(12) United States Patent
Campbell et al.

(10) Patent No.: US 8,969,349 B2
(45) Date of Patent: Mar. 3, 2015

(54) SUBSTITUTED QUINOXALINES AND QUINOXALINONES AS PDE-10 INHIBITORS

(75) Inventors: John Emmerson Campbell, Cambridge, MA (US); Michael Charles Hewitt, Somerville, MA (US); Philip Jones, Danvers, MA (US); Linghong Xie, Southborough, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

(21) Appl. No.: 13/700,051

(22) PCT Filed: May 26, 2011

(86) PCT No.: PCT/US2011/038057
§ 371 (c)(1),
(2), (4) Date: Mar. 7, 2013

(87) PCT Pub. No.: WO2011/150156
PCT Pub. Date: Dec. 1, 2011

(65) Prior Publication Data
US 2013/0158003 A1 Jun. 20, 2013

Related U.S. Application Data

(60) Provisional application No. 61/348,683, filed on May 26, 2010, provisional application No. 61/411,410, filed on Nov. 8, 2010.

(51) Int. Cl.
| | | |
|---|---|---|
| A61K 31/498 | (2006.01) | |
| C07D 241/40 | (2006.01) | |
| C07D 403/06 | (2006.01) | |
| C07D 401/06 | (2006.01) | |
| C07D 471/04 | (2006.01) | |
| C07D 471/14 | (2006.01) | |
| C07D 487/04 | (2006.01) | |
| C07D 491/056 | (2006.01) | |
| C07D 498/14 | (2006.01) | |
| C07D 519/00 | (2006.01) | |
| C07D 401/14 | (2006.01) | |
| C07D 405/14 | (2006.01) | |
| C07D 409/06 | (2006.01) | |
| C07D 409/14 | (2006.01) | |

(Continued)

(52) U.S. Cl.
CPC ............ C07D 403/06 (2013.01); C07D 401/06 (2013.01); C07D 471/04 (2013.01); C07D 471/14 (2013.01); C07D 487/04 (2013.01); C07D 491/056 (2013.01); C07D 498/14 (2013.01); C07D 519/00 (2013.01); C07D 401/14 (2013.01); C07D 405/14 (2013.01); C07D 409/06 (2013.01); C07D 409/14 (2013.01); C07D 413/06 (2013.01); C07D 417/06 (2013.01); C07D 498/04 (2013.01)

USPC .......... 514/249; 544/350; 544/353; 546/268.1; 548/217; 548/235; 548/262.4; 548/305.1; 548/335.1; 548/373.1; 549/59; 549/505

(58) Field of Classification Search
CPC ............................ A61K 31/498; C07D 241/40
USPC ................ 514/249; 544/350, 353; 546/268.1; 548/217, 235, 262.4, 305.1, 335.1, 548/373.1; 549/59, 505
See application file for complete search history.

(56) References Cited

U.S. PATENT DOCUMENTS

| | | |
|---|---|---|
| 4,036,840 A | 7/1977 | O'Brien et al. |
| 5,217,980 A | 6/1993 | Janssens et al. |

(Continued)

FOREIGN PATENT DOCUMENTS

| | | |
|---|---|---|
| JP | H02-64553 A1 | 5/1990 |
| WO | WO-2004/076451 A1 | 9/2004 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Choate, Hall & Stewart LLP; Daniel A. Klein; Andrea L. Reid

(57) ABSTRACT

Provided herein are compounds of formula A-L-B, and pharmaceutically acceptable salts and stereoisomers thereof, wherein A is

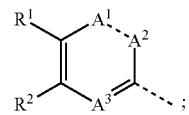

$R^1$ and $R^2$ together with the carbon atoms to which they are attached form a 1,2-phenylene ring optionally substituted with one or more $R^{11}$; L is —C($R^6$)$_2$—C($R^6$)$_2$—; B is a heteroaromatic group defined herein; and -$A^1$-$A^2$- , $A^3$, $R^{11}$ and $R^6$ are defined herein. Also disclosed are methods of their synthesis, pharmaceutical compositions comprising the compounds, and methods of their use. In one embodiment, the compounds provided herein are useful for the treatment, prevention, and/or management of various disorders, such as CNS disorders and metabolic disorders, including, but not limited to, e.g., neurological disorders, psychosis, schizophrenia, obesity, and diabetes.

25 Claims, No Drawings

(51) Int. Cl.
*C07D 413/06* (2006.01)
*C07D 417/06* (2006.01)
*C07D 498/04* (2006.01)

(56) References Cited

U.S. PATENT DOCUMENTS

2007/0299078 A1* 12/2007 Niu et al. .................. 514/249
2010/0028299 A1   2/2010 Einav et al.

FOREIGN PATENT DOCUMENTS

| WO | WO-2005/030769 A1 | 4/2005 |
| WO | WO-2005/061496 A1 | 7/2005 |
| WO | WO-2006/072828 A2 | 7/2006 |
| WO | WO-2007/077490 A2 | 7/2007 |
| WO | WO-2007/100880 A1 | 9/2007 |
| WO | WO-2007/129183 A2 | 11/2007 |
| WO | WO-2008/020302 A2 | 2/2008 |
| WO | WO-2008/046757 A1 | 4/2008 |
| WO | WO-2009/094442 A2 | 7/2009 |
| WO | WO-2009/143156 A2 | 11/2009 |
| WO | WO-2009/152825 A1 | 12/2009 |
| WO | WO 2010/054067 | 5/2010 |
| WO | WO 2010/054078 | 5/2010 |
| WO | WO-2010/132999 A1 | 11/2010 |
| WO | WO-2011/053559 A1 | 5/2011 |

OTHER PUBLICATIONS

Hackam, et al. JAMA, 296(14), 2006, 1731-1732.*
Kolasa, T. et al., Heteroarylmethoxyphenylalkoxy-iminoalkylcarboxylic acids as leukotriene biosynthesis inhibitors, Journal of Medicinal Chemistry, 43(4):690-705 (2000).
Reiter, J. et al., On triazoles. XXXV. The Reaction of 5-amino-1,2,4-triazoles with di- and triketones, Journal of Heterocyclic Chemistry, 32(2):407-417 (1995).

* cited by examiner

SUBSTITUTED QUINOXALINES AND QUINOXALINONES AS PDE-10 INHIBITORS

This application is the national stage entry of PCT/US2011/038057, filed May 26, 2011, which claims priority to U.S. Provisional Patent Application No. 61/348,683, filed May 26, 2010, and U.S. Provisional Patent Application No. 61/411,410, filed Nov. 8, 2010, the contents of all of which are hereby incorporated herein by reference in their entireties.

I. FIELD

Provided herein are heteroaryl compounds useful for treating various disorders or diseases, such as disorders or diseases of the central nervous system and metabolic disorders. Also provided herein are compositions comprising the compounds, and methods of use thereof.

II. BACKGROUND

Central nervous system (CNS) disorders affect a wide range of the population with differing severity. For example, schizophrenia is a psychopathic disorder of unknown origin, which usually appears for the first time in early adulthood and is marked by characteristics, such as, psychotic symptoms, phasic progression and development, and deterioration in social behavior and professional capability. Characteristic psychotic symptoms include disorders of thought content (e.g., multiple, fragmentary, incoherent, implausible or simply delusional contents, or ideas of persecution) and of mentality (e.g., loss of association, flight of imagination, incoherence, or incomprehensibility), as well as disorders of perceptibility (e.g., hallucinations), emotions (e.g., superficial or inadequate emotions), self-perceptions, intentions, impulses, and inter-human relationships, and psychomotoric disorders (e.g., catatonia). Other symptoms are also associated with this disorder. See, e.g., *Diagnostic and Statistical Manual of Mental Disorders*, 4th Ed., American Psychiatric Association (1997) (DSM-IV™).

Schizophrenia can be classified into various subgroups. For example, the paranoid type is characterized by delusions and hallucinations and absence of thought disorder, disorganized behavior, and affective flattening. The disorganized type, also named hebephrenic schizophrenia, is characterized by the presence of both thought disorder and affective flattening. The cataconic type is characterized by prominent psychomotor disturbances, including symptoms of catatonic stupor and waxy flexibility. In the undifferentiated type, psychotic symptoms are present but the criteria for paranoid, disorganized, or catatonic types have not been met.

The symptoms of schizophrenia normally manifest themselves in three broad categories, i.e., positive, negative and cognitive symptoms. Positive symptoms are those that represent an excess of normal experiences, such as hallucinations, disorganized speech, and delusions. Negative symptoms are those where the patient suffers from a lack of normal experiences, such as anhedonia, lack of motivation, inability to experience pleasure, and lack of social interaction. The cognitive symptoms relate to cognitive impairment in schizophrenics, such as lack of sustained attention, impairment of memory, and deficits in decision making. The current antipsychotics are somewhat effective in treating the positive symptoms but are less effective in treating the negative or cognitive symptoms. For instance, the current typical or atypical anti-psychotics do not address cognitive or negative symptoms of schizophrenia, and only treat the positive symptoms in approximately 40% of patients.

Cognitive impairments include a decline in cognitive functions or cognitive domains, e.g., working memory, attention and vigilance, verbal learning and memory, visual learning and memory, reasoning and problem solving, e.g., executive function, speed of processing and/or social cognition. In particular, cognitive impairment may indicate deficits in attention, disorganized thinking, slow thinking, difficulty in understanding, poor concentration, impairment of problem solving, poor memory, difficulties in expressing thoughts, difficulties in integrating thoughts, feelings and behavior, or difficulties in extinction of irrelevant thoughts.

Agitation is a well-recognized behavioral disorder with a range of symptoms, including hostility, extreme excitement, poor impulse control, tension, and uncooperativeness. Agitation is common in the elderly and often associated with dementia such as those caused by Alzheimer's disease, Parkinson's disease, and Huntington's disease, and by diseases that affect blood vessels, such as stroke or multi-infarct dementia, which is caused by multiple strokes in the brain. An estimated five percent of people aged 65 and older and up to 20 percent of those aged 80 and older are affected by dementia. Of these sufferers, nearly half exhibit behavioral disturbances, such as agitation, wandering, and violent outbursts. Agitated behaviors can also be manifested in cognitively intact elderly people and by those with psychiatric disorders other than dementia.

Dementia is characterized by several cognitive impairments including significant memory deficit and can stand alone, or be an underlying characteristic feature of a variety of diseases, including but not limited to, Alzheimer's disease, Parkinson's disease, Huntington's disease, and multiple sclerosis.

Thus, there remains a great need for effective treatments of various CNS disorders.

Cyclic nucleotide phosphodiesterases (PDEs) are a super family of enzymes encoded by twenty-one genes, and are subdivided into eleven known families based on structure and function. PDEs are modular enzymes having a catalytic domain in the C-terminal portion of the protein and regulatory elements in the N-terminal portion. PDEs hydrolyze the phosphodiester bond of cyclic nucleotides, e.g., cyclic adenosine monophosphate (cAMP) and cyclic guanosine monophosphate (cGMP), converting them into the corresponding monophosphates. cAMP and cGMP function as intracellular second messengers regulating a wide range of intracellular processes. For instance, in neurons cAMP and cGMP activate cyclic-nucleotide-dependent kinases and the subsequent phosphorylation of proteins involved in acute regulation of synaptic transmission and in neuronal differentiation and survival. PDEs are therefore important regulators of a wide variety of physiological processes. PDEs are expressed differentially throughout the organism and cyclic nucleotide signaling is highly compartmentalized within individual cells. Thus, different PDE isozymes can serve distinct physiological functions. Compounds that can selectively inhibit distinct PDE families or isozymes may offer additional therapeutic benefits, fewer side effects, or both.

PDE-10 was first reported in 1999 (Soderling et al., *Proc. Natl. Acad. Sci.*, 1999, 96, 7071-76; Loughney et al., *Gene*, 1999, 234, 109-17; Fujishige et al., *J. Biol. Chem.*, 1999, 274, 18438-45). Homology screening revealed mouse PDE-10A as the first member of the PDE-10 family of enzymes. The human PDE-10 sequence is highly homologous to both the rat and mouse PDE-10 enzymes. The PDE-10 family of enzymes has a lower degree of sequence homology as compared to previously identified PDE families. PDE-10 can hydrolyze both cAMP ($K_m$=0.26 μM) and cGMP ($K_m$=7.2 μM), and has a five-fold greater $V_{max}$ for cGMP than for cAMP.

PDE-10A is primarily expressed in the brain, also found in testes. PDE-10A mRNA and protein are abundant in brain tissues, and are mainly detected at high levels in the medium spiny neurons (MSN) of the striatum, a distribution conserved across mammalian species. The striatal MSNs provide input to the basal ganglia circuit, affecting action selection and execution, and suppressing undesired responses to sensory stimuli. PDE-10A has become an emerging target for the development of new anti-psychotics. Inhibitors of PDE-10A have been shown to increase cAMP and cGMP levels in striatal tissue and have demonstrated efficacy against not only positive but also negative and cognitive symptoms of schizophrenia in animals. PDE-10A is also useful in treating metabolic disorders, such as diabetes, obesity, and metabolic syndrome.

Citation of any references in this Section of the application is not to be construed as an admission that such reference is prior art to the present application.

III. SUMMARY

Provided herein are compounds of formula (I), or pharmaceutically acceptable salts or stereoisomers thereof:

$$A\text{-}L\text{-}B \quad (I),$$

wherein A, L, and B are defined herein elsewhere. The compounds are useful for treating various diseases or disorders, such as CNS disorders and metabolic disorders.

Also provided herein are compositions and dosage forms comprising, a compound provided herein, and one or more pharmaceutically acceptable excipient(s). Compositions and dosage forms provided herein may further comprise one or more additional active ingredients.

Also provided herein are methods for the treatment, prevention, and/or management of various disorders, such as a CNS disorder or a metabolic disorder, e.g., the treatment, prevention, and/or amelioration of one or more symptoms of a disorder, using the compounds and compositions provided herein. In one embodiment, the disorders provided herein include, but are not limited to, schizophrenia, psychosis, cognitive disorders, mood disorders, attention deficit disorders, and neurodegenerative diseases. In one embodiment, the disorders include, but are not limited to, neurological disorder, schizophrenia, schizophrenia-related disorder, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, disease having a psychosis component, psychotic disorder, brief psychotic disorder, Alzheimer's psychosis, Parkinson's psychosis, shared psychotic disorder, substance-induced psychotic disorder (e.g., cocaine, alcohol, amphetamine), psychotic disorder due to a general medical condition, psychoaffective disorder, aggression, delirium, excitative psychosis, Tourette's syndrome, manic disorder, organic psychosis, NOS psychosis, convulsion, seizure, agitation, posttraumatic stress disorder, behavior disorder, neurodegenerative disease, Huntington's disease, Alzheimer's disease, Parkinson's disease, dyskinesia, dementia, mood disorder, bipolar disorder, anxiety, depression, major depressive disorder, unipolar depression, treatment resistant depression, dysthymia, affective disorder, seasonal affective disorder, obsessive-compulsive disorder, attention deficit disorder (ADD), attention deficit hyperactivity disorder (ADHD), vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome (RLS), multiple sclerosis, sleep disorder, substance abuse or dependency (e.g., nicotine, cocaine), addiction, eating disorder, autism, obesity, undesirable weight retention or weight gain, metabolic syndrome, diabetes, non-insulin dependent diabetes, impaired glucose tolerance, and hyperglycemia.

In one embodiment, provided herein is a method of treating, preventing, and/or managing schizophrenia or related disorders, including but not limited to, schizoaffective disorder, schizophreniform disorder, paraphrenia, paranoid personality disorder, schizoid personality disorder, and schizotypal personality disorder; a disease having a psychosis component, including but not limited to, Alzheimer's psychosis, Parkinson's psychosis, shared psychotic disorder, and substance-induced psychotic disorder; cognitive impairment, including but not limited to, cognitive impairment associated with schizophrenia, cognitive deficit in Alzheimer's disease, and cognitive deficit in Parkinson's disease; mood disorder, including but not limited to, bipolar disorder; attention deficit disorder, including but not limited to attention deficit hyperactive disorder; neurodegenerative disease, including but not limited to, Huntington's disease; or depression, including but not limited to, major depressive disorder, unipolar depression, and treatment resistant depression. In one embodiment, provided herein is a method of treating, preventing, and/or managing a disorder provided herein elsewhere (e.g., a CNS disorder or a metabolic disorder), in a subject, such as a mammal, e.g., human, rodent (e.g., mice and rats), cat, dog, and non-human primate, among others. In one embodiment, provided herein is a method of treating, preventing, and/or ameliorating one or more symptoms associated with a disorder provided herein elsewhere (e.g., a CNS disorder or a metabolic disorder), in a subject, such as a mammal, e.g., human, rodent (e.g., mice and rats), cat, dog, and non-human primate, among others. In one embodiment, the method comprises contacting a compound provided herein with a PDE enzyme. In one embodiment, the method comprises contacting a compound provided herein with a PDE enzyme expressed in the central nervous system. In one embodiment, the method comprises contacting a compound provided herein with PDE-10A. In one embodiment, the method comprises contacting a cell with a compound provided herein. In an exemplary embodiment, the cell is a brain cell, such as, e.g., a MSN cell, a neuronal cell, or a glial cell.

IV. DETAILED DESCRIPTION

Unless defined otherwise, all technical and scientific terms used herein have the same meaning as those commonly understood by one of ordinary skill in the art. All publications and patents referred to herein are incorporated by reference herein in their entireties.

A. Definitions

As used in the specification and the accompanying claims, the indefinite articles "a" and "an" and the definite article "the" include plural as well as singular referents, unless the context clearly dictates otherwise.

As used herein, and unless otherwise indicated, the term "alkyl" refers to a linear or branched saturated monovalent hydrocarbon radical, wherein the alkyl may be optionally substituted with one or more substituents. In certain embodiments, the alkyl is a linear saturated monovalent hydrocarbon radical that has 1 to 20 ($C_{1\text{-}20}$), 1 to 15 ($C_{1\text{-}15}$), 1 to 12 ($C_{1\text{-}12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$, or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl, isopropyl), butyl (including all isomeric forms, e.g., n-butyl, isobutyl, t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is optionally substituted as described herein elsewhere. In some embodiments, the alkyl is optionally substituted with one or more halo.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" also encompasses radicals having "cis" and "trans" configurations, or alternatively, "E" and "Z" configurations, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenyl is optionally substituted as described herein elsewhere. In some embodiments, the alkenyl is optionally substituted with one or more halo.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—$CH_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is optionally substituted as described herein elsewhere. In some embodiments, the alkynyl is optionally substituted with one or more halo.

As used herein, and unless otherwise specified, the term "cycloalkyl" refers to a cyclic fully or partially saturated bridged and/or non-bridged hydrocarbon radical or ring system, which may be optionally substituted with one or more substituents. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentadienyl, cyclohexyl, cyclohexenyl, cycloheptyl, decalinyl, and adamantyl. In certain embodiments, the cycloalkyl is optionally substituted as described herein elsewhere. In some embodiments, the cycloalkyl is optionally substituted with one or more halo.

As used herein, and unless otherwise specified, the term "heteroalkyl" refers to a stable straight or branched chain consisting of the stated number of carbon atoms and from one or more, in one embodiment, one to three, heteroatoms selected from the group consisting of O, N, Si, and S, and wherein the nitrogen and sulfur atoms are optionally oxidized and the nitrogen heteroatom can optionally be quaternized. In one embodiment, the heteroatom(s) O and N can be placed at any interior position of the heteroalkyl group. In one embodiment, the heteroatom(s) S and Si can be placed at any position of the heteroalkyl group (e.g., interior or terminal position), including the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms can be consecutive, such as, for example, —$CH_2$—NH—O—$CH_3$ and —$CH_2$—O—Si($CH_3$)$_3$. In certain embodiments, the heteroalkyl is optionally substituted as described herein elsewhere. In some embodiments, the heteroalkyl is optionally substituted with one or more halo.

As used herein, and unless otherwise specified, the term "alkoxyl" or "alkoxy" refers to a stable straight or branched chain, or cyclic hydrocarbon radical, or combinations thereof, consisting of the stated number of carbon atoms and from one or more, in one embodiment, one to three, O atoms, wherein at least one O atom is at the position where the alkoxyl or alkoxy group is attached to the remainder of the molecule. Examples of alkoxyl include, but are not limited to, —O—$CH_3$, —O—$CF_3$, —O—$CH_2$—$CH_3$, —O—$CH_2$—$CH_2$—$CH_3$, —O—CH—($CH_3$)$_2$, and —O—$CH_2$—$CH_2$—O—$CH_3$. In one embodiment, the alkoxyl is optionally substituted as described herein elsewhere. In some embodiments, the alkoxyl is optionally substituted with one or more halo.

As used herein, and unless otherwise specified, the term "aminoalkyl" or "alkylamino" refers to a stable straight or branched chain, or cyclic hydrocarbon radical, or combinations thereof, consisting of the stated number of carbon atoms and from one or more, in one embodiment, one to three, N atoms, wherein at least one N atom is at the position where the aminoalkyl or alkylamino group is attached to the remainder of the molecule. Examples of aminoalkyl include, but are not limited to, —NH—$CH_3$, —N($CH_3$)$_2$, —NH—$CH_2$—$CH_3$, —N($CH_3$)—$CH_2$—$CH_3$, —NH—CH—($CH_3$)$_2$, —NH—$CH_2$—$CH_2$—NH—$CH_3$, and —NH—$CH_2$—$CH_2$—N($CH_3$)$_2$. In one embodiment, the aminoalkyl is optionally substituted as described herein elsewhere. In some embodiments, the aminoalkyl is optionally substituted with one or more halo.

As used herein, and unless otherwise specified, the term "aryl" refers to an optionally substituted monocyclic or multicyclic radical or ring system that contains at least one aromatic hydrocarbon ring. In certain embodiments, the aryl has from 6 to 20, from 6 to 15, or from 6 to 10 ring atoms. Examples of aryl groups include, but are not limited to, phenyl, naphthyl, fluorenyl, azulenyl, anthryl, phenanthryl, pyrenyl, biphenyl, and terphenyl. In certain embodiments, aryl also refers to bicyclic, tricyclic, or tetracyclic carbon rings, where one of the rings is aromatic and the other(s) of the rings may be saturated, partially unsaturated, or aromatic, for example, dihydronaphthyl, indenyl, indanyl, or tetrahydronaphthyl (tetralinyl). In certain embodiments, aryl may be a bicyclic, tricyclic, or tetracyclic ring system, where at least one of the rings is aromatic and one or more of the ring(s) may be saturated or partially unsaturated optionally containing one or more heteroatoms independently selected from O, S, and N. In certain embodiments, the aryl is optionally substituted with one or more substituents as described herein elsewhere.

As used herein, and unless otherwise specified, the term "arylalkyl" or "aralkyl" refers to a monovalent alkyl group substituted with aryl. An example of aralkyl includes, but is not limited to, benzyl. In certain embodiments, both alkyl and aryl may be optionally substituted with one or more substituents as described herein elsewhere.

As used herein, and unless otherwise specified, the term "heteroarylalkyl" or "heteroaralkyl" refers to a monovalent alkyl group substituted with heteroaryl. In certain embodiments, both alkyl and heteroaryl may be optionally substituted with one or more substituents as described herein elsewhere.

As used herein, and unless otherwise specified, the term "heteroaryl" refers to an optionally substituted monocyclic or multicyclic radical or ring system which contains at least one aromatic ring having one or more heteroatoms independently selected from O, S, and N. In one embodiment, each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, heteroaryl also refers to bicyclic, tricyclic, or tetracyclic rings, where one of the rings is aromatic having one or more heteroatoms independently selected from O, S, and N, and the other(s) of the rings may be saturated, partially unsaturated, or aromatic and may be carbocyclic or contain one or more heteroatoms independently selected from O, S, and N. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents as described herein elsewhere.

As used herein, and unless otherwise specified, the term "heterocycloalkyl" or "heterocyclyl" refers to an optionally substituted monocyclic or multicyclic radical or ring system which contains at least one non-aromatic saturated or partially saturated ring having one or more heteroatoms independently selected from O, S, and N. In certain embodiments, the heterocyclyl or heterocycloalkyl group has from 3 to 20, from 3 to 15, from 3 to 10, from 3 to 8, from 4 to 7, or from 5 to 6 ring atoms. In certain embodiments, the heterocyclyl or heterocycloalkyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, the ring carbon atoms may be optionally substituted with oxo, and some rings may be partially or fully saturated, or aromatic. The heterocycloalkyl or heterocyclyl may be attached to the main structure at a heteroatom or a carbon atom which results in the creation of a stable compound. Examples include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, when the heterocyclyl or heterocycloalkyl ring contains one or more O, the heterocyclyl or heterocycloalkyl may also be referred to as "cycloalkoxyl." In certain embodiments, the heterocyclyl or heterocycloalkyl is optionally substituted with one or more substituents as described herein elsewhere.

As used herein, and unless otherwise specified, the term "halogen", "halide" or "halo" refers to fluorine, chlorine, bromine, and iodine.

As used herein, and unless otherwise specified, the term "hydrogen" encompasses proton ($^1$H), deuterium ($^2$H), tritium ($^3$H), and/or mixtures thereof. In a compound described herein, one or more positions occupied by hydrogen may be enriched with deuterium and/or tritium. Such isotopically enriched analogs may be prepared from suitable isotopically labeled starting material obtained from a commercial source or prepared using known literature procedures.

As used herein, and unless otherwise specified, the term "optionally substituted" is intended to mean that a group, such as an alkyl, alkenyl, alkynyl, cycloalkyl, heteroalkyl, alkoxyl, aminoalkyl, aryl, aralkyl, heteroaralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—NO$_2$), oxo (=O), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) R$^b$ and R$^c$ together with the N atom to which they are attached form heteroaryl or heterocyclyl, optionally substituted with one or more, in one embodiment, one, two, three, or four, substituents $Q^1$. As used herein, all groups that can be substituted are "optionally substituted," unless otherwise specified.

In one embodiment, each $Q^1$ is independently selected from the group consisting of (a) cyano, halo, oxo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

As used herein, and unless otherwise specified, the term "pharmaceutically acceptable salts" refers to salts prepared from pharmaceutically acceptable non-toxic acids, including inorganic acids and organic acids; or from pharmaceutically acceptable non-toxic bases, including inorganic bases and organic bases. In one embodiment, suitable non-toxic acids include, but are not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, and p-toluenesulfonic.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceu-* tical Additives, 3rd Edition, Ash and Ash Eds., Gower Publishing Company: 2007; Pharmaceutical Preformulation and Formulation, 2nd Edition, Gibson Ed., CRC Press LLC: Boca Raton, Fla., 2009.

As used herein, and unless otherwise specified, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

As used herein, and unless otherwise specified, the terms "drug" and "therapeutic agent" refer to a compound, or a pharmaceutical composition thereof, which is administered to a subject for treating, preventing, managing, or ameliorating one or more symptoms of a condition, disorder, or disease.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, "amelioration" of the symptoms of a particular disorder by administration of a particular pharmaceutical composition refers to any lessening, whether permanent or temporary, lasting or transient, that can be attributed to or associated with the administration of the composition.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise specified, the term "neurological disorder" refers to any condition of the central or peripheral nervous system of a mammal. The term "neurological disorder" includes, but is not limited to, neurodegenerative diseases (e.g., Alzheimer's disease, Parkinson's disease and amyotrophic lateral sclerosis), neuropsychiatric diseases (e.g., schizophrenia and anxieties, such as general anxiety disorder), and affective disorders (e.g., depression and attention deficit disorder). Exemplary neurological disorders include, but are not limited to, MLS (cerebellar ataxia), Huntington's disease, Down syndrome, multi-infarct dementia, depression (e.g., major depressive disorder, dysthymia, and bipolar depressive disorder), dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder. An exemplary method would also include treating or preventing loss of neuronal function characteristic of neurodegenerative disorder.

As used herein, and unless otherwise specified, the terms "psychosis," "schizophrenia," "obsessive-compulsive disorder," "substance abuse," "anxiety," "eating disorders," "migraine," and other CNS disorders described herein elsewhere are used herein in a manner consistent with their accepted meanings in the art. See, e.g., *Diagnostic and Statistical Manual of Mental Disorders*, 4$^{th}$ Ed., American Psychiatric Association (1997) (DSM-IV™).

As used herein, and unless otherwise specified, the term "affective disorder" includes depression, attention deficit disorder, attention deficit disorder with hyperactivity, bipolar and manic conditions, and the like. The terms "attention deficit disorder" (ADD) and "attention deficit disorder with hyperactivity" (ADDH), or attention deficit/hyperactivity disorder (AD/HD), are used herein in accordance with the accepted meanings as found in the *Diagnostic and Statistical Manual of Mental Disorders*, 4$^{th}$ Ed., American Psychiatric Association (1997) (DSM-IV™).

As used herein, and unless otherwise specified, the term "depression" includes all forms of depression including, but not limited to, major depressive disorder (MDD), bipolar disorder, seasonal affective disorder (SAD), dysthymia, and treatment resistant depression. "Major depressive disorder" is used herein interchangeably with "unipolar depression" and "major depression." "Depression" may also include any condition commonly associated with depression, such as all forms of fatigue (e.g., chronic fatigue syndrome) and cognitive deficits.

As used herein, and unless otherwise specified, the term "pain" refers to an unpleasant sensory and emotional experience. The term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (See, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In addition, The term "pain" includes pain resulting from dysfunction of the nervous system: organic pain states that share clinical features of neuropathic pain and possible common pathophysiology mechanisms, but are not initiated by an identifiable lesion in any part of the nervous system.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, and unless otherwise specified, the terms "overweight" and "obese" refer to adult persons 18 years or older having a greater than ideal body weight (e.g., greater than ideal body fat) that can be measured by the body mass index (BMI), which is generally correlated with total body fat and the relative risk of suffering from premature death or disability due to diseases as a consequence of the overweight or obese condition. BMI is calculated by weight in kilograms divided by height in meters squared ($kg/m^2$), or alternatively by weight in pounds, multiplied by 703, divided by height in inches squared ($lbs \times 703/in^2$). Overweight individuals typically have a BMI of between about 25 and about 29, whereas obese individuals typically have a BMI of about 30 or more (see, e.g., National Heart, Lung, and Blood Institute, Clinical Guidelines on the Identification, Evaluation, and Treatment of Overweight and Obesity in Adults, The Evidence Report, Washington, D.C., U.S. Department of Health and Human Services, NIH publication no. 98-4083, 1998). Other means for indicating excess body weight, excess body fat, and obesity include direct measure of body fat and/or waist-to-hip ratio measurements.

As used herein, and unless otherwise specified, the term "metabolic syndrome" is used according to its usual meaning in the art. The American Heart Association characterizes metabolic syndrome as having at least three or more of the following symptoms: 1) elevated waist circumference [>102 cm (40 inches) in men; >88 cm (35 inches) in women]; 2) elevated triglycerides [≥150 mg/dL (>1.695 mmol/L) or drug treatment for elevated triglycerides]; 3) reduced HDL cholesterol [<40 mg/dL (1.036 mmol/L) in men; <50 mg/dL (1.295 mmol/L) in women; or drug treatment for reduced HDL-C]; 4) elevated blood pressure [≥130/85 mmHg or drug treatment for hypertension]; and 5) elevated fasting glucose [≥110 mg/dL or drug treatment for elevated glucose]. According to the World Health Organization, metabolic syndrome includes individuals suffering from diabetes, impaired glucose tolerance, impaired fasting glucose, or insulin resistance plus two or more of the following symptoms: 1) high blood pressure [≥160/90 mmHg]; 2) hyperlipdemia [triglyceride concentration ≥150 mg/dL (1.695 mmol/L) and/or HDL cholesterol <35 mg/dL (0.9 mmol/L) in men and <39 mg/dL (1.0 mmol/L) in women]; 3) central obesity [waist-to-hip ratio of >0.90 for men and >0.85 for women and/or BMI >30 $kg/m^2$]; and 4) microalbuminuria [urinary albumin excretion rate ≥20 μg/min or an albumin-to-creatinine ratio ≥20 mg/kg).

B. Compounds

In one embodiment, provided herein is a compound of formula (I):

or a pharmaceutically acceptable salt or stereoisomer thereof, wherein

L is $-C(R^6)_2-C(R^6)_2-$, $-C(R^6)=C(R^6)-$, $-N(R^{10})-C(R^6)_2-$, $-O-C(R^6)_2-$, $-C(R^6)_2-N(R^{10})-$, $-C(R^6)_2-O-$, $-C(R^6)_2-S-$, $-S-$, $-(CH_2)_p-S-(CH_2)_q-$, or $-(CH_2)_u-$;

A is

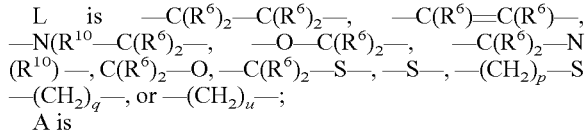

B is

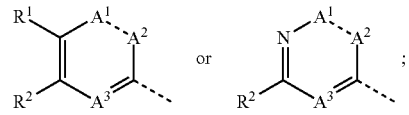

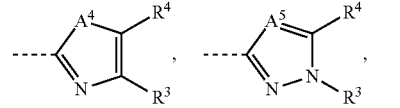

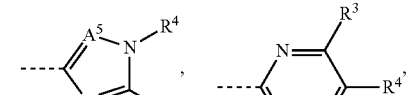

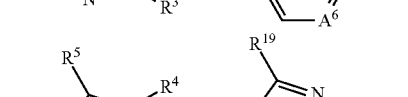

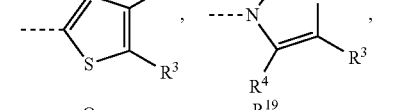

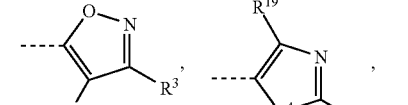


$-A^1-A^2-$ is $-NR^7-C(=O)-$, $-C(=O)-NR^7-$, $-O-C(=O)-$, $-C(=O)-O-$, $-N=CR^8-$, $-CR^8=N-$, $-CR^8=CR^8-$, or $-N=N-$;

$A^3$ is N or $CR^9$;

$A^4$ is $NR^5$, O, or S;

$A^5$ is $CR^5$ or N;

$A^6$ is N or $CR^5$;

$R^1$ and $R^2$ are each independently (i) hydrogen, cyano, or halo; or (ii) $(C_1-C_{10})$alkyl, $(C_2-C_{10})$alkenyl, $(C_1-C_{10})$alkoxyl, $(C_1-C_{10})$aminoalkyl, $(C_1-C_{10})$heteroalkyl, $(C_3-C_{10})$cycloalkyl, (6 to 10 membered)aryl, (5 to 10 membered)heteroaryl, (3 to 12 membered)heterocyclyl, hydroxyl, amino, imino, amido, carbonyl, thiol, sulfinyl, or sulfonyl, each of which is optionally substituted with one or more $R^{11}$; or (iii) $R^1$ and $R^2$ together with the carbon atoms to which they are attached form a ring optionally substituted with one or more $R^{11}$;

$R^3$ and $R^4$ are each independently (i) hydrogen, cyano, or halo; or (ii) $(C_1-C_{10})$alkyl, $(C_2-C_{10})$alkenyl, $(C_1-C_{10})$alkoxyl, $(C_1-C_{10})$aminoalkyl, $(C_1-C_{10})$heteroalkyl, $(C_3-C_{10})$cycloalkyl, (6 to 10 membered)aryl, (5 to 10 membered)heteroaryl, (3 to 12 membered)heterocyclyl, hydroxyl, amino, imino, amido, carbonyl, thiol, sulfinyl, or sulfonyl, each of which is optionally substituted with one or more $R^{11}$; or (iii) $R^3$ and $R^4$ together with the atoms to which they are attached form a ring optionally substituted with one or more $R^{11}$;

$R^5$ is (i) hydrogen, cyano, or halo; or (ii) $(C_1-C_{10})$alkyl, $(C_2-C_{10})$alkenyl, $(C_1-C_{10})$alkoxyl, $(C_1-C_{10})$aminoalkyl, $(C_1-C_{10})$heteroalkyl, $(C_3-C_{10})$cycloalkyl, (6 to 10 membered)aryl, (5 to 10 membered)heteroaryl, (3 to 12 membered)heterocyclyl, hydroxyl, amino, imino, amido, carbonyl, thiol, sulfinyl, or sulfonyl, each of which is optionally substituted with one or more $R^{11}$; or (iii) $R^4$ and $R^5$ together with the atoms to which they are attached form a ring optionally substituted with one or more $R^{11}$;

$R^{19}$ is (i) hydrogen, cyano, or halo; or (ii) $(C_1-C_{10})$alkyl, $(C_2-C_{10})$alkenyl, $(C_1-C_{10})$alkoxyl, $(C_1-C_{10})$aminoalkyl, $(C_1-C_{10})$heteroalkyl, $(C_3-C_{10})$cycloalkyl, (6 to 10 membered)aryl, (5 to 10 membered)heteroaryl, (3 to 12 membered)heterocyclyl, hydroxyl, amino, imino, amido, carbonyl, thiol, sulfinyl, or sulfonyl, each of which is optionally substituted with one or more $R^{11}$;

$R^{20}$ is (i) hydrogen; or (ii) $(C_1-C_{10})$alkyl, $(C_2-C_{10})$alkenyl, $(C_1-C_{10})$heteroalkyl, $(C_3-C_{10})$cycloalkyl, (6 to 10 membered)aryl, (5 to 10 membered)heteroaryl, (3 to 12 membered) heterocyclyl, carbonyl, or sulfonyl, each of which is optionally substituted with one or more $R^{11}$;

each occurrence of $R^6$ is independently hydrogen, halo, or $(C_1-C_6)$alkyl optionally substituted with one or more halo;

$R^7$ is hydrogen or $(C_1-C_6)$alkyl optionally substituted with one or more halo;

each occurrence of $R^8$ is independently (i) hydrogen, cyano, or halo; or (ii) $(C_1-C_{10})$alkyl, $(C_2-C_{10})$alkenyl, $(C_1-C_{10})$alkoxyl, $(C_1-C_{10})$aminoalkyl, $(C_1-C_{10})$heteroalkyl, $(C_3-C_{10})$cycloalkyl, (6 to 10 membered)aryl, (5 to 10 membered) heteroaryl, (3 to 12 membered) heterocyclyl, hydroxyl, amino, imino, amido, carbonyl, thiol, sulfinyl, or sulfonyl, each of which is optionally substituted with one or more $R^{11}$;

$R^9$ is hydrogen, cyano, halo, $(C_1-C_6)$alkyl optionally substituted with one or more halo, or $(C_1-C_6)$alkoxyl optionally substituted with one or more halo;

$R^{10}$ is hydrogen or $(C_1-C_6)$alkyl optionally substituted with one or more halo;

each occurrence of $R^{11}$ is independently hydrogen, halogen, cyano, =O, $-OR^{13}$, $-NR^{13}R^{14}$, $-N(R^{13})C(O)R^{14}$, $-C(O)NR^{13}R^{14}$, $-C(O)R^{13}$, $-C(O)OR^{13}$, $-OC(O)R^{13}$, $-SR^{13}$, $-S(O)R^{13}$, $-S(O)_2R^{13}$, $-S(O)_2NR^{13}R^{14}$, $(C_1-C_{10})$alkyl optionally substituted with one or more $R^{12}$, $(C_1-C_{10})$heteroalkyl optionally substituted with one or more $R^{12}$, $(C_3-C_{10})$cycloalkyl optionally substituted with one or more $R^{12}$, $(C_7-C_{12})$aralkyl optionally substituted with one or more $R^{12}$, $(C_3-C_{12})$heteroaralkyl optionally substituted with one or more $R^{12}$, (6 to 10 membered)aryl optionally substituted with one or more $R^{12}$, (5 to 10 membered)heteroaryl optionally substituted with one or more $R^{12}$, or (3 to 12 membered) heterocyclyl optionally substituted with one or more $R^{12}$;

each occurrence of $R^{12}$ is independently hydrogen, $(C_1-C_6)$alkyl optionally substituted with one or more $R^{13}$, $(C_3-C_6)$cycloalkyl optionally substituted with one or more $R^{13}$, halogen, cyano, =O, $-OR^{13}$, $-NR^{13}R^{14}$, $-N(R^{13})C(O)R^{14}$, $-C(O)NR^{13}R^{14}$, $-C(O)R^{13}$, $-C(O)OR^{13}$, $-OC(O)R^{13}$, $-SR^{13}$, $-S(O)R^{13}$, $-S(O)_2R^{13}$, or $-S(O)_2NR^{13}R^{14}$;

each occurrence of $R^{13}$ and $R^{14}$ is independently hydrogen, $(C_1-C_6)$alkyl, $(C_1-C_6)$ heteroalkyl, $(C_3-C_6)$cycloalkyl, $(C_7-C_{10})$aralkyl; $(C_3-C_{12})$heteroaralkyl, (6 to 10 membered)aryl, (5 to 10 membered)heteroaryl, or (3 to 12 membered)heterocyclyl; or $R^{13}$ and $R^{14}$ together may form a 3 to 10 membered ring; and u is 2 or 3; and p and q are each independently 0, 1, or 2, provided that when one of p and q is 0, the other is 1 or 2.

In one embodiment, L is $-C(R^6)_2-C(R^6)_2-$, $-C(R^6)=C(R^6)-$, $-N(R^{10})-C(R^6)_2-$, $-O-C(R^6)_2-$, $-C(R^6)_2-N(R^{10})-$, $-C(R^6)_2-O-$, $-C(R^6)_2-S-$, or $-S-$.

In one embodiment, L is $-C(R^6)_2-C(R^6)_2-$. In one embodiment, L is $-C(R^6)=C(R^6)-$. In one embodiment, L is $-N(R^{10})-C(R^6)_2-$. In one embodiment, L is $-O-C(R^6)_2-$. In one embodiment, L is $-C(R^6)_2N-(R^{10})-$. In one embodiment, L is $-C(R^6)_2-O-$. In one embodiment, L is $-C(R^6)_2-S-$. In one embodiment, L is $-S-$.

In one embodiment, L is $-(CH_2)_p-S-(CH_2)_q-$, $-CH=CH-$, or $-(CH_2)_u-$. In one embodiment, L is $-(CH_2)_p-S-(CH_2)_q-$. In one embodiment, L is $-CH=CH-$. In one embodiment, L is $-(CH_2)_u-$.

In one embodiment, A is

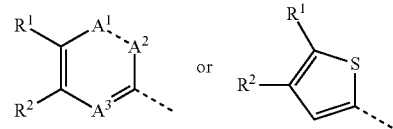

In one embodiment, A is

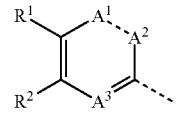

In one embodiment, -$A^1$-$A^2$- is $-NR^7-C(=O)-$. In one embodiment, -$A^1$-$A^2$- is $-C(=O)-NR^7-$. In one embodiment, -$A^1$-$A^2$- is $-O-C(=O)-$. In one embodiment, -$A^1$-$A^2$- is $-C(=O)-O-$. In one embodiment, -$A^1$-$A^2$- is $-N=CR^8-$. In one embodiment, -$A^1$-$A^2$- is $-CR^8=N-$. In one embodiment, -$A^1$-$A^2$- is $-CR^8=CR^8-$. In one embodiment, -$A^1$-$A^2$- is $-N=N-$.

In one embodiment, $A^3$ is N. In one embodiment, $A^3$ is $CR^9$.

In one embodiment, $A^4$ is $NR^5$. In one embodiment, $A^4$ is O. In one embodiment, $A^4$ is S.

In one embodiment, $A^5$ is N. In one embodiment, $A^5$ is $CR^5$.

In one embodiment, $A^6$ is N. In one embodiment, $A^6$ is $CR^5$.

In one embodiment, $R^1$ is hydrogen. In one embodiment, $R^1$ is cyano. In one embodiment, $R^1$ is halo. In one embodiment, $R^1$ is optionally substituted $(C_1-C_{10})$alkyl. In one embodiment, $R^1$ is optionally substituted $(C_2-C_{10})$alkenyl. In one embodiment, $R^1$ is optionally substituted $(C_1-C_{10})$alkoxyl. In one embodiment, $R^1$ is optionally substituted $(C_1-C_{10})$aminoalkyl. In one embodiment, $R^1$ is optionally substituted $(C_1-C_{10})$heteroalkyl. In one embodiment, $R^1$ is optionally substituted $(C_3-C_{10})$cycloalkyl. In one embodiment, $R^1$ is optionally substituted (6 to 10 membered)aryl. In one embodiment, $R^1$ is optionally substituted (5 to 10 membered)heteroaryl. In one embodiment, $R^1$ is optionally substituted (3 to 12 membered)heterocyclyl. In one embodiment, $R^1$ is optionally substituted hydroxyl. In one embodiment, $R^1$ is optionally substituted amino. In one embodiment, $R^1$ is optionally substituted imino. In one embodiment, $R^1$ is optionally substituted amido. In one embodiment, $R^1$ is optionally substituted carbonyl. In one embodiment, $R^1$ is optionally substituted thiol. In one embodiment, $R^1$ is optionally substituted sulfinyl. In one embodiment, $R^1$ is optionally substituted sulfonyl. In one embodiment, $R^1$ is optionally substituted with one or more $R^{11}$.

In one embodiment, $R^2$ is hydrogen. In one embodiment, $R^2$ is cyano. In one embodiment, $R^2$ is halo. In one embodiment, $R^2$ is optionally substituted $(C_1-C_{10})$alkyl. In one embodiment, $R^2$ is optionally substituted $(C_2-C_{10})$alkenyl. In one embodiment, $R^2$ is optionally substituted $(C_1-C_{10})$alkoxyl. In one embodiment, $R^2$ is optionally substituted $(C_1-C_{10})$aminoalkyl. In one embodiment, $R^2$ is optionally substituted $(C_1-C_{10})$heteroalkyl. In one embodiment, $R^2$ is optionally substituted $(C_3-C_{10})$cycloalkyl. In one embodiment, $R^2$ is optionally substituted (6 to 10 membered)aryl. In one embodiment, $R^2$ is optionally substituted (5 to 10 membered)heteroaryl. In one embodiment, $R^2$ is optionally substituted (3 to 12 membered)heterocyclyl. In one embodiment, $R^2$ is optionally substituted hydroxyl. In one embodiment, $R^2$ is optionally substituted amino. In one embodiment, $R^2$ is optionally substituted imino. In one embodiment, $R^2$ is optionally substituted amido. In one embodiment, $R^2$ is optionally substituted carbonyl. In one embodiment, $R^2$ is optionally substituted thiol. In one embodiment, $R^2$ is optionally substituted sulfinyl. In one embodiment, $R^2$ is optionally substituted sulfonyl. In one embodiment, $R^2$ is optionally substituted with one or more $R^{11}$.

In one embodiment, $R^1$ and $R^2$ together with the atoms to which they are attached form a ring optionally substituted with one or more $R^{11}$. In one embodiment, $R^1$ and $R^2$ together with the atoms to which they are attached form an optionally substituted aromatic ring. In one embodiment, $R^1$ and $R^2$ together with the atoms to which they are attached form an optionally substituted non-aromatic ring. In one embodiment, $R^1$ and $R^2$ together with the atoms to which they are attached form an optionally substituted partially saturated ring. In one embodiment, $R^1$ and $R^2$ together with the atoms to which they are attached form an optionally substituted 5-membered ring (which is further fused to the adjacent 6-membered ring to form a 9-membered fused ring system). In one embodiment, $R^1$ and $R^2$ together with the atoms to which they are attached form an optionally substituted 6-membered ring (which is further fused to the adjacent 6-membered ring to form a 10-membered fused ring system). In one embodiment, $R^1$ and $R^2$ together with the atoms to which they are attached form an optionally substituted 9-membered ring (which is further fused to the adjacent 6-membered ring to form a 13-membered fused ring system). In one embodiment, $R^1$ and $R^2$ together with the atoms to which they are attached form an optionally substituted 10-membered ring (which is further fused to the adjacent 6-membered ring to form a 14-membered fused ring system). In one embodiment, $R^1$ and $R^2$ together with the atoms to which they are attached form an optionally substituted phenyl ring. In one embodiment, $R^1$ and $R^2$ together with the atoms to which they are attached form an optionally substituted pyridyl ring. In one embodiment, $R^1$ and $R^2$ together with the atoms to which they are attached form an optionally substituted pyrimidinyl ring. In one embodiment, $R^1$ and $R^2$ together with the atoms to which they are attached form an optionally substituted pyrazinyl ring. In one embodiment, $R^1$ and $R^2$ together with the atoms to which they are attached form an optionally substituted benzothiophenyl ring. In one embodiment, $R^1$ and $R^2$ together with the atoms to which they are attached form an optionally substituted benzofuranyl ring. In one embodiment, $R^1$ and $R^2$ together with the atoms to which they are attached form an optionally substituted indolyl ring. In one embodiment, $R^1$ and $R^2$ together with the atoms to which they are attached form an optionally substituted benzimidazolyl ring. In one embodiment, $R^1$ and $R^2$ together with the atoms to which they are attached form an optionally substituted benzoxazolyl ring. In one embodiment, $R^1$ and $R^2$ together with the atoms to which they are attached form an optionally substituted benzothiazolyl ring. In one embodiment, $R^1$ and $R^2$ together with the atoms to which they are attached form an optionally substituted thienopyridinyl ring. In one embodiment, $R^1$ and $R^2$ together with the atoms to which they are attached form an optionally substituted furopyridinyl ring. In one embodiment, $R^1$ and $R^2$ together with the atoms to which they are attached form an optionally substituted pyrrolopyridinyl ring. In one embodiment, $R^1$ and $R^2$ together with the atoms to which they are attached form an optionally substituted naphthyl ring. In one embodiment, $R^1$ and $R^2$ together with the atoms to which they are attached form an optionally substituted quinoxalinyl ring. In one embodiment, $R^1$ and $R^2$ together with the atoms to which they are attached form an optionally substituted quinazolinyl ring. In one embodiment, $R^1$ and $R^2$ together with the atoms to which they are attached form an optionally substituted cinnolinyl ring. In one embodiment, $R^1$ and $R^2$ together with the atoms to which they are attached form an optionally substituted naphthyridinyl ring. In one embodiment, $R^1$ and $R^2$ together with the atoms to which they are attached form an optionally substituted quinolinyl ring. In one embodiment, $R^1$ and $R^2$ together with the atoms to which they are attached form an optionally substituted benzo[d][1,3]dioxolyl ring. In one embodiment, $R^1$ and $R^2$ together with the atoms to which they are attached form an optionally substituted 5-membered heteroaryl ring (e.g., pyrrole, pyrazole, imidazole, triazole, oxazole, thiazole, isoxazole, isothiazole, furan, and thiophene). In one embodiment, $R^1$ and $R^2$ together with the atoms to which they are attached form an optionally substituted ring having one or more (in one embodiment, one, two, three, or four) additional hetero-atoms selected from the group consisting of O, S, and N. In one embodiment, $R^1$ and $R^2$ together with the atoms to which they are attached form an optionally substituted ring having no additional hetero-atom.

In one embodiment, $R^3$ is hydrogen. In one embodiment, $R^3$ is cyano. In one embodiment, $R^3$ is halo. In one embodiment, $R^3$ is optionally substituted $(C_1-C_{10})$alkyl. In one embodiment, $R^3$ is optionally substituted $(C_2-C_{10})$alkenyl. In one embodiment, $R^3$ is optionally substituted $(C_1-C_{10})$alkoxyl. In one embodiment, $R^3$ is optionally substituted $(C_1-C_{10})$aminoalkyl. In one embodiment, $R^3$ is optionally substituted ($C_1$-$C_{10}$)heteroalkyl. In one embodiment, $R^3$ is optionally substituted ($C_3$-$C_{10}$)cycloalkyl. In one embodiment, $R^3$ is optionally substituted (6 to 10 membered)aryl. In one embodiment, $R^3$ is optionally substituted (5 to 10 membered)heteroaryl. In one embodiment, $R^3$ is optionally substituted (3 to 12 membered)heterocyclyl. In one embodiment, $R^3$ is optionally substituted hydroxyl. In one embodiment, $R^3$ is optionally substituted amino. In one embodiment, $R^3$ is optionally substituted imino. In one embodiment, $R^3$ is optionally substituted amido. In one embodiment, $R^3$ is optionally substituted carbonyl. In one embodiment, $R^3$ is optionally substituted thiol. In one embodiment, $R^3$ is optionally substituted sulfinyl. In one embodiment, $R^3$ is optionally substituted sulfonyl. In one embodiment, $R^3$ is optionally substituted with one or more $R^{11}$.

In one embodiment, $R^3$ is (i) hydrogen; or (ii) ($C_1$-$C_{10}$)alkyl, ($C_2$-$C_{10}$)alkenyl, ($C_1$-$C_{10}$)heteroalkyl, ($C_3$-$C_{10}$)cycloalkyl, (6 to 10 membered)aryl, (5 to 10 membered) heteroaryl, (3 to 12 membered)heterocyclyl, carbonyl, or sulfonyl, each of which is optionally substituted with one or more $R^{11}$.

In one embodiment, $R^4$ is hydrogen. In one embodiment, $R^4$ is cyano. In one embodiment, $R^4$ is halo. In one embodiment, $R^4$ is optionally substituted ($C_1$-$C_{10}$)alkyl. In one embodiment, $R^4$ is optionally substituted ($C_2$-$C_{10}$)alkenyl. In one embodiment, $R^4$ is optionally substituted ($C_1$-$C_{10}$) alkoxyl. In one embodiment, $R^4$ is optionally substituted ($C_1$-$C_{10}$)aminoalkyl. In one embodiment, $R^4$ is optionally substituted ($C_1$-$C_{10}$)heteroalkyl. In one embodiment, $R^4$ is optionally substituted ($C_3$-$C_{10}$)cycloalkyl. In one embodiment, $R^4$ is optionally substituted (6 to 10 membered)aryl. In one embodiment, $R^4$ is optionally substituted (5 to 10 membered)heteroaryl. In one embodiment, $R^4$ is optionally substituted (3 to 12 membered)heterocyclyl. In one embodiment, $R^4$ is optionally substituted hydroxyl. In one embodiment, $R^4$ is optionally substituted amino. In one embodiment, $R^4$ is optionally substituted imino. In one embodiment, $R^4$ is optionally substituted amido. In one embodiment, $R^4$ is optionally substituted carbonyl. In one embodiment, $R^4$ is optionally substituted thiol. In one embodiment, $R^4$ is optionally substituted sulfinyl. In one embodiment, $R^4$ is optionally substituted sulfonyl. In one embodiment, $R^4$ is optionally substituted with one or more $R^{11}$.

In one embodiment, $R^4$ is (i) hydrogen; or (ii) ($C_1$-$C_{10}$)alkyl, ($C_2$-$C_{10}$)alkenyl, ($C_1$-$C_{10}$)heteroalkyl, ($C_3$-$C_{10}$)cycloalkyl, (6 to 10 membered)aryl, (5 to 10 membered) heteroaryl, (3 to 12 membered)heterocyclyl, carbonyl, or sulfonyl, each of which is optionally substituted with one or more $R^{11}$.

In one embodiment, $R^3$ and $R^4$ together with the atoms to which they are attached form a ring optionally substituted with one or more $R^{11}$. In one embodiment, $R^3$ and $R^4$ together with the atoms to which they are attached form an optionally substituted 5-membered ring (which is further fused to the adjacent 5- or 6-membered ring). In one embodiment, $R^3$ and $R^4$ together with the atoms to which they are attached form an optionally substituted 6-membered ring (which is further fused to the adjacent 5- or 6-membered ring). In one embodiment, $R^3$ and $R^4$ together with the atoms to which they are attached form an optionally substituted 9-membered ring (which is further fused to the adjacent 5- or 6-membered ring). In one embodiment, $R^3$ and $R^4$ together with the atoms to which they are attached form an optionally substituted 10-membered ring (which is further fused to the adjacent 5- or 6-membered ring). In one embodiment, $R^3$ and $R^4$ together with the atoms to which they are attached form an optionally substituted aromatic ring. In one embodiment, $R^3$ and $R^4$ together with the atoms to which they are attached form an optionally substituted non-aromatic ring. In one embodiment, $R^3$ and $R^4$ together with the atoms to which they are attached form an optionally substituted partially saturated ring. In one embodiment, $R^3$ and $R^4$ together with the atoms to which they are attached form an optionally substituted phenyl ring. In one embodiment, $R^3$ and $R^4$ together with the atoms to which they are attached form an optionally substituted pyridyl ring. In one embodiment, $R^3$ and $R^4$ together with the atoms to which they are attached form an optionally substituted pyrimidinyl ring. In one embodiment, $R^3$ and $R^4$ together with the atoms to which they are attached form an optionally substituted pyrazinyl ring. In one embodiment, $R^3$ and $R^4$ together with the atoms to which they are attached form an optionally substituted benzothiophenyl ring. In one embodiment, $R^3$ and $R^4$ together with the atoms to which they are attached form an optionally substituted benzofuranyl ring. In one embodiment, $R^3$ and $R^4$ together with the atoms to which they are attached form an optionally substituted indolyl ring. In one embodiment, $R^3$ and $R^4$ together with the atoms to which they are attached form an optionally substituted benzimidazolyl ring. In one embodiment, $R^3$ and $R^4$ together with the atoms to which they are attached form an optionally substituted benzoxazolyl ring. In one embodiment, $R^3$ and $R^4$ together with the atoms to which they are attached form an optionally substituted benzothiazolyl ring. In one embodiment, $R^3$ and $R^4$ together with the atoms to which they are attached form an optionally substituted thienopyridinyl ring. In one embodiment, $R^3$ and $R^4$ together with the atoms to which they are attached form an optionally substituted furopyridinyl ring. In one embodiment, $R^3$ and $R^4$ together with the atoms to which they are attached form an optionally substituted pyrrolopyridinyl ring. In one embodiment, $R^3$ and $R^4$ together with the atoms to which they are attached form an optionally substituted naphthyl ring. In one embodiment, $R^3$ and $R^4$ together with the atoms to which they are attached form an optionally substituted quinoxalinyl ring. In one embodiment, $R^3$ and $R^4$ together with the atoms to which they are attached form an optionally substituted quinazolinyl ring. In one embodiment, $R^3$ and $R^4$ together with the atoms to which they are attached form an optionally substituted cinnolinyl ring. In one embodiment, $R^3$ and $R^4$ together with the atoms to which they are attached form an optionally substituted naphthyridinyl ring. In one embodiment, $R^3$ and $R^4$ together with the atoms to which they are attached form an optionally substituted quinolinyl ring. In one embodiment, $R^3$ and $R^4$ together with the atoms to which they are attached form an optionally substituted benzo[d][1,3]dioxolyl ring. In one embodiment, $R^3$ and $R^4$ together with the atoms to which they are attached form an optionally substituted 5-membered non-aromatic ring. In one embodiment, $R^3$ and $R^4$ together with the atoms to which they are attached form an optionally substituted 6-membered non-aromatic ring. In one embodiment, $R^3$ and $R^4$ together with the atoms to which they are attached form an optionally substituted 9-membered non-aromatic ring. In one embodiment, $R^3$ and $R^4$ together with the atoms to which they are attached form an optionally substituted 10-membered non-aromatic ring. In one embodiment, $R^3$ and $R^4$ together with the atoms to which they are attached form an optionally substituted 9-membered partially saturated ring. In one embodiment, $R^3$ and $R^4$ together with the atoms to which they are attached form an optionally substituted 10-membered partially saturated ring. In one embodiment, $R^3$ and $R^4$ together with the atoms to which they are attached form an optionally substituted ring having one or more (in one embodiment, one, two, three, or four) additional heteroatoms selected from the group consisting of O, S, and N. In one embodiment, $R^3$ and $R^4$ together with the atoms to which they are attached form an optionally substituted ring having no additional heteroatom.

In one embodiment, $R^5$ is hydrogen. In one embodiment, $R^5$ is cyano. In one embodiment, $R^5$ is halo. In one embodiment, $R^5$ is optionally substituted $(C_1-C_{10})$alkyl. In one embodiment, $R^5$ is optionally substituted $(C_2-C_{10})$alkenyl. In one embodiment, $R^5$ is optionally substituted $(C_1-C_{10})$alkoxyl. In one embodiment, $R^5$ is optionally substituted $(C_1-C_{10})$aminoalkyl. In one embodiment, $R^5$ is optionally substituted $(C_1-C_{10})$heteroalkyl. In one embodiment, $R^5$ is optionally substituted $(C_3-C_{10})$cycloalkyl. In one embodiment, $R^5$ is optionally substituted (6 to 10 membered)aryl. In one embodiment, $R^5$ is optionally substituted (5 to 10 membered)heteroaryl. In one embodiment, $R^5$ is optionally substituted (3 to 12 membered)heterocyclyl. In one embodiment, $R^5$ is optionally substituted hydroxyl. In one embodiment, $R^5$ is optionally substituted amino. In one embodiment, $R^5$ is optionally substituted imino. In one embodiment, $R^5$ is optionally substituted amido. In one embodiment, $R^5$ is optionally substituted carbonyl. In one embodiment, $R^5$ is optionally substituted thiol. In one embodiment, $R^5$ is optionally substituted sulfinyl. In one embodiment, $R^5$ is optionally substituted sulfonyl. In one embodiment, $R^5$ is optionally substituted with one or more $R^{11}$.

In one embodiment, $R^5$ is (i) hydrogen; or (ii) $(C_1-C_{10})$alkyl, $(C_2-C_{10})$alkenyl, $(C_1-C_{10})$heteroalkyl, $(C_3-C_{10})$cycloalkyl, (6 to 10 membered)aryl, (5 to 10 membered)heteroaryl, (3 to 12 membered)heterocyclyl, carbonyl, or sulfonyl, each of which is optionally substituted with one or more $R^{11}$.

In one embodiment, $R^4$ and $R^5$ together with the atoms to which they are attached form a ring optionally substituted with one or more $R^{11}$. In one embodiment, $R^4$ and $R^5$ together with the atoms to which they are attached form an optionally substituted 5-membered ring (which is further fused to the adjacent 5- or 6-membered ring). In one embodiment, $R^4$ and $R^5$ together with the atoms to which they are attached form an optionally substituted 6-membered ring (which is further fused to the adjacent 5- or 6-membered ring). In one embodiment, $R^4$ and $R^5$ together with the atoms to which they are attached form an optionally substituted 9-membered ring (which is further fused to the adjacent 5- or 6-membered ring). In one embodiment, $R^4$ and $R^5$ together with the atoms to which they are attached form an optionally substituted 10-membered ring (which is further fused to the adjacent 5- or 6-membered ring). In one embodiment, $R^4$ and $R^5$ together with the atoms to which they are attached form an optionally substituted aromatic ring. In one embodiment, $R^4$ and $R^5$ together with the atoms to which they are attached form an optionally substituted non-aromatic ring. In one embodiment, $R^4$ and $R^5$ together with the atoms to which they are attached form an optionally substituted partially saturated ring. In one embodiment, $R^4$ and $R^5$ together with the atoms to which they are attached form an optionally substituted ring having one or more (in one embodiment, one, two, three, or four) additional hetero-atoms selected from the group consisting of O, S, and N. In one embodiment, $R^4$ and $R^5$ together with the atoms to which they are attached form an optionally substituted ring having no additional hetero-atom.

In one embodiment, $R^{19}$ is hydrogen. In one embodiment, $R^{19}$ is cyano. In one embodiment, $R^{19}$ is halo. In one embodiment, $R^{19}$ is optionally substituted $(C_1-C_{10})$alkyl. In one embodiment, $R^{19}$ is optionally substituted $(C_2-C_{10})$alkenyl. In one embodiment, $R^{19}$ is optionally substituted $(C_1-C_{10})$alkoxyl. In one embodiment, $R^{19}$ is optionally substituted $(C_1-C_{10})$aminoalkyl. In one embodiment, $R^{19}$ is optionally substituted $(C_1-C_{10})$heteroalkyl. In one embodiment, $R^{19}$ is optionally substituted $(C_3-C_{10})$cycloalkyl. In one embodiment, $R^{19}$ is optionally substituted (6 to 10 membered) aryl. In one embodiment, $R^{19}$ is optionally substituted (5 to 10 membered)heteroaryl. In one embodiment, $R^{19}$ is optionally substituted (3 to 12 membered)heterocyclyl. In one embodiment, $R^{19}$ is optionally substituted hydroxyl. In one embodiment, $R^{19}$ is optionally substituted amino. In one embodiment, $R^{19}$ is optionally substituted imino. In one embodiment, $R^{19}$ is optionally substituted amido. In one embodiment, $R^{19}$ is optionally substituted carbonyl. In one embodiment, $R^{19}$ is optionally substituted thiol. In one embodiment, $R^{19}$ is optionally substituted sulfinyl. In one embodiment, $R^{19}$ is optionally substituted sulfonyl. In one embodiment, $R^{19}$ is optionally substituted with one or more $R^{11}$.

In one embodiment, $R^{20}$ is hydrogen. In one embodiment, $R^{20}$ is optionally substituted $(C_1-C_{10})$alkyl. In one embodiment, $R^{20}$ is optionally substituted $(C_2-C_{10})$alkenyl. In one embodiment, $R^{20}$ is optionally substituted $(C_1-C_{10})$heteroalkyl. In one embodiment, $R^{20}$ is optionally substituted $(C_3-C_{10})$cycloalkyl. In one embodiment, $R^{20}$ is optionally substituted (6 to 10 membered)aryl. In one embodiment, $R^{20}$ is optionally substituted (5 to 10 membered)heteroaryl. In one embodiment, $R^{20}$ is optionally substituted (3 to 12 membered)heterocyclyl. In one embodiment, $R^{20}$ is optionally substituted carbonyl. In one embodiment, $R^{20}$ is optionally substituted sulfonyl. In one embodiment, $R^{20}$ is optionally substituted with one or more $R^{11}$.

In one embodiment, $R^6$ is hydrogen. In one embodiment, $R^6$ is halo. In one embodiment, $R^6$ is $(C_1-C_6)$alkyl optionally substituted with one or more halo.

In one embodiment, $R^7$ is hydrogen. In one embodiment, $R^7$ is $(C_1-C_6)$alkyl optionally substituted with one or more halo.

In one embodiment, $R^8$ is hydrogen. In one embodiment, $R^8$ is cyano. In one embodiment, $R^8$ is halo. In one embodiment, $R^8$ is optionally substituted $(C_1-C_{10})$alkyl. In one embodiment, $R^8$ is optionally substituted $(C_2-C_{10})$alkenyl. In one embodiment, $R^8$ is optionally substituted $(C_1-C_{10})$alkoxyl. In one embodiment, $R^8$ is optionally substituted $(C_1-C_{10})$aminoalkyl. In one embodiment, $R^8$ is optionally substituted $(C_1-C_{10})$heteroalkyl. In one embodiment, $R^8$ is optionally substituted $(C_3-C_{10})$cycloalkyl. In one embodiment, $R^8$ is optionally substituted (6 to 10 membered)aryl. In one embodiment, $R^8$ is optionally substituted (5 to 10 membered)heteroaryl. In one embodiment, $R^8$ is optionally substituted (3 to 12 membered)heterocyclyl. In one embodiment, $R^8$ is optionally substituted hydroxyl. In one embodiment, $R^8$ is optionally substituted amino. In one embodiment, $R^8$ is optionally substituted imino. In one embodiment, $R^8$ is optionally substituted amido. In one embodiment, $R^8$ is optionally substituted carbonyl. In one embodiment, $R^8$ is optionally substituted thiol. In one embodiment, $R^8$ is optionally substituted sulfinyl. In one embodiment, $R^8$ is optionally substituted sulfonyl. In one embodiment, $R^8$ is optionally substituted with one or more $R^{11}$.

In one embodiment, $R^9$ is hydrogen. In one embodiment, $R^9$ is cyano. In one embodiment, $R^9$ is halo. In one embodiment, $R^9$ is $(C_1-C_6)$alkyl optionally substituted with one or more halo. In one embodiment, $R^9$ is $(C_1-C_6)$alkoxyl optionally substituted with one or more halo.

In one embodiment, $R^{10}$ is hydrogen. In one embodiment, $R^{10}$ is $(C_1-C_6)$alkyl optionally substituted with one or more halo.

In one embodiment, $R^{11}$ is hydrogen. In one embodiment, $R^{11}$ is halogen. In one embodiment, $R^{11}$ is cyano. In one embodiment, $R^{11}$ is =O. In one embodiment, $R^{11}$ is —$OR^{13}$. In one embodiment, $R^{11}$ is —$NR^{13}R^{14}$. In one embodiment, $R^{11}$ is —$N(R^{13})C(O)R^{14}$. In one embodiment $R^{11}$ is $C(O)NR^{13}R^{14}$. In one embodiment $R^{11}$ is $C(O)R^{13}$. In one embodiment, $R^{11}$ is —$C(O)OR^{13}$. In one embodiment, $R^{11}$ is —$OC(O)R^{13}$. In one embodiment, $R^{11}$ is —$SR^{13}$. In one embodiment, $R^{11}$ is —$S(O)R^{13}$. In one embodiment, $R^{11}$ is —$S(O)_2R^{13}$. In one embodiment, $R^{11}$ is —$S(O)_2NR^{13}R^{14}$. In one embodiment, $R^{11}$ is $(C_1-C_{10})$alkyl optionally substituted with one or more $R^{12}$. In one embodiment, $R^{11}$ is $(C_1-C_{10})$heteroalkyl optionally substituted with one or more $R^{12}$. In one embodiment, $R^{11}$ is $(C_3-C_{10})$cycloalkyl optionally substituted with one or more $R^{12}$. In one embodiment, $R^{11}$ is $(C_7-C_{12})$aralkyl optionally substituted with one or more $R^{12}$. In one embodiment, $R^{11}$ is $(C_3-C_{12})$heteroaralkyl optionally substituted with one or more $R^{12}$. In one embodiment, $R^{11}$ is (6 to 10 membered)aryl optionally substituted with one or more $R^{12}$. In one embodiment, $R^{11}$ is (5 to 10 membered) heteroaryl optionally substituted with one or more $R^{12}$. In one embodiment, $R^{11}$ is (3 to 12 membered)heterocyclyl optionally substituted with one or more $R^{12}$.

In one embodiment, $R^{12}$ is hydrogen. In one embodiment, $R^{12}$ is $(C_1-C_6)$alkyl optionally substituted with one or more $R^{13}$. In one embodiment, $R^{12}$ is $(C_3-C_6)$cycloalkyl optionally substituted with one or more $R^{13}$. In one embodiment, $R^{12}$ is halogen. In one embodiment, $R^{12}$ is cyano. In one embodiment, $R^{12}$ is =O. In one embodiment, $R^{12}$ is —$OR^{13}$. In one embodiment, $R^{12}$ is —$NR^{13}R^{14}$. In one embodiment, $R^{12}$ is —$N(R^{13})C(O)R^{14}$. In one embodiment, $R^{12}$ is —$C(O)NR^{13}R^{14}$. In one embodiment, $R^{12}$ is —$C(O)R^{13}$. In one embodiment, $R^{12}$ is —$C(O)OR^{13}$. In one embodiment, $R^{12}$ is —$OC(O)R^{13}$. In one embodiment, $R^{12}$ is —$SR^{13}$. In one embodiment, $R^{12}$ is —$S(O)R^{13}$. In one embodiment, $R^{12}$ is —$S(O)_2R^{13}$. In one embodiment, $R^{12}$ is —$S(O)_2NR^{13}R^{14}$.

In one embodiment, $R^{13}$ is hydrogen. In one embodiment, $R^{13}$ is $(C_1-C_6)$alkyl. In one embodiment, $R^{13}$ is $(C_1-C_6)$heteroalkyl. In one embodiment, $R^{13}$ is $(C_3-C_6)$cycloalkyl. In one embodiment, $R^{13}$ is $(C_7-C_{10})$aralkyl. In one embodiment, $R^{13}$ is $(C_3-C_{12})$heteroaralkyl. In one embodiment, $R^{13}$ is (6 to 10 membered)aryl. In one embodiment, $R^{13}$ is (5 to 10 membered)heteroaryl. In one embodiment, $R^{13}$ is (3 to 12 membered)heterocyclyl.

In one embodiment, $R^{14}$ is hydrogen. In one embodiment, $R^{14}$ is $(C_1-C_6)$alkyl. In one embodiment, $R^{14}$ is $(C_1-C_6)$heteroalkyl. In one embodiment, $R^{14}$ is $(C_3-C_6)$cycloalkyl. In one embodiment, $R^{14}$ is $(C_7-C_{10})$aralkyl. In one embodiment, $R^{14}$ is $(C_3-C_{12})$heteroaralkyl. In one embodiment, $R^{14}$ is (6 to 10 membered)aryl. In one embodiment, $R^{14}$ is (5 to 10 membered)heteroaryl. In one embodiment, $R^{14}$ is (3 to 12 membered)heterocyclyl.

In one embodiment, $R^{13}$ and $R^{14}$ together form a 3 to 10 membered ring.

In one embodiment, u is 2. In one embodiment, u is 3.

In one embodiment, p is 0. In one embodiment, p is 1. In one embodiment, p is 2. In one embodiment, q is 0. In one embodiment, q is 1. In one embodiment, q is 2. In one embodiment, p is 0 and q is 1 or 2. In one embodiment, q is 0 and p is 1 or 2.

Any of the combinations of A, B, L, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{19}$, $R^{20}$, $A^1$, $A^2$, $A^3$, $A^4$, $A^5$, $A^6$, u, p, and q are encompassed by this disclosure and specifically provided herein.

In one embodiment, L is —$CH_2$—$CH_2$—, —CH=CH—, —O—$CH_2$—, NH—$CH_2$—, —$CH_2$—O—, —$CH_2$—NH—, —$CH_2$—S—, or —S—. In one embodiment, L is —$CH_2$—$CH_2$—. In one embodiment, L is —CH=CH—. In one embodiment, L is —O—$CH_2$—. In one embodiment, L is —NH—$CH_2$—. In one embodiment, L is —$CH_2$—O—. In one embodiment, L is —$CH_2$—NH—. In one embodiment, L is —$CH_2$—S—. In one embodiment, L is —S—.

In one embodiment, provided herein is a compound of formula (I), or a pharmaceutically acceptable salt or stereoisomer thereof, wherein A is

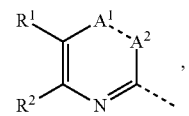

wherein $R^1$, $R^2$, $A^1$, and $A^2$ are defined herein elsewhere.

In one embodiment, provided herein is a compound of formula (I), or a pharmaceutically acceptable salt or stereoisomer thereof, wherein B is

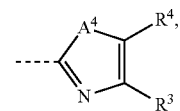

wherein $R^3$, $R^4$ and $A^4$ are defined herein elsewhere.

In one embodiment, provided herein is a compound of formula (I-A), or a pharmaceutically acceptable salt or stereoisomer thereof,

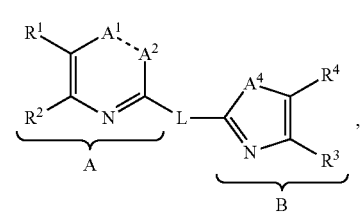

(I-A)

wherein $R^1$, $R^2$, $R^3$, $R^4$, $A^1$, $A^2$, $A^4$ and L are defined herein elsewhere.

In one embodiment, L is —$(CH_2)_2$— or —CH=CH—. In one embodiment, $A^1$-$A^2$ is $CR^8$=$CR^8$ such that A is pyridine, $CR^8$=N such that A is pyrimidine, or N=$CR^8$ such that A is pyrazine, optionally substituted with one or more substituent(s) selected from $R^1$, $R^2$, and $R^8$, wherein $R^1$, $R^2$, and $R^8$ are defined herein elsewhere. In one embodiment, A is pyridine, pyrimidine, or pyrazine, optionally substituted with one or more methyl, ethyl, $CF_3$, halo (e.g., F, Cl, or Br), cyano, carboxamido, imidazolyl, or pyridyl; or two adjacent substituents together with the atoms to which they are attached form a 5- or 6-membered ring. In one embodiment, A is optionally substituted quinoxalin-2(1H)-one. In one embodiment, $R^3$ is optionally substituted phenyl or pyridyl. In one embodiment, $A^4$ is $NR^5$, and $R^5$ is (i) hydrogen; or (ii) $(C_1-C_{10})$alkyl, $(C_2-C_{10})$alkenyl, $(C_1-C_{10})$heteroalkyl, $(C_3-C_{10})$cycloalkyl, (6 to 10 membered) aryl, (5 to 10 membered) heteroaryl, (3 to 12 membered) heterocyclyl, carbonyl, or sulfonyl, each of which is optionally substituted with one or more $R^{11}$; or (iii) $R^4$ and $R^5$ together with the atoms to which they are attached form a ring optionally substituted with one or more $R^{11}$. In one embodiment, $R^5$ is hydrogen or methyl. In one embodiment, $R^4$ is H. In one embodiment, $R^3$ and $R^4$ together with the atoms to which they are attached form an optionally substituted aryl or heteroaryl (e.g., benzene, pyridine, naphthylene, or quinoline). In one embodiment, A is optionally substituted pyridyl. In one embodiment, A is optionally substituted pyrimidyl. In one embodiment, A is optionally substituted pyridazinyl. In one embodiment, A is optionally substituted with one or more halo, cyano, hydroxyl, methyl, ethyl, CF$_3$, methoxy, ethoxy, OCF$_3$, amido, aryl, heteroaryl, cycloalkyl, or heterocyclyl. Specific examples include, but are not limited to, the following:

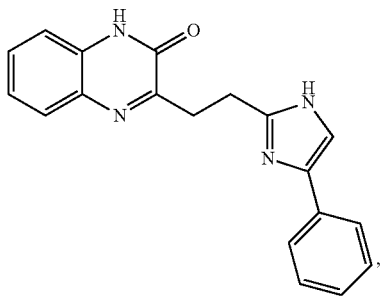

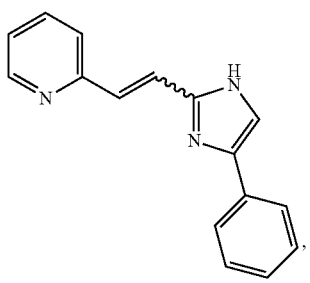

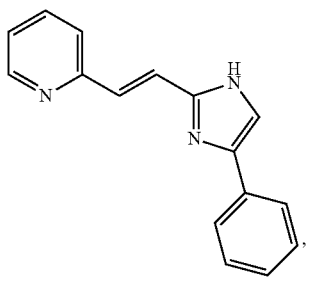

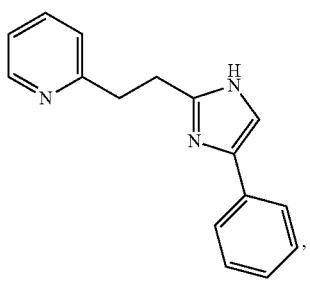

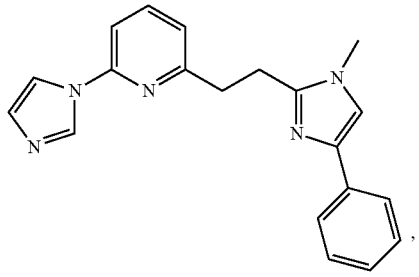

-continued

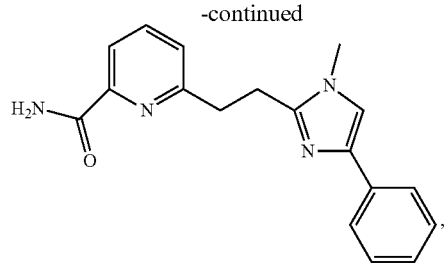

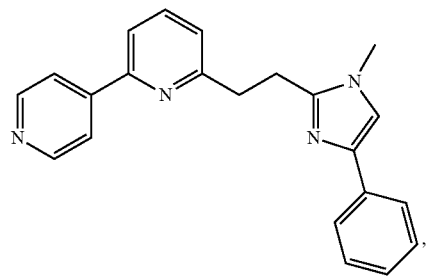

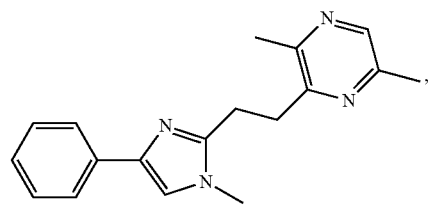

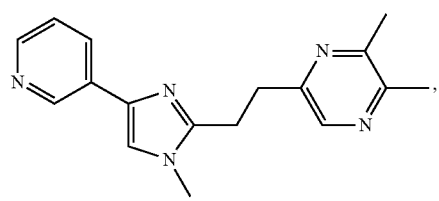

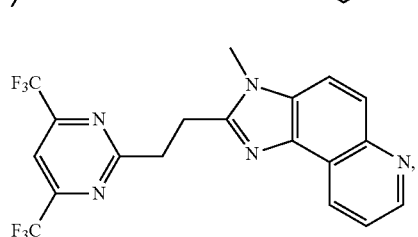

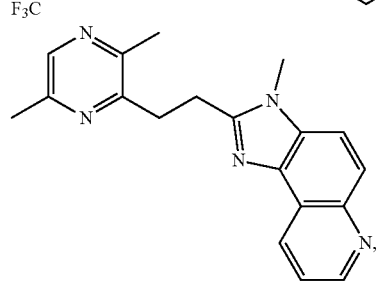

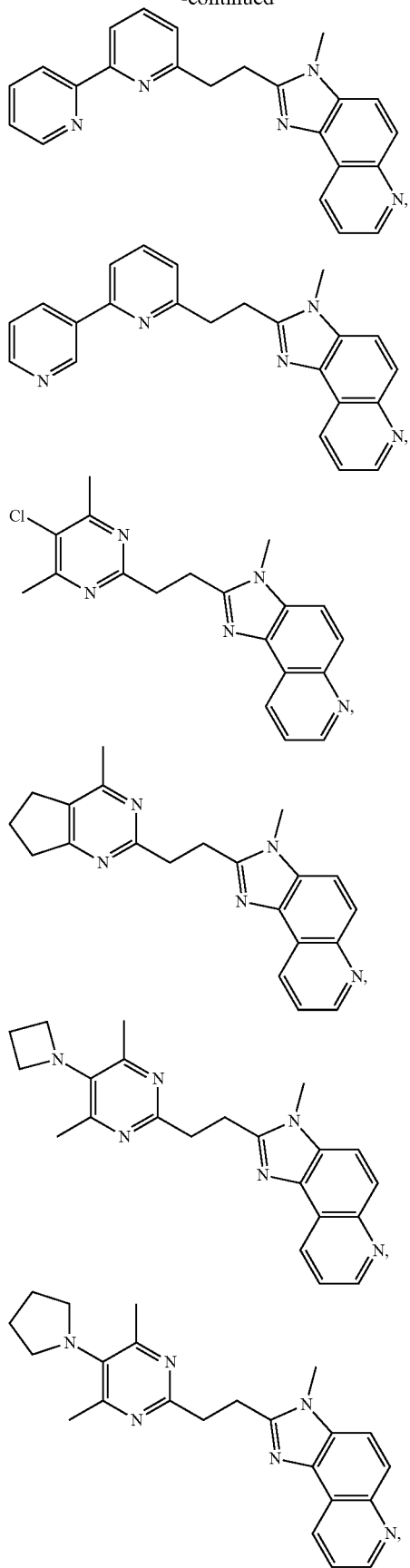
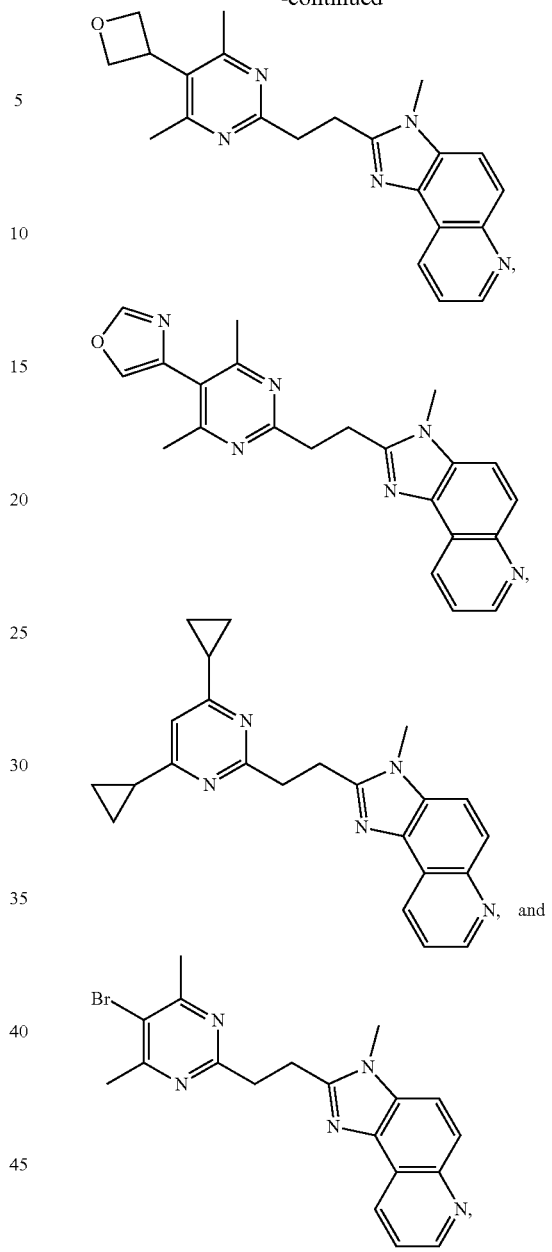

In one embodiment, $A^4$ is $NR^5$. In one embodiment, $R^5$ is H or $CH_3$. In one embodiment, $A^4$ is NH or $NCH_3$.

In one embodiment, $A^6$ is CH or N.

In one embodiment, $R^3$ is hydrogen. In one embodiment, $R^3$ is halo (e.g., F, Cl, or Br) or cyano. In one embodiment, $R^3$ is methyl, phenyl, pyridyl, furanyl, thienyl, benzofuranyl, naphthyl, quinolinyl, or benzodioxolyl, each of which is optionally substituted with one or more $R^{11}$. In one embodiment, $R^3$ is methyl, phenyl or pyridyl, each of which is optionally substituted with one or more $R^{11}$. In one embodiment, $R^3$ is alkyl, aryl, or heteroaryl, each of which is optionally substituted with one or more $R^{11}$.

In one embodiment, $R^4$ is hydrogen. In one embodiment, $R^4$ is halo (e.g., F, Cl, or Br) or cyano. In one embodiment, $R^4$ is methyl, phenyl or pyridyl, each of which is optionally substituted with one or more $R^{11}$. In one embodiment, $R^4$ is methyl, phenyl, pyridyl, furanyl, thienyl, benzofuranyl, naphthyl, quinolinyl, or benzodioxolyl, each of which is optionally substituted with one or more $R^{11}$. In one embodiment, $R^4$ is alkyl, aryl, or heteroaryl, each of which is optionally substituted with one or more $R^{11}$.

In one embodiment, $R^3$ and $R^4$ together with the atoms to which they are attached form a phenyl, pyridyl, pyrimidyl, pyrazinyl, naphthyl, quinolinyl, or benzodioxolyl ring, which is optionally substituted with one or more $R^{11}$.

In one embodiment, each occurrence of $R^8$ is independently hydrogen, halo (e.g., F, Cl, or Br), cyano, $CH_3$, $OCH_3$, $CF_3$, or $OCF_3$. In one embodiment, each occurrence of $R^8$ is independently hydrogen, fluoro, chloro, cyano, $CH_3$, or $CF_3$. In one embodiment, each occurrence of $R^8$ is independently hydrogen or $CH_3$. In one embodiment, $R^8$ is hydrogen.

In one embodiment, each occurrence of $R^{11}$ is independently hydrogen, fluoro, chloro, $CH_3$, $OCH_3$, $CF_3$, $OCF_3$, OH, ethyl, propyl, isopropyl, t-butyl, or phenyl.

In one embodiment, B is selected from the group consisting of:

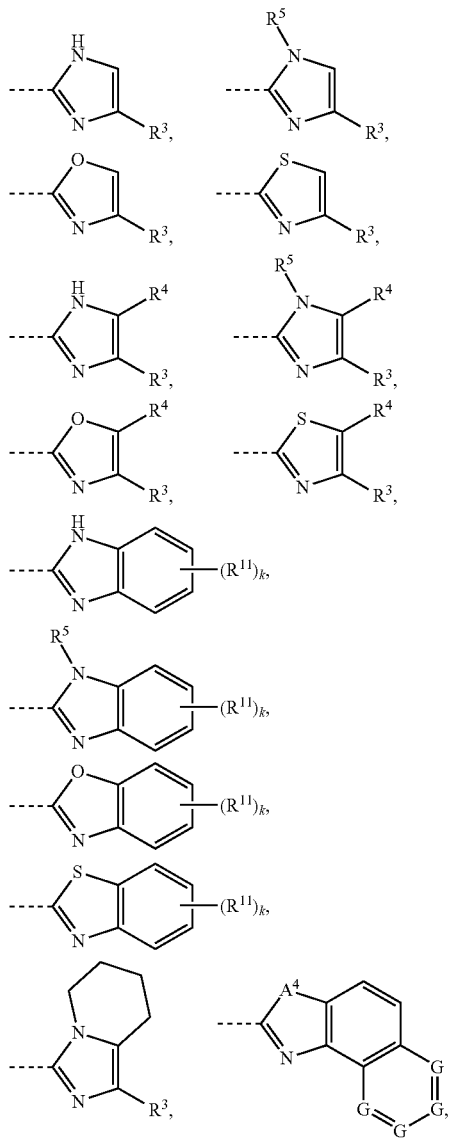

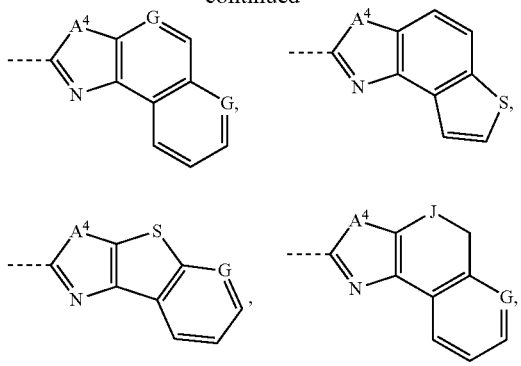

wherein $R^3$, $R^4$, $R^5$, $R^{11}$, and $A^4$ are defined herein elsewhere; k is 0, 1, 2, 3, or 4; each occurrence of G is independently CH or N; and J is O, S, NH or $CH_2$.

In one embodiment, $R^3$ is hydrogen. In one embodiment, $R^3$ is alkyl, aryl, or heteroaryl, each of which is optionally substituted with one or more $R^{11}$. In one embodiment, $R^3$ is (i) hydrogen; or (ii) alkyl, aryl, or heteroaryl, each of which is optionally substituted with one or more $R^{11}$.

In one embodiment, $R^4$ is hydrogen. In one embodiment, $R^4$ is alkyl, aryl, or heteroaryl, each of which is optionally substituted with one or more $R^{11}$. In one embodiment, $R^4$ is (i) hydrogen; or (ii) alkyl, aryl, or heteroaryl, each of which is optionally substituted with one or more $R^{11}$.

In one embodiment, $R^5$ is hydrogen. In one embodiment, $R^5$ is alkyl, aryl, or heteroaryl, each of which is optionally substituted with one or more $R^{11}$. In one embodiment, $R^5$ is (i) hydrogen; or (ii) alkyl, aryl, or heteroaryl, each of which is optionally substituted with one or more $R^{11}$.

In one embodiment, $R^{11}$ is hydrogen. In one embodiment, $R^{11}$ is alky, aryl or heteroaryl, each of which is optionally substituted with one or more $R^{12}$. In one embodiment, $A^4$ is O, S, NH, or $NR^5$. In one embodiment, each occurrence of $R^{11}$ is independently (i) hydrogen; or (ii) alky, aryl or heteroaryl, each of which is optionally substituted with one or more $R^{12}$.

In one embodiment, B is

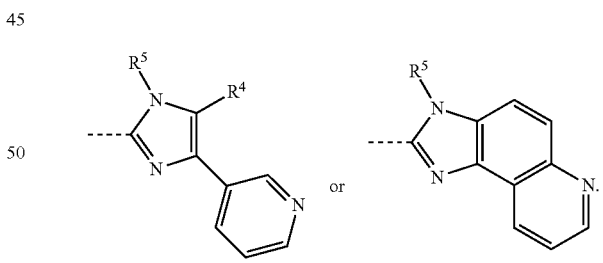

In one embodiment, provided herein is a compound of formula (I) or formula (I-A), or a pharmaceutically acceptable salt or stereoisomer thereof, wherein L is —$CH_2$—$CH_2$—.

In one embodiment, provided herein is a compound of formula (I) or formula (I-A), or a pharmaceutically acceptable salt or stereoisomer thereof, wherein $A^4$ is $NR^5$.

In one embodiment, provided herein is a compound of formula (I) or formula (I-A), or a pharmaceutically acceptable salt or stereoisomer thereof, wherein $A^4$ is $NR^5$, and L is —$CH_2$—$CH_2$—.

In one embodiment, -A$^1$-A$^2$- is NR$^7$C(O)—. In one embodiment. -A$^1$-A$^2$- is —C(O)NR$^7$—. In one embodiment, -A$^1$-A$^2$- is —N═CH—. In one embodiment, -A$^1$-A$^2$- is —CH═N—. In one embodiment, -A$^1$-A$^2$- is —CH═CH—. In one embodiment, -A$^1$-A$^2$- is —N═N—. In one embodiment, R$^7$ is hydrogen. In one embodiment, R$^7$ is methyl. In one embodiment, R$^7$ is alkyl. In one embodiment, R$^1$ and R$^2$ together with the atoms to which they are attached form a phenyl ring, optionally substituted with one or more R$^{11}$. In one embodiment, R$^1$ and R$^2$ together with the atoms to which they are attached form a pyridyl ring, optionally substituted with one or more R$^{11}$.

In one embodiment, provided herein is a compound of formula (I) or (I-A), or a pharmaceutically acceptable salt or stereoisomer thereof, wherein R$^1$ and R$^2$ together with the carbon atoms to which they are attached form an optionally substituted pyridyl ring. In one embodiment, A is optionally substituted pyrido[4,3-d]pyrimidin-4(3H)-one or pyrido[3,4-d]pyrimidin-4(3H)-one. In one embodiment, A is pyrido[2,3-b]pyrazine, pyrido[3,4-b]pyrazine, or naphthyridinyl, each of which is optionally substituted. In one embodiment, A is pyridylpyrimidyl or naphthyridinyl, each of which is optionally substituted. In one embodiment, A is optionally substituted with one or more halo (e.g., F, Cl, or Br), cyano, methyl, or CF$_3$. In one embodiment, L is —(CH$_2$)$_2$— or —CH═CH—. In one embodiment, R$^3$ is optionally substituted phenyl or pyridyl (e.g., optionally substituted with one or more F, Cl, Br, cyano, methyl, or CF$_3$). In one embodiment, R$^4$ is H. In one embodiment, A$^4$ is NR$^5$, and R$^5$ is hydrogen or methyl. In one embodiment, R$^3$ and R$^4$ together with the atoms to which they are attached form an optionally substituted aryl or heteroaryl (e.g., benzene, pyridine, naphthylene, or quinoline). Specific examples include, but are not limited to, the following:

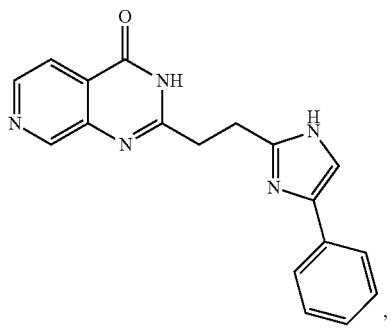

,

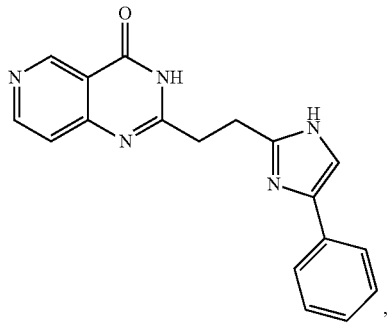

,

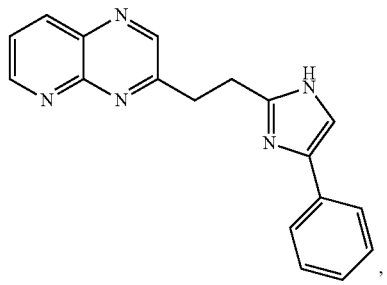

,

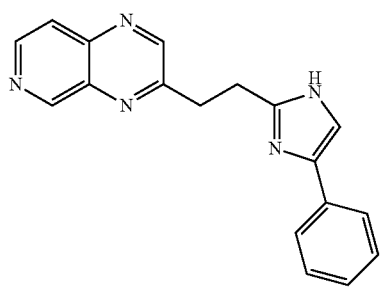

,

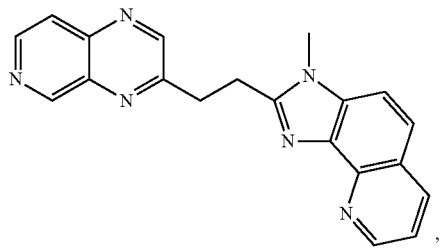

,

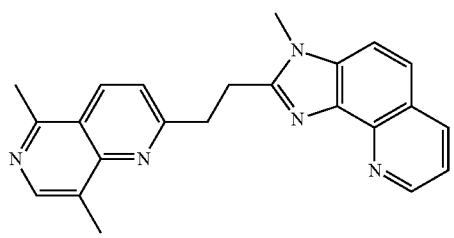

,

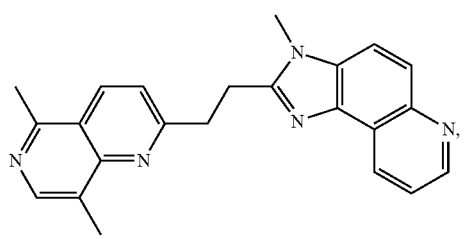

,

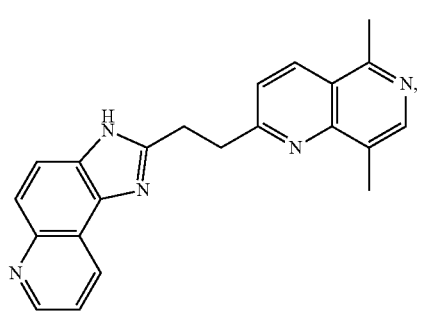

,

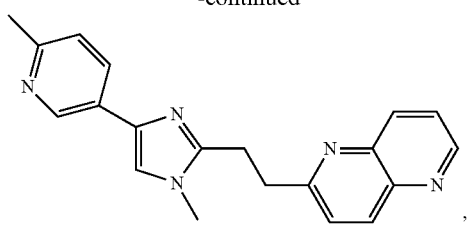
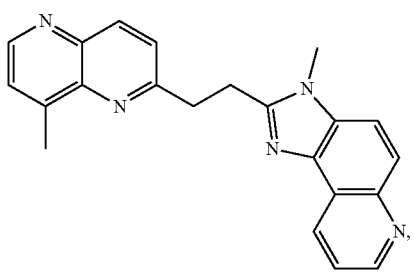
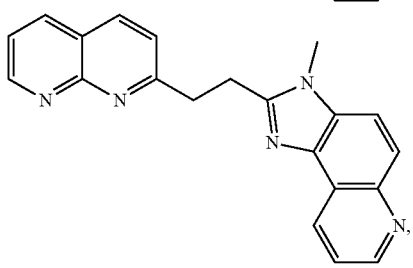
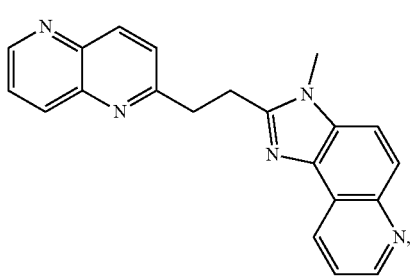
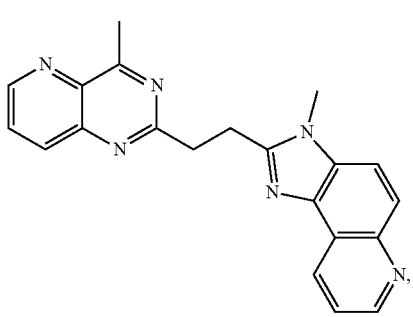
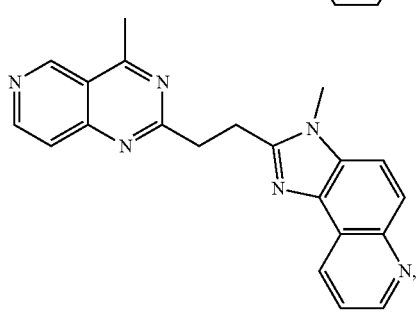
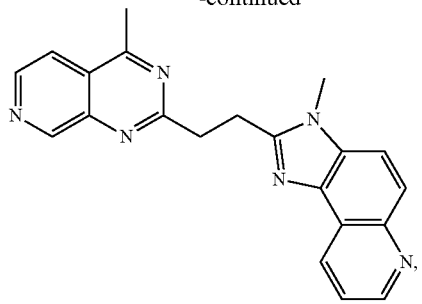
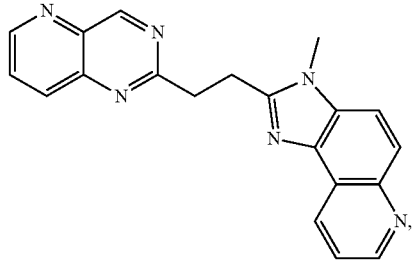
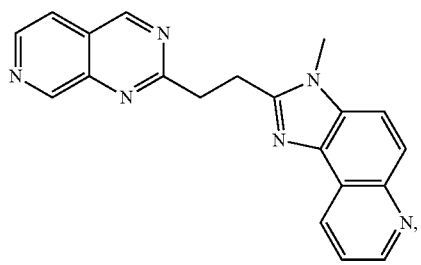
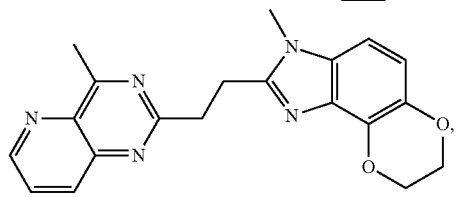
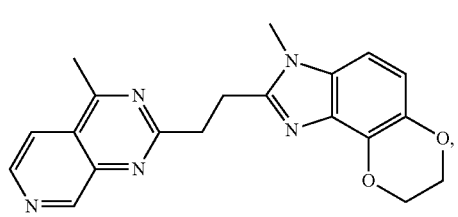
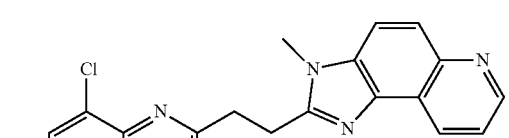, and
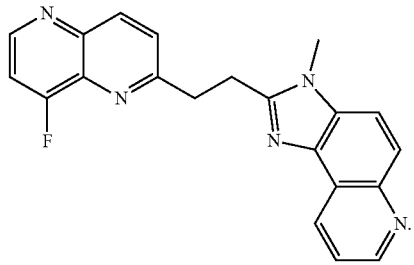

In one embodiment, provided herein is a compound of formula (I) or (I-A), or a pharmaceutically acceptable salt or stereoisomer thereof, wherein

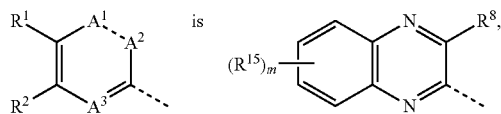 is 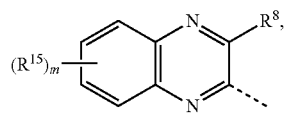

wherein $R^8$ is defined herein elsewhere; each occurrence of $R^{15}$ is independently: (i) hydrogen, halo, cyano, —$OR^{13}$, —$NR^{13}R^{14}$, —$N(R^{13})C(O)R^{14}$, —$C(O)NR^{13}R^{14}$, —$C(O)R^{13}$, —$C(O)OR^{13}$, —$OC(O)R^{13}$, —$SR^{13}$, —$S(O)R^{13}$, —$S(O)_2R^{13}$, —$S(O)_2NR^{13}R^{14}$, $(C_1-C_{10})$alkyl optionally substituted with one or more $R^{12}$, $(C_1-C_{10})$heteroalkyl optionally substituted with one or more $R^{12}$, $(C_3-C_{10})$cycloalkyl optionally substituted with one or more $R^{12}$, $(C_7-C_{12})$aralkyl optionally substituted with one or more $R^{12}$, $(C_3-C_{12})$heteroaralkyl optionally substituted with one or more $R^{12}$, (6 to 10 membered)aryl optionally substituted with one or more $R^{12}$, (5 to 10 membered) heteroaryl optionally substituted with one or more $R^{12}$, or (3 to 12 membered) heterocyclyl optionally substituted with one or more $R^{12}$; or (ii) when two occurrences of $R^{15}$ are attached to adjacent carbon atoms, the two adjacent occurrences of $R^{15}$ together with the carbon atoms to which they are attached may form a ring, optionally substituted with one or more $R^{11}$; wherein $R^{11}$, $R^{12}$, $R^{13}$, and $R^{14}$ are defined herein elsewhere; and m is 0, 1, 2, 3, or 4. In one embodiment, $R^8$ is hydrogen or methyl. In one embodiment, L is —$(CH_2)_2$— or —CH═CH—. In one embodiment, L is —O—$CH_2$—, —NH—$CH_2$—, —$CH_2$—O—, —$CH_2$—S—, or —S—. In one embodiment, A is quinoxalinyl optionally substituted with one or more halo (e.g., F, Cl, or Br), cyano, methyl, ethyl, $CF_3$, $OCH_3$, or $OCF_3$. In one embodiment, $R^3$ is optionally substituted cycloalkyl (e.g., cyclopropyl, cyclobutyl, cyclopentyl, or cyclohexyl), phenyl, pyridyl, furanyl, or thienyl (e.g., optionally substituted with one or more F, Cl, Br, cyano, methyl, or $CF_3$). In one embodiment, $R^4$ is H. In one embodiment, $A^4$ is $NR^5$, and $R^5$ is hydrogen or methyl. In one embodiment, $R^3$ and $R^4$ together with the atoms to which they are attached form an optionally substituted aryl or heteroaryl (e.g., phenyl, pyridyl, naphthyl, quinolinyl, tetrahydroquinolinyl, dihydrobenzodioxinyl, or benzodioxolyl ring, in one embodiment, each of which is optionally substituted with one or more F, Cl, Br, cyano, methyl, ethyl, propyl, butyl, OH, $OCH_3$, $CF_3$, or $OCF_3$). In one embodiment, $R^4$ and $R^5$ together with the atoms to which they are attached form an optionally substituted 5- or 6-membered ring. In one embodiment, $A^4$ is O or S. Specific examples include, but are not limited to, the following:

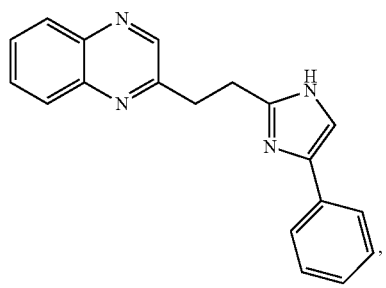

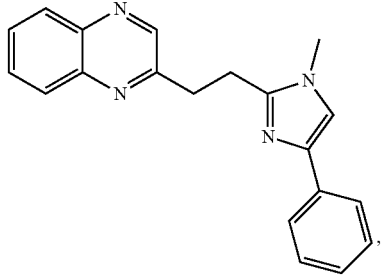

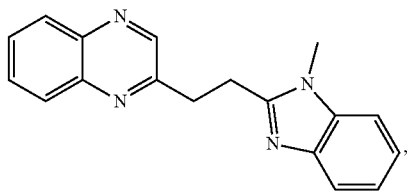

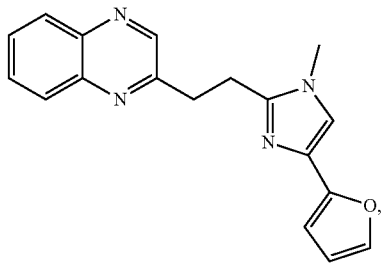

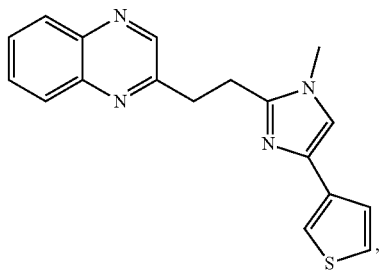

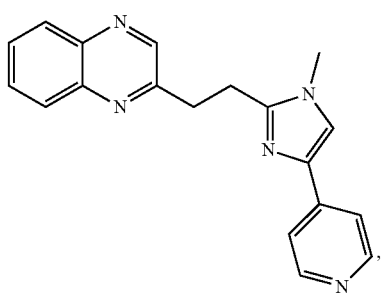

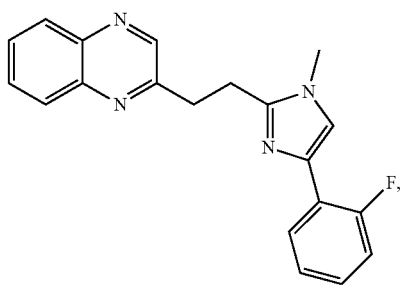

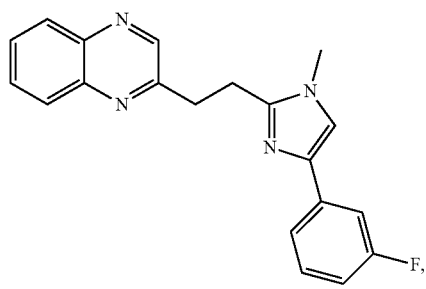
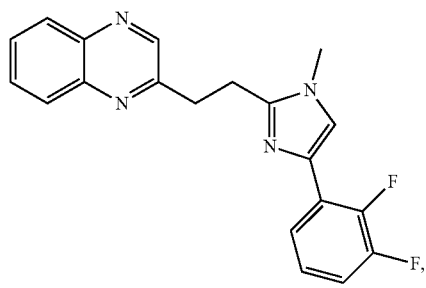
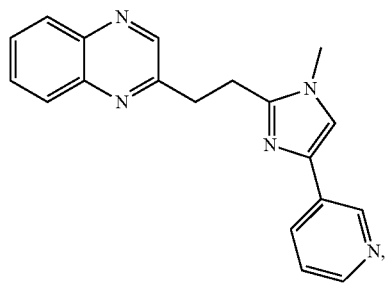
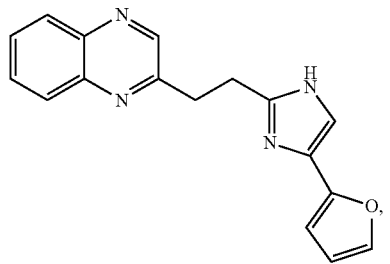
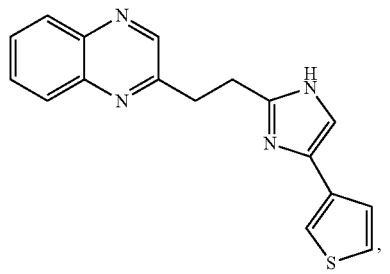
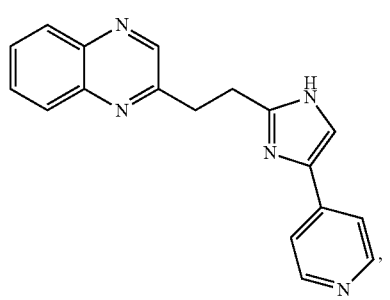
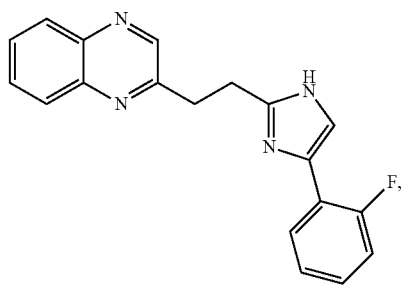
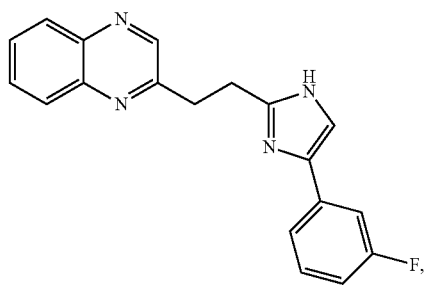
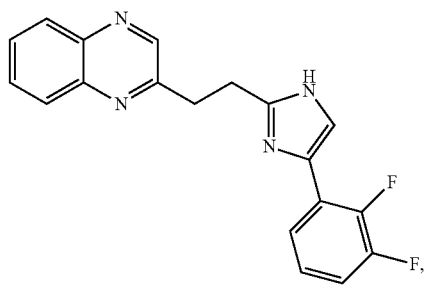
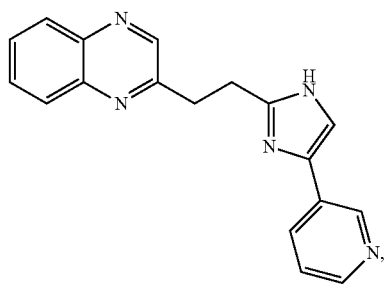
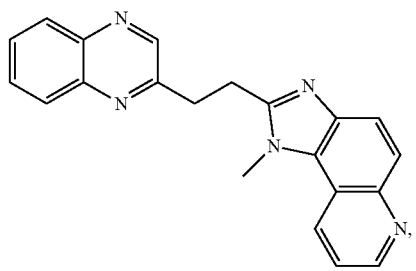
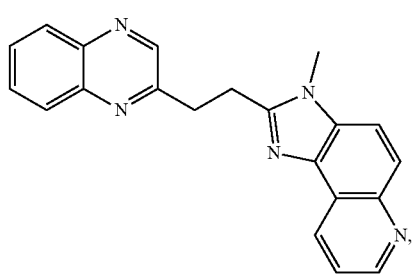

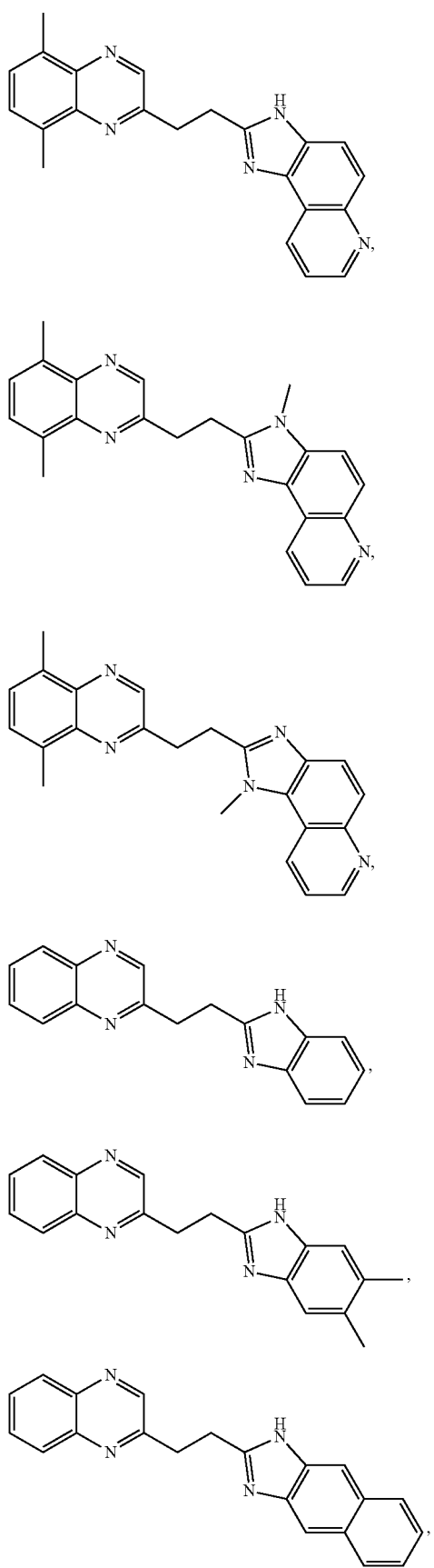
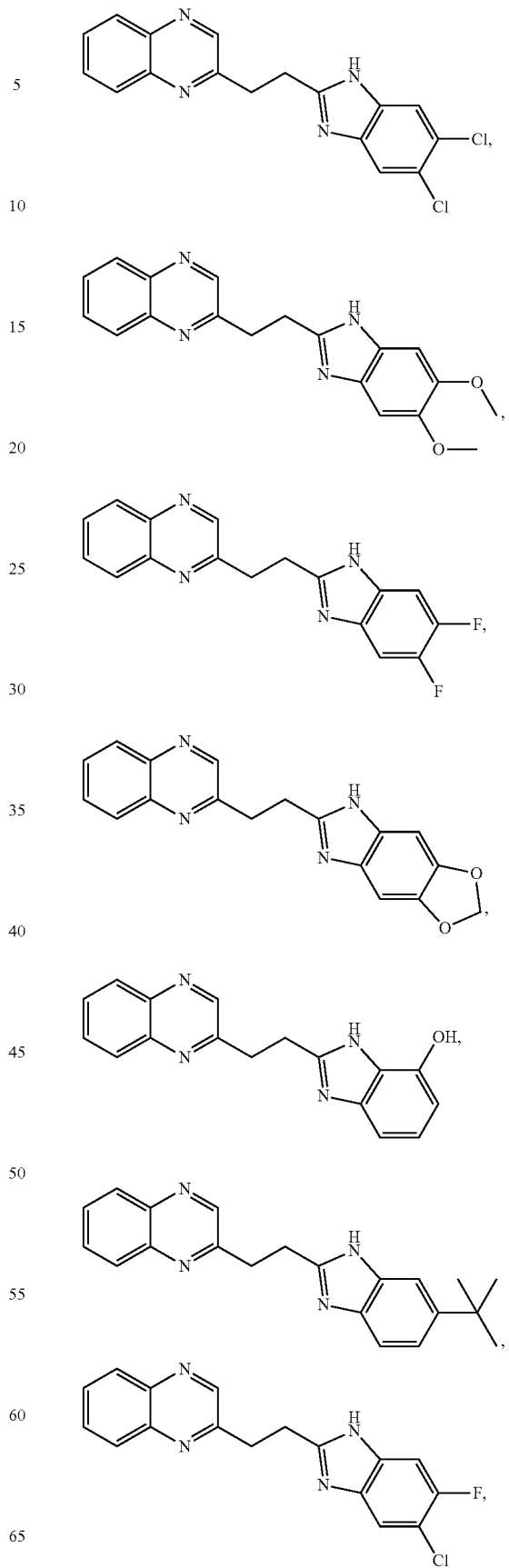

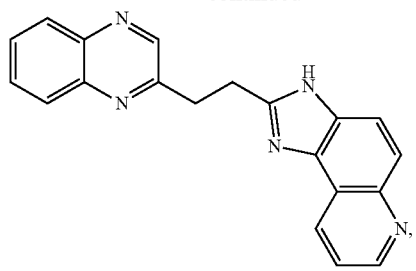
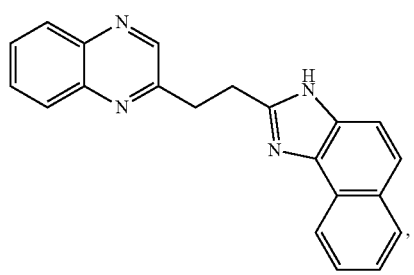
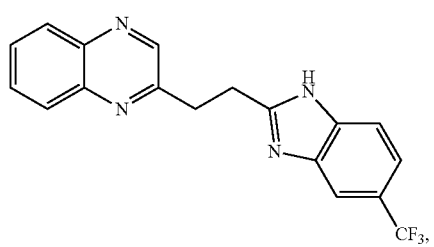
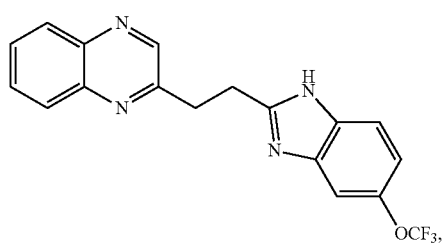
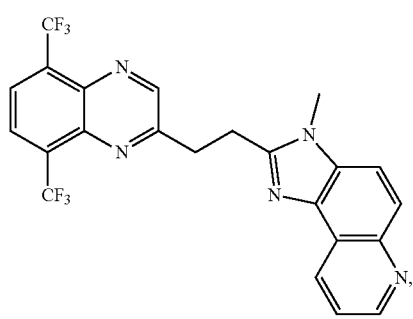
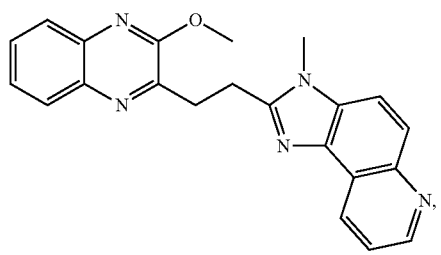
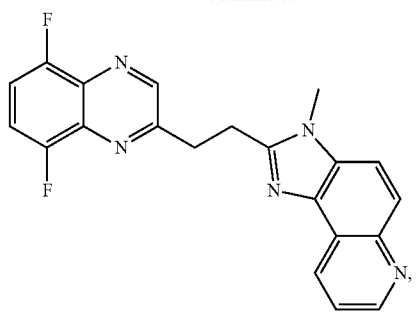
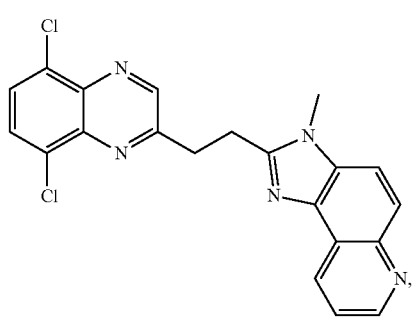
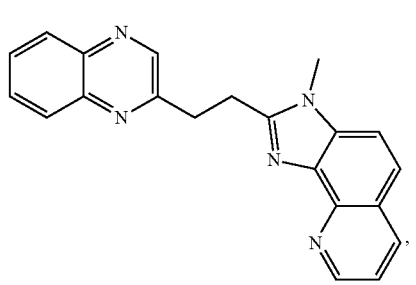
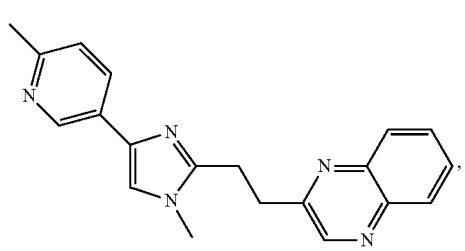
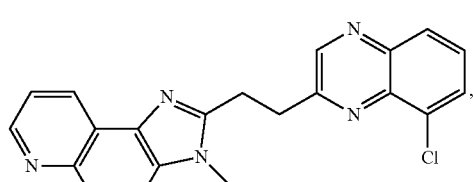
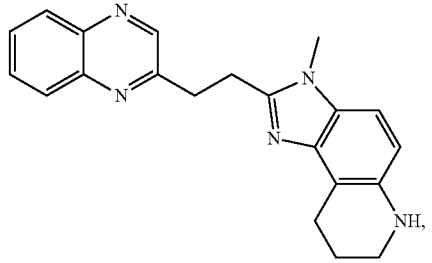

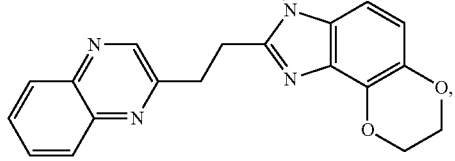
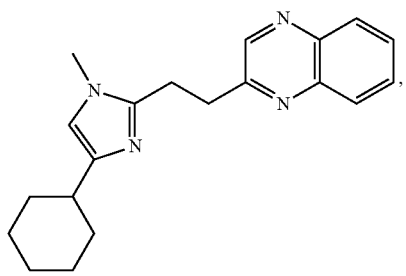
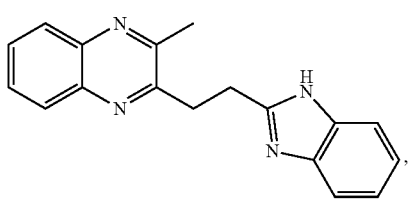
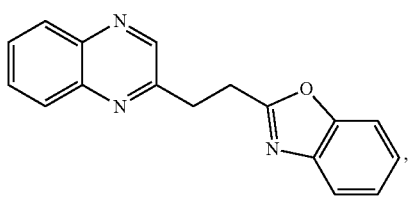
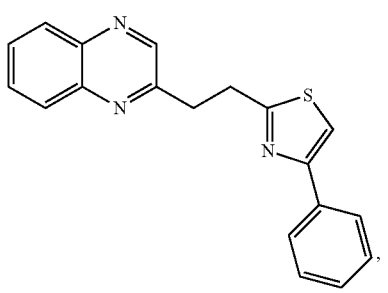
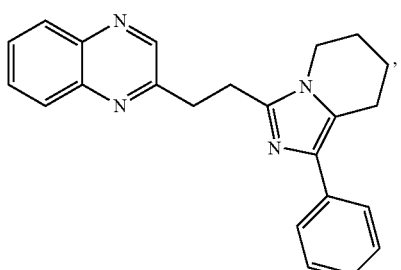
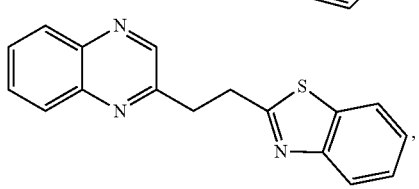
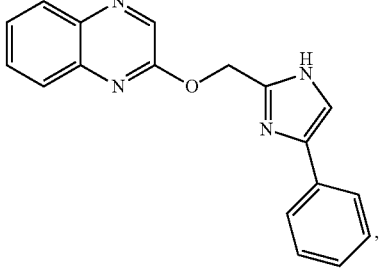
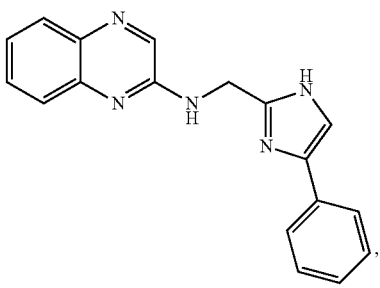
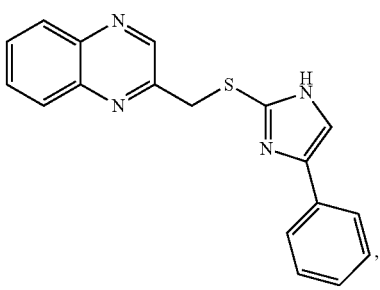
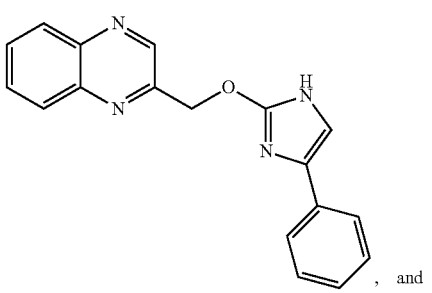
, and
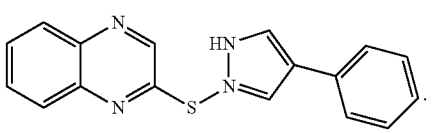
.
In one embodiment, provided herein is a compound of formula (I) or formula (I-A), or a pharmaceutically acceptable salt or stereoisomer thereof, wherein
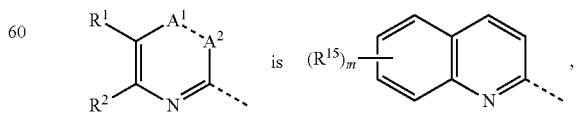
wherein each occurrence of $R^{15}$ is independently: (i) hydrogen, halo, cyano, —$OR^{13}$, —$NR^{13}R^{14}$, —$N(R^{13})C(O)R^{14}$, —$C(O)NR^{13}R^{14}$, —$C(O)R^{13}$, —$C(O)OR^{13}$, —$OC(O)R^{13}$, —SR$^{13}$, —S(O)R$^{13}$, —S(O)$_2$R$^{13}$, —S(O)$_2$NR$^{13}$R$^{14}$, (C$_1$-C$_{10}$)alkyl optionally substituted with one or more R$^{12}$, (C$_1$-C$_{10}$)heteroalkyl optionally substituted with one or more R$^{12}$, (C$_3$-C$_{10}$)cycloalkyl optionally substituted with one or more R$^{12}$, (C$_7$-C$_{12}$)aralkyl optionally substituted with one or more R$^{12}$, (C$_3$-C$_{12}$)heteroaralkyl optionally substituted with one or more R$^{12}$, (6 to 10 membered)aryl optionally substituted with one or more R$^{12}$, (5 to 10 membered) heteroaryl optionally substituted with one or more R$^{12}$, or (3 to 12 membered) heterocyclyl optionally substituted with one or more R$^{12}$; or (ii) when two occurrences of R$^{15}$ are attached to adjacent carbon atoms, the two adjacent occurrences of R$^{15}$ together with the carbon atoms to which they are attached may form a ring, optionally substituted with one or more R$^{11}$; wherein R$^{11}$, R$^{12}$, R$^{13}$, and R$^{14}$ are defined herein elsewhere; and m is 0, 1, 2, 3, or 4. In one embodiment, R$^8$ is hydrogen or methyl. In one embodiment, L is —(CH$_2$)$_2$— or —CH=CH—. In one embodiment, A is quinolinyl optionally substituted with one or more halo (e.g., F, Cl, or Br), cyano, methyl, ethyl, CF$_3$, OCH$_3$, or OCF$_3$. In one embodiment, A is optionally substituted phenanthrolinyl. In one embodiment, R$^3$ is optionally substituted phenyl, pyridyl, furanyl, or thienyl (e.g., optionally substituted with one or more F, Cl, Br, cyano, methyl, or CF$_3$). In one embodiment, R$^4$ is H. In one embodiment, A$^4$ is NR$^5$, and R$^5$ is hydrogen or methyl. In one embodiment, R$^3$ and R$^4$ together with the atoms to which they are attached form an optionally substituted aryl or heteroaryl (e.g., benzene, pyridine, naphthylene, or quinoline, in one embodiment, each of which is optionally substituted with one or more F, Cl, Br, cyano, methyl, ethyl, propyl, butyl, OH, OCH$_3$, CF$_3$, or OCF$_3$). Specific examples include, but are not limited to, the following:

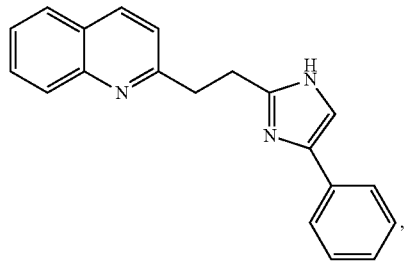

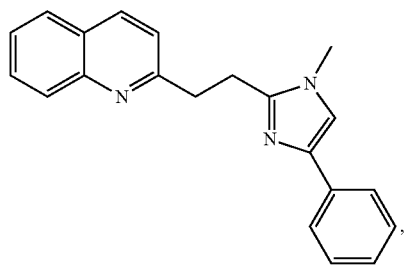

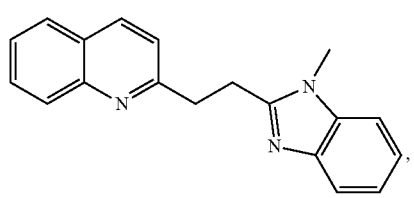

-continued

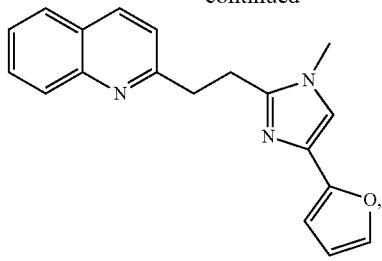

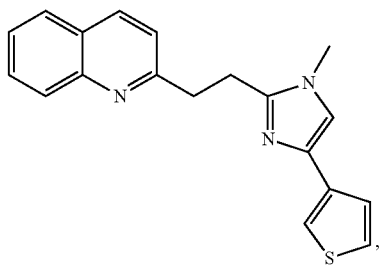

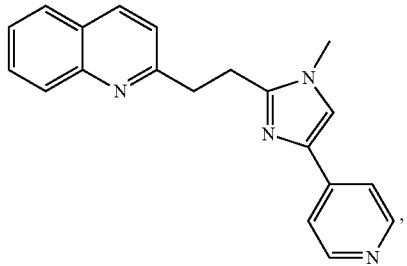

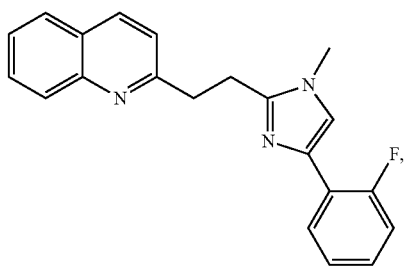

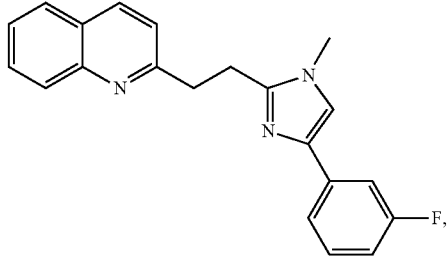

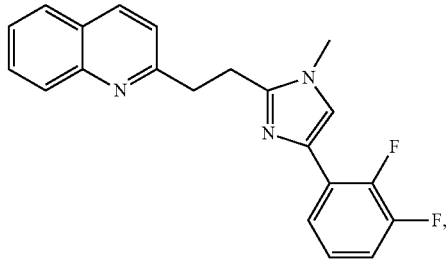

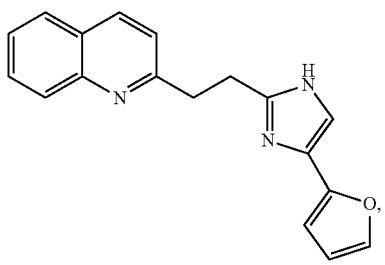
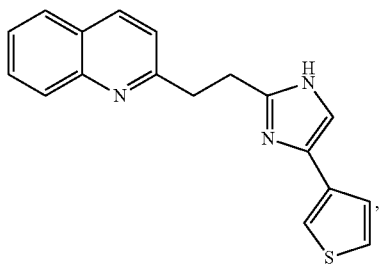
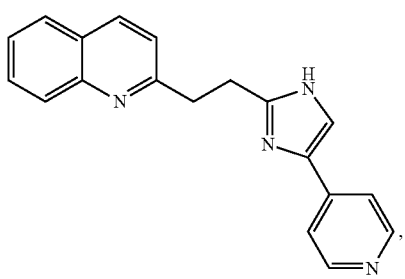
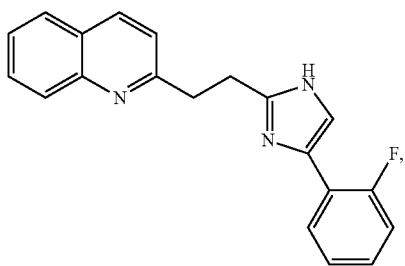
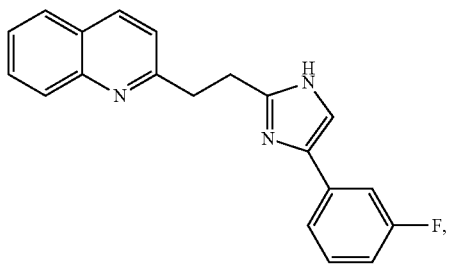
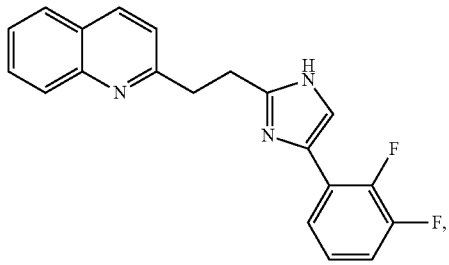
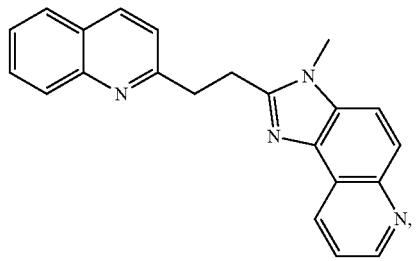
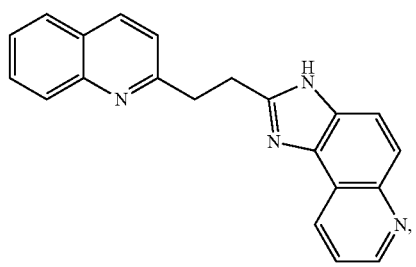
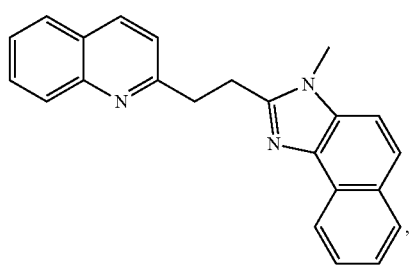
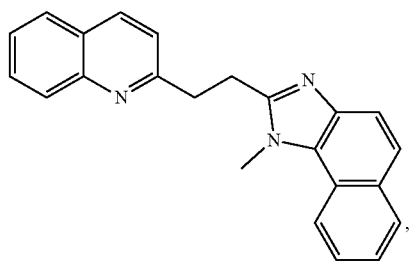
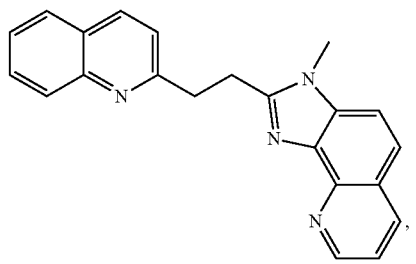
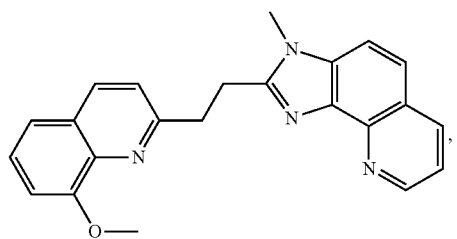

-continued

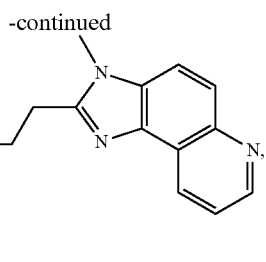

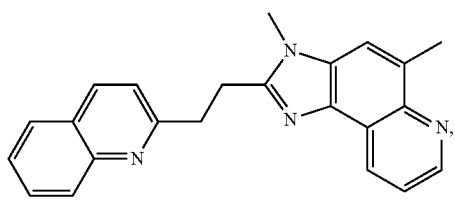

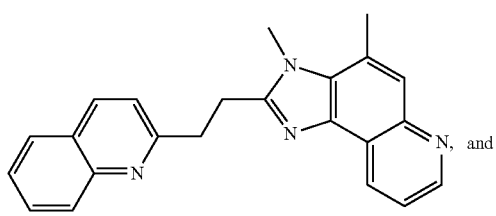

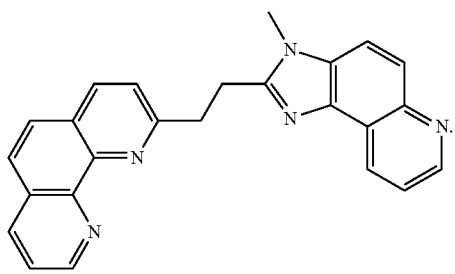

In one embodiment, provided herein is a compound of formula (I) or formula (I-A), or a pharmaceutically acceptable salt or stereoisomer thereof, wherein

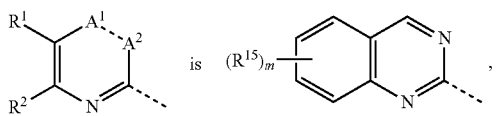

wherein each occurrence of $R^{15}$ is independently: (i) hydrogen, halo, cyano, —$OR^{13}$, —$NR^{13}R^{14}$, —$N(R^{13})C(O)R^{14}$, $C(O)NR^{13}R^{14}$, —$C(O)R^{13}$, —$C(O)OR^{13}$, —$OC(O)R^{13}$, —$SR^{13}$, —$S(O)R^{13}$, —$S(O)_2R^{13}$, —$S(O)NR^{13}R^{14}$, ($C_1$-$C_{10}$) alkyl optionally substituted with one or more $R^{12}$, ($C_1$-$C_{10}$) heteroalkyl optionally substituted with one or more $R^{12}$, ($C_3$-$C_{10}$)cycloalkyl optionally substituted with one or more $R^{12}$, ($C_7$-$C_{12}$)aralkyl optionally substituted with one or more $R^{12}$, ($C_3$-$C_{12}$)heteroaralkyl optionally substituted with one or more $R^{12}$, (6 to 10 membered)aryl optionally substituted with one or more $R^{12}$, (5 to 10 membered) heteroaryl optionally substituted with one or more $R^{12}$, or (3 to 12 membered) heterocyclyl optionally substituted with one or more $R^{12}$; or (ii) when two occurrences of $R^{15}$ are attached to adjacent carbon atoms, the two adjacent occurrences of $R^{15}$ together with the carbon atoms to which they are attached may form a ring, optionally substituted with one or more $R^{11}$; wherein $R^{11}$, $R^{12}$, $R^{13}$, and $R^{14}$ are defined herein elsewhere; and m is 0, 1, 2, 3, or 4. In one embodiment, $R^8$ is hydrogen or methyl. In one embodiment, L is —$(CH_2)_2$— or —CH=CH—. In one embodiment, A is quinazolinyl optionally substituted with one or more halo (e.g., F, Cl, or Br), cyano, methyl, ethyl, $CF_3$, $OCH_3$, or $OCF_3$. In one embodiment, $R^3$ is optionally substituted phenyl, pyridyl, furanyl, or thienyl (e.g., optionally substituted with one or more F, Cl, Br, cyano, methyl, or $CF_3$). In one embodiment, $R^4$ is H. In one embodiment, $A^4$ is $NR^5$, and $R^5$ is hydrogen or methyl. In one embodiment, $R^3$ and $R^4$ together with the atoms to which they are attached form an optionally substituted aryl or heteroaryl (e.g., benzene, pyridine, naphthylene, or quinoline, in one embodiment, each of which is optionally substituted with one or more F, Cl, Br, cyano, methyl, ethyl, propyl, butyl, OH, $OCH_3$, $CF_3$, or $OCF_3$). In one embodiment, $R^3$ and $R^4$ together with the atoms to which they are attached form an optionally substituted heterocyclyl ring (e.g., 2,3-dihydrobenzo[b][1,4]dioxine). Specific examples include, but are not limited to, the following:

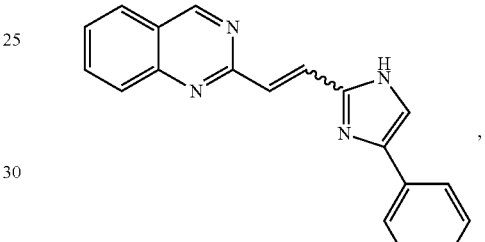

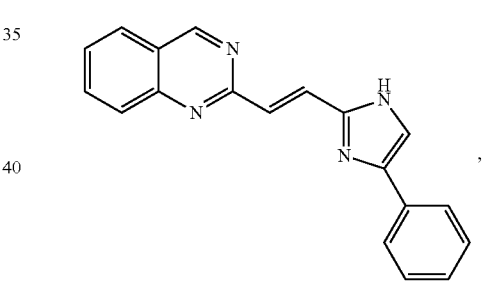

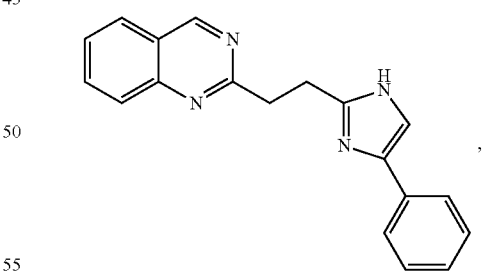

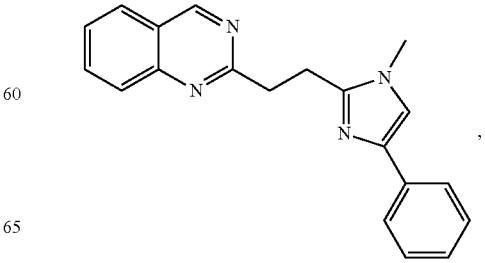

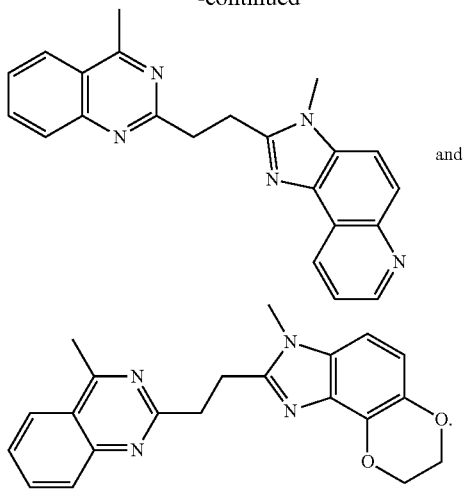

In one embodiment, provided herein is a compound of formula (I) or formula (I-A), or a pharmaceutically acceptable salt or stereoisomer thereof, wherein

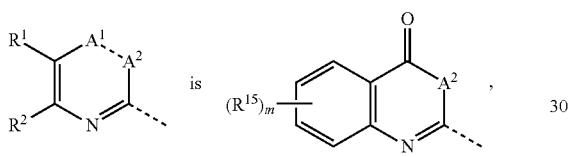

wherein $A^2$ is NH, NCH$_3$, or O; each occurrence of $R^{15}$ is independently: (i) hydrogen, halo, cyano, —OR$^{13}$, —NR$^{13}$R$^{14}$, —N(R$^{13}$)C(O)R$^{14}$, —C(O)NR$^{13}$R$^{14}$, —C(O)R$^{13}$, —C(O)OR$^{13}$, —OC(O)R$^{13}$, —SR$^{13}$, —S(O)R$^{13}$, —S(O)$_2$R$^{13}$, —S(O)$_2$NR$^{13}$R$^{14}$, (C$_1$-C$_{10}$)alkyl optionally substituted with one or more R$^{12}$, (C$_1$-C$_{10}$)heteroalkyl optionally substituted with one or more R$^{12}$, (C$_3$-C$_{10}$)cycloalkyl optionally substituted with one or more R$^{12}$, (C$_7$-C$_{12}$)aralkyl optionally substituted with one or more R$^{12}$, (C$_3$-C$_{12}$)heteroaralkyl optionally substituted with one or more R$^{12}$, (6 to 10 membered)aryl optionally substituted with one or more R$^{12}$, (5 to 10 membered)heteroaryl optionally substituted with one or more R$^{12}$, or (3 to 12 membered) heterocyclyl optionally substituted with one or more R$^{12}$; or (ii) when two occurrences of R$^{15}$ are attached to adjacent carbon atoms, the two adjacent occurrences of R$^{15}$ together with the carbon atoms to which they are attached may form a ring, optionally substituted with one or more R$^{11}$; wherein R$^{11}$, R$^{12}$, R$^{13}$, and R$^{14}$ are defined herein elsewhere; and m is 0, 1, 2, 3, or 4. In one embodiment, L is —(CH$_2$)$_2$— or —CH═CH—. In one embodiment, each R$^{15}$ is independently halo (e.g., F, Cl, or Br), cyano, methyl, ethyl, CF$_3$, OCH$_3$, or OCF$_3$. In one embodiment, two adjacent occurrences of R$^{15}$ together with the carbon atoms to which they are attached form an optionally substituted phenyl. In one embodiment, R$^3$ is optionally substituted phenyl, pyridyl, furanyl, benzofuranyl, thienyl, benzodioxolyl, naphthyl, or quinolinyl (e.g., optionally substituted with one or more F, Cl, Br, cyano, methyl, CF$_3$, or phenyl). In one embodiment, R$^4$ is H. In one embodiment, R$^4$ is phenyl. In one embodiment, A$^4$ is NR$^5$, and R$^5$ is hydrogen or methyl. In one embodiment, R$^3$ and R$^4$ together with the atoms to which they are attached form an optionally substituted aryl or heteroaryl (e.g., benzene, pyridine, naphthylene, or quinoline, in one embodiment, each of which is optionally substituted with one or more F, Cl, Br, cyano, methyl, ethyl, propyl, butyl, OH, OCH$_3$, CF$_3$, or OCF$_3$). In one embodiment, A$^4$ is O or S. Specific examples include, but are not limited to, the following:

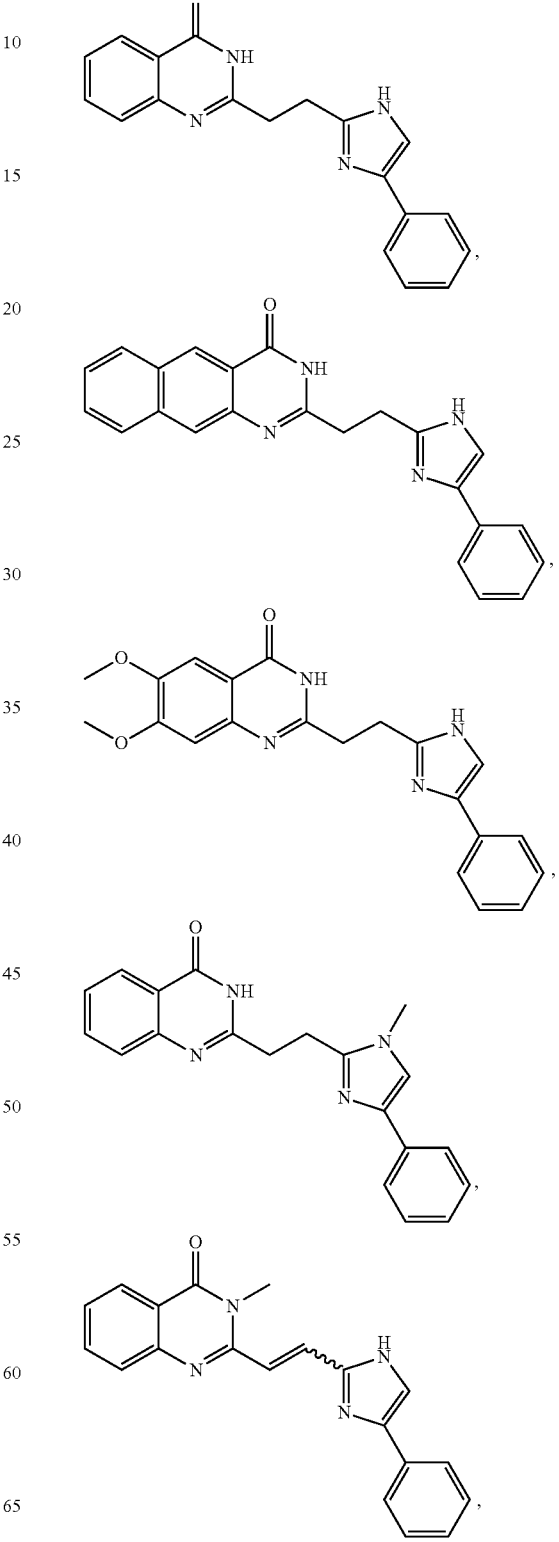

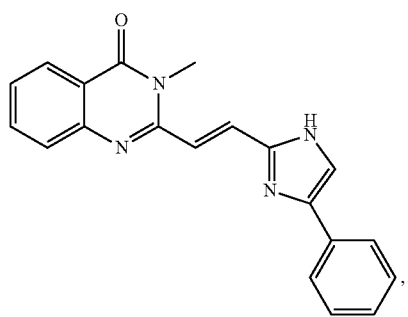
,
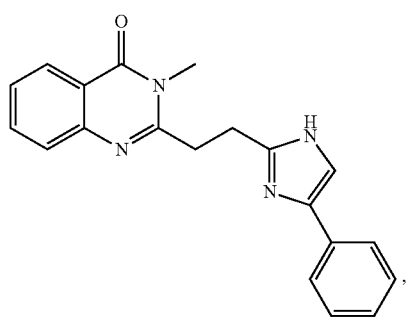
,
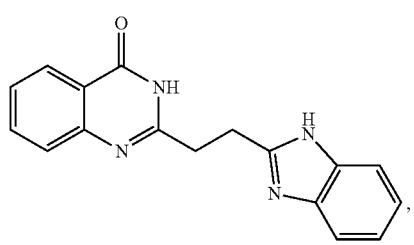
,
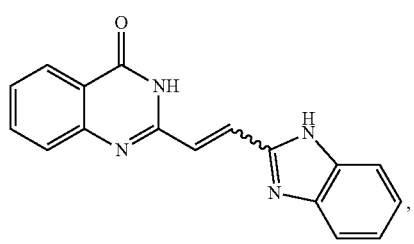
,
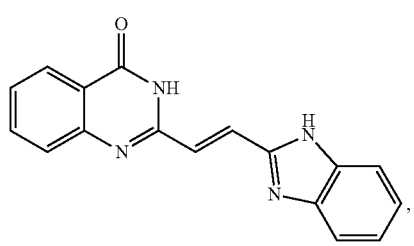
,
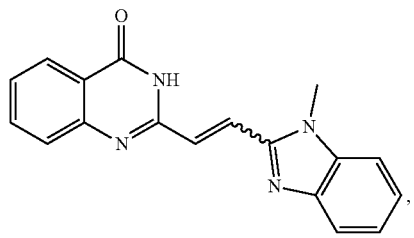
,
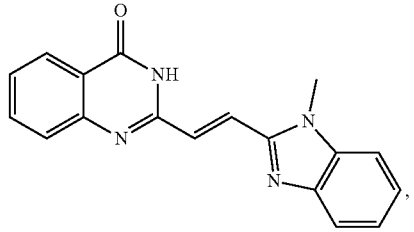
,
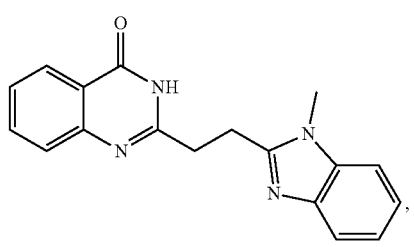
,
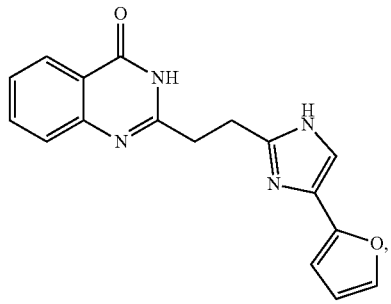
,
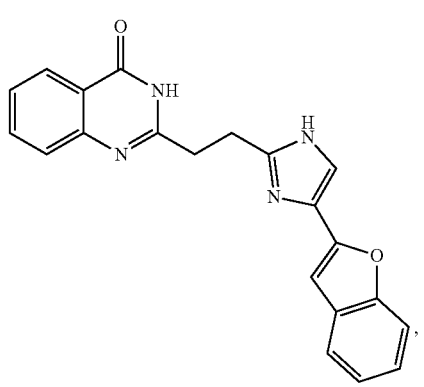
,
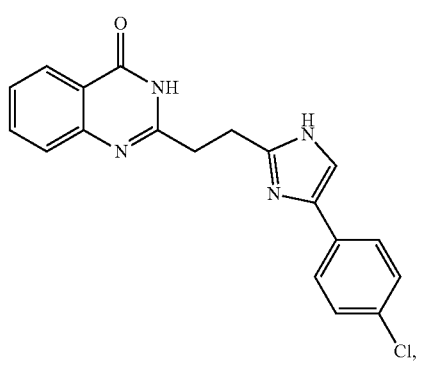
,

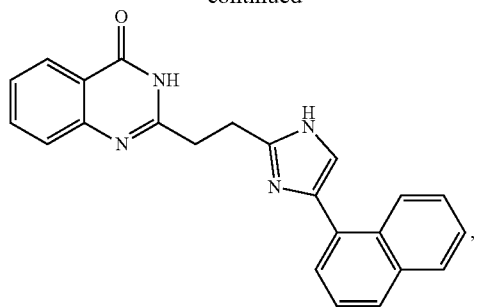
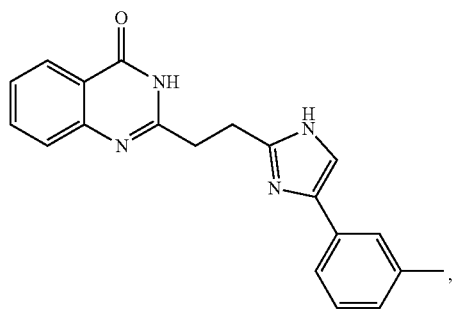
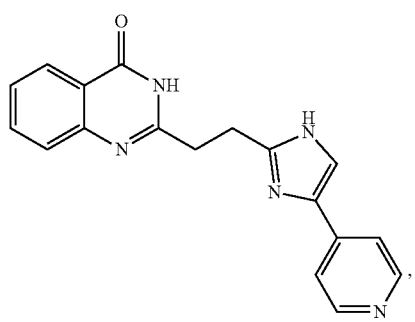
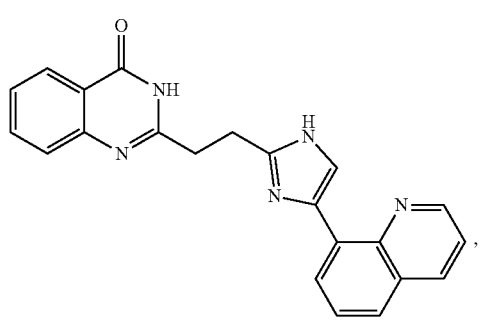
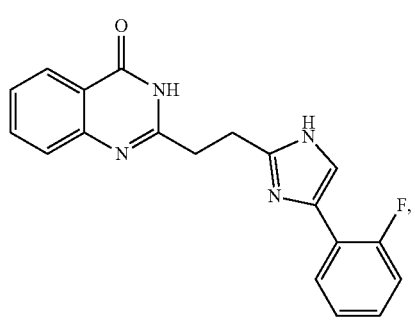
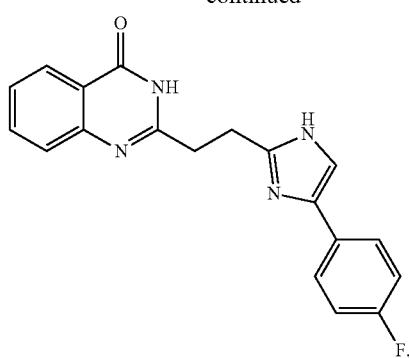
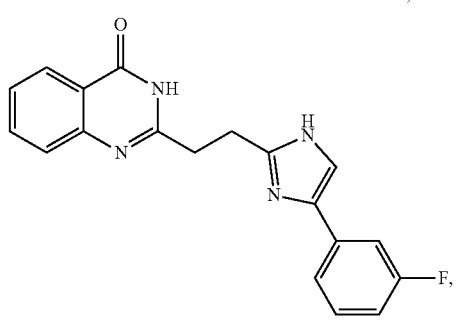
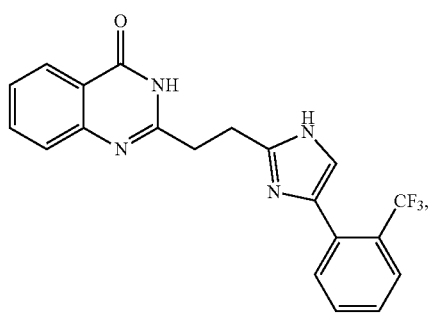
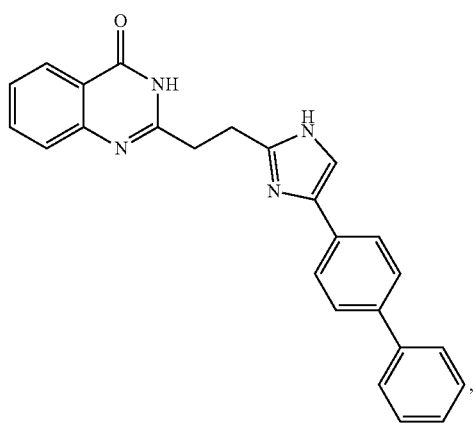
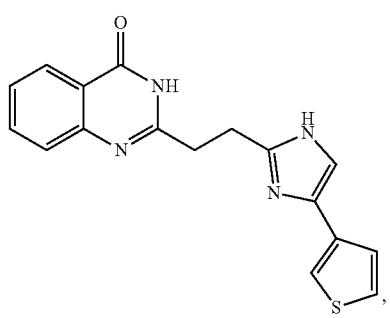

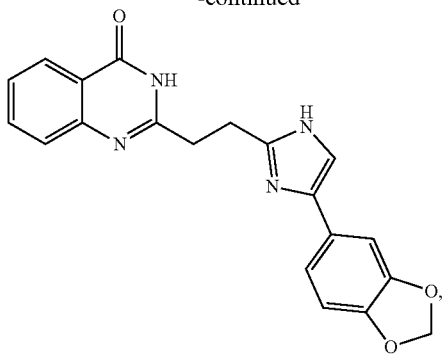

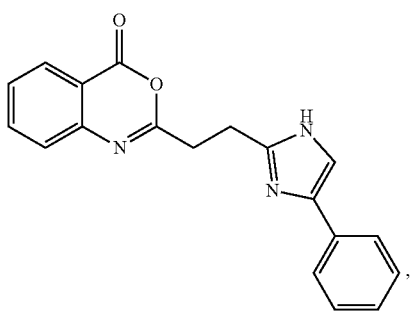

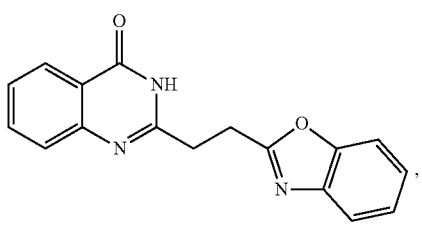

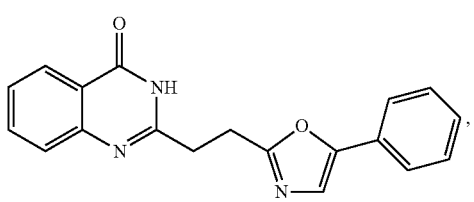

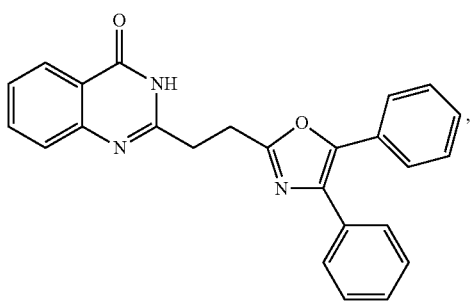

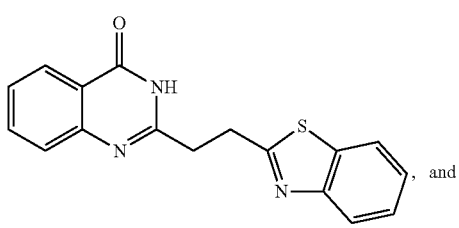

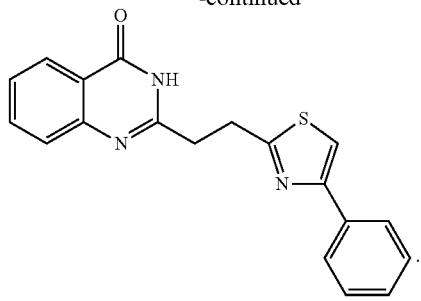

In one embodiment, provided herein is a compound of formula (I), or a pharmaceutically acceptable salt or stereoisomer thereof, wherein A is

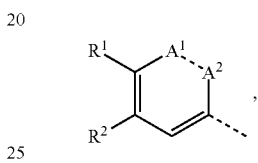

wherein $R^1$, $R^2$, $A^1$ and $A^2$ are defined herein elsewhere. In one embodiment, A is optionally substituted phenyl or naphthyl. In one embodiment, A is optionally substituted isoquinolinyl. In one embodiment, A is optionally substituted isoquinolin-1(2H)-onyl. In one embodiment, L is —(CH$_2$)$_2$— or —CH═CH—. In one embodiment, B is optionally substituted phenylimidazolyl. Specific examples include, but are not limited to, the following:

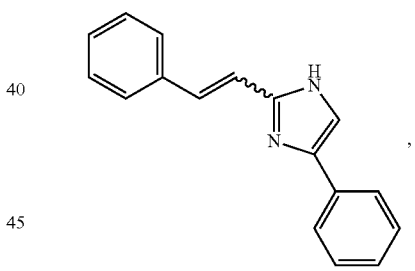

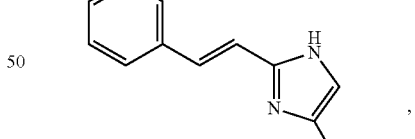

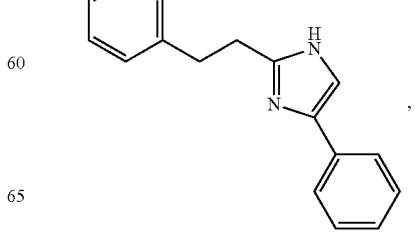

-continued

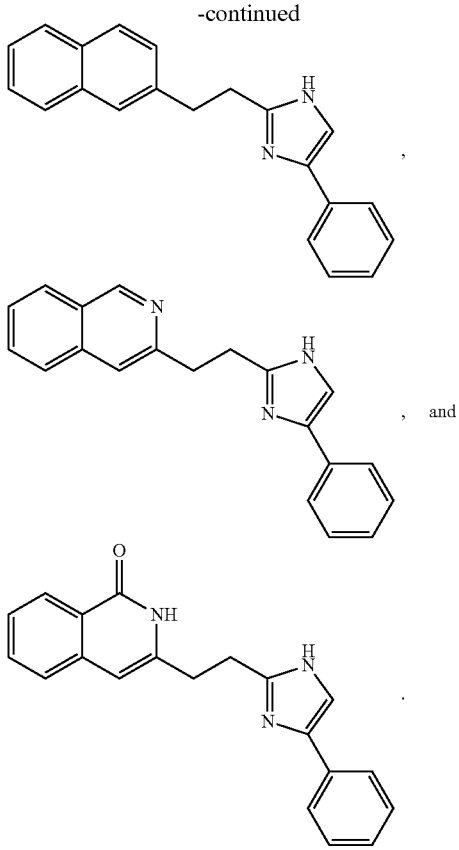

, and

In one embodiment, provided herein is a compound of formula (I), or a pharmaceutically acceptable salt or stereoisomer thereof, wherein B is

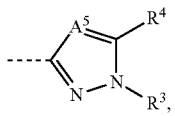

wherein $R^3$, $R^4$, and $A^5$ are defined herein elsewhere. In one embodiment, $A^5$ is CH. In one embodiment, $R^3$ is phenyl and $R^4$ is H. In one embodiment, $A^5$ is N. In one embodiment, $R^3$ is H and $R^4$ is pyridyl. In one embodiment, specific examples include, but are not limited to, the following:

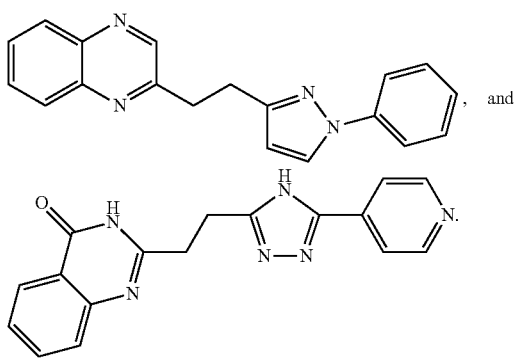

In one embodiment, $A^5$ is N. In one embodiment, $A^5$ is $CR^5$. In one embodiment, $R^3$ and $R^4$ together with the atoms to which they are attached form an optionally substituted ring. In one embodiment, $R^3$ and $R^4$ together with the atoms to which they are attached form an optionally substituted 9- to 10-membered heteroaryl ring (i.e., B is an optionally substituted 12- to 13-membered heteroaryl).

In one embodiment, $A^5$ is CH. In one embodiment, $R^4$ is hydrogen. In one embodiment, $R^3$ is alkyl, aryl, or heteroaryl, each of which is optionally substituted with one or more $R^{11}$.

In one embodiment, $A^5$ is N. In one embodiment, $R^3$ is hydrogen. In one embodiment, $R^4$ is alkyl, aryl, or heteroaryl, each of which is optionally substituted with one or more $R^{11}$.

In one embodiment, provided herein is a compound of formula (I), or a pharmaceutically acceptable salt or stereoisomer thereof, wherein
B is

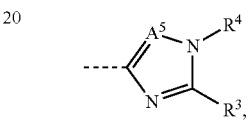

wherein $R^3$, $R^4$, and $A^5$ are defined herein elsewhere.

In one embodiment, $A^5$ is N. In one embodiment, $R^3$ and $R^4$ together with the atoms to which they are attached form an optionally substituted ring. In one embodiment, $R^3$ and $R^4$ together with the atoms to which they are attached form an optionally substituted 9- to 10-membered heteroaryl ring (i.e., B is an optionally substituted 12- to 13-membered heteroaryl).

In one embodiment, $A^5$ is $CR^5$. In one embodiment, $R^5$ is H or $CH_3$. In one embodiment, $R^3$ and $R^4$ together with the atoms to which they are attached form an optionally substituted ring. In one embodiment, $R^3$ and $R^4$ together with the atoms to which they are attached form an optionally substituted pyridyl ring. In one embodiment, A is an optionally substituted 6- to 10-membered ring (e.g., quinoxalinyl or quinolinyl) (examples of optional substituents are provided herein elsewhere). Specific examples include, but are not limited to, the following:

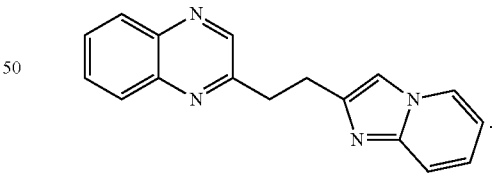

In one embodiment, $A^5$ is $CR^5$. In one embodiment, $R^5$ is H, halo, $CH_3$, cycloalkyl (e.g., cyclopropyl), or heterocyclyl (e.g., pyrrolidinyl, piperidinyl, piperazinyl, or morpholinyl) In one embodiment, $R^3$ and $R^4$ together with the atoms to which they are attached form an optionally substituted pyrimidinyl, pyrazinyl, or pyridazinyl ring. In one embodiment, A is an optionally substituted 6- to 10-membered ring (e.g., pyrimidinyl, pyridylpyrimidyl, quinoxalinyl, or quinolinyl) (examples of optional substituents are provided herein elsewhere). Specific examples include, but are not limited to, the following:

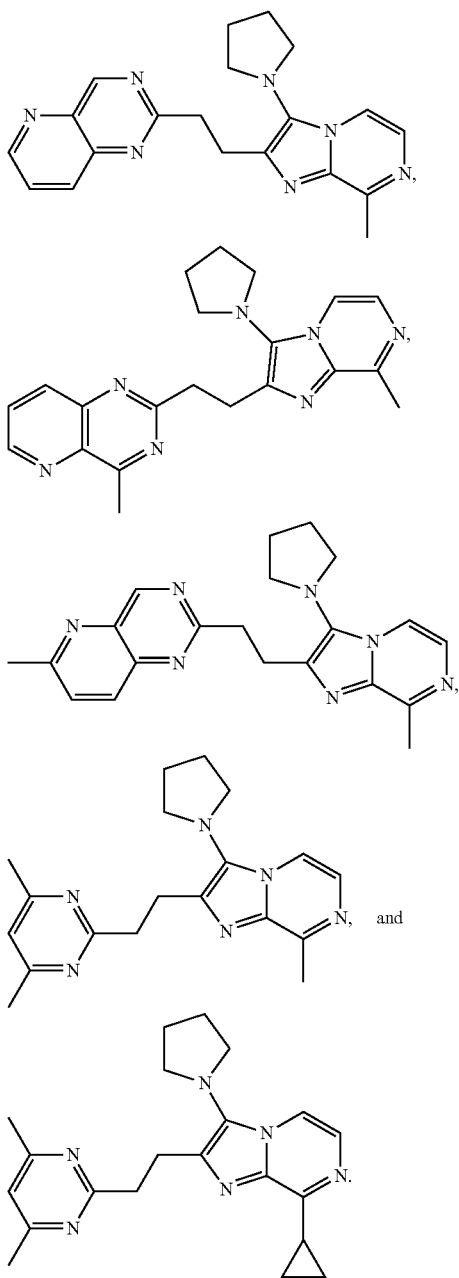

In one embodiment, $A^5$ is $CR^5$. In one embodiment, $R^5$ is H or $CH_3$. In one embodiment, $R^3$ and $R^4$ together with the atoms to which they are attached form a 9- to 10-membered heteroaryl ring (e.g., a 9- to 10-membered heteroaryl ring having 1, 2, or 3 nitrogen ring atoms). In one embodiment, $R^3$ and $R^4$ together with the atoms to which they are attached form a 10-membered heteroaryl ring having at least two nitrogen ring atoms (e.g., 2, 3, or 4 nitrogen ring atoms). In one embodiment, L is —$(CH_2)_2$— or —CH═CH—. In one embodiment, L is —O—$CH_2$— or —$CH_2$—O—. In one embodiment, A is an optionally substituted 6- to 10-membered heteroaryl ring. In one embodiment, A is pyridyl, pyrimidyl, pyrazinyl, pyridylpyrimidyl, quinazolinyl, 6,7-dihydro-5H-cyclopenta[d]pyrimidinyl, dihydro-naphthyridinonyl, tetrahydro-naphthyridinyl, quinoxalinyl, quinolinyl, or naphthyridinyl, each of which is optionally substituted (e.g., with one or more halo, e.g., F, Cl, or Br, cyano, methyl, ethyl, $CF_3$, $OCH_3$, $OCF_3$, or heterocyclyl, e.g., pyrrolidinyl). In one embodiment, A is quinoxalinyl, quinolinyl, or naphthyridinyl, each of which is optionally substituted with one or more halo (e.g., F, Cl, or Br), cyano, methyl, ethyl, $CF_3$, $OCH_3$, or $OCF_3$. Specific examples include, but are not limited to, the following:

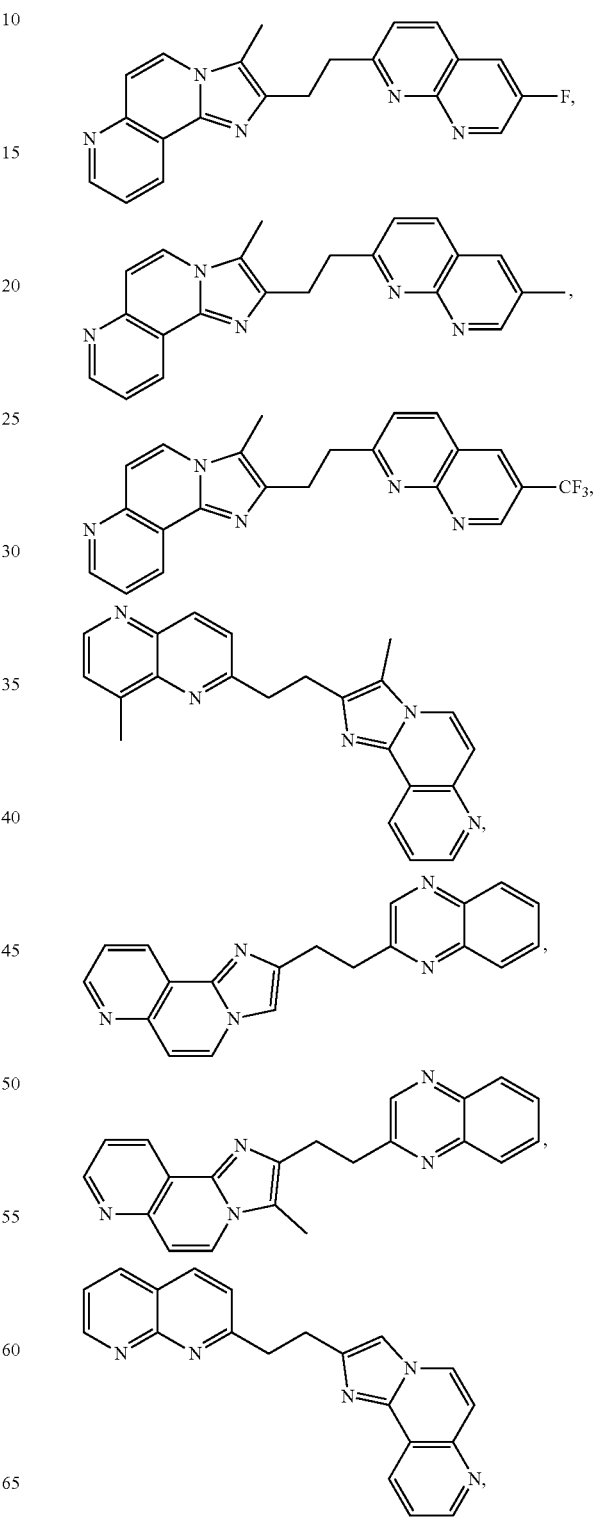

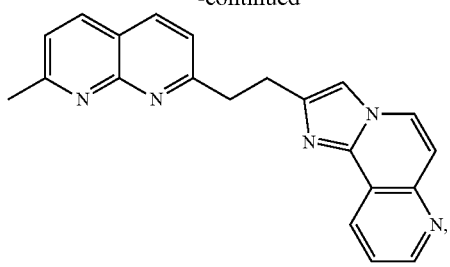
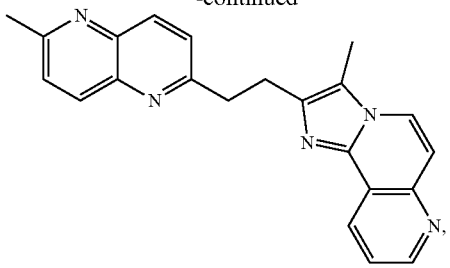
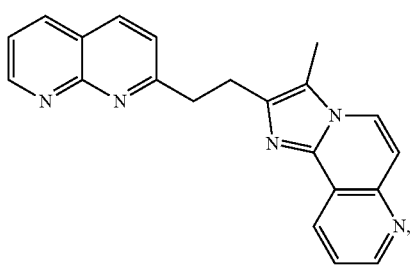
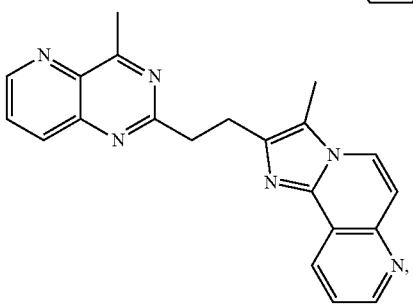
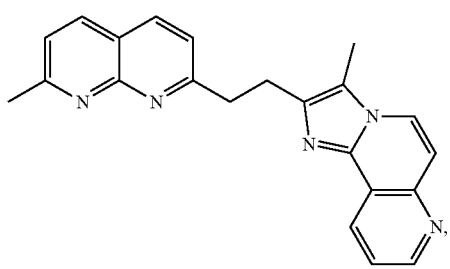
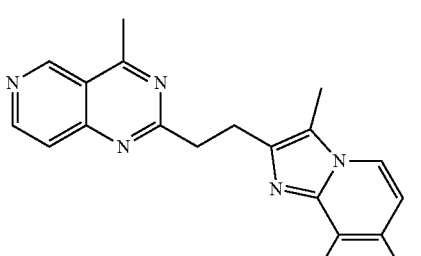
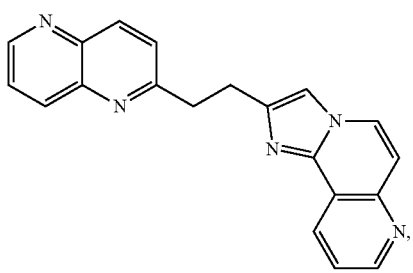
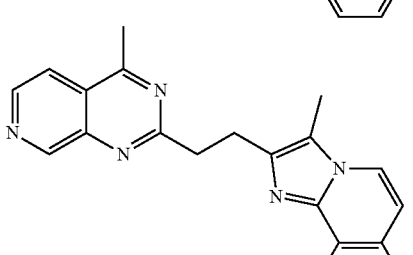
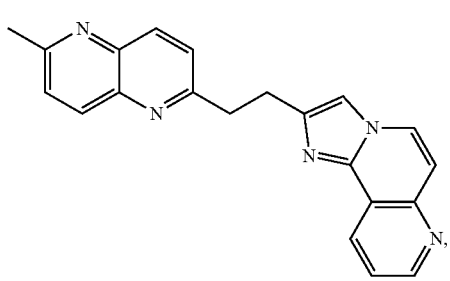
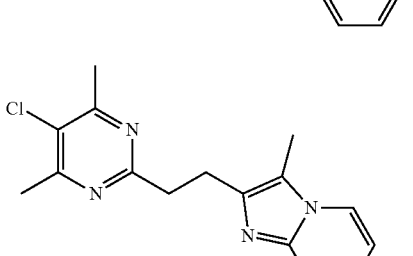
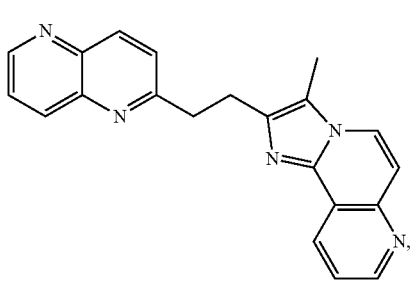
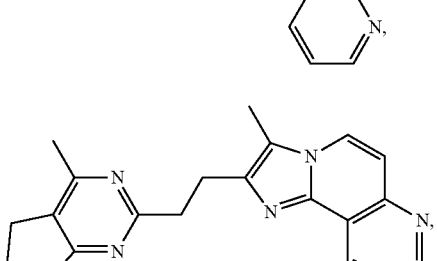

65
-continued
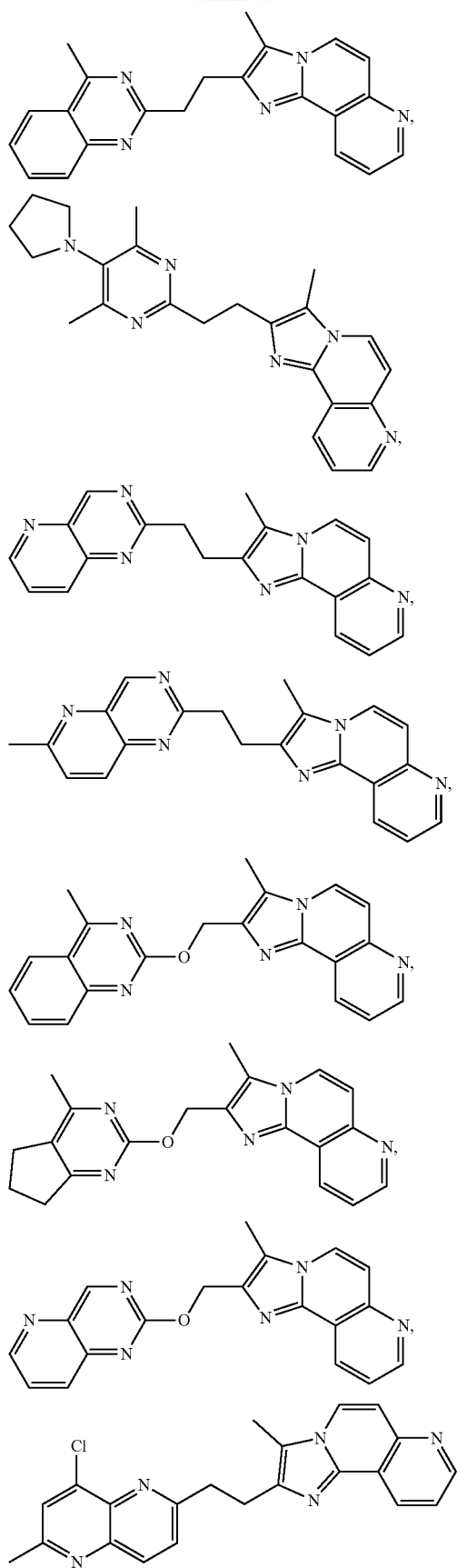
66
-continued
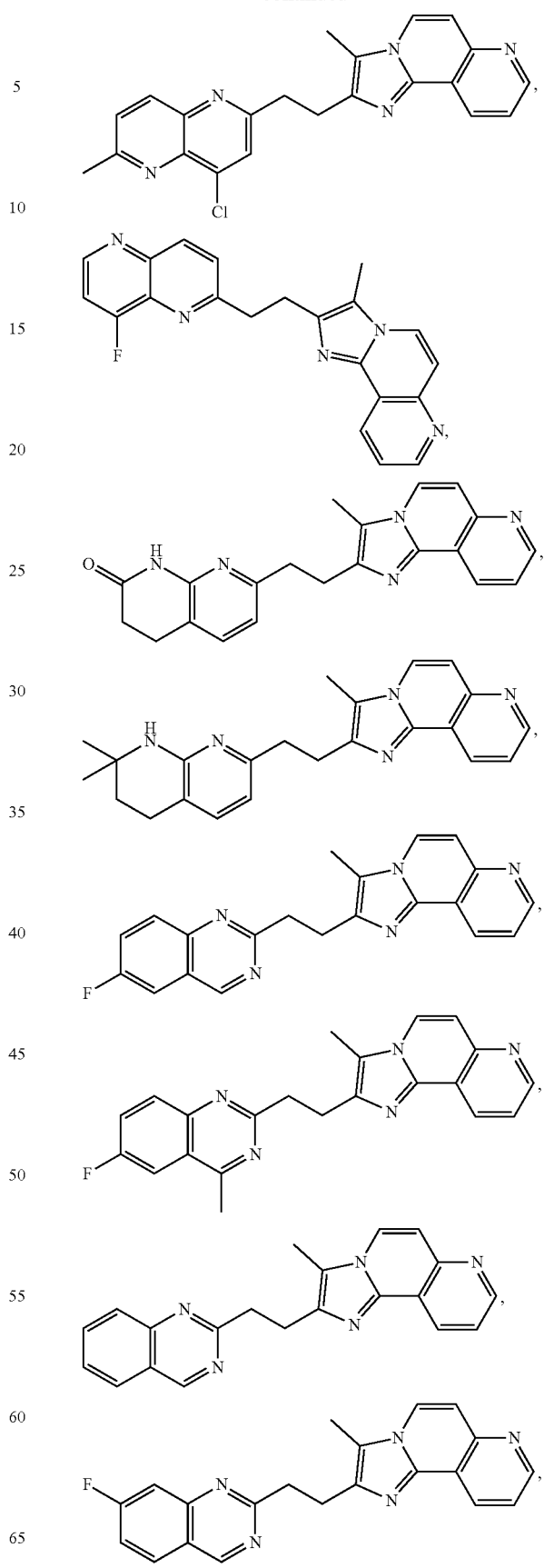

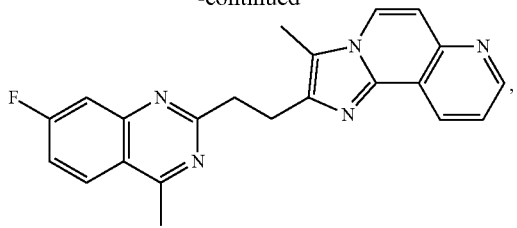

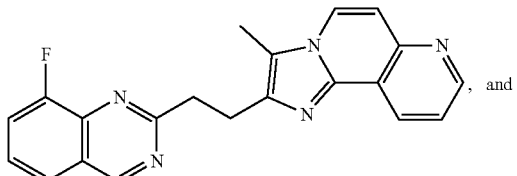

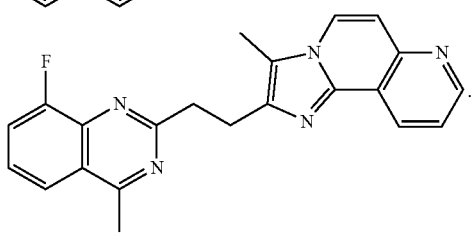

In one embodiment, $A^5$ is $CR^5$. In one embodiment, $R^5$ is H, halo, $CH_3$, cycloalkyl (e.g., cyclopropyl), or heterocyclyl (e.g., pyrrolidinyl, piperidinyl, piperazinyl, or morpholinyl). In one embodiment, $R^3$ and $R^4$ together with the atoms to which they are attached form a 9- to 10-membered heteroaryl or heterocyclyl ring (e.g., a 9- to 10-membered ring having 1, 2, 3, or 4 hetero atoms, such as one or more N, O, and/or S). Specific examples include, but are not limited to, the following:

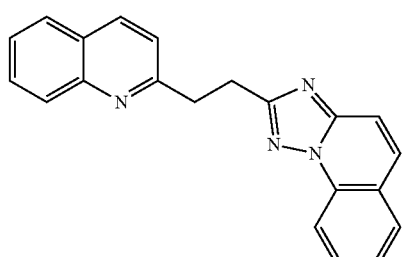

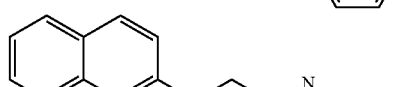

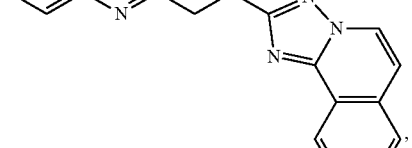

In one embodiment, provided herein is a compound of formula (I), or a pharmaceutically acceptable salt or stereoisomer thereof, wherein B is

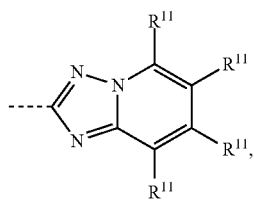

wherein each occurrence of $R^{11}$ may be the same or different, and is defined herein elsewhere. In one embodiment, two adjacent occurrences of $R^{11}$ together with the atoms to which they are attached form an optionally substituted 5- or 6-membered aryl or heteroaryl (e.g., phenyl, thienyl, pyridyl, pyrimidyl, or pyrazinyl ring, in one embodiment, optionally substituted with one or more F, Cl, cyano, methyl, $OCH_3$, $CF_3$, or $OCF_3$). In one embodiment, the other two occurrences of $R^{11}$ is H, halo (e.g., F, Cl, or Br), cyano, or methyl. In one embodiment, L is —$(CH_2)_2$— or —CH=CH—. In one embodiment, A is an optionally substituted 6- to 10-membered heteroaryl or heterocyclyl ring. In one embodiment, A is an optionally substituted 10-membered heteroaryl or heterocyclyl ring. In one embodiment, A is pyridyl, pyrimidyl, pyrazinyl, pyridylpyrimidyl, quinazolinyl, 6,7-dihydro-5H-cyclopenta[d]pyrimidinyl, dihydro-naphthyridinonyl, tetrahydro-naphthyridinyl, quinoxalinyl, quinolinyl, or naphthyridinyl, each of which is optionally substituted (e.g., with one or more halo, e.g., F, Cl, or Br, cyano, methyl, ethyl, $CF_3$, $OCH_3$, or $OCF_3$). In one embodiment, A is quinoxalinyl, quinolinyl, or naphthyridinyl, each of which is optionally substituted with one or more halo (e.g., F, Cl, or Br), cyano, methyl, ethyl, $CF_3$, $OCH_3$, or $OCF_3$. Specific examples include, but are not limited to, the following:

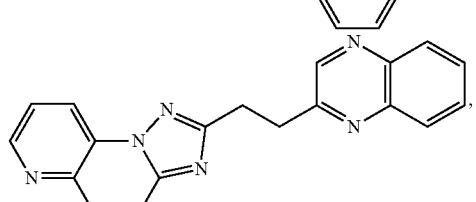

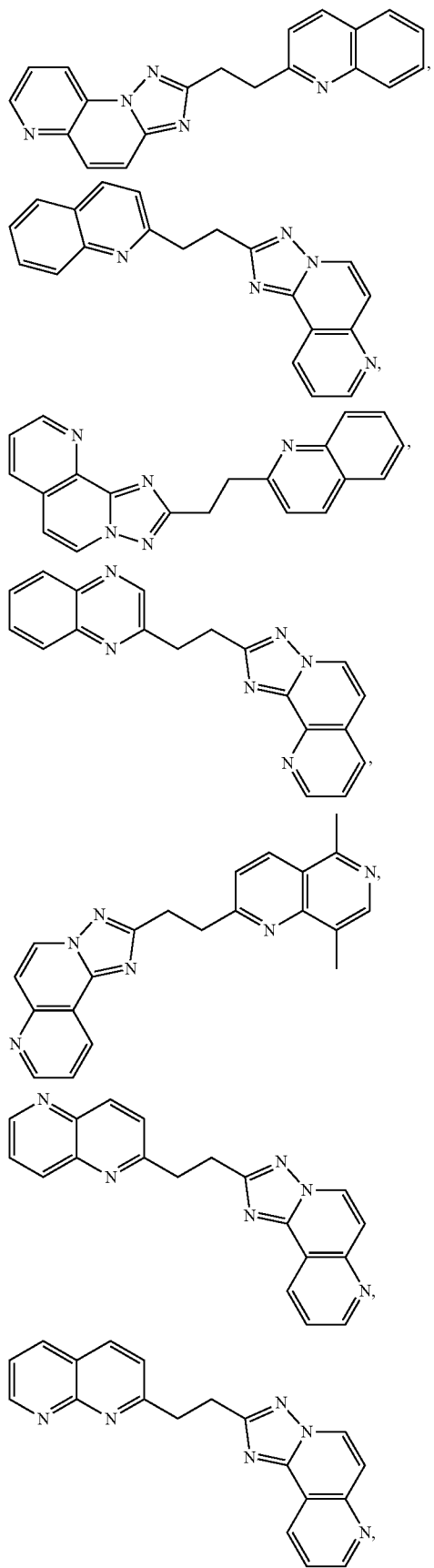
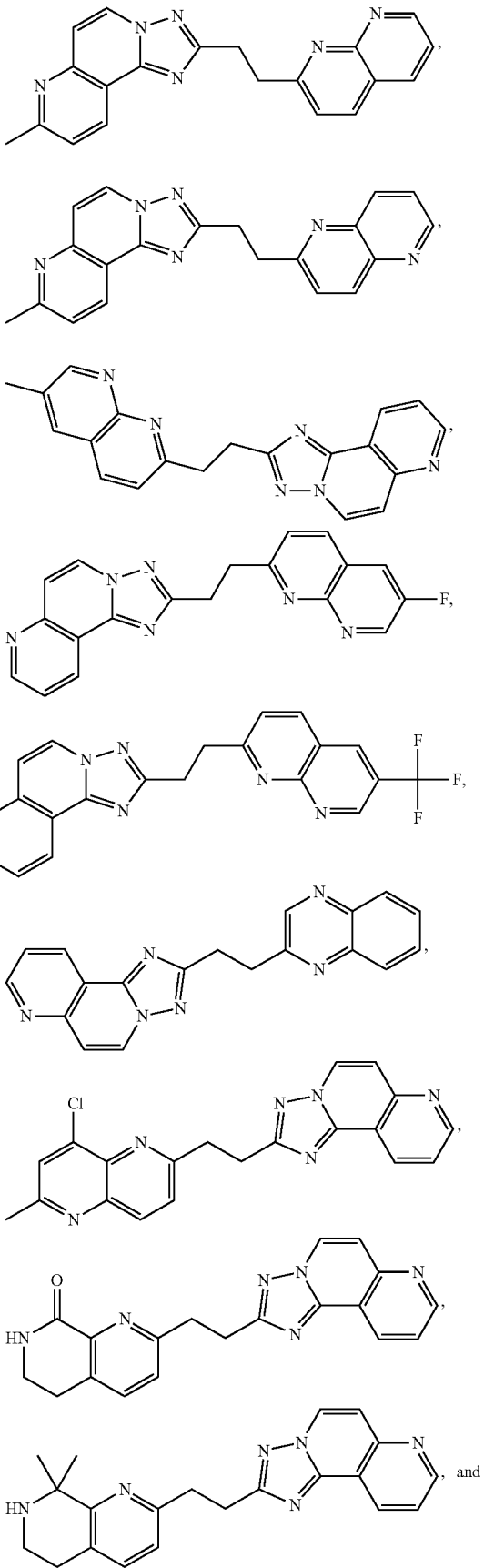

-continued

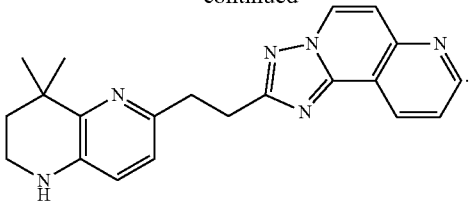

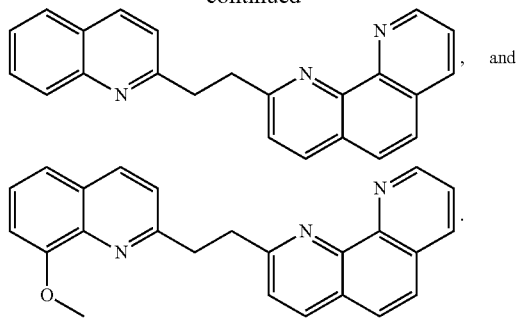

In one embodiment, $A^5$ is CH. In one embodiment, $R^4$ is hydrogen or methyl. In one embodiment, $R^3$ is alkyl, aryl, or heteroaryl, each of which is optionally substituted with one or more $R^{11}$.

In one embodiment, $A^5$ is N. In one embodiment, $R^4$ is hydrogen. In one embodiment, $R^3$ is alkyl, aryl, or heteroaryl, each of which is optionally substituted with one or more $R^{11}$.

In one embodiment, $A^5$ is N or CH. In one embodiment, $A^5$ is CH. In one embodiment, $R^3$ and $R^4$ together with the atoms to which they are attached form a pyridyl ring, which is optionally substituted with one or more $R^{11}$.

In one embodiment, provided herein is a compound of formula (I), or a pharmaceutically acceptable salt or stereoisomer thereof, wherein
B is

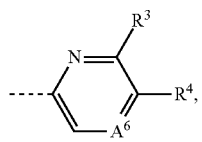

wherein $R^3$, $R^4$, and $A^6$ are defined herein elsewhere. In one embodiment, B is optionally substituted pyridyl (e.g., pyridyl optionally substituted with phenyl). In one embodiment, B is optionally substituted quinoxalinyl, quinolinyl, or phenanthrolinyl. In one embodiment, A is quinoxalinyl, quinolinyl, or naphthyridinyl, each of which is optionally substituted with one or more halo (e.g., F, Cl, or Br), cyano, methyl, ethyl, $CF_3$, $OCH_3$, or $OCF_3$. In one embodiment, L is —$(CH_2)_2$— or —CH=CH—. Specific examples include, but are not limited to, the following:

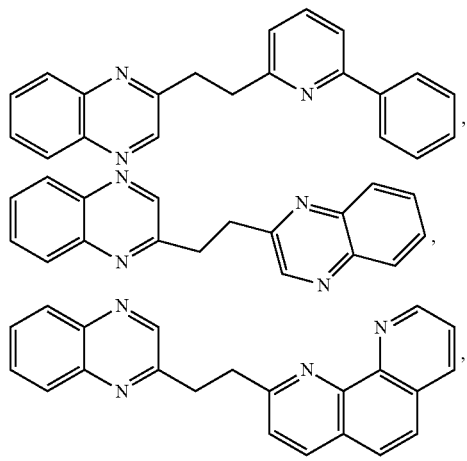

In one embodiment, $A^6$ is CH. In one embodiment, $A^6$ is N. In one embodiment, $R^4$ is hydrogen. In one embodiment, $R^3$ is alkyl, aryl, or heteroaryl, each of which is optionally substituted with one or more $R^{11}$.

In one embodiment, provided herein is a compound of formula (I), or a pharmaceutically acceptable salt or stereoisomer thereof, wherein
B is

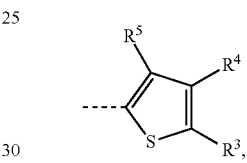

wherein A, L, $R^3$, $R^4$, and $R^5$ are defined herein elsewhere. In one embodiment, L is —$(CH_2)_2$— or —CH=CH—. In one embodiment, A is quinazolin-4(3H)-onyl. In one embodiment, B is thienyl substituted with phenyl. Specific examples include, but are not limited to, the following:

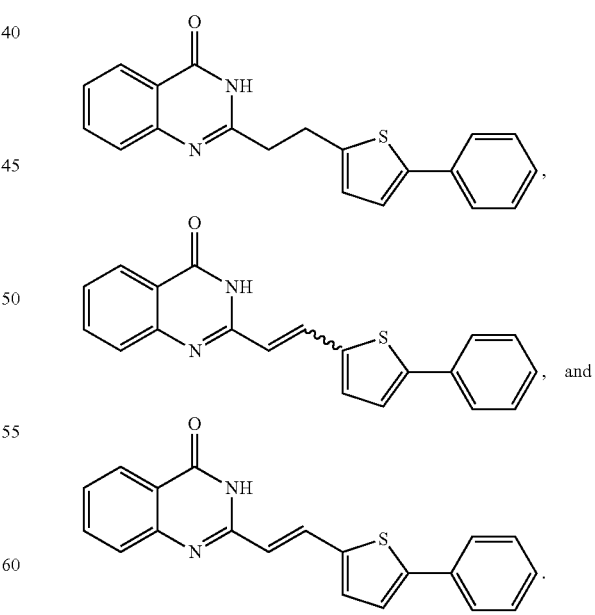

In one embodiment, $R^4$ is hydrogen. In one embodiment, $R^5$ is hydrogen. In one embodiment, $R^3$ is alkyl, aryl, or heteroaryl, each of which is optionally substituted with one or more $R^{11}$.

In one embodiment, provided herein is a compound of formula (I), or a pharmaceutically acceptable salt or stereoisomer thereof, wherein
B is

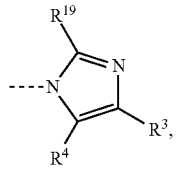

wherein $R^3$, $R^4$, and $R^{19}$ are defined herein elsewhere. In one embodiment, B is phenylimidazolyl. In one embodiment, L is —(CH$_2$)$_2$— or —CH=CH—. In one embodiment, A is quinazolin-4(3H)-onyl. Specific examples include, but are not limited to, the following:

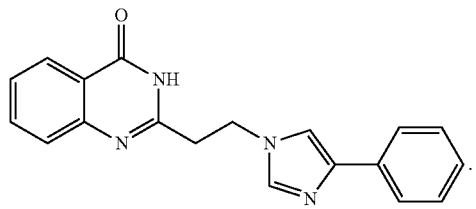 [SMILES: O=c1[nH]c(CCn2cnc(-c3ccccc3)c2)nc2ccccc12]

In one embodiment, $R^4$ is hydrogen. In one embodiment, $R^3$ is alkyl, aryl, or heteroaryl, each of which is optionally substituted with one or more $R^{11}$. In one embodiment, $R^{19}$ is hydrogen.

In one embodiment, provided herein is a compound of formula (I), or a pharmaceutically acceptable salt or stereoisomer thereof, wherein
B is

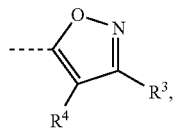

wherein $R^3$ and $R^4$ are defined herein elsewhere. In one embodiment, B is phenylisoxazolyl. In one embodiment, L is —(CH$_2$)$_2$— or —CH=CH—. In one embodiment, A is quinazolin-4(3H)-onyl. Specific examples include, but are not limited to, the following:

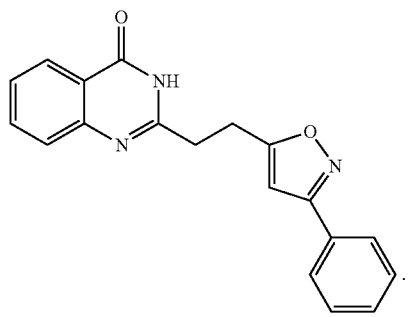 [SMILES: O=c1[nH]c(CCc2cc(-c3ccccc3)no2)nc2ccccc12]

In one embodiment, $R^4$ is hydrogen. In one embodiment, $R^3$ is alkyl, aryl, or heteroaryl, each of which is optionally substituted with one or more $R^{11}$.

In one embodiment, provided herein is a compound of formula (I), or a pharmaceutically acceptable salt or stereoisomer thereof, wherein
B is

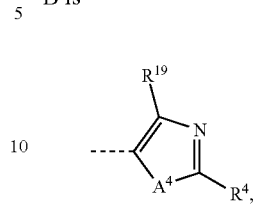

wherein $R^4$, $R^{19}$, and $A^4$ are defined herein elsewhere. In one embodiment, B is phenyloxazolyl. In one embodiment, L is —(CH$_2$)$_2$— or —CH=CH—. In one embodiment, A is quinoxalinyl. Specific examples include, but are not limited to, the following:

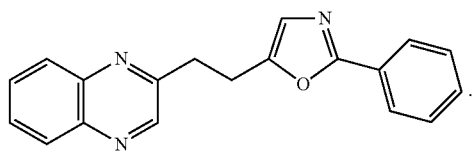 [SMILES: c1ccc(-c2ncc(CCc3cnc4ccccc4n3)o2)cc1]

In one embodiment, $R^4$ is alkyl, aryl, or heteroaryl, each of which is optionally substituted with one or more $R^{11}$. In one embodiment, $R^{19}$ is hydrogen. In one embodiment, $A^4$ is O.

In one embodiment, provided herein is a compound of formula (I), or a pharmaceutically acceptable salt or stereoisomer thereof, wherein
B is

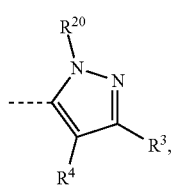

wherein $R^3$, $R^4$, and $R^{20}$ are defined herein elsewhere. In one embodiment, B is phenyl-1H-pyrazolyl, optionally substituted with methyl. In one embodiment, L is —(CH$_2$)$_2$— or —CH=CH—. In one embodiment, A is quinazolin-4(3H)-onyl. Specific examples include, but are not limited to, the following:

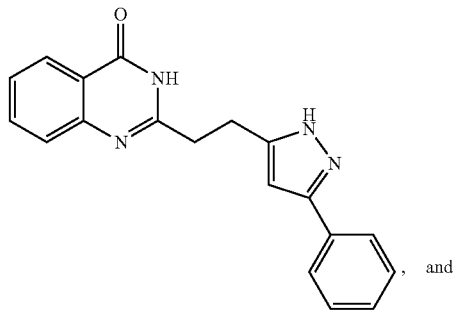

, and

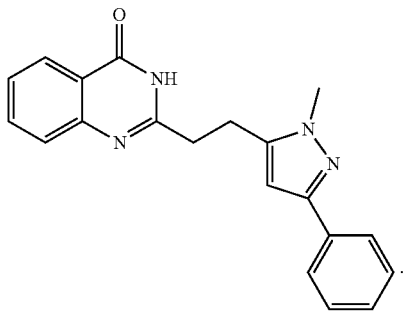

In one embodiment, $R^{20}$ is hydrogen or methyl. In one embodiment, $R^4$ is hydrogen. In one embodiment, $R^3$ is alkyl, aryl, or heteroaryl, each of which is optionally substituted with one or more $R^{11}$.

In one embodiment, provided herein is a compound of formula (I):

A-L-B  (I), or a pharmaceutically acceptable salt or stereoisomer thereof, wherein A is

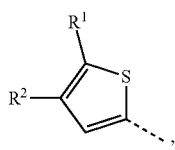

and L, B, $R^1$, and $R^2$ are defined herein elsewhere. In one embodiment, L is —(CH$_2$)$_2$— or —CH═CH—. In one embodiment, B is phenylimidazolyl. Specific examples include, but are not limited to, the following:

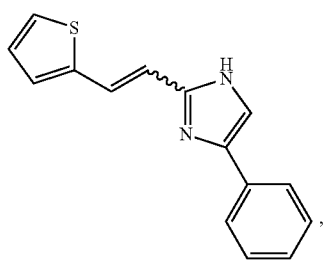

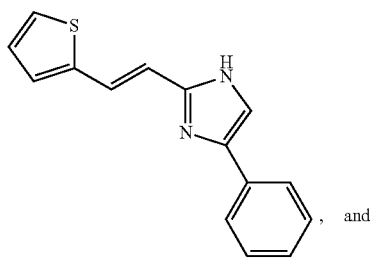, and

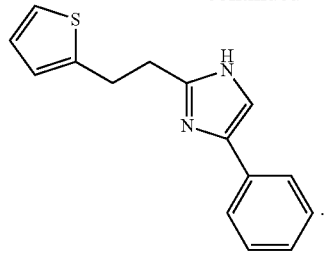

In one embodiment, provided herein is a compound of formula (I) or formula (I-A), or a pharmaceutically acceptable salt or stereoisomer thereof, wherein

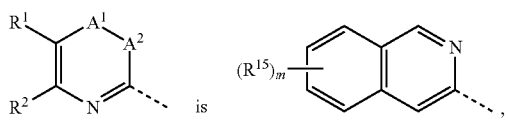

wherein each occurrence of $R^{15}$ is independently: (i) hydrogen, halo, cyano, —OR$^{13}$, —NR$^{13}$R$^{14}$, —N(R$^{13}$)C(O)R$^{14}$, —C(O)NR$^{13}$, R$^{14}$, —C(O)R$^{13}$, —C(O)OR$^{13}$, —OC(O)R$^{13}$, —SR$^{13}$, —S(O)R$^{13}$, —S(O)$_2$R$^{13}$, —S(O)$_2$NR$^{13}$R$^{14}$, (C$_1$-C$_{10}$)alkyl optionally substituted with one or more R$^{12}$, (C$_1$-C$_{10}$)heteroalkyl optionally substituted with one or more R$^{12}$, (C$_3$-C$_{10}$)cycloalkyl optionally substituted with one or more R$^{12}$, (C$_7$-C$_{12}$)aralkyl optionally substituted with one or more R$^{12}$, (C$_3$-C$_{12}$)heteroaralkyl optionally substituted with one or more R$^{12}$, (6 to 10 membered)aryl optionally substituted with one or more R$^{12}$, (5 to 10 membered) heteroaryl optionally substituted with one or more R$^{12}$, or (3 to 12 membered) heterocyclyl optionally substituted with one or more R$^{12}$; or (ii) when two occurrences of R$^{15}$ are attached to adjacent carbon atoms, the two adjacent occurrences of R$^{15}$ together with the carbon atoms to which they are attached may form a ring, optionally substituted with one or more R$^{11}$; wherein R$^{11}$, R$^{12}$, R$^{13}$, and R$^{14}$ are defined herein elsewhere; and m is 0, 1, 2, 3, or 4.

In one embodiment, provided herein is a compound of formula (I) or formula (I-A), or a pharmaceutically acceptable salt or stereoisomer thereof, wherein

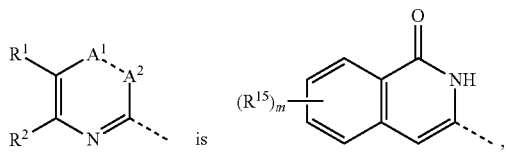

wherein each occurrence of R$^{15}$ is independently:
(i) hydrogen, halo, cyano, —OR$^{13}$, —NR$^{13}$R$^{14}$, —N(R$^{13}$)C(O)R$^{14}$, —C(O)NR$^{13}$R$^{14}$, —C(O)R$^{13}$, —C(O)OR$^{13}$, —OC(O)R$^{13}$, —SR$^{13}$, —S(O)R$^{13}$, —S(O)$_2$R$^{13}$, —S(O)$_2$NR$^{13}$R$^{14}$, (C$_1$-C$_{10}$)alkyl optionally substituted with one or more R$^{12}$, (C$_1$-C$_{10}$)heteroalkyl optionally substituted with one or more R$^{12}$, (C$_3$-C$_{10}$)cycloalkyl optionally substituted with one or more R$^{12}$, (C$_7$-C$_{12}$)aralkyl optionally substituted with one or more R$^{12}$, (C$_3$-C$_{12}$)heteroaralkyl optionally substituted with one or more R$^{12}$, (6 to 10 membered)aryl optionally substituted with one or more R$^{12}$, (5 to 10 membered) heteroaryl optionally substituted with one or more $R^{12}$, or (3 to 12 membered)heterocyclyl optionally substituted with one or more $R^{12}$; or (ii) when two occurrences of $R^{15}$ are attached to adjacent carbon atoms, the two adjacent occurrences of $R^{15}$ together with the carbon atoms to which they are attached may form a ring, optionally substituted with one or more $R^{11}$; wherein $R^{11}$, $R^{12}$, $R^{13}$, and $R^{14}$ are defined herein elsewhere; and m is 0, 1, 2, 3, or 4.

In one embodiment, provided herein is a compound of formula (I) or formula (I-A), or a pharmaceutically acceptable salt or stereoisomer thereof, wherein

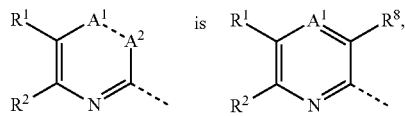

wherein $R^1$, $R^2$, and $R^8$ are defined herein elsewhere, and $A^1$ is N or $CR^8$. In one embodiment, each occurrence of $R^8$ may be the same or different. In one embodiment, $A^1$ is N or CH. In one embodiment, $R^8$ is hydrogen. In one embodiment, $R^1$ and $R^2$ together with the carbon atoms to which they are attached form an optionally substituted phenyl ring. In one embodiment, $R^1$ and $R^2$ together with the carbon atoms to which they are attached form an optionally substituted pyridyl ring.

In one embodiment, provided herein is a compound of formula (I) or formula (I-A), or a pharmaceutically acceptable salt or stereoisomer thereof, wherein

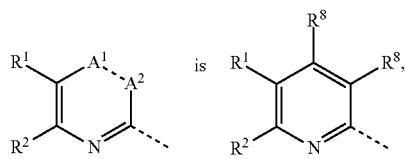

wherein $R^1$, $R^2$, and $R^8$ are defined herein elsewhere. In one embodiment, the two occurrences of $R^8$ may be the same or different. In one embodiment, $R^1$ and $R^2$ are hydrogen. In one embodiment, $R^1$ and $R^2$ together with the carbon atoms to which they are attached form an optionally substituted phenyl ring. In one embodiment, $R^1$ and $R^2$ together with the carbon atoms to which they are attached form an optionally substituted pyridyl ring.

In one embodiment, provided herein is a compound of formula (I) or formula (I-A), or a pharmaceutically acceptable salt or stereoisomer thereof, wherein

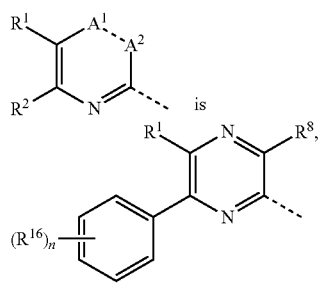

wherein $R^1$ and $R^8$ are defined herein elsewhere; each occurrence of $R^{16}$ is independently $R^{11}$; wherein $R^{11}$ is defined herein elsewhere; and n is 0, 1, 2, 3, 4, or 5.

In one embodiment, provided herein is a compound of formula (I) or formula (I-A), or a pharmaceutically acceptable salt or stereoisomer thereof, wherein

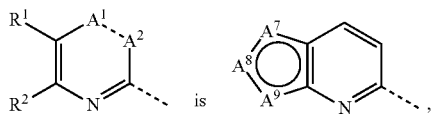

wherein $A^7$, $A^8$ and $A^9$ are each independently O, S, N, $CR^{17}$, or $NR^{18}$, wherein $A^7$, $A^8$ and $A^9$ together with the two carbon atoms to which they are attached form a stable five-membered heteroaryl ring (e.g., a heteroaryl ring provided herein elsewhere); each occurrence of $R^{17}$ is independently $R^{11}$; each occurrence of $R^{18}$ is hydrogen, —C(O)$NR^{13}R^{14}$, —C(O)$R^{13}$, —C(O)$OR^{13}$, —S(O)$_2R^{13}$, $(C_1$-$C_{10})$alkyl optionally substituted with one or more $R^{12}$, $(C_1$-$C_{10})$heteroalkyl optionally substituted with one or more $R^{12}$, $(C_3$-$C_{10})$cycloalkyl optionally substituted with one or more $R^{12}$, $(C_7$-$C_{12})$aralkyl optionally substituted with one or more $R^{12}$, $(C_3$-$C_{12})$heteroaralkyl optionally substituted with one or more $R^{12}$, (6 to 10 membered)aryl optionally substituted with one or more $R^{12}$, (5 to 10 membered)heteroaryl optionally substituted with one or more $R^{12}$, or (3 to 12 membered)heterocyclyl optionally substituted with one or more $R^{12}$; wherein $R^{11}$, $R^{12}$, $R^{13}$, and $R^{14}$ are as defined herein elsewhere.

In one embodiment, provided herein is a compound of formula (I), or a pharmaceutically acceptable salt or stereoisomer thereof, wherein
B is

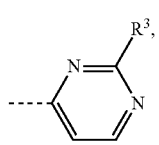

wherein $R^3$ are defined herein elsewhere. In one embodiment, $R^3$ is alkyl, aryl, or heteroaryl, each of which is optionally substituted with one or more $R^{11}$.

In one embodiment, provided herein is a compound of formula (I), or a pharmaceutically acceptable salt or stereoisomer thereof, wherein
B is

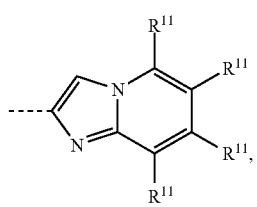

wherein $R^{11}$ is defined herein elsewhere. In one embodiment, each occurrence of $R^{11}$ may be the same or different from each other.

Any of the combinations of A, B, L, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $A^1$, $A^2$, $A^3$, $A^4$, $A^5$, $A^6$, $A^7$, $A^8$, $A^9$, m, n, k, G, J, u, p, and q are encompassed by this disclosure and specifically provided herein.

In one embodiment, provided herein is a compound of formula (I-B):

D-L-E (I-B), or a pharmaceutically acceptable salt or stereoisomer thereof, wherein
L is —(CH$_2$)$_u$—, CH=CH—, or —(CH$_2$)$_p$—S—(CH$_2$)$_q$—;
D is

E is

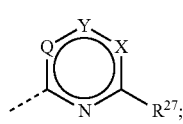

X is N or CR$^{26}$;
each Y is independently N or CR;
each Z is independently N or C;
Q is independently N or CR$^{25}$;
provided that D contains 1, 2, 3, or 4 nitrogen ring atoms;
each occurrence of R is independently hydrogen, halo, cyano, (C$_1$-C$_6$)alkyl, (C$_1$-C$_6$)alkoxyl, (C$_1$-C$_6$)hydroxyalkyl, aryl, or heteroaryl; each of which is optionally substituted;
R$^{25}$ is hydrogen, halo, cyano, (C$_1$-C$_6$)alkyl, (C$_3$-C$_8$)cycloalkyl, (C$_1$-C$_6$)alkoxyl, (C$_1$-C$_6$)hydroxyalkyl, CH$_2$CN, CH$_2$C(O)NH$_2$, (C$_7$-C$_{12}$)aralkyl, or alkyl-heterocycloalkyl; each of which is optionally substituted;
R$^{26}$ and R$^{27}$ are independently hydrogen, halo, cyano, (C$_1$-C$_6$)alkyl, (C$_1$-C$_6$)alkoxyl, aryl, or heteroaryl; each of which is optionally substituted; or R$^{26}$ and R$^{27}$ together with the atoms to which they are attached form an optionally substituted cycloalkyl, aryl, heteroaryl, or heterocyclyl ring;
u is 2 or 3; and
p and q are each independently 0, 1, or 2, provided that when one of p and q is 0, the other is 1 or 2.

In one embodiment, L is —(CH$_2$)$_u$—. In one embodiment, L is —CH=CH—. In one embodiment, L is —(CH$_2$)$_p$—S—(CH$_2$)$_q$—.

In one embodiment, u is 2. In one embodiment, u is 3.

In one embodiment, p is 0. In one embodiment, p is 1. In one embodiment, p is 2. In one embodiment, q is 0. In one embodiment, q is 1. In one embodiment, q is 2. In one embodiment, when p is 0, q is 1 or 2. In one embodiment, when q is 0, p is 1 or 2.

In one embodiment, L is —CH$_2$—CH$_2$—, —CH$_2$—CH$_2$—CH$_2$—, —CH$_2$—S—, —CH=CH—, —S—CH$_2$—CH$_2$—, —CH$_2$—S—CH$_2$—, or —CH$_2$—CH$_2$—S—. In one embodiment, L is —CH$_2$—CH$_2$—. In one embodiment, L is —CH$_2$—CH$_2$—CH$_2$—. In one embodiment, L is —S—CH$_2$—. In one embodiment, L is —CH$_2$—S—. In one embodiment, L is —CH=CH—. In one embodiment, L is S—CH$_2$—CH$_2$—. In one embodiment, L is —CH$_2$—S—CH$_2$—. In one embodiment, L is —CH$_2$—CH$_2$—S—. In one embodiment, L is —CH$_2$—CH$_2$—, —CH$_2$—CH$_2$—CH$_2$—, or —CH=CH—.

In one embodiment, D contains from 1 to 2, from 1 to 3, from 1 to 4, from 2 to 3, from 2 to 4, or from 3 to 4 nitrogen ring atoms. In one embodiment, D contains one nitrogen ring atom. In one embodiment, D contains two nitrogen ring atoms. In one embodiment, D contains three nitrogen ring atoms. In one embodiment, D contains four nitrogen ring atoms.

In one embodiment, D is:

wherein Y is defined herein elsewhere.

In one embodiment, D is:

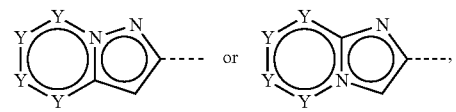

wherein Y is defined herein elsewhere.

In one embodiment, D is:

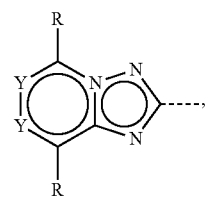

wherein R and Y are defined herein elsewhere.

In one embodiment, R is halo, cyano, (C$_1$-C$_6$)alkyl, (C$_1$-C$_6$)alkoxyl, (C$_1$-C$_6$)hydroxyalkyl, aryl, or heteroaryl; each of which is optionally substituted. In one embodiment, R is halo, cyano, (C$_1$-C$_6$)alkyl, or (C$_1$-C$_6$)alkoxyl, each of which is optionally substituted.

In one embodiment, D is:

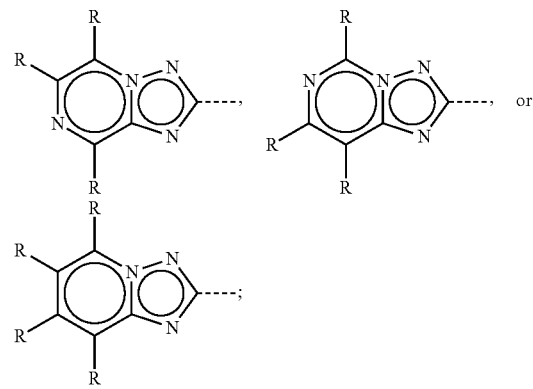

wherein R is defined herein elsewhere.

In one embodiment, D is optionally substituted with up to three substituents. In one embodiment, up to three occurrences of R substituting D are not hydrogen.

In one embodiment, D is:

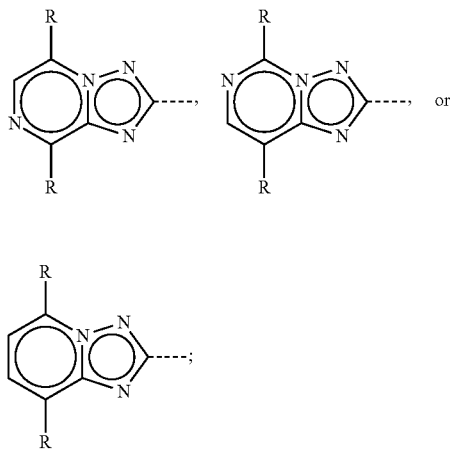

wherein R is defined herein elsewhere.

In one embodiment, each occurrence of R is independently hydrogen or methyl.

In one embodiment, D is:

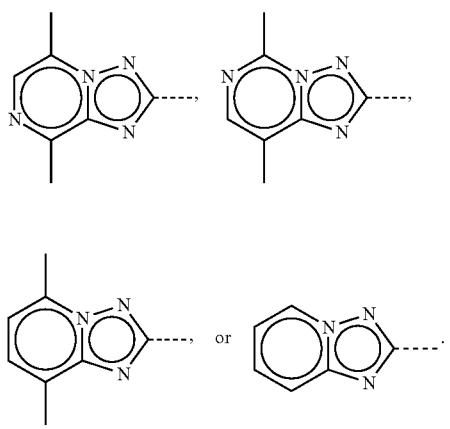

In one embodiment, E contains from 1 to 2, from 1 to 3, from 1 to 4, from 2 to 3, from 2 to 4, or from 3 to 4 nitrogen ring atoms. In one embodiment, E contains one nitrogen ring atom. In one embodiment, E contains two nitrogen ring atoms. In one embodiment, E contains three nitrogen ring atoms. In one embodiment, E contains four nitrogen ring atoms.

In one embodiment, E is optionally substituted with up to one, up to two, up to three, up to four, or up to five substituents.

In one embodiment, E is:

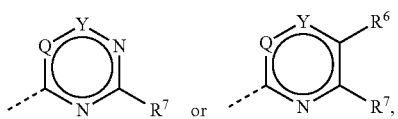

wherein Q, Y, $R^{26}$, and $R^{27}$ are defined herein elsewhere.

In one embodiment, E is:

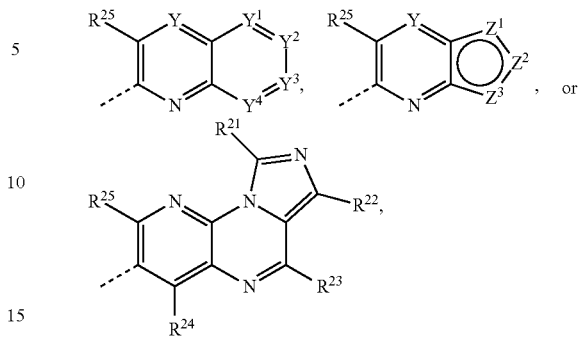

wherein Y and $R^{25}$ are defined herein elsewhere;
$Y^1$ is N or $CR^{21}$; $Y^2$ is N or $CR^{22}$; $Y^3$ is N or $CR^{23}$; and $Y^4$ is N or $CR^{24}$; provided that at least one of $Y^1$, $Y^2$, $Y^3$, and $Y^4$ is not N;
$Z^1$ is N, O, S, $CR^{21}$, or $NR^{21}$; $Z^2$ is N, O, S, $CR^{22}$, or $NR^{22}$; and $Z^3$ is N, O, S, $CR^{23}$, or $NR^{23}$; provided that $Z^1$, $Z^2$, and $Z^3$ together with the carbon atoms to which they are attached form a stable 5-membered heteroaryl;
each occurrence of $R^{21}$, $R^{22}$, $R^{23}$, and $R^{24}$ is independently hydrogen, halo, cyano, $(C_1-C_6)$alkyl, $(C_2-C_6)$alkenyl, $(C_2-C_6)$alkynyl, $(C_1-C_6)$heteroalkyl, $(C_1-C_6)$alkoxyl, $(C_1-C_6)$aminoalkyl, $(C_1-C_6)$hydroxyalkyl, $CH_2CN$, $CH_2C(O)NH_2$, $(C_3-C_8)$cycloalkyl, aryl, heteroaryl, heterocyclyl, aralkyl, heteroaralkyl, or alkyl-heterocycloalkyl; each of which is optionally substituted; and two adjacent $R^{21}$, $R^{22}$, $R^{23}$, and $R^{24}$ may together with the atoms to which they are attached form an optionally substituted aromatic or non-aromatic ring.

In one embodiment, one of $Y^1$, $Y^2$, $Y^3$, and $Y^4$ is N, and the other three are carbon (e.g., $CR^{21}$, $CR^{22}$, $CR^{23}$, or $CR^{24}$). In one embodiment, two of $Y^1$, $Y^2$, $Y^3$, and $Y^4$ are N, and the other two are carbon (e.g., $CR^{21}$, $CR^{22}$, $CR^{23}$, or $CR^{24}$). In one embodiment, three of $Y^1$, $Y^2$, $Y^3$, and $Y^4$ are N, and the other one is carbon (e.g., $CR^{21}$, $CR^{22}$, $CR^{23}$, or $CR^{24}$).) In one embodiment, $Y^1$, $Y^2$, $Y^3$, and $Y^4$ are all carbon (e.g., $CR^{21}$, $CR^{22}$, $CR^{23}$, or $CR^{24}$).

In one embodiment, E is:

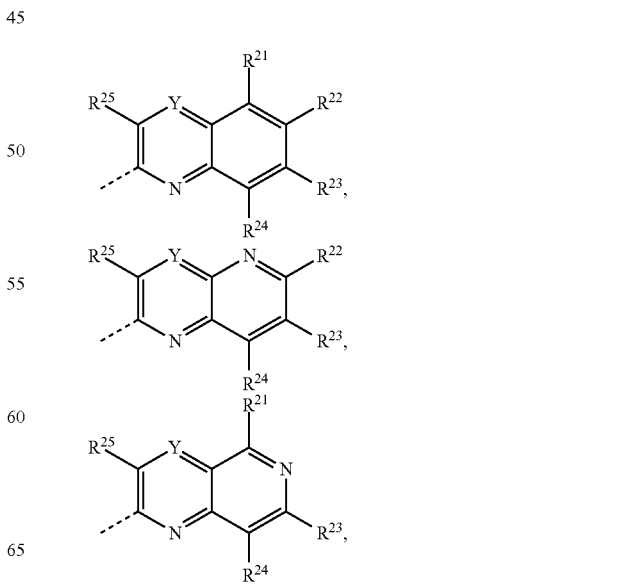

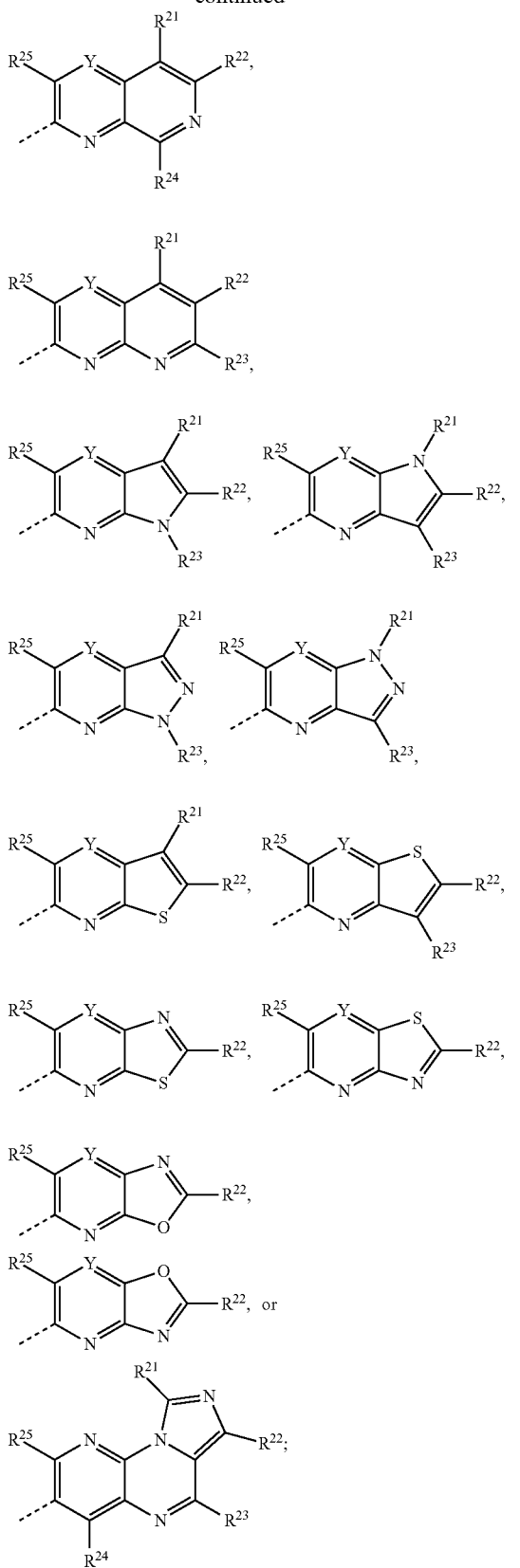
In one embodiment, E is:
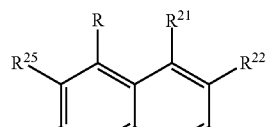
wherein Y, $R^{21}$, $R^{22}$, $R^{23}$, $R^{24}$, and $R^{25}$ are defined herein elsewhere.

-continued

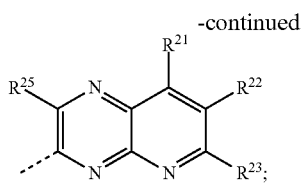

wherein R, $R^{21}$, $R^{22}$, $R_{23}$, $R^{24}$, and $R^{25}$ are defined herein elsewhere. In some embodiments, R is hydrogen. In some embodiments, $R^{21}$, $R^{22}$, $R^{23}$, $R^{24}$, and $R^{25}$ are each independently hydrogen, halo (e.g., fluoro or chloro), cyano, ($C_1$-$C_4$) alkyl (e.g., methyl or $CF_3$), or ($C_1$-$C_4$)alkoxyl (e.g., methoxyl or $OCF_3$). In some embodiments, $R^{21}$ and $R^{22}$, $R^{22}$ and $R^{23}$, or $R^{23}$ and $R^{24}$ together with the carbon atoms to which they are attached form an optionally substituted ring, such as, e.g., a benzene, pyridine, pyrimidine, pyrazine, pyridazine, thiophene, furan, pyrrole, imidazole, pyrazole, oxazole, isoxazole, thiazole, or isothiazole ring; or a 5- to 7-membered non-aromatic carbocyclic or heterocyclic ring, wherein the non-aromatic heterocyclic ring contains one to two heteroatom(s) independently selected from N, O, and S.

In one embodiment, E is not:

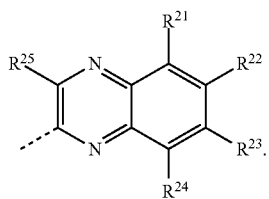

In one embodiment, E is:

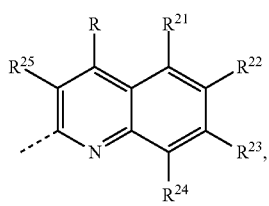

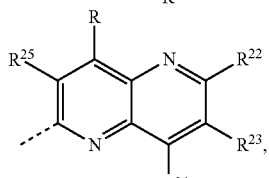

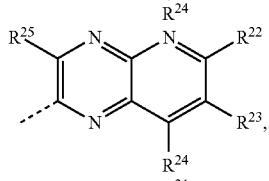

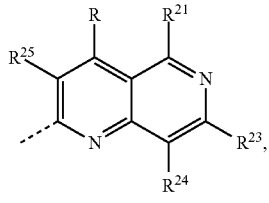

-continued

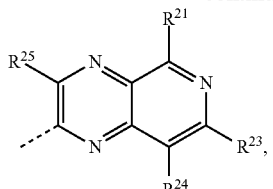

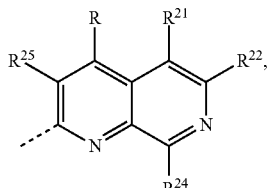

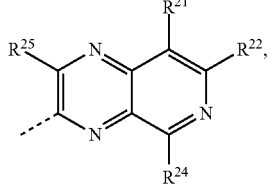

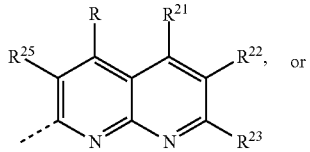, or

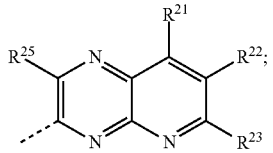

wherein R, $R^{21}$, $R^{22}$, $R_{23}$, $R^{24}$, and $R^{25}$ are defined herein elsewhere. In some embodiments, R is hydrogen. In some embodiments, $R^{21}$, $R^{22}$, $R^{23}$, $R^{24}$, and $R^{25}$ are each independently hydrogen, halo (e.g., fluoro or chloro), cyano, ($C_1$-$C_4$) alkyl (e.g., methyl or $CF_3$), or ($C_1$-$C_4$)alkoxyl (e.g., methoxyl or $OCF_3$). In some embodiments, $R^{21}$ and $R^{22}$, $R^{22}$ and $R^{23}$, or $R^{23}$ and $R^{24}$ together with the carbon atoms to which they are attached form an optionally substituted ring, such as, e.g., a benzene, pyridine, pyrimidine, pyrazine, pyridazine, thiophene, furan, pyrrole, imidazole, pyrazole, oxazole, isoxazole, thiazole, or isothiazole ring; or a 5- to 7-membered non-aromatic carbocyclic or heterocyclic ring, wherein the non-aromatic heterocyclic ring contains one to two heteroatom(s) independently selected from N, O, and S.

In one embodiment, E is:

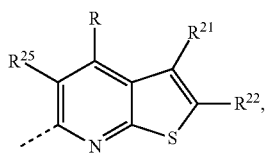

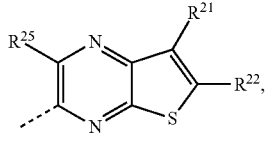

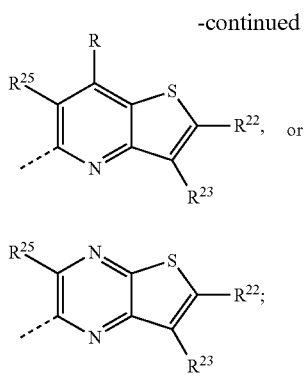

wherein R, $R^{21}$, $R^{22}$, $R^{23}$, and $R^{25}$ are defined herein elsewhere. In some embodiments, R is hydrogen. In some embodiments, $R^{21}$, $R^{22}$, $R^{23}$, and $R^{25}$ are each independently hydrogen, halo (e.g., fluoro or chloro), cyano, $(C_1-C_4)$alkyl (e.g., methyl or $CF_3$), or $(C_1-C_4)$alkoxyl (e.g., methoxyl or $OCF_3$). In some embodiments, $R^{21}$ and $R^{22}$, or $R^{22}$ and $R^{23}$ together with the carbon atoms to which they are attached form an optionally substituted ring, such as, e.g., a benzene, pyridine, pyrimidine, pyrazine, pyridazine, thiophene, furan, pyrrole, imidazole, pyrazole, oxazole, isoxazole, thiazole, or isothiazole ring; or a 5- to 7-membered non-aromatic carbocyclic or heterocyclic ring, wherein the non-aromatic heterocyclic ring contains one to two heteroatom(s) independently selected from N, O, and S.

In one embodiment, X is $CR^{26}$. In one embodiment, X is N.

In one embodiment, Y is N. In one embodiment, Y is CR. In one embodiment, Y is CH. In one embodiment, Y is CMe. One occurrence of Y may be the same or different from another occurrence of Y.

In one embodiment, Z is N. In one embodiment, Z is C. One occurrence of Z may be the same or different from another occurrence of Z. In one embodiment, one of the two occurrences of Z is C and the other is N. In one embodiment, one of the two occurrences of Z is N. In one embodiment, one of the two occurrences of Z is C. In one embodiment, at least one of the two occurrences of Z is N. In one embodiment, the two occurrences of Z are not both C.

In one embodiment, the two occurrences of Z are not both N.

In one embodiment, Q is N. In one embodiment, Q is $CR^{25}$.

In one embodiment, R is hydrogen. In one embodiment, R is halo. In one embodiment, R is cyano. In one embodiment, R is $(C_1-C_6)$alkyl. In one embodiment, R is methyl. In one embodiment, R is $(C_1-C_6)$alkoxyl. In one embodiment, R is $(C_1-C_6)$ hydroxyalkyl. In one embodiment, R is aryl. In one embodiment, R is heteroaryl. In one embodiment, R is not hydrogen. In one embodiment, R is halo, cyano, $(C_1-C_6)$alkyl, $(C_1-C_6)$alkoxyl, $(C_1-C_6)$hydroxyalkyl, aryl, or heteroaryl; each of which is optionally substituted. In one embodiment, R is a monovalent radical (e.g., two adjacent occurrences of R do not together with the atoms to which they are attached form a ring). Each occurrence of R may be optionally substituted. One occurrence of R may be the same or different from another occurrence of R.

In one embodiment, $R^{25}$ is hydrogen. In one embodiment, $R^{25}$ is halo. In one embodiment, $R^{25}$ is cyano. In one embodiment, $R^{25}$ is $(C_1-C_6)$alkyl. In one embodiment, $R^{25}$ is $(C_3-C_8)$ cycloalkyl. In one embodiment, $R^{25}$ is $(C_1-C_6)$alkoxyl. In one embodiment, $R^{25}$ is $(C_1-C_6)$hydroxyalkyl. In one embodiment, $R^{25}$ is $CH_2CN$. In one embodiment, $R^{25}$ is $CH_2C(O)NH_2$.

In one embodiment, $R^{25}$ is $(C_7-C_{12})$aralkyl. In one embodiment, $R^{25}$ is alkyl-heterocycloalkyl. Each embodiment of $R^{25}$ may be optionally substituted.

In one embodiment, $R^{26}$ is hydrogen. In one embodiment, $R^{26}$ is halo. In one embodiment, $R^{26}$ is cyano. In one embodiment, $R^{26}$ is $(C_1-C_6)$alkyl. In one embodiment, $R^{26}$ is $(C_1-C_6)$ alkoxyl. In one embodiment, $R^{26}$ is aryl. In one embodiment, $R^{26}$ is heteroaryl. Each embodiment of $R^{26}$ may be optionally substituted.

In one embodiment, $R^{27}$ is hydrogen. In one embodiment, $R^{27}$ is halo. In one embodiment, $R^{27}$ is cyano. In one embodiment, $R^{27}$ is $(C_1-C_6)$alkyl. In one embodiment, $R^{27}$ is $(C_1-C_6)$ alkoxyl. In one embodiment, $R^{27}$ is aryl. In one embodiment, $R^{27}$ is heteroaryl. Each embodiment of $R^{27}$ may be optionally substituted.

In one embodiment, $R^{26}$ and $R^{27}$ together with the atoms to which they are attached form an optionally substituted aromatic or non-aromatic monocyclic or multicyclic ring, including but not limited to, phenyl, pyridyl, pyrimidyl, pyrazinyl, pyridazinyl, imidazolyl, thienyl, furanyl, pyrrolyl, quinolinyl, or benzothiophenyl ring. The ring may be optionally substituted as defined herein elsewhere.

In one embodiment, $R^{21}$ is hydrogen. In one embodiment, $R^{21}$ is halo. In one embodiment, $R^{21}$ is cyano. In one embodiment, $R^{21}$ is $(C_1-C_6)$alkyl. In one embodiment, $R^{21}$ is $(C_2-C_6)$ alkenyl. In one embodiment, $R^{21}$ is $(C_2-C_6)$alkynyl. In one embodiment, $R^{21}$ is $(C_1-C_6)$heteroalkyl. In one embodiment, $R^{21}$ is $(C_1-C_6)$alkoxyl. In one embodiment, $R^{21}$ is $(C_1-C_6)$ aminoalkyl. In one embodiment, $R^{21}$ is $(C_1-C_6)$hydroxyalkyl. In one embodiment, $R^{21}$ is $CH_2CN$. In one embodiment, $R^{21}$ is $CH_2C(O)NH_2$. In one embodiment, $R^{21}$ is $(C_3-C_8)$cycloalkyl. In one embodiment, $R^{21}$ is aryl. In one embodiment, $R^{21}$ is heteroaryl. In one embodiment, $R^{21}$ is heterocyclyl. In one embodiment, $R^{21}$ is $(C_7-C_{12})$aralkyl. In one embodiment, $R^{21}$ is heteroaralkyl. In one embodiment, $R^{21}$ is alkyl-heterocycloalkyl. Each embodiment of $R^{21}$ may be optionally substituted.

In one embodiment, $R^{22}$ is hydrogen. In one embodiment, $R^{22}$ is halo. In one embodiment, $R^{22}$ is cyano. In one embodiment, $R^{22}$ is $(C_1-C_6)$alkyl. In one embodiment, $R^{22}$ is $(C_2-C_6)$ alkenyl. In one embodiment, $R^{22}$ is $(C_2-C_6)$alkynyl. In one embodiment, $R^{22}$ is $(C_1-C_6)$heteroalkyl. In one embodiment, $R^{22}$ is $(C_1-C_6)$alkoxyl. In one embodiment, $R^{22}$ is $(C_1-C_6)$ aminoalkyl. In one embodiment, $R^{22}$ is $(C_1-C_6)$hydroxyalkyl. In one embodiment, $R^{22}$ is $CH_2CN$. In one embodiment, $R^{22}$ is $CH_2C(O)NH_2$. In one embodiment, $R^{22}$ is $(C_3-C_8)$cycloalkyl. In one embodiment, $R^{22}$ is aryl. In one embodiment, $R^{22}$ is heteroaryl. In one embodiment, $R^{22}$ is heterocyclyl. In one embodiment, $R^{22}$ is $(C_7-C_{12})$aralkyl. In one embodiment, $R^{22}$ is heteroaralkyl. In one embodiment, $R^{22}$ is alkyl-heterocycloalkyl. Each embodiment of $R^{22}$ may be optionally substituted.

In one embodiment, $R^{23}$ is hydrogen. In one embodiment, $R^{23}$ is halo. In one embodiment, $R^{23}$ is cyano. In one embodiment, $R^{23}$ is $(C_1-C_6)$alkyl. In one embodiment, $R^{23}$ is $(C_2-C_6)$ alkenyl. In one embodiment, $R^{23}$ is $(C_2-C_6)$alkynyl. In one embodiment, $R^{23}$ is $(C_1-C_6)$heteroalkyl. In one embodiment, $R^{23}$ is $(C_1-C_6)$alkoxyl. In one embodiment, $R^{23}$ is $(C_1-C_6)$ aminoalkyl. In one embodiment, $R^{23}$ is $(C_1-C_6)$hydroxyalkyl. In one embodiment, $R^{23}$ is $CH_2CN$. In one embodiment, $R^{23}$ is $CH_2C(O)NH_2$. In one embodiment, $R^{23}$ is $(C_3-C_8)$cycloalkyl. In one embodiment, $R^{23}$ is aryl. In one embodiment, $R^{23}$ is heteroaryl. In one embodiment, $R^{23}$ is heterocyclyl. In one embodiment, $R^{23}$ is $(C_7-C_{12})$aralkyl. In one embodiment, $R^{23}$ is heteroaralkyl. In one embodiment, $R^{23}$ is alkyl-heterocycloalkyl. Each embodiment of $R^{23}$ may be optionally substituted.

In one embodiment, $R^{24}$ is hydrogen. In one embodiment, $R^{24}$ is halo. In one embodiment, $R^{24}$ is cyano. In one embodiment, $R^{24}$ is $(C_1-C_6)$alkyl. In one embodiment, $R^{24}$ is $(C_2-C_6)$alkenyl. In one embodiment, $R^{24}$ is $(C_2-C_6)$alkynyl. In one embodiment, $R^{24}$ is $(C_1-C_6)$heteroalkyl. In one embodiment, $R^{24}$ is $(C_1-C_6)$alkoxyl. In one embodiment, $R^{24}$ is $(C_1-C_6)$aminoalkyl. In one embodiment, $R^{24}$ is $(C_1-C_6)$hydroxyalkyl. In one embodiment, $R^{24}$ is $CH_2CN$. In one embodiment, $R^{24}$ is $CH_2C(O)NH_2$. In one embodiment, $R^{24}$ is $(C_3-C_8)$cycloalkyl. In one embodiment, $R^{24}$ is aryl. In one embodiment, $R^{24}$ is heteroaryl. In one embodiment, $R^{24}$ is heterocyclyl. In one embodiment, $R^{24}$ is $(C_7-C_{12})$aralkyl. In one embodiment, $R^{24}$ is heteroaralkyl. In one embodiment, $R^{24}$ is alkyl-heterocycloalkyl. Each embodiment of $R^{24}$ may be optionally substituted.

In one embodiment, $R^{21}$ and $R^{22}$, $R^{22}$ and $R^{23}$ or $R^{23}$ and $R^{24}$ together with the atoms to which they are attached form an optionally substituted aromatic or non-aromatic ring, including but not limited to, phenyl, pyridyl, pyrimidyl, pyrazinyl, pyridazinyl, imidazolyl, thienyl, thiazolyl, or 5- or 6-membered heterocyclyl ring. Other embodiments of the optionally substituted aromatic or non-aromatic ring are provided herein elsewhere.

In one embodiment, provided herein is a compound of formula (II-A):

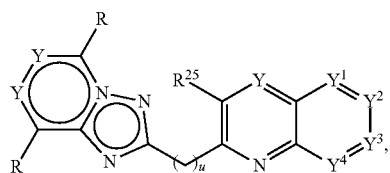

(II-A)

or a pharmaceutically acceptable salt or stereoisomer thereof, wherein Y, R, u, $R^{25}$, $Y^1$, $Y^2$, $Y^3$, and $Y^4$ are defined herein elsewhere.

In one embodiment, provided herein is a compound of formula (II-B):

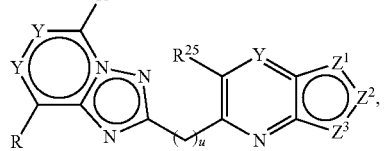

(II-B)

or a pharmaceutically acceptable salt or stereoisomer thereof, wherein Y, R, u, $R^{25}$, $Z^1$, $Z^2$, and $Z^3$ are defined herein elsewhere. In one embodiment, $Z^2$ is $CR^{22}$, and (i) $Z^1$ is S and $Z^3$ is $CR^{23}$, or (ii) $Z^1$ is $CR^{21}$ and $Z^3$ is S; wherein $R^{21}$, $R^{22}$, and $R^{23}$ are defined herein elsewhere. In one embodiment, R is H or Me. In one embodiment, Y is N or CH. In one embodiment, $R^{21}$, $R^{22}$, and $R^{23}$ are H; or $R^{22}$ and $R^{23}$, or $R^{21}$ and $R^{22}$, together with the carbon atoms to which they are attached form an optionally substituted phenyl ring. Specific examples include, but are not limited to the following:

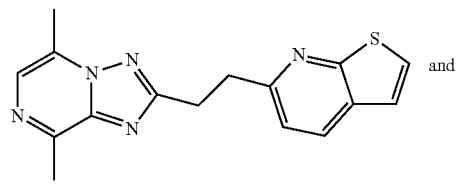

and

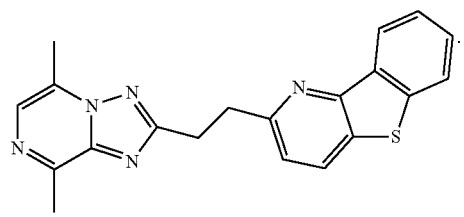

In one embodiment, provided herein is a compound of formula (III-A):

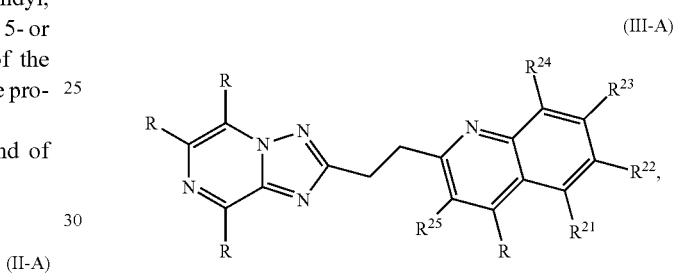

(III-A)

or a pharmaceutically acceptable salt or stereoisomer thereof, wherein R, $R^{21}$, $R^{22}$, $R^{23}$, $R^{24}$, and $R^{25}$ are defined herein elsewhere. In one embodiment, R is H or Me. In one embodiment, $R^{21}$, $R^{22}$, $R^{23}$, $R^{24}$, and $R^{25}$ are each independently H, halo (e.g., F, Cl, or Br), methyl, or $CF_3$. In one embodiment, $R^{23}$ and $R^{24}$ together with the carbon atoms to which they are attached form an optionally substituted phenyl, pyridyl, pyrimidyl, pyrazinyl, tetrahydropyridinyl, or 3,4-dihydro-2H-1,4-oxazinyl ring. Specific examples include, but are not limited to:

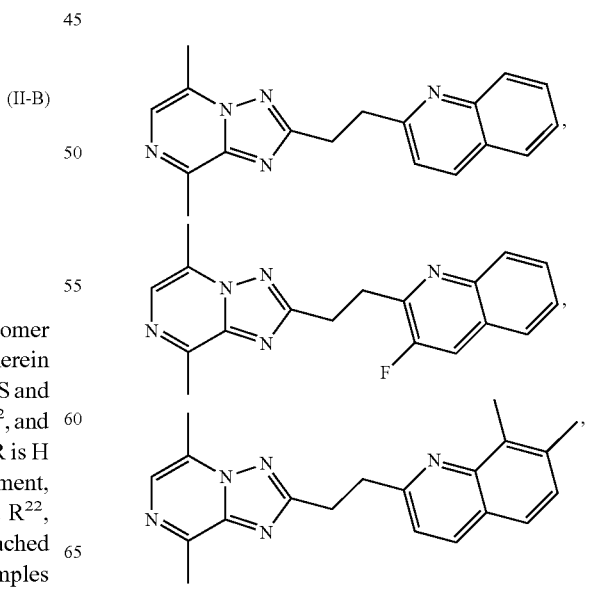

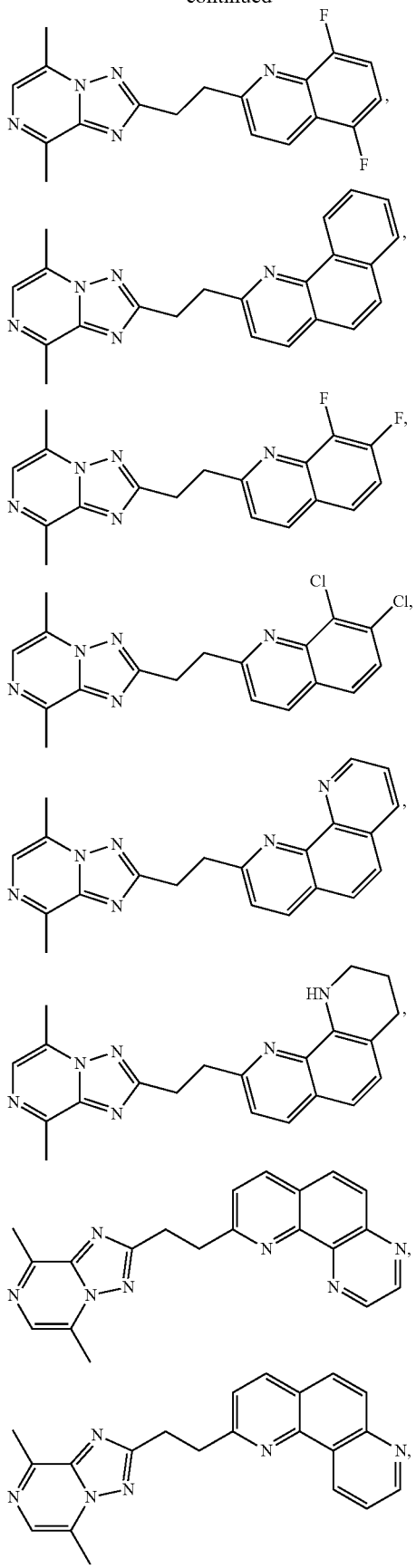

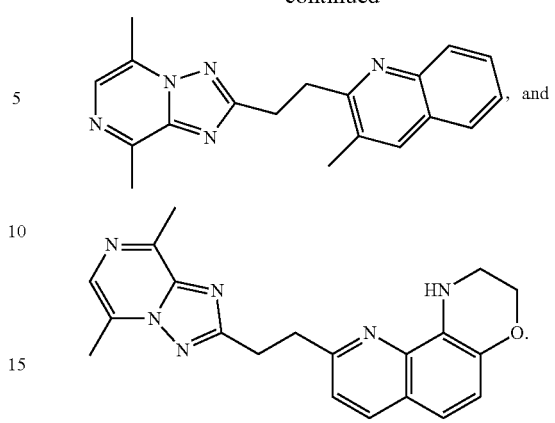

In one embodiment, provided herein is a compound of formula (III-B):

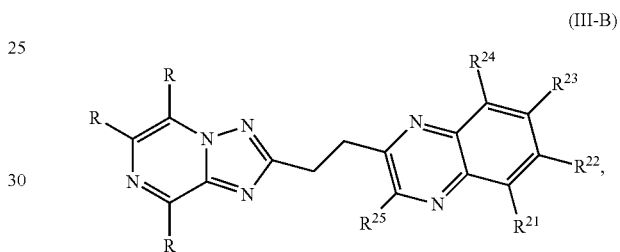

(III-B)

or a pharmaceutically acceptable salt or stereoisomer thereof, wherein R, $R^{21}$, $R^{22}$, $R^{23}$, $R^{24}$, and $R^{25}$ are defined herein elsewhere. In one embodiment, R is H or Me. In one embodiment, $R^{21}$, $R^{22}$, $R^{23}$, $R^{24}$, and $R^{25}$ are each independently H, halo (e.g., F, Cl, or Br), methyl, or $CF_3$. Specific examples include, but are not limited to:

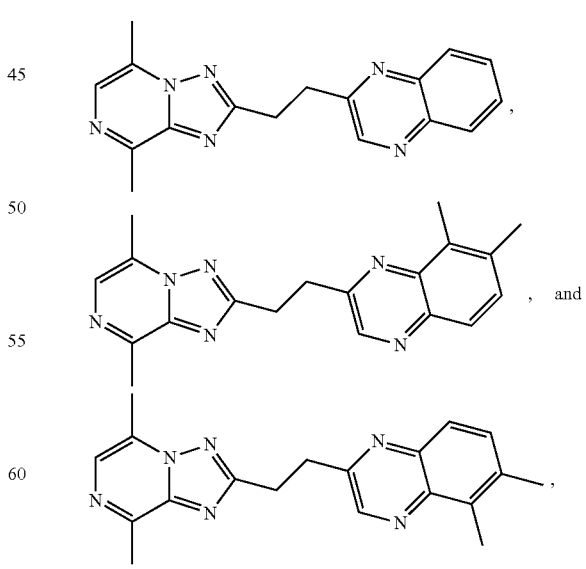

In one embodiment, provided herein is a compound of formula (III-C):

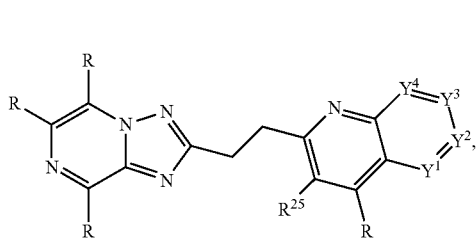
(III-C)

or a pharmaceutically acceptable salt or stereoisomer thereof, wherein R, $Y^1$, $Y^2$, $Y^3$, $Y^4$, and $R^{25}$ are defined herein elsewhere. In one embodiment, at least one of $Y^1$, $Y^2$, $Y^3$, and $Y^4$ is N. In one embodiment, one of $Y^1$, $Y^2$, $Y^3$, and $Y^4$ is N and the other three of $Y^1$, $Y^2$, $Y^3$, and $Y^4$ are substituted C as defined herein elsewhere. In one embodiment, R is H or Me. In one embodiment, $R^{21}$, $R^{22}$, $R^{23}$, $R^{24}$, and $R^{25}$ are each independently H, halo (e.g., F, Cl, or Br), methyl, or $CF_3$. Specific examples include, but are not limited to:

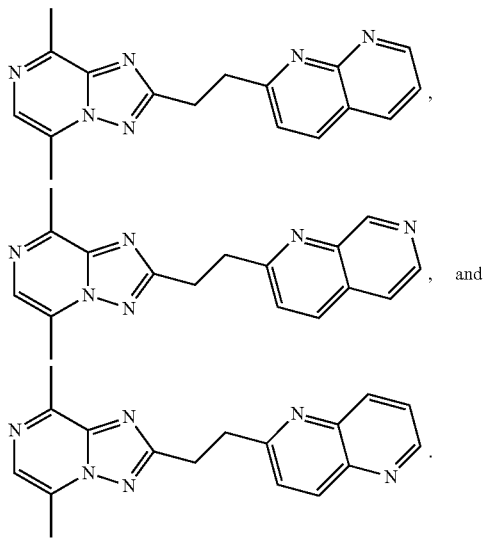

In one embodiment, provided herein is a compound of formula (III-D):

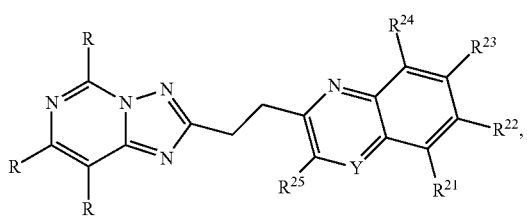
(III-D)

or a pharmaceutically acceptable salt or stereoisomer thereof, wherein R, Y, $R^{21}$, $R^{22}$, $R^{23}$, $R^{24}$, and $R^{25}$ are defined herein elsewhere. In one embodiment, R is H or Me. In one embodiment, Y is CH or N. In one embodiment, $R^{21}$, $R^{22}$, $R^{23}$, $R^{24}$, and $R^{25}$ are each independently H, halo (e.g., F, Cl, or Br), methyl, or $CF_3$. Specific examples include, but are not limited to:

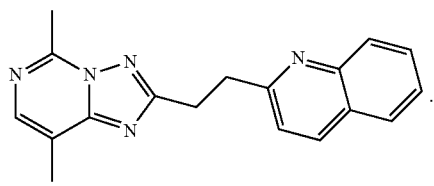 [SMILES: Cc1cnc(C)n2nc(CCc3ccc4ccccc4n3)nc12]

In one embodiment, provided herein is a compound of formula (III-E):

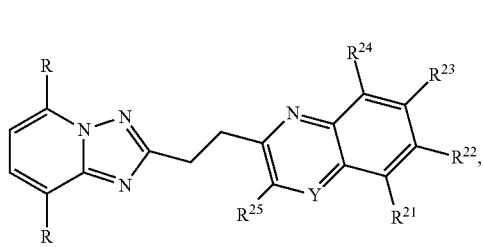
(III-E)

or a pharmaceutically acceptable salt or stereoisomer thereof, wherein R, Y, $R^{21}$, $R^{22}$, $R^{23}$, $R^{24}$, and $R^{25}$ are defined herein elsewhere. In one embodiment, R is H or Me. In one embodiment, Y is N or CH. In one embodiment, $R^{21}$, $R^{22}$, $R^{23}$, $R^{24}$, and $R^{25}$ are each independently H, halo (e.g., F, Cl, or Br), methyl, or $CF_3$. In one embodiment, $R^{23}$ and $R^{24}$ together with the carbon atoms to which they are attached form an optionally substituted phenyl, pyridyl, pyrazinyl, or pyrimidyl ring. Specific examples include, but are not limited to:

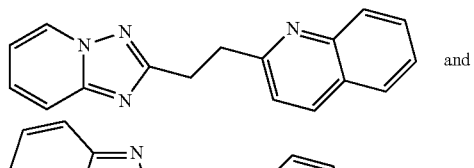
and
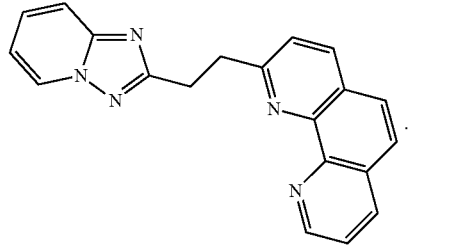

In one embodiment, provided herein is a compound of formula (III-F):

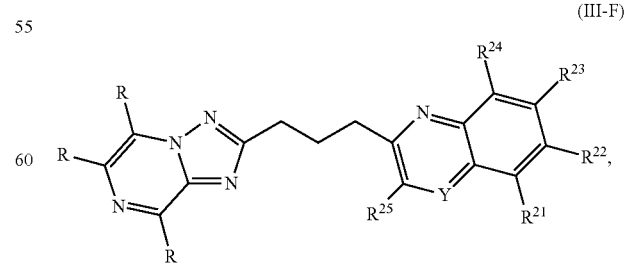
(III-F)

or a pharmaceutically acceptable salt or stereoisomer thereof, wherein R, Y, $R^{21}$, $R^{22}$, $R^{23}$, $R^{24}$, and $R^{25}$ are defined herein elsewhere. In one embodiment, R is H or Me. In one embodiment, Y is N or CH. In one embodiment, $R^{21}$, $R^{22}$, $R^{23}$, $R^{24}$, and $R^{25}$ are each independently H, halo (e.g., F, Cl, or Br), methyl, or $CF_3$. Specific examples include, but are not limited to:
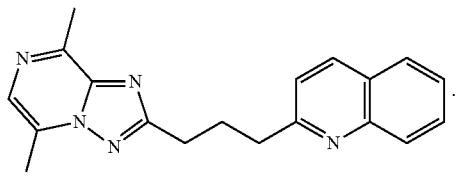 [SMILES: Cc1ncc(C)n2nc(CCCc3ccc4ccccc4n3)nc12]
In one embodiment, the compound of formula (I-B) is not:
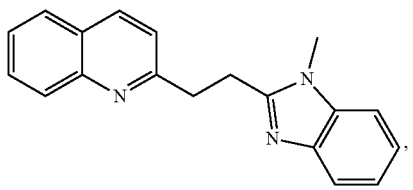
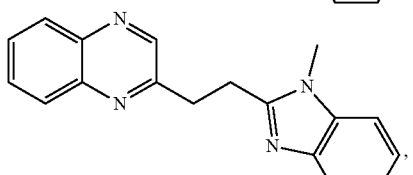
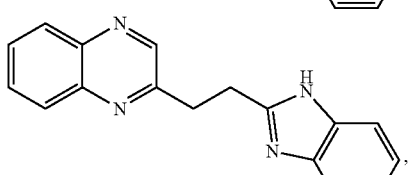
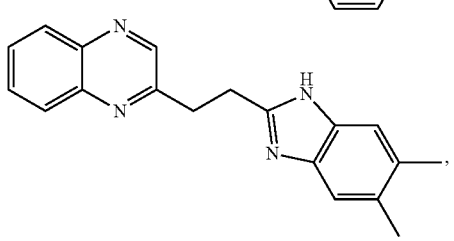
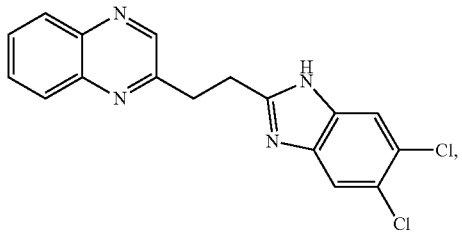
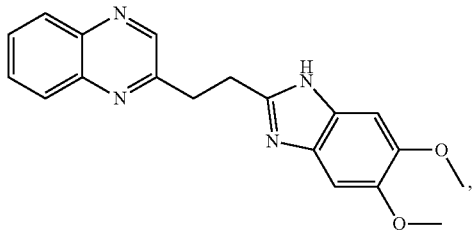
-continued
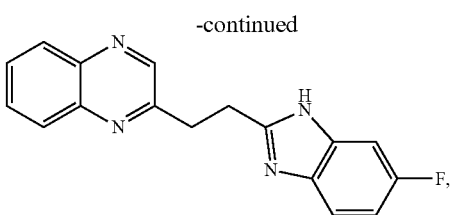
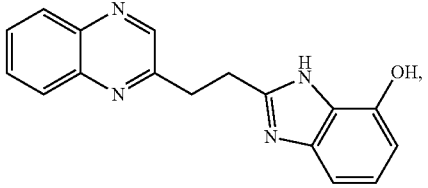
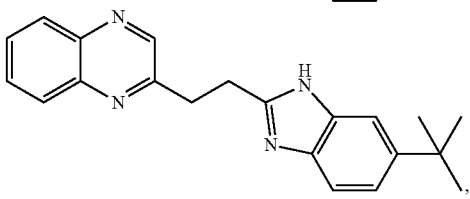
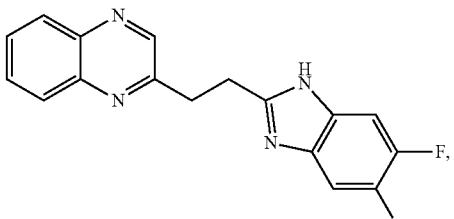
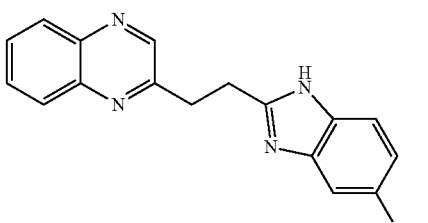
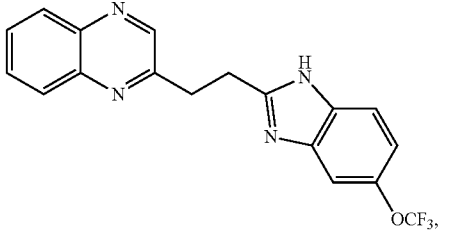
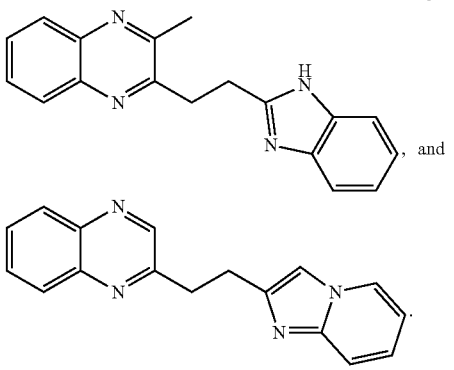

Any of the combinations of D, E, L, X, Y, Z, $Y^1$, $Y^2$, $Y^3$, $Y^4$, $Z^1$, $Z^2$, $Z^3$, Q, R, $R^{21}$, $R^{22}$, $R^{23}$, $R^{24}$, $R^{25}$, $R^{26}$, $R^{27}$, u, p and q are encompassed by this disclosure and specifically provided herein.

It should be noted that if there is a discrepancy between a depicted structure and a chemical name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. Where the compound provided herein contains an alkenyl or alkenylene group, the compound may exist as one geometric (i.e., cis/trans) isomer or a mixture of geometric (i.e., cis/trans) isomers.

Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contain, for example, an aromatic moiety. It follows that a single compound may exhibit more than one type of isomerism. Unless otherwise specified, a structure is intended to encompass any corresponding tautomeric forms.

Unless otherwise specified, the term "compound" referred to herein, such as, e.g., a compound of formula (I), (I-A), (I-B), (II-A), (II-B), (III-A), (III-B), (III-C), (III-D), (III-E), or (III-F) is intended to encompass one or more of the following: a free base of the compound or a salt thereof, a stereoisomer or a mixture of two or more stereoisomers, a solid form (e.g., a crystal form or an amorphous form) or a mixture of two or more solid forms thereof, or a solvate (e.g., a hydrate) thereof. In certain embodiments, the term "compound" referred to herein is intended to encompass a pharmaceutical acceptable form of the compound, including but not limited to, a free base, a pharmaceutically acceptable salt, a stereoisomer or a mixture of two or more stereoisomers, a solid form (e.g., a crystal form or an amorphous form) or a mixture of two or more solid forms, a solvate (e.g., a hydrate), or a cocrystal thereof. In one embodiment, the term "compound" referred to herein, such as, e.g., a compound of formula (I), (I-A), (I-B), (II-A), (II-B), (III-A), (III-B), (III-C), (III-D), (III-E), or (III-F) is intended to encompass a solvate (e.g., a hydrate) thereof.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. In some instances, for compounds that undergo epimerization in vivo, one of skill in the art will recognize that administration of a compound in its (R) form is equivalent to administration of the compound in its (S) form, and vice versa. Conventional techniques for the preparation/isolation of individual enantiomers include synthesis from a suitable optically pure precursor, asymmetric synthesis from achiral starting materials, or resolution of an enantiomeric mixture, for example, by chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

In one embodiment, the compounds provided herein are modulators of a PDE enzyme. In one embodiment, the compounds provided herein are inhibitors of a PDE enzyme. In one embodiment, the compounds provided herein are inhibitors of PDE-10. In one embodiment, the compounds provided herein are inhibitors of PDE-10A. In one embodiment, the compounds provided herein are selective inhibitors of PDE-10. In one embodiment, the compounds provided herein are selective inhibitors of PDE-10A. In one embodiment, the compounds provided herein are active in one or more animal models for a disorder provided herein elsewhere. In one embodiment, the compounds provided herein are active in one or more animal models for a CNS disorder provided herein elsewhere. In one embodiment, the compounds provided herein are active in one or more animal models for psychosis, schizophrenia, or antipsychotic activity, including without limitation, the conditioned avoidance response (CAR) assay, and any other animal models for psychosis, schizophrenia or antipsychotic activity that are known in the art. In one embodiment, the compounds provided herein are active in one or more animal models for psychosis, schizophrenia, or antipsychotic activity, including but not limited to, conditioned avoidance response (CAR), pre-pulse inhibition (PPI), PCP-induced hyperlocomotion, and other animal models provided herein elsewhere. In one embodiment, compounds that are active in in vitro assays (e.g., PDE-10A inhibition) or in vivo models for psychosis, schizophrenia or antipsychotic activity (e.g., CAR) are further optimized to improve the potency in in vitro and in vivo assays and drug-like properties such as, e.g., solubility and lipophilicity. In one embodiment, the compounds provided herein are useful for treating, preventing, or ameliorating one or more symptoms of schizophrenia, including, positive, negative, and cognitive symptoms. In one embodiment, the compounds provided herein induce fewer side effects, such as weight gain, in a subject treated with the compound. In one embodiment, the compounds provided herein induce fewer side effects, such as extrapyramidal side effects, in a subject treated with the compound. In one embodiment, the compounds provided herein are active in one or more animal models for obesity, undesirable weight retention or weight gain, metabolic syndrome, diabetes, non-insulin dependent diabetes, impaired glucose tolerance, or hyperglycemia, including without limitation, in vivo glucose tolerance test (GTT), diet-induced obesity model, obesity food intake model, and any other animal models known in the art or provided herein elsewhere. In one embodiment, compounds that are active in in vitro assays (e.g., PDE-10A inhibition) or in vivo models for obesity, undesirable weight retention or weight gain, metabolic syndrome, diabetes, non-insulin dependent diabetes, impaired glucose tolerance, or hyperglycemia are further optimized to improve the potency in in vitro and in vivo assays and drug-like properties such as, e.g., solubility and lipophilicity.

C. Synthetic Schemes

Schemes below provide exemplary synthetic methods for the preparation of the compounds provided herein. One of ordinary skills in the art will understand that similar methods may be employed to prepare the compounds provided herein. In other words, one of ordinary skills in the art will recognize that suitable adjustments to reagents, protecting groups, reaction conditions, and reaction sequences may be employed to prepare a desired embodiment. The reactions may be scaled upwards or downwards to suit the amount of material to be prepared.

In one embodiment, the compound of formula (I) may be prepared following Schemes 1-8, using suitable starting materials known in the art and/or available from a commercial source. In one embodiment, the starting materials of Scheme 1-8 may be prepared from commercially available compounds using procedures and conditions known in the art.

Scheme 1

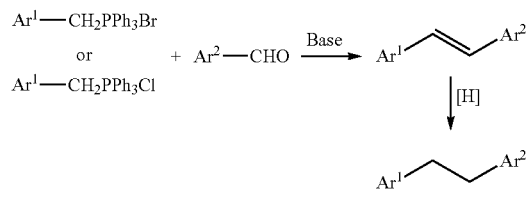

In one embodiment, a suitable triphenylphosphine halide is reacted with a suitable aldehyde or ketone in the presence of a base to render a substituted ethylene (Scheme 1), which may be further reduced (e.g., by hydrogenation) to render a substituted ethane compound as shown in Scheme 1. In one embodiment, $Ar^1$ or $Ar^2$ may be further converted to other suitable embodiments of $Ar^1$ or $Ar^2$ (e.g., transformation of substitution groups) using procedures and conditions known in the art.

In one embodiment, a suitable $Ar^1$—$CH_3$ is reacted with a suitable aldehyde in the presence of acid (e.g., acetic acid, zinc chloride, heating) to render a substituted ethylene (Scheme 2), which may be further reduced (e.g., by hydrogenation) to render a substituted ethane compound as shown in Scheme 2. In one embodiment, $Ar^1$ or $Ar^2$ may be further converted to other suitable embodiments of $Ar^1$ or $Ar^2$ (e.g., transformation of substitution groups) using procedures and conditions known in the art.

Scheme 2

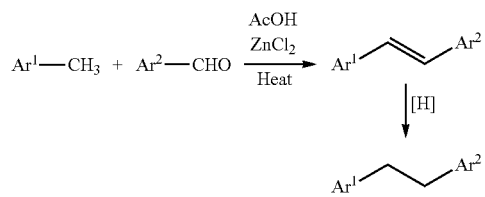

Scheme 3

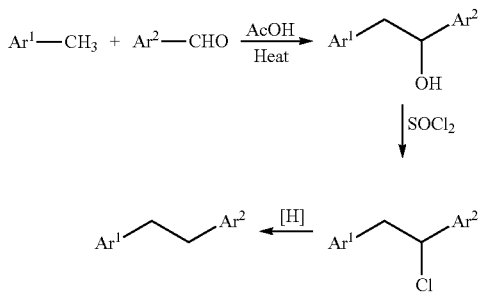

In another embodiment, a suitable $Ar^1$—$CH_3$ is reacted with a suitable aldehyde in the presence of acid (e.g., acetic acid, heating) to render a substituted hydroxylethylene compound (Scheme 3), which is converted to the corresponding chloride (e.g., using $SOCl_2$) and reduced (e.g., using Pd on Carbon) to render a substituted ethane compound as shown in Scheme 3. In one embodiment, $Ar^1$ or $Ar^2$ may be further converted to other suitable embodiments of $Ar^1$ or $Ar^e$ (e.g., transformation of substitution groups) using procedures and conditions known in the art.

Scheme 4

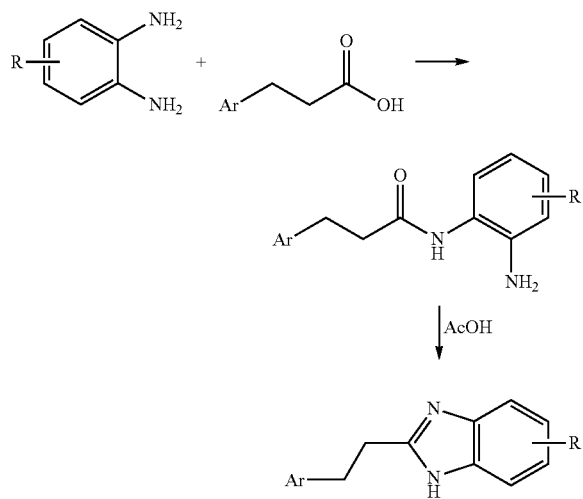

In one embodiment, a suitable substituted diaminoaryl or substituted diaminoheteroaryl is reacted with a suitable substituted propionic acid under amide coupling conditions to yield the corresponding amide (Scheme 4), which is cyclized under acidic condition (e.g., acetic acid) to render a substituted ethyl-imidazole compound as shown in Scheme 4. In one embodiment, the diaminoaryl or diaminoheteroaryl compound is substituted with one or more R, a suitable substituent, which may be the same or different. In one embodiment, Ar or R may be further converted to other suitable embodiments of Ar or R (e.g., transformation of substitution groups) using procedures and conditions known in the art. In one embodiment, the imidazole ring may be further alkylated to render an N-substituted imidazole compound.

Scheme 5

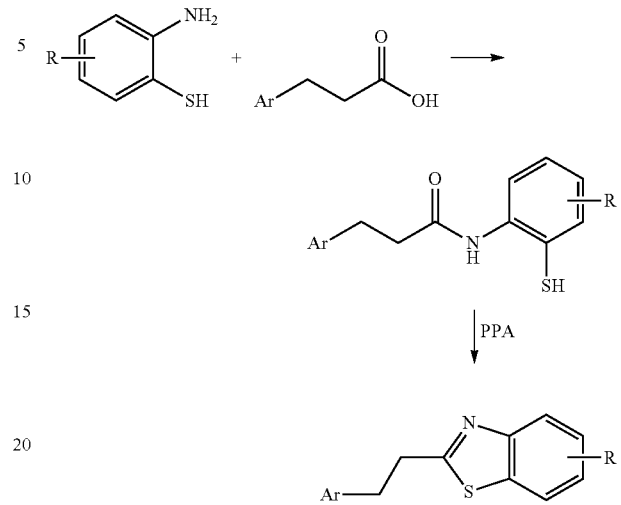

In one embodiment, a suitable substituted aminothioaryl or substituted aminothioheteroaryl is reacted with a suitable substituted propionic acid under amide coupling conditions to yield the corresponding amide (Scheme 5), which is cyclized under acidic condition (e.g., PPA) to render a substituted ethyl-thiazole compound as shown in Scheme 5. In one embodiment, the aminothioaryl or aminothioheteroaryl compound is substituted with one or more R, a suitable substituent, which may be the same or different. In one embodiment, Ar or R may be further converted to other suitable embodiments of Ar or R (e.g., transformation of substitution groups) using procedures and conditions known in the art.

Scheme 6

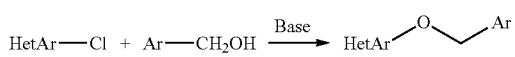

In one embodiment, a suitable heteroaryl chloride is reacted with a suitable substituted hydroxymethyl compound in the presence of base to yield the corresponding heteroaryl ether compound as shown in Scheme 6. In one embodiment, HetAr or Ar may be further converted to other suitable embodiments of HetAr or Ar (e.g., transformation of substitution groups) using procedures and conditions known in the art.

Scheme 7

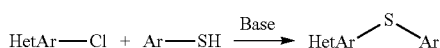

In one embodiment, a suitable heteroaryl chloride is reacted with a suitable substituted thioaryl or thioheteroaryl compound in the presence of base to yield the corresponding heteroaryl thioether compound as shown in Scheme 7. In one embodiment, HetAr or Ar may be further converted to other suitable embodiments of HetAr or Ar (e.g., transformation of substitution groups) using procedures and conditions known in the art.

Scheme 8

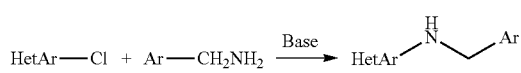

In one embodiment, a suitable heteroaryl chloride is reacted with a suitable substituted aminomethyl compound in the presence of base to yield the corresponding aminoheteroaryl compound as shown in Scheme 8. In one embodiment, HetAr or Ar may be further converted to other suitable embodiments of HetAr or Ar (e.g., transformation of substitution groups) using procedures and conditions known in the art.

In other embodiments, the compounds provided herein may be prepared using the general procedures described herein below. In one embodiment, the compounds provided herein may be prepared using General Procedure A. In one embodiment, the compounds provided herein may be prepared using General Procedure B. In one embodiment, the compounds provided herein may be prepared using General Procedure C. In one embodiment, the compounds provided herein may be prepared using General Procedure D. In one embodiment, the compounds provided herein may be prepared using General Procedure E. In one embodiment, the compounds provided herein may be prepared using General Procedure F. In one embodiment, the compounds provided herein may be prepared using General Procedure G. In one embodiment, the compounds provided herein may be prepared using General Procedure H. In one embodiment, the compounds provided herein may be prepared using General Procedure I. In one embodiment, the compounds provided herein may be prepared using General Procedure J. In one embodiment, the compounds provided herein may be prepared using General Procedure K. In one embodiment, the compounds provided herein may be prepared using General Procedure L. In one embodiment, the compounds provided herein may be prepared using General Procedure M. In one embodiment, the compounds provided herein may be prepared using General Procedure N. In one embodiment, the compounds provided herein may be prepared using General Procedure O. In one embodiment, the compounds provided herein may be prepared using General Procedure P. In one embodiment, the compounds provided herein may be prepared using General Procedure Q. In one embodiment, the compounds provided herein may be prepared using General Procedure R. In one embodiment, the compounds provided herein may be prepared using General Procedure S. In one embodiment, the compounds provided herein may be prepared using General Procedure T. In one embodiment, the compounds provided herein may be prepared using General Procedure U. In one embodiment, the compounds provided herein may be prepared using General Procedure V. In one embodiment, the compounds provided herein may be prepared using General Procedure W. In one embodiment, the compounds provided herein may be prepared using General Procedure X. In one embodiment, the compounds provided herein may be prepared using General Procedure Y. In one embodiment, the compounds provided herein may be prepared using General Procedure Z. In one embodiment, the compounds provided herein may be prepared using any one or more of General Procedures AA to ZZ. In one embodiment, the compounds provided herein may be prepared using General Procedure AAA. In one embodiment, the compounds provided herein may be prepared using General Procedure BBB.

In one embodiment, the compound of formula (I-B) may be prepared following Schemes 9-11, using suitable starting materials known in the art and/or available from a commercial source. In one embodiment, the starting materials of Schemes 9-11 may be prepared from commercially available compounds using procedures and conditions known in the art. Exemplary procedures and conditions are provided herein elsewhere.

Scheme 9

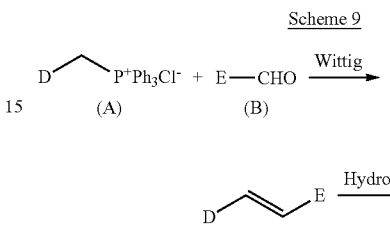

In one embodiment, a suitable triphenylphosphine halide (e.g., methyltriphenylphosphine chloride) is reacted with a suitable aldehyde in the presence of a base to render a substituted alkene, which may be further reduced (e.g., by hydrogenation) to render a substituted alkane compound as shown in Scheme 9. In one embodiment, D or E may be further converted to other suitable embodiments of D or E (e.g., transformation of substitution groups) using procedures and conditions known in the art.

Conditions and starting materials other than the Wittig reaction may be employed in the preparation of a compound of formula (I-B). For example, in one embodiment, a suitable D-$CH_3$ may be reacted with a suitable aldehyde in the presence of acid (e.g., acetic acid, zinc chloride, heating) to render a substituted alkene, which may be further reduced (e.g., by hydrogenation) to render a substituted alkane compound as shown in Scheme 10. In one embodiment, D or E may be further converted to other suitable embodiments of D or E (e.g., transformation of substitution groups) using procedures and conditions known in the art.

Scheme 10

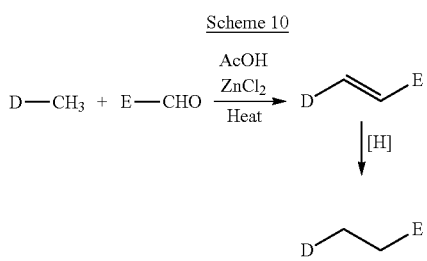

In another embodiment, a suitable D-$CH_3$ is reacted with a suitable aldehyde in the presence of acid (e.g., acetic acid, heating) to render a substituted hydroxylethylene compound (Scheme 11), which is converted to the corresponding chloride (e.g., using $SOCl_2$) and reduced (e.g., using Pd on Carbon) to render a substituted alkane compound as shown in Scheme 11. In one embodiment, D or E may be further converted to other suitable embodiments of D or E (e.g., transformation of substitution groups) using procedures and conditions known in the art.

Scheme 11

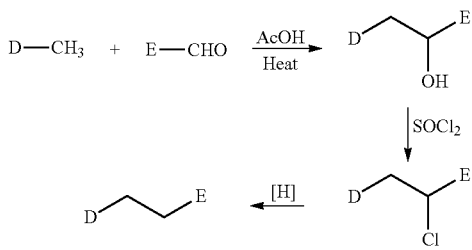

In certain embodiments, the compounds provided herein are prepared as a mixture of two or more stereoisomers or diastereoisomers. In one embodiment, the stereoisomers or diastereoisomers are separated using techniques known to those skilled in the art, including but not limited to, chiral column chromatography and chiral resolution by forming a salt with a suitable chiral counterion. In certain embodiments, the compounds provided herein are prepared following one or more stereoselective reaction(s). In some embodiment, the compounds provided herein are prepared as a substantially pure stereoisomer.

D. Methods of Use

1. Modulation of PDE Enzyme Activity

In one embodiment, provided herein is a method of binding a compound provided herein to a PDE enzyme, such as, PDE-10, in one embodiment, PDE-10A. The method comprises contacting the PDE enzyme with a compound provided herein. In one embodiment, the binding to PDE enzyme is assessed using an in vitro binding assay, such as those known in the art.

In one embodiment, provided herein is a method of modulating (e.g., inhibiting or augmenting) the activity of a PDE enzyme, such as, PDE-10, in one embodiment, PDE-10A. In one embodiment, provided herein is a method of inhibiting the activity of a PDE enzyme, such as, PDE-10, in one embodiment, PDE-10A. In one embodiment, the method comprises contacting a PDE enzyme, such as PDE-10A, with a compound provided herein, in vitro or in vivo. In one embodiment, the PDE enzyme, such as PDE-10A, is contacted by a compound provided herein by administering to a subject a therapeutically effective amount of the compound provided herein, or a pharmaceutically acceptable salt or stereoisomer thereof. The subject may be a human. In one embodiment, the PDE enzyme is PDE-10. In one embodiment, the PDE enzyme is PDE-10A.

In other embodiments, the compound provided herein inhibits the activity of a PDE enzyme, such as PDE-10A. Inhibition of PDE activity may be measured using assays known in the art. In some embodiments, the activity of the PDE enzyme is inhibited or reduced by about 1%, about 5%, about 10%, about 20%, about 30%, about 40%, about 50%, about 60%, about 70%, about 80%, about 90%, about 95%, about 99% or more than about 99%, as compared with activity without contacting the PDE enzyme with a compound provided herein (e.g., vehicle condition). In one embodiment, the inhibition of enzyme activity is dose dependent. Exemplary assay methods include, but are not limited to, in vitro binding assays and in vitro functional assays. In one embodiment, the functional assay utilizes an appropriate cell-line expressing a desired PDE enzyme, such as PDE-10A. In one embodiment, the functional assay utilizes a PDE enzyme purified following expression using an appropriate recombinant system. In one embodiment, inhibition of PDE enzyme activity may be assessed using a fluorescent assay, e.g., utilizing a fluorescently-labeled cAMP/cGMP substrate. In one embodiment, the functional assay utilizes synaptosomes isolated from brain tissue of an appropriate organism. In one embodiment, the assay is carried out in vivo and involves treatment of a test subject (e.g., a rodent) with a compound provided herein. In one embodiment, a test subject is treated with a reference compound or vehicle, as positive or negative controls. In one embodiment, the assay is followed by isolation of brain tissue and ex vivo analysis of substrate concentration (e.g., cAMP or cGMP) in the brain tissue. In one embodiment, the assay is followed by isolation of brain microdialysates and ex vivo analysis of substrate concentration (e.g., cAMP or cGMP) in the microdialysates.

In certain embodiments, provided herein are methods of inhibiting the activity of a PDE enzyme, e.g., PDE-10A, in a subject (e.g., human) comprising administering to the subject an effective amount of a compound provided herein. In some embodiments, the activity of PDE enzyme is inhibited by about 1%, about 5%, about 10%, about 20%, about 30%, about 40%, about 50%, about 60%, about 70%, about 80%, about 90%, about 95%, about 99%, or more than about 99%, when measured using an assay described herein elsewhere.

In one embodiment, provided herein is a method of inhibiting a PDE enzyme to increase the concentration of a cyclic nucleotide substrate. In one embodiment, the method includes contacting the cell with a compound provided herein. In one embodiment, the cell is a brain cell, such as a medium spiny neuron. In one embodiment, the enzyme inhibition occurs in vitro. In one embodiment, the enzyme inhibition occurs in vivo. Thus, in certain embodiments, provided herein are methods of increasing the level of a cyclic nucleotide substrate (e.g., cAMP or cGMP) comprising administering to a subject (e.g., human) an effective amount of a compound provided herein.

Inhibition of PDE enzyme can be shown, for example, by performing various in vitro functional assays utilizing a cell type which expresses a certain type of PDE enzyme, such as PDE-10A, together with an appropriate labeled cyclic nucleotide substrate. In some embodiments, the compounds provided herein inhibit the PDE enzyme in a dose-dependent manner, with an $EC_{50}$ of, for example, between about 0.1 nM and about 10 µM, between about 1 nM and about 1 µM, between about 1 nM and about 500 nM, and between about 1 nM and about 100 nM, in a functional PDE inhibition assay, such as those described herein. In one embodiment, the $EC_{50}$ is less than about 0.01 nM, less than about 0.1 nM, less than about 1 nM, less than about 3 nM, less than about 10 nM, less than about 30 nM, less than about 100 nM, less than about 300 nM, less than about 1000 nM, less than about 3000 nM, or less than about 10000 nM. In one embodiment, the $EC_{50}$ is about 0.01 nM, about 0.1 nM, about 1 nM, about 3 nM, about 10 nM, about 30 nM, about 100 nM, about 300 nM, about 1000 nM, about 3000 nM, or about 10000 nM.

2. Treatment, Prevention, and/or Management of Disorders

In one embodiment, provided herein is a method for the treatment, prevention, and/or management of various disorders, including a disorder of the central nervous system, comprising administering a compound or a composition provided herein. In one embodiment, provided herein is a method for the treatment, prevention, and/or amelioration of one or more symptoms of a disorder (e.g., a CNS disorder), comprising administering a compound or a composition provided herein. In one embodiment, the disorders provided herein include, but are not limited to, schizophrenia, psychosis, cognitive disorders, mood disorders, depression, attention deficit disorders, and neurodegenerative diseases. In one embodiment, the disorders include, but are not limited to, neurological disorder, schizophrenia, schizophrenia-related disorders, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, disease having a psychosis component, psychotic disorder, brief psychotic disorder, Alzheimer's psychosis, Parkinson's psychosis, shared psychotic disorder, substance-induced psychotic disorder (e.g., cocaine, alcohol, amphetamine), psychotic disorder due to a general medical condition, psychoaffective disorder, aggression, delirium, excitative psychosis, Tourette's syndrome, manic disorder, organic psychosis, NOS psychosis, convulsion, seizure, agitation, posttraumatic stress disorder, behavior disorder, neurodegenerative disease, Huntington's disease, Alzheimer's disease, Parkinson's disease, dyskinesia, dementia, mood disorder, bipolar disorder, anxiety, depression, major depressive disorder, unipolar depression, treatment resistant depression, dysthymia, affective disorder, seasonal affective disorder, obsessive-compulsive disorder, attention deficit disorder (ADD), attention deficit hyperactivity disorder (ADHD), vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome (RLS), multiple sclerosis, sleep disorder, substance abuse or dependency (e.g., nicotine, cocaine), addiction, eating disorder, autism, obesity, undesirable weight retention or weight gain, metabolic syndrome, diabetes, non-insulin dependent diabetes, impaired glucose tolerance, and hyperglycemia. In one embodiment, the disorder provided herein is a disorder known in the art that affects the central nervous system (i.e., a CNS disorder).

In one embodiment, provided herein is a method of administering a compound provided herein in a disease model that is known in the art. In one embodiment, the disease model is an animal model. In one embodiment, provided herein is a method of administering the compound provided herein in an animal model that is predictive of efficacy in the treatment of certain diseases in a human. The method comprises administering a compound provided herein in a subject. In one embodiment, the method comprises administering to a subject a therapeutically effective amount of a compound provided herein, or a pharmaceutically acceptable salt or stereoisomer thereof. In one embodiment, the method comprises treatment of a test subject (e.g., a mice or rat) with a compound provided herein. In one embodiment, the method comprises treatment of a test subject (e.g., a mouse or rat) with a compound provided herein as well as a reference compound. In one embodiment, the in vivo activity of the compound provided herein is dose dependent. In one embodiment, without being limited to a particular theory, the method provided herein comprises administering an effective amount of a compound provided herein to inhibit PDE-10 activity in a subject. In one embodiment, without being limited to a particular theory, the method provided herein comprises administering an effective amount of a compound provided herein to inhibit PDE-10A activity in a subject.

In one embodiment, the compounds provided herein are active in one or more animal models of schizophrenia or psychosis, such as conditioned avoidance responding (CAR), auditory gating (e.g., amphetamine-induced deficit in auditory gating), phencyclidine (PCP)-induced hyperlocomotion, stimulant-induced hyperlocomotion/hyperactivity, PCP-induced hyperactivity, and amphetamine-induced hyperactivity. In one embodiment, the compounds provided herein inhibit exploratory locomotor activity and/or hyperactivity caused by a dopamine releasing agent, such as amphetamine, and/or a NMDA receptor antagonist, such as phencyclidine (PCP). In one embodiment, the compounds provided herein inhibit conditioned avoidance responding. In one embodiment, the compounds provided herein are active in pre-pulse inhibition (PPI) of acoustic startle response model. In one embodiment, the compounds provided herein inhibit spontaneous locomotor activity. In one embodiment, the compounds provided herein improve cognitive function in a treated subject. In one embodiment, the compounds provided herein improve social interaction in a treated subject. In one embodiment, the compounds provided herein improve social cognition in a treated subject. In one embodiment, the compounds provided herein improve executive function in a treated subject. In one embodiment, the compounds provided herein caused reduced Parkinsonian side effects in a treated subject. In one embodiment, the compounds provided herein produce relatively low levels of catalepsy, as compared to other therapeutic agents. In one embodiment, the compounds provided herein provide a neuron-protective effect on neurons, such as medium spiny neurons, in a treated subject. In one embodiment, the compounds provided herein are active in a striatal quinolinic acid lesion model for Huntington's disease. In one embodiment, the compounds provided herein are active in dizocilpine-induced hyperactivity and stereotyped sniffing model for psychosis. In one embodiment, the compounds provided herein inhibit apomorphine-induced climbing. In one embodiment, the compounds provided herein inhibit N-methyl-D-aspartate antagonist-induced deficits in pre-pulse inhibition of acoustic startle response. In one embodiment, the compounds provided herein improve baseline sensory gating. In one embodiment, the compounds provided herein increase sociality in a social approach/social avoidance assay. In one embodiment, the compounds provided herein enhance social odor recognition. In one embodiment, the compounds provided herein improve novel object recognition. In one embodiment, the compounds provided herein are active in a disease model for a disorder provided herein elsewhere, which is known in the art. See, e.g., Grauer et al., Phosphodiesterase 10A Inhibitor Activity in Preclinical Models of the Positive, Cognitive, and Negative Symptoms of Schizophrenia, *Journal of Pharmacology and Experimental Therapeutics,* 2009, 331(2), 574-90; Threlfell et al., Inhibition of Phosphodiesterase 10A Increases the Responsiveness of Striatal Projection Neurons to Cortical Stimulation, *Journal of Pharmacology and Experimental Therapeutics,* 2009, 328(3), 785-95; Schmidt et al., Preclinical Characterization of Selective Phosphodiesterase 10A Inhibitors: A New Therapeutic Approach to the Treatment of Schizophrenia, *Journal of Pharmacology and Experimental Therapeutics,* 2008, 325 (2), 681-90.

In one embodiment, provided herein is a method of treating, preventing, and/or managing various disorders, including, but not limited to, a disorder of the central nervous system. In one embodiment, the method comprises administering to a subject (e.g., human) a therapeutically or prophylactically effective amount of a composition or a compound provided herein. In one embodiment, the subject is a human. In one embodiment, the subject is an animal. In one embodiment, the compounds provided herein are highly brain penetrable in the subject. In certain embodiments, the efficacious concentration of the compounds provided herein is less than 10 nM, less than 100 nM, less than 1 µM, less than 10 µM, less than 100 µM, or less than 1 mM. In one embodiment, the compound's activity may be assessed in various art-recognized animal models as described herein elsewhere or known in the literature.

In one embodiment, without being limited by a particular theory, the treatment, prevention, and/or management is done by administering a compound provided herein that has shown in vivo efficacy in an animal model predictive of efficacy in humans.

In one embodiment, provided herein is a method of treating, preventing, and/or managing a disorder related to a CNS disorder, a neurological disorder, schizophrenia, a schizophrenia-related disorder, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, a disease having a psychosis component, psychotic disorder, brief psychotic disorder, Alzheimer's psychosis, Parkinson's psychosis, shared psychotic disorder, substance-induced psychotic disorder (e.g., cocaine, alcohol, amphetamine), psychotic disorder due to a general medical condition, psychoaffective disorder, aggression, delirium, excitative psychosis, Tourette's syndrome, manic disorder, organic psychosis, NOS psychosis, convulsion, seizure, agitation, posttraumatic stress disorder, behavior disorder, neurodegenerative disease, Huntington's disease, Alzheimer's disease, Parkinson's disease, dyskinesias, dementia, mood disorder, bipolar disorder, anxiety, depression, major depressive disorder, unipolar depression, treatment resistant depression, dysthymia, affective disorder, seasonal affective disorder, obsessive-compulsive disorder, attention deficit disorder (ADD), attention deficit hyperactivity disorder (ADHD), vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome (RLS), multiple sclerosis, sleep disorder, substance abuse or dependency (e.g., nicotine, cocaine), addiction, eating disorder, autism, obesity, undesirable weight retention or weight gain, metabolic syndrome, diabetes, non-insulin dependent diabetes, impaired glucose tolerance, or hyperglycemia, comprising administering to a subject an effective amount of a compound provided herein.

In one embodiment, provided herein is a method of treating, preventing, and/or managing a neurological disorder as provided herein elsewhere, such as schizophrenia, psychosis, cognitive impairment, depression, Alzheimer's disease, Parkinson's disease, and attention deficit hyperactivity disorder (ADHD), and the like, comprising administering to a subject an effective amount of a compound provided herein.

In one embodiment, provided herein is a method of treating, preventing, and/or managing schizophrenia or a schizophrenia-related disorder, including but not limited to schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, and psychosis, comprising administering to a subject an effective amount of a compound provided herein. In one embodiment, the compounds provided herein treat, prevent, and/or ameliorate one or more positive symptoms of schizophrenia. In one embodiment, the compounds provided herein treat, prevent, and/or ameliorate one or more negative symptoms of schizophrenia. In one embodiment, the compounds provided herein treat, prevent, and/or ameliorate one or more cognitive symptoms of schizophrenia.

In one embodiment, provided herein is a method of treating, preventing, and/or managing a disease having a psychosis component, including but not limited to psychotic disorder, brief psychotic disorder, Alzheimer's psychosis, Parkinson's psychosis, shared psychotic disorder, substance-induced psychotic disorder (e.g., cocaine, alcohol, or amphetamine), psychotic disorder due to a general medical condition, psychoaffective disorder, aggression, delirium, excitative psychosis, Tourette's syndrome, manic disorder, organic psychosis, and NOS psychosis, comprising administering to a subject an effective amount of a compound provided herein.

In one embodiment, provided herein is a method of treating, preventing, and/or managing cognitive impairment, including but not limited to cognitive impairment associated with schizophrenia, cognitive deficit in Alzheimer's disease, cognitive deficit in Parkinson's disease, comprising administering to a subject an effective amount of a compound provided herein.

In one embodiment, provided herein is a method of treating, preventing, and/or managing mood disorder, bipolar disorder, anxiety, depression, major depressive disorder, unipolar depression, treatment resistant depression, dysthymia, affective disorder, seasonal affective disorder, or obsessive-compulsive disorder, comprising administering to a subject an effective amount of a compound provided herein.

In one embodiment, provided herein is a method of treating, preventing, and/or managing attention deficit disorder (ADD) or attention deficit hyperactivity disorder (ADHD), comprising administering to a subject an effective amount of a compound provided herein.

In one embodiment, provided herein is a method of treating, preventing, and/or managing a neurodegenerative disease, including but not limited to Huntington's disease, Alzheimer's disease, and Parkinson's disease, comprising administering to a subject an effective amount of a compound provided herein. In one embodiment, provided herein is a method of treating, preventing, and/or managing Huntington's disease, comprising administering to a subject an effective amount of a compound provided herein.

In one embodiment, provided herein is a method of treating, preventing, and/or managing agitation, posttraumatic stress disorder, or behavior disorder, comprising administering to a subject an effective amount of a compound provided herein.

In one embodiment, provided herein is a method of treating, preventing, and/or managing dementia, comprising administering to a subject an effective amount of a compound provided herein.

In one embodiment, provided herein is a method of treating, preventing, and/or managing vertigo, comprising administering to a subject an effective amount of a compound provided herein.

In one embodiment, provided herein is a method of treating, preventing, and/or managing pain, neuropathic pain, sensitization accompanying neuropathic pain, inflammatory pain, migraine or fibromyalgia, comprising administering to a subject an effective amount of a compound provided herein.

In one embodiment, provided herein is a method of treating, preventing, and/or managing movement disorder or restless leg syndrome (RLS), comprising administering to a subject an effective amount of a compound provided herein.

In one embodiment, provided herein is a method of treating, preventing, and/or managing multiple sclerosis, sleep disorder, substance abuse or dependency (e.g., nicotine, cocaine), addiction, eating disorder, or autism, comprising administering to a subject an effective amount of a compound provided herein.

In one embodiment, provided herein is a method of treating, preventing, and/or managing a disorder related to cognitive impairments, such as those associated with Alzheimer's disease, Parkinson's disease, schizophrenia, and attention deficit hyperactivity disorder (ADHD), and the like, comprising administering to a subject an effective amount of a compound provided herein. For example, without being limited by a particular theory, the compounds provided herein may have pro-cognitive effects, such as passive avoidance, novel object recognition, social recognition, and attention-set shifting. Further, without being limited by a particular theory, the compounds provided herein may improve social memory, increase the acquisition of an environment, and reverse scopolamine-induced deficits. The compounds provided herein may also reverse scopolamine-induced deficits in a passive avoidance memory test.

In one embodiment, provided herein is a method of treating, preventing, and/or managing a psychotic disorder or psychotic condition, including but not limited to, schizophrenia, delusional disorders and drug induced psychosis, comprising administering to a subject an effective amount of a compound provided herein.

In one embodiment, provided herein is a method of treating, preventing, and/or managing an anxiety disorder, including but not limited to, panic and obsessive-compulsive disorder, comprising administering to a subject an effective amount of a compound provided herein.

In one embodiment, provided herein is a method of treating, preventing, and/or managing a movement disorder, including but not limited to, Parkinson's disease and Huntington's disease, comprising administering to a subject an effective amount of a compound provided herein.

In one embodiment, the psychotic disorders provided herein that can be treated, prevented, and/or managed using a compound or a pharmaceutical composition provided herein include, but are not limited to, schizophrenia, e.g., of the paranoid, disorganized, catatonic, undifferentiated, and/or residual type; schizophreniform disorder; schizoaffective disorder, e.g., of the delusional and/or depressive type; delusional disorder; substance-induced psychotic disorder, e.g., psychosis induced by alcohol, amphetamine, cannabis, cocaine, hallucinogens, inhalants, opioids, and/or phencyclidine; personality disorder of the paranoid type; and personality disorder of the schizoid type.

In one embodiment, the movement disorders provided herein that can be treated, prevented, and/or managed using a compound or a pharmaceutical composition provided herein include, but are not limited to, Huntington's disease, dyskinesia associated with dopamine agonist therapy, Parkinson's disease, restless leg syndrome, and essential tremor.

In one embodiment, other disorders provided herein that can be treated, prevented, and/or managed using a compound or a pharmaceutical composition provided herein include, but are not limited to, obsessive-compulsive disorder, Tourette's syndrome, and tic disorders.

In one embodiment, provided herein is a method of treating, preventing, and/or managing an anxiety disorder, including but not limited to, panic disorder, agoraphobia, specific phobia, social phobia, obsessive-compulsive disorder, post-traumatic stress disorder, acute stress disorder, and generalized anxiety disorder, comprising administering to a subject an effective amount of a compound provided herein.

In one embodiment, provided herein is a method of treating, preventing, and/or managing a drug addiction, including but not limited to, an alcohol, amphetamine, cocaine, and/or opiate addiction, comprising administering to a subject an effective amount of a compound provided herein. In one embodiment, the drug addiction provided herein represents an abnormal desire for a drug and is generally characterized by motivational disturbances such a compulsion to take the desired drug and episodes of intense drug craving.

In one embodiment, provided herein is a method of treating, preventing, and/or managing a disorder comprising a symptom of deficiency in attention and/or cognition, comprising administering to a subject an effective amount of a compound provided herein. In one embodiment, deficiency in attention and/or cognition provided herein may represent a subnormal functioning in one or more cognitive aspects, such as, e.g., memory, intellect, learning ability, and/or logic ability, in a particular subject relative to other subjects within the same general population and/or age group. In one embodiment, deficiency in attention and/or cognition provided herein may represent a reduction in a particular sub-population's functioning in one or more cognitive aspects, such as, e.g., in age-related cognitive decline.

In one embodiment, the disorders comprising a symptom of deficiency in attention and/or cognition provided herein that can be treated, prevented, and/or managed with a compound or a pharmaceutical composition provided herein, include, but are not limited to, dementia, e.g., dementia in Alzheimer's disease, multi-infarct dementia, alcoholic dementia, drug-related dementia, dementia associated with intracranial tumors, dementia associated with cerebral trauma, dementia associated with Huntington's disease, dementia associated with Parkinson's disease, or AIDS-related dementia; delirium; amnestic disorder; post-traumatic stress disorder; mental retardation; learning disorder, e.g., reading disorder, mathematics disorder, or a disorder of written expression; attention-deficit/hyperactivity disorder; and age-related cognitive decline.

In one embodiment, provided herein is a method of treating, preventing, and/or managing a mood disorder or a mood episode, comprising administering to a subject an effective amount of a compound provided herein. In one embodiment, the mood disorders or mood episodes provided herein that can be treated, prevented, and/or managed with a compound or a pharmaceutical composition provided herein include, but are not limited to, major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; treatment resistant depression; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, e.g., bipolar I disorder, bipolar II disorder, and cyclothymic disorder.

In one embodiment, provided herein is a method of treating, preventing, and/or managing a neurodegenerative disorder or neurodegenerative condition, comprising administering to a subject an effective amount of a compound provided herein. In one embodiment, the neurodegenerative disorder or neurodegenerative condition provided herein that can be treated, prevented, and/or managed with a compound or a pharmaceutical composition provided herein represents a disorder or condition that is caused by the dysfunction and/or death of neurons in the central nervous system. The treatment of these disorders and conditions can be facilitated by administration of an agent which prevents the dysfunction or death of neurons at risk and/or enhances the function of damaged or healthy neurons to compensate for the loss of function caused by the dysfunction or death of at-risk neurons. In one embodiment, the neurodegenerative disorders or neurodegenerative conditions provided herein that can be treated, prevented, and/or managed with a compound or a pharmaceutical composition provided herein include, but are not limited to, Parkinson's disease; Huntington's disease; dementia, e.g., Alzheimer's disease, multi-infarct dementia, AIDS-related dementia, and Fronto temporal dementia; neurodegeneration associated with cerebral trauma; neurodegeneration associated with stroke; neurodegeneration associated with cerebral infarct; hypoglycemia-induced neurodegeneration; neurodegeneration associated with neurotoxin poisoning; and multi-system atrophy. In one embodiment, the neurodegenerative disorders or neurodegenerative conditions provided herein comprise neurodegeneration of striatal medium spiny neurons in a subject. In one embodiment, the neurodegenerative disorder or neurodegenerative condition is Huntington's disease.

In one embodiment, provided herein is a method of treating, preventing, and/or managing psychotic disorder, delusional disorder, drug induced psychosis, anxiety disorder, movement disorder, mood disorder, neurodegenerative disorder, or drug addiction, comprising administering to a subject an effective amount of a compound provided herein.

In one embodiment, provided herein is a method of treating, preventing, and/or managing a neurologic disorder, including but not limited to, dementia, Alzheimer's disease, multi-infarct dementia, alcoholic dementia, drug-related dementia, dementia associated with intracranial tumors, dementia associated with cerebral trauma, dementia associated with Huntington's disease, dementia associated with Parkinson's disease, AIDS-related dementia, delirium, amnestic disorder, post-traumatic stress disorder, mental retardation, learning disorder, reading disorder, mathematics disorder, disorder of written expression, attention-deficit-hyperactivity disorder, age-related cognitive decline, major depressive episode of the mild, moderate or severe type, manic or mixed mood episode, hypomanic mood episode, depressive episode with atypical features, depressive episode with melancholic features, depressive episode with catatonic features, mood episode with postpartum onset, post-stroke depression, major depressive disorder, dysthymic disorder, minor depressive disorder, premenstrual dysphoric disorder, post-psychotic depressive disorder of schizophrenia, a major depressive disorder superimposed on a psychotic disorder comprising a delusional disorder or schizophrenia, bipolar disorder, bipolar I disorder, bipolar II disorder, cyclothymic disorder, Parkinson's disease, Huntington's disease, dementia, Alzheimer's disease, multi-infarct dementia, AIDS-related dementia, Fronto temporal dementia, neurodegeneration associated with cerebral trauma, neurodegeneration associated with stroke, neurodegeneration associated with cerebral infarct, hypoglycemia-induced neurodegeneration, neurodegeneration associated with neurotoxin poisoning, multi-system atrophy, schizophrenia of a paranoid, disorganized, catatonic, undifferentiated or residual type, schizophreniform disorder; schizoaffective disorder of the delusional type or the depressive type, delusional disorder, substance-induced psychotic disorder, psychosis induced by alcohol, amphetamine, cannabis, cocaine, hallucinogens, inhalants, opioids, or phencyclidine, personality disorder of the paranoid type, and personality disorder of the schizoid type, comprising administering to a subject an effective amount of a compound provided herein.

In one embodiment, provided herein is a method of treating, preventing, and/or managing a neurologic disorder, including but not limited to, psychotic disorders, delusional disorders, drug induced psychosis, anxiety disorders, movement disorders, mood disorders, neurodegenerative disorders, and drug addiction, comprising administering to a subject an effective amount of a compound provided herein.

In one embodiment, provided herein is a method of treating, preventing, and/or managing substance abuse, comprising administering to a subject an effective amount of a compound provided herein. For example, without being limited by a particular theory, the compounds provided herein may alter methamphetamine self-administration in rats, and therefore the compounds provided herein may ameliorate the craving for addictive drugs.

In one embodiment, provided herein is a method of using the compounds provided herein as psycho-stimulants, which may lack the abuse liabilities generally associated with other classes of psycho-stimulants.

In one embodiment, provided herein is a method of treating, preventing, and/or managing movement disorders, such as Parkinson's disease, L-dopa induced dyskineasias, peak dose dyskinesas, restless leg syndrome (RLS), and Huntington's disease, comprising administering to a subject an effective amount of a compound provided herein.

In some embodiments, the compounds provided herein are active in at least one model, which can be used to measure the activity of the compounds and estimate their efficacy in treating a CNS disorder. For example, the compounds provided herein are active in at least one model for schizophrenia, such as, e.g., conditioned avoidance responding, amphetamine-induced deficit in auditory gating, phencyclidine-induced hyperlocomotion or hyperactivity, and amphetamine-induced hyperactivity models. The compounds are active when they induce a desired response in the animal (e.g., mice) by a statistically significant amount compared to vehicle-treated animals.

In other embodiments, provided herein is a method of effecting a therapeutic effect as described herein elsewhere. The method comprises administering to a subject (e.g., a mammal) a therapeutically effective amount of a compound or a composition provided herein. The particular therapeutic effects may be measured using any model system known in the art and described herein, such as those involving an animal model of a disease.

In some embodiments, the neurological disorder provided herein is: depression (e.g., major depressive disorder, bipolar disorder, unipolar disorder, treatment resistant depression, dysthymia, and seasonal affective disorder); cognitive deficits; fibromyalgia; pain (e.g., neuropathic pain); sleep related disorders (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; posttraumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic conditions; dysthymic disorder; cyclothymic disorder; obesity; and substance abuse or dependency (e.g., cocaine addiction, nicotine addiction). In another embodiment, the compounds provided herein are useful to treat, prevent, and/or manage two or more conditions/disorders, which are co-morbid, such as psychosis and depression.

Neurological disorders may also include cerebral function disorders, including without limitation, senile dementia, Alzheimer's type dementia, cognition, memory loss, amnesia/amnestic syndrome, lowering of attention, speech disorders, autism, and hyperkinetic syndrome.

Neuropathic pain includes, without limitation, post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated, prevented, and/or managed using the methods, compounds, and/or compositions provided herein include, but are not limited to: obesity, overweight, metabolic syndrome, diabetes, non-insulin dependent diabetes, impaired glucose tolerance, and hyperglycemia.

In one embodiment, the neurological disorder is excessive daytime sleepiness. In another embodiment, the neurological disorder is cognitive impairment. In another embodiment, the neurological disorder is mood disorders. In another embodiment, the neurological disorder is movement disorders. In another embodiment, the neurological disorder is schizophrenia. In another embodiment, the neurological disorder is attention disorders. In another embodiment, the neurological disorder is anxiety disorder. In another embodiment, the neurological disorder is seizure. In another embodiment, the neurological disorder is psychosis. In another embodiment, the neurological disorder is vertigo. In another embodiment, the neurological disorder is pain. In another embodiment, the neurological disorder is neuropathic pain. In another embodiment, the neuropathic pain is diabetic neuropathy.

In one embodiment, the neurological disorder is a neurodegenerative disease. In one embodiment, the neurodegenerative disease is Parkinson's disease. In another embodiment, the neurodegenerative disorder is Alzheimer's disease.

In one embodiment, the compounds described herein treat, prevent, and/or manage a central nervous disorder, without causing addiction to said compounds.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. The dosage may be formulated as a single or multiple unit dosage formulation. In one embodiment, the compound is given in single or divided doses per day.

In some embodiments, the compounds disclosed herein may be used in combination with one or more second active agents to treat, prevent, and/or manage disorders described herein.

In certain embodiments, the second active agent is an antipsychotic agent. In certain embodiments, the second active agent is an atypical antipsychotic agent. In certain embodiments, the second active agent is an agent that is useful for the treatment of Alzheimer's disease. In certain embodiments, the second active agent is a cholinesterase inhibitor. In certain embodiments, the second active agent is an antidepressant, including, but not limited to, an SNRI, SSRI, TCA, or an MAOI.

In certain embodiments, the second active agent is lurasidone, olanzapine, risperidone, aripiprazole, amisulpride, asenapine, blonanserin, clozapine, clotiapine, iloperidone, mosapramine, paliperidone, quetiapine, remoxipride, sertindole, sulpiride, ziprasidone, zotepine, pimavanserin, loxapine, donepezil, rivastigmine, memantine, galantamine, tacrine, amphetamine, methylphenidate, atomoxetine, modafinil, sertraline, fluoxetine, duloxetine, venlafaxine, phenelzine, selegiline, imipramine, desipramine, clomipramine, or L-DOPA.

3. Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, stereoisomer, solvate, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intra-arterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., *Remington's Pharmaceutical Sciences,* 18th Ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising, active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

In other embodiments, dosage forms comprise the second active ingredient. The specific amount of the second active agent will depend on the specific agent used, the diseases or disorders being treated or managed, and the amount(s) of a compound provided herein, and any optional additional active agents concurrently administered to the patient.

(a) Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's The Science and Practice of Pharmacy,* 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a freeflowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, and optional excipients, such as anhydrous lactose, microcrystalline cellulose, polyvinylpyrrolidone, stearic acid, colloidal anhydrous silica, and gelatin.

(b) Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

(c) Parenteral Dosage Forms

Parenteral dosage forms can be administered to patients by various routes including, but not limited to, subcutaneous, intravenous (including bolus injection), intramuscular, and intra-arterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

(d) Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

4. Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

V. EXAMPLES

Certain embodiments are illustrated by the following non-limiting examples.

A. General Procedures for Compound Synthesis

In the examples below, unless otherwise indicated, all temperatures are set forth in degrees Celsius and all parts and percentages are by weight. Reagents may be purchased from commercial suppliers, such as Sigma-Aldrich® Chemical Company, and may be used without further purification unless otherwise indicated. Reagents may also be prepared following standard literature procedures known to those skilled in the art. Solvents may be purchased from Aldrich in Sure-Seal® bottles and used as received. All solvents may be purified using standard methods known to those skilled in the art, unless otherwise indicated.

The reactions set forth below were done generally at ambient temperature, unless otherwise indicated. The reaction flasks were fitted with rubber septa for introduction of substrates and reagents via syringe. Analytical thin layer chromatography (TLC) was performed using glass-backed silica gel pre-coated plates and eluted with appropriate solvent ratios (v/v). Reactions were assayed by TLC or liquid chromatography mass spectroscopy (LCMS), and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (see, e.g., Still et al., *J. Org. Chem.,* 43: 2923 (1978)) was performed using silica gel 60 or various medium-pressure liquid chromatography (MPLC) systems (such as Biotage® or ISCO® separation systems).

The compound structures in the examples below were confirmed by one or more of the following methods: proton magnetic resonance spectroscopy, mass spectroscopy, elemental microanalysis, and melting point. Proton nuclear magnetic resonance ($^1$H NMR) spectra were determined using a NMR spectrometer operating at a certain field strength. Chemical shifts are reported in parts per million (ppm, δ) downfield from an internal standard, such as tetramethylsilane (TMS). Alternatively, $^1$H NMR spectra were referenced to signals from residual protons in deuterated solvents as follows: $CDCl_3$=7.25 ppm; DMSO-$d_6$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

In one embodiment, in the schemes below, $R^{51}$, $R^{52}$, $R^{53}$, $R^{54}$, $R^{55}$, $R^{56}$, $R^{57}$, $R^{58}$, $R^{59}$, $R^{60}$, $R^{61}$, and $R^{62}$ are each independently a suitable substituent; HetAr is heteroaryl; and Ar, $Ar^1$, and $Ar^2$ are each independently aryl or heteroaryl. In the scheme for General Procedure A, A and B are each independently N or $CR^{61}$. In one embodiment, $R^{61}$ is H. In the scheme for General Procedure L, $X^1$ and $X^2$ are each independently N or $CR^{62}$. In one embodiment, $R^{62}$ is H.

1. General Procedure A

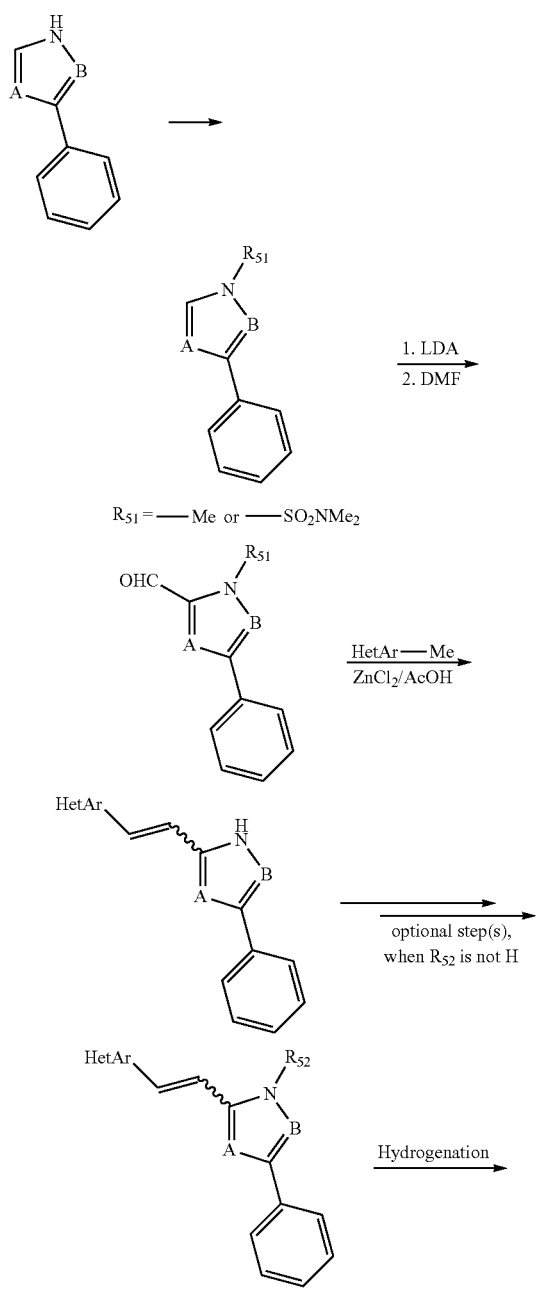

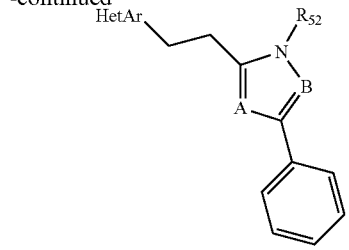

(a)
N,N-Dimethyl-4-phenyl-1H-imidazole-1-sulfonamide

To a solution of 5-phenyl-1H-imidazole (5 g, 34.7 mmol) and $K_2CO_3$ (6 g, 41.6 mmol) in N,N-dimethylformamide (DMF) (20 mL) was added dimethylsulfamoyl chloride (4.11 mL, 38.2 mmol) drop wise at room temperature. The resulting mixture was stirred at room temperature for 4 h and then diluted with water (500 mL). The resulting solid was collected by vacuum filtration and dried to give the desired product (7 g). LC-MS: m/z 252 (M+H+).

(b) 2-Formyl-N,N-dimethyl-4-phenyl-1H-imidazole-1-sulfonamide

To a solution of diisopropylamine (12 mL, 85.3 mmol) in tetrahydrofuran (THF) (50 mL) was added n-butyllithium (n-BuLi) (34 mL, 85.3 mmol) dropwise at 0° C. The reaction mixture was stirred for 0.5 h to form a solution of lithium diisopropylamide (LDA). A solution of N,N-dimethyl-5-phenyl-1H-imidazole-1-sulfonamide (10.7 g, 42.6 mmol) in anhydrous THF (40 mL) was prepared and cooled to −78° C. To this solution was added dropwise at −78° C. the LDA solution, and the reaction mixture was stirred at −78° C. for additional 0.5 h. Anhydrous DMF (9.9 mL, 128 mmol) was then added rapidly and the mixture was stirred at −60° C. to −30° C. for 2 h. While the mixture was vigorously stirred, 10% HCl was added dropwise until pH 5. The aqueous layer was extracted with EtOAc (200 mL×3). The combined organic layers were dried over $Na_2SO_4$, filtered, and concentrated to give the desired product as a solid (12.5 g). LC-MS: m/z 280 (M+H+).

(c) (E,Z)-2-(2-(5-Phenyl-1H-imidazol-2-yl)vinyl)quinoxaline

A mixture of 2-formyl-N,N-dimethyl-4-phenyl-1H-imidazole-1-sulfonamide (500 mg, 1.79 mmol), 2-methylquinoxaline (258 mg, 1.79 mmol), and a catalytic amount of $ZnCl_2$ in glacial acetic acid (10 mL) was stirred at 110° C. for 18 h. The reaction mixture was cooled to room temperature, pH was adjusted to 8 with $Na_2CO_3$, and extracted with EtOAc (50 mL×3). The organic layer was dried over $Na_2SO_4$, filtered, and concentrated. The resulting crude product was purified by column chromatography to give 90 mg of the desired product. LC-MS: m/z 299 (M+H+).

(d) 2-(2-(5-Phenyl-1H-imidazol-2-yl)ethyl)quinoxaline (E,Z)-2-(2-(5-Phenyl-1H-imidazol-2-yl)vinyl)quinoxaline (90 mg) was dissolved in MeOH (5 mL). To the mixture was added a catalytic amount of Pd on carbon. A vacuum was applied and the reaction vessel containing the reaction mixture was back filled with hydrogen gas, three times. After the completion of the reaction, the mixture was filtered and the solid was rinsed with methanol. The filtrate was concentrated and purified by column chromatography to give the desired product (21.6 mg). LC-MS: m/z 301 (M+H$^+$).

2. General Procedure B

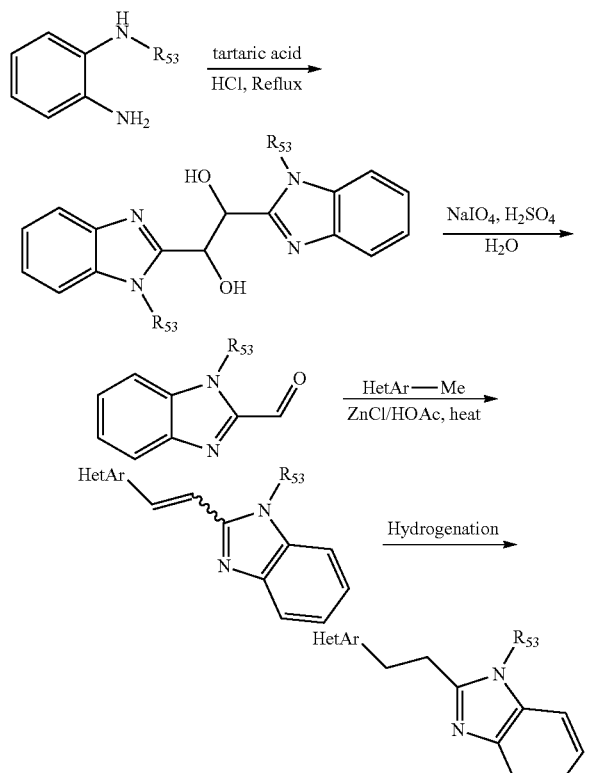

(a) 1,2-Bis(1-methyl-1H-benzo[d]imidazol-2-yl)ethane-1,2-diol

N-Methylbenzene-1,2-diamine (13.5 g, 85.4 mmol) and tartaric acid (6.4 g, 42.6 mmol) were dissolved in 4 N aqueous HCl (100 mL), and the solution was stirred at reflux overnight. After cooling to room temperature, the precipitate was collected by vacuum filtration and re-dissolved in water (200 mL), and the pH of the resulting mixture was adjusted to 8 with aqueous NH$_4$OH solution. The precipitate was collected by vacuum filtration and dried to give 6.86 g of the desired product, which was used for the next step without further purification. LC-MS: m/z 323 (M+H$^+$).

(b) 1-Methyl-1H-benzo[d]imidazole-2-carbaldehyde

To a solution of 1,2-bis(1-methyl-1H-benzo[d]imidazol-2-yl)ethane-1,2-diol (4.9 g, 15.2 mmol) and NaIO$_4$ (3.3 g, 15.2 mmol) in water (150 mL) was added 3 N aqueous H$_2$SO$_4$ (18 mL) dropwise. After stirring at ambient temperature overnight, the mixture was adjusted to pH 8 with aqueous Na$_2$CO$_3$. The precipitate was collected by vacuum filtration and washed with water and ethanol. The solid was dried to give 3.11 g of the desired product. LC-MS: m/z 161 (M+H$^+$).

(c) 2-((E,Z)-2-(1-Methyl-1H-benzo[d]imidazol-2-yl)vinyl)quinazolin-4(3H)-one

The title compound was prepared from 1-methyl-1H-benzo[d]imidazole-2-carbaldehyde and 2-methylquinazolin-4(3H)-one according to General Procedure A-(c). LC-MS: m/z 303 (M+H$^+$).

(d) 2-(2-(1-Methyl-1H-benzo[d]imidazol-2-yl)ethyl)quinazolin-4(3H)-one

The title compound was prepared from 2-((E,Z)-2-(1-methyl-1H-benzo[d]imidazol-2-yl)vinyl)quinazolin-4(3H)-one according to General Procedure A-(d). LC-MS: m/z 305.1 (M+H$^+$).

3. General Procedure C

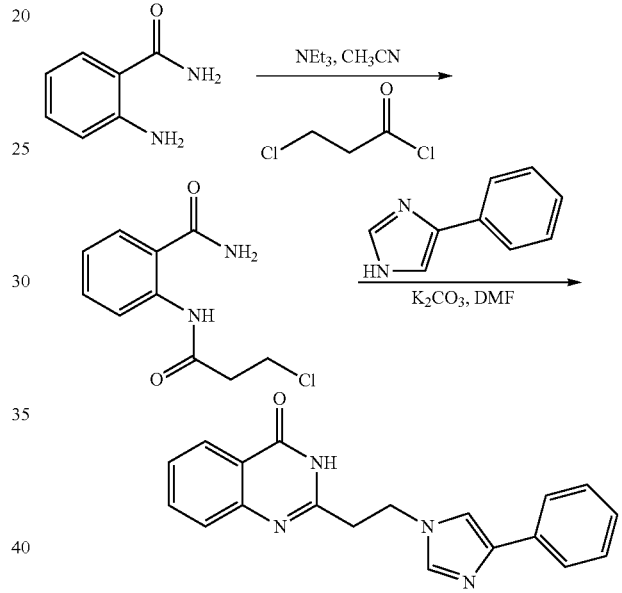

(a) 2-(3-Chloropropanamido)benzamide

To a solution of 2-aminobenzamide (500 mg, 3.68 mmol) and triethylamine (NEt$_3$) (450 mg, 4.41 mmol) in CH$_3$CN (30 mL) was added 3-chloropropanoyl chloride (0.45 mL, 4.41 mmol) dropwise at room temperature. After stirring overnight, the reaction mixture was concentrated to give the desired product (800 mg) as solid, which was used for the next step without further purification. LC-MS: m/z 227 (M+H$^+$).

(b) 2-(2-(4-Phenyl-1H-imidazol-1-yl)ethyl)quinazolin-4(3H)-one

A solution of 4-phenyl-1H-imidazole (500 mg, 3.47 mmol), 2-(3-chloropropanamido)benzamide (1.17 g, 5.21 mmol) and K$_2$CO$_3$ (717 mg, 5.20 mmol) in DMF (50 mL) was stirred at 110° C. overnight. After cooling to room temperature, the reaction mixture was diluted with water (200 mL) and extracted with EtOAc (100 mL×3). The organic layer was dried over Na$_2$SO$_4$, filtered and concentrated. The resulting product was washed with EtOAc and filtered to give the desired product (60 mg). LC-MS: m/z 317 (M+H$^+$).

4. General Procedure D

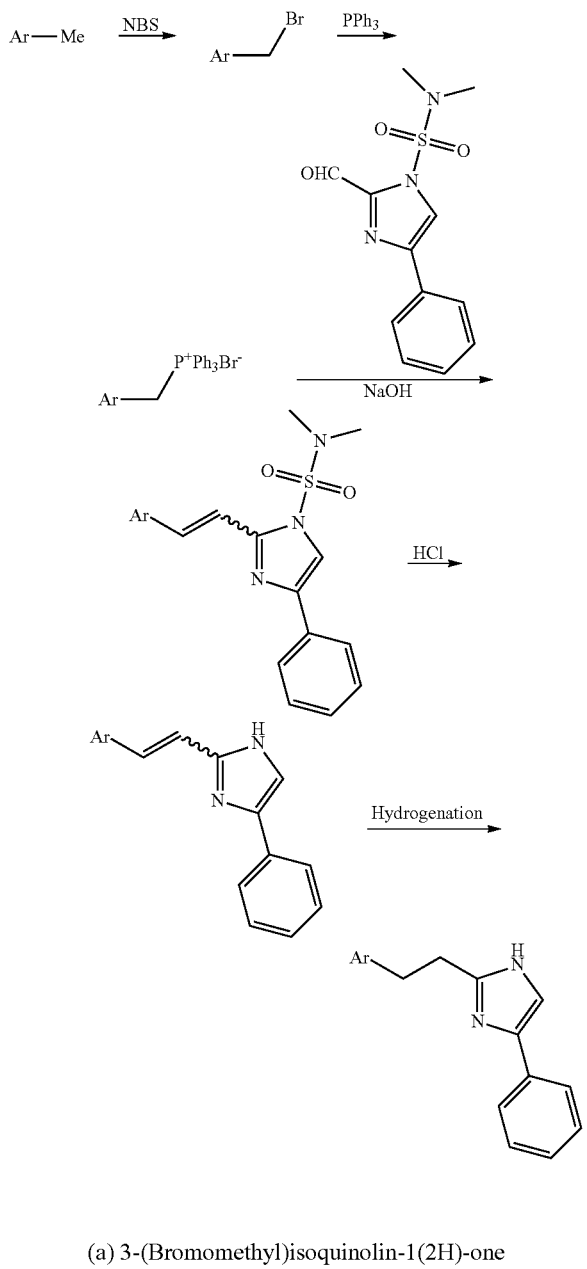

(a) 3-(Bromomethyl)isoquinolin-1(2H)-one

To a refluxing solution of 3-methylisoquinolin-1(2H)-one (1.7 g, 10.69 mmol) and 2-(4-biphenyl)-5-phenyloxazole (120 mg) in $CCl_4$ (30 mL) was added N-bromosuccinimide (1.9 g, 10.7 mmol) in portions. The reaction mixture was stirred at reflux for 2 h. After cooling to room temperature, the reaction mixture was diluted with EtOAc, filtered and concentrated to give the crude product, which was used for the next step without further purification. LC-MS: m/z 238 (M+H$^+$).

(b) ((1-oxo-1,2-dihydroisoquinolin-3-yl)methyl)triphenylphosphonium bromide

A solution of 3-(bromomethyl)isoquinolin-1(2H)-one and PPh$_3$ (1.8 g, 6.87 mmol) in 1,4-dioxane (50 mL) was refluxed for 2 h. After cooling to room temperature, the reaction mixture was filtered to give the desired product (317 mg). LC-MS: m/z 420 (M+H$^+$).

(c) (E,Z)-N,N-Dimethyl-2-(2-(1-oxo-1,2-dihydroisoquinolin-3-yl)vinyl)-4-phenyl-1H-imidazole-1-sulfonamide 2-Formyl-N,N-dimethyl-4-phenyl-1H-imidazole-1-sulfonamide (210 mg, 0.753 mmol) and ((1-oxo-1,2-dihydroisoquinolin-3-yl)methyl)triphenylphosphonium bromide (317 mg, 0.635 mmol) were dissolved in CHCl$_3$ (10 mL). Sodium hydroxide solution (2 mL, 50% w/w in H$_2$O) was added dropwise over 5 minutes and the resulting solution was stirred at room temperature for 0.5 h before diluting with H$_2$O (30 mL). The mixture was washed with CHCl$_3$ (50 mL×2), and the organic layer was dried over Na$_2$SO$_4$ and filtered. The filtrate was concentrated and purified by column chromatography to give the desired product (80 mg). LC-MS: m/z 421 (M+H$^+$).

(d) (E,Z)-3-(2-(4-Phenyl-1H-imidazol-2-yl)vinyl)isoquinolin-1(2H)-one

A solution of (E,Z)-N,N-dimethyl-2-(2-(1-oxo-1,2-dihydroisoquinolin-3-yl)vinyl)-4-phenyl-1H-imidazole-1-sulfonamide (80 mg, 0.19 mmol) and HCl (37% in water, 0.1 mL) in 1,4-dioxane (3 mL) was stirred at 90° C. for 2 h. After cooling to room temperature, the reaction mixture was filtered to give the desired product (40 mg). LC-MS: m/z 314 (M+H$^+$).

(e) 3-(2-(4-Phenyl-1H-imidazol-2-yl)ethyl)isoquinolin-1(2H)-one

The title compound was prepared according to General Procedure A-(d). LC-MS: m/z 316 (M+H$^+$).

5. General Procedure E

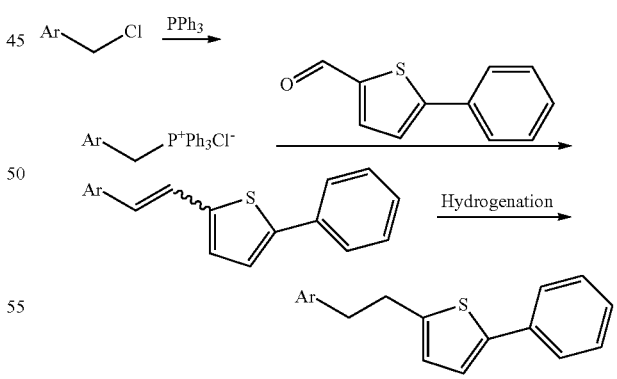

(a) ((4-Oxo-3,4-dihydroquinazolin-2-yl)methyl)triphenylphosphonium chloride was prepared according to General Procedure D-(b). LC-MS: m/z 421 (M+H$^+$). (b) (E,Z)-2-(2-(5-Phenylthiophen-2-yl)vinyl)quinazolin-4(3H)-one was prepared according to General Procedure D-(c). LC-MS: m/z 331 (M+H$^+$). (c) 2-(2-(5-Phenylthiophen-2-yl)ethyl)quinazolin-4(3H)-one was prepared according to General Procedure D-(e). LC-MS: m/z 333 (M+H$^+$).

6. General Procedure F

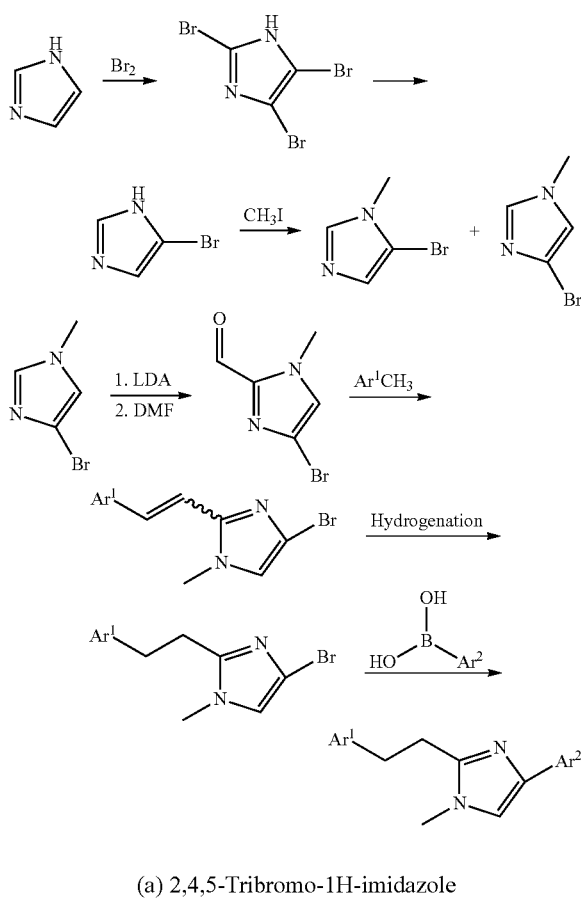

(a) 2,4,5-Tribromo-1H-imidazole

To a solution of imidazole (60 g, 0.88 mol) in chloroform (360 mL) was added bromine (138 g, 1 mol) in chloroform (100 mL) dropwise at room temperature. Then the mixture was stirred for 1 h. After removing the solvent, the residue was suspended in hot water, filtered and dried in vacuo to provide 64 g of the desired product as a white solid. GC-MS: 304 (M+).

(b) 5-Bromo-1H-imidazole 2,4,5-Tribromo-1H-imidazole (32 g, 0.105 mol) was refluxed with 20% aqueous sodium sulphite solution (66.34 g, 0.527 mol) for 8 h. The solid product precipitated upon cooling and was collected by vacuum filtration to yield 12.5 g of the desired product. LC-MS: 147, 149 (M+H$^+$).

(c) 4-Bromo-1-methyl-1H-imidazole

To a solution of 5-bromo-1H-imidazole (70 g, 0.48 mol) in THF (220 mL) in an ice bath was added 25% NaOH (70 mL). MeI (81 g, 0.57 mol) was then added dropwise at 7-8° C. The mixture was stirred at ambient temperature for 5 min, and then the solvent was removed under reduced pressure. The title compound (15 g) was obtained by fractional distillation. GC-MS: 160 (M+).

(d) 4-Bromo-1-methyl-1H-imidazole-2-carbaldehyde

The title compound was prepared according to General Procedure A-(b). GC-MS: 188 (M+).

(e) 2-((E,Z)-2-(4-Bromo-1-methyl-1H-imidazol-2-yl)vinyl)quinoline

The title compound was prepared according to General Procedure A-(c). LC-MS: m/z 314 (M+H$^+$).

(f) 2-(2-(4-Bromo-1-methyl-1H-imidazol-2-yl)ethyl)quinoline

To a solution of 2-((E,Z)-2-(4-bromo-1-methyl-1H-imidazol-2-yl)vinyl)quinoline (8.3 g, 26.4 mmol) in MeOH (150 mL) and THF (150 mL) was added 1 g of Raney-Ni catalyst and the mixture was stirred under hydrogen atmosphere for 2 h. The catalyst was then filtered off and the filtrate was concentrated and purified by column chromatography to afford 3.8 g of the desired product as a solid. LC-MS: m/z 316 (M+H$^+$).

(g) 2-(2-(1-Methyl-4-(thiophen-3-yl)-1H-imidazol-2-yl)ethyl)quinoline

A suspension of 2-(2-(4-bromo-1-methyl-1H-imidazol-2-yl)ethyl)quinoline (0.31 g, 0.980 mmol), thiophen-3-ylboronic acid (0.25 g, 1.960 mmol), and Pd(PPh$_3$)$_4$ (0.022 g, 0.441 mmol) in 1,4-dioxane (6 mL) under N$_2$ was stirred at room temperature for 0.5 h and then Na$_2$CO$_3$ (0.3105 g, 2.94 mmol) in water (1 mL) was added. The mixture was refluxed overnight. The mixture was then cooled to room temperature and partitioned between water and ethyl acetate (EtOAc). The separated organic layer was dried, filtered, and concentrated under reduced pressure. The residue was purified by column chromatography to afford 55.6 mg of the desired compound. LC-MS: m/z 320 (M+H$^+$).

7. General Procedure G

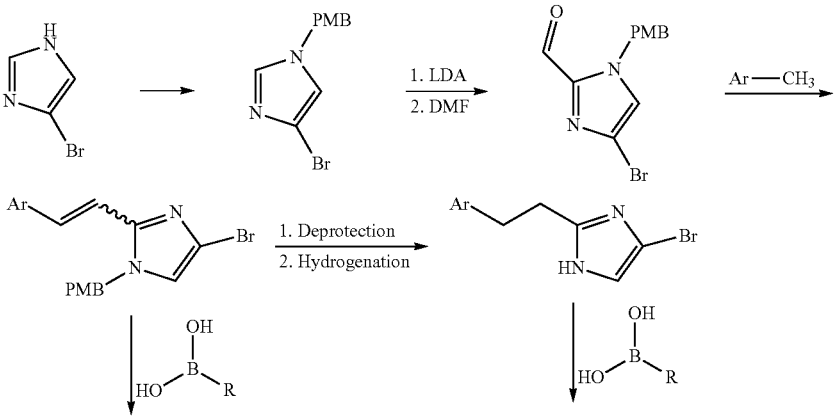

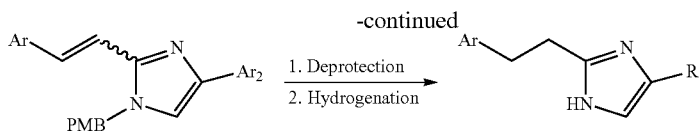

(a) 1-(4-Methoxybenzyl)-4-bromo-1H-imidazole

To a suspension of 5-bromo-1H-imidazole (10 g, 68.5 mmol) and $K_2CO_3$ (37.8 g, 274 mmol) in DMF (100 mL) was added 1-(chloromethyl)-4-methoxybenzene (11.8 g, 75.4 mmol) dropwise at room temperature. The resulting mixture was stirred for 16 hours, and then dichloromethane (DCM) was added. The mixture was successively washed with water and brine, dried and concentrated to give a residue that was purified by column chromatography to afford 12.3 g of the desired compound as a solid. LC-MS: m/z 267 (M+H$^+$).

(b) 1-(4-Methoxybenzyl)-4-bromo-1H-imidazole-2-carbaldehyde

The title compound was prepared according to General Procedure A-(b). LC-MS: m/z 295 (M+H$^+$).

(c) 24(E,Z)-2-(1-(4-Methoxybenzyl)-4-bromo-1H-imidazol-2-yl)vinyl)quinoline

The title compound was prepared according to General Procedure A-(c). LC-MS: m/z 420 (M+H$^+$).

(d) 2-((E,Z)-2-(4-Bromo-1H-imidazol-2-yl)vinyl)quinoline

A solution of 2-((E,Z)-2-(1-(4-methoxybenzyl)-4-bromo-1H-imidazol-2-yl)vinyl)quinoline (8.5 g, 0.02 mol) in $CH_3SO_3H$ (70 mL) was refluxed overnight. After cooling to room temperature, the reaction mixture was diluted with water (200 mL) and the pH was adjusted to 8-9 with aqueous $Na_2CO_3$. The resulting solid was filtered and purified by column chromatography to afford the desired product (4.3 g). LC-MS: m/z 300 (M+H$^+$).

(e) 2-(2-(4-Bromo-1H-imidazol-2-yl)ethyl)quinoline

The title compound was prepared according to General Procedure F-(f). LC-MS: m/z 302 (M+H$^+$).

(f) 2-(2-(4-(Pyridin-4-yl)-1H-imidazol-2-yl)ethyl)quinoline

The title compound was synthesized according to General Procedure F-(g). LC-MS: m/z 301 (M+H$^+$).

8. General Procedure H

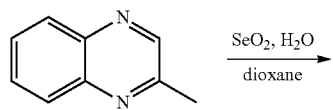

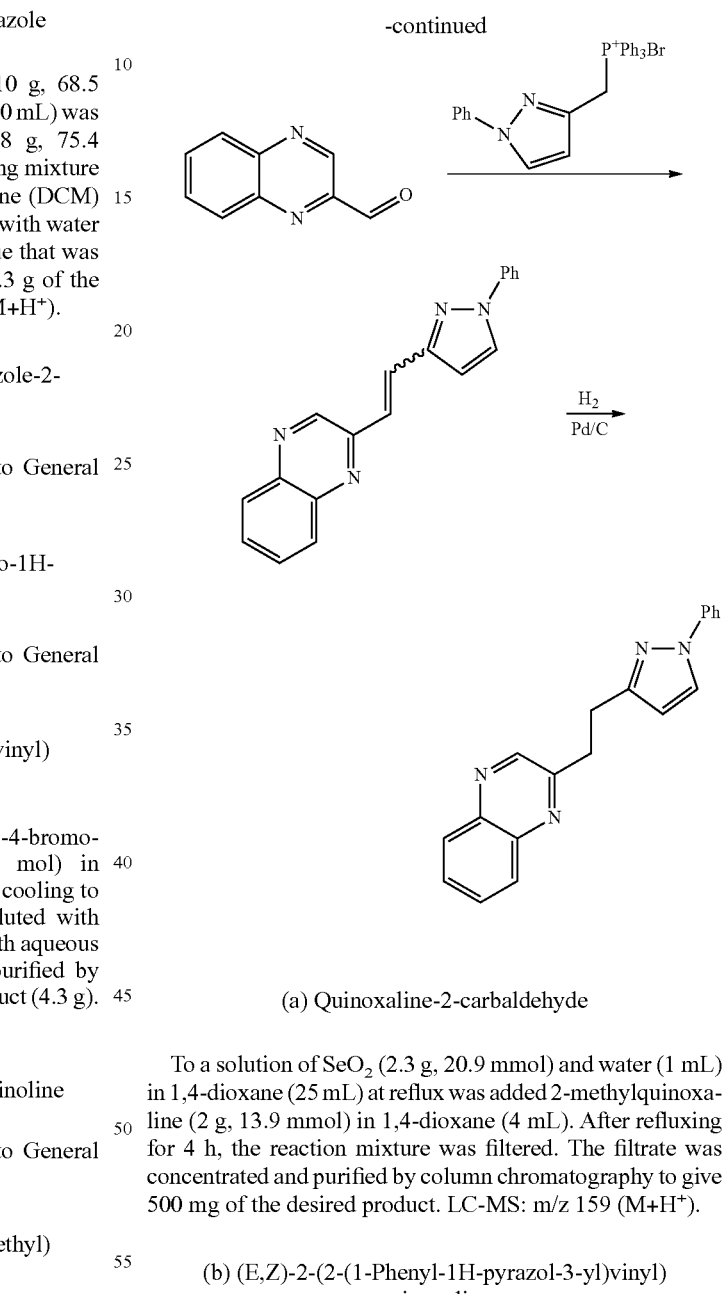

(a) Quinoxaline-2-carbaldehyde

To a solution of $SeO_2$ (2.3 g, 20.9 mmol) and water (1 mL) in 1,4-dioxane (25 mL) at reflux was added 2-methylquinoxaline (2 g, 13.9 mmol) in 1,4-dioxane (4 mL). After refluxing for 4 h, the reaction mixture was filtered. The filtrate was concentrated and purified by column chromatography to give 500 mg of the desired product. LC-MS: m/z 159 (M+H$^+$).

(b) (E,Z)-2-(2-(1-Phenyl-1H-pyrazol-3-yl)vinyl)quinoxaline

The title compound was synthesized according to General Procedure D-(c). LC-MS: m/z 299 (M+H$^+$).

(c) 2-(2-(1-Phenyl-1H-pyrazol-3-yl)ethyl)quinoxaline

The title compound was synthesized according to General Procedure A-(d). LC-MS: m/z 301 (M+H$^+$).

9. General Procedure I

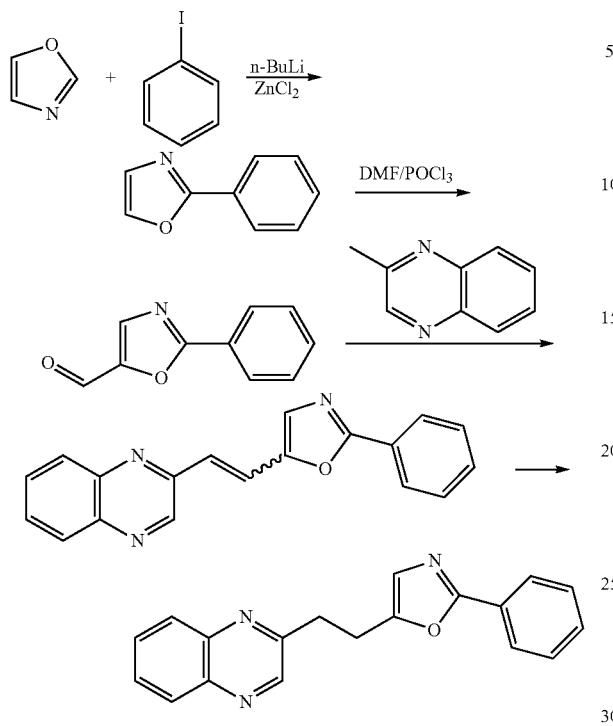

(a) 2-Phenyloxazole

To a solution of oxazole (0.5 g, 7 mmol) in anhydrous THF (10 mL) was added n-BuLi (3.5 mL, 8.8 mmol) dropwise at −65° C. After stirring for 10 min, anhydrous ZnCl$_2$ (2 g, 14.7 mmol) was added. The reaction mixture was allowed to warm to room temperature. Then Pd(PPh$_3$)$_4$ (0.3 g, 0.26 mmol) and iodobenzene (2 g, 9.8 mmol) were added. The reaction mixture was heated at 60° C. for 1 h. After quenching with water (20 mL), the solution was extracted with EtOAc (20 mL×3). The combined organic layers were dried over Na$_2$SO$_4$ and filtered. The filtrate was concentrated and purified by column chromatography to give 600 mg of the desired product. LC-MS: m/z 146 (M+H$^+$).

(b) 2-Phenyloxazole-5-carbaldehyde

To a 50 mL flask charged with DMF (5 mL) was added POCl$_3$ (0.7 g, 4.6 mmol) dropwise at 0° C. After stirring for 10 min, a solution of 2-phenyloxazole (0.6 g, 4.1 mmol) in DMF (5 mL) was added dropwise. The reaction mixture was heated to 100° C. and stirred for 48 h. After cooling to room temperature, the reaction mixture was poured into ice water and the pH was adjusted to 10 with 10% aqueous NaOH. The aqueous mixture was extracted with EtOAc (20 mL×3). The combined organic layers were dried over Na$_2$SO$_4$ and filtered. The filtrate was concentrated and purified by column chromatography to give 240 mg of the desired product. LC-MS: m/z 174 (M+H$^+$).

(c) (E,Z)-2-Phenyl-5-(2-(quinoxalin-2-yl)vinyl)oxazole

The title compound was prepared according to General Procedure A-(c). LC-MS: m/z 300 (M+H$^+$).

(d) 2-Phenyl-5-(2-(quinoxalin-2-yl)ethyl)oxazole

The title compound was prepared according to General Procedure A-(d). LC-MS: m/z 302 (M+H$^+$).

10. General Procedure J

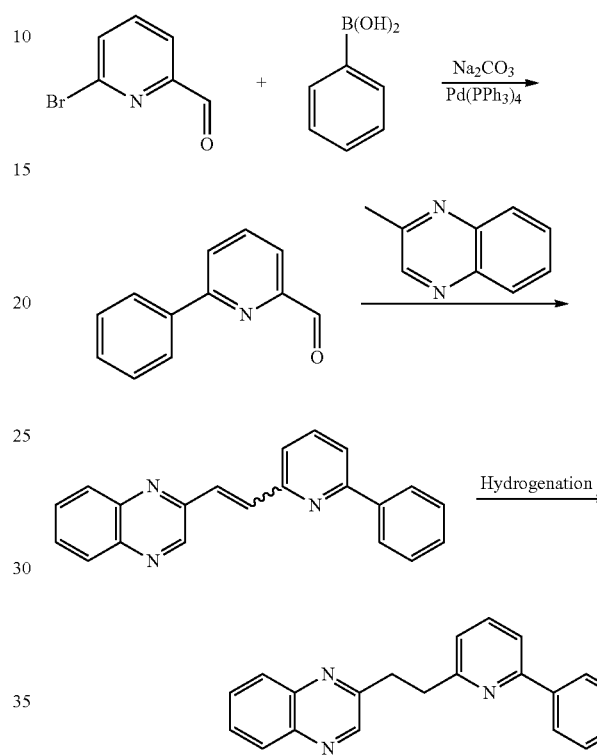

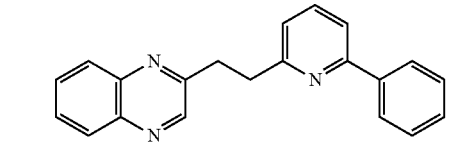

(a) 6-Phenylpicolinaldehyde was prepared according to General Procedure F-(g). GC-MS: 183 (M$^+$). (b) (E,Z)-2-(2-(6-Phenylpyridin-2-yl)vinyl)quinoxaline was prepared according to General Procedure A-(c). LC-MS: m/z 310 (M+H$^+$). (c) 2-(2-(6-Phenylpyridin-2-yl)ethyl)quinoxaline was prepared according to General Procedure A-(d). LC-MS: m/z 312 (M+H$^+$).

11. General Procedure K

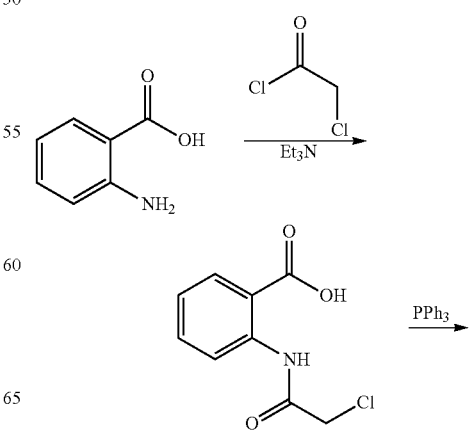

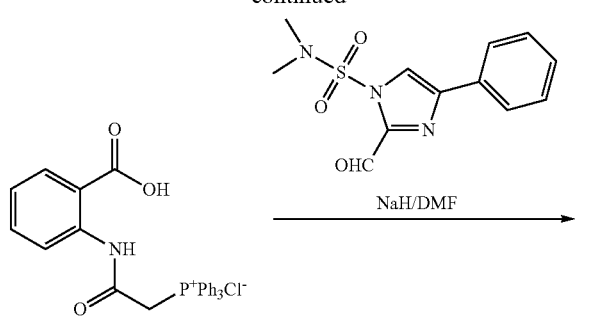
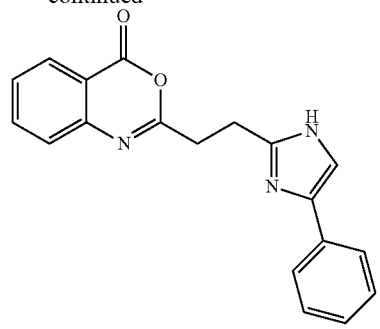

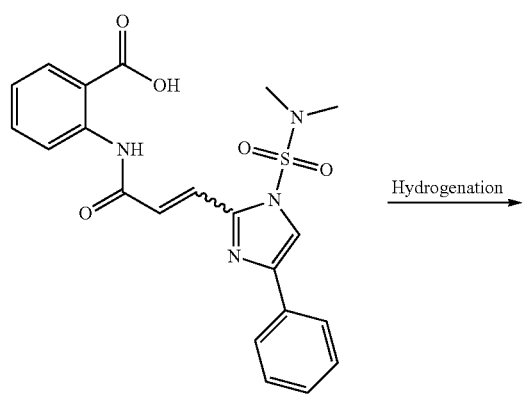

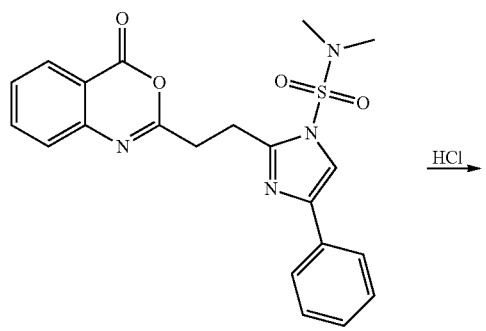

(a) 2-(2-Chloroacetamido)benzoic acid

The title compound was synthesized according to General Procedure C-(a). LC-MS: m/z 214 (M+H$^+$).

(b) (2-(2-Carboxyphenylamino)-2-oxoethyl)triphenylphosphonium chloride

The title compound was prepared according to General Procedure D-(b). LC-MS: m/z 440 (M+H$^+$).

(c) (E,Z)-2-(3-(1-(N,N-Dimethylsulfamoyl)-4-phenyl-1H-imidazol-2-yl)acrylamido)benzoic acid The title compound was prepared according to General Procedure D-(c). LC-MS: m/z 441 (M+H$^+$).

(d) 2-(3-(1-(N,N-Dimethylsulfamoyl)-4-phenyl-1H-imidazol-2-yl)propanamido)benzoic acid The title compound was prepared according to General Procedure A-(d). LC-MS: m/z 443 (M+H$^+$).

(e) N,N-Dimethyl-2-(2-(4-oxo-4H-benzo[d][1,3]oxazin-2-yl)ethyl)-4-phenyl-1H-imidazole-1-sulfonamide A solution of 2-(3-(1-(N,N-dimethylsulfamoyl)-4-phenyl-1H-imidazol-2-yl)propanamido)benzoic acid (150 mg, 0.339 mmol) in Ac$_2$O (10 mL) was stirred at reflux for 5 h. The reaction mixture was then concentrated to give a white solid (100 mg), which was used for the next step without further purification. LC-MS: m/z 425 (M+H$^+$).

(f) 2-(2-(4-Phenyl-1H-imidazol-2-yl)ethyl)-4H-benzo[d][1,3]oxazin-4-one

The title compound was prepared according to General Procedure D-(d). LC-MS: m/z 318 (M+H$^+$).

12. General Procedure L

General Procedure L-1

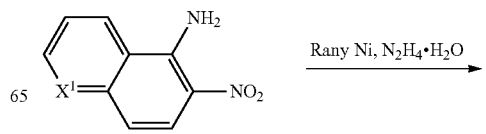

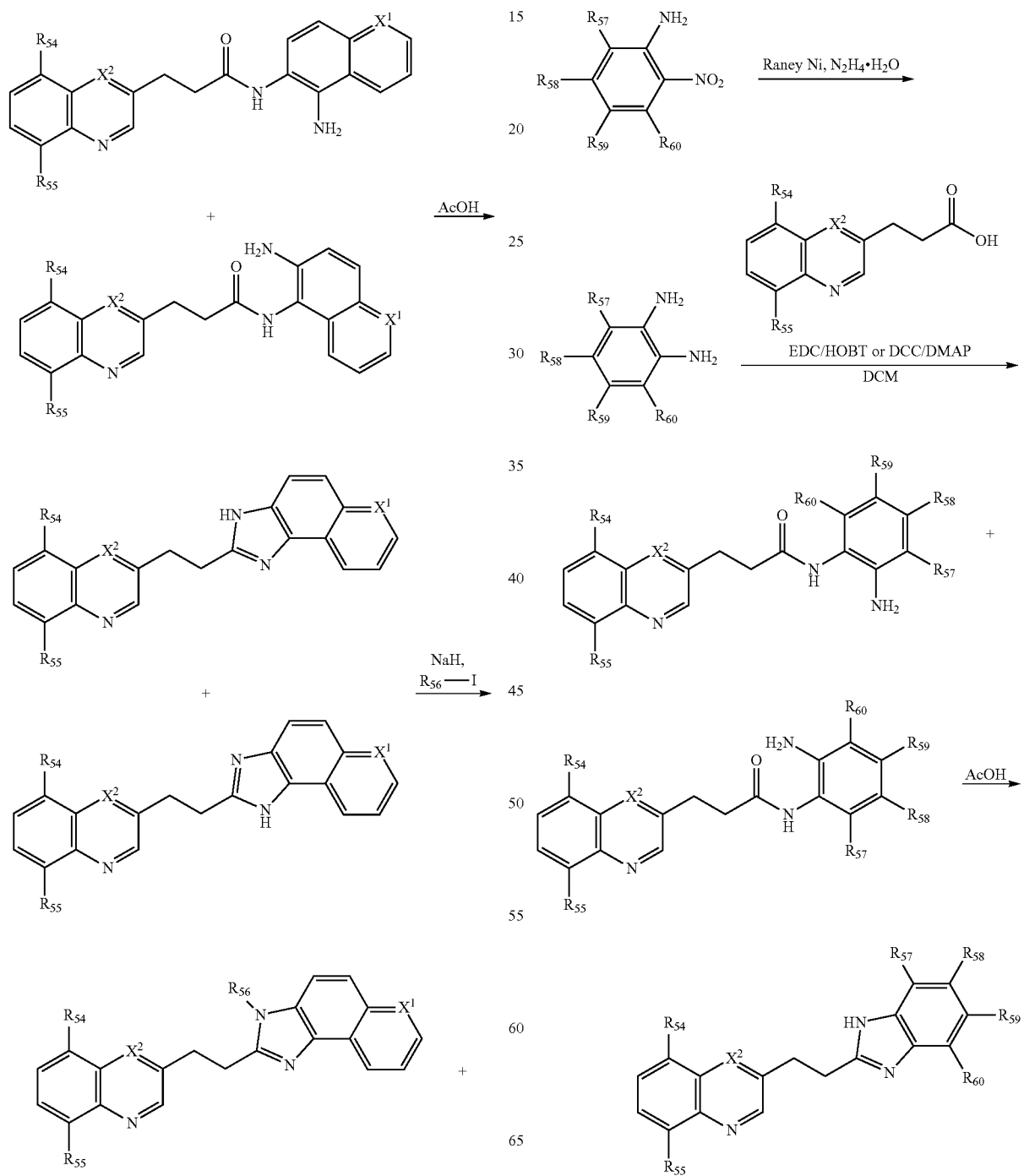
General Procedure L-2

(a) Quinoline-5,6-diamine

To a solution of 5-amine-6-nitroquinoline (500 mg, 2.7 mmol) in ethanol (20 mL) was added hydrazine hydrate (200 mg, 4 mmol) at room temperature. Then Raney Ni was added dropwise until the reaction mixture became clear. The mixture was filtered and the filtrate was collected and concentrated to obtain quinoline-5,6-diamine as a green solid (430 mg), which was used for the next step without further purification. MS (ESI) m/z 159 (M+H$^+$).

(b) N-(5-Aminoquinolin-6-yl)-3-(quinoxalin-2-yl) propanamide and N-(6-Aminoquinolin-5-yl)-3-(quinoxalin-2-yl)propanamide To a solution of 3-(quinoxalin-2-yl)propanoic acid (550 mg, 2.7 mmol) in DCM (30 mL) was added HOBt (550 mg, 4 mmol) and EDCI (780 mg, 4 mmol). After stirring for 30 minutes, quinoline-5,6-diamine (430 mg, 2.7 mmol) was added and the reaction was stirred for 3 hours. The mixture was washed with water (10 mL) and extracted with DCM (30 mL×3). The combined organic layers were dried over sodium sulfate, filtered, and concentrated to afford a yellow mixture which was purified by reverse phase chromatography. N-(5-Aminoquinolin-6-yl)-3-(quinoxalin-2-yl)propanamide (180 mg) and N-(6-aminoquinolin-5-yl)-3-(quinoxalin-2-yl)propanamide (80 mg) were isolated. MS (ESI) m/z 343 (M+H$^+$).

(c) 2-(2-(Quinoxalin-2-yl)ethyl)-3H-imidazo[4,5-f]quinoline

N-(5-Aminoquinolin-6-yl)-3-(quinoxalin-2-yl)propanamide (180 mg, 0.5 mmol) or N-(6-aminoquinolin-5-yl)-3-(quinoxalin-2-yl)propanamide (80 mg, 0.23 mmol) in acetic acid (5 mL or 2 mL, respectively) was heated to 60° C. and stirred for 2 hours. Excess acetic acid was removed under vacuum, and the residue was purified by column chromatography to afford 2-(2-(quinoxalin-2-yl)ethyl)-3H-imidazo[4,5-f]quinoline (150 mg) and 2-(2-(quinoxalin-2-yl)ethyl)-1H-imidazo[4,5-f]quinoline (60 mg). MS (ESI) m/z 325 (M+H$^+$).

(d) 3-Methyl-2-(2-(quinoxalin-2-yl)ethyl)-3H-imidazo[4,5-f]quinoline and 1-Methyl-2-(2-(quinoxalin-2-yl)ethyl)-1H-imidazo[4,5-f]quinoline To a solution of 2-(2-(quinoxalin-2-yl)ethyl)-3H-imidazo [4,5-f]quinoline (100 mg, 0.31 mmol) or 2-(2-(quinoxalin-2-yl)ethyl)-1H-imidazo[4,5-f]quinoline (60 mg, 0.18 mmol) in DMF (3 mL or 2 mL, respectively) cooled in an ice bath was added sodium hydride (12 mg, 0.31 mmol; or 7 mg, 0.18 mmol; respectively). After stirring for 30 minutes, iodomethane (44 mg, 0.31 mmol; or 25 mg, 0.18 mmol; respectively) was added and the mixture was stirred at room temperature for 2 hours. The reaction was quenched with water, washed with saturated sodium bicarbonate (10 mL), and extracted with DCM (20 mL×3). The combined organic layers were dried and concentrated to give a yellow solid as the free base. The free base may optionally be converted to a salt. For example, the free base was stirred in an HCl in methanol solution for 30 minutes to afford 3-methyl-2-(2-(quinoxalin-2-yl)ethyl)-3H-imidazo[4,5-f]quinoline hydrochloride (20 mg) or 1-methyl-2-(2-(quinoxalin-2-yl)ethyl)-M-imidazo[4,5-f]quinoline hydrochloride (25 mg) as a pale yellow solid.

13. General Procedure M

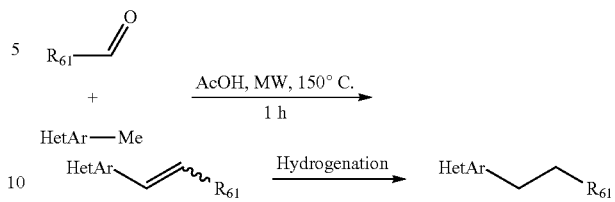

(a) (E/Z)-2-(2-(Benzo[d]oxazol-2-yl)vinyl)quinazolin-4 (3H)-one was prepared according to General Procedure A-(c) and heating in a microwave reactor. MS (ESI) m/z 290 (M+H$^+$). (b) 2-(2-(Benzo[d]oxazol-2-yl)ethyl)quinazolin-4 (3H)-one was prepared according to General Procedure A-(d) with methanol/THF as solvent. MS (ESI) m/z 292 (M+H$^+$).

14. Preparation of Aldehyde Intermediates

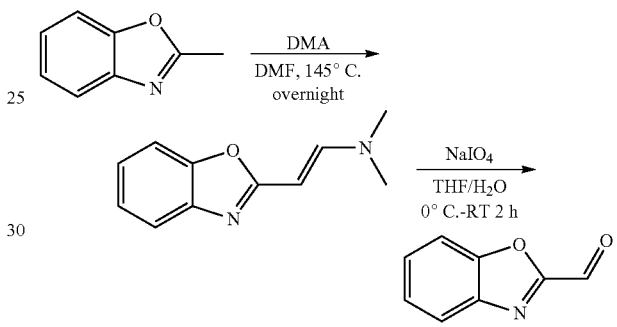

(a) (E)-2-(Benzo[d]oxazol-2-yl)-N,N-dimethylethenamine

A mixture of 2-methylbenzo[d]oxazole (3 g, 22.6 mmol) in DMF (3.2 g) and dimethyl acetamide (3.5 g, 29.3 mmol) was stirred under N$_2$ at 145° C. overnight. Then the solution was poured into ice-water and extracted with EtOAc (100 mL×2). The organic phase was washed, dried and concentrated. The residue was purified by column chromatography to get the title compound (2.2 g). MS (ESI) m/z 134 (M+H$^+$).

(b) Benzo[d]oxazole-2-carbaldehyde

To (E)-2-(benzo[d]oxazol-2-yl)-N,N-dimethylethenamine (1 g, 5.32 mmol) in THF (15 mL) at 0° C. was added water (15 mL) and NaIO$_4$ (3.4 g, 16 mmol). The resulting mixture was stirred at 0° C. for 10 min, then at room temperature for 2 h. To the solution was added H$_2$O and EtOAc and then the mixture was filtered. The clear solution was extracted with EtOAc and the organic phase was washed with aqueous NaHCO$_3$ solution. The organic phase was concentrated and the residue was purified by column chromatography to give the title compound (120 mg). MS (ESI) m/z 148 (M+H$^+$).

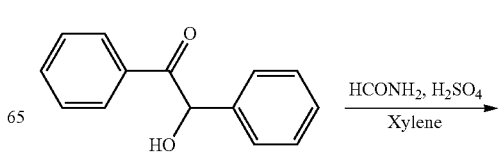

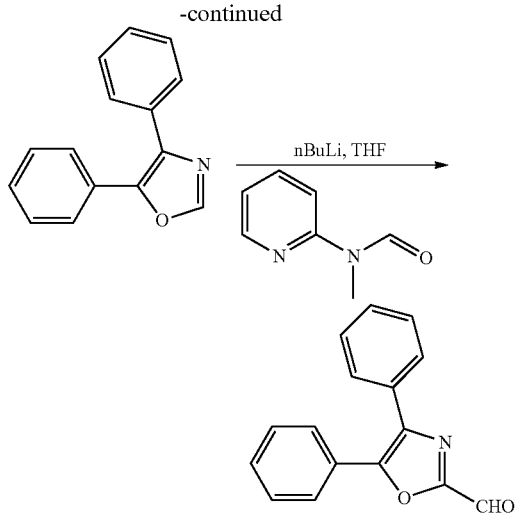

(c) 4,5-Diphenyloxazole

A mixture of benzoin (2.65 g, 12.5 mmol), formamide (10 mL), xylene (40 mL) and conc. H$_2$SO$_4$ (1 mL) was refluxed for 14 h with a dean-stark trap attached to remove water. After cooling to room temperature, water was added to the mixture. The organic layer was separated, washed, dried (with MgSO$_4$), and then distilled under reduced pressure to give 4,5-diphenyloxazole (1.93 g) as a yellow solid.

(d) 4,5-Diphenyloxazole-2-carbaldehyde n-BuLi (361 mg, 5.65 mmol) was added to a stirred and cooled (−78° C.) solution of 4,5-diphenyloxazole (500 mg, 2.26 mmol) in dry THF. The stirring was continued for 30 min at −78° C., and N-methyl-N-(pyridin-2-yl)formamide (461 mg, 3.39 mmol) was added. The resulting solution was stirred at −78° C. for 1 h, then quenched with H$_2$O. The mixture was extracted with EtOAc (3×20 mL), and the combined organic extracts were dried (MgSO$_4$) and concentrated. The crude product was purified by column chromatography to afford the desired product 4,5-diphenyloxazole-2-carbaldehyde (372 mg) as an orange oil.

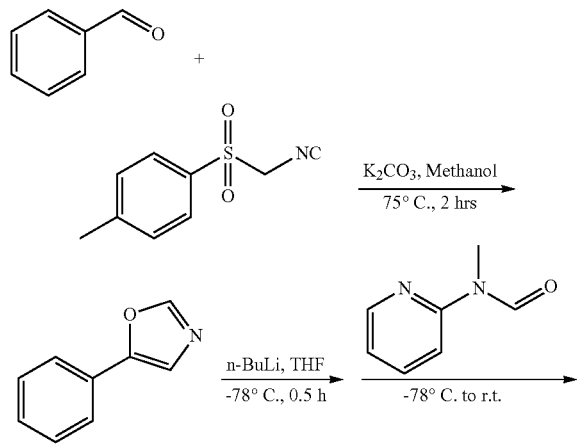

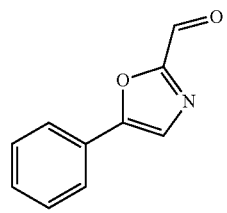

(e) 5-Phenyloxazole

A mixture of benzaldehyde (3 g, 28.3 mmol), 1-(isocyanomethylsulfonyl)-4-methylbenzene (5.5 g, 28.3 mmol) and K$_2$CO$_3$ (5.9 g, 42.5 mmol) in 60 mL methanol was refluxed for 2 h and then concentrated. 250 mL EtOAc was added and the mixture was washed with water and brine, dried, and concentrated to give 5-phenyl oxazole (3.4 g). MS (ESI) m/z 145 (M+H$^+$).

(f) 5-Phenyloxazole-2-carbaldehyde

The title compound was synthesized according to Synthetic Procedure 14-(d). MS (ESI) m/z 174 (M+H$^+$).

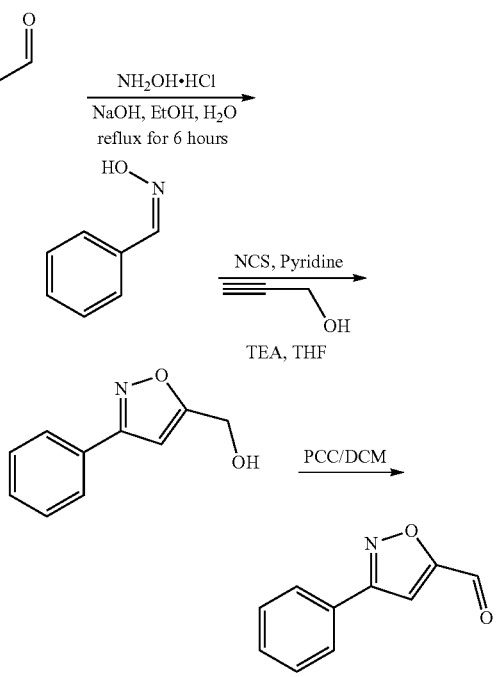

(g) (Z)-Benzaldehyde oxime

To a stirred solution of benzaldehyde (3 g, 28.3 mmol) in ethanol (50 mL) and water (30 mL), NH$_2$OH hydrochloride (3.9 g, 56.6 mmol) and sodium hydroxide (2.26 g, 56.6 mmol) were added. The mixture was heated at reflux for 6 hours. The resulting mixture was cooled to room temperature and extracted with EtOAc, and the organic layer was dried over anhydrous sodium sulfate. The solution was then concentrated under vacuum to give the title compound as an oil-like solid (3.4 g), which was used in the next step without further purification. MS (ESI) m/z 121 (M+H$^+$).

(h) (3-Phenylisoxazol-5-yl)methanol (Z)-Benzaldehyde oxime (3.4 g, 28.2 mmol) was dissolved in anhydrous THF (50 mL) and cooled to 0° C. N-Chlorosuccinimide (5.63 g, 42.3 mmol) and pyridine (221 mg, 2.8 mmol) were added and the mixture was stirred at room temperature for 1 hour. Prop-2-yn-1-ol (1.89 g, 33.4 mmol) and NEt₃ (286 mg, 2.8 mmol) were added and the mixture was heated at reflux for 2 hours. The reaction was cooled and quenched with water, extracted with EtOAc and dried over anhydrous sodium sulfate. The solution was concentrated under vacuum to give a crude product, which was purified by column chromatography to afford (3-phenylisoxazol-5-yl)methanol as a white solid (1.8 g).

(i) 3-Phenylisoxazole-5-carbaldehyde

To (3-phenylisoxazol-5-yl)methanol (0.9 g, 5.1 mmol) in DCM (10 mL) was added pyridinium chlorochromate (PCC) (2.1 g, 10.2 mmol) and the mixture was stirred at room temperature for 2 hours. The reaction was quenched with water, extracted with EtOAc and dried over anhydrous sodium sulfate. The solution was then concentrated under vacuum to give 3-phenylisoxazole-5-carbaldehyde as a light yellow solid (600 mg).

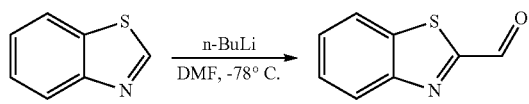

(j) Benzo[d]thiazole-2-carbaldehyde

To a solution of benzo[d]thiazole (1 g, 7 mmol) in DMF (10 mL) was added n-BuLi (8.4 mL, 21 mmol) over 15 min at −78° C. and the mixture was stirred at this temperature for 1 hour. The reaction was quenched with water, extracted with EtOAc and dried over anhydrous sodium sulfate. The solution was then concentrated under vacuum to give benzo[d]thiazole-2-carbaldehyde as a light yellow solid (500 mg).

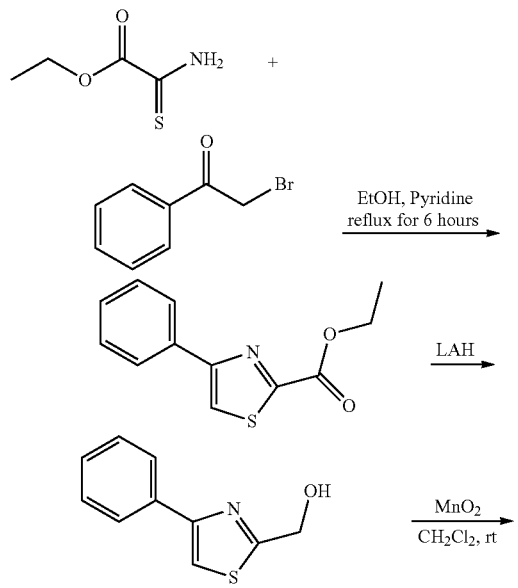

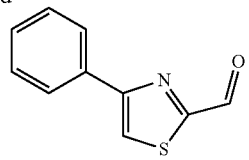

(k) Ethyl 4-phenylthiazole-2-carboxylate

To ethyl 2-amino-2-thioxoacetate (4 g, 30 mmol) in ethanol (50 mL) was added pyridine (0.24 g, 3 mmol). 2-Bromo-1-phenylethanone (5 g, 25 mmol) was added after 10 minutes and the mixture was then heated at reflux for 6 hours. The resulting mixture was washed with water and extracted with EtOAc and dried over anhydrous sodium sulfate. The solution was then concentrated under vacuum to give a crude product, which was purified by column chromatography to afford the title compound as a white solid (4.4 g). MS (ESI) m/z 233 (M+H⁺).

(l) (4-Phenylthiazol-2-yl)methanol

To ethyl 4-phenylthiazole-2-carboxylate (1 g, 4.3 mmol) in anhydrous THF was added LiAlH₄ and the mixture was stirred for 1 hour. The reaction was quenched with water, extracted with EtOAc and dried over anhydrous sodium sulfate. The solution was concentrated under vacuum to afford (4-phenylthiazol-2-yl)methanol as a white solid (0.9 g). MS (ESI) m/z 191 (M+H⁺).

(m) 4-Phenylthiazole-2-carbaldehyde

To (4-phenylthiazol-2-yl)methanol (900 mg, 4.7 mmol) in DCM (10 mL) was added MnO₂ (4 g, 47 mmol), and the mixture was stirred at room temperature for 3 hours. The reaction mixture was then filtered, washed with water, extracted with EtOAc and dried over anhydrous sodium sulfate. The solution was concentrated under vacuum to give a crude product, which was purified by column chromatography to afford the title compound as a yellow solid (360 mg).

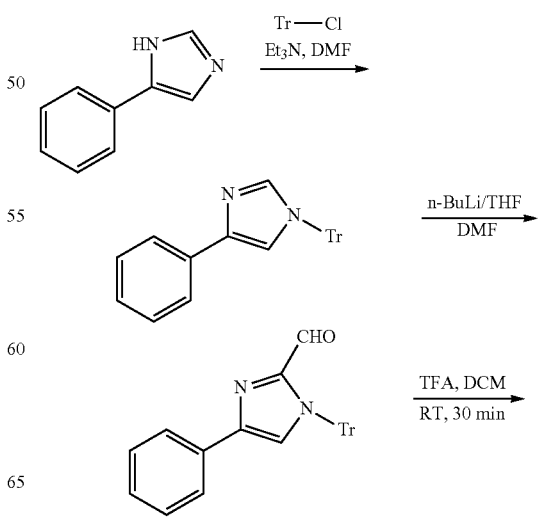

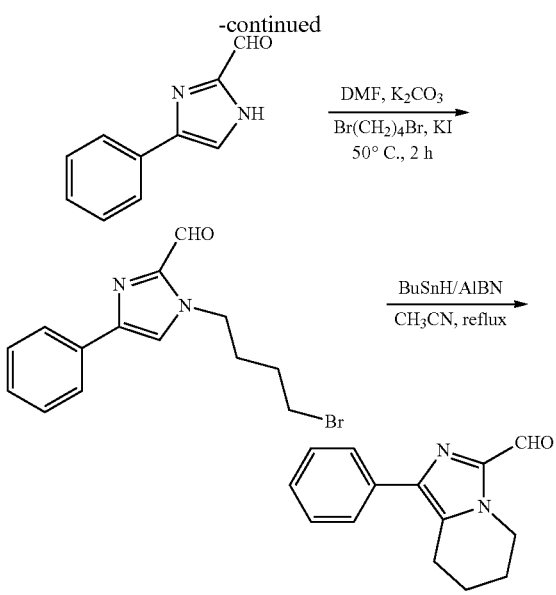

(n) 4-Phenyl-1-trityl-1H-imidazole

A solution of 5-phenyl-1H-imidazole (504 mg, 3.5 mmol) in DMF (10 mL) was cooled to 0° C., and then NEt₃ (530 mg, 5.25 mmol) was added, followed by the addition of (chloromethanetriyl)tribenzene (1.17 g, 4.2 mmol) in small portions. The resulting slurry was stirred at room temperature for 2 hours. The mixture was poured into ice-water (50 mL) and stirred until the ice melted. The resulting precipitate was collected and dissolved in DCM (100 mL). The solution was dried over sodium sulfate, filtered, concentrated and then purified by column chromatography to obtain 4-phenyl-1-trityl-1H-imidazole as a white solid (1.0 g). MS (ESI): m/z 387 (M+H)⁺.

(o) 4-Phenyl-1-trityl-1H-imidazole-2-carbaldehyde

The title compound was prepared according to Synthetic Procedure 14-(j). MS (ESI): m/z 415 (M+H)⁺.

(p) 4-Phenyl-1H-imidazole-2-carbaldehyde

To a solution of 4-phenyl-1-trityl-1H-imidazole-2-carbaldehyde (414 mg, 1 mmol) in DCM (10 mL) was added 2,2,2-trifluoroacetic acid (1 mL). After stirring at room temperature for 30 minutes, the solvent was removed in vacuo. The resulting residue was diluted with DCM (50 mL) and saturated sodium bicarbonate (50 mL). The aqueous layer was extracted with DCM (2×50 mL). The combined organic layers were dried over sodium sulfate, filtered, concentrated and then purified by column chromatography to give 4-phenyl-1H-imidazole-2-carbaldehyde as a white solid (160 mg). MS (ESI): m/z 173 (M+H)⁺.

(q) 1-(4-Bromobutyl)-4-phenyl-1H-imidazole-2-carbaldehyde

A mixture of 4-phenyl-1H-imidazole-2-carbaldehyde (1.79 g, 10.4 mmol), potassium carbonate (2.87 g, 20.8 mmol), potassium iodide (2.94 g, 17.7 mmol) and 1,4-dibromobutane (4.49 g, 20.8 mmol) in dry DMF (35 mL) were heated to 50° C. and stirred for 4 hours. The mixture was poured into ice-water (100 mL), and washed with EtOAc (2×80 mL). The combined organic layers were washed with brine (2×100 mL). The organic layer was dried over sodium sulfate, filtered, concentrated and then purified by column chromatography to give 1-(4-bromobutyl)-4-phenyl-1H-imidazole-2-carbaldehyde as a colorless oil (2.1 g). MS (ESI): m/z 308 (M+H)⁺.

(r) 1-Phenyl-5,6,7,8-tetrahydroimidazo[1,5-a]pyridine-3-carbaldehyde

A solution of 1-(4-bromobutyl)-4-phenyl-1H-imidazole-2-carbaldehyde (918 mg, 3 mmol) in dry acetonitrile (300 mL) was heated at reflux. (E)-2,2'-(Diazene-1,2-diyl)bis(2-methylbutanenitrile) (AIBN) (288 mg, 1.5 mmol) was added followed by addition of tributylstannane (1.93 g, 6.6 mmol) over the course of 2 hours. An additional aliquot of AIBN (288 mg, 1.5 mmol) was added 1 hour after the start of the reaction. The mixture was stirred under reflux for 2 hours. Acetonitrile was removed under reduced pressure. The obtained residue was purified by column chromatography to give 1-phenyl-5,6,7,8-tetrahydroimidazo[1,5-a]pyridine-3-carbaldehyde as a white solid (250 mg). MS (ESI): m/z 227 (M+H)⁺.

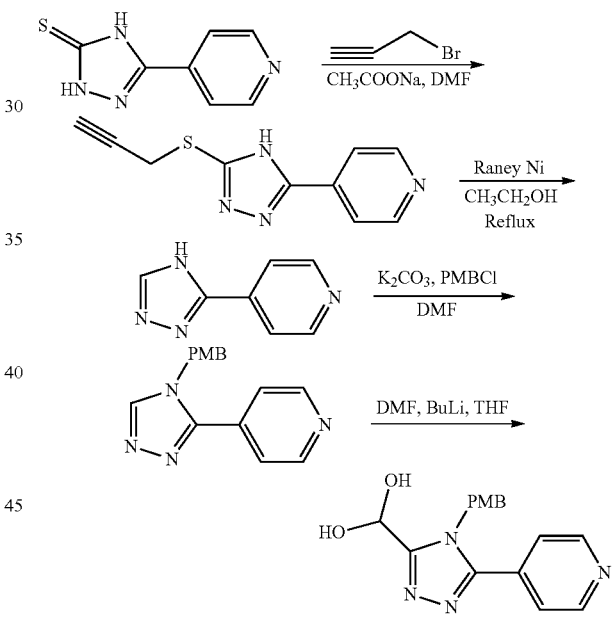

(s) 4-(5-(Prop-2-ynylthio)-4H-1,2,4-triazol-3-yl)pyridine

A mixture of 3-(pyridin-4-yl)-1H-1,2,4-triazole-5(4H)-thione (2 g, 11.2 mmol), 3-bromoprop-1-yne (1.47 g, 12.3 mmol) and sodium acetate (5.34 g, 65.1 mmol) in DMF (20 mL) was stirred for 6 h at room temperature. The reaction mixture was then poured into water (50 mL) and extracted with DCM. The combined organic layers were washed with water three times, dried with Na₂SO₄, filtered and concentrated to obtain the title compound (1.5 g).

(t) 4-(4H-1,2,4-Triazol-3-yl)pyridine

A mixture of 4-(5-(prop-2-ynylthio)-4H-1,2,4-triazol-3-yl)pyridine (1.6 g, 7.4 mmol) and Raney Ni in ethanol (30 mL) was stirred at reflux for 8 h. The reaction mixture was then filtered through a Celite pad and the solution was concentrated to obtain the crude compound. The crude product was purified by column chromatography to give 4-(4H-1,2,4-triazol-3-yl)pyridine (0.4 g).

(u) 4-(4-(4-Methoxybenzyl)-4H-1,2,4-triazol-3-yl)pyridine

A mixture of 4-(4H-1,2,4-triazol-3-yl)pyridine (0.56 g, 3.8 mmol), PMBCl (0.66 g, 4.2 mmol), and $K_2CO_3$ (2.12 g, 15.3 mmol) in DMF (10 mL) was stirred for 4 h at room temperature. The reaction mixture was then diluted with water and extracted with DCM. The combined organic layers were washed with water three times, dried with $Na_2SO_4$, filtered and concentrated. The crude product was purified by column chromatography to give 4-(4-(4-methoxybenzyl)-4H-1,2,4-triazol-3-yl)pyridine (0.60 g).

(v) (4-(4-Methoxybenzyl)-5-(pyridin-4-yl)-4H-1,2,4-triazol-3-yl)methanediol

The title compound was prepared according to Synthetic Procedure 14-(j).

15. 2-(2-(Quinoxalin-2-yl)ethyl)benzo[d]thiazole

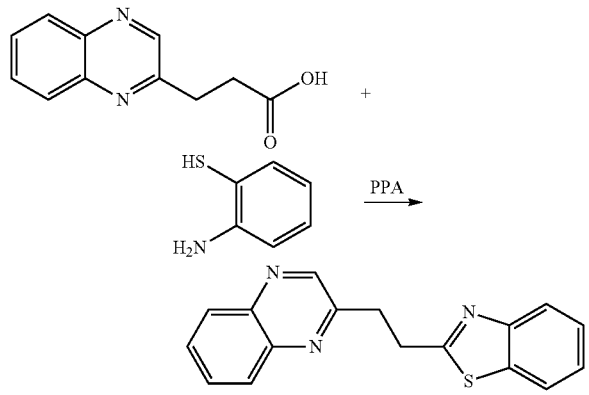

A mixture of 3-(quinoxalin-2-yl)propanoic acid (530 mg, 2.6 mmol) and 2-aminobenzenethiol (390 mg, 3.12 mmol) in PPA (7 g) was heated to 120° C. and stirred for 10 minutes. The reaction mixture was cooled and aqueous NaOH (20 mL) was added. The mixture was extracted with DCM (2×20 mL). The combined organic layers were dried over sodium sulfate, filtered, concentrated and then purified by prep-TLC to give 2-(2-(quinoxalin-2-yl)ethyl)benzo[d]thiazole as a yellow solid. (38 mg). MS (ESI) m/z 318 (M+H⁺).

16. 1,2-Di(quinoxalin-2-yl)ethane

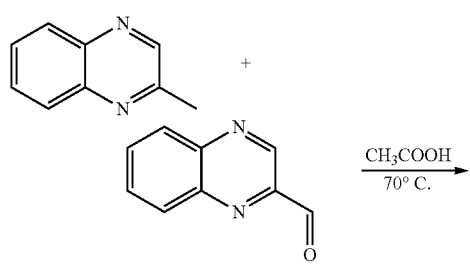

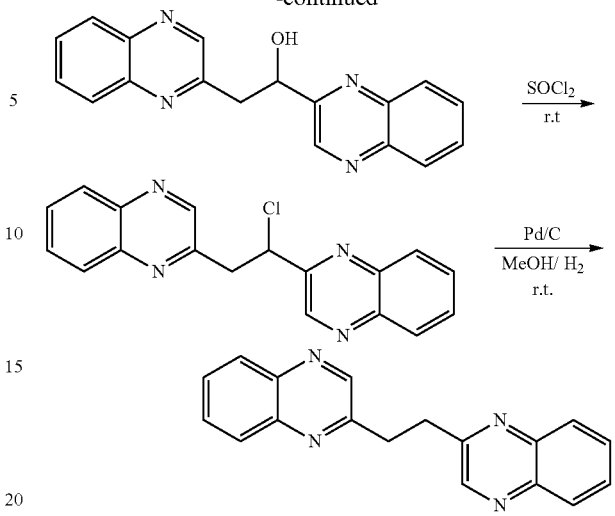

(a) 1,2-Di(quinoxalin-2-yl)ethanol

A solution of 2-methyl quinoxaline (0.11 g, 0.76 mmol) and quinoxaline-2-carbaldehyde (0.16 g, 0.63 mmol) in AcOH (2 mL) was stirred for 1 hour at 70° C. The reaction mixture was concentrated and purified with reverse phase column chromatography to afford 1,2-di(quinoxalin-2-yl)ethanol (0.05 g) as a yellow solid. MS (ESI) m/z 303.1 (M+H⁺).

(b) 2,2'-(1-Chloroethane-1,2-diyl)diquinoxaline

A solution of 1,2-di(quinoxalin-2-yl)ethanol (0.05 g, 0.166 mmol) in $SOCl_2$ (2 mL) was stirred at room temperature for 1 hour. The solution was then concentrated to afford 2,2'-(1-chloroethane-1,2-diyl)diquinoxaline (0.05 g) as a yellow solid. MS (ESI) m/z 321.1 (M+H⁺).

(c) 1,2-Di(quinoxalin-2-yl)ethane

The title compound was prepared according to General Procedure A-(d). MS (ESI) m/z 287.1 (M+H⁺).

17. 2-(2-(Imidazo[1,2-a]pyridin-2-yl)ethyl)quinoxaline

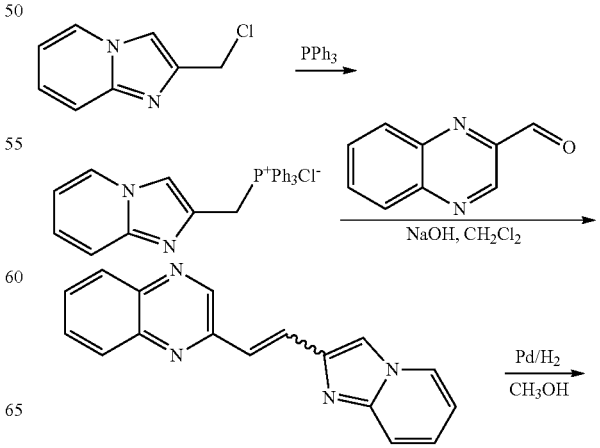

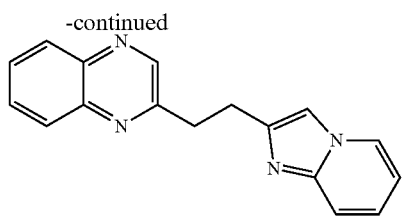

(a) (Imidazo[1,2-a]pyridin-2-ylmethyl)triphenylphosphonium chloride was prepared according to General Procedure D-(b). MS (ESI) m/z 393 (M+H⁺). (b) (E/Z)-2-(2-(Imidazo[1,2-a]pyridin-2-yl)vinyl)quinoxaline was prepared according to General Procedure D-(c). MS (ESI) m/z: 272.32 (M+H⁺). (c) 2-(2-(Imidazo[1,2-a]pyridin-2-yl)ethyl)quinoxaline was prepared according to General Procedure A-(d). MS (ESI) m/z 274.32 (M+H⁺).

18. 2-((4-Phenyl-1H-imidazol-2-yl)methoxy)quinoxaline

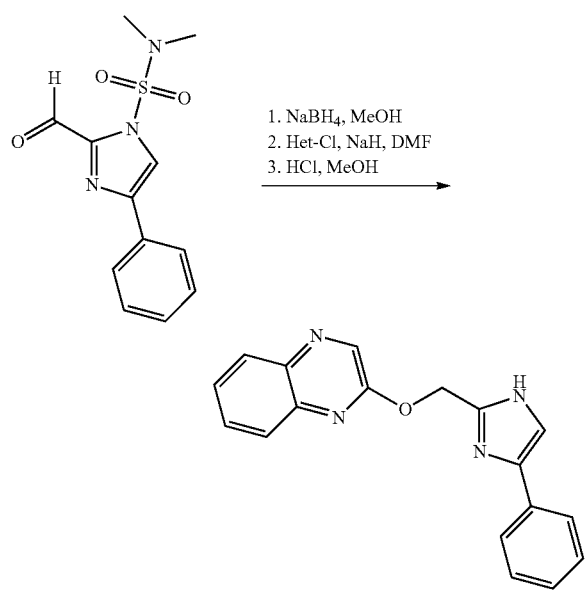

(a) 2-(Hydroxymethyl)-N,N-dimethyl-4-phenyl-1H-imidazole-1-sulfonamide

2-Formyl-N,N-dimethyl-4-phenyl-1H-imidazole-1-sulfonamide (221 mg, 0.79 mmol) was dissolved in anhydrous MeOH (10 mL) and NaBH$_4$ (89 mg, 2.37 mmol) was added in portions. Gas evolved and the suspension was stirred at room temperature. After 30 min, the crude reaction mixture was poured into H$_2$O and extracted with EtOAc (3×20 mL). The combined organic layers were washed with brine, dried (Na$_2$SO$_4$), filtered and concentrated to give crude 2-(hydroxymethyl)-N,N-dimethyl-4-phenyl-1H-imidazole-1-sulfonamide, which was used directly in the next reaction.

(b) N,N-Dimethyl-4-phenyl-2-((quinoxalin-2-yloxy)methyl)-1H-imidazole-1-sulfonamide 2-(Hydroxymethyl)-N,N-dimethyl-4-phenyl-1H-imidazole-1-sulfonamide (0.79 mmol) was dissolved in anhydrous DMF (5 mL) and cooled to 0° C. NaH (60% dispersion in mineral oil, 47 mg, 1.19 mmol) was added and the suspension was stirred for 2 min. 2-Chloroquinoxaline (195 mg, 1.19 mmol) in anhydrous DMF (3 mL) was added dropwise and the resulting suspension was allowed to warm to room temperature. After 2 h, MeOH (10 mL) was added slowly. The crude reaction mixture was poured into H$_2$O (30 mL) and extracted with Et$_2$O (3×30 mL). The combined organic layers were washed with brine, dried (Na$_2$SO$_4$), filtered and concentrated to give crude N,N-dimethyl-4-phenyl-2-((quinoxalin-2-yloxy)methyl)-1H-imidazole-1-sulfonamide, which was used directly in the next reaction.

(c) 2-((4-Phenyl-1H-imidazol-2-yl)methoxy)quinoxaline

The title compound was prepared according to General Procedure D-(d). LC-MS m/z 303 (M+H⁺).

19. 2-(4-Phenyl-1H-imidazol-2-ylthio)quinoxaline

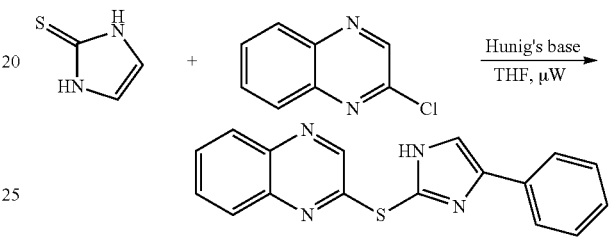

1H-Imidazole-2(3H)-thione (241 mg, 0.92 mmol) and 2-chloroquinoxaline (166 mg, 1.01 mmol) were combined in anhydrous THF (10 mL) in a microwave vial. To the suspension was added Hunig's base (320 µL, 1.84 mmol). The resulting clear yellow solution was heated in the microwave (130° C., 30 min), then concentrated and purified by column chromatography. 2-(4-Phenyl-1H-imidazol-2-ylthio)quinoxaline was obtained as a yellowish oil. LC-MS m/z 305 (M+H⁺).

20. N-((4-Phenyl-1H-imidazol-2-yl)methyl)quinoxalin-2-amine

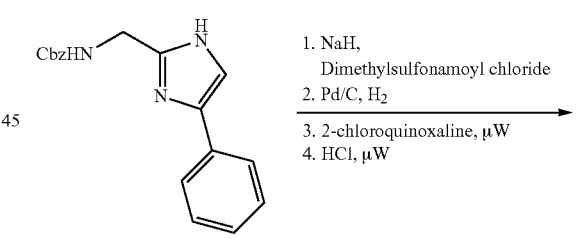

J. Med. Chem. 2007, 50, 4710

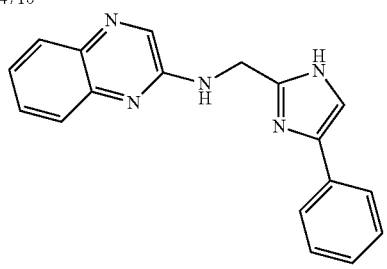

(a) Benzyl (1-(N,N-dimethylsulfamoyl)-4-phenyl-1H-imidazol-2-yl)methylcarbamate

The title compound was prepared according to Kitigawa et al., *J. Med. Chem.*, 2007, 50, 4710.

(b) 2-(Aminomethyl)-N,N-dimethyl-4-phenyl-1H-imidazole-1-sulfonamide

Benzyl (1-(N,N-dimethylsulfamoyl)-4-phenyl-1H-imidazol-2-yl)methylcarbamate (235 mg, 0.56 mmol) was dissolved in anhydrous DMF (5 mL) and Pd on carbon (about 5 mg, catalytic) was added. The vessel containing the solution was purged with $H_2$, and the vessel was sealed. A $H_2$ balloon was attached. Another 10 mg of Pd on carbon was added after 8 h, and the suspension was stirred at room temperature for 48 hours (total). The suspension was filtered through Celite, washing with EtOAc (30 mL), and the washes were concentrated to give crude 2-(aminomethyl)-N,N-dimethyl-4-phenyl-1H-imidazole-1-sulfonamide.

(c) N,N-Dimethyl-4-phenyl-2-((quinoxalin-2-ylamino)methyl)-1H-imidazole-1-sulfonamide 2-(Aminomethyl)-N,N-dimethyl-4-phenyl-1H-imidazole-1-sulfonamide (0.56 mmol), 2-chloroquinoxaline (138 mg, 0.84 mmol), and Hunig's base (195 µL, 1.12 mmol) were dissolved in anhydrous THF (4.5 mL) in a microwave vial. The vial was heated in the microwave (180° C., 40 min), then poured into saturated aqueous $K_2CO_3$ solution (50 mL). The layers were separated and the aqueous phase was extracted with EtOAc (3×30 mL). The combined organic phases were washed with saturated aqueous NaCl (1×50 mL), dried ($Na_2SO_4$), filtered and concentrated to give N,N-dimethyl-4-phenyl-2-((quinoxalin-2-ylamino)methyl)-1H-imidazole-1-sulfonamide.

(d) N((4-Phenyl-1H-imidazol-2-yl)methyl)quinoxalin-2-amine

N,N-Dimethyl-4-phenyl-2-((quinoxalin-2-ylamino)methyl)-1H-imidazole-1-sulfonamide was dissolve in MeOH (5 mL) and 1 M HCl aqueous solution (4.5 mL) was added. The suspension was heated in the microwave (120° C., 40 min) and then poured into a separatory funnel. The phases were separated and the aqueous phase (pH about 2) was washed with $Et_2O$ (2×20 mL). The combined organic layers were discarded and the aqueous phase was made basic (pH about 10) by the slow addition of saturated aqueous $K_2CO_3$ (10 mL). The basic aqueous phase was extracted with EtOAc (3×40 mL). The combined organic phases were washed with saturated aqueous NaCl (1×50 mL), dried ($Na_2SO_4$), filtered and concentrated to give crude N((4-phenyl-1H-imidazol-2-yl)methyl)quinoxalin-2-amine. The material was purified by reverse phase HPLC (Gilson) to give N-((4-phenyl-1H-imidazol-2-yl)methyl)quinoxalin-2-amine as a clear oil. LC-MS m/z 302 (M+H$^+$).

21. 2-(2-(1H-Benzo[d]imidazol-2-yl)ethyl)-3-methylquinoxaline

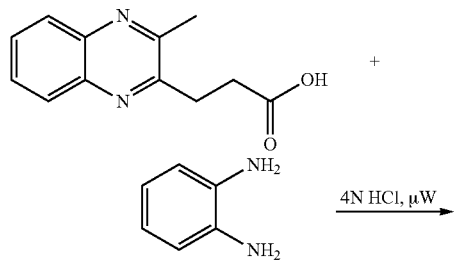

3-(3-Methylquinoxalin-2-yl)propanoic acid (98 mg, 0.45 mmol) and benzene-1,2-diamine (98 mg, 0.45 mmol) were suspended in 4 M HCl in 1,4-dioxane (6 mL) and heated in the microwave (150° C., 2.5 h). The crude reaction was poured into saturated aqueous $Na_2CO_3$ solution (30 mL) and extracted with EtOAc (3×50 mL). The organic layers were combined, washed with brine (1×50 mL), dried ($Na_2SO_4$), filtered and concentrated. The crude material was purified by RPLC (Gilson). Fractions containing the compound were combined, diluted with EtOAc and washed with saturated aqueous $Na_2CO_3$, dried ($Na_2SO_4$), filtered and concentrated to give 2-(2-(1H-benzo[d]imidazol-2-yl)ethyl)-3-methylquinoxaline (8 mg) as an orange oil. LC-MS m/z 289 (M+H$^+$).

22. 2-((4-Phenyl-1H-imidazol-2-yloxy)methyl)quinoxaline and 2-((4-phenyl-1H-imidazol-2-ylthio)methyl)quinoxaline

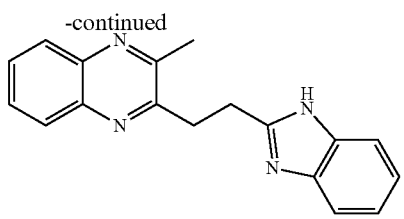

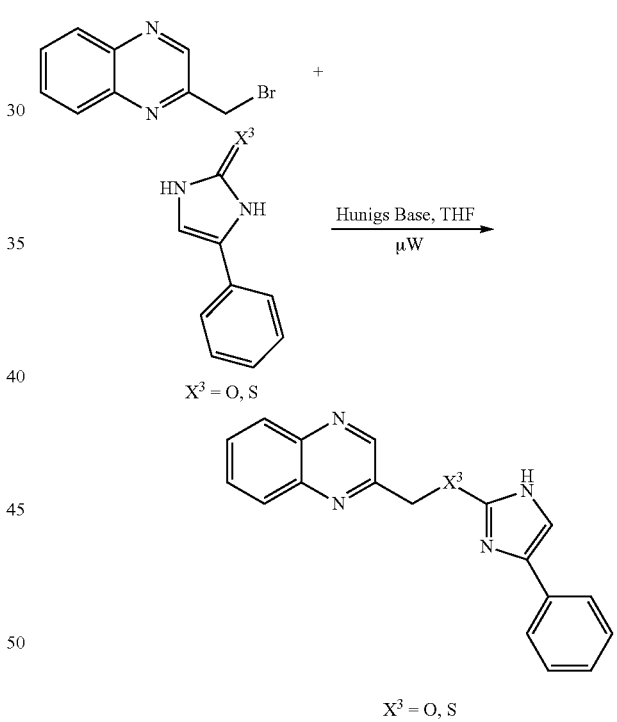

The title compounds were prepared according to Synthetic Procedure 19. Purification by reverse phase HPLC provided the title compounds as oils.

23. General Procedure N; 2-(2-(5,8-Dimethyl-[1,2,4]triazolo[1,5-a]pyrazin-2-yl)ethyl)quinoline (Compound 125)

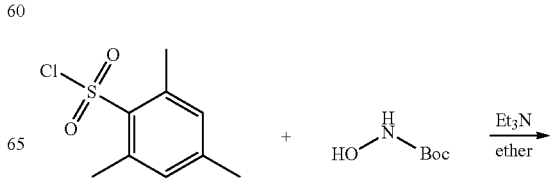

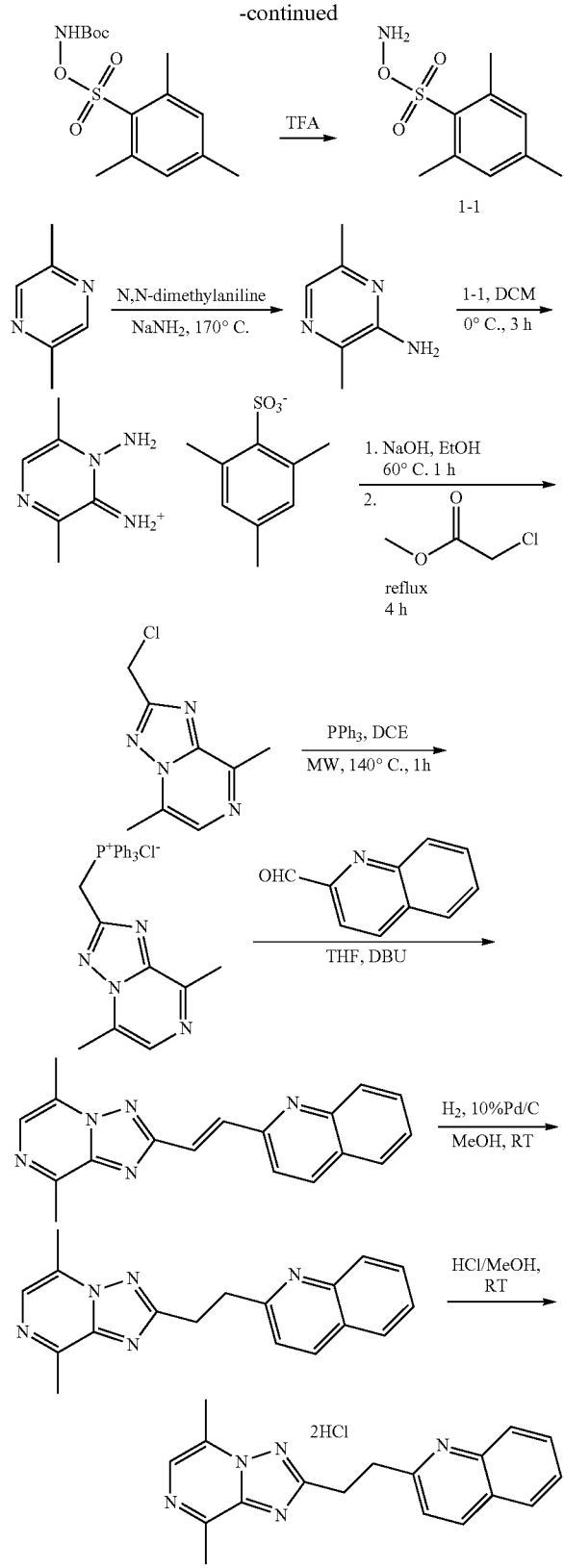

(a) O-(Mesitylsulfonyl)hydroxylamine

To a solution of 2,4,6-trimethylbenzene-1-sulfonyl chloride (30 g, 0.148 mol) and tert-butyl hydroxycarbamate (18 g, 0.148 mol) in ether (500 mL), was added Et₃N (15 g, 0.148 mol) dropwise over 1 h. The reaction mixture was stirred at room temperature for 4 h, then filtered. The filtrate was then concentrated under reduced pressure. The product was purified by column to give tert-butyl mesitylsulfonyloxycarbamate as a white solid (31 g). MS (ESI): m/z 338 [M+Na]⁺.

A solution of tert-butyl mesitylsulfonyloxycarbamate (3 g, 9.5 mmol) in trifluoroacetic acid (7 mL) was stirred at 10° C. for 40 min, then poured into ice/water (10 mL) and the resulting solid was collected by filtration. The solid was dissolved in DCM (12 mL), dried with Na₂SO₄, and filtered. The solution containing O-(mesitylsulfonyl)hydroxylamine was used without further purification.

(b) 3,6-Dimethylpyrazin-2-amine

A mixture of 2,5-dimethylpyrazine (14 g, 0.13 mol) in N,N-dimethylaniline (50 mL) was heated to 170° C. and NaNH₂ (22 g, 0.56 mol) was added in portions. The reaction mixture was stirred at 170° C. for 1 h, and the solvent was removed. The product was purified by column chromatography to give 3,6-dimethylpyrazin-2-amine as a brown solid (1.6 g). MS (ESI): m/z 124 [M+H]⁺.

(c) 1-Amino-3,6-dimethylpyrazin-2(1H)-iminium 2,4,6-trimethylbenzenesulfonate

A mixture of 3,6-dimethylpyrazin-2-amine (1.23 g, 10 mmol) in DCM (20 mL) was cooled to 0° C. and a solution of O-(mesitylsulfonyl)hydroxylamine (4.3 g, 20 mmol) was added slowly. The reaction mixture was allowed to warm to room temperature, stirred for 3 h and then filtered. The solid collected was washed with DCM (50 mL) to give 1-amino-3,6-dimethylpyrazin-2(1H)-iminium 2,4,6-trimethylbenzenesulfonate as a brown solid (2.0 g). MS (ESI): m/z 139 [M-199]⁺.

(d) 2-(Chloromethyl)-5,8-dimethyl-[1,2,4]triazolo[1,5-a]pyrazine

A mixture of 1-amino-3,6-dimethylpyrazin-2(1H)-iminium 2,4,6-trimethylbenzenesulfonate (2.0 g, 5.9 mmol) and sodium hydroxide (480 mg, 12 mmol) in ethanol (20 mL) was stirred at 60° C. for 1 h; methyl 2-chloroacetate (1.34 g, 12.4 mmol) was then added slowly. The reaction mixture heated at reflux for 4 h, then the solvent was removed. The product was purified by column chromatography to give 2-(chloromethyl)-5,8-dimethyl-[1,2,4]triazolo[1,5-a]pyrazine as a yellow solid (420 mg). MS (ESI): m/z 197 [M+H]⁺.

(e) ((5,8-Dimethyl-[1,2,4]triazolo[1,5-a]pyrazin-2-yl)methyl)triphenylphosphonium chloride The title compound was prepared according to General Procedure D-(b). MS (ESI): m/z 424 [M-35]⁺.

(f) (E)-2-(2-(5,8-Dimethyl-[1,2,4]triazolo[1,5-a]pyrazin-2-yl)vinyl)quinoline

The title compound was prepared according to General Procedure D-(c) to give the compound as a yellow solid (386 mg). MS (ESI): m/z 302 [M+H]⁺.

(g) 2-(2-(5,8-Dimethyl-[1,2,4]triazolo[1,5-a]pyrazin-2-yl)ethyl)quinoline

The title compound was prepared according to General Procedure A-(d). MS (ESI): m/z 304 [M+H]⁺.

(h) Dihydrochloride salt of 2-(2-(5,8-dimethyl-[1,2,4]triazolo[1,5-a]pyrazin-2-yl)ethyl)quinoline 2-(2-(5,8-Dimethyl-[1,2,4]triazolo[1,5-a]pyrazin-2-yl)ethyl)quinoline (390 mg, 1.28 mmol) was dissolved in 5 mL of a solution of hydrogen chloride in methanol, stirred for 1 h and concentrated to give the dihydrochloride salt as a pale yellow solid (480 mg). MS (ESI): m/z 304 [M+H]$^+$.

24. 2-(2-(5,8-Dimethyl-[1,2,4]triazolo[1,5-c]pyrimidin-2-yl)ethyl)quinoline (Compound 126)

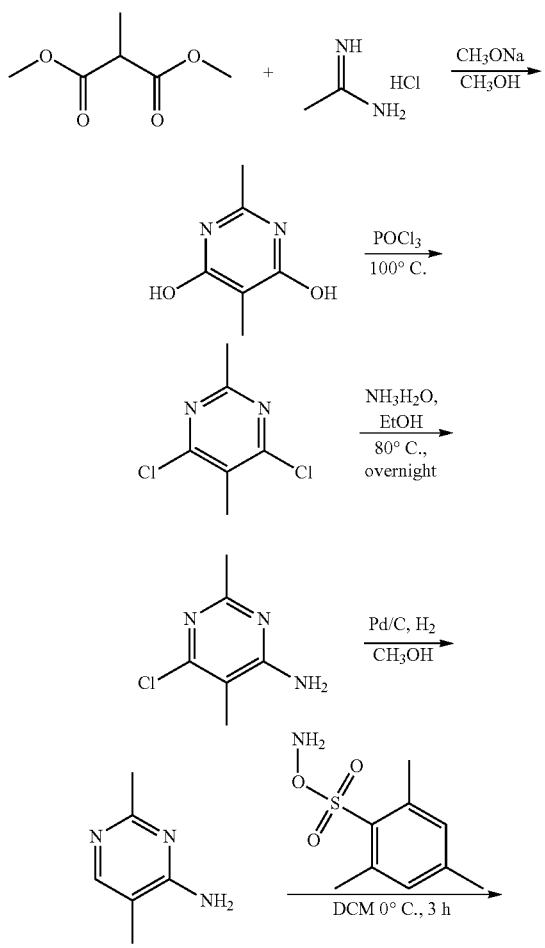

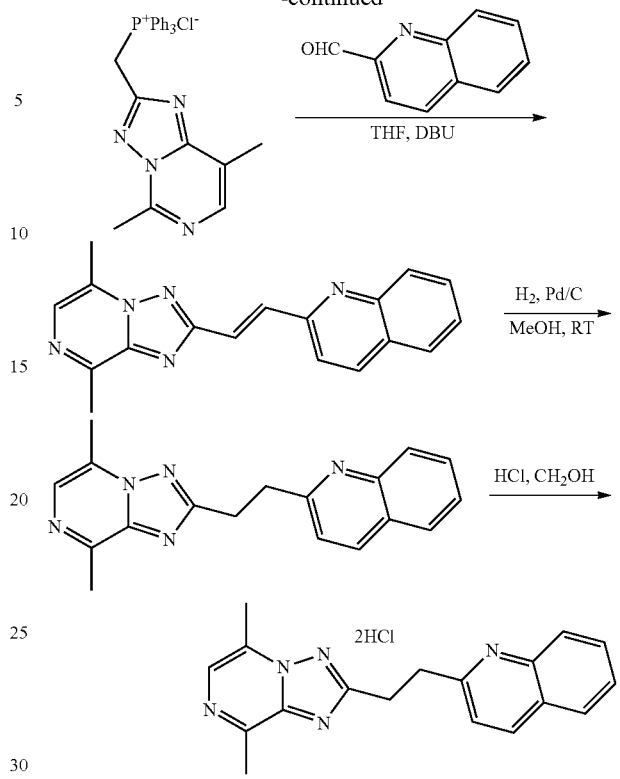

(a) 2,5-Dimethylpyrimidine-4,6-diol

A solution of CH$_3$ONa (5.02 g, 93 mmol) in CH$_3$OH (31 mL) was cooled to 0° C. Acetamidine hydrochloride (3.21 g, 34 mmol) was added slowly. The reaction mixture was stirred at 0° C. for 30 min. Then dimethyl 2-methylmalonate (4.5 g, 31 mmol) was added. The mixture was stirred at 75° C. for 4 h, during which time a precipitate formed. The solid was filtered and dissolved in water and HCl (conc.) was added until pH 1-2. The white precipitate was filtered, and dried in vacuum to give 2,5-dimethylpyrimidine-4,6-diol as a white solid (3.41 g). MS (ESI): m/z 141 [M+H]$^+$.

(b) 4,6-Dichloro-2,5-dimethylpyrimidine

A mixture of 2,5-dimethylpyrimidine-4,6-diol (3.41 g, 24.4 mmol) in POCl$_3$ (40 mL) was heated to 100° C. and stirred overnight. After cooling to room temperature, the reaction mixture was poured into water (50 mL) and sodium hydroxide aqueous solution (sat.) was added to the mixture until pH 8-9. The mixture was extracted with EtOAc (150 mL×3). The combined organic layers were washed with brine (100 mL), dried over Na$_2$SO$_4$, and concentrated under reduced pressure to give crude 4,6-dichloro-2,5-dimethylpyrimidine as a yellow solid (2.80 g). MS (ESI): m/z 178 [M+H]$^+$.

(c) 6-Chloro-2,5-dimethylpyrimidin-4-amine

A microwave vial was charged with 4,6-dichloro-2,5-dimethylpyrimidine (523 mg, 2.95 mmol) and ammonium hydroxide (8 mL) in ethanol (4 mL). The vial was heated to 80° C. and stirred for 8 h. After concentration under reduced pressure, the reaction mixture was extracted with EtOAc (15 mL×8). The combined organic layers were washed with brine (30 mL), dried over Na₂SO₄ and concentrated to give 6-chloro-2,5-dimethylpyrimidin-4-amine as a yellow solid (411 mg). MS (ESI): m/z 158 [M+H]⁺.

(d) 2,5-Dimethylpyrimidin-4-amine

The title compound was prepared according to General Procedure A-(d). MS (ESI): m/z 124 [M+H]⁺.

(e) 3-Amino-2,5-dimethylpyrimidin-4(3H)-iminium 2,4,6-trimethylbenzenesulfonate

The title compound was prepared according to General Procedure N-(d). MS (ESI): m/z 139 [M-199]⁺.

(f) 2-(Chloromethyl)-5,8-dimethyl-[1,2,4]triazolo[1,5-c]pyrimidine

The title compound was prepared according to General Procedure N-(e). MS (ESI): m/z 197 [M+H]⁺.

(g) ((5,8-Dimethyl-[1,2,4]triazolo[1,5-c]pyrimidin-2-yl)methyl)triphenylphosphonium chloride The title compound was prepared according to General Procedure D-(b). The crude product was used in the next step without further purification.

(h) (E/Z)-2-(2-(5,8-Dimethyl-[1,2,4]triazolo[1,5-c]pyrimidin-2-yl)vinyl)quinoline The title compound was prepared according to General Procedure D-(c). MS (ESI): m/z 302 [M+H]⁺.

(i) 2-(2-(5,8-Dimethyl-[1,2,4]triazolo[1,5-c]pyrimidin-2-yl)ethyl)quinoline

The title compound was prepared according to General Procedure A-(d) MS (ESI): m/z 304 [M+H]⁺.

(j) 2-(2-(5,8-Dimethyl-[1,2,4]triazolo[1,5-c]pyrimidin-2-yl)ethyl)quinoline hydrochloride salt The title compound was prepared according to General Procedure N-(h). MS (ESI): m/z 304 [M+H]⁺.

25. Synthesis of quinoline and quinoxaline derivatives (Compounds 127-142)

The procedures outlined above in Examples 23 and 24 for the synthesis of 2-(2-(5,8-dimethyl-[1,2,4]triazolo[1,5-a]pyrazin-2-yl)ethyl)quinoline and 2-(2-(5,8-dimethyl-[1,2,4]triazolo[1,5-c]pyrimidin-2-yl)ethyl)quinoline were also carried out with other suitable carbaldehydes, including but not limited to, substituted quinoline 2-carbaldehydes and substituted or unsubstituted quinoxaline 2-carbaldehydes, which may be commercially available or prepared using known literature conditions, to prepare other embodiments of the compounds disclosed herein. The synthesis of exemplary carbaldehydes is described below. The carbaldehydes were then used as starting material in the preparation of various embodiments of the compounds provided herein elsewhere.

(a) 7,8-Difluoro-2-methylquinoline

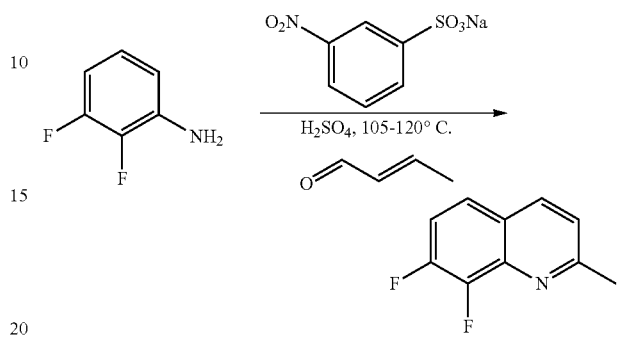

Sodium 3-nitrobenzenesulfonate (2.7 g, 12 mmol) was dissolved in H₂O (3 mL), and oleum (4 mL) was added to the mixture. 2,3-Difluoroaniline was then added to the mixture. The mixture was heated to 105° C. and (E)-but-2-enal (2.34 g, 33.4 mmol) was added dropwise. The mixture was stirred at 120° C. for 1 h. Then the mixture was poured into ice (50 g), and solid NaOH was added until pH 12. The mixture was extracted with EtOAc (50 mL×3). The combined organic layers were dried over anhydrous Na₂SO₄, filtered and concentrated under reduced pressure. The crude product was purified by column chromatography to afford 7,8-difluoro-2-methylquinoline (1.5 g) as a white solid.

(b) 7,8-Difluoroquinoline-2-carbaldehyde

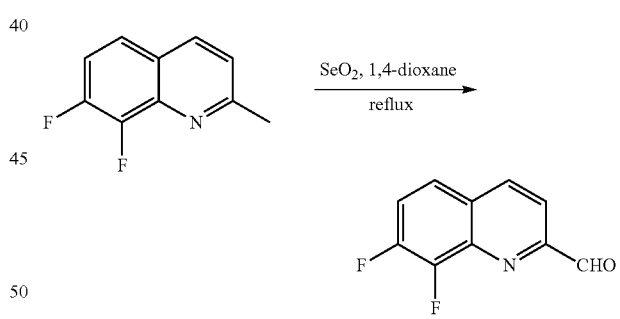

The title compound was prepared according to General Procedure H-(a).

(c) 2-(Dibromomethyl)benzo[h]quinoline

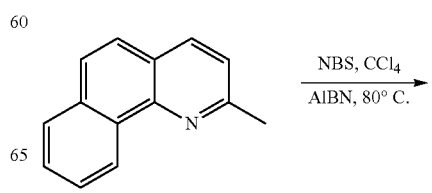

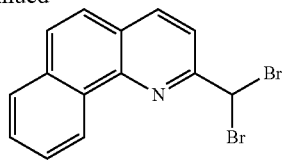

A mixture of 2-methylbenzo[h]quinoline (0.193 g, 1.0 mmol), 1-bromopyrrolidine-2,5-dione (NBS) (600 mg, 3.3 mmol), and AIBN (50 mg, 0.3 mmol) in CCl$_4$ (5 mL) was stirred at 80° C. for 4 h. H$_2$O (20 mL) and DCM (20 mL) were added to the mixture and the layers were separated. The aqueous layer was extracted with DCM (20 mL×2). The combined organic layers were washed with brine and dried over anhydrous Na$_2$SO$_4$ The organic layers were concentrated and purified by column chromatography to afford 2-(dibromomethyl)benzo[h]quinoline (0.2 g) as a white solid.

(d) Benzo[h]quinoline-2-carbaldehyde

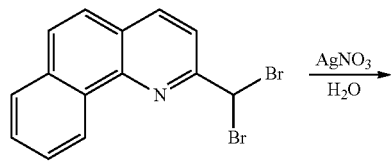

To a mixture of 2-(dibromomethyl)benzo[h]quinoline (52 mg, 0.148 mmol) in EtOH (2 mL) and THF (1 mL) was added a solution of AgNO$_3$ (75 mg, 0.444 mmol) in H$_2$O (1 mL). The mixture was stirred at reflux for 2 h. The solid was filtered off and the organic solvent was removed under reduced pressure. DCM (5 mL) was added and the layers were separated. The aqueous layer was extracted with DCM (5 mL×2). The combined organic layers were washed with brine (2 mL) and dried by anhydrous Na$_2$SO$_4$. The organic layer was concentrated to give benzo[h]quinoline-2-carbaldehyde (30 mg) as a yellow solid.

(e) 2-Methyl-1,8-naphthyridine

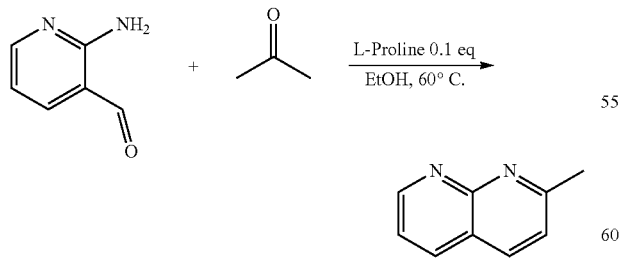

To a suspension of 2-aminonicotinaldehyde (732 mg, 6 mmol) and L-proline (69 mg, 0.6 mmol) in EtOH (15 mL) was added acetone (1.74 g, 30 mmol). Then the mixture was heated at reflux and stirred for 8 h. The resulting mixture was concentrated under reduced pressure to give a residue, which was washed with water (10 mL) and extracted with DCM (15 mL×3). The combined organic layers were washed with brine (10 mL), dried over anhydrous sodium sulfate, and concentrated under reduced pressure to afford the crude product 2-methyl-1,8-naphthyridine as a yellow solid (768 mg). MS (ESI): m/z 145 [M+H]$^+$. See e.g., *Bioorg. Med. Chem. Lett.*, 2005, 15, 2679-84.

(f) 1,8-Naphthyridine-2-carbaldehyde

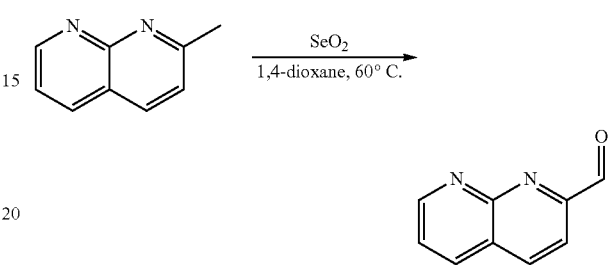

The title compound was prepared according to General Procedure H-(a). MS (ESI): m/z 159 [M+H]$^+$.

(g) 2-Methyl-1,5-naphthyridine

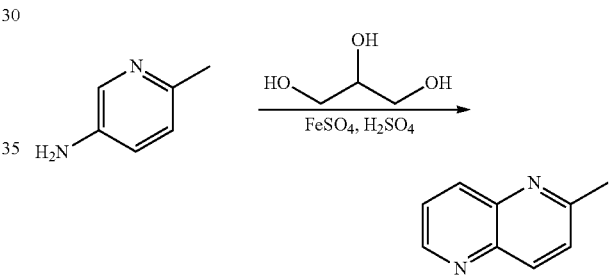

A mixture of concentrated sulfuric acid (14 mL), boric acid (1.55 g, 39 mmol), sodium m-nitrobenzenesulfonate (11.30 g, 50 mmol), and iron sulfate heptahydrate (0.90 g, 3.23 mmol) was stirred at room temperature. Glycerol (8 mL) was added to the mixture followed by 3-amino-6-picoline (2.79 g, 25 mmol) and water (14 mL). The mixture was heated at 135° C. for 18 h. The reaction mixture was cooled to room temperature, basified using 4 N aqueous sodium hydroxide to pH 8, and extracted with EtOAc (50 mL×3). The organic extracts were combined, concentrated, and the residue was purified by column chromatography to afford 2-methyl-1,5-naphthyridine (2.01 g) as a light brown crystalline solid. MS (ESI): m/z 145 [M+H]$^+$. See, e.g., *J. Med. Chem.* 2004, 47, 4494-4506.

(h) 1,5-Naphthyridine-2-carbaldehyde

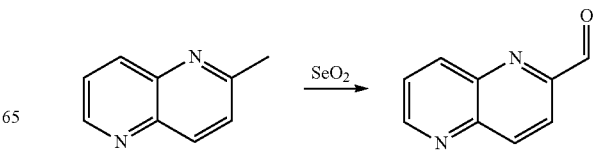

The title compound was prepared according to General Procedure H-(a). MS (ESI): m/z 159 [M+H]⁺.

(i) 2,7-Dimethyl-1,8-naphthyridine and 2,6-dimethyl-1,5-naphthyridine

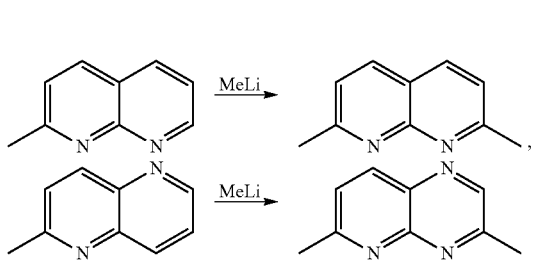

The title compounds were prepared according to *J. Org. Chem.* 1990, 55, 2838-2842.

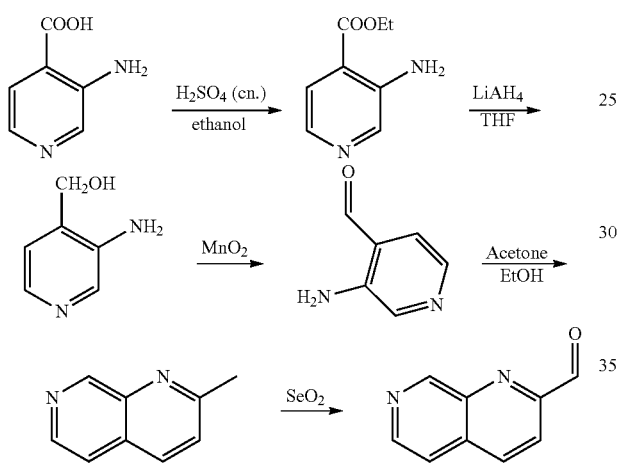

(j) Ethyl 3-aminoisonicotinate

To an ice-cold suspension of 3-aminoisonicotinic acid (8 g, 58 mmol) in ethanol (36 mL) and toluene (36 mL) was added concentrated sulfuric acid (6.4 mL), and the mixture was stirred for 24 h. The solvents were removed under reduced pressure, the residue was dissolved in water, and the solution was adjusted to pH 8 with concentrated ammonium hydroxide to give ethyl 3-aminoisonicotinate (6.5 g). MS (ESI): m/z 167 [M+H]⁺.

(k) (3-Aminopyridin-4-yl)methanol

The title compound was prepared according to General Procedure 14-(l). MS (ESI): m/z 125 [M+H]⁺.

(l) 3-Aminoisonicotinaldehyde

The title compound was prepared according to General Procedure 14-(m). MS (ESI): m/z 123 [M+H]⁺. See, e.g., *Aust. J. Chem.,* 1993, 46, 987-93.

(m) 2-Methyl-1,7-naphthyridine

The title compound was prepared according to General Procedure 25-(e). MS (ESI): m/z 145 [M+H]⁺.

(n) 1,7-Naphthyridine-2-carbaldehyde

The title compound was prepared according to General Procedure H-(a). MS (ESI): m/z 159 [M+H]⁺.

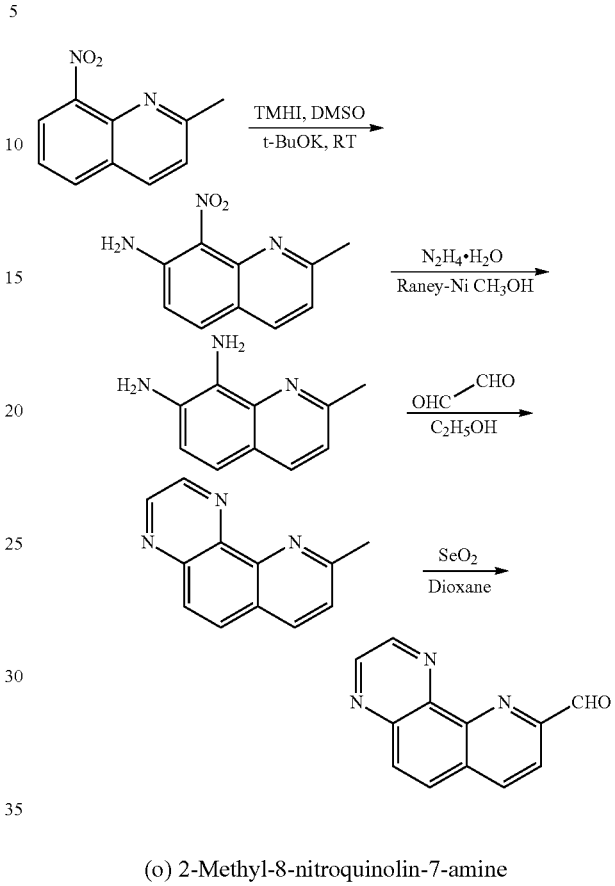

(o) 2-Methyl-8-nitroquinolin-7-amine

To a solution of 2-methyl-8-nitroquinoline (1.88 g, 10 mmol) and 1,1,1-trimethylhydrazinium iodide (3.03 g, 15 mmol) in anhydrous dimethyl sulfoxide (20 mL) was added potassium tert-butoxide as a solid (3.36 g, 30 mmol). The mixture was stirred at room temperature for 1 h. The mixture was then poured into saturated aqueous ammonium chloride, and extracted with EtOAc. The organic layer was concentrated and purified by column chromatography to give 2-methyl-8-nitroquinolin-7-amine as a yellow solid (300 mg). MS (ESI): m/z 204 (M+H)⁺.

(p) 2-Methylquinoline-7,8-diamine

The title compound was prepared according to General Procedure L-(a). MS (ESI): m/z 174 (M+H)⁺.

(q) 9-Methylpyrido[2,3-f]quinoxaline

To a solution of 2-methylquinoline-7,8-diamine (255 mg, 1.48 mmol) in ethanol (3 mL) was added glyoxal (103 mg, 1.78 mmol). The mixture was stirred at room temperature for 2 h. The mixture was then concentrated to give 9-methylpyrido[2,3-f]quinoxaline as a yellow solid (300 mg). MS (ESI): m/z 196 (M+H)⁺.

(r) Pyrido[2,3-f]quinoxaline-9-carbaldehyde

The title compound was prepared according to General Procedure H-(a). MS (ESI): m/z 210 (M+H)⁺.

26. General Procedure O

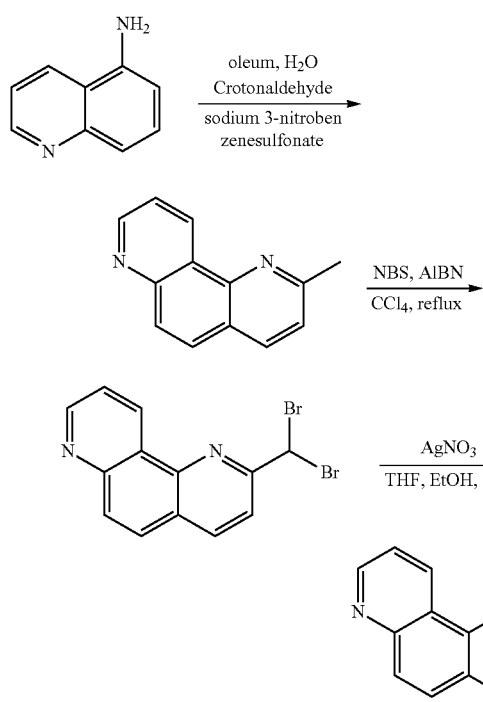

(s) 2-Methyl-1,7-phenanthroline

To a mixture of sodium 3-nitrobenzenesulfonate (2.88 g, 12.8 mmol) in oleum (12 mL) and water (12 mL) was added quinolin-5-amine (3.09 g, 21.4 mmol). The mixture was stirred and heated to 105° C. Crotonaldehyde (3.00 g, 42.8 mmol) was added dropwise over 15 min. The resulting mixture was stirred at 105° C. for 16 h. The mixture was then poured into ice (50 g), and the pH value was adjusted to 11 with 1 N aqueous sodium hydroxide solution. The mixture was extracted with EtOAc (3×60 mL), and the combined organic layers were dried over anhydrous sodium sulfate and concentrated under reduced pressure. The residue was purified by column chromatography to afford 2-methyl-1,7-phenanthroline as a yellow solid (2.10 g). MS (ESI) m/z 195.1 (M+H)$^+$.

(t) 2-(Dibromomethyl)-1,7-phenanthroline

To a solution of 2-methyl-1,7-phenanthroline (582 mg, 3.0 mmol) in tetrachloromethane (20 mL) was added N-bromosuccinimide (2.14 g, 12.0 mmol) and 2,2'-azobis(2-methylpropionitrile) (100 mg). The mixture was stirred at reflux for 5 h. Then saturated sodium bicarbonate aqueous solution (20 mL) was added. The resulting mixture was extracted with DCM (3×20 mL). The extracts were dried over anhydrous sodium sulfate and concentrated under reduced pressure to give 2-(dibromomethyl)-1,7-phenanthroline as a yellow solid (1.2 g). MS (ESI) m/z 350.9 (M+H)$^+$.

(u) 1,7-Phenanthroline-2-carbaldehyde

The title compound was prepared according to General Procedure 25-(d). MS (ESI) m/z 209.0 (M+H)$^+$.

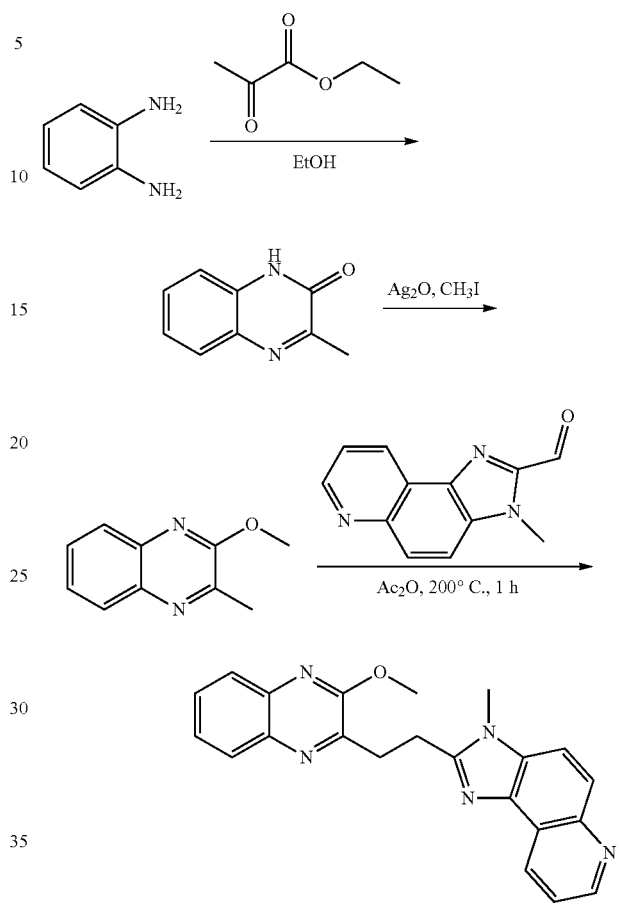

(a) 3-Methylquinoxalin-2(1H)-one

A solution of benzene-1,2-diamine (10.8 g, 100 mmol) in ethanol (500 mL) was treated with a solution of ethyl-2-oxopropanoate (11.22 g, 110 mmol) slowly at 0° C., and the resulting suspension was stirred at room temperature for 1 h, then filtered. An off-white solid was collected (15.85 g). MS (ESI): m/z 161 [M+H]$^+$.

(b) 2-Methoxy-3-methylquinoxaline

A suspension of 3-methylquinoxalin-2(1H)-one (3.2 g, 20 mmol), silver oxide (5.56 g, 24 mmol), and methyl iodide (5.68 g, 40 mmol) in toluene (100 mL) was heated to 100° C. for 16 h. After cooling to room temperature, the reaction mixture was filtered, concentrated, and purified by column chromatography to afford the title compound as an orange solid (2.11 g). MS (ESI): m/z 175 [M+H]$^+$.

(c) 2-(2-(3-Methoxyquinoxalin-2-yl)ethyl)-3-methyl-3H-imidazo[4,5-f]quinoline

The title compound was prepared according to General Procedure A-(c).

27. General Procedure P

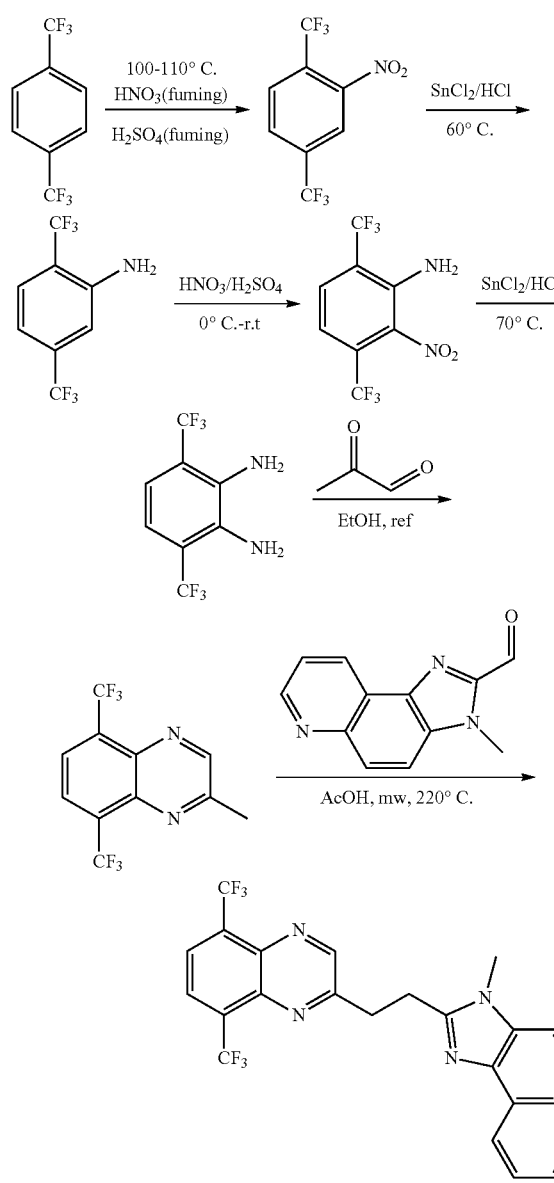

(a) 2-Nitro-1,4-bis(trifluoromethyl)benzene 1,4-Bis(trifluoromethyl)benzene (10.06 g, 47 mmol) in fuming sulfuric acid (20 g) was cooled to 0° C. Fuming nitric acid (8 g) was added cautiously. The mixture was heated to 100° C. and stirred for 1 hour. A mixture of fuming nitric acid (6 g) and fuming sulfuric acid (12 g) was added, and the mixture was heated to 110° C. and stirred for 6 hours. After cooling to r.t., the mixture was poured into ice water (150 g) cautiously, and extracted with chloroform (100 mL×3). The combined organic layers were washed with water (100 mL×2), 10% sodium hydroxide aqueous solution (100 mL×2), and then water (100 mL×2). The resulting organic layers were dried over sodium sulfate, filtered, and concentrated to afford 2-nitro-1,4-bis(trifluoromethyl)benzene as an oil (3.3 g).

(b) 2,5-Bis(trifluoromethyl)benzenamine

To a solution of 2-nitro-1,4-bis(trifluoromethyl)benzene (3.3 g, 12.7 mmol) in methanol (15 mL) was added a solution of $SnCl_2.H_2O$ (8.57 g, 38.1 mmol) in conc. HCl (15 mL) at room temperature, and the mixture was heated to 50° C. and stirred for 4 hours. Methanol was removed, and the aqueous solution was basified with conc. NaOH solution until pH 10. The suspension was diluted with EtOAc (100 mL), and the mixture was stirred at room temperature for 30 minutes and filtered. The solid was discarded, and the filtrate was washed with brine (50 mL), dried over sodium sulfate, and filtered. The solution was concentrated to give 2,5-bis(trifluoromethyl)benzenamine as a yellow oil (2.5 g). MS (ESI): m/z 230 $[M+H]^+$.

(c) 2-Nitro-3,6-bis(trifluoromethyl)benzenamine

Nitric acid (7 mL) was added to sulfuric acid (10 mL) cautiously at 0° C. 2,5-Bis(trifluoromethyl)benzenamine (2 g, 8.7 mmol) was added in small portions at 0° C. over 20 minutes and the resulting slurry was stirred at 0° C. to room temperature for 3 hours. The mixture was poured into ice water (100 mL) and basified with sodium hydroxide solution, and extracted with EtOAc (80 mL×3). The combined organic layers were washed with brine (80 mL), dried over sodium sulfate, filtered and concentrated to give a crude product of 2-nitro-3,6-bis(trifluoromethyl)benzenamine (containing isomers) which was used in the next step without further purification (2.3 g). MS (ESI): m/z 275 $[M+H]^+$

(d) 3,6-Bis(trifluoromethyl)benzene-1,2-diamine

To a solution of 2-nitro-3,6-bis(trifluoromethyl)benzenamine (2.3 g, 8.4 mmol) in methanol (10 mL) was added a solution of $SnCl_2.H_2O$ (7.56 g, 33.6 mmol) in concentrated HCl (15 mL). The mixture was heated to 50° C. and stirred for 2 hours. Methanol was removed in vacuum and the aqueous solution was basified with sodium hydroxide solution. The suspension was diluted with EtOAc (150 mL), and the mixture was stirred at room temperature for 30 minutes and filtered. The filtrate was washed with brine (100 mL), dried over sodium sulfate, and filtered. The solution was concentrated to give a crude product of 3,6-bis(trifluoromethyl)benzene-1,2-diamine (1.5 g). MS (ESI): m/z 245 $[M+H]^+$

(e) 2-Methyl-5,8-bis(trifluoromethyl)quinoxaline

The title compound was prepared according to General Procedure 25-(q) from 2-oxopropanal, after heating at reflux for 2 h. $^1$H-NMR (400 MHz, $CDCl_3$): δ 8.94 (s, 1H), 8.14 (d, 1H, J=7.6 Hz), 8.10 (d, 1H, J=8.0 Hz), 2.87 (s, 3H). MS (ESI): m/z 281 $[M+H]^+$

(f) 2-(2-(5,8-Bis(trifluoromethyl)quinoxalin-2-yl)ethyl)-3-methyl-3,1-imidazo[4,5-f]quinoline The title compound was prepared according to General Procedure A-(c).

28. General Procedure Q

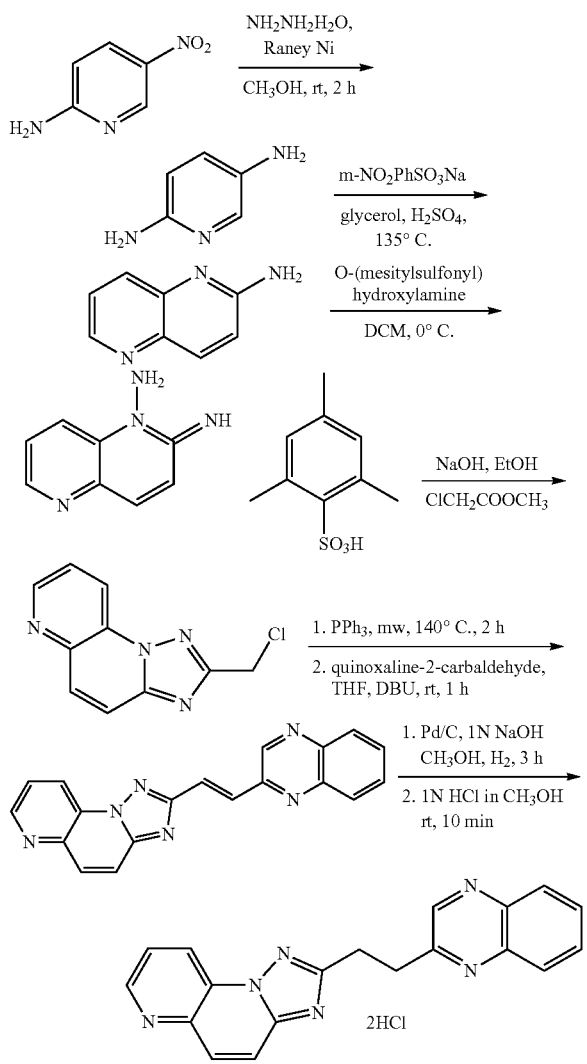

(a) Pyridine-2,5-diamine

The title compound was prepared according to General Procedure L-(a). MS (ESI): m/z 110.1 [M+H]+.

(b) 1,5-Naphthyridin-2-amine

A mixture of pyridine-2,5-diamine (5.2 g, 71% pure, 33.9 mmol), glycerol (15.6 g, 169.5 mmol), sodium 3-nitrobenzenesulphonate (15.2 g, 67.8 mmol), sulfuric acid (20 mL), and water (30 mL) was heated to 135° C. and stirred at this temperature for 16 h. The mixture was cooled to room temperature and then poured into ice water (150 g). The pH of the reaction mixture was adjusted to 9 with saturated sodium hydroxide aqueous solution. Then the mixture was extracted with EtOAc (3×100 mL). The extracts were dried over sodium sulfate, concentrated under reduce pressure to give the crude product. The crude product was purified by column chromatography to give 2.0 g of 1,5-naphthyridin-2-amine as a yellow solid.

MS (ESI): m/z 146.1 [M+H]+.

(c) 2-Imino-1,5-naphthyridin-1(2H)-amine 2,4,6-trimethylbenzenesulfonate

The title compound was prepared according to General Procedure N-(d). MS (ESI): m/z 161.1 [M+H]+.

(d) 2-(Chloromethyl)-[1,2,4]triazolo[1,5-a][1,5]naphthyridine

The title compound was prepared according to General Procedure N-(e). MS (ESI): m/z 219.0 [M+H]+.

(e) (E)-2-(2-(Quinoxalin-2-yl)vinyl)-[1,2,4]triazolo[1,5-a][1,5]naphthyridine The title compound was prepared according to General Procedure D-(c). MS (ESI): m/z 325.1 [M+H]+.

(f) 2-(2-(Quinoxalin-2-yl)ethyl)-[1,2,4]triazolo[1,5-a][1,5]naphthyridine hydrochloride salt To a solution of (E)-2-(2-(quinoxalin-2-yl)vinyl)-[1,2,4]triazolo[1,5-a][1,5]naphthyridine (32 mg, 0.099 mmol) in 1 N sodium hydroxide aqueous solution (1 mL) and methanol (2 mL) was added Pd/C (10%, 5 mg). The mixture was stirred under hydrogen at room temperature for 16 h. The mixture was filtered and the filtrate was concentrated, and purified by reverse phase prep-HPLC to give 15 mg of 2-(2-(quinoxalin-2-yl)ethyl)-[1,2,4]triazolo[1,5-a][1,5]naphthyridine as a yellow solid.

A solution of 2-(2-(quinoxalin-2-yl)ethyl)-[1,2,4]triazolo[1,5-a][1,5]naphthyridine (15 mg, 0.046 mmol) in 1 N HCl in methanol was stirred at room temperature for 10 min. The solvent was removed under reduce pressure to give 18 mg of 2-(2-(quinoxalin-2-yl)ethyl)-[1,2,4]triazolo[1,5-a][1,5]naphthyridine hydrochloride as a yellow solid. MS (ESI): m/z 327.1 [M+H]+.

29. General Procedure R

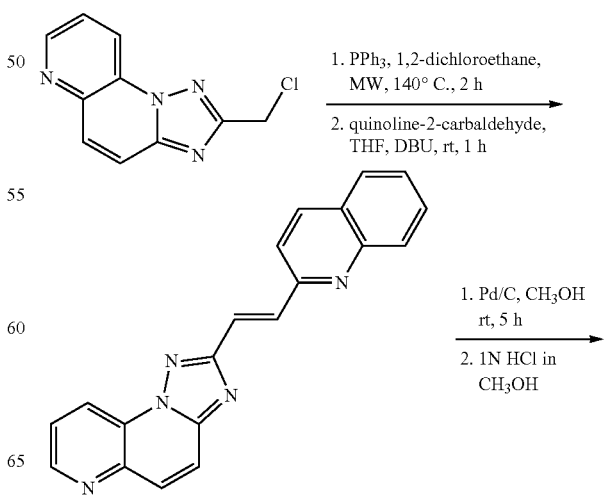

-continued

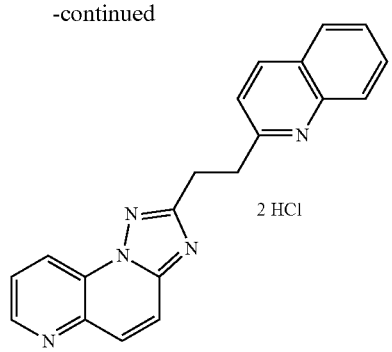

2 HCl (a) (E)-2-(2-(Quinolin-2-yl)vinyl)-[1,2,4]triazolo[1,5-a][1,5]naphthyridine was prepared according to General Procedure D-(b) and D-(c). MS (ESI): m/z 324.1 [M+H]+. (b) 2-(2-(Quinolin-2-yl)ethyl)-[1,2,4]triazolo[1,5-a][1,5]naphthyridine was prepared according to General Procedure A-(d) and N-(h). MS (ESI): m/z 326.1 [M+H]+.

30. General Procedure S

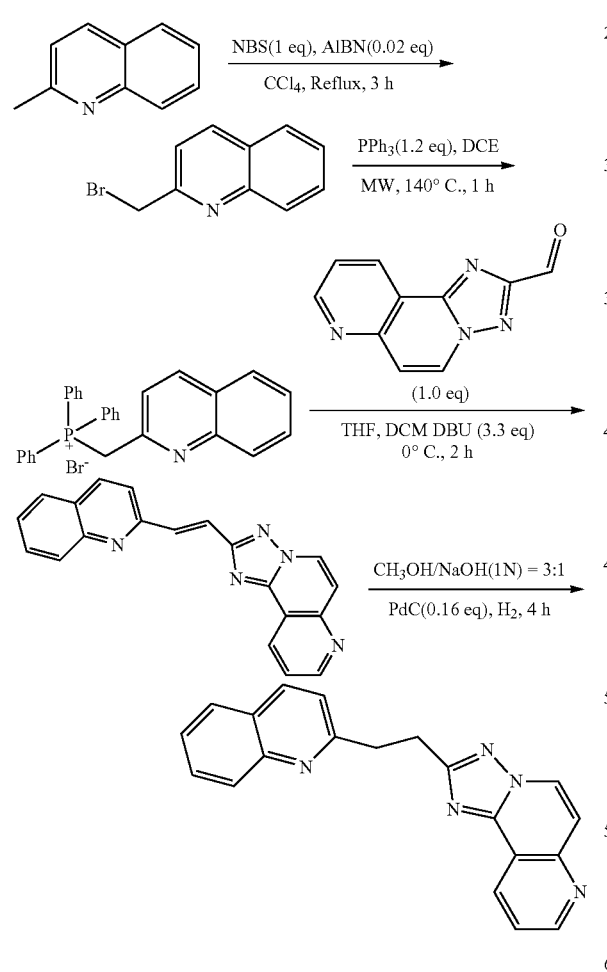

(a) 2-(Bromomethyl)quinoline was prepared according to General Procedure 25-(c) using NBS. MS (ESI): m/z=222.1 [M+H]+ (b) Triphenyl(quinolin-2-ylmethyl)phosphonium bromide was prepared according to General Procedure D-(b). MS (ESI): m/z=404.1 [M+H]+ (c) (E)-2-(2-(Quinolin-2-yl)vinyl)-[1,2,4]triazolo[5,1-f][1,6]naphthyridine was prepared according to General Procedure H-(b). MS (ESI): m/z=324.1 [M+H]+ (d) 2-(2-(Quinolin-2-yl)ethyl)-[1,2,4]triazolo[5,1-f][1,6]naphthyridine was prepared according to General Procedure Q-(f).

31. General Procedure T

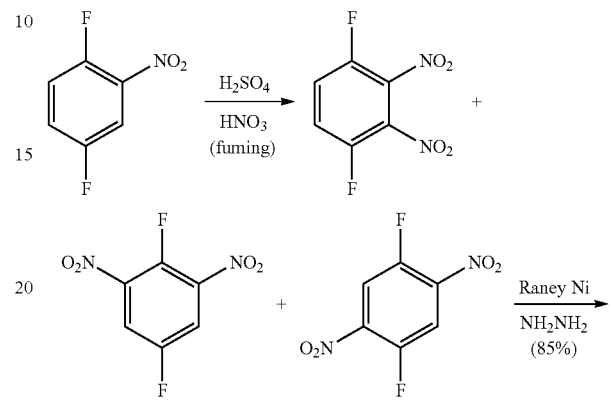

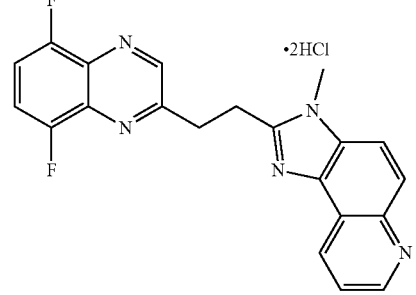

(a) 1,4-Difluoro-2,3-dinitrobenzene The title compound was prepared according to General Procedure P-(c). MS (ESI): m/z 205 [M+H]+. (b) 3,6-Difluorobenzene-1,2-diamine was prepared according to General Procedure L-(a). MS (ESI): m/z 145 [M+H]+. (c) 5,8-Difluoro-2-methylquinoxaline was prepared according to General Procedure 25-(q) from 2-oxopropanal. MS (ESI): m/z 181 [M+H]+. (d) 2-(2-(5,8-Difluoroquinoxalin-2-yl)ethyl)-3-methyl-3H-imidazo[4,5-f]quinoline was prepared according to General Procedure A-(c) after heating at 200° C. in a microwave for 3 h.

32. General Procedure U

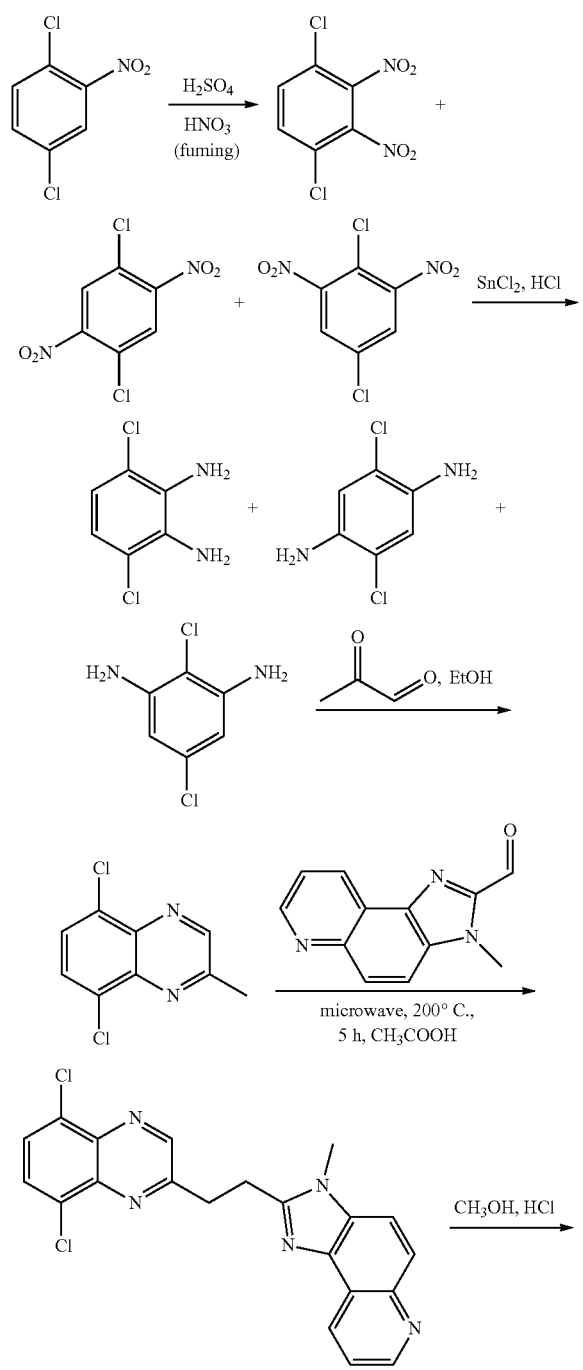

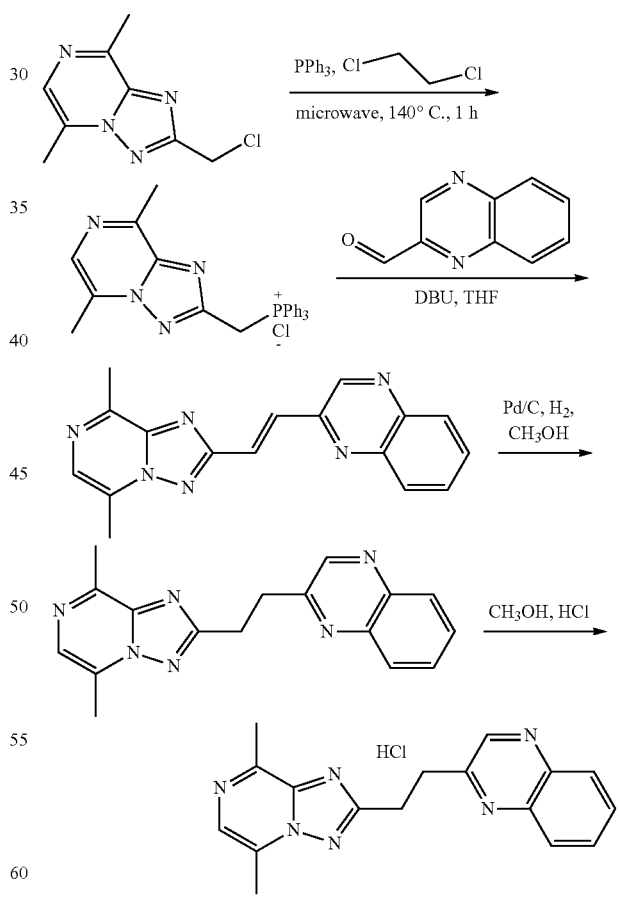

(a) 1,4-Dichloro-2,3-dinitrobenzene was prepared according to General Procedure P-(c). MS (ESI): m/z 238 [M+H]+. (b) 3,6-Dichlorobenzene-1,2-diamine was prepared according to General Procedure P-(b). MS (ESI): m/z 178 [M+H]+. (c) 5,8-Dichloro-2-methylquinoxaline was prepared according to General Procedure 25-(q) from 2-oxopropanal. MS (ESI): m/z 213 [M+H]+. (d) 2-(2-(5,8-Dichloroquinoxalin-2-yl)ethyl)-3-methyl-3H-imidazo[4,5-f]quinoline was prepared according to General Procedure A-(c) after heating at 200° C. in a microwave for 3 h.

33. General Procedure V (a) (5,8-Dimethyl-[1,2,4]triazolo[1,5-a]pyrazin-2-yl)methyl)triphenylphosphonium chloride was prepared according to General Procedure D-(b). MS (ESI): m/z 423 [M]+. (b) (E)-2-(2-(5,8-Dimethyl-[1,2,4]triazolo[1,5-a]pyrazin-2-yl)vinyl)quinoxaline was prepared according to General Procedure D-(c). MS (ESI): m/z 303 [M+H]⁺. (c) 2-(2-(5,8-Dimethyl-[1,2,4]triazolo[1,5-a]pyrazin-2-yl)ethyl)quinoxaline was prepared according to General Procedure A-(d). See, e.g., Recueil des Travaux Chimiques des Pays-Bas, 1963, (82), 988-995.

34. General Procedure W

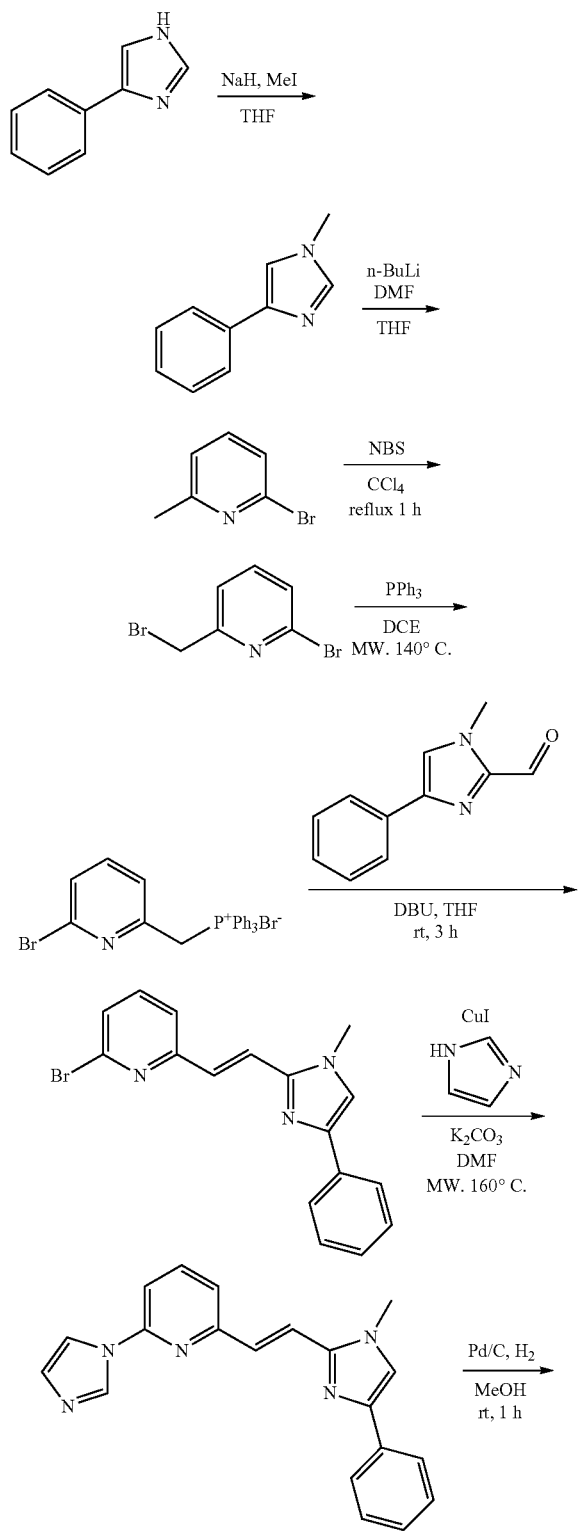

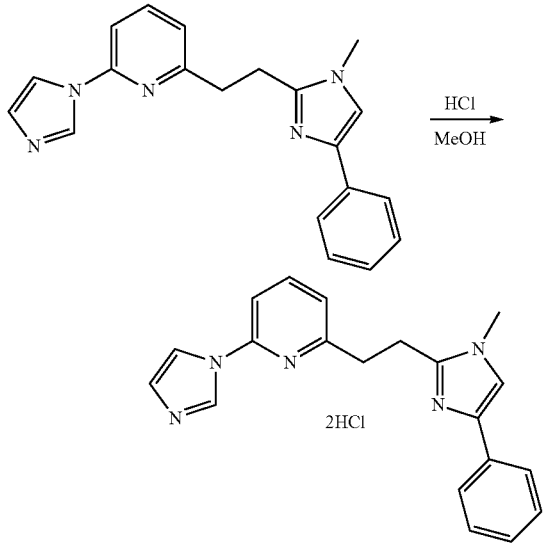

(a) 1-Methyl-4-phenyl-1H-imidazole

The title compound was prepared according to General Procedure L-(d). MS (ESI): m/z 159 [M+H]⁺.

(b) 1-Methyl-4-phenyl-1H-imidazole-2-carbaldehyde

The title compound was prepared according to General Procedure 14-(j). MS (ESI): m/z 187 [M+H]⁺.

(c) 2-Bromo-6-(bromomethyl)pyridine

The title compound was prepared according to General Procedure 25-(c) using 1 equivalent of NBS. MS (ESI): m/z 250 [M+H]⁺.

(d) ((6-Bromopyridin-2-yl)methyl)triphenylphosphonium bromide

The title compound was prepared according to General Procedure D-(b).

(e) 2-Bromo-6-(2-(1-methyl-4-phenyl-1H-imidazol-2-yl)vinyl)-pyridine

The title compound was prepared according to General Procedure D-(c). MS (ESI): m/z 340 [M+H]⁺.

(f) 2-(1H-Imidazol-1-yl)-6-(2-(1-methyl-4-phenyl-1H-imidazol-2-yl)vinyl)pyridine 2-Bromo-6-(2-(1-methyl-4-phenyl-1H-imidazol-2-yl)vinyl)pyridine (102 mg, 0.3 mmol), imidazole (41 mg, 0.6 mmol), CuI (6 mg, 0.03 mmol), and K₂CO₃ (124 mg, 0.9 mmol) were mixed in dimethylformamide (2 mL). The resulting solution was heated for 5 h in a microwave reactor held at a constant temperature of 160° C. The crude product was purified using reverse phase column chromatography to give 2-(1H-imidazol-1-yl)-6-(2-(1-methyl-4-phenyl-1H-imidazol-2-yl)-vinyl)pyridine (57 mg). MS (ESI): m/z 328 [M+H]⁺.

(g) 2-(1H-Imidazol-1-yl)-6-(2-(1-methyl-4-phenyl-1H-imidazol-2-yl)ethyl)pyridine The title compound was prepared according to General Procedure A-(d).

35. General Procedure X

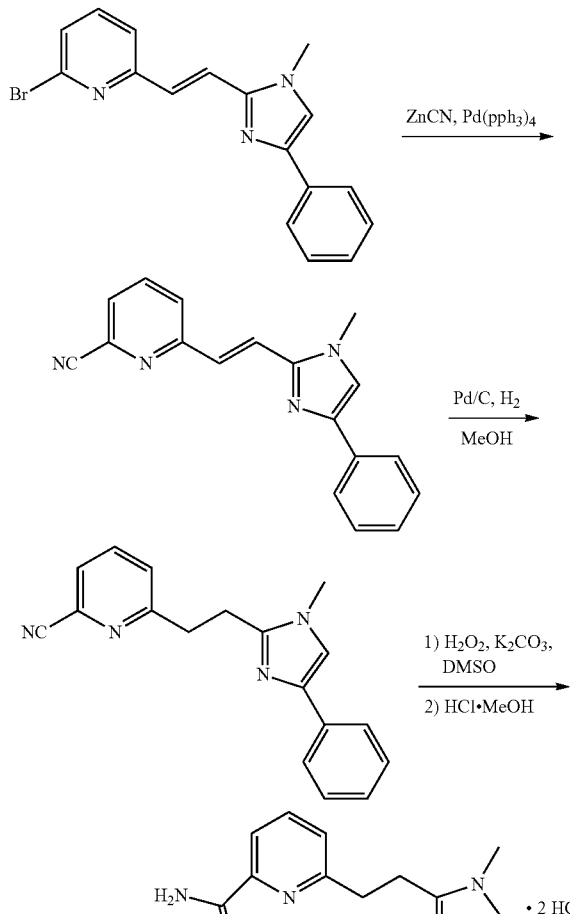

(a) 6-(2-(1-Methyl-4-phenyl-1H-imidazol-2-yl)vinyl)-picolinonitrile

To a solution of 2-bromo-6-(2-(1-methyl-4-phenyl-1H-imidazol-2-yl)vinyl)pyridine (120 mg, 0.354 mmol) in dry DMF (3 mL) was added cyanozinc (97 mg, 1.062 mmol) and tetrakis(triphenylphosphine)palladium(0) (41 mg, 0.035 mmol). The mixture was stirred at 130° C. for 3 h in a microwave. The residue was then filtered. The filtrate was concentrated and purified by reverse phase column chromatography to yield 6-(2-(1-methyl-4-phenyl-1H-imidazol-2-yl)vinyl)-picolinonitrile (100 mg) as a yellow solid. MS (ESI): m/z 287 [M+H]+.

(b) 6-(2-(1-Methyl-4-phenyl-1H-imidazol-2-yl)ethyl)-picolinonitrile

The title compound was prepared according to General Procedure A-(d). MS (ESI): m/z 289 [M+H]+.

(c) 6-(2-(1-Methyl-4-phenyl-1H-imidazol-2-yl)ethyl)picolinamide

To a solution of 6-(2-(1-methyl-4-phenyl-1H-imidazol-2-yl)ethyl)-picolinonitrile (10 mg, 0.035 mmol) in dimethyl sulfoxide (2 mL) at 0° C. was added potassium carbonate (24 mg, 0.175 mmol) and hydrogen peroxide (12 mg, 0.350 mmol). After stirring at room temperature for 1 h, the mixture was quenched with sat. NaHSO4 (aq.), and extracted with EtOAc (30 mL×2). The organic phase was dried and concentrated under reduced pressure. The residue was purified by prep-HPLC to give a white solid (3 mg). MS (ESI): m/z 307 [M+H]+.

The solid was dissolved in 3 mL HCl/MeOH and stirred at r.t for 1 h. The mixture was concentrated under reduced pressure to give a yellow solid (3.3 mg). MS (ESI): m/z 307 [M+H]+.

36. General Procedure Y

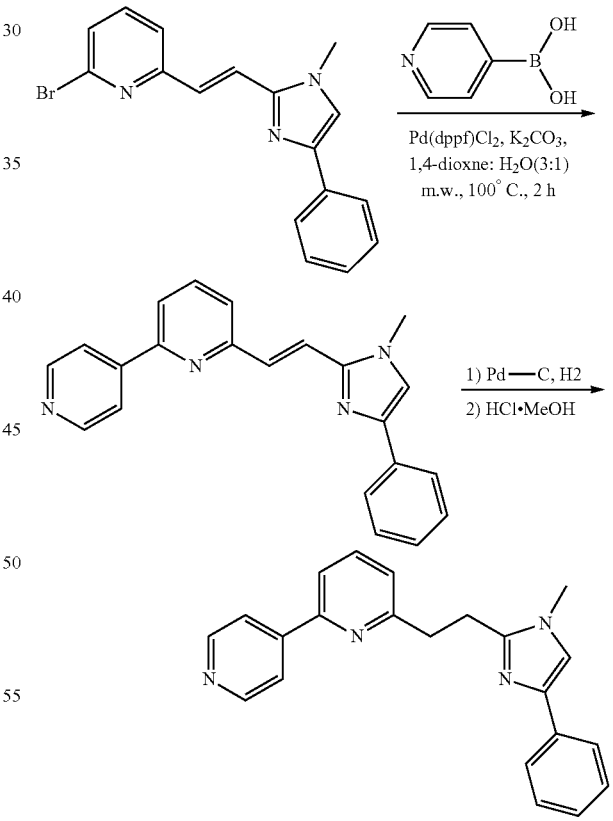

(a) 6-(2-(1-Methyl-4-phenyl-1H-imidazol-2-yl)vinyl)-2,4'-bipyridine 6-(2-(1-Methyl-4-phenyl-1H-imidazol-2-yl)vinyl)-2,4'-bipyridine was prepared according to General Procedure F-(g). MS (ESI): m/z 339 [M+H]+. (b) 6-(2-(1-Methyl-4-phenyl-1H-imidazol-2-yl)ethyl)-2,4'-bipyridine hydrochloride salt was prepared according to General Procedure A-(d) and N-(h). MS (ESI): m/z 341 [M+H]+.

37. General Procedure Z

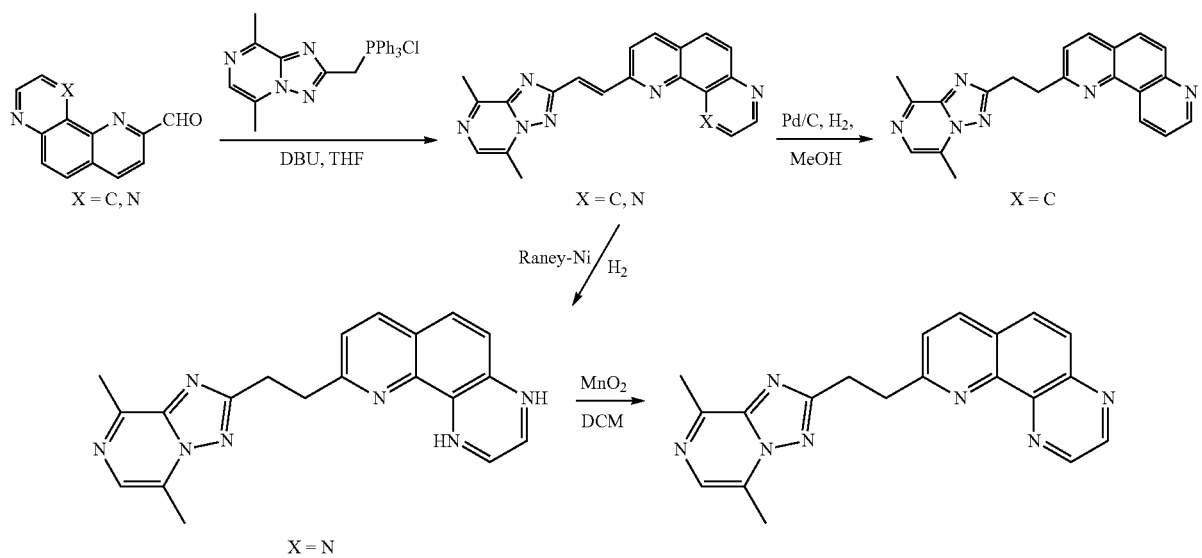

(a) (E)-2-(2-(5,8-Dimethyl-[1,2,4]triazolo[1,5a]pyrazin-2-yl)vinyl)-1,7-phenanthroline and (E)-9-(2-(5,8-dimethyl-[1,2,4]triazolo[1,5-a]pyrazin-2-yl)vinyl)pyrido[2,3-f]quinoxaline were prepared according to General Procedure D-(c). MS (ESI): m/z 353 [M+H]$^+$. (b) 2-(2-(5,8-Dimethyl-[1,2,4]triazolo[1,5-a]pyrazin-2-yl)ethyl)-1,7-phenanthroline was prepared according to General Procedure A-(d). MS (ESI): m/z 355 [M+H]$^+$. (c) 9-(2-(5,8-Dimethyl-[1,2,4]triazolo[1,5-a]pyrazin-2-yl)ethyl)pyrido[2,3-f]quinoxaline was prepared according to General Procedures F-(f) and 14-(m).

38. General Procedure AA

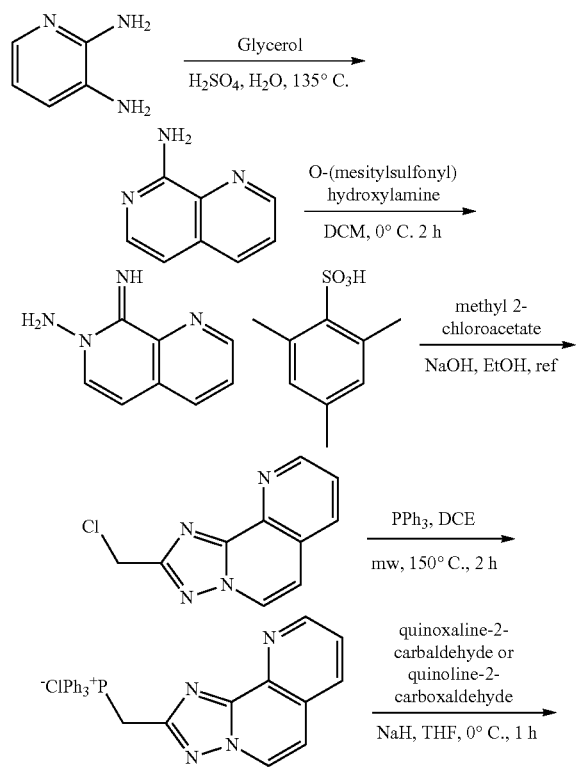

-continued

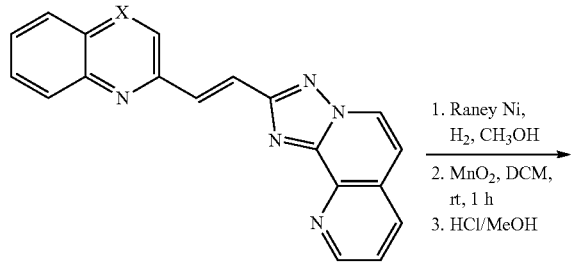

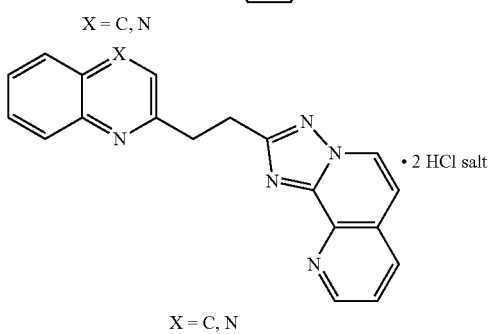

(a) 1,7-Naphthyridin-8-amine was prepared according to General Procedure Q-(b). MS (ESI): m/z 146.1 [M+H]$^+$. (b) 8-Imino-1,7-naphthyridin-7(8H)-amine 2,4,6-trimethylbenzenesulfonate was prepared according to General Procedure N-(d). MS (ESI): m/z 161.1 [M+H]$^+$. (c) 2-(Chloromethyl)-[1,2,4]triazolo[1,5-h][1,7]naphthyridine was prepared according to General Procedure N-(e). MS (ESI): m/z 219.0 [M+H]$^+$. (d) ([1,2,4]Triazolo[1,5-h][1,7]naphthyridin-2-ylmethyl)triphenylphosphonium chloride was prepared according to General Procedure D-(b). MS (ESI): m/z 445 [M]$^+$. (e) (E)-2-(2-(Quinolin-2-yl)vinyl)-[1,2,4]triazolo[1,5-h][1,7]naphthyridine and (E)-2-(2-(Quinoxalin-2-yl)vinyl)-[1,2,4]triazolo[1,5-h][1,7]naphthyridine were prepared according to General Procedure D-(c). MS (ESI): m/z 324.1 [M+H]$^+$. (f) 2-(2-(Quinolin-2-yl)ethyl)-[1,2,4]triazolo[1,5-h][1,7]naphthyridine hydrochloride salt and 2-(2-(Quinoxalin-2-yl)ethyl)-[1,2,4]triazolo[1,5-h][1,7]naphthyridine hydrochloride salt were prepared according to General Procedures A-(d) and N-(h).

39. General Procedure BB

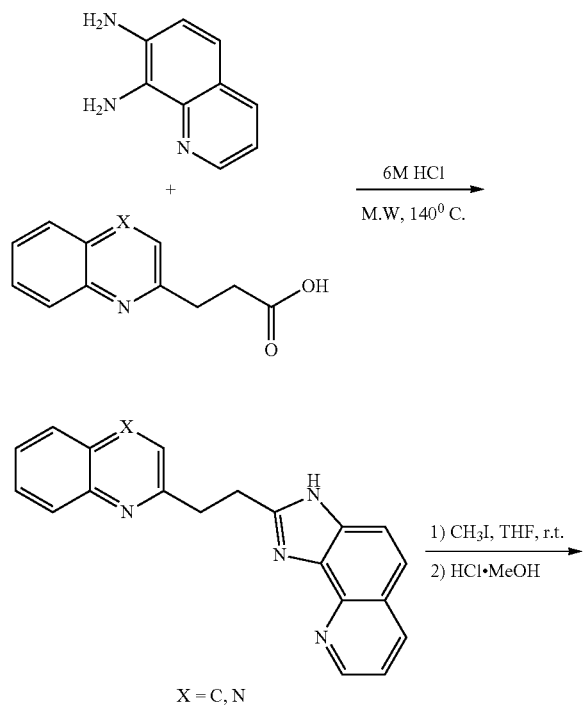

X = C, N (a) 2-(2-(Quinolin-2-yl)ethyl)-3H-imidazo[4,5-h]quinoline and 2-(2-(Quinoxalin-2-yl)ethyl)-3H-imidazo[4,5-h] quinoline were prepared according to Synthetic Procedure 21 using 6 M HCl and after heating at 140° C. in a microwave reactor. MS (ESI): m/z 326 [M+H]$^+$. (b) 3-Methyl-2-(2-(quinolin-2-yl)ethyl)-3H-imidazo[4,5-h]quinoline and 3-methyl-2-(2-(quinoxalin-2-yl)ethyl)-3H-imidazo[4,5-h] quinoline hydrochloride were prepared according to General Procedure L-(d) using THF as solvent and General Procedure N-(h).

40. General Procedure CC

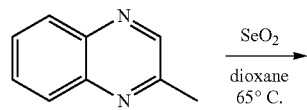

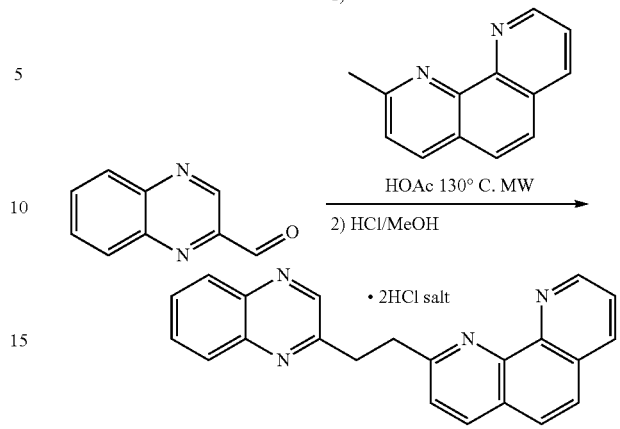

(a) Quinoxaline-2-carbaldehyde was prepared according to General Procedure H-(a). MS (ESI): m/z 159.1 [M+H]$^+$. (b) 2-(2-(Quinoxalin-2-yl)ethyl)-1,10-phenanthroline hydrochloride was prepared according to General Procedures A-(c) and N-(h).

41. General Procedure DD

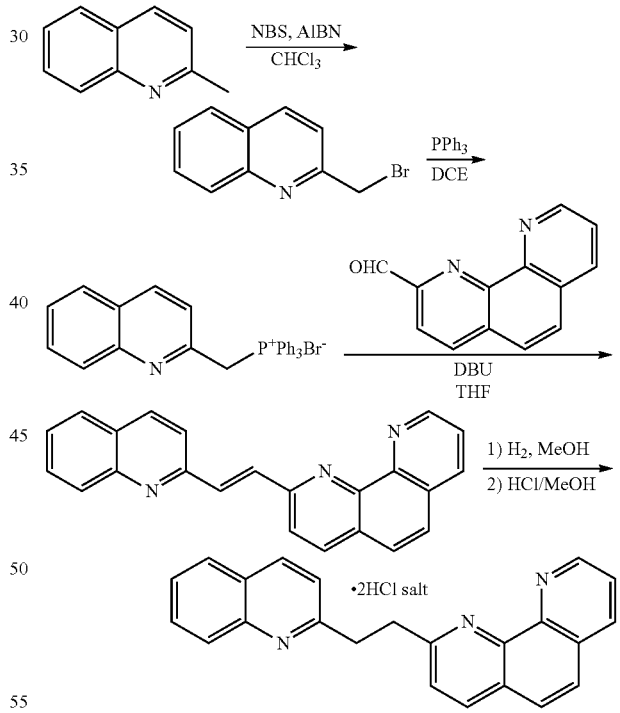

(a) 2-(Bromomethyl)quinoline was prepared according to General Procedure 25-(c) using 1 equivalent of NBS. MS (ESI): m/z 221 [M+H]$^+$. (b) Triphenyl(quinolin-2-ylmethyl) phosphonium bromide was prepared according to General Procedure D-(b). MS (ESI): m/z 404 [1\4]$^+$. (c) (E)-2-(2-(Quinolin-2-yl)vinyl)-1,10-phenanthroline was prepared according to General Procedure D-(c). MS (ESI): m/z 334.1 [M+H]$^+$. (d) 2-(2-(Quinolin-2-yl)ethyl)-1,10-phenanthroline hydrochloride was prepared according to General Procedures F-(f) and N-(h).

42. General Procedure EE

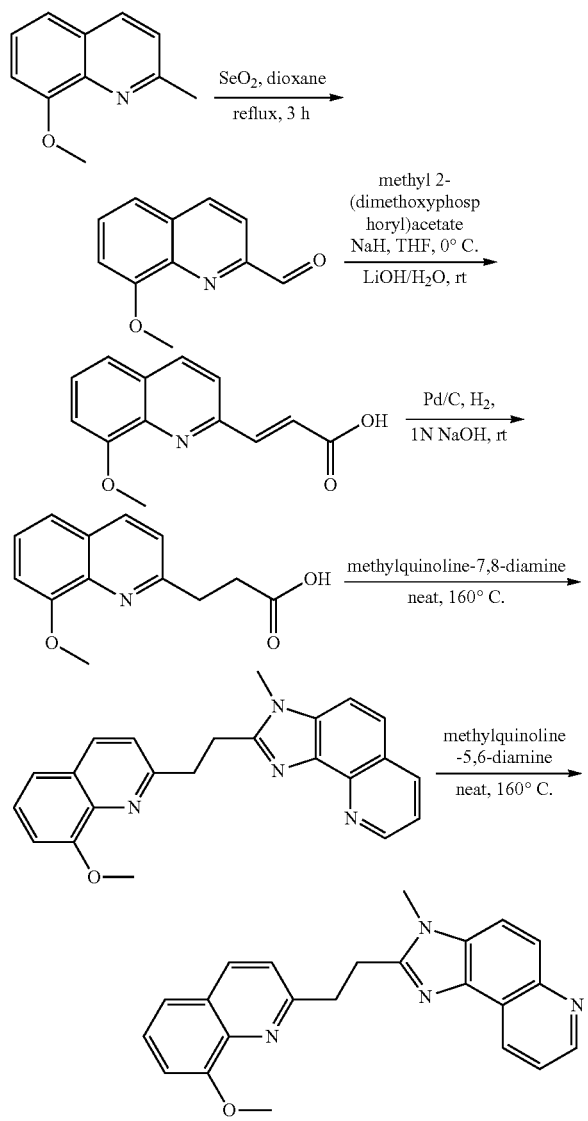

(a) 8-Methoxyquinoline-2-carbaldehyde

The title compound was prepared according to General Procedure H-(a). MS (ESI): m/z 188.1 [MA-]+.

(b) (E)-3-(8-Methoxyquinolin-2-yl)acrylic acid

To a suspension of sodium hydride (60%) (0.8 mg, 20.0 mmol) in tetrahydrofuran (80 mL) was added methyl 2-(dimethoxyphosphoryl)acetate (2.65 mg, 12 mmol) dropwise at 0° C. After the addition was completed, the mixture was stirred for 30 min at 0° C. A solution of 8-methoxyquinoline-2-carbaldehyde (1.87 g, 10.0 mmol) in tetrahydrofuran (20 mL) was then added dropwise over a period of 50 min. The mixture was stirred at 0° C. for 1 h. A solution of lithium hydroxide hydrate (1.26 g, 30.0 mmol) in water (20 mL) was added cautiously to the solution. The resulting mixture was stirred at room temperature overnight. The reaction mixture was concentrated under reduced pressure. To the residue was added water (20 mL), and the pH of the aqueous layer was then adjust to 4 with 1 N hydrogen chloride solution. The precipitate was collected by filtration and then dried in vacuum to give 1.9 g of the product as a white solid. MS (ESI): m/z 230.1 [M+H]+.

(c) 3-(8-Methoxyquinolin-2-yl)propanoic acid

The title compound was prepared according to General Procedure Q-(f). MS (ESI): m/z 232.1 [M+H]+.

(d) 2-(2-(8-Methoxyquinolin-2-yl)ethyl)-3-methyl-3H-imidazo[4,5-h]quinoline and 2-(2-(8-Methoxyquinolin-2-yl)ethyl)-3-methyl-3H-imidazo[4,5-f]quinoline A mixture of 3-(8-methoxyquinolin-2-yl)propanoic acid (116 mg, 0.5 mmol) and methylquinoline-7,8-diamine (260 mg, 1.5 mmol) or methylquinoline-5,6-diamine (70 mg, 0.4 mmol) was stirred at 160° C. for 1 h under nitrogen. After cooling to room temperature, the residue was purified by column chromatography.

43. General Procedure FF

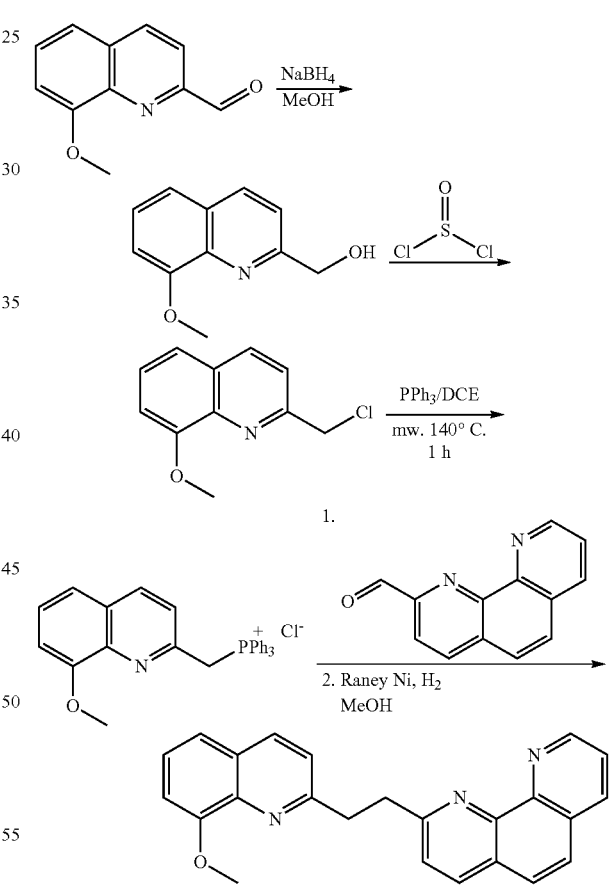

(a) (8-Methoxyquinolin-2-yl)methanol

The title compound was prepared according to General Procedure 18-(a). MS (ESI): m/z 190.1 [M+H]+.

(b) 2-(Chloromethyl)-8-methoxyquinoline

A mixture of (8-methoxyquinolin-2-yl)methanol (1.0 g, 5.3 mmol) and N,N-dimethylformamide (39 mg, 0.53 mmol)

in sulfurous dichloride (20 mL) was stirred at room temperature for 2 h. The reaction mixture was concentrated and ice water was added. The pH of the aqueous layer was adjusted to 7 with 10 N sodium hydroxide solution. The mixture was extracted with DCM (30 mL×3). The combined organic phase was dried with anhydrous sodium sulfate, concentrated, and purified by column chromatography to give 0.66 g of the product as a yellow solid. MS (ESI): m/z 208.0 [M+H]$^+$.

(c) ((8-Methoxyquinolin-2-yl)methyl)triphenylphosphonium chloride

The title compound was prepared according to General Procedure D-(b). MS (ESI): m/z 434.2 [M]$^+$.

(d) (E)-2-(2-(8-Methoxyquinolin-2-yl)vinyl)-1,10-phenanthroline

The title compound was prepared according to General Procedure D-(c). MS (ESI): m/z 364.1 [M+H]$^+$.

(e) 2-(2-(8-Methoxyquinolin-2-yl)ethyl)-1,10-phenanthroline

The title compound was prepared according to General Procedure F-(f).

44. General Procedure GG

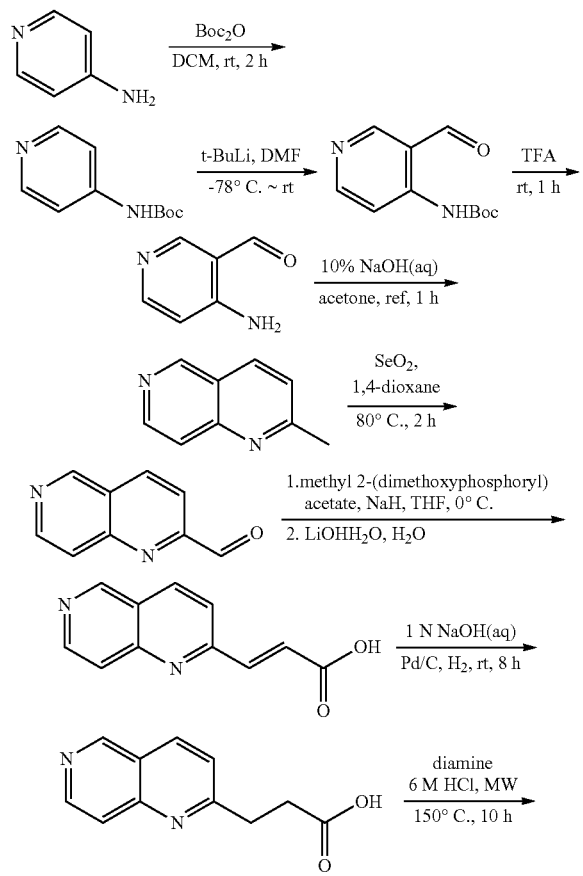

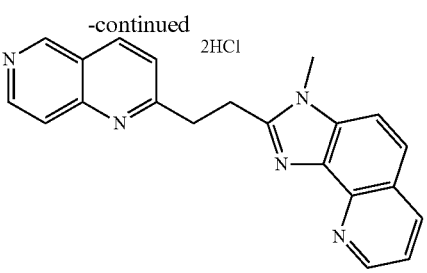

(a) tert-Butyl pyridin-4-ylcarbamate

To a solution of pyridin-4-amine (2.35 g, 25.0 mmol) in DCM (150 mL) was added di-tert-butyl dicarbonate (5.40 g, 25.0 mmol). The mixture was stirred at room temperature for 2 h. The solvent was removed under reduced pressure. The residue was purified by column chromatography to give 3.6 g of the product as a white solid. MS (ESI): m/z 195.1 [M+H]$^+$.

(b) tert-Butyl-3-formylpyridin-4-ylcarbamate

The title compound was prepared according to General Procedure A-(b). MS (ESI): m/z 223.1 [M+H]$^+$.

(c) 4-Aminonicotinaldehyde

The title compound was prepared according to General Procedure N-(a). MS (ESI): m/z 123.1 [M+H]$^+$.

(d) 2-Methyl-1,6-naphthyridine

The title compound was prepared according to General Procedure 25-(e). MS (ESI): m/z 145.1 [M+H]$^+$.

(e) 1,6-Naphthyridine-2-carbaldehyde

The title compound was prepared according to General Procedure H-(a). MS (ESI): m/z 177.1 [M+H]$^+$.

(f) (E)-3-(1,6-Naphthyridin-2-yl)acrylic acid

The title compound was prepared according to General Procedure EE-(b). MS (ESI): m/z 201.1 [M+H]$^+$.

(g) 3-(1,6-Naphthyridin-2-yl)propanoic acid

A mixture of (E)-3-(1,6-naphthyridin-2-yl)acrylic acid (300 mg, 1.50 mmol) and Pd/C (30 mg, 10%) in 1 N sodium hydroxide aqueous solution (8 mL) was stirred under H$_2$ for 8 h at room temperature, and then filtered. The solution was acidified to pH 4 with 1 N aqueous hydrogen chloride solution. The precipitate was collected by filtration and dried in vacuum to give 220 mg of the product as a yellow solid. MS (ESI): m/z 203.1 [M+H]$^+$.

(h) 2-(2-(1,6-Naphthyridin-2-yl)ethyl)-3-methyl-3H-imidazo[4,5-h]quinoline hydrochloride salt The title compound was prepared according to Synthetic Procedure 21 and General Procedure N-(h). MS (ESI): m/z 340.1 [M+H]$^+$.

45. General Procedure HH

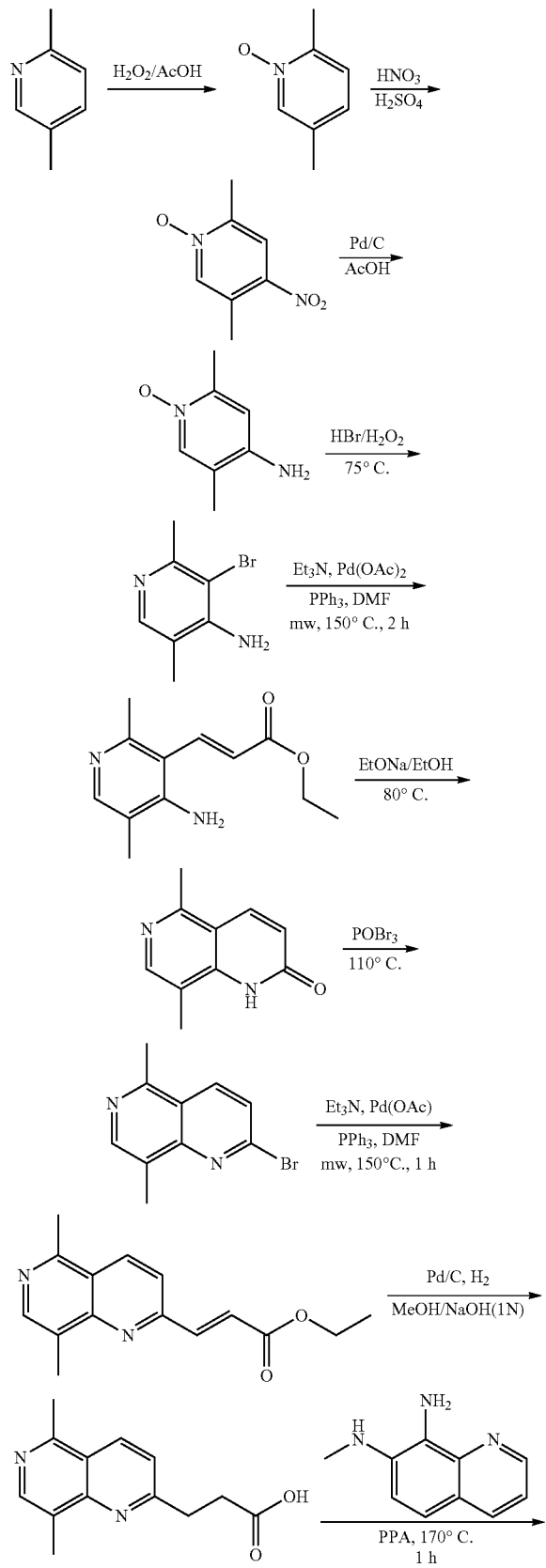

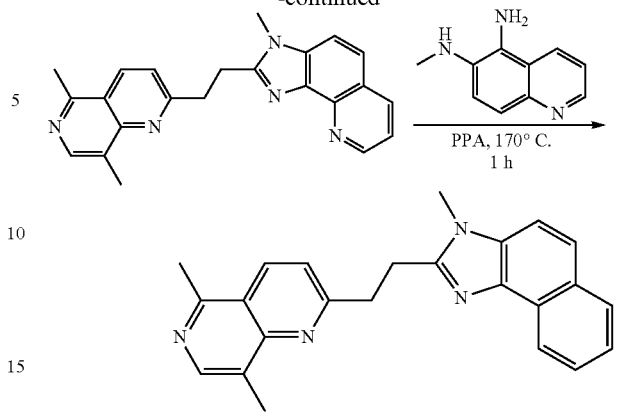

(a) 2,5-Dimethylpyridine N-Oxide

A mixture of 2,5-dimethylpyridine (12.5 g, 0.12 mol) and 30% hydrogen peroxide (30 mL) in acetic acid (25 mL) was stirred at 90° C. for 48 h. The reaction mixture was diluted with water (50 mL) and concentrated to a volume of approximately 25 mL. The concentrated solution was neutralized with solid sodium carbonate, extracted with DCM (100 mL×3), dried with anhydrous sodium sulfate, and concentrated to give 14.4 g of the product as a yellow oil. MS (ESI): m/z 124.1 [M+H]$^+$.

(b) 2,5-Dimethyl-4-nitropyridine N-Oxide

To 75 mL of concentrated sulfuric acid at 0° C. was added 2,5-dimethylpyridine N-oxide (10 g, 0.08 mol) dropwise. 5.6 mL of fuming nitric acid (0.13 mol) was added to the mixture. The mixture was heated at 90° C. for 6 h, cooled, poured onto 500 mg ice, and neutralized with 120 mL of 50% sodium hydroxide solution. The solution was extracted with DCM (250 mL×5), and the combined organic phase was dried with anhydrous sodium sulfate and concentrated to give 7.0 g of the crude product as a yellow solid, which was used for the next step without further purification. MS (ESI): m/z 169.1 [M+H]$^+$.

(c) 2,5-Dimethylpyridin-4-amine

A mixture of 2,5-dimethyl-4-nitropyridine N-oxide (7.0 g, 41.7 mmol) and 10% Pd/C (1.2 g) in acetic acid (60 mL) was stirred under hydrogen at 60° C. for 18 h. The solution was cooled, filtered, and diluted with water (100 mL). The aqueous mixture was neutralized with solid sodium carbonate. The solution was extracted with DCM (250 mL×5), and the combined organic phase was dried with anhydrous sodium sulfate and concentrated to give 4.6 g of the product as a yellow solid. MS (ESI): m/z 123.1 [M+H]$^+$.

(d) 3-Bromo-2,5-dimethylpyridin-4-amine

A mixture of 2,5-dimethylpyridin-4-amine (3.57 g, 29.3 mmol) in 48% hydrogen bromide aqueous solution (40 mL) was heated to 75° C. Then 15% hydrogen peroxide (7 mL) was added dropwise over 30 min. The reaction mixture was stirred at 75° C. for 1 h, and concentrated under reduced pressure. The pH of the solution was adjusted to 9 with 1 N sodium hydroxide solution. The aqueous mixture was extracted with DCM (250 mL×3), and the combined organic phase was washed with saturated sodium chloride solution (250 mL×1), dried with sodium sulfate, and concentrated to give 5.0 g of the product as a yellow solid. MS (ESI): m/z 203.1 [M+H]$^+$.

(e) (E)-Ethyl 3-(4-amino-2,5-dimethylpyridin-3-yl)acrylate

A mixture of 3-bromo-2,5-dimethylpyridin-4-amine (5.0 g, 25 mmol), ethyl acrylate (5.0 g, 50 mmol), diacetoxypalladium (1.12 g, 5.0 mmol), PPh$_3$ (3.28 g, 12.5 mmol), and NEt$_3$ (7.6 g, 75 mmol) in DMF (50 mL) was heated in a microwave reactor at 150° C. for 2 h. The reaction mixture was cooled, diluted with water (100 mL), and extracted with DCM (250 mL×3). The combined organic layers were washed with saturated sodium chloride solution (100 mL×3), dried with sodium sulfate, concentrated, and purified by column chromatography to give 5.0 g of the product as a yellow solid. MS (ESI): m/z 221.2 [M+H]$^+$.

(f) 5,8-Dimethyl-1,6-naphthyridin-2(1H)-one

A mixture of (E)-ethyl 3-(4-amino-2,5-dimethylpyridin-3-yl)acrylate (5 g, 22.7 mmol) and sodium ethanolate (6.2 g, 91 mmol) in ethanol (100 mL) was heated to 80° C. for 2 h. The reaction mixture was concentrated and diluted with water (50 mL). The aqueous phase was extracted with EtOAc (100 mL×3), and the combined organic layers were washed with saturated sodium chloride solution, dried with sodium sulfate, and concentrated to give 2.3 g of the product as a yellow solid. MS (ESI): m/z 175.1 [M+H]$^+$.

(g) 2-Bromo-5,8-dimethyl-1,6-naphthyridine

A mixture of 5,8-dimethyl-1,6-naphthyridin-2(1H)-one (2.1 g, 12 mmol) and phosphoryl tribromide (5 g) was heated to 110° C. for 1 h, cooled, diluted with ice water, and neutralized with saturated sodium bicarbonate solution. The aqueous phase was extracted with DCM (100 mL×3), and the combined organic layers were dried with sodium sulfate and purified by column chromatography to give 0.63 g of the product as a pale white solid. MS (ESI): m/z 237.0 [M+H]$^+$.

(h) (E)-Ethyl 3-(5,8-dimethyl-1,6-naphthyridin-2-yl)acrylate

A mixture of 2-bromo-5,8-dimethyl-1,6-naphthyridine (0.63 g, 2.7 mmol), ethyl acrylate (0.53 g, 5.4 mmol), diacetoxypalladium (121 mg, 0.5 mmol), PPh$_3$ (0.35 g, 1.4 mmol), and NEt$_3$ (0.82 g, 8.1 mmol) in N,N-dimethylformamide (5 mL) was heated in a microwave reactor at 150° C. for 1 h. The reaction mixture was diluted with water (20 mL) and extracted with EtOAc (50 mL×3). The combined organic layers were washed with saturated sodium chloride solution (50 mL×3), dried with sodium sulfate and concentrated to give 0.6 g of the crude product as a yellow solid, which was used for the next step without further purification. MS (ESI): m/z 257.1 [M+H]$^+$.

(i) 3-(5,8-Dimethyl-1,6-naphthyridin-2-yl)propanoic acid

The title compound was prepared according to General Procedure Q-(f). MS (ESI): m/z 231.1 [M+H]$^+$.

(j) 2-(2-(5,8-Dimethyl-1,6-naphthyridin-2-yl)ethyl)-3-methyl-3H-imidazo[4,5-h]quinoline The title compound was prepared according to General Procedure EE-(d) using polyphosphoric acid after heating at 170° C. for 1 h.

(k) 2-(2-(5,8-Dimethyl-1,6-naphthyridin-2-yl)ethyl)-3-methyl-3H-imidazo[4,5-f]quinoline The title compound was prepared according to General Procedure EE-(d) using polyphosphoric acid after heating at 170° C. for 1 h.

(l) 2-(2-(5,8-Dimethyl-1,6-naphthyridin-2-yl)ethyl)-3H-imidazo[4,5-f]quinoline

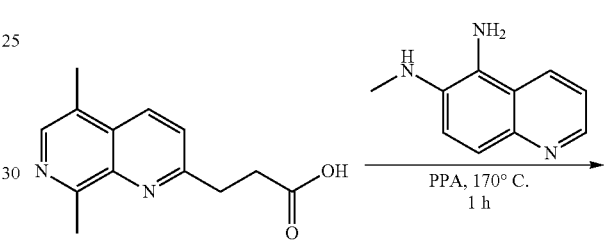

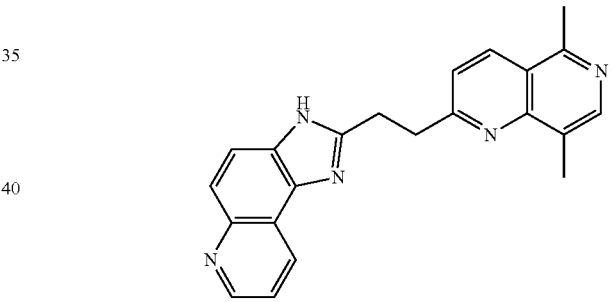

The title compound was prepared according to General Procedure EE-(d) using polyphosphoric acid after heating at 170° C. for 1 h.

(m) 2-(2-(5,8-Dimethyl-1,6-naphthyridin-2-yl)ethyl)-[1,2,4]triazolo[5,1-f][1,6]naphthyridine

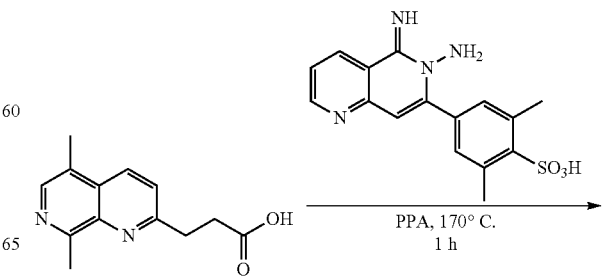

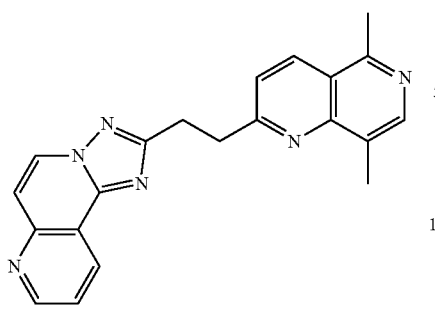

The title compound was prepared according to General Procedure N-(e).

46. General Procedure II

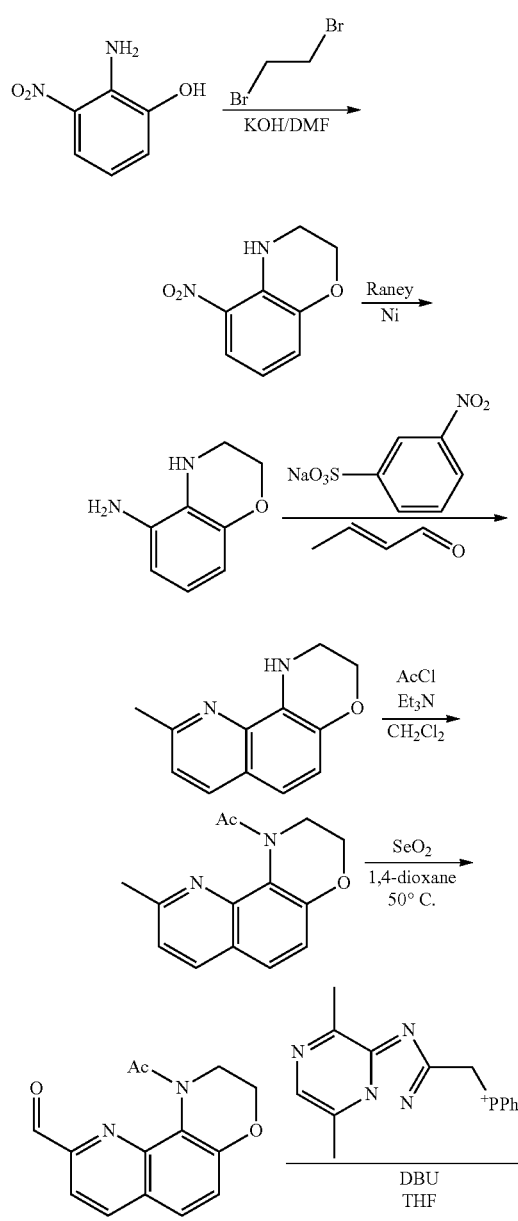

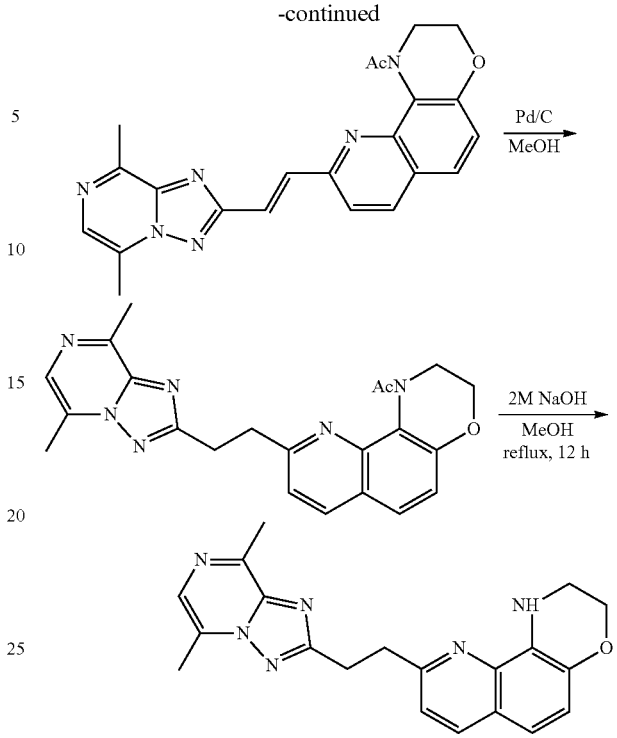

(a) 5-Nitro-3,4-dihydro-2H-benzo[b][1,4]oxazine

To a solution of 2-amino-3-nitrophenol (15.0 g, 97 mmol) and 1,2-dibromoethane (29.1 g, 155 mmol) in dimethylformamide (80 mL) was added KOH (10.9 g, 194 mmol) at 180° C. After stirring at 200° C. for 2 days, the mixture was poured to 150 g water. The mixture was concentrated under reduced pressure. The crude product was purified using column chromatography to give the title compound (2.50 g) as a red solid. MS (ESI): m/z 181 [M+H]$^+$ (b) 3,4-Dihydro-2H-benzo[b][1,4]oxazin-5-amine The title compound was prepared according to General Procedure L-(a). MS (ESI): m/z 151 [M+H]$^+$.

(c) 9-Methyl-2,3-dihydro-1H-[1,4]oxazino[2,3-h]quinoline

The title compound was prepared according to General Procedure 25-(a). MS (ESI): m/z 201 [M+H]$^+$ (d) 1-(9-Methyl-2,3-dihydro-[1,4]oxazino[2,3-h]quinolin-1-yl)ethanone To a solution of 9-methyl-2,3-dihydro-1H-[1,4]oxazino[2,3-h]quinoline (200 mg, 1.0 mmol) and NEt$_3$ (304 mg, 3.0 mmol) in DCM (5 mL) was added acetyl chloride (157 mg, 2.0 mmol) at room temperature. After stirring at room temperature for 1 h, the mixture was washed with water (10 mL×3). The organic phase was dried over anhydrous Na$_2$SO$_4$ and filtered. The filtrate was concentrated to give the title compound (170 mg) as a yellow solid. MS (ESI): m/z 243 [M+H]$^+$.

(e) 1-Acetyl-2,3-dihydro-1H-[1,4]oxazino[2,3-h]quinoline-9-carbaldehyde

The title compound was prepared according to General Procedure H-(a). MS (ESI): m/z 257 [M+H]$^+$.

(f) (E)-1-(9-(2-(5,8-Dimethyl-[1,2,4]triazolo[1,5-a]pyrazin-2-yl)vinyl)-2,3-dihydro-[1,4]oxazino[2,3-h]quinolin-1-yl)ethanone The title compound was prepared according to General Procedure D-(c). MS (ESI): m/z 401 [M+H]$^+$.

(g) 1-(9-(2-(5,8-Dimethyl-[1,2,4]triazolo[1,5-a]pyrazin-2-yl)ethyl)-2,3-dihydro-[1,4]oxazino[2,3-h]quinolin-1-yl)ethanone The title compound was prepared according to General Procedure A-(d). MS (ESI): m/z 403 [M+H]$^+$.

(h) 9-(2-(5,8-Dimethyl-[1,2,4]triazolo[1,5-a]pyrazin-2-yl)ethyl)-2,3-dihydro-1H-[1,4]oxazino[2,3-h]quinoline To a solution of 1-(9-(2-(5,8-dimethyl-[1,2,4]triazolo[1,5-a]pyrazin-2-yl)ethyl)-2,3-dihydro-[1,4]oxazino[2,3-h]quinolin-1-yl)ethanone (10 mg, 0.025 mmol) in methanol (1 mL) was added 2 M NaOH (0.05 mL, 0.1 mmol) at room temperature. After stirring the mixture at 100° C. for 12 h, the solvent was removed. The crude product was purified using reverse phase column chromatography (7 mg).

47. General Procedure JJ

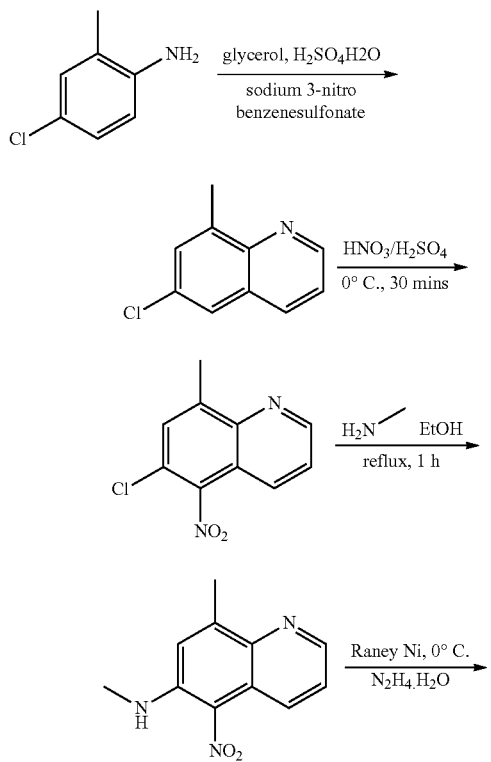

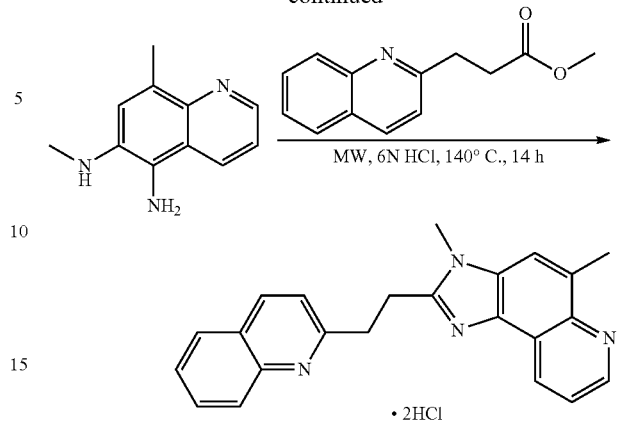

(a) 6-Chloro-8-methylquinoline

The title compound was prepared according to General Procedure Q-(b). MS (ESI): m/z 178 [M+H]$^+$.

(b) 6-Chloro-8-methyl-5-nitroquinoline

The title compound was prepared according to General Procedure P-(c). MS (ESI): m/z 223 [M+H]$^+$.

(c) N,8-Dimethyl-5-nitroquinolin-6-amine

A mixture of 6-chloro-8-methyl-5-nitroquinoline (420 mg, 1.9 mmol) in methanamine as a solution in ethyl alcohol (30 mL) was heated to 80° C. and stirred for 1 h. After concentration under reduced pressure, the reaction mixture was extracted with DCM (50 mL). The organic layer was washed with water (20 mL×2), dried over Na$_2$SO$_4$, and concentrated under reduced pressure to give 410 mg of N,8-dimethyl-5-nitroquinolin-6-amine as a yellow solid. MS (ESI): m/z 218 [M+H]$^+$.

(d) N$^6$,8-Dimethylquinoline-5,6-diamine

The title compound was prepared according to General Procedure L-(a). MS (ESI): m/z 188 [M+H]$^+$.

(e) 3,5-Dimethyl-2-(2-(quinolin-2-yl)ethyl)-3H-imidazo[4,5-f]quinoline hydrochloride salt The title compound was prepared according to Synthetic Procedure 21 using a microwave reactor, and General Procedure N-(h). MS (ESI): m/z 353 [M+H]$^+$.

48. General Procedure KK

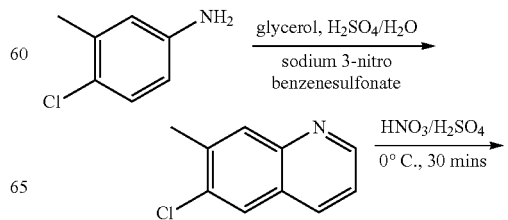

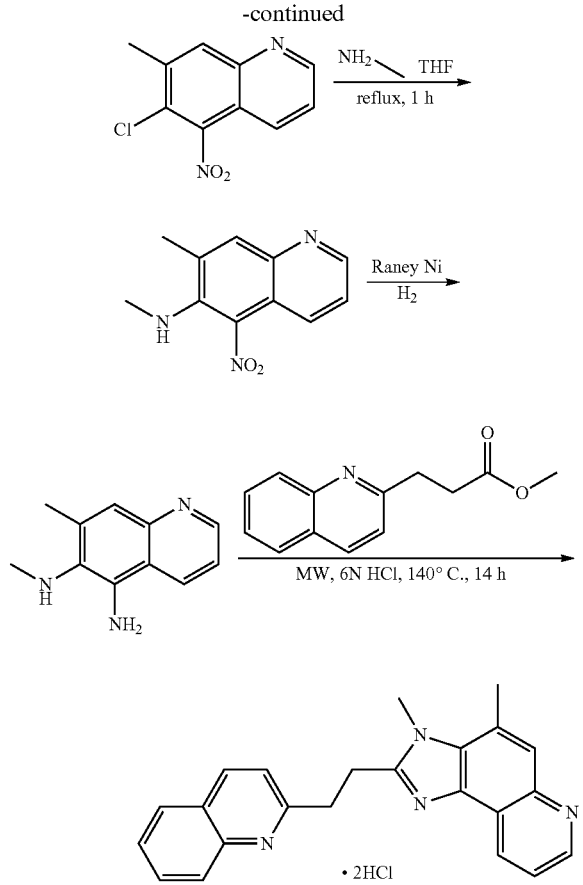

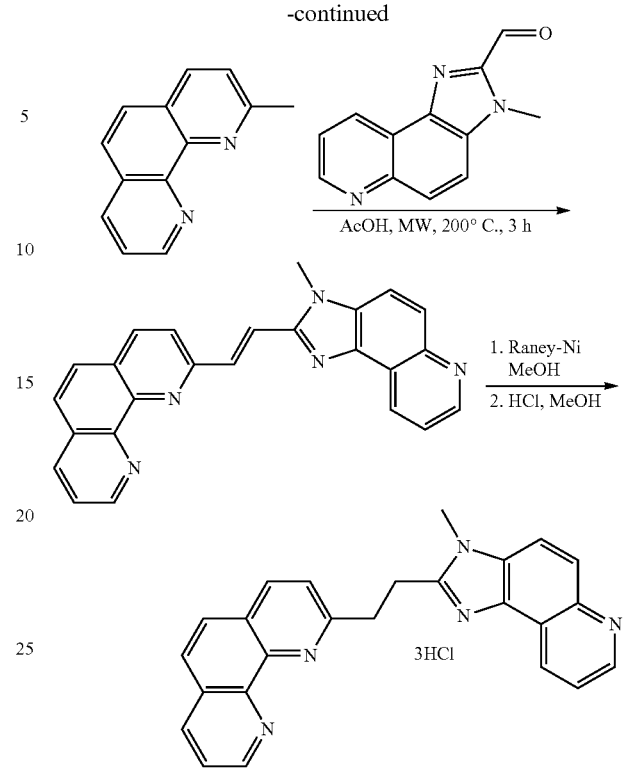

(a) 6-Chloro-7-methylquinoline was prepared according to General Procedure Q-(b). MS (ESI): m/z 178 [M+H]$^+$. (b) 6-Chloro-7-methyl-5-nitroquinoline was prepared according to General Procedure P-(c). MS (ESI): m/z 223 [M+H]$^+$. (c) N,7-Dimethyl-5-nitroquinolin-6-amine was prepared according to General Procedure JJ-(c). MS (ESI): m/z 218 [M+H]$^+$. (d) N$^6$,7-Dimethylquinoline-5,6-diamine was prepared according to General Procedure L-(a). MS (ESI): m/z 188 [M+H]$^+$. (e) 3,4-Dimethyl-2-(2-(quinolin-2-yl)ethyl)-3H-imidazo[4,5-f]quinoline hydrochloride salt was prepared according to Synthetic Procedure 21 using a microwave reactor, and General Procedure N-(h). MS (ESI): m/z 353 [M+H]$^+$ 49. General Procedure LL

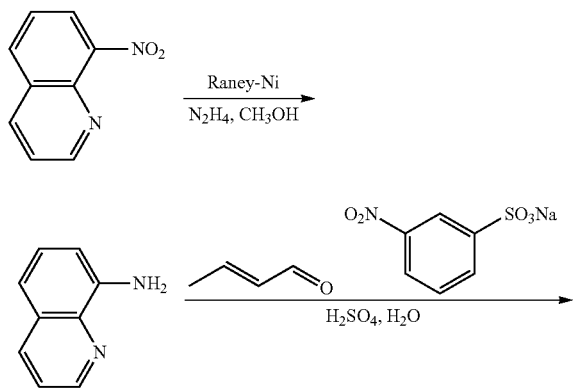

(a) Quinolin-8-amine was prepared according to General Procedure L-(a). MS (ESI): m/z 145 [M+H]$^+$. (b) 2-Methyl-1,10-phenanthroline was prepared according to General Procedure 25-(a). MS (ESI): m/z 195 [M+H]$^+$. (c) (E)-2-(2-(3-Methyl-3H-imidazo[4,5-f]quinolin-2-yl)vinyl)-1,10-phenanthroline was prepared according to General Procedure A-(c). MS (ESI): m/z 388 [M+H]$^+$. (d) 2-(2-(3-Methyl-3H-imidazo[4,5-f]quinolin-2-yl)ethyl)-1,10-phenanthroline hydrochloride salt was prepared according to General Procedure F-(f) and N-(h). MS (ESI): m/z 390 [M+H]$^+$.

50. General Procedure MM

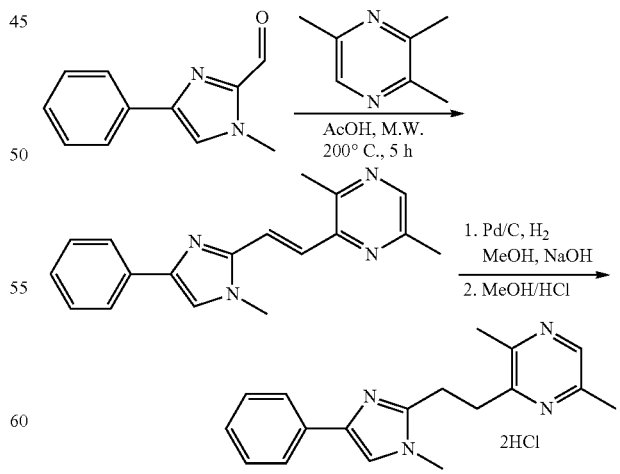

(a) 2,5-Dimethyl-3-(2-(1-methyl-4-phenyl-1H-imidazol-2-yl)vinyl)pyrazine was prepared according to General Procedure A-(c). MS (ESI): m/z 291 [M+H]$^+$. (b) 2,5-Dimethyl-3-(2-(1-methyl-4-phenyl-1H-imidazol-2-yl)ethyl)pyrazine hydrochloride salt was prepared according to General Procedure Q-(f) and N-(h). MS (ESI): m/z 293.1 [M+H]+.

51. General Procedure NN

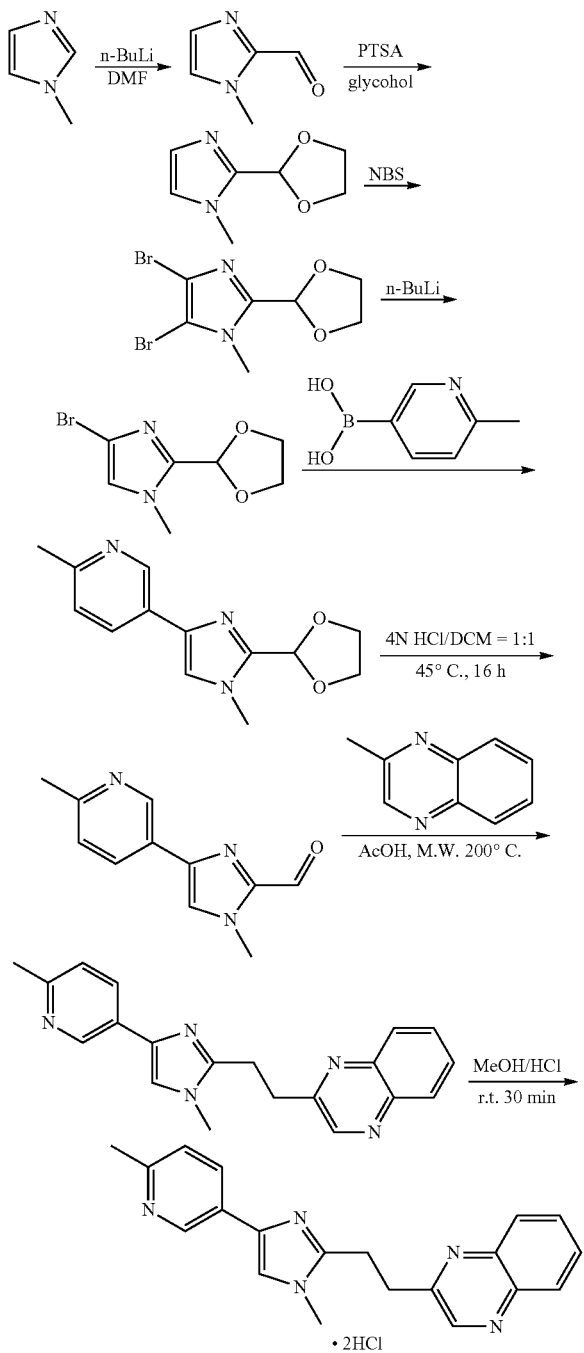

(a) 1-Methyl-1H-imidazole-2-carbaldehyde

The title compound was prepared according to General Procedure A-(b). MS (ESI): m/z 111.1 [M+H]+.

(b) 2-(1,3-Dioxolan-2-yl)-1-methyl-1H-imidazole

A mixture of 1-methyl-1H-imidazole-2-carbaldehyde (24 g, 218 mmol), p-TsOH (16.2 g, 87 mmol), glycol (27 g, 437 mmol), and toluene (700 mL) was heated to 120° C. in a Dean-Stark apparatus for 16 h. Then the mixture was cooled to room temperature, pH was adjusted to 9 with saturated sodium bicarbonate solution at 0° C., and the mixture was extracted with EtOAc (500 mL×2). The organic layers were washed with water (200 mL) and brine (100 mL), dried, filtered, then concentrated to give a red oil (12 g). MS (ESI): m/z 155.1 [M+H]+.

(c) 4,5-Dibromo-2-(1,3-dioxolan-2-yl)-1-methyl-1H-imidazole

A mixture of 2-(1,3-dioxolan-2-yl)-1-methyl-1H-imidazole (9 g, 58.4 mmol), NBS (20.8 g, 116.8 mmol), 2,2'-azobis (2-methylpropionitrile) (478 mg, 2.92 mmol), and chloroform (200 mL) was heated to 62° C. for 16 h under N2. Then the mixture was cooled to room temperature, filtered, and concentrated; and the residue was purified by column chromatography to provide a light yellow solid (3.6 g). MS (ESI): m/z 313 [M+H]+.

(d) 4-Bromo-2-(1,3-dioxolan-2-yl)-1-methyl-1H-imidazole

To a solution of 4,5-dibromo-2-(1,3-dioxolan-2-yl)-1-methyl-1H-imidazole (1 g, 3.2 mmol) in dry THF (20 mL) was added n-BuLi (2.5 M in hexane, 1.28 mL, 3.2 mmol) dropwise at −68° C. over 30 min. The reaction mixture was stirred at the same temperature for 2 h and then was allowed to warm to r.t. over 1 h. 10 mL of water was added slowly at 0° C. to quench the reaction. The residue was extracted with EtOAc (50 mL×2) and the combined organic layers were washed with water (20 mL) and brine (20 mL), dried, and concentrated to give a yellow oil (678 mg). MS (ESI): m/z 233 [M+H]+.

(e) 5-(2-(1,3-Dioxolan-2-yl)-1-methyl-1H-imidazol-4-yl)-2-ethylpyridine

The title compound was prepared according to General Procedure F-(g). MS (ESI): m/z 245 [M+H]+.

(f) 1-Methyl-4-(6-methylpyridin-3-yl)-1H-imidazole-2-carbaldehyde

A mixture of 5-(2-(1,3-dioxolan-2-yl)-1-methyl-1H-imidazol-4-yl)-2-ethylpyridine (140 mg, 0.571 mmol), DCM (5 mL), and 4 N HCl (5 mL) was heated to 45° C. for 16 h. Then the mixture was cooled to room temperature, the pH was adjusted to 6 with saturated sodium bicarbonate solution at 0° C., and the mixture was concentrated to give a crude product. 30 mL of CH3CN was added and the mixture was filtered. The filtrate was then concentrated to afford a white solid (90 mg). MS (ESI): m/z 202.1 [M+H]+.

(g) 2-(2-(1-Methyl-4-(6-methylpyridin-3-yl)-1H-imidazol-2-yl)ethyl)quinoxaline hydrochloride salt The title compound was prepared according to General Procedure A-(c) and N-(h). MS (ESI): m/z 293.1 [M+H]+.

52. General Procedure OO

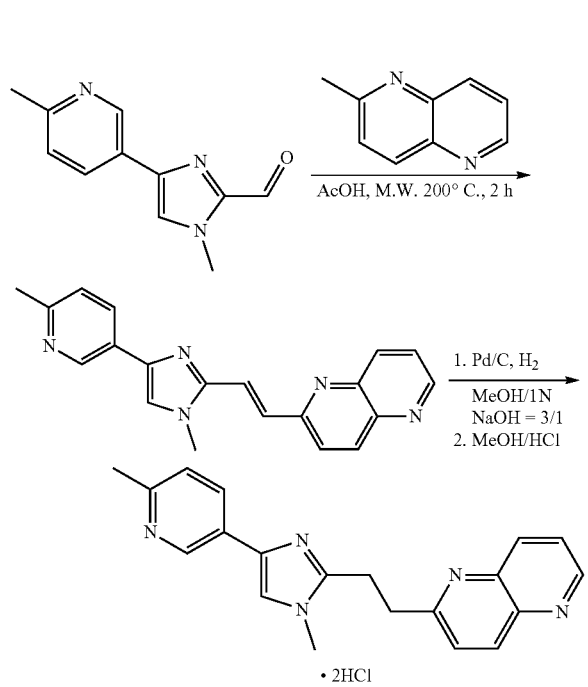

(a) (E)-2-(2-(1-Methyl-4-(6-methylpyridin-3-yl)-1H-imidazol-2-yl)vinyl)-1,5-naphthyridine was prepared according to General Procedure A-(c). (b) 2-(2-(1-Methyl-4-(6-methylpyridin-3-yl)-1H-imidazol-2-yl)ethyl)-1,5-naphthyridine hydrochloride salt was prepared according to General Procedures A-(d) and N-(h).

53. General Procedure PP

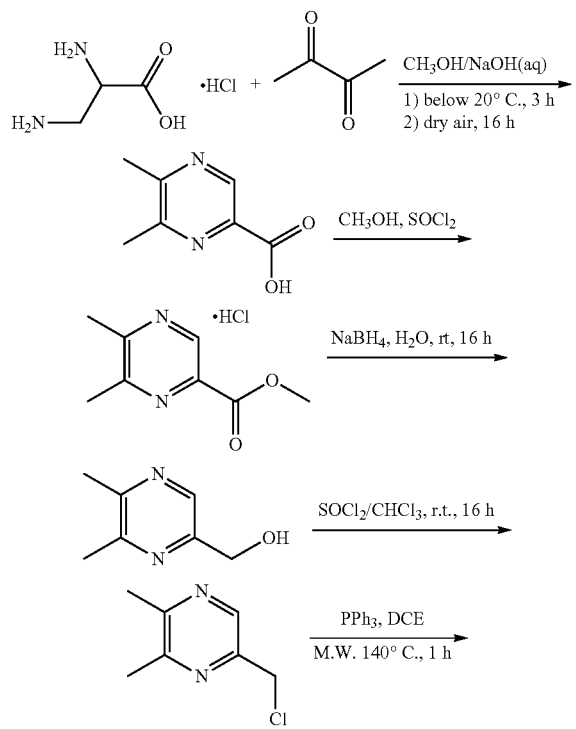

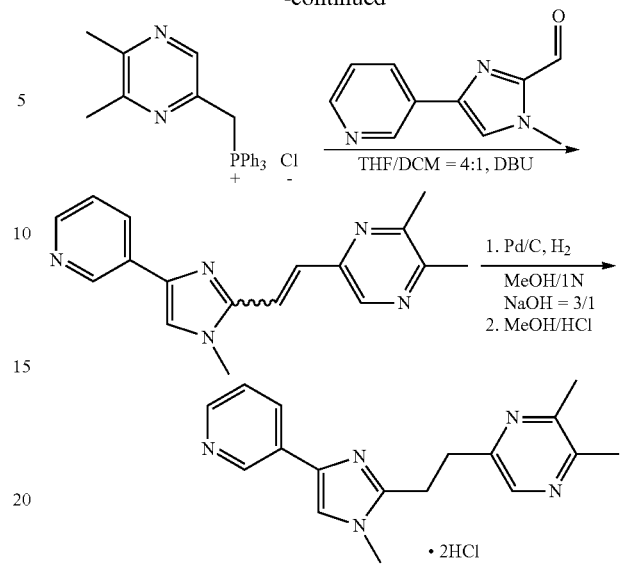

(a) 5,6-Dimethylpyrazine-2-carboxylic acid

To a solution of 2,3-diaminopropanoic acid hydrochloride (1 g, 7.11 mmol) in methanol (63 mL) was added sodium hydroxide (1.42 g, 28.4 mmol) at 10° C., and then the mixture was degassed with $N_2$. After 30 min, biacetyl (612 mg, 7.11 mmol) was added and the reaction mixture was stirred at the same temperature for 3 h. Dry air was passed through the reaction mixture for 16 h. The solvent was then removed under reduced pressure, the residue was dissolved in water (7 mL), and the solution was adjusted to pH 2 with concentrated HCl slowly at 0° C., and the mixture was filtered. The yellow solid (580 mg) was used in the next step without further purification. MS (ESI): m/z 153.1 $[M+H]^+$.

(b) Methyl 5,6-dimethylpyrazine-2-carboxylate hydrochloride

To a solution of 5,6-dimethylpyrazine-2-carboxylic acid (580 mg, 3.82 mmol) in methanol (20 mL) was added thionyl chloride (1.82 g, 15.3 mmol) slowly at 0° C. and the mixture was stirred for 2 h and then heated to reflux for 16 h. The reaction was then cooled to r.t. and concentrated to give the crude product as a yellow solid (700 mg). MS (ESI): m/z 167.1 $[M+H]^+$.

(c) (5,6-Dimethylpyrazin-2-yl)methanol

To a solution of methyl 5,6-dimethylpyrazine-2-carboxylate hydrochloride (340 mg, 1.68 mmol) in water (10 mL) was added sodium borohydride (320 mg, 8.4 mmol) in 5 portions at 0° C. Then the mixture was allowed to warm to room temperature and stirred for 16 h. The solvent was then removed under reduced pressure, chloroform (30 mL) was added, the mixture was filtered, and the filtrate was concentrated under reduced pressure to give an off yellow solid (125 mg). MS (ESI): m/z 139.1 $[M+H]^+$.

(d) 5-(Chloromethyl)-2,3-dimethylpyrazine hydrochloride

The title compound was prepared according to General Procedure FF-(b). MS (ESI): m/z 157.1 $[M+H]^+$.

(e) ((5,6-Dimethylpyrazin-2-yl)methyl)triphenylphosphonium chloride

The title compound was prepared according to General Procedure D-(b). MS (ESI): m/z 383.1 [M–Cl]+.

(f) 2,3-Dimethyl-5-(2-(1-methyl-4-(pyridin-3-yl)-1H-imidazol-2-yl)vinyl)pyrazine The title compound was prepared according to General Procedure D-(c). MS (ESI): m/z 292.1 [M+H]+.

(g) 2,3-Dimethyl-5-(2-(1-methyl-4-(pyridin-3-yl)-1H-imidazol-2-yl)ethyl)pyrazine The title compound was prepared according to General Procedure Q-(f). See, e.g., *Chem. Ber.*, 1967, 100, 555-559.

54. General Procedure QQ

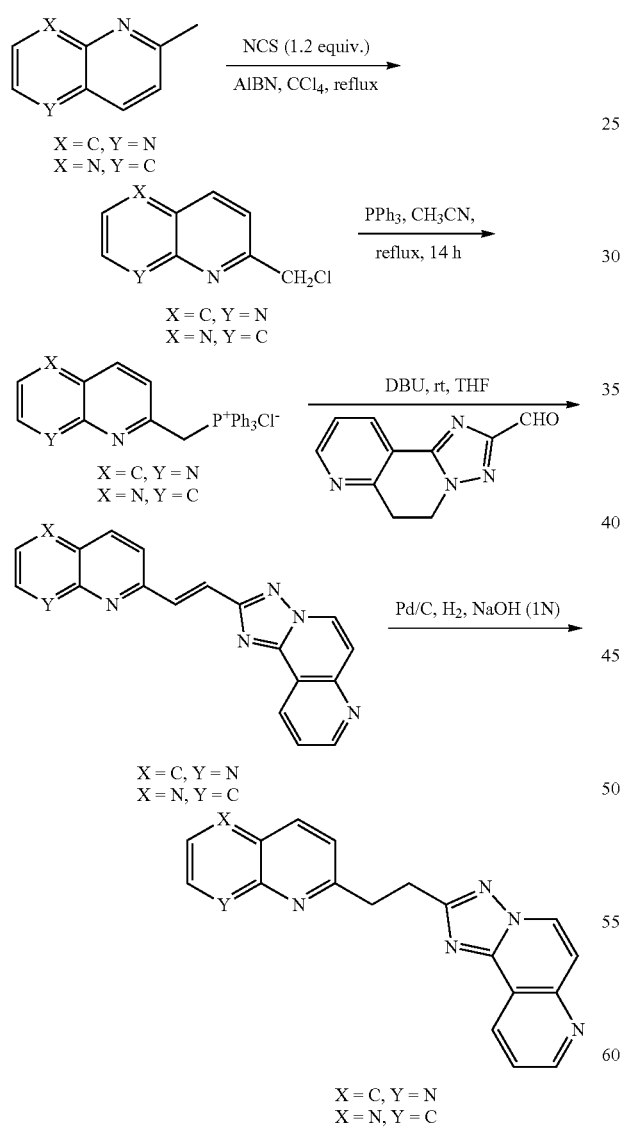

(a) 2-(Chloromethyl)-1,5-naphthyridine and 2-(Chloromethyl)-1,8-naphthyridine were prepared according to General Procedure 25-(c) using 1 equivalent of NCS. MS (ESI): m/z 179 [M+H]+. (b) ((1,5-Naphthyridin-2-yl)methyl)triphenylphosphonium chloride and ((1,8-Naphthyridin-2-yl)methyl)triphenylphosphonium chloride were prepared according to General Procedure D-(b). MS (ESI): m/z 405 [M–Cl]+. (c) 2-(2-(1,5-Naphthyridin-2-yl)vinyl)-[1,2,4]triazolo[5,1-f]-[1,6]naphthyridine and 2-(2-(1,8-naphthyridin-2-yl)vinyl)-[1,2,4]triazolo[5,1-f][1,6]naphthyridine were prepared according to General Procedure D-(c). MS (ESI): m/z 325 [M+H]+. (d) 2-(2-(1,5-Naphthyridin-2-yl)ethyl)-[1,2,4]triazolo[5,1-f]-[1,6]naphthyridine and 2-(2-(1,8-naphthyridin-2-yl)ethyl)-[1,2,4]triazolo[5,1-f][1,6]naphthyridine were prepared according to General Procedure Q-(f).

55. General Procedure RR

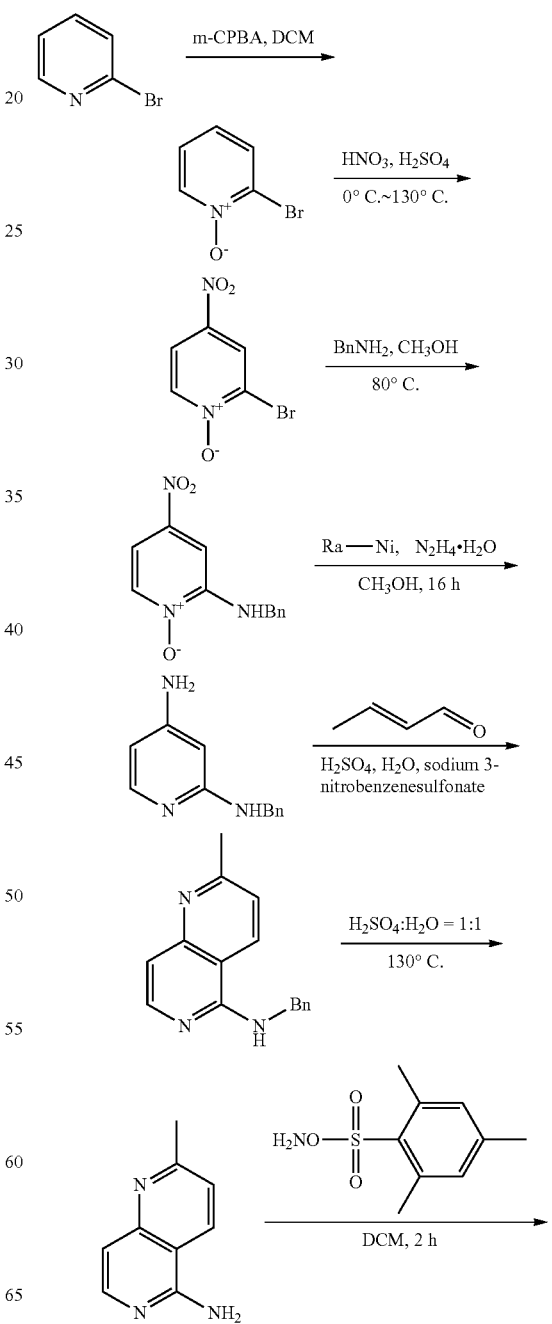

-continued

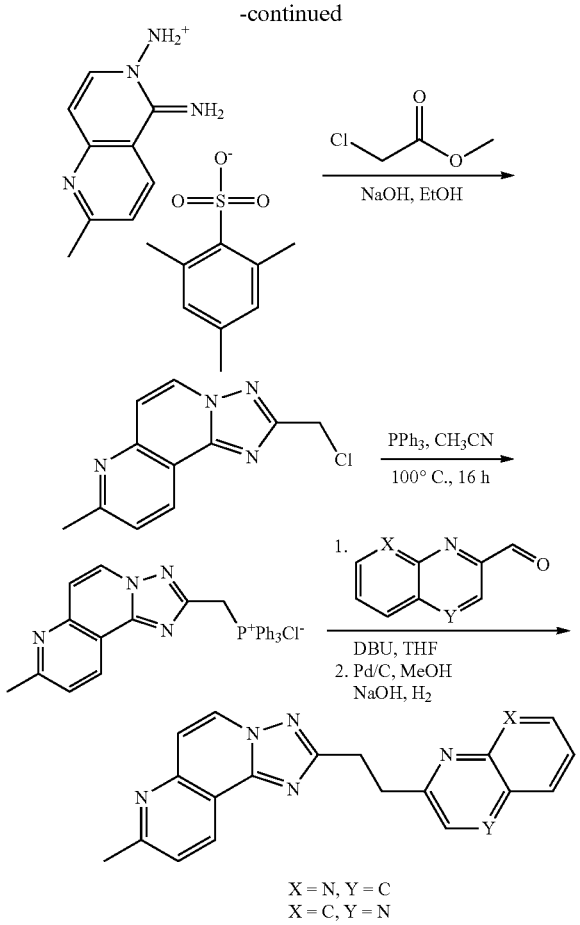

X = N, Y = C
X = C, Y = N (a) N-Oxide-2-bromopyridine

To a mixture of 2-bromopyridine (4.74 g, 30.0 mmol) in DCM (60 mL) was added 3-chlorobenzoperoxoic acid (7.22 g, 42.0 mmol). The mixture was stirred at room temperature for 16 h. Water (200 mL) was added and the mixture was extracted with DCM (200 mL×3). The organic layer was separated and dried with anhydrous sodium sulfate. The solution was concentrated under reduced pressure. The crude product was purified by column chromatography. The product (5.06 g) was obtained as a white solid. MS (ESI): m/z 172, 174 [M+H]$^+$.

(b) N-Oxide-2-bromo-4-nitropyridine

To a solution of N-oxide-2-bromopyridine (5.06 g, 29.6 mmol) in fuming sulfuric acid (100 mL) was added fuming nitric acid (2.84 g, 44.4 mmol) at 0° C. The resulting mixture was heated to 135° C. After stirring for 3 hours at this temperature, fuming nitric acid (0.95 g, 14.8 mmol) was added and the mixture was stirred for 1 hour. The mixture was cooled to room temperature and poured into ice water (300 mL). The aqueous layer was extracted with EtOAc (300 mL×2). The combined organic layers were washed with sat. sodium bicarbonate (200 mL×5). The organic phase was concentrated under reduced pressure, and a brown solid (2.73 g) was obtained. MS (ESI): m/z 219, 221 [M+H]$^+$.

(c) N$_2$-Benzylpyridine-2,4-diamine

The title compound was prepared according to General Procedure L-(a). MS (ESI): m/z 200 [M+H]$^+$.

(d) N-Benzyl-2-methyl-1,6-naphthyridin-5-amine

The title compound was prepared according to General Procedure 25-(a). MS (ESI): m/z 250 [M+H]$^+$.

(e) 2-Methyl-1,6-naphthyridin-5-amine

N-Benzyl-2-methyl-1,6-naphthyridin-5-amine (1.42 g, 5.7 mmol) was dissolved in sulfuric acid (6 mL) and water (3 mL). The solution was heated to 130° C. and stirred for 3 hours. The reaction mixture was poured into ice water and neutralized with sodium hydroxide adjusting pH to 8-10. The solution was then concentrated under reduced pressure. The solid was triturated in ethanol (30 mL×2) and filtered. The filtrate was concentrated to dryness and purified by reverse phase column chromatography, and a brown solid (485 mg) was obtained. MS (ESI): m/z 160 [M+H]$^+$.

(f) 6-Amino-2-methyl-1,6-naphthyridin-5(6H)-iminium

The title compound was prepared according to General Procedure N-(d-e). MS (ESI): m/z 233 [M+H]$^+$.

(g) ((8-Methyl-[1,2,4]triazolo[5,1-f][1,6]naphthyridin-2-yl)methyl)triphenylphosphonium chloride The title compound was prepared according to General Procedure D-(b). MS (ESI): m/z 459 [M+H]$^+$.

(h) (E)-2-(2-(1,8-Naphthyridin-2-yl)vinyl)-8-methyl-[1,2,4]triazolo[5,1-f][1,6]naphthyridine The title compound was prepared according to General Procedure D-(c). MS (ESI): m/z 339 [M+H]$^+$.

(i) 2-(2-(1,8-Naphthyridin-2-yl)ethyl)-8-methyl-[1,2,4]triazolo[5,1-f][1,6]naphthyridine The title compound was prepared according to General Procedure Q-(f).

(j) 2-(2-(1,5-Naphthyridin-2-yl)ethyl)-8-methyl-[1,2,4]triazolo[5,1-f][1,6]naphthyridine The title compound was prepared according to General Procedure D-(c) and Q-(f). See, e.g., *J. Mol. Structure*, 1997, 415, 53-63.

56. General Procedure SS

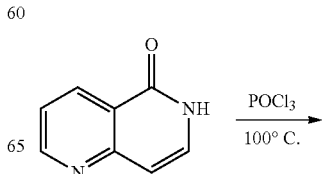

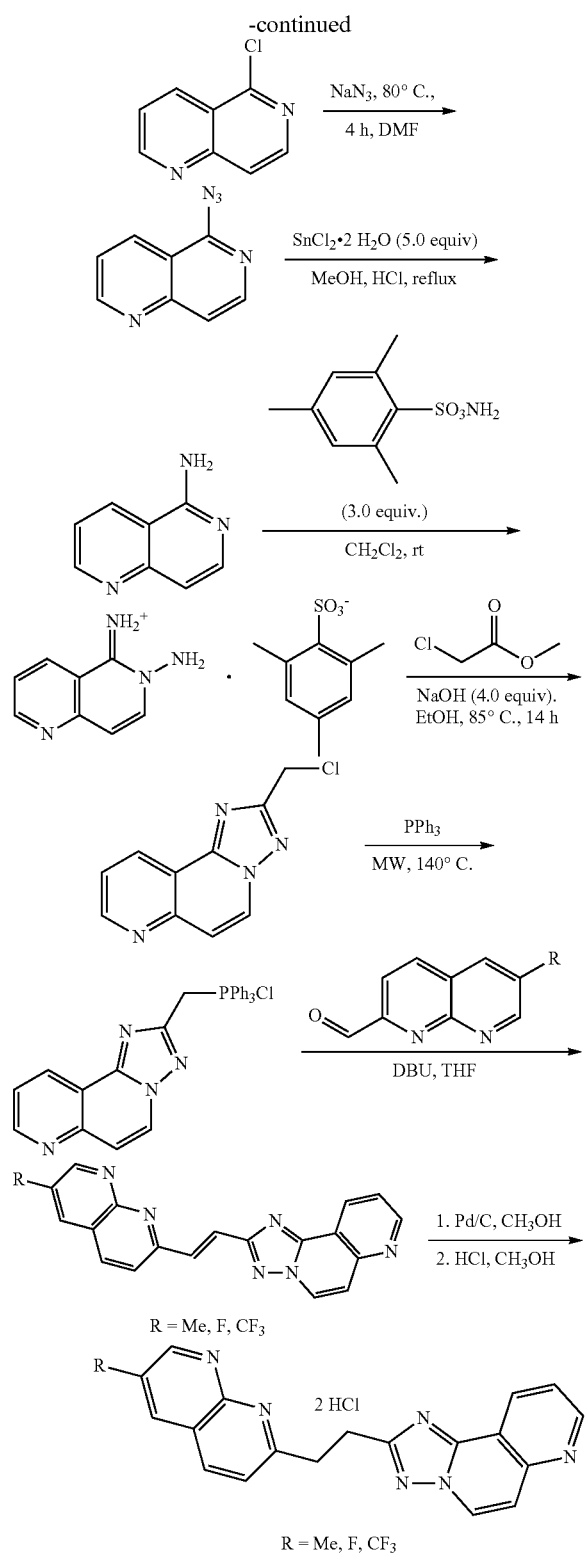

aqueous solution) was added to adjust the pH to 9. The mixture was extracted with EtOAc (200 mL×3). The combined organic layers were dried over sodium sulfate and concentrated under vacuum to give 3.3 g of the crude product as a yellow solid. MS (ESI): m/z 165 [M+H]+.

(b) 5-Azido-1,6-naphthyridine

To a solution of 5-chloro-1,6-naphthyridine (3.3 g, 20.1 mmol) in DMF (40 mL) was added sodium azide (6.0 g, 88.5 mmol). The mixture was stirred at 80° C. overnight. The mixture was poured into water (120 mL). The aqueous phase was extracted with EtOAc (150 mL×4). The combined organic layers were washed with brine (100 mL×3), dried over sodium sulfate, and concentrated under reduced pressure to give 3.4 g of the crude product as a brown solid. MS (ESI): m/z 172 [M+H]+.

(c) 1,6-Naphthyridin-5-amine

To a suspension of 5-azido-1,6-naphthyridine (3.4 g, 19.9 mmol) in methanol (40 mL) was added hydrochloric acid (30 mL). Stannous chloride dihydrate (22.5 g, 99.5 mmol) was added. The mixture was stirred at 75° C. for 3.5 h. A yellow precipitate formed. The mixture was filtered to give a yellow solid. The solid was suspended in EtOAc (200 mL). Sodium hydroxide (saturated aqueous solution) was added to adjust pH to 9. A white precipitate formed. The mixture was filtered and the filtrate was extracted with EtOAc (200 mL×6). The organic phase was dried over sodium sulfate and concentrated under reduced pressure to give 2.0 g of the crude product as a yellow solid. MS (ESI): m/z 146 [M+H]+.

(d) 6-Amino-1,6-naphthyridin-5(6H)-iminium 2,4,6-trimethylbenzenesulfonate

The title compound was prepared according to General Procedure N-(d). MS (ESI): m/z 161 [M+H]+.

(e) 2-(Chloromethyl)-[1,2,4]triazolo[5,1-f][1,6]naphthyridine

The title compound was prepared according to General Procedure N-(e). MS (ESI): m/z 219 [M+H]+.

(f) ([1,2,4]Triazolo[5,1-f][1,6]naphthyridin-2-ylmethyl)triphenylphosphonium chloride The title compound was prepared according to General Procedure D-(b). MS (ESI): m/z 445 [M]+.

(g) (E)-2-(2-(6-Methyl-1,8-naphthyridin-2-yl)vinyl)-[1,2,4]triazolo[5,1-f][1,6]naphthyridine The title compound was prepared according to General Procedure D-(c). MS (ESI): m/z 339 [M+H]+.

(h) 2-(2-(6-Methyl-1,8-naphthyridin-2-yl)ethyl)-[1,2,4]triazolo[5,1-f][1,6]naphthyridine hydrochloride salt The title compound was prepared according to General Procedures A-(d) and N-(h). MS (ESI): m/z 341 [M+H]+.

(a) 5-Chloro-1,6-naphthyridine

A solution of 1,6-naphthyridin-5(6H)-one (3.2 g, 21.9 mmol) in phosphoryl trichloride (50 mL) was stirred at 100° C. overnight. The solvent was removed under vacuum. The residue was cooled to 0° C. Sodium hydroxide (saturated

(i) 2-(2-(6-Fluoro-1,8-naphthyridin-2-yl)ethyl)-[1,2,4]triazolo[5,1-f][1,6]naphthyridine hydrochloride salt The title compound was prepared according to General Procedures D-(c), A-(d), and N-(h). MS (ESI): m/z 345 [M+H]⁺.

(j) 2-(2-(6-(Trifluoromethyl)-1,8-naphthyridin-2-yl)ethyl)-[1,2,4]triazolo[5,1-f][1,6]naphthyridine hydrochloride salt The title compound was prepared according to General Procedures D-(c), A-(d), and N-(h). MS (ESI): m/z 395 [M+H]⁺.

57. General Procedure TT

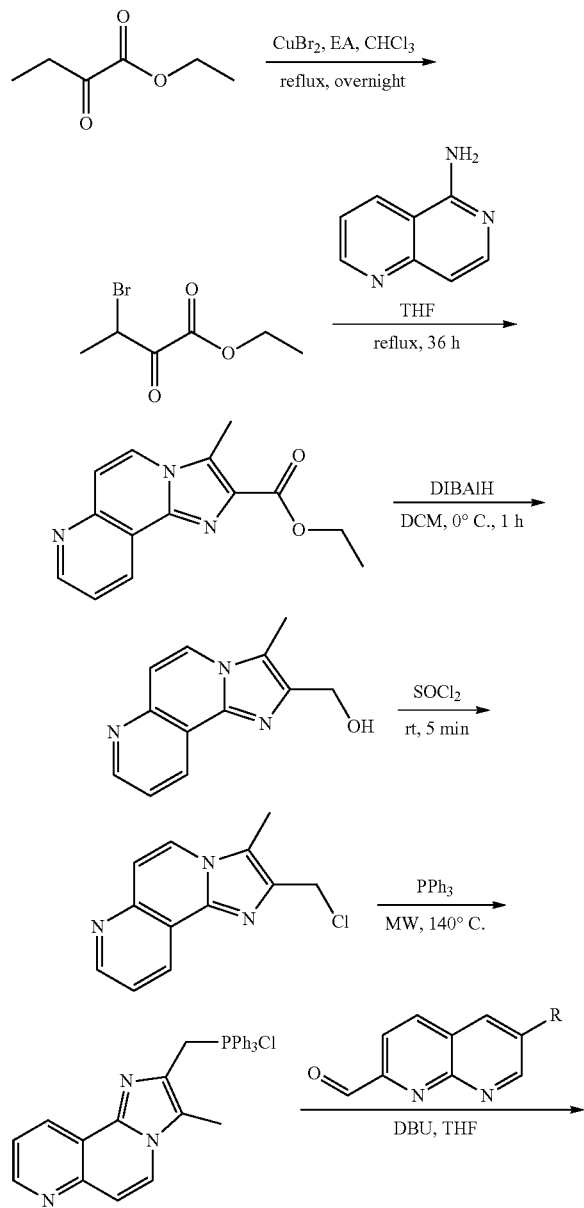

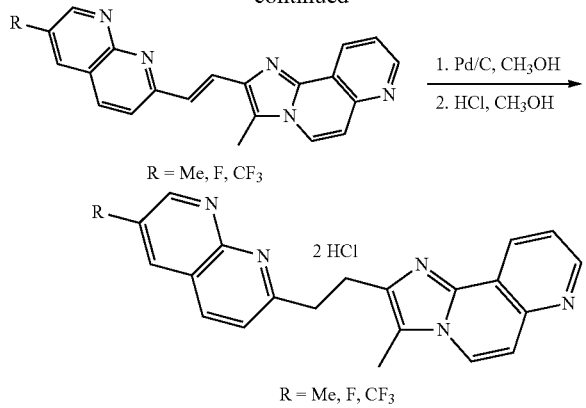

(a) Ethyl 3-bromo-2-oxobutanoate

To a suspension of CuBr$_2$ (20.6 g, 92.3 mmol) in EtOAc (500 mL) was added a solution of ethyl 2-oxobutanoate (4.0 g, 30.7 mmol) in 250 mL of chloroform. The mixture was heated at reflux for 18 h, cooled, and filtered through a short pad of silica gel. The solvent was removed under reduced pressure to give the product as a light green liquid (3.8 g).

(b) Methyl 3-methylimidazo[2,1-f][1,6]naphthyridine-2-carboxylate

A solution of 1,6-naphthyridin-5-amine (700 mg, 4.83 mmol) in tetrahydrofuran (25 mL) was added ethyl 3-bromo-2-oxobutanoate (1.51 g, 7.24 mmol). The mixture was stirred at reflux for 36 h. Then the mixture was concentrated under reduced pressure, and purified by column chromatography to give 740 mg of the product as a yellow solid. MS (ESI): m/z 256.1 [M+H]⁺.

(c) (3-Methylimidazo[2,1-f][1,6]naphthyridin-2-yl)methanol

A solution of methyl 3-methylimidazo[2,1-f][1,6]naphthyridine-2-carboxylate (100 mg, 0.39 mmol) in DCM (8 mL) was cooled to 0° C. Diisobutylaluminium hydride (1 M in cyclohexane, 1.2 mL, 1.2 mmol) was added dropwise over 10 min. Then the mixture was stirred at 0° C. for 1 h. 2 mL of saturated ammonium chloride aqueous solution was added slowly to quench the reaction. Then 5 mL of saturated sodium bicarbonate aqueous solution was added. The mixture was extracted with DCM (3×10 mL). The combined organic layers were dried over sodium sulfate, filtered, and concentrated to give the crude product. The crude product was purified by column chromatography to give 42 mg of the product as a yellow solid. MS (ESI) m/z 214.1 [M+H]⁺.

(d) 2-(Chloromethyl)-3-methylimidazo[2,1-f][1,6]naphthyridine

The title compound was prepared according to General Procedure FF-(b). MS (ESI): m/z 232.1 [M+H]⁺.

(e) ((3-Methylimidazo[2,1-f][1,6]naphthyridin-2-yl)methyl)triphenylphosphonium chloride The title compound was prepared according to General Procedure D-(b). MS (ESI): m/z 458 [M]⁺.

(f) 2-(2-(6-Fluoro-1,8-naphthyridin-2-yl)ethyl)-3-methylimidazo[2,1-f][1,6]naphthyridine The title compound was prepared according to General Procedures D-(c), A-(d), and N-(h). MS (ESI): m/z 358.1 [M+H]⁺.

(g) 3-Methyl-2-(2-(6-methyl-1,8-naphthyridin-2-yl)ethyl)imidazo[2,1-f][1,6]naphthyridine hydrochloride salt The title compound was prepared according to General Procedures A-(d) and N-(h). MS (ESI): m/z 354.1 [M+H]⁺.

(h) 3-Methyl-2-(2-(6-(trifluoromethyl)-1,8-naphthyridin-2-yl)ethyl)imidazo[2,1-f][1,6]naphthyridine hydrochloride salt The title compound was prepared according to General Procedures A-(d) and N-(h). MS (ESI): m/z 408.1 [M+H]⁺. See, e.g., WO2010/126163; *J. Org. Chem.* 2002, 67, 1102-1108.

58. General Procedure UU

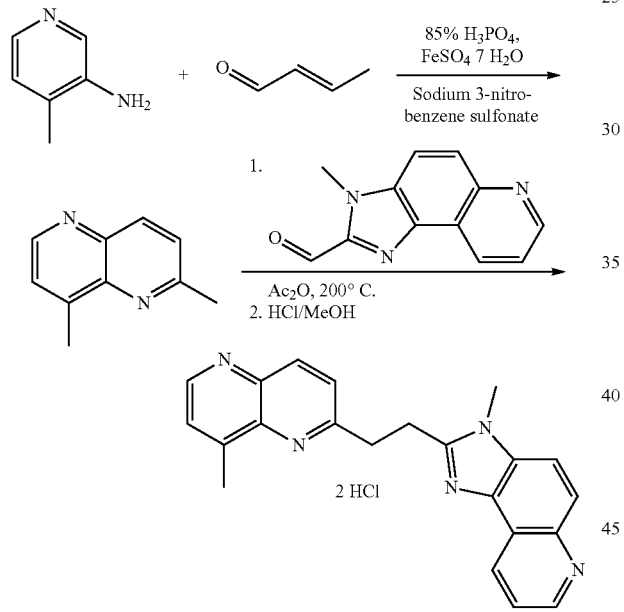

(a) 2,8-Dimethyl-1,5-naphthyridine was prepared according to General Procedure 25-(g). MS (ESI): m/z 159.7 [M+H]⁺. (b) 3-Methyl-2-(2-(8-methyl-1,5-naphthyridin-2-yl)ethyl)-3H-imidazo[4,5-f]quinoline hydrochloride salt was prepared according to General Procedures A-(c) and N-(h).

59. General Scheme VV

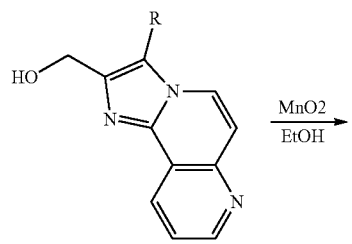

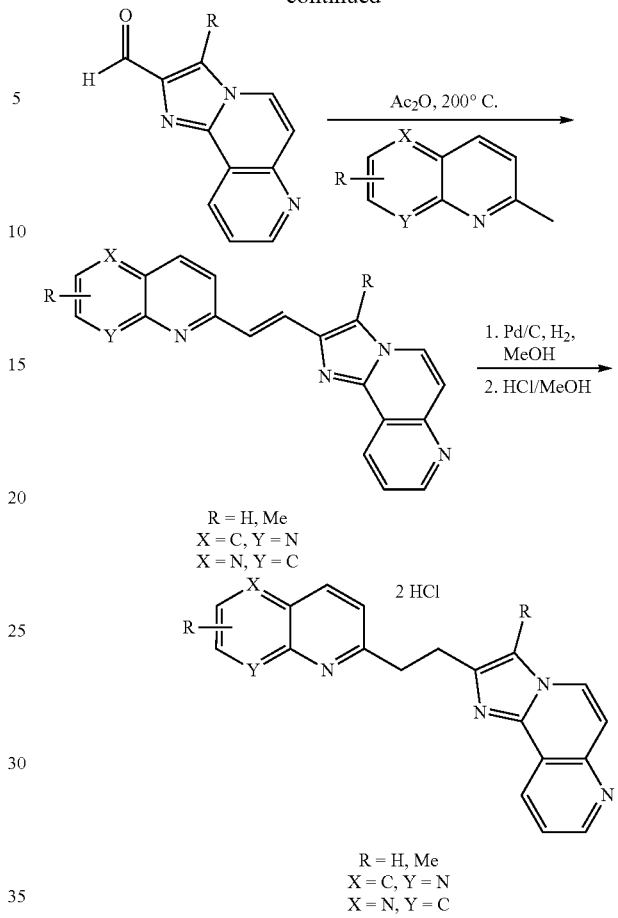

R = H, Me
X = C, Y = N
X = N, Y = C (a) 3-Methylimidazo[2,1-f][1,6]naphthyridine-2-carbaldehyde was prepared according to General Procedure 14-(m). MS (ESI): m/z 212.0 [M+H]⁺. (b) 3-Methyl-2-(2-(8-methyl-1,5-naphthyridin-2-yl)vinyl)imidazo[2,1-f][1,6]naphthyridine was prepared according to General Procedure A-(c). MS (ESI): m/z 352.1 [M+H]⁺. (c) 3-Methyl-2-(2-(8-methyl-1,5-naphthyridin-2-yl)ethyl)imidazo[2,1-f][1,6]naphthyridine was prepared according to General Procedures A-(d) and N-(h). ESI MS: m/z 354.1 [M+H]⁺. (d) 2-(2-(1,8-Naphthyridin-2-yl)ethyl)imidazo[2,1-a]isoquinoline was prepared according to General Procedures A-(c), A-(d), and N-(i). ESI MS: m/z 326 [M+H]⁺. (e) 2-(2-(7-Methyl-1,8-naphthyridin-2-yl)ethyl)imidazo[2,1-a]isoquinoline was prepared according to General Procedures A-(c), A-(d), and N-(h). ESI MS: m/z 340 [M+H]⁺. (f) 2-(2-(1,8-Naphthyridin-2-yl)ethyl)-3-methylimidazo[2,1-a]isoquinoline was prepared according to General Procedures A-(c), A-(d), and N-(h). ESI MS: m/z 340 [M+H]⁺. (g) 3-Methyl-2-(2-(7-methyl-1,8-naphthyridin-2-yl)ethyl)imidazo[2,1-a]isoquinoline was prepared according to General Procedures A-(c), A-(d), and N-(h). ESI MS: m/z 354.5 [M+H]⁺. (h) 2-(2-(1,5-Naphthyridin-2-yl)ethyl)imidazo[2,1-a]isoquinoline was prepared according to General Procedures A-(c), A-(d), and N-(h). ESI MS: m/z 326 [M+H]⁺. (i) 2-(2-(6-Methyl-1,5-naphthyridin-2-yl)ethyl)imidazo[2,1-a]isoquinoline was prepared according to General Procedures A-(c), A-(d), and N-(h). ESI MS: m/z 340 [M+H]⁺. (j) 2-(2-(1,5-Naphthyridin-2-yl)ethyl)-3-methylimidazo[2,1-a]isoquinoline was prepared according to General Procedures A-(c), A-(d), and N-(h). ESI MS: m/z 340 [M+H]⁺. (k) 3-Methyl-2-(2-(6-methyl-1,5-naphthyridin-2- yl)ethyl)imidazo[2,1-a]isoquinoline was prepared according to General Procedures A-(c), A-(d), and N-(h). ESI MS: m/z 354.5 [M+H]+.

60. General Procedure WW

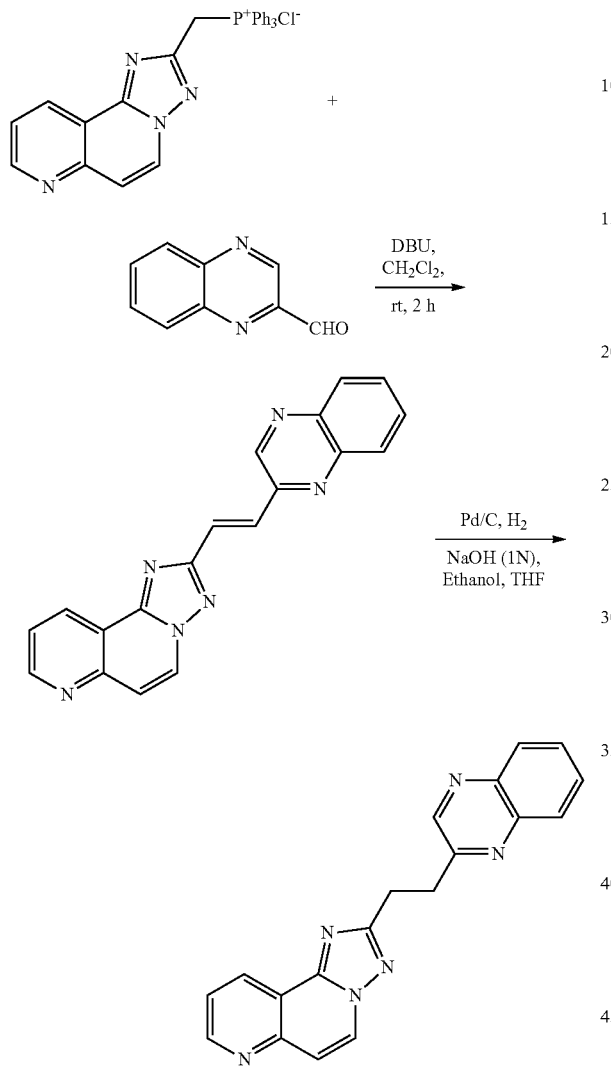

2-(2-(Quinoxalin-2-yl)ethyl)-[1,2,4]triazolo[5,1-f][1,6] Naphthyridine was prepared according to General Procedures D-(c) and Q-(f).

61. General Procedure XX

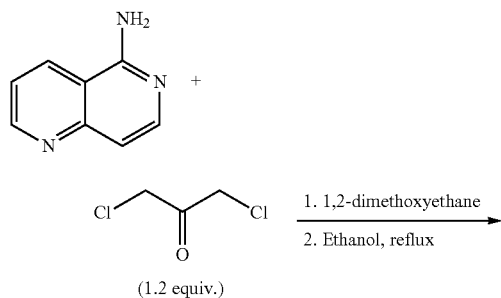

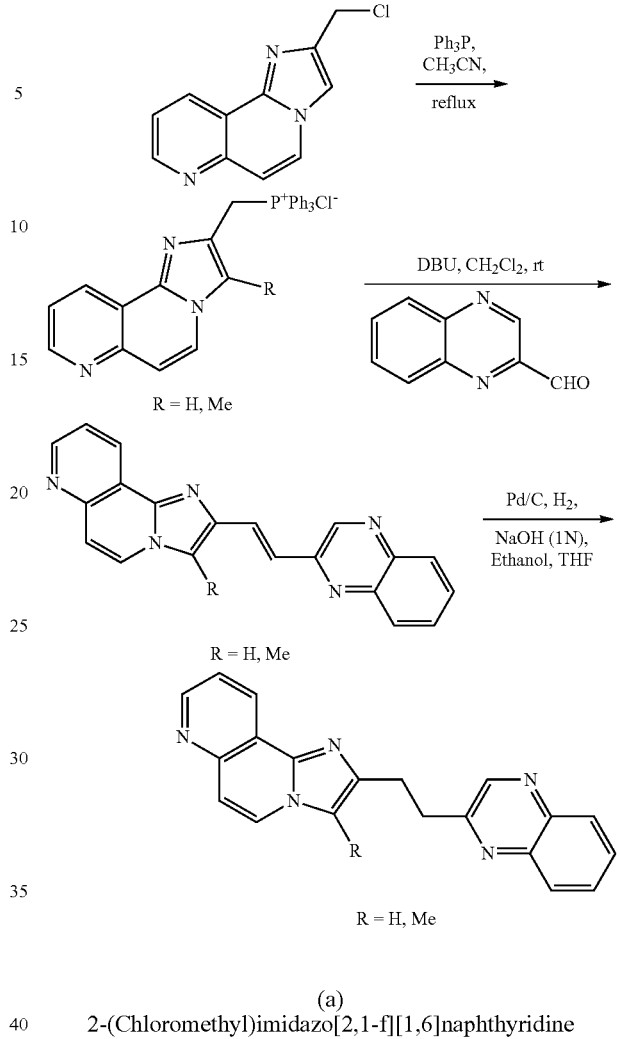

(a) 2-(Chloromethyl)imidazo[2,1-f][1,6]naphthyridine

To a solution of 1,6-naphthyridin-5-amine (145 mg, 1 mmol) in 1,2-dimethoxyethane (5 mL) was added 1,3-dichloropropan-2-one (140 mg, 1.1 mmol). The solid dissolved immediately and a white precipitate was observed. The mixture was stirred at room temperature for 1 h, and then was cooled to 0° C. for 20 min. The resulting mixture was filtered to give a white solid. The precipitate was suspended in EtOH (40 mL) and heated at reflux. After refluxing for 2 h, the reaction mixture was concentrated under reduced pressure. The residue was dissolved in water and saturated aqueous NaHCO₃ solution was added to adjust the pH value to 7. A white suspension formed during the course of addition. The resulting mixture was stirred for 20 min and then filtered to give 2-(chloromethyl)imidazo[2,1-f][1,6]naphthyridine as a white solid (130 mg). MS (ESI): m/z 218 [M+H]+.

(b) (Imidazo[2,1-f][1,6]naphthyridin-2-ylmethyl) triphenyl phosphonium chloride

The title compound was prepared according to General Procedure D-(b). MS (ESI): m/z 444 [M−35]+.

(c) 2-(2-(Quinoxalin-2-yl)ethyl)imidazo[2,1-f][1,6] naphthyridine and 3-methyl-2-(2-(quinoxalin-2-yl) ethyl)imidazo[2,1-f][1,6]naphthyridine The title compounds were prepared according to General Procedures D-(c) and Q-(f).

62. General Procedure YY

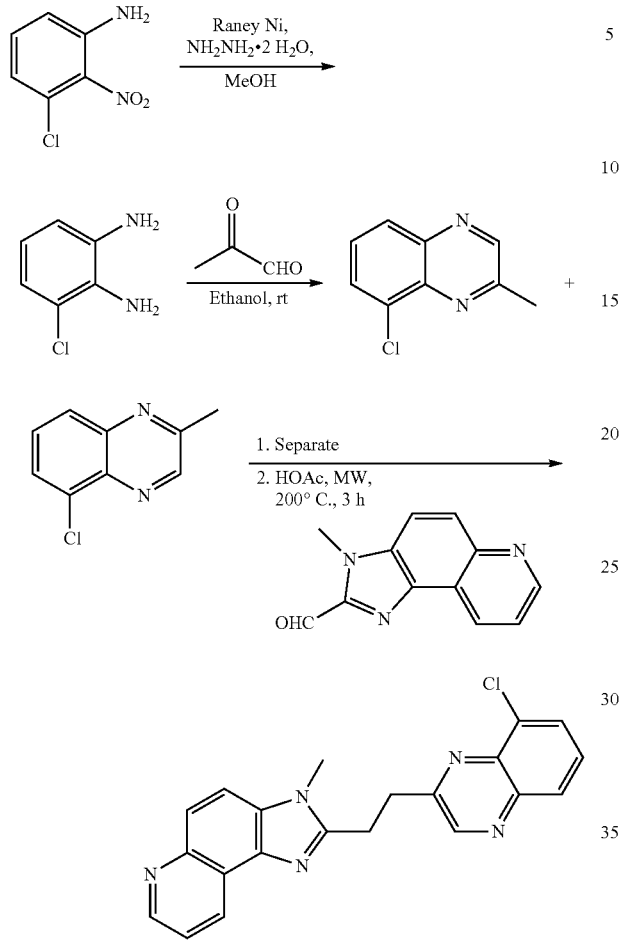

(a) 3-Chlorobenzene-1,2-diamine was prepared according to General Procedure L-(a). MS (ESI): m/z 143 [M+H]⁺. (b) 8-Chloro-2-methylquinoxaline and 5-chloro-2-methyl quinoxaline was prepared according to General Procedure 25-(p). MS (ESI): m/z 179 [M+H]⁺. (c) 2-(2-(8-Chloroquinoxalin-2-yl)ethyl)-3-methyl-3H-imidazo[4,5-f]quinoline was prepared according to General Procedure A-(d).

63. General Procedure ZZ

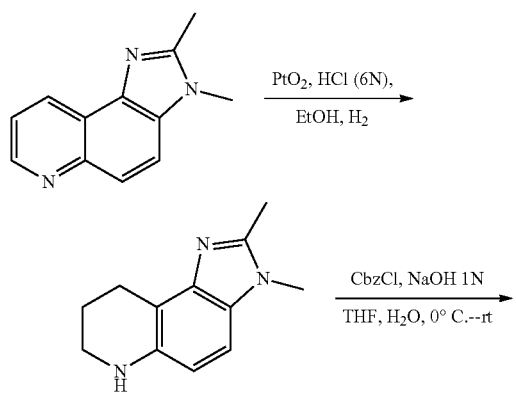

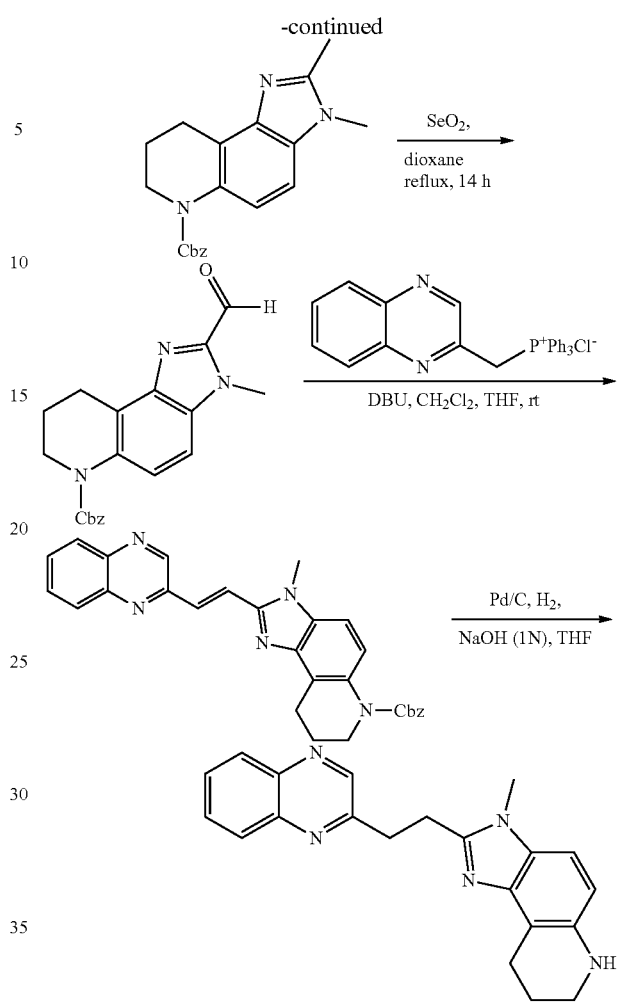

(a) 2,3-Dimethyl-6,7,8,9-tetrahydro-3H-imidazo[4,5-f]quinoline

A mixture of 2,3-dimethyl-3H-imidazo[4,5-f]quinoline (0.40 g, 2.03 mmol) and platinum(IV) oxide (24 mg, 0.11 mmol) in HCl (6 N, 2 mL) and ethanol (10 mL) was stirred at room temperature under H₂ for 24 h. Then ethanol was removed under reduced pressure and the residue was dissolved in EtOAc (20 mL) and sat. NaHCO₃ (3 mL), filtered through Celite, washed with EtOAc (10 mL×3), and separated. The water layer was then extracted with EtOAc (10 mL×3). The combined organic layers were dried with Na₂SO₄ and filtered; and the solvent was removed under reduced pressure to give a yellow solid. The residue was used in the next step without further purification (320 mg). MS (ESI): m/z 202 [M+H]⁺.

(b) Benzyl 2,3-dimethyl-8,9-dihydro-3H-imidazo[4,5-f]quinoline-6(7H)-carboxylate A solution of 2,3-dimethyl-6,7,8,9-tetrahydro-3H-imidazo[4,5-f]quinoline (400 mg, 2 mmol) in tetrahydrofuran (10 mL) was stirred at 0° C. Then NaOH (1 N, 10 mL, 10 mmol) was added to the solution and the mixture was stirred at 0° C. for 10 minutes. Phenyl carbonochloridate (1.02 g, 6 mmol) was then added and the mixture was stirred at 0° C. for 1 hour. The layers were then separated and the water layer was extracted with EtOAc (10 mL×3). The combined organic layers were dried with Na$_2$SO$_4$ and filtered; and the solvent was removed under reduced pressure. The residue was purified with prep-TLC to give the product as a yellow oil (0.53 g). MS (ESI): m/z 336 [M+H]$^+$.

(c) Benzyl 2-formyl-3-methyl-8,9-dihydro-3H-imidazo[4,5-f]quinoline-6(7H)-carboxylate The title compound was prepared according to General Procedure H-(a). MS (ESI): m/z 350 [M+H]$^+$.

(d) 3-Methyl-2-(2-(quinoxalin-2-yl)ethyl)-6,7,8,9-tetrahydro-3H-imidazo[4,5-f]quinoline The title compound was prepared according to General Procedures D-(c) and Q-(f).

64. General Procedure AAA

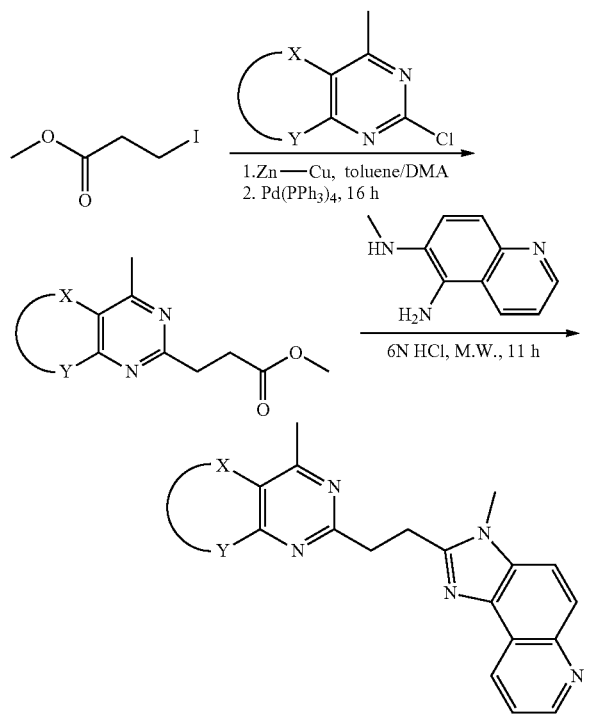

(a) Methyl 3-iodopropanoate

To a solution of methyl 3-bromopropanoate (20 g, 0.12 mol) in acetone (40 mL) was added sodium iodide (23.4 g, 0.156 mol), and the resulting mixture was heated to 55° C. for 16 h. The mixture was then filtered, the filter cake was rinsed with ethyl ether (50 mL), and the filtrate was concentrated under reduced pressure. The residue was dissolved in ethyl ether (100 mL) and washed with ice water (2×50 mL), brine (30 mL), dried over anhydrous sodium sulfate, and filtered; and the solution was concentrated to provide a red oil (11 g).

(b) Methyl-3-(4,6-dimethylpyrimidin-2-yl)propanoate

A suspension of Zn—Cu couple (3.45 g) in toluene/N,N-dimethylacetamide (14:1, 30 mL) was degassed by bubbling N$_2$ through the suspension for 15 min. Then methyl 3-iodopropanoate (1.96 g, 9.14 mmol) was added to the suspension, and the resulting mixture was heated at 110° C. for 6 h.

The reaction mixture was allowed to cool to 70° C., and 2-chloro-4,6-dimethylpyrimidine (961 mg, 6.77 mmol) and tetrakis(triphenylphosphine) palladium (235 mg, 0.203 mmol) were added. The reaction mixture was maintained at 70° C. for 22 h. Upon cooling to r.t., the mixture was filtered, and the filter cake was rinsed with ether (10 mL×3). The filtrate was extracted with 1 M hydrochloric acid (75 mL×2). The acidic extracts were basified with the addition of sodium bicarbonate, and the resulting solution was extracted with ether (75 mL×2). The combined organic layers were dried over anhydrous sodium sulfate and the solution was concentrated to give a residue, which was purified by prep-TLC to afford methyl 3-(4,6-dimethylpyrimidin-2-yl)propanoate as a pale-yellow solid (120 mg). MS (ESI): m/z 195 [M+H]$^+$.

(c) 2-(2-(4,6-Dimethylpyrimidin-2-yl)ethyl)-3-methyl-3H-imidazo[4,5-f]quinoline

The title compound was prepared according to Synthetic Procedure 21.

(d) 3-Methyl-2-(2-(4-methylquinazolin-2-yl)ethyl)-3H-imidazo[4,5-f]quinoline

The title compound was prepared according to Generic Procedure AAA (a-c).

(e) 3-Methyl-2-(2-(4-methyl-6,7-dihydro-5H-cyclopenta[d]pyrimidin-2-yl)ethyl)-3H-imidazo[4,5-f]quinoline The title compound was prepared according to Generic Procedure AAA (a-c).

65. General Procedure BBB

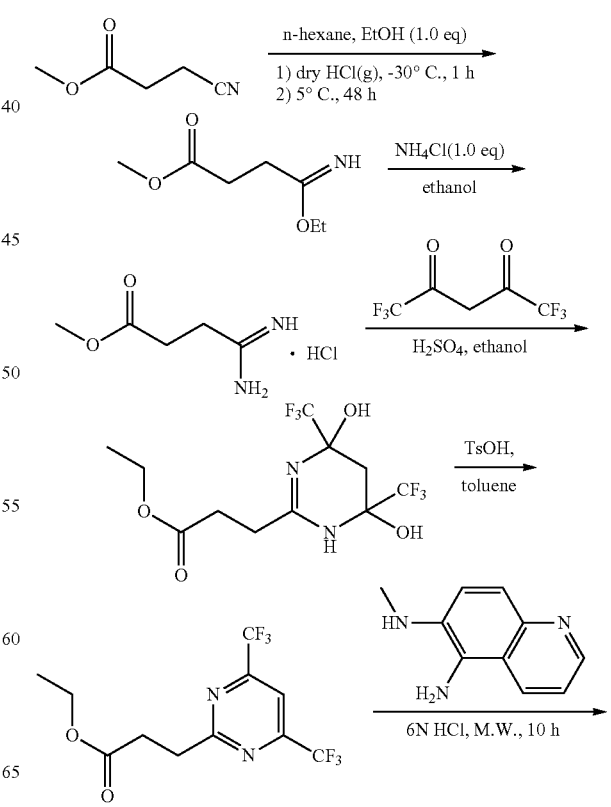

-continued

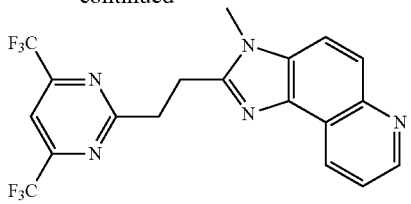

(a) Methyl 4-ethoxy-4-iminobutanoate

A solution of methyl 3-cyanopropanoate (1.5 g, 13.3 mmol) and ethanol (0.61 g, 13.3 mmol) in n-hexane (15 mL) was cooled to −30° C., and anhydrous hydrogen chloride was bubbled into the solution for 1 h. The mixture was allowed to stand overnight at about −15° C., then at 5-10° C. for 16 h. The solvent was decanted, and the residue was diluted with diethyl ether (30 mL×2) and a solution of $K_2CO_3$ (3.67 g, 26.6 mmol) in water (25 mL), the organic layer was washed with water (20 mL) and brine (10 mL), dried, and concentrated to give a colorless oil (1.34 g). MS (ESI): m/z 160 [M+H]$^+$.

(b) Methyl 4-ethoxy-4-iminobutanoate

To a solution of methyl 4-ethoxy-4-iminobutanoate (1.34 g, 8.4 mmol) in ethanol (25 mL) was added ammonium chloride (450 mg, 8.4 mmol), and the reaction mixture was heated at reflux for 16 h. The reaction was then cooled to room temperature and filtered, and the filtrate was concentrated to provide methyl 4-amino-4-iminobutanoate hydrochloride (1 g) as a white solid. MS (ESI): m/z 131 [M+H]$^+$.

(c) Ethyl 3-(4,6-dihydroxy-4,6-bis(trifluoromethyl)-1,4,5,6-tetrahydropyrimidin-2-yl)propanoate To a solution of methyl 4-ethoxy-4-iminobutanoate (800 mg, 4.8 mmol) and 1,1,1,5,5,5-hexafluoropentane-2,4-dione (1.2 g, 4.8 mmol) in ethanol (40 mL) was added concentrated $H_2SO_4$ (2 drops). Then the resulting mixture was heated at reflux for 16 h. The reaction was then cooled to room temperature, and the mixture was neutralized with saturated sodium carbonate solution to pH 7, and then extracted with EtOAc (50 mL×3). The combined organic layers were washed with brine (30 mL), dried over anhydrous sodium sulfate, and concentrated under reduced pressure to provide a white solid as the crude product (400 mg), which was used in the next step without purification. MS (ESI): m/z 353.1 [M+H]$^+$.

(d) Ethyl 3-(4,6-bis(trifluoromethyl)pyrimidin-2-yl)propanoate

A mixture of ethyl 3-(4,6-dihydroxy-4,6-bis(trifluoromethyl)-1,4,5,6-tetrahydropyrimidin-2-yl)propanoate (400 mg, 1.14 mmol), p-toluenesulfonic acid (210 mg, 1.14 mmol), and toluene was heated to 110° C. for 2 h. The reaction was then cooled to room temperature, the mixture was neutralized with saturated sodium carbonate solution to pH 7 and then extracted with EtOAc (50 mL×3). The combined organic layers were washed with brine (30 mL), dried over anhydrous sodium sulfate, and concentrated under reduced pressure; and the residue was purified by prep-TLC to give the title compound (100 mg). MS (ESI): m/z 317 [M+H]$^+$ (e) 2-(2-(4,6-bis(Trifluoromethyl)pyrimidin-2-yl)ethyl)-3-methyl-3H-imidazo[4,5-f]quinoline The title compound was prepared according to General Procedure 21. See, e.g., Chem. Commun., 2009, 2145-2147.

B. Compounds

The following compounds were prepared using the above procedures.

| Compound No. | Structure | Method of Preparation | Analytical Data |
|---|---|---|---|
| 1 | 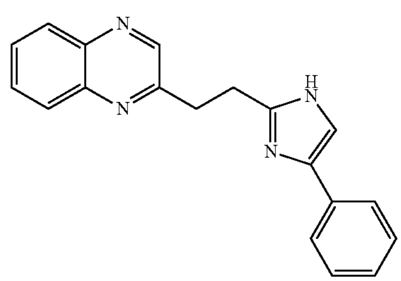 [SMILES: c1ccc(-c2c[nH]c(CCc3cnc4ccccc4n3)n2)cc1] | A | LC-MS: m/z 301.4 (M + H$^+$); $^1$H NMR (CDCl$_3$); δ 8.80 (s, 1H), 8.14-8.08 (m, 2H), 7.84-7.65 (m, 3H), 7.40-7.35 (t, J = 7.6 Hz, 3H), 7.24-7.23 (m, 2H), 3.55-3.41 (m, 4H). |
| 2 | 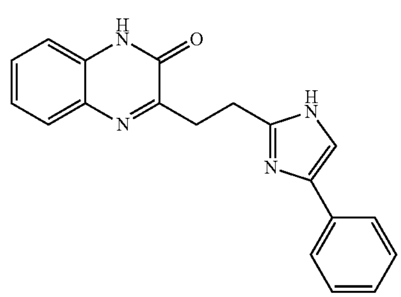 [SMILES: O=c1[nH]c2ccccc2nc1CCc1nc(-c2ccccc2)c[nH]1] | A | LC-MS: m/z 317.1 (M + H$^+$); $^1$H NMR (CD$_3$OD); δ 7.81 (d, J = 7.9 Hz, 1H), 7.65 (d, J = 7.7 Hz, 2H), 7.54-7.49 (m, 1H), 7.38-7.19 (m, 6H), 3.36-3.32 (m, 2H), 3.28-3.25 (m, 2H). |

-continued

| Compound No. | Structure | Method of Preparation | Analytical Data |
|---|---|---|---|
| 3 | 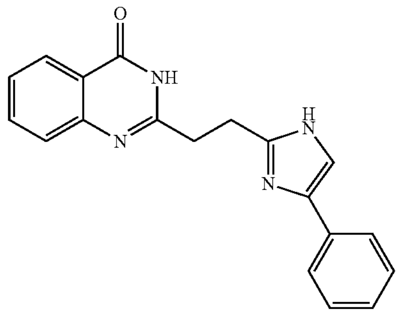 [SMILES: O=c1[nH]c(CCc2nc(-c3ccccc3)c[nH]2)nc2ccccc12] | A | MS (ESI) m/z 317.4 (M + H)+; $^1$H NMR (400 MHz, DMSO-d$_6$): δ 11.93 (s, 1H), 12.56 (s, 1H), 8.09 (d, J = 7.6 Hz, 1H), 7.80-7.74 (m, 3H), 7.61 (d, J = 8.0 Hz, 1H), 7.47 (m, 2H), 7.32 (m, 2H), 7.16 (m, 1H), 3.17-3.14 (m, 2H), 3.10-3.07 (m, 2H). |
| 4 | 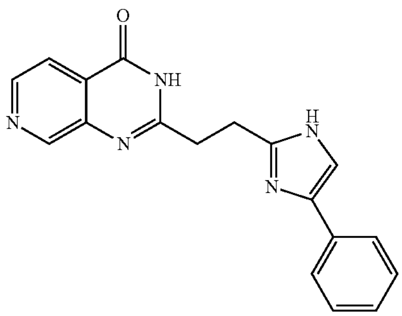 [SMILES: O=c1[nH]c(CCc2nc(-c3ccccc3)c[nH]2)nc2cnccc12] | A | MS (ESI) m/z 318.4 (M + H)+; $^1$H NMR (400 MHz, DMSO-d$_6$): δ 15.24 (brs, 1H), 14.63 (brs, 1H), 9.04 (s, 1H), 8.66 (d, J = 5.2 Hz, 1H), 8.04 (q, J = 5.2 Hz, 2H), 7.91 (d, J = 7.6 Hz, 2H), 7.51 (m, 2H), 7.44 (m, 1H), 3.51 (q, J = 6.8 Hz, 2H), 3.37 (q, J = 6.6 Hz, 2H). |
| 5 | 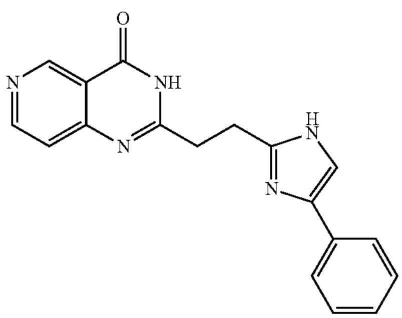 [SMILES: O=c1[nH]c(CCc2nc(-c3ccccc3)c[nH]2)nc2ccncc12] | A | MS (ESI) m/z 318.4 (M + H)+; $^1$H NMR (400 MHz, DMSO-d$_6$): δ 9.25 (s, 1H), 8.78 (d, J = 5.6 Hz, 1H), 7.71 (d, J = 7.6 Hz, 2H), 7.51 (dd, $^1$J = 4.8 Hz, $^2$J = 0.4 Hz, 1H), 7.45 (brs, 1H), 7.33 (t, J = 7.6 Hz, 2H), 7.16 (t, J = 7.6 Hz, 1H), 3.12-3.17 (m, 4H). |
| 6 | 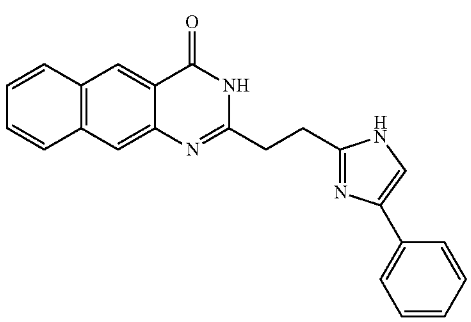 [SMILES: O=c1[nH]c(CCc2nc(-c3ccccc3)c[nH]2)nc2cc3ccccc3cc12] | A | MS (ESI) m/z 367.4 (M + H)+; $^1$H NMR (400 MHz, DMSO-d$_6$): δ 12.4 (s, 1H), 11.97 (s, 1H), 8.81 (s, 1H), 8.19 (d, J = 8.8 Hz, 2H), 8.08 (d, J = 8.8 Hz, 1H), 7.78 (s, 2H), 7.65 (t, 1H), 7.58 (t, 1H), 7.50 (s, 1H), 7.33 (m, 2H), 7.15 (m, 1H), 3.20 (m, 2H), 3.12 (m, 2H). |
| 7 | 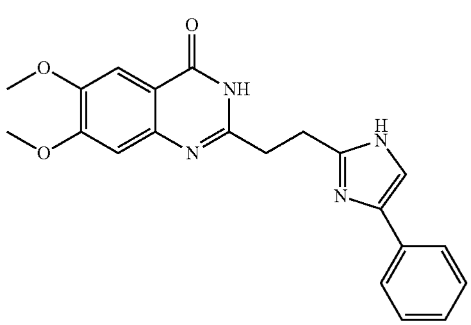 [SMILES: COc1cc2nc(CCc3nc(-c4ccccc4)c[nH]3)[nH]c(=O)c2cc1OC] | A | MS (ESI) m/z 377.41 (M + H)+; $^1$H NMR (400 MHz, CDCl$_3$): δ 8.85 (d, J = 1.6 Hz, 1H), 7.76 (d, J = 8.0 Hz, 2H), 7.37 (s, 1H), 7.30-7.34 (m, 2H), 7.14 (q, J = 4.3 Hz, 1H), 6.84 (s, 1H), 3.81 (s, 3H), 3.78 (s, 3H), 3.02 (q, J = 3.8 Hz, 2H), 2.84 (q, J = 3.8 Hz, 2H). |

| Compound No. | Structure | Method of Preparation | Analytical Data |
|---|---|---|---|
| 8 | 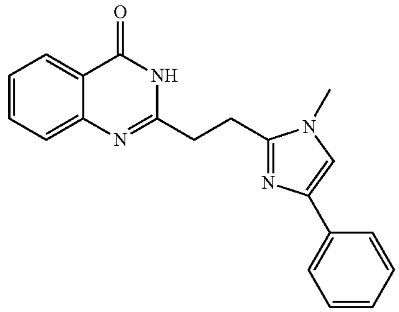 [SMILES: Cn1cc(-c2ccccc2)nc1CCc1nc2ccccc2c(=O)[nH]1] | A | LC-MS: m/z 331.4 (M + H⁺); ¹H NMR (CDCl₃): δ 13.79 (s, 1H), 8.32-8.29 (dd, $^1J$ = 7.9 Hz, $^2J$ = 1.1 Hz, 1H), 7.93-7.90 (m, 2H), 7.77-7.66 (m, 2H), 7.49-7.43 (t, J = 7.7 Hz, 3H), 7.31-7.26 (t, J = 7.4 Hz, 1H), 7.14 (s, 1H), 3.64 (s, 3H), 3.37-3.33 (m, 2H), 3.17-3.13 (m, 2H). |
| 9 | 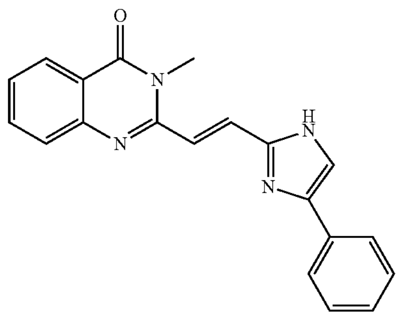 [SMILES: Cn1c(/C=C/c2nc(-c3ccccc3)c[nH]2)nc2ccccc2c1=O] | A | LC-MS: m/z 329.4 (M + H⁺); ¹H NMR (CDCl₃): δ 8.32-8.29 (d, J = 7.9 Hz, 1H), 7.91-7.86 (m, 2H), 7.78-7.67 (m, 3H), 7.49-7.42 (m, 4H), 7.35-7.33 (m, 2H), 3.82 (s, 3H). |
| 10 | 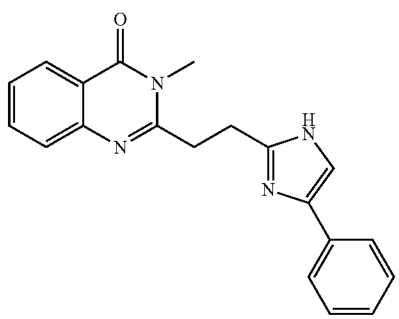 [SMILES: Cn1c(CCc2nc(-c3ccccc3)c[nH]2)nc2ccccc2c1=O] | A | LC-MS: m/z 331.4 (M + H⁺); ¹H NMR (CD₃OD); δ 8.22-8.19 (dd, $^1J$ = 8.0 Hz, $^2J$ = 1.2 Hz, 1H), 7.79-7.76 (m, 1H), 7.70-7.64 (m, 3H), 7.53-7.47 (t, J = 8.1 Hz, 1H), 7.38-7.33 (t, J = 7.6 Hz, 2H), 7.29 (s, 1H), 7.25-7.22 (m, 1H), 3.67 (s, 3H), 3.37 (s, 4H). |
| 11 | 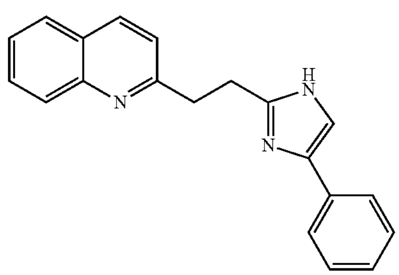 [SMILES: c1ccc(-c2c[nH]c(CCc3ccc4ccccc4n3)n2)cc1] | A | LC-MS: m/z 300.4 (M + H⁺); ¹H NMR (CDCl₃); δ 11.30 (s, 1H), 8.16-8.14 (m, 2H), 7.86 (d, J = 8.2 Hz, 1H), 7.79 (t, J = 7.0 Hz, 2H), 7.62-7.55 (m, 2H), 7.41-7.35 (m, 3H), 7.24-7.21 (m, 2H), 3.50-3.44 (m, 4H). |
| 12 | 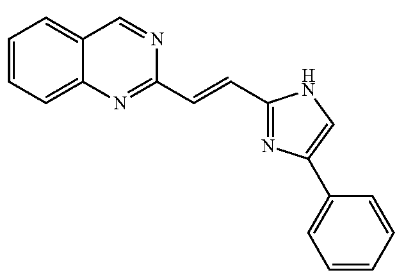 [SMILES: C(=C\c1nc(-c2ccccc2)c[nH]1)/c1ncc2ccccc2n1] | A | LC-MS: m/z 299.3 (M + H⁺); ¹H NMR (CDCl₃): δ 12.80 (s, 1H), 13.05 (s, 1H), 8.14 (d, J = 8.0 Hz, 1H), 8.03-7.86 (m, 6H), 7.74 (m, 1H), 7.52 (d, J = 16.3 Hz, 1H), 7.39 (s, 1H), 7.24 (s, 1H). |

-continued

| Compound No. | Structure | Method of Preparation | Analytical Data |
|---|---|---|---|
| 13 | 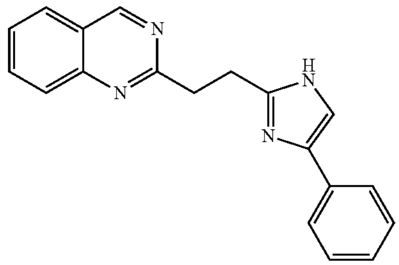 [SMILES: c1ccc(-c2c[nH]c(CCc3ncc4ccccc4n3)n2)cc1] | A | LC-MS: m/z 301.3 (M + H+); 1H NMR (CDCl3): δ 9.44 (s, 1H), 8.08-7.97 (m, 3H), 7.72-7.67 (m, 3H), 7.38 (t, J = 7.5 Hz, 2H), 7.25-7.21 (m, 2H), 3.67-3.63 (m, 2H), 3.50-3.46 (m, 2H). |
| 14 | 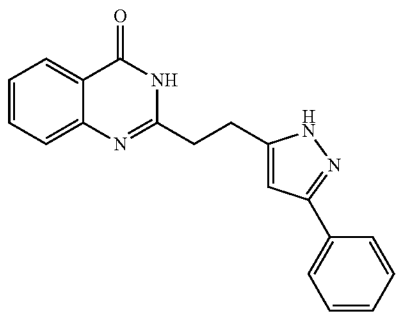 [SMILES: O=c1[nH]c(CCc2cc(-c3ccccc3)n[nH]2)nc2ccccc12] | A | LC-MS: m/z 317 (M + H+); 1H NMR (CD3OD): δ 8.20 (dd, 1J = 7.6 Hz, 2J = 1.1 Hz, 1H), 7.83-7.79 (m, 1H), 7.69 (d, J = 8.3 Hz, 3H), 7.54-7.51 (m, 1H), 7.42-7.29 (m, 3H), 6.50 (s, 1H), 3.22-3.20 (m, 2H), 3.10-3.08 (m, 2H). |
| 15 | 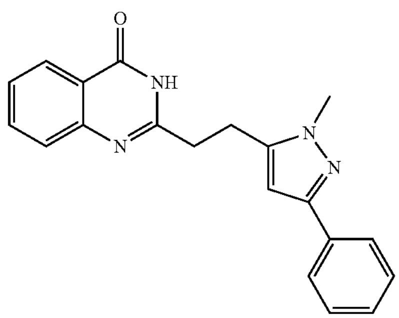 [SMILES: Cn1nc(-c2ccccc2)cc1CCc1nc2ccccc2c(=O)[nH]1] | A | LC-MS: m/z 331 (M + H+); 1H NMR (CD3OD): δ 8.21 (d, J = 7.9 Hz, 1H), 7.86-7.81 (m, 1H), 7.70 (d, J = 7.1 Hz, 3H), 7.52 (t, J = 7.6 Hz, 1H), 7.39-7.26 (m, 3H), 6.50 (s, 1H), 3.91 (s, 3H), 3.28-3.23 (m, 2H), 3.13-3.08 (m, 2H). |
| 16 | 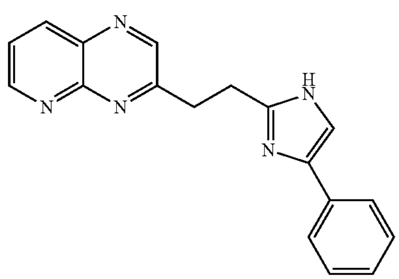 [SMILES: c1ccc(-c2c[nH]c(CCc3cnc4cccnc4n3)n2)cc1] | A | LC-MS: m/z 302.4 (M + H+); 1H NMR (CD3OD): δ 9.12 (dd, 1J = 4.3 Hz, 2J = 1.8 Hz, 1H), 8.91 (s, 1H), 8.57 (dd, 1J = 8.4 Hz, 2J = 1.7 Hz, 1H), 7.85 (dd, 1J = 8.4 Hz, 2J = 4.3 Hz, 1H), 7.63 (d, J = 7.5 Hz, 2H), 7.37-7.32 (t, J = 7.6 Hz, 2H), 7.26-7.19 (m, 2H), 3.63-3.58 (m, 2H), 3.43-3.38 (m, 2H). |
| 17 | 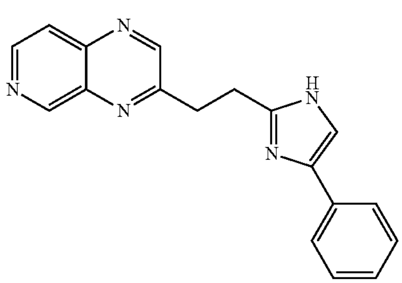 [SMILES: c1ccc(-c2c[nH]c(CCc3cnc4ccncc4n3)n2)cc1] | A | LC-MS: m/z 302.4 (M + H+). |

| Compound No. | Structure | Method of Preparation | Analytical Data |
|---|---|---|---|
| 18 | 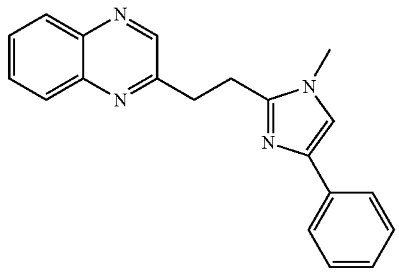 [SMILES: Cn1cc(-c2ccccc2)nc1CCc1cnc2ccccc2n1] | A | LC-MS: m/z 315 (M + H$^+$); $^1$H NMR (CDCl$_3$): δ 9.35 (s, 1H), 7.97 (d, J = 8.1 Hz, 1H), 7.91-7.87 (m, 2H), 7.71 (d, J = 8.4 Hz, 2H), 7.63-7.59 (m, 1H), 7.34-7.31 (m, 2H), 7.21-7.17 (m, 1H), 7.07 (d, J = 1.1 Hz, 1H), 3.71-3.66 (m, 5H), 3.42-3.38 (m, 2H). |
| 19 | 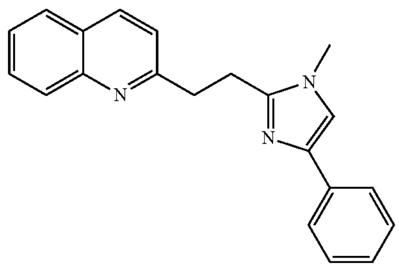 [SMILES: Cn1cc(-c2ccccc2)nc1CCc1ccc2ccccc2n1] | A | LC-MS: m/z 314 (M + H$^+$); $^1$H NMR (CDCl$_3$): δ 8.05 (d, J = 8.4 Hz, 1H), 8.01 (d, J = 8.4 Hz, 1H), 7.77-7.73 (m, 3H), 7.70-7.66 (m, 1H), 7.50-7.46 (m, 1H), 7.37-7.33 (m, 2H), 7.27 (d, J = 8.4 Hz, 1H), 7.25-7.18 (m, 1H), 6.98 (s, 1H), 3.52-3.48 (m, 2H), 3.46 (s, 3H), 3.30-3.26 (m, 2H); $^{13}$C NMR (CDCl$_3$): 161.4, 148.3, 148.1, 140.2, 136.4, 134.7, 129.5, 128.9, 128.7, 127.8, 127.0, 126.5, 126.0, 124.9, 122.1, 116.4, 37.48, 32.86, 26.34. |
| 20 | 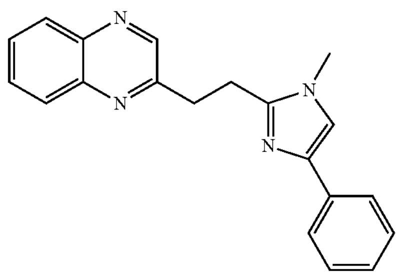 [SMILES: Cn1cc(-c2ccccc2)nc1CCc1cnc2ccccc2n1] | A | LC-MS: m/z 315 (M + H$^+$); $^1$H NMR (CDCl$_3$): δ 8.82 (s, 1H), 8.08-8.02 (m, 2H), 7.75-7.69 (m, 4H), 7.36-7.32 (m, 2H), 7.22-7.20 (m, 1H), 7.02 (s, 1H), 3.75-3.57 (m, 2H), 3.55 (s, 3H), 3.31-3.28 (m, 2H). |
| 21 | 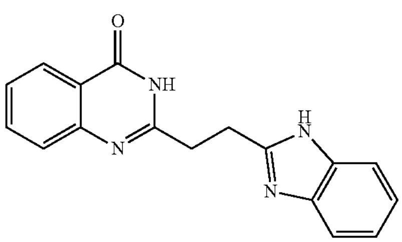 [SMILES: O=c1[nH]c(CCc2nc3ccccc3[nH]2)nc2ccccc12] | B | LC-MS: m/z 291.1 (M + H$^+$); $^1$H NMR (DMSO-d$_6$): δ 12.36 (s, 1H), 12.28 (s, 1H), 8.09 (dd, $^1$J = 7.8 Hz, $^2$J = 1.1 Hz, 1H), 7.80-7.74 (m, 1H), 7.58 (d, J = 8.0 Hz, 1H), 7.49-7.36 (m, 3H), 7.11 (d, J = 5.3 Hz, 2H), 3.41-3.36 (m, 2H), 3.21-3.16 (m, 2H). |
| 22 | 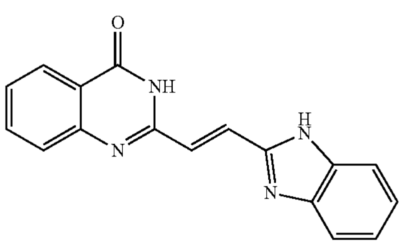 [SMILES: O=c1[nH]c(/C=C/c2nc3ccccc3[nH]2)nc2ccccc12] | B | LC-MS: m/z 289.1 (M + H$^+$); $^1$H NMR (DMSO-d$_6$): δ 12.95 (s, 1H), 12.60 (s, 1H), 8.14 (d, J = 7.8 Hz, 1H), 7.94 (d, J = 16.1 Hz, 1H), 7.87-7.81 (m, 1H), 7.73-7.62 (m, 2H), 7.55-7.50 (m, 2H), 7.44 (d, J = 16.1 Hz, 1H), 7.25 (s, 2H). |
| 23 | 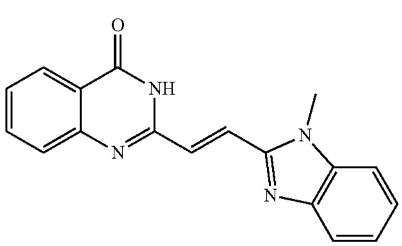 [SMILES: Cn1c(/C=C/c2nc3ccccc3c(=O)[nH]2)nc2ccccc21] | B | LC-MS: m/z 303.2 (M + H$^+$); $^1$H NMR (DMSO-d$_6$): δ 12.55 (s, 1H), 8.16-8.08 (m, 2H), 7.87-7.82 (m, 1H), 7.75-7.68 (m, 2H), 7.66 (dd, $^1$J = 11.9 Hz, $^2$J = 1.5 Hz, 1H), 7.57-7.50 (m, 2H), 7.34-7.24 (m, 2H), 3.98 (s, 3H). |

| Compound No. | Structure | Method of Preparation | Analytical Data |
|---|---|---|---|
| 24 | 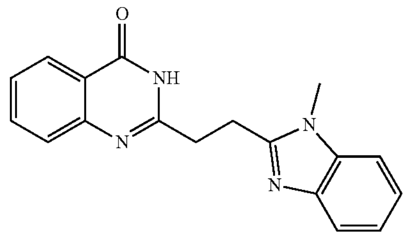 [SMILES: Cn1c(CCc2nc3ccccc3c(=O)[nH]2)nc2ccccc21] | B | LC-MS: m/z 305.1 (M + H⁺); ¹H NMR (DMSO-d₆): δ 12.34 (s, 1H), 8.08 (d, J = 7.4 Hz, 1H), 7.79-7.74 (m, 1H), 7.60-7.43 (m, 4H), 7.21-7.11 (m, 2H), 3.81 (s, 3H), 3.45-3.39 (m, 2H), 3.25-3.20 (m, 2H). |
| 25 | 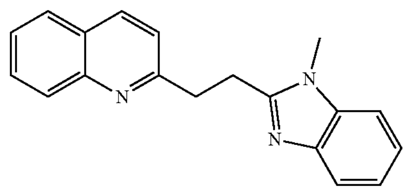 [SMILES: Cn1c(CCc2ccc3ccccc3n2)nc2ccccc21] | B | LC-MS: m/z 288 (M + H⁺); ¹H NMR (CDCl₃): δ 8.05-8.03 (m, 2H), 7.79-7.68 (m, 3H), 7.50 (t, 1H), 7.31 (d, J = 8.4 Hz, 1H), 7.28-7.23 (m, 3H), 3.71 (s, 3H), 3.66-3.62 (m, 2H), 3.52-3.47 (m, 2H). |
| 26 | 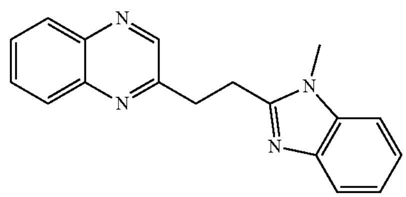 [SMILES: Cn1c(CCc2cnc3ccccc3n2)nc2ccccc21] | B | LC-MS: m/z 289 (M + H⁺); ¹H NMR (CDCl₃): δ 8.82 (s, 1H), 8.06-8.00 (m, 2H), 7.73-7.68 (m, 3H), 7.26-7.21 (m, 3H), 3.74 (s, 3H), 3.72-3.69 (m, 2H), 3.50-3.46 (m, 2H). |
| 27 | 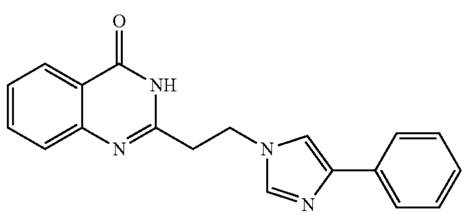 [SMILES: O=c1[nH]c(CCn2cnc(-c3ccccc3)c2)nc2ccccc12] | C | LC-MS: m/z 317 (M + H⁺); ¹H NMR (DMSO-d₆): δ 12.27 (s, 1H), 8.08 (d, J = 7.4 Hz, 1H), 7.82-7.64 (m, 6H), 7.49 (t, J = 14.7 Hz, 1H), 7.35-7.30 (t, J = 7.4 Hz, 1H), 7.19-7.14 (m, 1H), 4.49-4.45 (t, J = 6.8 Hz, 2H), 3.17-3.12 (t, J = 13.5 Hz, 2H). |
| 28 | 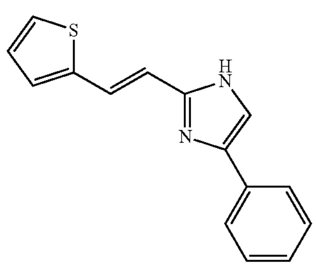 [SMILES: C(=C\c1cccs1)/c1nc(-c2ccccc2)c[nH]1] | D | LC-MS: m/z 253.3 (M + H⁺); ¹H NMR (CDCl₃): δ 7.72 (d, J = 7.3 Hz, 2H), 7.49 (d, J = 16.1 Hz, 1H), 7.42-7.34 (m, 3H), 7.30-7.25 (m, 1H), 7.19 (d, J = 5.0 Hz, 1H), 7.02-7.01 (m, 1H), 6.80-6.93 (m, 1H), 6.80 (d, J = 16.1 Hz, 1H). |
| 29 | 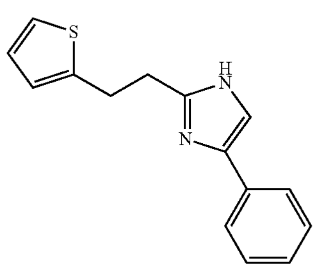 [SMILES: c1ccc(-c2c[nH]c(CCc3cccs3)n2)cc1] | D | LC-MS: m/z 255.3 (M + H⁺); ¹H NMR (CDCl₃): δ 7.68-7.65 (m, 2H), 7.36 (t, J = 7.6 Hz, 2H), 7.25-7.17 (m, 3H), 6.89 (dd, ¹J = 5.1 Hz, ²J = 3.5 Hz, 1H), 6.83 (d, J = 3.2 Hz, 1H), 3.33-3.27 (m, 2H), 3.11-3.06 (m, 2H). |

| Compound No. | Structure | Method of Preparation | Analytical Data |
|---|---|---|---|
| 30 | 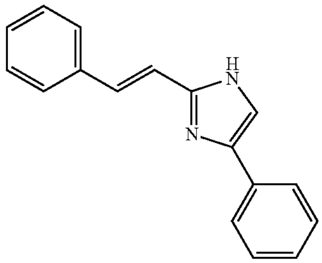 [SMILES: C(=C\c1nc(-c2ccccc2)c[nH]1)/c1ccccc1] | D | LC-MS: m/z 247.3 (M + H⁺); ¹H NMR (CD$_3$OD): δ 7.75 (d, J = 7.8 Hz, 2H), 7.60-7.57 (m, 2H), 7.45-7.37 (m, 6H), 7.31 (dd, ¹J = 12.3 Hz, ²J = 7.2 Hz, 2H), 7.06 (d, J = 16.6 Hz, 1H). |
| 31 | 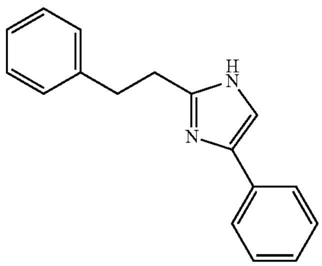 [SMILES: c1ccc(CCc2nc(-c3ccccc3)c[nH]2)cc1] | D | LC-MS: m/z 249.3 (M + H⁺); ¹H NMR (CD$_3$OD): δ 7.82-7.75 (m, 3H), 7.67-7.64 (m, 3H), 7.47-7.33 (m, 4H), 7.27-7.20 (m, 1H), 3.26-3.21 (m, 2H), 3.16-3.10 (m, 2H). |
| 32 | 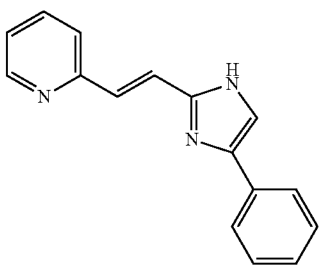 [SMILES: C(=C\c1nc(-c2ccccc2)c[nH]1)/c1ccccn1] | D | LC-MS: m/z 248.3 (M + H⁺); ¹H NMR (CD$_3$OD): δ 8.60 (dd, ¹J = 4.9 Hz, ²J = 0.8 Hz, 1H), 7.88-7.84 (m, 1H), 7.79-7.76 (m, 2H), 7.64-7.61 (m, 2H), 7.53 (s, 2H), 7.48-7.43 (t, J = 7.5 Hz, 2H), 7.38-7.34 (m, 2H). |
| 33 | 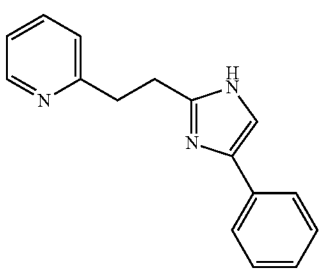 [SMILES: c1ccc(-c2c[nH]c(CCc3ccccn3)n2)cc1] | D | LC-MS: m/z 250.3 (M + H⁺); ¹H NMR (CD$_3$OD): δ 8.50-8.47 (m, 1H), 7.77-7.71 (m, 1H), 7.65 (d, J = 7.4 Hz, 2H), 7.36 (t, J = 7.6 Hz, 2H), 7.29-7.19 (m, 4H), 3.27-3.21 (m, 2H), 3.17-3.12 (m, 2H). |
| 34 | 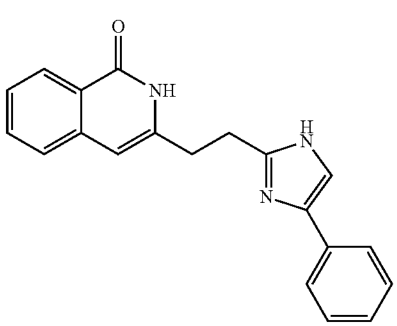 [SMILES: O=c1[nH]c(CCc2nc(-c3ccccc3)c[nH]2)cc2ccccc12] | D | LC-MS: m/z 316.3 (M + H⁺); ¹H NMR (DMSO-d$_6$ + D$_2$O): δ 8.11 (d, J = 8.1 Hz, 1H), 7.87 (s, 1H), 7.68-7.62 (m, 3H), 7.52-7.38 (m, 5H), 6.31 (s, 1H), 3.30 (t, J = 7.2 Hz, 2H), 3.00 (t, J = 7.2 Hz, 2H). |

| Compound No. | Structure | Method of Preparation | Analytical Data |
|---|---|---|---|
| 35 | 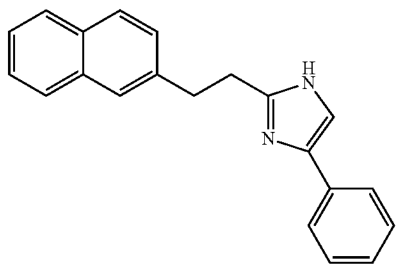 [SMILES: c1ccc(-c2c[nH]c(CCc3ccc4ccccc4c3)n2)cc1] | D | LC-MS: m/z 299.1 (M + H⁺); ¹H NMR (DMSO-d₆): δ 7.87-7.82 (m, 3H), 7.75-7.70 (m, 3H), 7.50 (m, 4H), 7.32 (t, J = 7.4 Hz, 2H), 7.18-7.13 (m, 1H), 3.22-3.16 (m, 2H), 3.06-3.01 (m, 2H). |
| 36 | 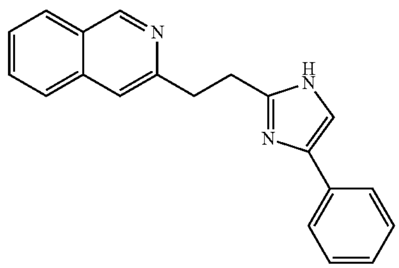 [SMILES: c1ccc(-c2c[nH]c(CCc3cc4ccccc4cn3)n2)cc1] | D | LC-MS: m/z 300.1 (M + H⁺); ¹H NMR (CD₃OD): δ 9.23 (s, 1H), 8.08 (d, J = 8.6 Hz, 1H), 7.86-7.83 (m, 1H), 7.75 (t, J = 8.1 Hz, 1H), 7.66-7.61 (m, 4H), 7.38-7.33 (t, J = 7.6 Hz, 2H), 7.25-7.22 (m, 2H), 3.41-3.35 (m, 2H), 3.26-3.21 (m, 2H). |
| 37 | 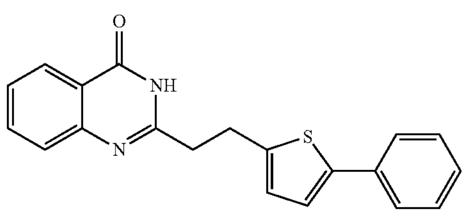 [SMILES: O=c1[nH]c(CCc2ccc(-c3ccccc3)s2)nc2ccccc12] | E | LC-MS: m/z 333 (M + H⁺); ¹H NMR (DMSO-d₆) δ 12.25 (s, 1H), 8.09 (dd, ¹J = 7.9 Hz, ²J = 1.3 Hz, 1H), 7.82-7.76 (m, 1H), 7.63 (d, J = 7.8 Hz, 1H), 7.57-7.54 (m, 2H), 7.50-7.45 (t, J = 8.0 Hz, 1H), 7.38 (t, J = 7.5 Hz, 2H), 7.31-7.23 (m, 2H), 6.92 (d, J = 3.6 Hz, 1H), 3.32-3.29 (m, 2H), 3.02-2.99 (m, 2H). |
| 38 | 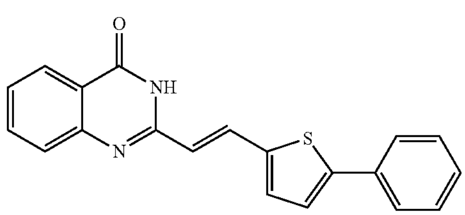 [SMILES: O=c1[nH]c(/C=C/c2ccc(-c3ccccc3)s2)nc2ccccc12] | E | LC-MS: m/z 331 (M + H⁺); ¹H NMR (DMSO-d₆): δ 12.31 (s, 1H), 8.14 (d, J = 7.2 Hz, 1H), 7.96-7.88 (m, 2H), 7.76-7.72 (m, 2H), 7.67-7.45 (m, 5H), 7.39-7.34 (m, 1H), 7.26 (d, J = 12.6 Hz, 1H), 6.16 (d, J = 12.5 Hz, 1H). |
| 39 | 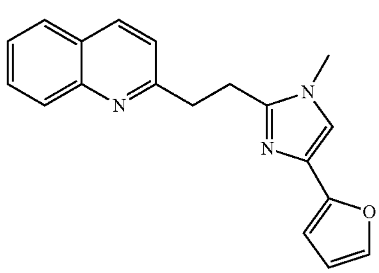 [SMILES: Cn1cc(-c2ccco2)nc1CCc1ccc2ccccc2n1] | F | LC-MS: m/z 304.4 (M + H⁺); ¹H NMR (DMSO-d₆ + D₂O): δ 8.25 (d, J = 8.6 Hz, 1H), 7.94 (t, J = 8.3 Hz, 2H), 7.73 (t, J = 5.3 Hz, 1H), 7.52-7.44 (m, 3H), 7.25 (s, 1H), 6.48-6.46 (m, 2H), 3.53 (s, 3H), 3.36-3.31 (m, 2H), 3.16-3.11 (m, 2H). |
| 40 | 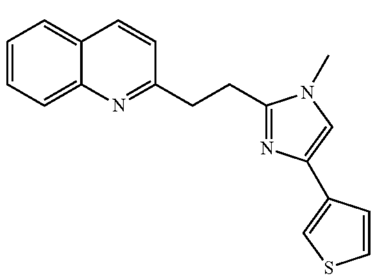 [SMILES: Cn1cc(-c2ccsc2)nc1CCc1ccc2ccccc2n1] | F | LC-MS: m/z 320.4 (M + H⁺); ¹H NMR (DMSO-d₆ + D₂O): δ 8.25 (d, J = 8.5 Hz, 1H), 7.94 (dd, ¹J = 12.0 Hz, ²J = 8.5 Hz, 2H), 7.73 (t, J = 7.7 Hz, 1H), 7.56-7.51 (m, 2H), 7.47-7.44 (m, 2H), 7.34 (d, J = 4.9 Hz, 1H), 7.27 (s, 1H), 3.53 (s, 3H), 3.53-3.30 (m, 2H), 3.17-3.12 (m, 2H). |

-continued

| Compound No. | Structure | Method of Preparation | Analytical Data |
|---|---|---|---|
| 41 | 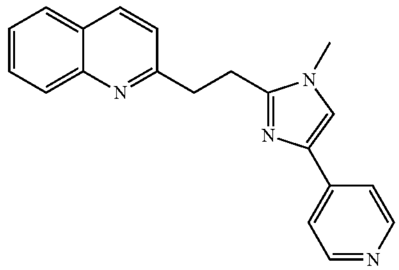 [SMILES: Cn1cc(-c2ccncc2)nc1CCc1ccc2ccccc2n1] | F | LC-MS: m/z 315.4 (M + H$^+$); $^1$H NMR (CDCl$_3$): δ 8.57-8.55 (m, 2H), 8.09-8.04 (m, 2H), 7.81 (d, J = 8.0 Hz, 1H), 7.72 (t, J = 8.4 Hz, 1H), 7.63-7.61 (m, 2H), 7.55-7.50 (m, 1H), 7.32 (d, J = 8.5 Hz, 1H), 7.22 (s, 1H), 3.58 (s, 3H), 3.56-3.51 (m, 2H), 3.35-3.30 (m, 2H). |
| 42 | 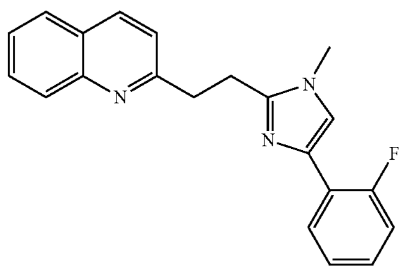 [SMILES: Cn1cc(-c2ccccc2F)nc1CCc1ccc2ccccc2n1] | F | LC-MS: m/z 332.4 (M + H$^+$); $^1$H NMR (CDCl$_3$): δ 8.20-8.14 (m, 1H), 8.05 (d, J = 8.3 Hz, 2H), 7.80 (d, J = 8.2 Hz, 1H), 7.74-7.69 (m, 1H), 7.52 (t, J = 15.1 Hz, 1H), 7.31 (d, J = 8.4 Hz, 1H), 7.22-7.14 (m, 3H), 7.11-7.04 (m, 1H), 3.56-3.51 (m, 5H), 3.34-3.29 (m, 2H). |
| 43 | 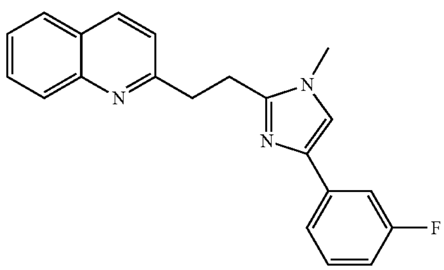 [SMILES: Cn1cc(-c2cccc(F)c2)nc1CCc1ccc2ccccc2n1] | F | LC-MS: m/z 332.4 (M + H$^+$); $^1$H NMR (CDCl$_3$): δ 8.05 (d, J = 8.3 Hz, 2H), 7.80 (d, J = 8.0 Hz, 1H), 7.74-7.68 (t, J = 8.3 Hz, 1H), 7.51-7.44 (m, 3H), 7.34-7.29 (m, 2H), 7.04 (s, 1H), 6.90 (t, J = 8.4 Hz, 1H), 3.55-3.50 (m, 5H), 3.33-3.28 (m, 2H). |
| 44 | 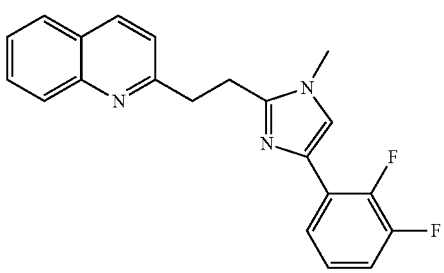 [SMILES: Cn1cc(-c2cccc(F)c2F)nc1CCc1ccc2ccccc2n1] | F | LC-MS: m/z 350.2 (M + H$^+$); $^1$H NMR (DMSO-d$_6$): δ 8.47 (d, J = 8.5 Hz, 1H), 8.01 (d, J = 8.0 Hz, 1H), 7.95-7.90 (m, 2H), 7.81 (t, J = 15.0 Hz, 1H), 7.65-7.59 (m, 2H), 7.54-7.41 (m, 2H), 7.35-7.28 (m, 1H), 3.84 (s, 3H), 3.56-3.47 (m, 4H). |
| 45 | 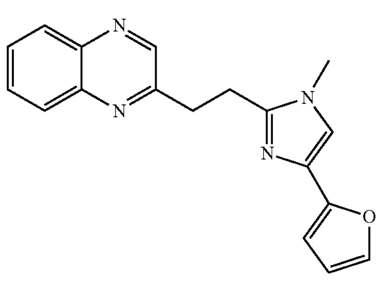 [SMILES: Cn1cc(-c2ccco2)nc1CCc1cnc2ccccc2n1] | F | LC-MS: m/z 305.2 (M + H$^+$); $^1$H NMR (CDCl$_3$): δ 8.81 (s, 1H), 8.12-8.09 (m, 1H), 7.97-7.94 (m, 1H), 7.79-7.72 (m, 2H), 7.40 (d, J = 1.4 Hz, 1H), 7.04-6.97 (m, 2H), 6.47 (dd, $^1$J = 3.4 Hz, $^2$J = 1.2 Hz, 1H), 3.84 (s, 3H), 3.76-3.72 (m, 2H), 3.62-3.57 (m, 2H). |

| Compound No. | Structure | Method of Preparation | Analytical Data |
|---|---|---|---|
| 46 | 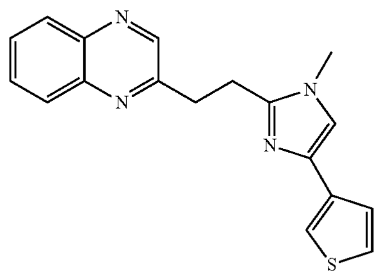 [SMILES: Cn1cc(-c2ccsc2)nc1CCc1cnc2ccccc2n1] | F | LC-MS: m/z 321.1 (M + H⁺); ¹H NMR (CDCl₃): δ 8.83 (s, 1H), 8.11-8.03 (m, 2H), 7.79-7.70 (m, 2H), 7.54 (s, 1H), 7.33-7.31 (m, 2H), 6.94 (s, 1H), 3.63-3.59 (m, 5H), 3.35-3.30 (m, 2H). |
| 47 | 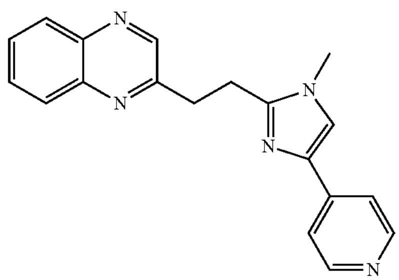 [SMILES: Cn1cc(-c2ccncc2)nc1CCc1cnc2ccccc2n1] | F | LC-MS: m/z 316.4 (M + H⁺); ¹H NMR (CDCl₃): δ 8.86 (s, 1H), 8.57-7.55 (m, 2H), 8.12-8.03 (m, 2H), 7.80-7.70 (m, 2H), 7.76-7.59 (m, 2H), 7.28 (s, 1H), 3.65-3.59 (m, 5H), 3.37-3.32 (m, 2H). |
| 48 | 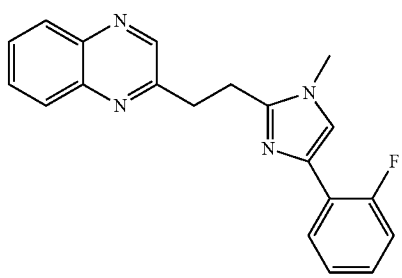 [SMILES: Cn1cc(-c2ccccc2F)nc1CCc1cnc2ccccc2n1] | F | LC-MS: m/z 333.3 (M + H⁺); ¹H NMR (CDCl₃): δ 8.87 (s, 1H), 8.17-8.04 (m, 3H), 7.80-7.70 (m, 2H), 7.27-7.25 (m, 1H), 7.21-7.16 (m, 2H), 7.10-7.03 (m, 1H), 3.65-3.58 (m, 5H), 3.37-3.31 (m, 2H). |
| 49 | 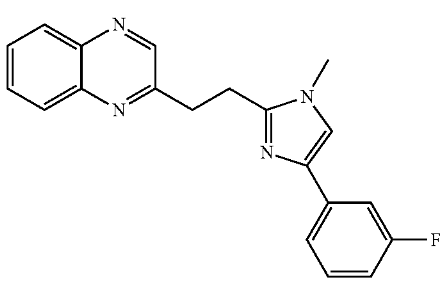 [SMILES: Cn1cc(-c2cccc(F)c2)nc1CCc1cnc2ccccc2n1] | F | LC-MS: m/z 333.4 (M + H⁺); ¹H NMR (CDCl₃): δ 8.85 (s, 1H), 8.12-8.03 (m, 3H), 7.80-7.70 (m, 2H), 7.51-7.42 (m, 2H), 7.35-7.29 (m, 1H), 7.07 (s, 1H), 6.90 (t, J = 8.4 Hz, 1H), 3.65-3.60 (m, 5H), 3.36 (t, J = 14.9 Hz, 1H). |
| 50 | 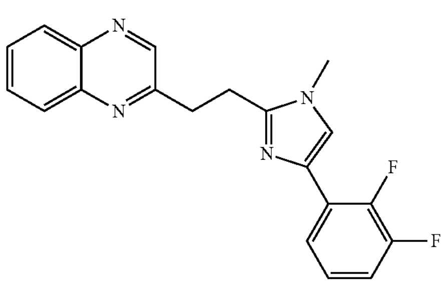 [SMILES: Cn1cc(-c2cccc(F)c2F)nc1CCc1cnc2ccccc2n1] | F | LC-MS: m/z 351.4 (M + H⁺); ¹H NMR (CDCl₃): δ 8.86 (s, 1H), 8.11-8.03 (m, 2H), 7.90-7.85 (m, 1H), 7.75 (t, J = 7.4 Hz, 3H), 7.14-7.07 (m, 1H), 7.01-6.95 (m, 1H), 3.65-3.58 (m, 5H), 3.34 (t, J = 14.7 Hz, 2H). |

| Compound No. | Structure | Method of Preparation | Analytical Data |
|---|---|---|---|
| 51 | 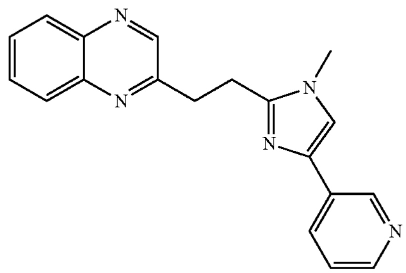 [SMILES: Cn1cc(-c2cccnc2)nc1CCc1cnc2ccccc2n1] | F | LC-MS: m/z 316.4 (M + H$^+$). |
| 52 | 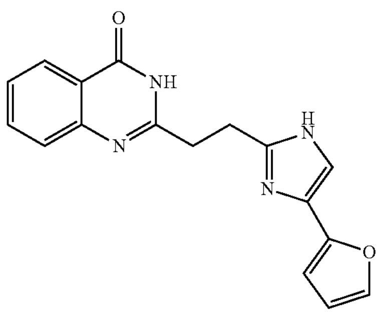 [SMILES: O=c1[nH]c(CCc2nc(-c3ccco3)c[nH]2)nc2ccccc12] | G-1 | MS (ESI) m/z 307 (M + H$^+$); $^1$H NMR (400 MHz, CD$_3$OD): δ 8.21-8.17 (m, 1H), 7.81-7.79 (m, 1H), 7.68 (d, J = 8.0 Hz, 1H), 7.54-7.49 (m, 1H), 7.46 (t, J = 0.8 Hz, 1H), 7.20 (s, 1H), 6.57 (d, J = 3.2 Hz, 1H), 6.48-6.46 (m, 1H), 3.26 (t, J = 2.0 Hz, 2H), 3.13 (t, J = 2.0 Hz, 2H). |
| 53 | 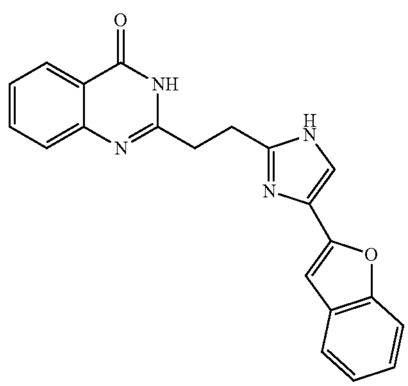 [SMILES: O=c1[nH]c(CCc2nc(-c3cc4ccccc4o3)c[nH]2)nc2ccccc12] | G-1 | MS (ESI) m/z 357 (M + H$^+$); $^1$H NMR (400 MHz, DMSO-d$_6$): δ 8.09-8.08 (m, 2H), 7.76-7.74 (m, 2H), 7.65 (d, J = 8.0 Hz, 1H), 7.54-7.45 (m, 2H), 7.42-7.34 (m, 3H), 3.44 (t, J = 2.0 Hz, 2H), 3.23 (t, J = 2.0 Hz, 2H). |
| 54 | 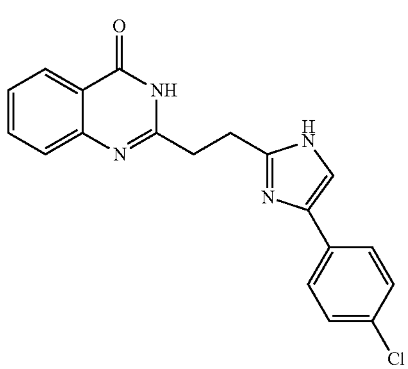 [SMILES: O=c1[nH]c(CCc2nc(-c3ccc(Cl)cc3)c[nH]2)nc2ccccc12] | G-1 | MS (ESI) m/z 351 (M + H$^+$); $^1$H NMR (400 MHz, DMSO-d$_6$): δ 8.09 (d, J = 8.0 Hz, 1H), 7.80-7.74 (m, 3H), 7.62-7.60 (d, J = 8.0 Hz, 1H), 7.56 (s, 1H), 7.47 (t, J = 8.0 Hz, 1H), 7.36 (d, J = 8.4 Hz, 2H), 3.16-3.13 (m, 2H), 3.09-3.05 (m, 2H). |

-continued

| Compound No. | Structure | Method of Preparation | Analytical Data |
|---|---|---|---|
| 55 | 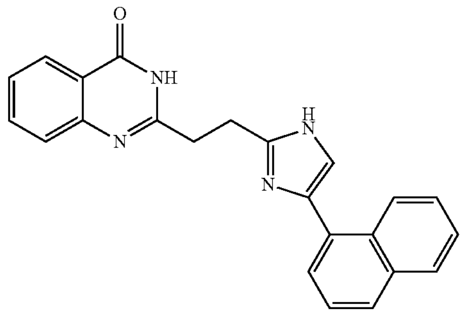 [SMILES: O=c1[nH]c(CCc2nc(-c3cccc4ccccc34)c[nH]2)nc2ccccc12] | G-1 | MS (ESI) m/z 367.1 (M + H⁺); $^1$H NMR (400 MHz, DMSO-d$_6$): δ 8.12-8.05 (m, 3H), 7.90 (s, 1H), 7.54-7.49 (m, 1H), 7.86-7.77 (m, 1H), 7.65-7.59 (m, 3H), 7.56-7.48 (m, 2H), 7.45-7.41 (m, 1H), 3.49 (t, J = 6.8 Hz, 2H), 3.26 (t, J = 6.8 Hz, 2H). |
| 56 | 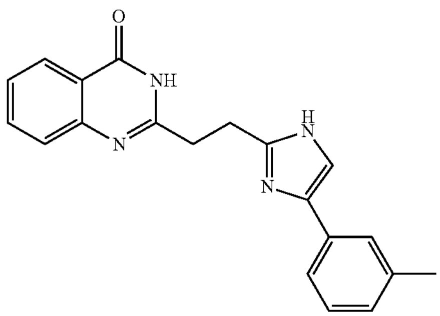 [SMILES: Cc1cccc(-c2c[nH]c(CCc3nc4ccccc4c(=O)[nH]3)n2)c1] | G-1 | MS (ESI) m/z 331.4 (M + H⁺); $^1$H NMR (400 MHz, DMSO-d$_6$): δ 12.58 (s, 1H), 11.93 (s, 1H), 8.10 (d, J = 7.6 Hz, 1H), 7.78 (q, J = 7.4 Hz, 1H), 7.62-7.45 (m, 5H), 7.21 (q, J = 7.4 Hz, 1H), 6.98 (d, J = 6.8 Hz, 1H), 3.15 (q, J = 6.6 Hz, 2H), 3.08 (q, J = 6.8 Hz, 2H), 2.31 (s, 3H). |
| 57 | 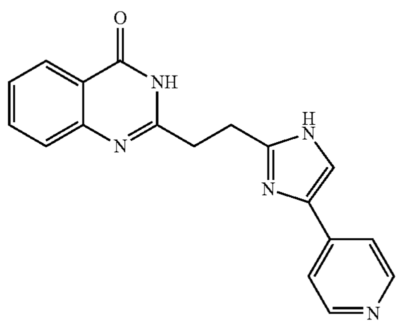 [SMILES: O=c1[nH]c(CCc2nc(-c3ccncc3)c[nH]2)nc2ccccc12] | G-2 | MS (ESI) m/z 318.1 (M + H⁺); $^1$H NMR (400 MHz, CD$_3$OD): δ 8.47 (d, J = 6.0 Hz, 2H), 8.19 (t, J = 13.6 Hz, 1H), 7.82 (d, J = 7.2 Hz, 1H), 7.75 (d, J = 5.2 Hz, 2H), 7.68 (d, J = 7.6 Hz, 2H), 7.52 (t, J = 7.6 Hz, 1H), 3.30 (t, J = 7.6 Hz, 2H), 3.17 (t, J = 7.6 Hz, 2H). |
| 58 | 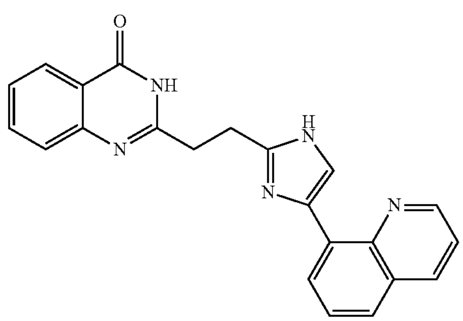 [SMILES: O=c1[nH]c(CCc2nc(-c3cccc4cccnc34)c[nH]2)nc2ccccc12] | G-2 | MS (ESI) m/z 368 (M + H⁺); $^1$H NMR (400 MHz, DMSO-d$_6$): δ 9.00-8.98 (m, 1H), 8.55-8.52 (m, 1H), 8.38 (s, 1H), 8.25-8.23 (m, 1H), 8.11 (t, J = 8.0 Hz, 2H), 7.80-7.74 (m, 2H), 7.70 (dd, $^1$J = 8.4 Hz, $^2$J = 4.4 Hz, 1H), 7.54 (d, J = 7.6 Hz, 1H), 7.49 (t, J = 8.0 Hz, 1H), 3.55 (t, J = 6.8 Hz, 2H), 3.27 (t, J = 6.8 Hz, 2H). |
| 59 | 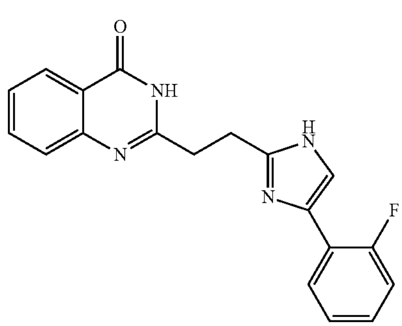 [SMILES: O=c1[nH]c(CCc2nc(-c3ccccc3F)c[nH]2)nc2ccccc12] | G-2 | MS (ESI) m/z 335.1 (M + H⁺); $^1$H NMR (400 MHz, CD$_3$OD): δ 8.07 (dd, $^1$J = 7.6 Hz, $^2$J = 0.8 Hz, 1H), 7.69-7.63 (m, 3H), 7.47 (d, J = 8.0 Hz, 1H), 7.42-7.38 (m, 2H), 7.28-7.20 (m, 2H), 3.48 (t, J = 6.8 Hz, 2H), 3.21 (t, J = 6.8 Hz, 2H). |

| Compound No. | Structure | Method of Preparation | Analytical Data |
|---|---|---|---|
| 60 | 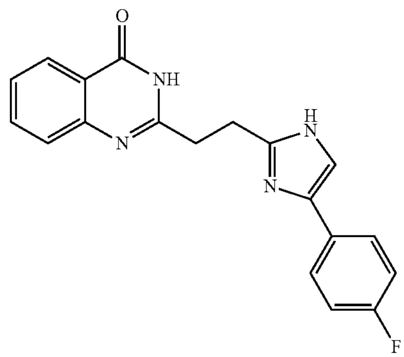 [SMILES: O=c1[nH]c(CCc2nc(-c3ccc(F)cc3)c[nH]2)nc2ccccc12] | G-2 | MS (ESI) m/z 335.1 (M + H$^+$); $^1$H NMR (400 MHz, CD$_3$OD): δ 8.17 (dd, $^1J$ = 8.0 Hz, $^2J$ = 0.4 Hz, 1H), 7.79-7.72 (m, 4H), 7.57 (d, J = 7.6 Hz, 1H), 7.51-7.47 (m, 1H), 7.29-7.24 (m, 2H), 3.57 (t, J = 6.8 Hz, 2H), 3.30 (t, J = 6.8 Hz, 2H). |
| 61 | 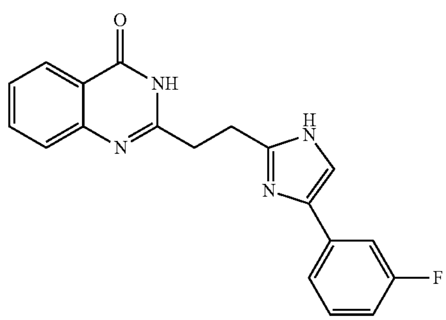 [SMILES: O=c1[nH]c(CCc2nc(-c3cccc(F)c3)c[nH]2)nc2ccccc12] | G-2 | MS (ESI) m/z 335.1 (M + H$^+$); $^1$H NMR (400 MHz, CD$_3$OD): δ 8.18 (dd, $^1J$ = 8.0 Hz, $^2J$ = 1.2 Hz, 1H), 7.79-7.77 (m, 1H), 7.64-7.61 (m, 2H), 7.54-7.51 (m, 2H), 7.49-7.45 (m, 2H), 7.09-7.08 (m, 1H), 3.44 (t, J = 7.2 Hz, 2H), 3.24 (t, J = 7.2 Hz, 2H). |
| 62 | 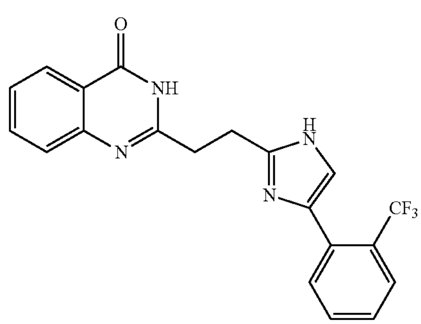 [SMILES: O=c1[nH]c(CCc2nc(-c3ccccc3C(F)(F)F)c[nH]2)nc2ccccc12] | G-2 | MS (ESI) m/z 385.1 (M + H$^+$); $^1$H NMR (400 MHz, CD$_3$OD): δ 8.19 (dd, $^1J$ = 8.0 Hz, $^2J$ = 1.2 Hz, 1H), 7.92-7.89 (m, 1H), 7.81-7.74 (m, 3H), 7.62-7.50 (m, 4H), 3.58 (t, J = 6.8 Hz, 2H), 3.33-3.30 (t, J = 6.8 Hz, 2H). |
| 63 | 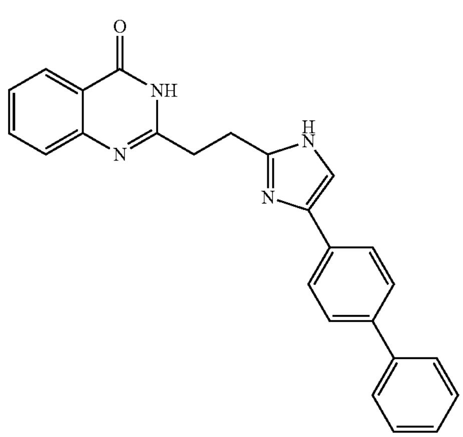 [SMILES: O=c1[nH]c(CCc2nc(-c3ccc(-c4ccccc4)cc3)c[nH]2)nc2ccccc12] | G-2 | MS (ESI) m/z 393.2 (M + H$^+$); $^1$H NMR (400 MHz, CD$_3$OD): δ 8.19 (dd, $^1J$ = 8.0 Hz, $^2J$ = 1.2 Hz, 1H), 7.82 (s, 1H), 7.80-7.75 (m, 5H), 7.69-7.66 (m, 2H), 7.59 (d, J = 7.6 Hz, 1H), 7.52-7.45 (m, 3H), 7.41-7.38 (m, 1H), 3.59 (t, J = 7.2 Hz, 2H), 3.34 (t, J = 7.2 Hz, 2H). |

| Compound No. | Structure | Method of Preparation | Analytical Data |
|---|---|---|---|
| 64 | 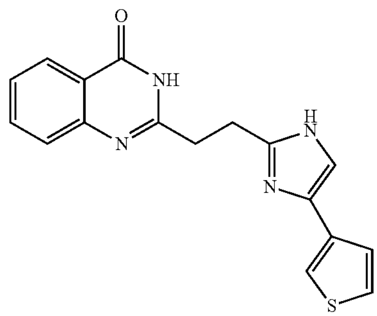 [SMILES: O=c1[nH]c(CCc2nc(-c3ccsc3)c[nH]2)nc2ccccc12] | G-1 | MS (ESI) m/z 323 (M + H$^+$); $^1$H NMR (400 MHz, DMSO-d$_6$): δ 12.58 (s, 1H), 11.97 (s, 1H), 8.10 (d, J = 7.2 Hz, 1H), 7.78 (t, J = 7.2 Hz, 1H), 7.61 (d, J = 8.0 Hz, 1H), 7.56-7.50 (m, 2H), 7.47 (t, J = 6.8 Hz, 1H), 7.41 (d, J = 0.8 Hz, 1H), 7.29 (brs, 1H), 3.19-3.10 (m, 2H), 3.10-3.04 (m, 2H). |
| 65 | 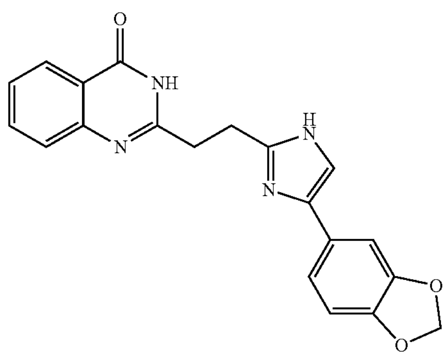 [SMILES: O=c1[nH]c(CCc2nc(-c3ccc4c(c3)OCO4)c[nH]2)nc2ccccc12] | G-1 | MS (ESI) m/z 361 (M + H$^+$); $^1$H NMR (400 MHz, CD$_3$OD): δ 8.09 (d, J = 8.0 Hz, 1H), 7.80-7.76 (m, 1H), 7.61 (d, J = 2.0 Hz, 1H), 7.47 (d, J = 8.0 Hz, 1H), 7.41 (s, 1H), 7.29-7.27 (m, 1H), 7.14-7.09 (m, 1H), 6.88-6.85 (m, 1H), 6.00 (s, 2H), 3.15-3.10 (m, 2H), 3.08-3.04 (m, 2H). |
| 66 | 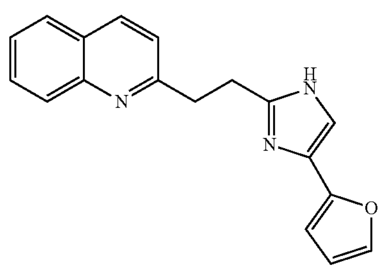 [SMILES: c1coc(-c2c[nH]c(CCc3ccc4ccccc4n3)n2)c1] | G-1 | LC-MS: m/z 290.3 (M + H$^+$); $^1$H NMR (DMSO-d$_6$): δ 8.27-8.24 (m, J = 8.4, 1H), 7.94 (dd, $^1$J = 11.6 Hz, $^2$J = 8.3 Hz, 2H), 7.73 (t, J = 8.3 Hz, 1H), 7.54 (d, J = 6.9 Hz, 1H), 7.22 (s, 1H), 6.48 (d, J = 4.9 Hz, 2H), 3.36-3.30 (m, 2H), 3.17-3.12 (m, 2H). |
| 67 | 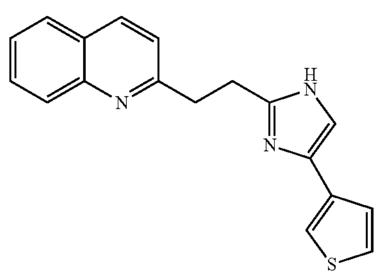 [SMILES: c1ccc2nc(CCc3nc(-c4ccsc4)c[nH]3)ccc2c1] | G-1 | LC-MS: m/z 306.4 (M + H$^+$); $^1$H NMR (DMSO-d$_6$): δ 8.27-8.24 (d, J = 8.5 Hz, 1H), 7.94 (dd, $^1$J = 12.1 Hz, $^2$J = 8.3 Hz, 2H), 7.73 (t, J = 7.0 Hz, 1H), 7.56-7.37 (m, 6H), 3.36-3.31 (m, 2H), 3.17-3.11 (m, 2H). |
| 68 | 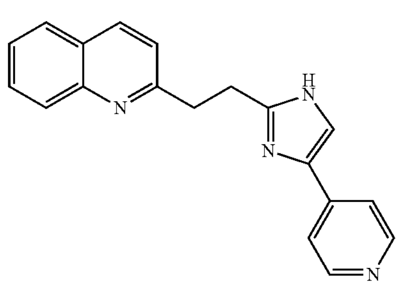 [SMILES: c1ccc2nc(CCc3nc(-c4ccncc4)c[nH]3)ccc2c1] | G-1 | LC-MS: m/z 301.4 (M + H$^+$); $^1$H NMR (CDCl$_3$): δ 8.47 (d, J = 6.2 Hz, 2H), 8.27 (d, J = 8.5 Hz, 1H), 8.01 (d, J = 8.2 Hz, 1H), 7.91 (d, J = 8.1 Hz, 1H), 7.75 (m, 3H), 7.66 (s, 1H), 7.58 (t, J = 7.0 Hz, 1H), 7.41 (d, J = 8.5 Hz, 1H), 3.46-3.42 (m, 2H), 3.27-3.24 (m, 2H). |

-continued

| Compound No. | Structure | Method of Preparation | Analytical Data |
|---|---|---|---|
| 69 | 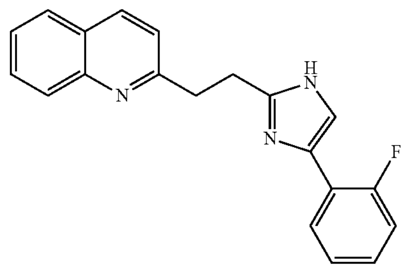 [SMILES: Fc1ccccc1-c1c[nH]c(CCc2ccc3ccccc3n2)n1] | G-1 | LC-MS: m/z 318.1 (M + H+); 1H NMR (CD3OD): δ 8.25 (d, J = 8.5 Hz, 1H), 8.03 (m, 1H), 7.91-7.83 (m, 2H), 7.75 (t, J = 8.4 Hz, 1H), 7.48 (t, J = 8.0 Hz, 1H), 7.41-7.33 (m, 2H), 7.26-7.10 (m, 3H), 3.46-3.40 (m, 2H), 3.33-3.26 (m, 2H). |
| 70 | 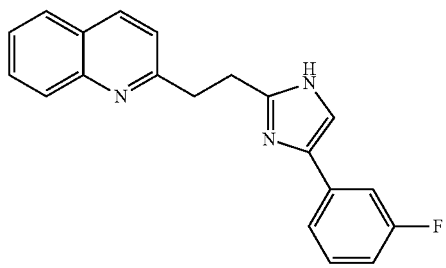 [SMILES: Fc1cccc(-c2c[nH]c(CCc3ccc4ccccc4n3)n2)c1] | G-1 | LC-MS: m/z 318.2 (M + H+); 1H NMR (CD3OD): δ 8.25 (d, J = 8.4 Hz, 1H), 8.01 (d, J = 8.5 Hz, 1H), 7.89 (d, J = 8.0, 1H), 7.75 (t, J = 8.3 Hz, 1H), 7.59-7.54 (m, 1H), 7.48-7.32 (m, 5H), 6.96 (t, J = 8.5 Hz, 1H), 3.44-3.39 (m, 2H), 3.33-3.25 (m, 2H). |
| 71 | 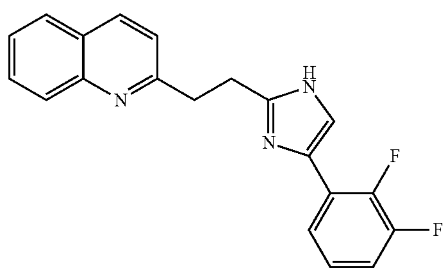 [SMILES: Fc1cccc(-c2c[nH]c(CCc3ccc4ccccc4n3)n2)c1F] | G-1 | LC-MS: m/z 336.4 (M + H+); 1H NMR (CDCl3): δ 8.15 (t, J = 7.8 Hz, 2H), 7.87-7.77 (m, 3H), 7.61-7.56 (m, 1H), 7.47 (d, J = 3.3 Hz, 1H), 7.37 (d, J = 8.5 Hz, 1H), 7.14-7.07 (m, 1H), 7.04-6.96 (m, 1H), 3.49-3.41 (m, 4H). |
| 72 | 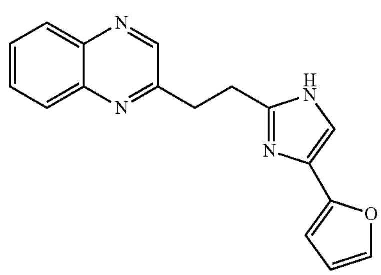 [SMILES: c1coc(-c2c[nH]c(CCc3cnc4ccccc4n3)n2)c1] | G-1 | LC-MS: m/z 291.4 (M + H+); 1H NMR (CDCl3): δ 8.81 (s, 1H), 8.15 (d, J = 7.8 Hz, 2H), 7.87-7.77 (m, 2H), 7.40 (s, 1H), 7.17 (s, 1H), 6.60 (s, 1H), 6.46 (s, 1H), 3.56-3.52 (m, 2H), 3.45-3.41 (m, 2H). |
| 73 | 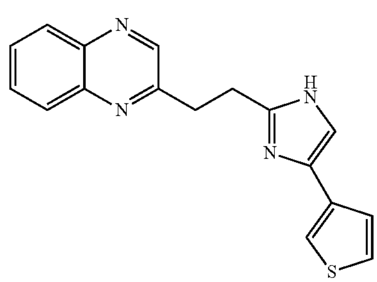 [SMILES: c1ccc2nc(CCc3nc(-c4ccsc4)c[nH]3)cnc2c1] | G-1 | LC-MS: m/z 307.1 (M + H+); 1H NMR (CDCl3): δ 8.82 (s, 1H), 8.16-8.09 (t, J = 19.0 Hz, 2H), 7.86-7.77 (m, 2H), 7.48 (s, 1H), 7.34-7.33 (m, 2H), 7.11 (s, 1H), 3.57-3.53 (m, 2H), 3.46-3.42 (m, 2H). |

| Compound No. | Structure | Method of Preparation | Analytical Data |
|---|---|---|---|
| 74 | 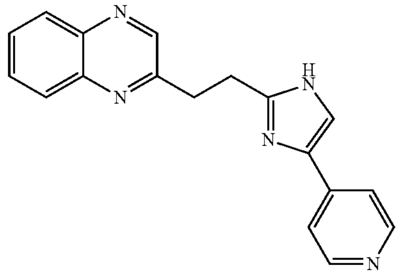 [SMILES: c1ccc2nc(CCc3nc(-c4ccncc4)c[nH]3)cnc2c1] | G-1 | LC-MS: m/z 302 (M + H$^+$); $^1$H NMR (CD$_3$OD): δ 8.78 (s, 1H), 8.50 (t, J = 6.0 Hz, 2H), 8.06 (dd, $^1$J = 6.5 Hz, $^2$J = 2.1 Hz, 2H), 7.85-7.78 (m, 5H), 3.31-3.52 (m, 2H), 3.42-3.37 (m, 2H). |
| 75 | 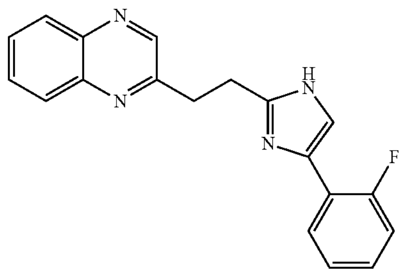 [SMILES: Fc1ccccc1-c1c[nH]c(CCc2cnc3ccccc3n2)n1] | G-1 | LC-MS: m/z 319.4 (M + H$^+$); $^1$H NMR (CDCl$_3$): δ 8.83 (s, 1H), 8.15 (t, J = 7.9 Hz, 3H), 7.87-7.76 (m, 2H), 7.42-7.41 (d, J = 2.5 Hz, 1H), 7.21-7.10 (m, 3H), 3.58-3.54 (m, 2H), 3.49-3.45 (m, 2H). |
| 76 | 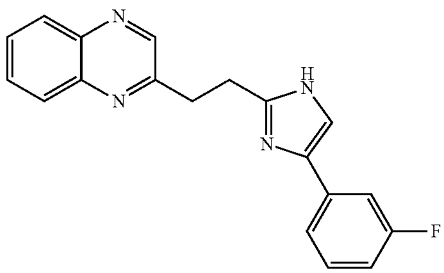 [SMILES: Fc1cccc(-c2c[nH]c(CCc3cnc4ccccc4n3)n2)c1] | G-1 | LC-MS: m/z 319.2 (M + H$^+$); $^1$H NMR (CDCl$_3$): δ 8.83 (s, 1H), 8.16-8.10 (m, 2H), 7.87-7.77 (m, 2H), 7.51 (s, 1H), 7.40-7.32 (m, 1H), 7.24 (s, 1H), 6.95-6.90 (t, J = 7.4 Hz, 1H), 3.61-3.54 (m, 2H), 3.47-3.43 (m, 2H). |
| 77 | 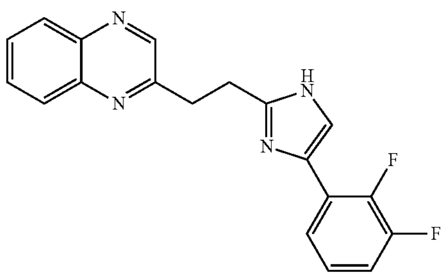 [SMILES: Fc1cccc(-c2c[nH]c(CCc3cnc4ccccc4n3)n2)c1F] | G-1 | LC-MS: m/z 337.1 (M + H$^+$); $^1$H NMR (CDCl$_3$): δ 8.84 (s, 1H), 8.14 (d, J = 6.5 Hz, 2H), 7.88-7.77 (m, 3H), 7.46 (d, J = 3.2 Hz, 1H), 7.13-7.01 (m, 2H), 3.58-3.54 (m, 2H), 3.49-3.45 (m, 2H). |
| 78 | 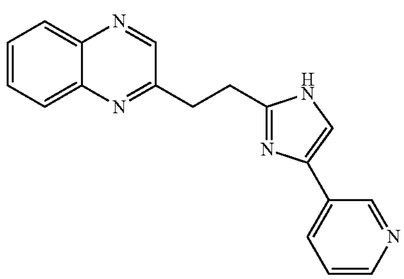 [SMILES: c1cncc(-c2c[nH]c(CCc3cnc4ccccc4n3)n2)c1] | G-1 | LC-MS: m/z 302.4 (M + H$^+$); $^1$H NMR (CDCl$_3$): δ 8.94 (s, 1H), 8.87 (s, 1H), 8.64 (d, J = 4.3 Hz, 1H), 8.24 (dd, $^1$J = 8.7 Hz, $^2$J = 1.7 Hz, 1H), 8.10-8.06 (m, 1H), 8.00-7.97 (m, 2H), 7.85-7.80 (m, 2H), 7.65 (dd, $^1$J = 8.1 Hz, $^2$J = 5.0 Hz, 1H), 3.67 (t, J = 3.5 Hz, 3H), 3.62 (s, 1H). |
| 79 | 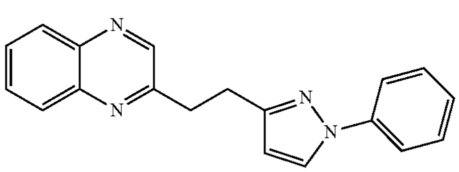 [SMILES: c1ccc(-n2ccc(CCc3cnc4ccccc4n3)n2)cc1] | H | LC-MS: m/z 301 (M + H$^+$); $^1$H NMR (CDCl$_3$): δ 8.79 (s, 1H), 8.09 (dd, $^1$J = 6.1 Hz, $^2$J = 2.0 Hz, 2H), 7.82-7.70 (m, 3H), 7.65 (d, J = 7.7 Hz, 2H), 7.44 (t, J = 7.9 Hz, 2H), 7.29-7.24 (m, 1H), 6.26-6.25 (m, 1H), 3.52-3.47 (m, 2H), 3.36-3.31 (m, 2H). |

| Compound No. | Structure | Method of Preparation | Analytical Data |
|---|---|---|---|
| 80 | 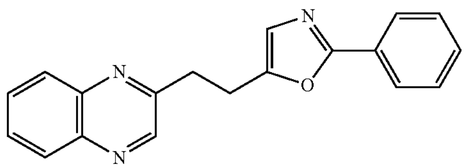 [SMILES: c1ccc(-c2ncc(CCc3cnc4ccccc4n3)o2)cc1] | I | LC-MS: m/z 302 (M + H$^+$); $^1$H NMR (CDCl$_3$): δ 8.78 (s, 1H), 8.13-8.07 (m, 2H), 7.99-7.95 (m, 2H), 7.82-7.73 (m, 2H), 7.48-7.39 (m, 3H), 6.91 (s, 1H), 3.49-3.44 (m, 2H), 3.40-3.35 (m, 2H). |
| 81 | 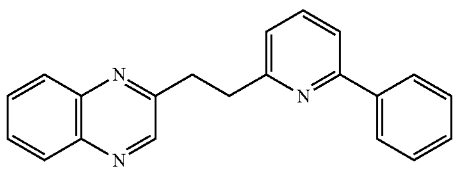 [SMILES: c1ccc(-c2cccc(CCc3cnc4ccccc4n3)n2)cc1] | J | LC-MS: m/z 312 (M + H$^+$); $^1$H NMR (CDCl$_3$): δ 8.77 (s, 1H), 8.09 (dd, $^1$J = 6.4 Hz, $^2$J = 2.0 Hz, 2H), 8.00-7.97 (m, 2H), 7.80-7.71 (m, 2H), 7.68-7.63 (m, 1H), 7.59-7.56 (m, 1H), 7.50-7.39 (m, 3H), 7.12 (d, J = 7.4 Hz, 1H), 3.65-3.60 (m, 2H), 3.50-3.45 (m, 2H). |
| 82 | 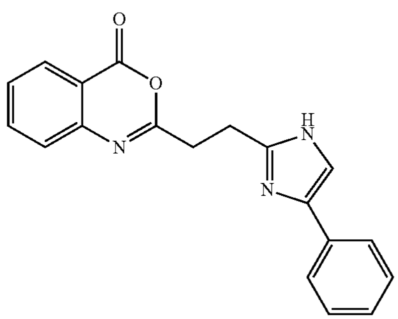 [SMILES: O=c1oc(CCc2nc(-c3ccccc3)c[nH]2)nc2ccccc12] | K | LC-MS: m/z 318 (M + H$^+$); $^1$H NMR (DMSO-d$_6$) δ 11.63 (s, 1H), 8.48 (d, J = 7.9 Hz, 1H), 7.98 (dd, $^1$J = 7.9 Hz, $^2$J = 1.5 Hz, 1H), 7.69 (d, J = 7.3 Hz, 2H), 7.59-7.48 (m, 2H), 7.33 (t, J = 7.7 Hz, 2H), 7.19 (m, 2H), 3.04-2.99 (m, 2H), 2.90-2.86 (m, 2H). |
| 83 | 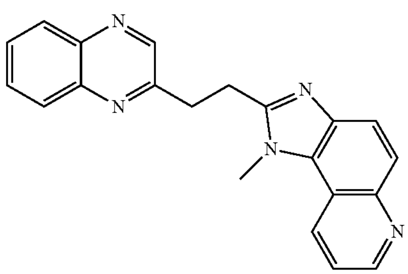 [SMILES: Cn1c(CCc2cnc3ccccc3n2)nc2ccc3ncccc3c21] | L-1 | MS (ESI): m/z 340 (M + H$^+$); HCl salt; $^1$H NMR (400 MHz, CDCl$_3$): δ 9.43 (d, J = 8.0 Hz, 1H), 9.07-9.05 (m, 1H), 8.94 (s, 1H), 8.28 (d, J = 8.0 Hz, 1H), 8.15 (d, J = 8.0 Hz, 1H), 7.74-7.72 (m, 1H), 7.68-7.64 (m, 1H), 7.30-7.22 (m, 3H), 3.80-3.77 (m, 5H), 3.54 (t, J = 7.2 Hz, 2H). |
| 84 | 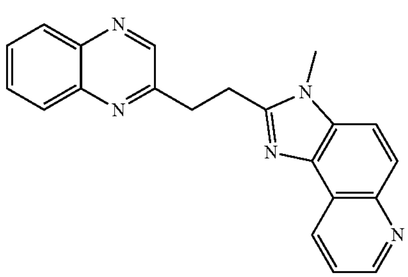 [SMILES: Cn1c(CCc2cnc3ccccc3n2)nc2c3cccnc3ccc21] | L-1 | MS (ESI): m/z 340 (M + H$^+$); HCl salt; $^1$H NMR (400 MHz, CDCl$_3$): δ 8.93-8.89 (m, 3H), 8.08-8.02 (m, 2H), 7.94 (d, J = 8.0 Hz, 1H), 7.75-7.69 (m, 2H), 7.66 (d, J = 8.0 Hz, 1H), 7.52-7.49 (m, 1H), 3.88 (s, 3H), 3.75 (t, J = 7.2 Hz, 2H), 3.60 (t, J = 7.2 Hz, 2H). |
| 85 | 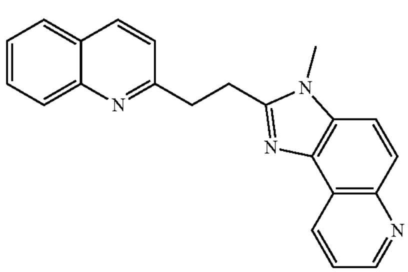 [SMILES: Cn1c(CCc2ccc3ccccc3n2)nc2c3cccnc3ccc21] | L-1 | MS (ESI): m/z 339 (M + H$^+$); HCl salt; $^1$H NMR (400 MHz, CDCl$_3$): δ 8.97-8.95 (m, 1H), 8.90 (dd, $^1$J = 3.2 Hz, $^2$J = 1.2 Hz, 1H), 8.04 (t, J = 6.8 Hz, 2H), 7.94 (d, J = 7.2 Hz, 1H), 7.78 (d, J = 7.6 Hz, 1H), 7.73-7.69 (m, 1H), 7.65 (d, J = 6.8 Hz, 1H), 7.53-7.49 (m, 2H), 7.31 (d, J = 6.8 Hz, 1H), 3.80 (s, 3H), 3.68-3.64 (m, 2H), 3.61-3.58 (m, 2H). |

-continued

| Compound No. | Structure | Method of Preparation | Analytical Data |
|---|---|---|---|
| 86 | 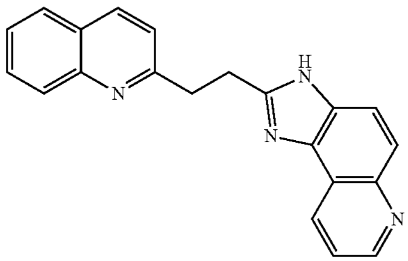 [SMILES: c1ccc2nc(CCc3nc4c(ccc5ncccc54)[nH]3)ccc2c1] | L-1 | MS (ESI): m/z 326 (M + H$^+$); HCl salt; $^1$H NMR (400 MHz, CDCl$_3$), δ 8.90-8.82 (m, 2H), 8.21 (t, J = 8.8 Hz, 2H), 7.94-7.82 (m, 4H), 7.61 (t, J = 8.0 Hz, 1H), 7.52-7.49 (m, 1H), 7.41 (d, J = 8.4 Hz, 1H), 3.66 (t, J = 4.0 Hz, 2H), 3.59 (t, J = 5.2 Hz, 2H). |
| 87 | 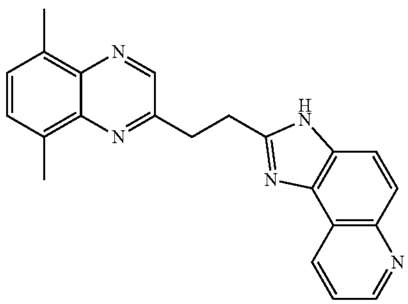 [SMILES: Cc1ccc(C)c2nc(CCc3nc4c(ccc5ncccc54)[nH]3)cnc12] | L-1 | MS (ESI): m/z 354 (M + H$^+$); HCl salt; $^1$H NMR (500 MHz, DMSO-d$_6$), δ 9.49 (d, J = 8.0 Hz, 1H), 9.17 (d, J = 4.5 Hz, 1H), 8.99 (s, 1H), 8.26-8.21 (m, 2H), 8.01 (dd, $^1$J = 8.0 Hz, $^2$J = 4.5 Hz, 1H), 7.45 (d, J = 7.5 Hz, 1H), 7.39 (d, J = 7.0 Hz, 1H), 3.97 (t, J = 7.0 Hz, 2H), 3.81 (t, J = 7.0 Hz, 2H), 2.62 (s, 3H), 2.18 (s, 3H). |
| 88 | 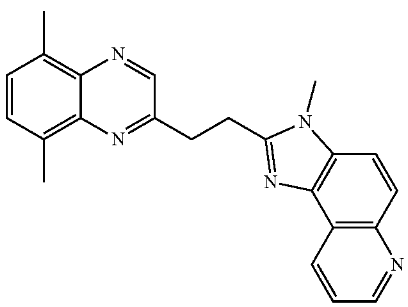 [SMILES: Cc1ccc(C)c2nc(CCc3nc4c5cccnc5ccc4n3C)cnc12] | L-1 | MS (ESI): m/z 368 (M + H$^+$); $^1$H NMR (400 MHz, CDCl$_3$): δ 8.95-8.92 (m, 1H), 8.89 (dd, $^1$J = 4.4 Hz, $^2$J = 1.6 Hz, 1H), 8.84 (s, 1H), 7.95 (d, J = 8.8 Hz, 1H), 7.67 (d, J = 9.2 Hz, 1H), 7.51 (dd, $^1$J = 8.0 Hz, $^2$J = 4.0 Hz, 1H), 7.45 (d, J = 14.0 Hz, 1H), 7.43 (d, J = 4.0 Hz, 1H), 3.87 (s, 3H), 3.76-3.72 (m, 2H), 3.65-3.61 (m, 2H), 2.73 (s, 3H), 2.70 (s, 3H). 1D NOESY: δ 3.87 and 7.67 have NOE. |
| 89 | 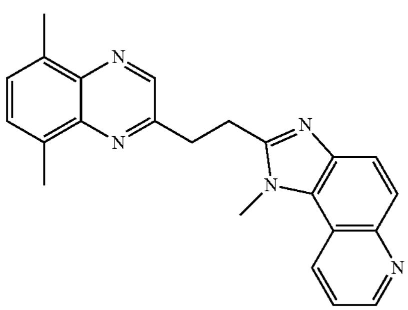 [SMILES: Cc1ccc(C)c2nc(CCc3nc4ccc5ncccc5c4n3C)cnc12] | L-1 | MS (ESI): m/z 368 (M + H$^+$); $^1$H NMR (400 MHz, CDCl$_3$): δ 8.90 (d, J = 3.2 Hz, 1H), 8.84 (s, 1H), 8.70 (d, J = 8.0 Hz, 1H), 8.08 (d, J = 8.8 Hz, 1H), 7.96 (d, J = 8.8 Hz, 1H), 7.49-7.44 (m, 3H), 4.23 (s, 3H), 3.78-3.74 (m, 2H), 3.65-3.61 (m, 2H), 2.73 (s, 3H), 2.71 (s, 3H). 1D NOESY: δ 8.70 and 4.23 have NOE. |
| 90 | 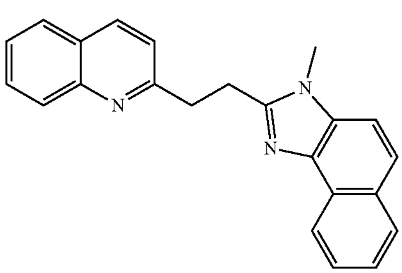 [SMILES: Cn1c(CCc2ccc3ccccc3n2)nc2c3ccccc3ccc21] | L-1 | MS (ESI): m/z 338 (M + H$^+$); $^1$H NMR (400 MHz, CDCl$_3$): δ 8.66 (d, J = 8.0 Hz, 1H), 8.06 (d, J = 8.4 Hz, 1H), 8.01 (d, J = 8.8 Hz, 1H), 7.92 (d, J = 8.0 Hz, 1H), 7.77 (d, J = 8.0 Hz, 1H), 7.72-7.68 (m, 1H), 7.66-7.60 (m, 2H), 7.52-7.44 (m, 2H), 7.40 (d, J = 8.8 Hz, 1H), 7.31 (d, J = 8.4 Hz, 1H), 3.74 (s, 3H), 3.67-3.63 (m, 2H), 3.59-3.55 (m, 2H). |

-continued

| Compound No. | Structure | Method of Preparation | Analytical Data |
|---|---|---|---|
| 91 | 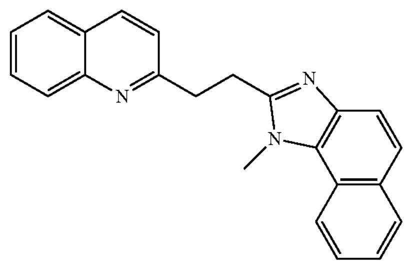 [SMILES: Cn1c(CCc2ccc3ccccc3n2)nc2ccc3ccccc3c21] | L-1 | MS (ESI): m/z 338 (M + H$^+$); $^1$H NMR (400 MHz, CDCl$_3$): δ 8.38 (d, J = 8.4 Hz, 1H), 8.06 (d, J = 8.0 Hz, 1H), 8.05 (d, J = 8.0 Hz, 1H), 7.99 (d, J = 8.0 Hz, 1H), 7.86 (d, J = 8.8 Hz, 1H), 7.78 (d, J = 8.0 Hz, 1H), 7.73-7.66 (m, 2H), 7.57-7.44 (m, 3H), 7.33 (d, J = 8.4 Hz, 1H), 4.19 (s, 3H), 3.70-3.66 (m, 2H), 3.61-3.57 (m, 2H). |
| 92 | 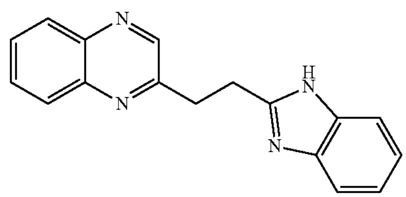 [SMILES: c1ccc2nc(CCc3nc4ccccc4[nH]3)cnc2c1] | L-2 | LC-MS: m/z 275 (M + H$^+$); HCl salt; $^1$H NMR (CD$_3$OD): δ 8.94 (s, 1H), 8.03-8.01 (m, 1H), 7.83-7.75 (m, 3H), 7.69-7.67 (m, 2H), 7.51-7.49 (m, 2H), 3.78 (s, 4H). |
| 93 | 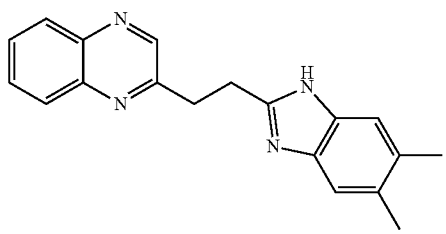 [SMILES: Cc1cc2nc(CCc3cnc4ccccc4n3)[nH]c2cc1C] | L-2 | MS (ESI): m/z 303.2 (M + H$^+$); HCl salt; $^1$H NMR (400 MHz, CDCl$_3$): δ 7.80 (s, 1H), 8.11 (m, 2H), 7.79 (m, 2H), 7.32 (s, 2H), 3.60 (m, 2H), 3.54 (m, 2H), 2.34 (s, 6H). |
| 94 | 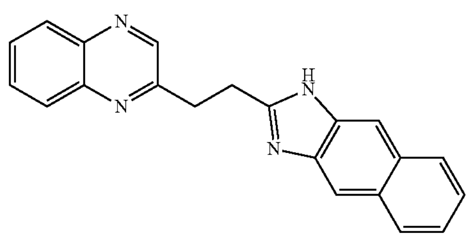 [SMILES: c1ccc2cc3[nH]c(CCc4cnc5ccccc5n4)nc3cc2c1] | L-2 | MS (ESI): m/z 325.1 (M + H$^+$); HCl salt; $^1$H NMR (400 MHz, CDCl$_3$): δ 8.85 (s, 1H), 8.14 (m, 2H), 7.99 (s, 2H), 7.94 (m, 2H), 7.80 (m, 2H), 7.40 (m, 2H), 3.66 (m, 4H). |
| 95 | 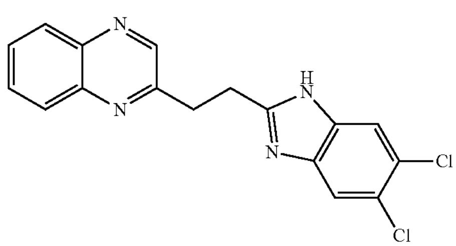 [SMILES: Clc1cc2nc(CCc3cnc4ccccc4n3)[nH]c2cc1Cl] | L-2 | MS (ESI): m/z 343.0 (M + H$^+$); HCl salt; $^1$H NMR (400 MHz, CDCl$_3$): δ 8.79 (s, 1H), 8.19 (d, J = 12.4 Hz, 2H), 7.52 (m, 2H), 7.22 (m, 2H), 3.60 (m, 2H), 3.48 (m, 2H). |
| 96 | 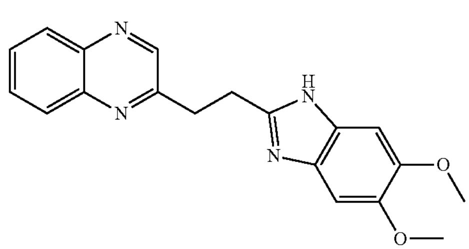 [SMILES: COc1cc2nc(CCc3cnc4ccccc4n3)[nH]c2cc1OC] | L-2 | MS (ESI): m/z 335.0 (M + H$^+$); HCl salt; $^1$H NMR (400 MHz, CDCl$_3$): δ 8.61 (s, 1H), 7.59 (s, 2H), 7.32 (d, J = 13.2 Hz, 2H), 7.23 (m, 2H), 4.09 (s, 3H), 4.06 (s, 3H), 3.54 (s, 4H). |

| Compound No. | Structure | Method of Preparation | Analytical Data |
|---|---|---|---|
| 97 | 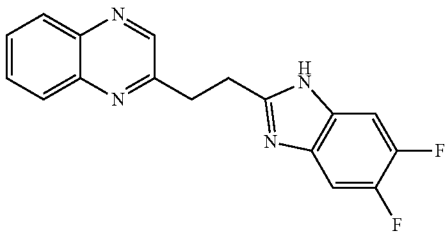 [SMILES: Fc1cc2nc(CCc3cnc4ccccc4n3)[nH]c2cc1F] | L-2 | MS (ESI): m/z 311.0 (M + H+); HCl salt; ¹H NMR (400 MHz, CDCl₃): δ 8.78 (s, 1H), 7.83 (m, 2H), 7.55 (m, 2H), 7.23 (m, 2H), 3.64 (m, 2H), 3.56 (m, 2H). |
| 98 | 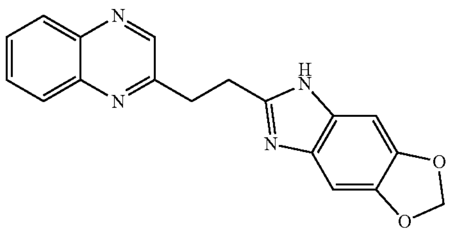 [SMILES: c1ccc2nc(CCc3nc4cc5c(cc4[nH]3)OCO5)cnc2c1] | L-2 | MS (ESI): m/z 319.1 (M + H+); HCl salt; ¹H NMR (400 MHz, CDCl₃): δ 8.78 (s, 1H), 7.83 (m, 2H), 7.55 (m, 2H), 7.23 (m, 2H), 6.20 (s, 2H), 3.64 (m, 2H), 3.56 (m, 2H). |
| 99 | 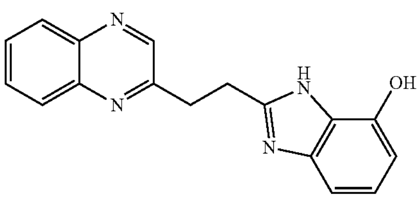 [SMILES: Oc1cccc2nc(CCc3cnc4ccccc4n3)[nH]c12] | L-2 | MS (ESI): m/z 291.1 (M + H+); HCl salt; ¹H NMR (400 MHz, CDCl₃): δ 8.81 (s, 1H), 8.09 (m, 2H), 7.81 (m, 2H), 7.05 (m, 2H), 6.69 (d, J = 8.4 Hz, 1H), 3.59 (m, 2H), 3.44 (m, 2H). |
| 100 | 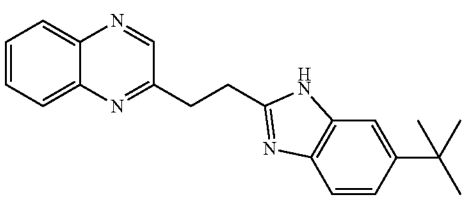 [SMILES: CC(C)(C)c1ccc2nc(CCc3cnc4ccccc4n3)[nH]c2c1] | L-2 | MS (ESI): m/z 331.2 (M + H+); HCl salt; ¹H NMR (400 MHz, CDCl₃): δ 8.81 (s, 1H), 8.12 (m, 2H), 7.81 (m, 2H), 7.50 (m, 2H), 7.31 (m, 1H), 3.61 (m, 4H), 1.37 (m, 9H). |
| 101 | 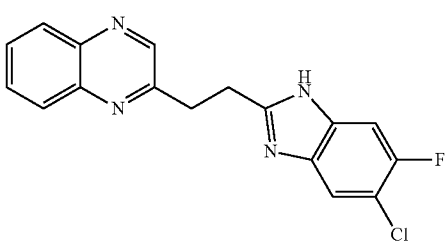 | L-2 | MS (ESI): m/z 327.0 (M + H+); HCl salt; ¹H NMR (400 MHz, CD₃OD): δ 8.76 (s, 1H), 8.00 (m, 2H), 7.77 (m, 2H), 7.51 (d, J = 6.8 Hz, 1H), 7.30 (d, J = 11.2 Hz, 1H), 3.59 (t, J = 7.2 Hz, 2H), 3.48 (t, J = 7.2 Hz, 2H). |
| 102 | 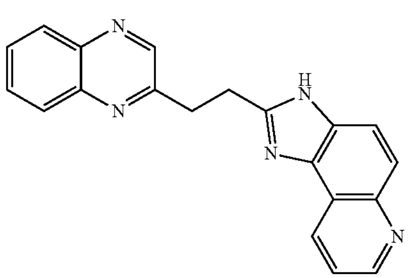 [SMILES: c1ccc2nc(CCc3nc4c(ccc5ncccc54)[nH]3)cnc2c1] | L-2 | MS (ESI): m/z 326.1 (M + H+); HCl salt; ¹H NMR (400 MHz, CDCl₃): δ 8.91 (m, 2H), 8.87 (s, 1H), 8.17 (m, 2H), 7.93 (d, J = 9.2 Hz, 1H), 7.85 (m, 3H), 7.52 (m, 1H), 3.68 (m, 4H). |

| Compound No. | Structure | Method of Preparation | Analytical Data |
|---|---|---|---|
| 103 | 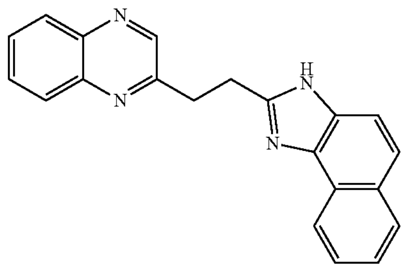 [SMILES: c1ccc2c(c1)ccc1[nH]c(CCc3cnc4ccccc4n3)nc12] | L-2 | MS (ESI): m/z 325.1 (M + H⁺); HCl salt; ¹H NMR (400 MHz, CDCl₃): δ 8.70 (s, 1H), 8.36 (d, J = 8.0 Hz, 1H), 8.04 (d, J = 7.6 Hz, 1H), 7.92 (d, J = 8.0 Hz, 1H), 7.72 (m, 4H), 7.52 (t, J = 8.0 Hz, 1H), 7.44 (t, J = 8.0 Hz, 1H), 3.60 (m, 4H). |
| 104 | 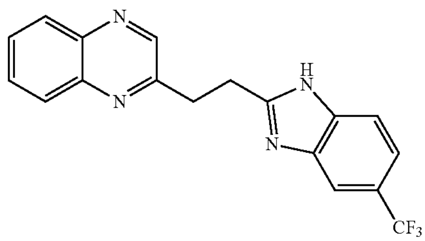 [SMILES: FC(F)(F)c1ccc2[nH]c(CCc3cnc4ccccc4n3)nc2c1] | L-2 | MS (ESI): m/z 343.1 (M + H⁺); HCl salt; ¹H NMR (400 MHz, CDCl₃): δ 8.91 (m, 1H), 8.41 (d, J = 12.4 Hz, 1H), 8.23 (t, J = 9.2 Hz, 1H), 7.93 (m, 1H), 7.58 (s, 2H), 7.23 (m, 2H), 3.70 (t, J = 6.8 Hz, 2H), 3.58 (t, J = 6.8 Hz, 2H). |
| 105 | 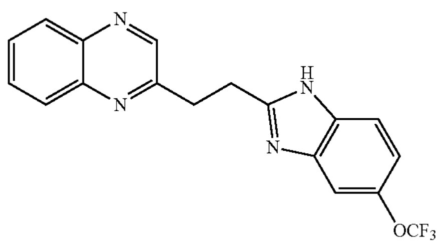 [SMILES: FC(F)(F)Oc1ccc2[nH]c(CCc3cnc4ccccc4n3)nc2c1] | L-2 | MS (ESI): m/z 359.1 (M + H⁺); HCl salt; ¹H NMR (400 MHz, DMSO-d₆): δ 12.32 (s, 1H), 9.00 (d, J = 7.6 Hz, 1H), 8.20 (m, 1H), 8.03 (m, 1H), 7.80 (m, 1H), 7.45 (s, 2H), 7.11 (m, 2H), 3.60 (t, J = 6.4 Hz, 2H), 3.43 (t, J = 6.4 Hz, 2H). |
| 106 | 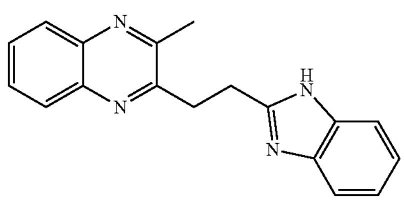 [SMILES: Cc1nc2ccccc2nc1CCc1nc2ccccc2[nH]1] | #21 | LC-MS: m/z 289 (M + H⁺); ¹H NMR (CD₃OD): δ 7.96-7.92 (m, 2H), 7.72-7.68 (m, 2H), 7.51-7.49 (m, 2H), 7.18-7.16 (m, 2H), 3.57 (s, 4H), 2.71 (s, 3H). |
| 107 | 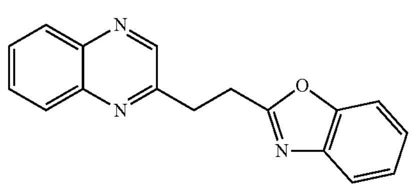 [SMILES: c1ccc2nc(CCc3nc4ccccc4o3)cnc2c1] | M | MS (ESI): m/z 276 (M + H⁺); ¹H NMR (400 MHz, CDCl₃): δ 8.86 (s, 1H), 8.12-8.04 (m, 2H), 7.78-7.68 (m, 3H), 7.52-7.49 (m, 1H), 7.34-7.32 (m, 2H), 3.71-3.60 (m, 4H). |
| 108 | 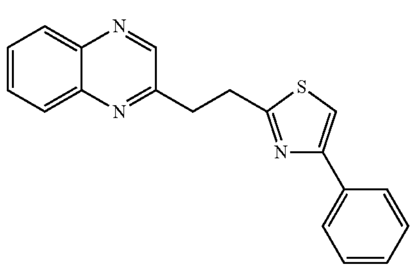 [SMILES: c1ccc(-c2csc(CCc3cnc4ccccc4n3)n2)cc1] | M | MS (ESI): m/z 318 (M + H⁺); ¹H NMR (400 MHz, CDCl₃): δ 8.80 (s, 1H), 8.10-8.07 (m, 2H), 7.87-7.86 (m, 2H), 7.78-7.72 (m, 2H), 7.43-7.40 (m, 2H), 7.34-7.31 (m, 2H), 3.69 (t, J = 5.8 Hz, 2H), 3.61 (t, J = 5.8 Hz, 2H). |

-continued

| Compound No. | Structure | Method of Preparation | Analytical Data |
| --- | --- | --- | --- |
| 109 | 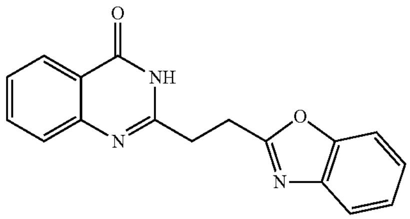 [SMILES: O=c1[nH]c(CCc2nc3ccccc3o2)nc2ccccc12] | M | MS (ESI): m/z 292 (M + H⁺); ¹H NMR (400 MHz, DMSO-d₆): δ 8.06 (d, J = 6.0 Hz, 1H), 7.67 (m, 3H), 7.50 (d, J = 6.0 Hz, 1H), 7.41 (t, J = 5.4 Hz, 1H), 7.35 (m, 2H), 3.40 (t, J = 5.7 Hz, 2H), 3.20 (t, J = 5.7 Hz, 2H). |
| 110 | 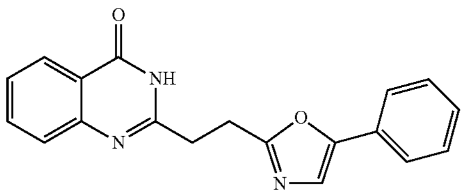 [SMILES: O=c1[nH]c(CCc2ncc(-c3ccccc3)o2)nc2ccccc12] | M | MS (ESI): m/z 318 (M + H⁺); ¹H NMR (400 MHz, DMSO-d₆): δ 8.07 (d, J = 5.7 Hz, 1H), 7.71 (t, J = 6.0 Hz, 1H), 7.57 (d, J = 5.7 Hz, 2H), 7.53 (d, J = 6.0 Hz, 1H), 7.37 (m, 4H), 7.27 (t, J = 5.4 Hz, 1H), 3.32 (t, J = 5.6 Hz, 2H), 3.15 (t, J = 5.6 Hz, 2H). |
| 111 | 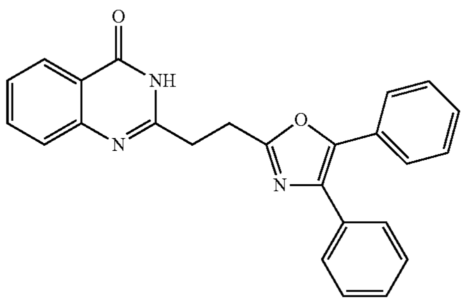 [SMILES: O=c1[nH]c(CCc2nc(-c3ccccc3)c(-c3ccccc3)o2)nc2ccccc12] | M | MS (ESI): m/z 394 (M + H⁺); ¹H NMR (400 MHz, DMSO-d₆): δ 8.09 (m, 1H), 7.78 (m, 1H), 7.60 (d, J = 8.0 Hz, 1H), 7.53 (m, 2H), 7.47 (m, 3H), 7.36 (m, 6H), 3.16 (m, 2H), 3.37 (m, 2H). |
| 112 | 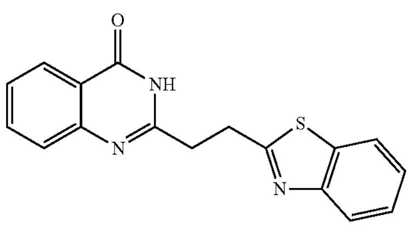 [SMILES: O=c1[nH]c(CCc2nc3ccccc3s2)nc2ccccc12] | M | MS (ESI): m/z 308 (M + H⁺), ¹H NMR (400 MHz, CDCl₃): δ 8.09 (d, J = 9.2 Hz, 1H), 8.04 (d, J = 7.6 Hz, 1H), 7.93 (d, J = 8.0 Hz, 1H), 7.80-7.75 (m, 1H), 7.62-7.59 (d, J = 8.0 Hz, 1H), 7.49-7.45 (m, 2H), 7.41-7.37 (m, 1H), 3.63 (t, J = 7.2 Hz, 2H), 3.22 (t, J = 7.2 Hz, 2H). |
| 113 | 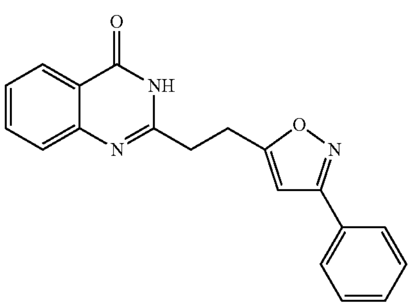 [SMILES: O=c1[nH]c(CCc2cc(-c3ccccc3)no2)nc2ccccc12] | M | MS (ESI): m/z 318 (M + H⁺); ¹H NMR (400 MHz, CDCl₃): δ 8.10 (d, J = 7.6 Hz, 1H), 7.84-7.76 (m, 3H), 7.62 (d, J = 7.6 Hz, 1H), 7.50-7.46 (m, 4H), 6.86 (s, 1H), 3.34-3.32 (m, 2H), 3.10-3.06 (t, J = 8.4 Hz, 2H). |
| 114 | 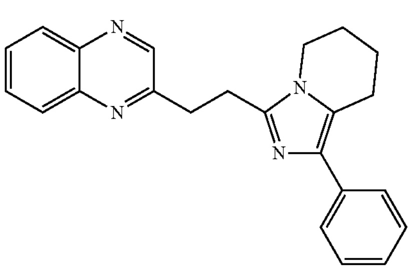 [SMILES: c1ccc(-c2nc(CCc3cnc4ccccc4n3)n3c2CCCC3)cc1] | M | MS (ESI): m/z 355 (M + H⁺); ¹H NMR (400 MHz, CDCl₃): δ 8.86 (s, 1H), 8.09-8.07 (m, 1H), 8.03 (m, 1H), 7.76-7.66 (m, 4H), 7.39-7.36 (m, 2H), 7.22-7.19 (m, 1H), 3.90 (t, J = 5.2 Hz, 2H), 3.61 (t, J = 6.0 Hz, 2H), 3.29 (t, J = 6.4 Hz, 2H), 2.96 (t, J = 5.2 Hz, 2H), 1.95-1.93 (m, 2H), 1.83-1.80 (m, 2H). |

-continued

| Compound No. | Structure | Method of Preparation | Analytical Data |
|---|---|---|---|
| 115 | 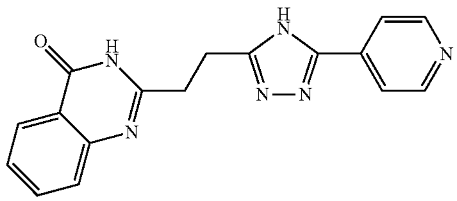 [SMILES: O=c1[nH]c(CCc2nnc(-c3ccncc3)[nH]2)nc2ccccc12] | M | MS (ESI): m/z 318 (M + H$^+$); $^1$H NMR (400 MHz, DMSO-d$_6$) δ 8.66-8.65 (m, 2H), 8.09 (d, J = 8.0 Hz, 1H), 7.87-7.88 (m, 2H), 7.79 (t, J = 8.0 Hz, 1H), 7.59 (d, J = 8.0 Hz, 1H), 7.47 (t, J = 8.0 Hz, 1H), 3.28 (t, J = 6.0 Hz, 2H), 3.13 (t, J = 6.0 Hz, 2H). |
| 116 | 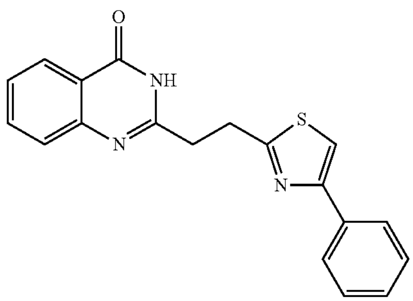 [SMILES: O=c1[nH]c(CCc2nc(-c3ccccc3)cs2)nc2ccccc12] | M | MS (ESI): m/z 334 (M + H$^+$); $^1$H NMR (400 MHz, CDCl$_3$): δ 8.31 (d, J = 8.4 Hz, 1H), 8.01 (d, J = 7.6 Hz, 2H), 7.79-7.71 (m, 2H), 7.51-7.47 (m, 3H), 7.46-7.26 (m, 2H), 3.59-3.56 (m, 2H), 3.37-3.34 (m, 2H). |
| 117 | 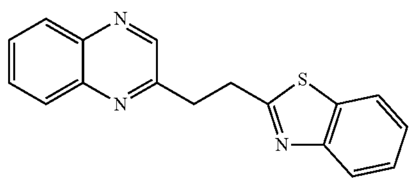 [SMILES: c1ccc2nc(CCc3nc4ccccc4s3)cnc2c1] | #15 | MS (ESI): m/z 292 (M + H$^+$); $^1$H NMR (400 MHz, CDCl$_3$): δ 8.81 (s, 1H), 8.10-8.06 (m, 2H), 7.99-7.96 (m, 1H), 7.83-7.72 (m, 3H), 7.48-7.44 (m, 1H), 7.37-7.33 (m, 1H), 3.79-3.75 (m, 2H), 3.68-3.64 (m, 2H). |
| 118 | 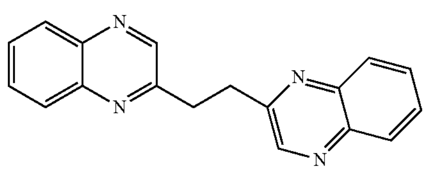 [SMILES: c1ccc2nc(CCc3cnc4ccccc4n3)cnc2c1] | #16 | MS (ESI): m/z 287.1 (M + H$^+$); $^1$H NMR (400 MHz, CDCl$_3$): δ 8.84 (s, 2H), 8.05 (m, 4H), 7.73 (m, 4H), 3.68 (s, 4H). |
| 119 | 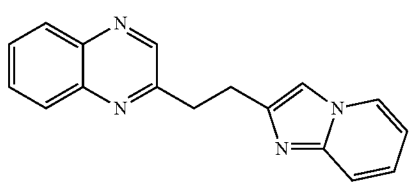 [SMILES: c1ccc2nc(CCc3cn4ccccc4n3)cnc2c1] | #17 | MS (ESI) m/z 275.0 (M + H$^+$); $^1$H NMR (400 MHz, CD$_3$OD): δ 8.68 (s, 1H), 8.23 (m, 1H), 8.00 (m, 2H), 7.75 (m, 2H), 7.53 (s, 1H), 7.42 (m, 1H), 7.21 (m, 1H), 6.79 (m, 1H), 3.46 (m, 2H), 3.31 (m, 2H). |
| 120 | 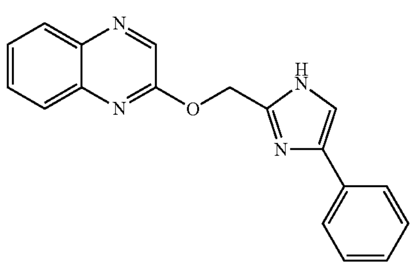 [SMILES: c1ccc(-c2c[nH]c(COc3cnc4ccccc4n3)n2)cc1] | #18 | LC-MS: m/z 303 (M + H$^+$); $^1$H NMR (CDCl$_3$): δ 8.38 (d, J = 2.6 Hz, 1H), 7.99 (d, J = 8.1 Hz, 1H), 7.81 (d, J = 8.1 Hz, 1H), 7.70-7.56 (m, 4H), 7.35-7.20 (m, 4H), 5.58 (d, J = 2.6 Hz, 2H). |
| 121 | 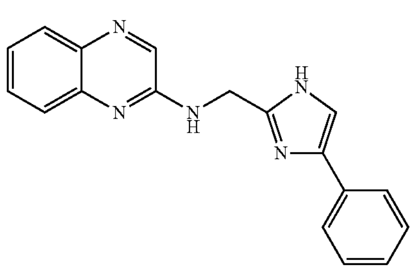 [SMILES: c1ccc(-c2c[nH]c(CNc3cnc4ccccc4n3)n2)cc1] | #20 | LC-MS: m/z 302 (M + H$^+$); $^1$H NMR (CDCl$_3$): δ 8.25 (s, 1H), 7.91 (d, J = 8.1 Hz, 1H), 7.77 (d, J = 8.4 Hz, 1H), 7.67-7.62 (m, 3H), 7.46-7.42 (m, 1H), 7.37-7.33 (m, 2H), 7.25-7.22 (m, 2H), 4.78 (d, J = 5.1 Hz, 2H). |

| Compound No. | Structure | Method of Preparation | Analytical Data |
|---|---|---|---|
| 122 | 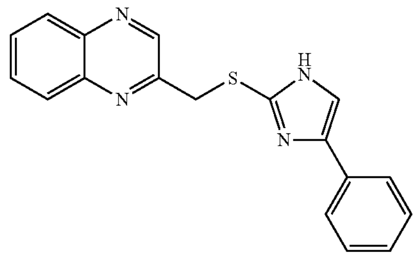 [SMILES: c1ccc(-c2c[nH]c(SCc3cnc4ccccc4n3)n2)cc1] | #22 | ¹H NMR (CD₃OD): δ 9.18 (s, 1H), 9.04 (s, 1H), 8.07-8.02 (m, 2H), 7.81-7.78 (m, 2H), 7.73-7.71 (m, 2H), 7.33-7.29 (m, 2H), 7.25-7.23 (m, 1H), 5.65 (s, 2H). |
| 123 | 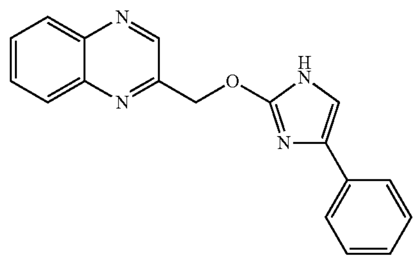 [SMILES: c1ccc(-c2c[nH]c(OCc3cnc4ccccc4n3)n2)cc1] | #22 | ¹H NMR (CD₃OD): δ 8.99-8.98 (m, 1H), 8.09-8.08 (m, 2H), 7.84-7.82 (m, 2H), 7.71-7.69 (m, 1H), 7.63-7.61 (m, 1H), 7.55-7.53 (m, 1H), 7.44-7.23 (m, 3H), 5.23 (d, J = 4.0 Hz, 1H), 4.91-4.90 (m, 1H). |
| 124 | 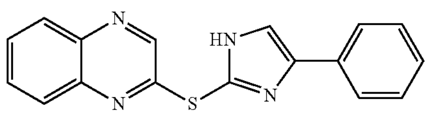 [SMILES: c1ccc(-c2c[nH]c(Sc3cnc4ccccc4n3)n2)cc1] | #19 | LC-MS: m/z 305 (M + H⁺); ¹H NMR (CDCl₃): δ 8.56 (s, 1H), 8.00-7.98 (m, 1H), 7.87 (d, J = 8.1 Hz, 1H), 7.72-7.63 (m, 4H), 7.50 (s, 1H), 7.39-7.34 (m, 2H), 7.32-7.24 (m, 1H). |

Compounds 127 to 142 were prepared following the exemplary procedures for the synthesis of Compounds 125 and 126, except using suitable carbaldehydes as starting materials. Unless otherwise specified, these compounds were prepared as a free base. Suitable salts of these compounds may be prepared using suitable acids and methods known to those of skill in the art, for example, as exemplified for Compounds 125 and 126.

| Compound Number | Structure | Analytical Data |
|---|---|---|
| 125 | 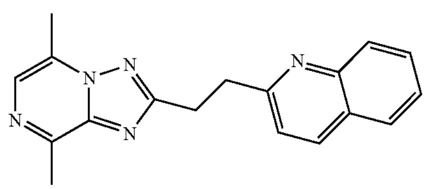 [SMILES: Cc1ncc(C)n2nc(CCc3ccc4ccccc4n3)nc12] | MS (ESI) m/z: 304.1 (M + H)⁺; HCl salt; ¹H NMR (400 MHz, CDCl₃): δ 8.06 (t, J = 9.2 Hz, 2H), 7.82 (d, J = 0.8 Hz, 1H), 7.78 (dd, ¹J = 8.0 Hz, ²J = 0.8 Hz, 1H), 7.69 (ddd, ¹J = 8.4 Hz, ²J = 7.2 Hz, ³J = 1.6 Hz, 1H), 7.50 (ddd, ¹J = 8.4 Hz, ²J = 6.8 Hz, ³J = 0.8 Hz, 1H), 7.38 d, J = 8.8 Hz, 1H), 3.61-3.58 (m, 4H), 2.88 (s, 3H), 2.69 (s, 3H). |
| 126 | 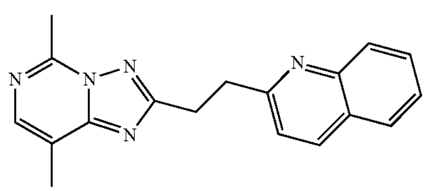 [SMILES: Cc1cnc(C)n2nc(CCc3ccc4ccccc4n3)nc12] | MS (ESI) m/z: 304.2 (M + H)⁺; HCl salt; ¹H NMR (400 MHz, DMSO-d₆): δ 8.28 (d, J = 8.4 Hz, 1H), 8.01 (s, 1H), 7.95 (t, J = 8.4 Hz, 2H), 7.73 (dt, ¹J = 8.4 Hz, ²J = 0.8 Hz, 1H), 7.58-7.53 (m, 2H), 3.50-3.33 (m, 4H), 2.81 (s, 3H), 2.44 (s, 3H). |
| 127 | 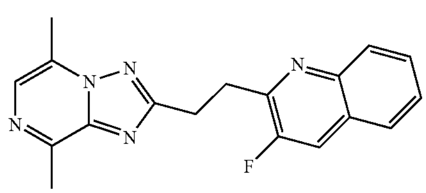 [SMILES: Cc1ncc(C)n2nc(CCc3nc4ccccc4cc3F)nc12] | MS (ESI) m/z: 322.1 (M + H)⁺; ¹H NMR (400 MHz, CDCl₃): δ 8.06 (d, J = 8.4 Hz, 1H), 7.82 (m, 1H), 7.77-7.71 (m, 2H), 7.63 (m, 1H), 7.54 (m, 1H), 3.63 (m, 4H), 2.87 (s, 3H), 2.68 (s, 3H). |

-continued

| Compound Number | Structure | Analytical Data |
|---|---|---|
| 128 | 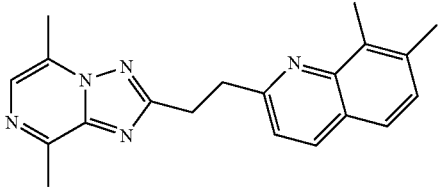 [SMILES: Cc1ccc2ccc(CCc3nc4c(C)ncc(C)n4n3)nc2c1C] | MS (ESI) m/z 332.1 (M + H)+; 1H NMR (400 MHz, CDCl3): δ 7.99-7.98 (d, J = 7.6 Hz, 1H), 7.82 (s, 1H), 7.54-7.52 (d, J = 8.0 Hz, 1H), 7.30 (m, 2H), 3.65 (m, 4H), 2.89 (s, 3 H), 2.73 (s, 3H), 2.71 (s, 3H), 2.49 (s, 3H). |
| 129 | 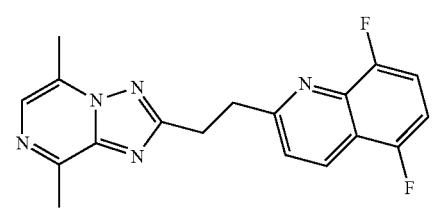 [SMILES: Cc1ncc(C)n2nc(CCc3ccc4c(F)ccc(F)c4n3)nc12] | MS (ESI) m/z 340.1 (M + H)+; 1H NMR (400 MHz, CDCl3): δ 8.34-8.31 (m, 1H), 7.83 (s, 1H), 7.52-7.50 (d, J = 8.8 Hz, 1H), 7.30 (m, 1H), 7.09 (m, 1 H), 3.67-3.58 (m, 4H), 2.88 (s, 3H), 2.69 (s, 3 H). |
| 130 | 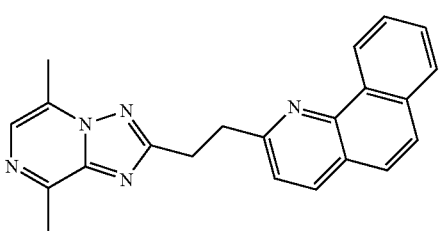 [SMILES: Cc1ncc(C)n2nc(CCc3ccc4ccc5ccccc5c4n3)nc12] | MS (ESI) m/z 354.2 (M + H)+; 1H NMR (400 MHz, CDCl3): δ 9.34 (m, 1H), 8.09 (m, 1H), 7.88 (m, 1H), 7.87 (s, 1H), 7.75 (s, 1H), 7.69 (m, 2H), 7.48 (m, 1H), 7.26 (m, 1H), 3.72 (m, 4H), 2.90 (s, 3H), 2.71 (s, 3H). |
| 131 | 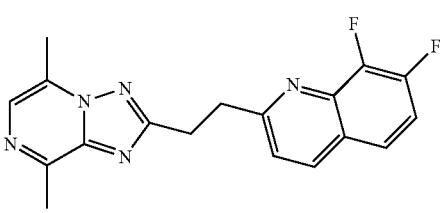 [SMILES: Cc1ncc(C)n2nc(CCc3ccc4ccc(F)c(F)c4n3)nc12] | MS (ESI) m/z 340.1 (M + H)+; 1H NMR (400 MHz, CDCl3): δ 8.08-8.05 (d, J = 8.8 Hz, 1H), 7.83 (s, 1H), 7.53 (m, 1H), 7.42-7.36 (m, 2H), 3.66-3.59 (m, 4H), 2.88 (s, 3H), 2.70 (s, 3H). |
| 132 | 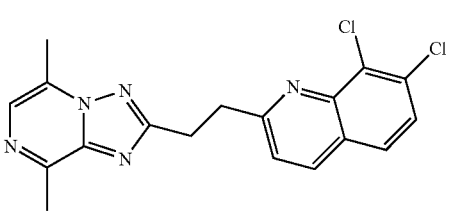 [SMILES: Cc1ncc(C)n2nc(CCc3ccc4ccc(Cl)c(Cl)c4n3)nc12] | MS (ESI) m/z: 372.1 (M + H)+; 1H NMR (400 MHz, CDCl3): δ 8.07 (d, J = 8.4 Hz, 1H), 7.83 (s, 1H), 7.65 (d, J = 8.8 Hz, 1H), 7.52 (d, J = 8.8 Hz, 1H), 7.45 (d, J = 8.4 Hz, 1H), 3.66 (m, 4 H), 2.89 (s, 3H), 2.70 (s, 3H). |
| 133 | 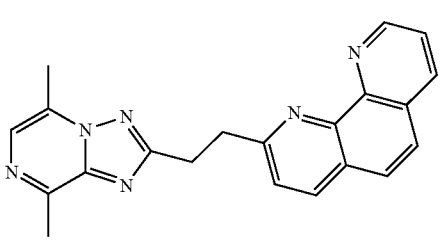 [SMILES: Cc1ncc(C)n2nc(CCc3ccc4ccc5cccnc5c4n3)nc12] | MS (ESI) m/z: 355.2 (M + H)+; 1H NMR (400 MHz, CDCl3): δ 9.25 (dd, 1J = 4.4 Hz, 2J = 1.2 Hz, 1H), 8.28 (dd, 1J = 8.0 Hz, 2J = 1.2 Hz, 1H), 8.19 (d, J = 8.0 Hz, 1H), 7.79 (m, 3H), 7.65 (m, 2H), 3.84 (m, 2H), 3.66 (m, 2H), 2.88 (s, 3H), 2.70 (s, 3H). |
| 134 | 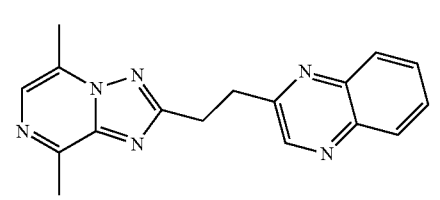 [SMILES: Cc1ncc(C)n2nc(CCc3cnc4ccccc4n3)nc12] | MS (ESI): m/z 305 (M + H)+; 1H NMR (400 MHz, CDCl3): δ 8.82 (s, 1H), 8.08-8.04 (m, 2H), 7.82 (d, J = 0.4 Hz, 1H), 7.77-7.69 (m, 2H), 3.67-3.62 (m, 4H), 2.87 (s, 3H), 2.67 (s, 3H). |

-continued

| Compound Number | Structure | Analytical Data |
|---|---|---|
| 135 | 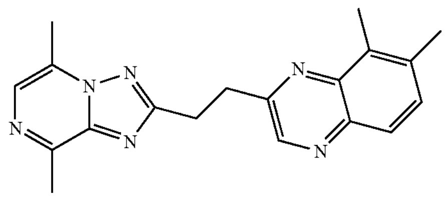 [SMILES: Cc1ccc2ncc(CCc3nc4c(C)ncc(C)n4n3)nc2c1C] | MS (ESI) m/z 333.2 (M + H)+; 1H NMR (400 MHz, DMSO-d6): δ 8.86 (s, 1H), 7.94 (s, 1H), 7.78 (d, J = 8.4 Hz, 1H), 7.61 (d, J = 8.8 Hz, 1H), 3.57-3.50 (m, 4H), 2.72 (s, 3H), 2.61 (s, 3H), 2.58 (s, 3H), 2.46 (s, 3H). |
| 136 | 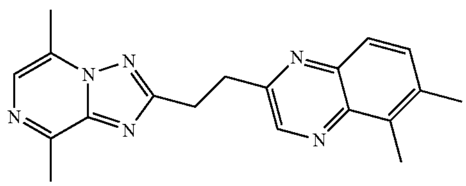 [SMILES: Cc1ccc2nc(CCc3nc4c(C)ncc(C)n4n3)cnc2c1C] | MS (ESI) m/z 333.2 (M + H)+; 1H NMR (400 MHz, CDCl3): δ 8.93 (s, 1 H), 7.97 (s, 1 H), 7.78 (d, J = 8.4 Hz, 1 H), 7.67 (d, J = 8.8 Hz, 1 H), 3.54-3.49 (m, 4 H), 2.74 (s, 3 H), 2.67 (s, 3 H), 2.63 (s, 3 H), 2.48 (s, 3 H). |
| 137 | 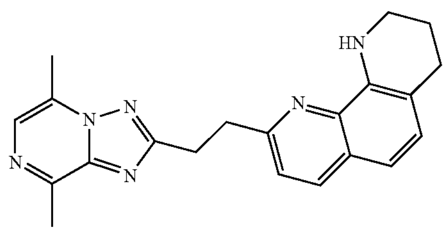 [SMILES: Cc1ncc(C)n2nc(CCc3ccc4ccc5c(c4n3)NCCC5)nc12] | MS (ESI): m/z: 359.2 (M + H)+; 1H NMR (400 MHz, CDCl3): δ 8.45 (d, J = 8.8 Hz, 1H), 8.05 (d, J = 0.8 Hz, 1H), 7.82 (d, J = 8.4 Hz, 1H), 7.71 (d, J = 8.8 Hz, 1H), 7.51 (d, J = 8.4 Hz, 1H), 3.75 (m, 4H), 3.60 (m, 2H), 3.11 (t, J = 6.0 Hz, 2H), 2.92 (s, 3H), 2.76 (s, 3H), 2.23 (m, 2H). |
| 138 | 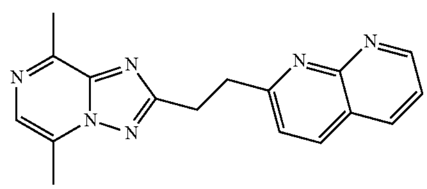 [SMILES: Cc1ncc(C)n2nc(CCc3ccc4cccnc4n3)nc12] | MS (ESI): m/z 305 [M + H]+; 1H-NMR (400 MHz, CDCl3): δ 9.09 (q, J = 2.0 Hz, 1H), 8.17 (q, J = 2.0 Hz, 1H), 8.11 (d, J = 8.4 Hz, 1H), 7.81 (d, J = 1.2 Hz, 1H), 7.48 (d, J = 8.4 Hz, 1H), 7.46 (q, J = 4.4 Hz, 1H), 3.68 (s, 4H), 2.87 (d, J = 0.8 Hz, 3H), 2.69 (s, 3H). |
| 139 | 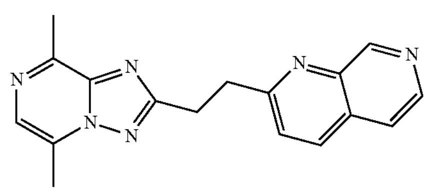 [SMILES: Cc1ncc(C)n2nc(CCc3ccc4ccncc4n3)nc12] | MS (ESI): m/z 305 [M + H]+; 1H-NMR (400 MHz, CDCl3): δ 9.47 (s, 1H), 8.60 (d, J = 5.6 Hz, 1H), 8.09 (d, J = 8.8 Hz, 1H), 7.84 (s, 1H), 7.64 (d, J = 6.0 Hz, 1H), 7.60 (d, J = 8.4 Hz, 1H), 3.66-3.63 (m, 4H), 2.89 (s, 3H), 2.70 (s, 3H). |
| 140 | 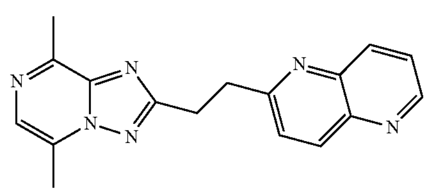 [SMILES: Cc1ncc(C)n2nc(CCc3ccc4ncccc4n3)nc12] | MS (ESI): m/z 305 [M + H]+; 1H-NMR (400 MHz, CDCl3): δ 8.92 (q, J = 1.6 Hz, 1H), 8.35 (q, J = 0.8 Hz, 1H), 8.32 (d, J = 8.8 Hz, 1H), 7.82 (d, J = 1.2 Hz, 1H), 7.63 (d, J = 8.4 Hz, 1H), 7.61 (d, J = 8.4 Hz, 1H), 3.63-3.60 (m, 4H), 2.88 (s, 3H), 2.69 (s, 3H). |
| 141 | 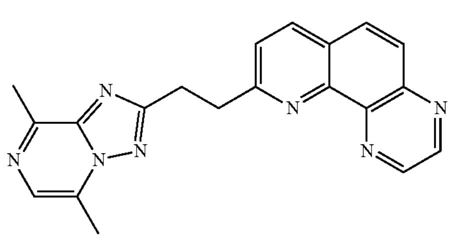 [SMILES: Cc1ncc(C)n2nc(CCc3ccc4ccc5nccnc5c4n3)nc12] | MS (ESI): m/z 356 (M + H)+; 1H NMR (400 MHz, CDCl3): δ 9.07 (s, 1H), 8.94 (s, 1H), 8.16 (d, J = 8.4 Hz, 1H), 7.97 (s, 2H), 7.75 (s, 1H), 7.62 (d, J = 8.0 Hz, 1H), 3.77 (t, J = 7.6 Hz, 2H), 3.56 (t, J = 7.6 Hz, 2H), 2.81 (s, 3H), 2.61 (s, 3H). |

-continued

| Compound Number | Structure | Analytical Data |
|---|---|---|
| 142 | 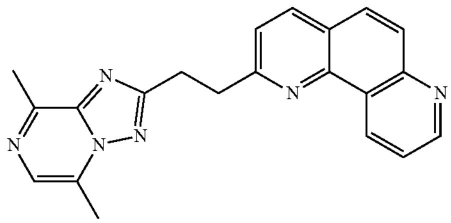 [SMILES: Cc1ncc(C)n2nc(CCc3ccc4ccc5ncccc5c4n3)nc12] | MS (ESI): m/z 355 [M + H]⁺; ¹H NMR (400 MHz, CDCl₃): δ 9.61 (d, J = 8.0 Hz, 1H), 9.03 (d, J = 2.8 Hz, 1H), 9.14 (d, J = 8.0 Hz, 1H), 8.02 (d, J = 9.2 Hz, 1H), 7.91 (d, J = 8.8 Hz, 1H), 7.82 (s, 1H), 7.58 (dd, $^1J$ = 8.4 Hz, $^2J$ = 4.4 Hz, 1H), 7.54 (d, J = 8.4 Hz, 1H), 3.72 (s, 4H), 2.90 (s, 3H), 2.71 (s, 3H). |

In other embodiments, the following compounds were prepared using the above procedures.

| Compound No. | Structure | Analytical Data |
|---|---|---|
| 143 | 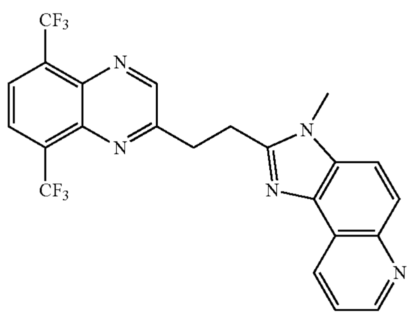 [SMILES: Cn1c(CCc2cnc3c(C(F)(F)F)ccc(C(F)(F)F)c3n2)nc2c3cccnc3ccc21] | MS (ESI): m/z 476 [M + H]⁺; ¹H NMR (400 MHz, CDCl₃): δ 9.15 (s, 1H), 8.87-8.83 (m, 2H), 8.10-8.05 (m, 2H), 7.92 (d, J = 9.2 Hz, 1H), 7.67 (d, J = 8.8 Hz, 1H), 7.47 (dd, $^1J$ = 8.4 Hz, $^2J$ = 4.4 Hz, 1H), 3.91 (s, 3H), 3.90 (t, J = 6.8 Hz, 2H), 3.65 (t, J = 7.2 Hz, 2H). |
| 144 | 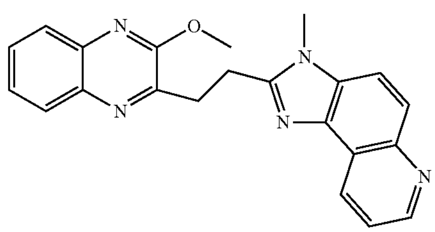 [SMILES: COc1nc2ccccc2nc1CCc1nc2c3cccnc3ccc2n1C] | MS (ESI): m/z 370 [M + H]⁺; ¹H NMR (400 MHz, CD₃OD): δ 8.81 (d, J = 7.2 Hz, 1H), 8.69 (dd, $^1J$ = 4.4 Hz, $^2J$ = 1.6 Hz, 1H), 7.89 (d, J = 8.8 Hz, 1H), 7.80 (d, J = 8.8 Hz, 1H), 7.66 (dd, $^1J$ = 8.0 Hz, $^2J$ = 1.6 Hz, 1H), 7.52-7.48 (m, 2H), 7.43-7.40 (m, 1H), 7.28-7.26 (m, 1H), 4.00 (s, 3H), 3.61 (s, 3H), 3.47-3.45 (m, 4H). |
| 145 | 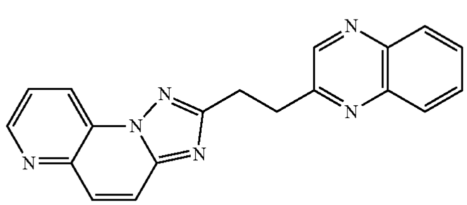 [SMILES: c1ccc2nc(CCc3nc4ccc5ncccc5n4n3)cnc2c1] | MS (ESI): m/z 327.1 [M + H]⁺; ¹H NMR (400 MHz, CDCl₃): δ 8.90 (dd, $^1J$ = 4.4 Hz, $^2J$ = 1.6 Hz, 1H), 8.85 (s, 1H), 8.73 (dd, $^1J$ = 8.4 Hz, $^2J$ = 0.8 Hz, 1H), 8.09-8.05 (m, 3H), 7.84 (d, J = 9.2 Hz, 1H), 7.75-7.71 (m, 2H), 7.66 (dd, $^1J$ = 8.8 Hz, $^2J$ = 4.8 Hz, 1H), 3.70-3.62 (m, 4H). |
| 146 | 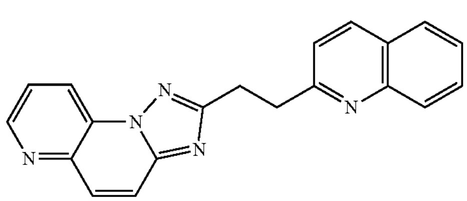 [SMILES: c1ccc2nc(CCc3nc4ccc5ncccc5n4n3)ccc2c1] | MS (ESI): m/z 326.1 [M + H]⁺; ¹H NMR (400 MHz, CDCl₃): δ 8.90 (dd, $^1J$ = 4.4 Hz, $^2J$ = 1.6 Hz, 1H), 8.77 (d, J = 8.4 Hz, 1H), 8.08-8.06 (m, 3H), 7.85 (d, J = 9.6 Hz, 1H), 7.78 (d, J = 8.4 Hz, 1H), 7.71-7.65 (m, 2H), 7.49 (t, J = 7.6 Hz, 1H), 7.40 (d, J = 8.4 Hz, 1H), 3.66-3.56 (m, 4H). |

| Compound No. | Structure | Analytical Data |
|---|---|---|
| 147 | 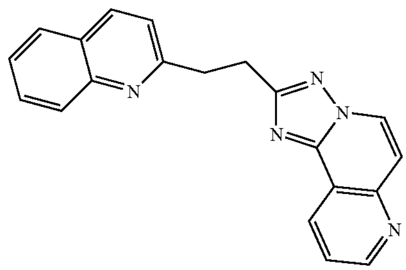 [SMILES: c1ccc2nc(CCc3nc4c5cccnc5ccn4n3)ccc2c1] | MS (ESI): m/z 326 [M + H]+; 1H NMR (400 MHz, CD3OD): δ 9.04 (dd, 1J = 1.6 Hz, 2J = 1.2 Hz, 1H), 8.93 (d, J = 8.4 Hz, 1H), 8.69 (d, J = 7.2 Hz, 1H), 8.25 (d, J = 8.0 Hz, 1H), 7.99 (d, J = 8.4 Hz, 1H), 7.89 (d, J = 8.0 Hz, 1H), 7.79 (dd, 1J = 4.8 Hz, 2J = 4.4 Hz, 1H), 7.75-7.71 (m, 1H), 7.57-7.49 (m, 3H), 3.62-3.31 (m, 4H). |
| 148 | 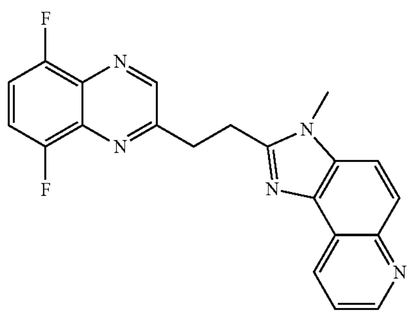 [SMILES: Cn1c(CCc2cnc3c(F)ccc(F)c3n2)nc2c3cccnc3ccc21] | MS (ESI): m/z 376 [M + H]+; 1H NMR (400 MHz, CDCl3): δ 9.06 (s, 1H), 8.87 (m, 2H), 7.94 (d, J = 10.0 Hz, 1H), 7.67 (d, J = 8.8 Hz, 1H), 7.50 (m, 1H), 7.32 (m, 2H), 3.96 (s, 3H), 3.87 (d, J = 7.2 Hz, 2H), 3.64 (d, J = 6.4 Hz, 2H). |
| 149 | 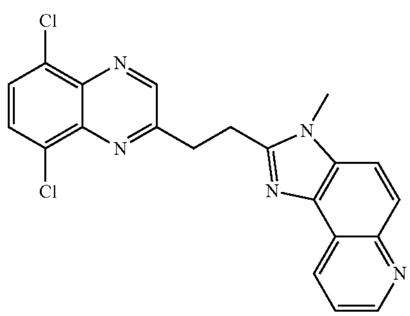 [SMILES: Cn1c(CCc2cnc3c(Cl)ccc(Cl)c3n2)nc2c3cccnc3ccc21] | MS (ESI): m/z 409 [M + H]+; 1H NMR (400 MHz, CDCl3): δ 9.08 (s, 1H), 8.89-8.87 (m, 2H), 7.94-7.92 (d, J = 8.8 Hz, 1H), 7.77-7.71 (dd, 1J = 14.8 Hz, 2J = 6.8 Hz, 2H), 7.67-7.65 (d, J = 9.2 Hz, 1H), 7.51-7.48 (m, 1H), 3.93 (s, 3H), 3.90-3.87 (m, 2H), 3.69-3.66 (m, 2H). |
| 150 | 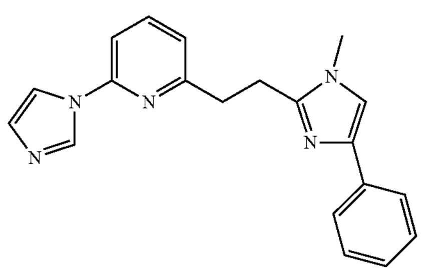 [SMILES: Cn1cc(-c2ccccc2)nc1CCc1cccc(-n2ccnc2)n1] | MS (ESI): m/z 330 [M + H]+; 1H NMR (400 MHz, CDCl3): δ 8.46 (t, J = 1.2 Hz, 1H), 7.74-7.69 (m, 3H), 7.64 (t, J = 1.2 Hz, 1H), 7.37-7.34 (m, 2H), 7.23-7.13 (m, 4H), 7.06 (s, 1H), 4.56 (s, 3H), 3.56-3.52 (m, 2H), 3.22-3.18 (m, 2H). |
| 151 | 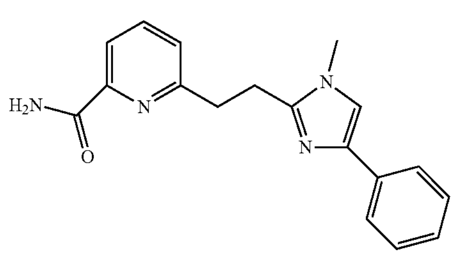 [SMILES: Cn1cc(-c2ccccc2)nc1CCc1cccc(C(N)=O)n1] | 1H-NMR(400 MHz, CDCl3): δ 8.05 (dd, 1J = 7.6 Hz, 2J = 0.8 Hz, 1H), 7.94 (brs, 1H), 7.77-7.72 (m, 3H), 7.38-7.32 (m, 3H), 7.24 (t, J = 7.6 Hz, 1H), 7.05 (s, 1H), 5.57 (brs, 1H), 3.48 (s, 3H), 3.35 (t, J = 7.6 Hz, 2H), 3.19 (t, J = 7.6 Hz, 2H). |

| Compound No. | Structure | Analytical Data |
|---|---|---|
| 152 | 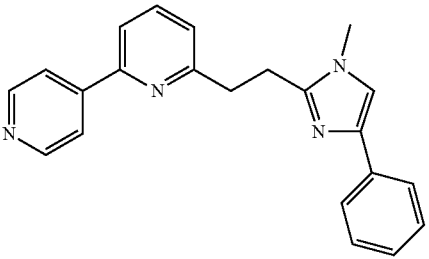 [SMILES: Cn1cc(-c2ccccc2)nc1CCc1cccc(-c2ccncc2)n1] | MS (ESI) m/z: 341 [M + H]+; 1H NMR (400 MHz, CDCl3): δ 8.71 (dd, 1J = 4.4 Hz, 2J = 2.0 Hz, 2H), 7.91 (dd, 1J = 4.0 Hz, 2J = 2.0 Hz, 2H), 7.75-7.72 (m, 2H), 7.69 (d, J = 7.6 Hz, 1H), 7.64 (dd, 1J = 7.6 Hz, 2J = 1.2 Hz, 1H), 7.34 (t, J = 7.6 Hz, 2H), 7.24 (d, J = 12.8 Hz, 2H), 7.04 (s, 1H), 3.52 (s, 3H), 3.40-3.37 (m, 2H), 3.28-3.23 (m, 2H). |
| 153 | 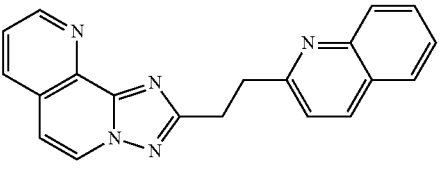 [SMILES: c1ccc2nc(CCc3nc4c5ncccc5ccn4n3)ccc2c1] | MS (ESI): m/z 326.1 [M + H]+; 1H NMR (400 MHz, CDCl3): δ 9.08 (d, J = 2.8 Hz, 1H), 8.38 (d, J = 7.2 Hz, 1H), 8.17 (d, J = 8.0 Hz, 1H), 8.09 (d, J = 8.4 Hz, 1H), 8.07 (d, J = 8.8 Hz, 1H), 7.77 (dd, 1J = 8.4 Hz, 2J = 1.2 Hz, 1H), 7.72-7.65 (m, 2H), 7.50 (dt, 1J = 8.0 Hz, 2J = 0.8 Hz, 1H), 7.40 (d, J = 8.0 Hz, 1H), 7.20 (d, J = 7.2 Hz, 1H), 3.73-3.69 (m, 2H), 3.63-3.59 (m, 2H). |
| 154 | 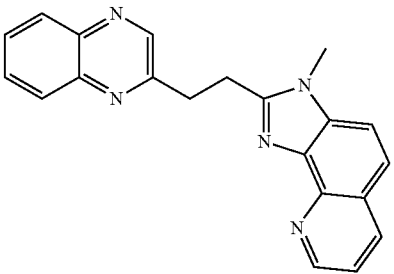 [SMILES: Cn1c(CCc2cnc3ccccc3n2)nc2c3ncccc3ccc21] | MS (ESI): m/z 340 [M + H]+; 1H NMR (400 MHz, CDCl3): δ 9.03 (d, J = 1.2 Hz, 1H), 8.34 (s, 1H), 8.23 (d, J = 1.6 Hz, 1H), 8.06 (m, 2H), 7.72 (m, 2H), 7.63 (d, J = 8.8 Hz, 1H), 7.53 (d, J = 8.8 Hz, 1H), 7.40 (m, 1H), 3.91 (m, 5H), 3.60 (t, J = 6.0 Hz, 2H). |
| 155 | 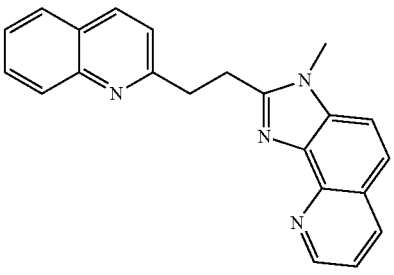 [SMILES: Cn1c(CCc2ccc3ccccc3n2)nc2c3ncccc3ccc21] | MS (ESI): m/z 339.0 [M + H]+; 1H NMR (400 MHz, CDCl3): δ 9.02 (dd, 1J = 4.0 Hz, 2J = 2.0 Hz, 1H), 8.22 (dd, 1J = 8.0 Hz, 2J = 2.0 Hz, 1H), 8.06 (d, J = 8.8 Hz, 1H), 8.02 (d, J = 8.4 Hz, 1H), 7.77 (dd, 1J = 8.0 Hz, 2J = 1.2 Hz, 1H), 7.77 (ddd, 1J = 8.4 Hz, 2J = 6.8 Hz, 3J = 1.2 Hz, 1H), 7.61 (d, J = 8.4 Hz, 1H), 7.49 (d, J = 8.4 Hz, 1H), 7.49 (ddd, 1J = 8.0 Hz, 2J = 6.8 Hz, 3J = 1.2 Hz, 1H), 7.40 (dd, 1J = 8.0 Hz, 2J = 4.4 Hz, 1H), 7.34 (d, J = 8.4 Hz, 1H), 3.82 (s, 3H), 3.80-3.76 (m, 2H), 3.61-3.57 (m, 2H). |
| 156 | 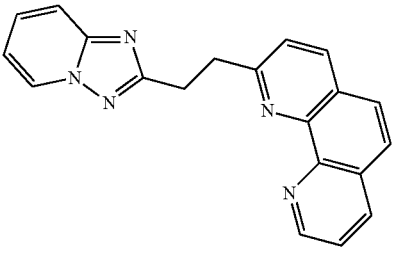 [SMILES: c1cnc2c(c1)ccc1ccc(CCc3nc4ccccn4n3)nc12] | MS (ESI): m/z 326 [M + H]+; 1H NMR (400 MHz, CD3OD): δ 8.97 (d, J = 3.6 Hz, 1H), 8.56 (d, J = 6.8 Hz, 1H), 8.35 (d, J = 1.6 Hz, 1H), 8.22 (d, J = 8.4 Hz, 1H), 7.77 (d, J = 9.2 Hz, 2H), 7.66 (m, 1H), 7.55 (m, 3H), 7.03 (td, J = 2.0 Hz, 1H), 3.59 (t, J = 8.0 Hz, 2H), 3.44 (t, J = 8.0 Hz, 2H). |
| 157 | 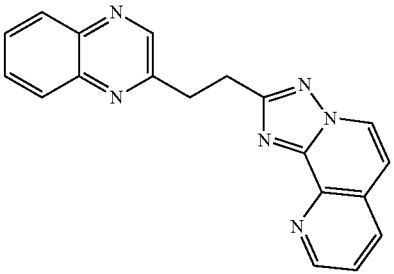 [SMILES: c1cnc2c(c1)ccn1nc(CCc3cnc4ccccc4n3)nc21] | MS (ESI) m/z 327 [M + H]+; 1H NMR (400 MHz, CDCl3): δ 9.07 (dd, 1J = 4.4 Hz, 2J = 1.6 Hz, 1H), 8.79 (s, 1H), 8.34 (d, J = 7.6 Hz, 1H), 8.16 (dd, 1J = 8.0 Hz, 2J = 1.6 Hz, 1H), 8.08-8.03 (m, 2H), 7.76-7.67 (m, 2H), 7.64 (dd, 1J = 8.0 Hz, 2J = 4.4 Hz, 1H), 7.19 (d, J = 6.8 Hz, 1H), 3.76-3.72 (m, 2H), 3.66-3.62 (m, 2H). |

| Compound No. | Structure | Analytical Data |
|---|---|---|
| 158 | 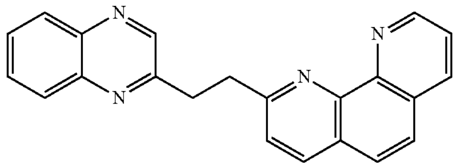 [SMILES: c1cnc2c(c1)ccc1ccc(CCc3cnc4ccccc4n3)nc12] | MS (ESI): m/z 337.1 [M + H]+; 1H NMR (400 MHz, CD3OD): δ 9.26 (d, J = 2.0 Hz, 1 H), 8.83 (s, 1 H), 8.26 (d, J = 1.6 Hz, 1 H), 8.16 (d, J = 8.4 Hz, 1H), 8.10-8.06 (m, 2H), 7.78-7.70 (m, 4 H), 7.65 (dd, 1J = 8.0 Hz, 2J = 4.4 Hz, 1 H), 7.57 (d, J = 8.4 Hz, 1 H), 3.83-3.79 (m, 2H), 3.73-3.69 (m, 2H). |
| 159 | 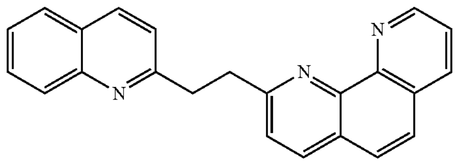 [SMILES: c1ccc2nc(CCc3ccc4ccc5cccnc5c4n3)ccc2c1] | MS (ESI): m/z 336 [M + H]+; 1H NMR (400 MHz, CD3OD): δ 9.14 (d, J = 3.6 Hz, 1H), 8.96 (d, J = 7.6 Hz, 1H), 8.78 (d, J = 8.4 Hz, 1H), 8.53 (d, J = 8.8 Hz, 1H), 8.17-8.07 (m, 5H), 7.97 (d, J = 7.2 Hz, 1H), 7.87 (d, J = 5.2 Hz, 2H), 7.75 (t, J = 7.2 Hz, 1H), 3.91 (t, J = 7.6 Hz, 2H), 3.77 (t, J = 7.2 Hz, 2H). |
| 160 | 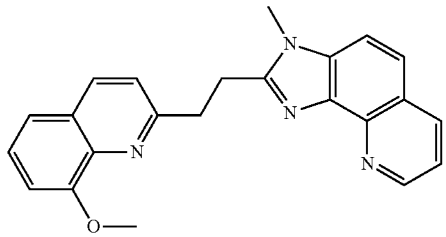 [SMILES: COc1cccc2ccc(CCc3nc4c5ncccc5ccc4n3C)nc12] | MS (ESI): m/z 369.1 [M + H]+; 1H NMR (400 MHz, CDCl3): δ 9.03 (dd, 1J = 4.4 Hz, 2J = 1.6 Hz, 1H), 8.23 (dd, 1J = 8.0 Hz, 2J = 2.0 Hz, 1H), 7.99 (d, J = 8.4 Hz, 1H), 7.61 (d, J = 9.2 Hz, 1H), 7.50 (d, J = 8.8 Hz, 1H), 7.42-7.34 (m, 4H), 7.07 (dd, 1J = 7.6 Hz, 2J = 1.2 Hz, 1H), 4.12 (s, 3H), 3.84 (t, J = 7.4 Hz, 2H), 3.81 (s, 3H), 3.60 (t, J = 7.6 Hz, 2H). |
| 161 | 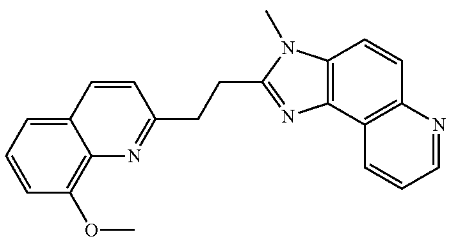 [SMILES: COc1cccc2ccc(CCc3nc4c5cccnc5ccc4n3C)nc12] | MS (ESI): m/z 369.1 [M + H]+; 1H NMR (400 MHz, CDCl3): δ 8.95 (t, J = 4.2 Hz, 1H), 8.89 (dd, 1J = 4.0 Hz, 2J =1.6 Hz, 1H), 7.99 (d, J = 8.4 Hz, 1H), 7.93 (d, J = 9.2 Hz, 1H), 7.64 (d, J = 8.8 Hz, 1H), 7.51 (dd, 1J = 8.8 Hz, 2J = 4.8 Hz, 1H), 7.42 (t, J = 7.8 Hz, 1H), 7.34 (t, J = 7.4 Hz, 1H), 7.06 (d, J = 6.8 Hz, 1H), 4.08 (s, 3H), 3.79 (s, 3H), 3.72 (t, J = 7.6 Hz, 2H), 3.59 (t, J = 7.2 Hz, 2H). |
| 162 | 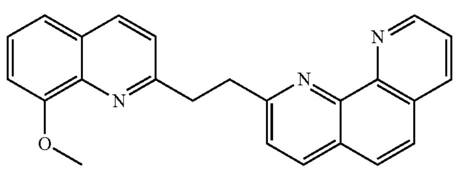 [SMILES: COc1cccc2ccc(CCc3ccc4ccc5cccnc5c4n3)nc12] | MS (ESI): m/z 366.1 [M + H]+; 1H NMR (400 MHz, CDCl3): δ 9.25 (dd, 1J = 4.0 Hz, 2J = 1.6 Hz, 1H), 8.26 (dd, 1J = 8.0 Hz, 2J = 2.0 Hz, 1H), 8.16 (d, J = 8.4 Hz, 1H), 8.05 (d, J = 8.4 Hz, 1H), 7.77 (dd, 1J = 12.8 Hz, 2J = 8.8 Hz, 2H), 7.66-7.62 (m, 2H), 7.48-7.36 (m, 3H), 7.07 (dd, 1J = 7.2 Hz, 2J = 0.8 Hz, 1H), 4.12 (s, 3H), 3.82-3.77 (m, 2H), 3.70-3.66 (m, 2H). |
| 163 | 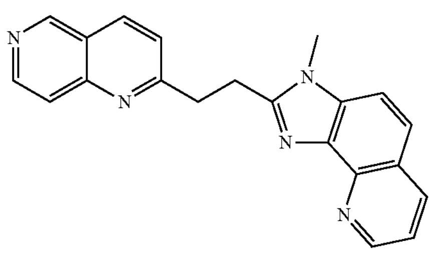 [SMILES: Cn1c(CCc2ccc3cnccc3n2)nc2c3ncccc3ccc21] | MS (ESI): m/z 340.1 [M + H]+; 1H NMR (400 MHz, CDCl3): δ 9.21 (s, 1H), 9.03 (dd, 1J = 1.2 Hz, 2J = 4.0 Hz, 1H), 8.73 (d, J = 6.0 Hz, 1H), 8.23 (dd, 1J = 1.2 Hz, 2J = 8.0 Hz, 1H), 8.16 (d, J = 8.4 Hz, 1H), 7.86 (d, J = 8.4 Hz, 1H), 7.63 (d, J = 8.8 Hz, 1H), 7.53 (d, J = 8.0 Hz, 1H), 7.51 (d, J = 8.4 Hz, 1H), 7.41 (dd, 1J = 4.0 Hz, 2J = 8.0 Hz, 1H), 3.91-3.87 (m, 5H), 3.63-3.59 (m, 2H). |
| 164 | 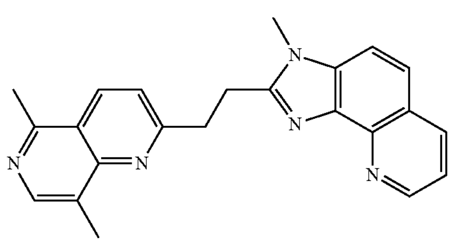 [SMILES: Cc1ncc(C)c2nc(CCc3nc4c5ncccc5ccc4n3C)ccc12] | MS (ESI): m/z 368.1 [M + H]+; 1H NMR (400 MHz, CDCl3): δ 9.01 (dd, 1J = 4.4 Hz, 2J = 1.6 Hz, 1H), 8.41 (s, 1H), 8.24 (d, J = 8.8 Hz, 1H), 8.22 (dd, 1J = 8.4 Hz, 2J = 1.6 Hz, 1H), 7.61 (d, J = 8.4 Hz, 1H), 7.51 (d, J = 8.8 Hz, 1H), 7.44 (d, J = 8.8 Hz, 1H), 7.40 (dd, 1J = 8.0 Hz, 2J = 4.0 Hz, 1H), 3.87 (s, 3H), 3.85 (dd, 1J = 5.6 Hz, 2J = 3.2 Hz, 2H), 3.63 (dd, 1J = 8.8 Hz, 2J = 6.4 Hz, 2H), 2.86 (s, 3H), 2.65 (s, 3H). |

-continued

| Compound No. | Structure | Analytical Data |
|---|---|---|
| 165 | 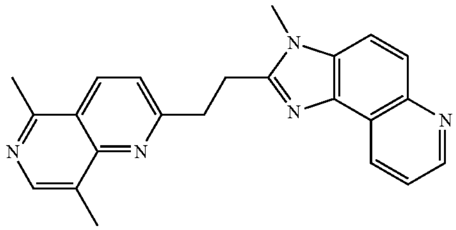 [SMILES: Cc1ncc(C)c2nc(CCc3nc4c5cccnc5ccc4n3C)ccc12] | MS (ESI): m/z 368.1 [M + H]⁺; ¹H NMR (400 MHz, CDCl₃): δ 8.95 (d, J = 8.4 Hz, 1H), 8.91 (dd, ¹J = 4.4 Hz, ²J = 1.6 Hz, 1H), 8.43 (s, 1H), 8.29 (d, J = 8.4 Hz, 1H), 7.97 (d, J = 9.2 Hz, 1H), 7.68 (d, J = 8.8 Hz, 1H), 7.53 (dd, ¹J = 8.4 Hz, ²J = 4.0 Hz, 1H), 7.45 (d, J = 8.8 Hz, 1H), 3.86 (s, 3H), 3.72-3.63 (m, 4H), 2.89 (s, 3H), 2.64 (s, 3H). |
| 166 | 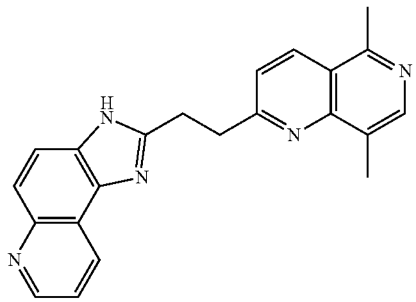 [SMILES: Cc1ncc(C)c2nc(CCc3nc4c(ccc5ncccc54)[nH]3)ccc12] | MS (ESI): m/z 354.1 [M + H]⁺; ¹H NMR (400 MHz, CDCl₃): δ 12.70 (s, 1H), 8.90 (d, J = 3.2 Hz, 2H), 8.51 (s, 1H), 8.40 (d, J = 8.8 Hz, 1H), 7.93 (d, J = 9.2 Hz, 1H), 7.82 (s, 1H), 7.48 (d, J = 8.4 Hz, 2H), 3.71-3.63 (m, 4H), 3.14 (s, 6H). |
| 167 | 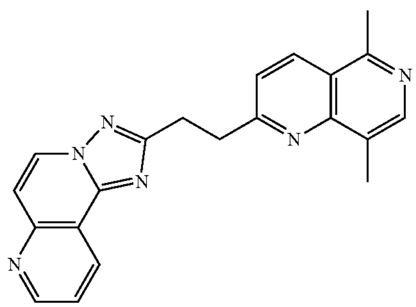 [SMILES: Cc1ncc(C)c2nc(CCc3nc4c5cccnc5ccn4n3)ccc12] | MS (ESI): m/z 355.1 [M + H]⁺; ¹H NMR (400 MHz, CDCl₃): δ 9.05 (dd, ¹J = 4.4 Hz, ²J = 1.6 Hz, 1H), 8.91 (d, J = 8.0 Hz, 1H), 8.50 (d, J = 7.6 Hz, 1H), 8.42 (s, 1H), 8.31 (d, J = 8.4 Hz, 1H), 7.64 (d, ¹J = 8.0 Hz, ²J = 4.8 Hz, 1H), 7.49 (dd, ¹J = 8.4 Hz, ²J = 7.6 Hz, 2H), 3.67 (s, 4H), 2.89 (s, 3H), 2.65 (s, 3H). |
| 168 | 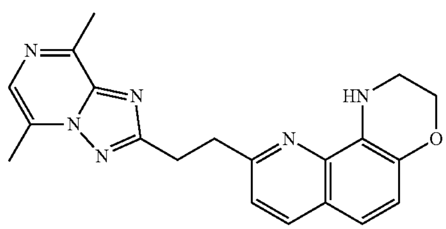 [SMILES: Cc1ncc(C)n2nc(CCc3ccc4ccc5c(c4n3)NCCO5)nc12] | MS (ESI): m/z 361 [M + H]⁺; ¹H NMR (400 MHz, DMSO-d₆): δ 8.06 (d, J = 8.4 Hz, 1H), 7.97 (s, 1H), 7.32 (d, J = 8.4 Hz, 1H), 7.04 (d, J = 8.8 Hz, 1H), 7.01 (d, J = 8.8 Hz, 1H), 6.11 (brs, 1H), 4.27 (t, J = 4.0 Hz, 2H), 3.52-3.44 (m, 6H), 2.76 (s, 3H), 2.66 (s, 3H). |
| 169 | 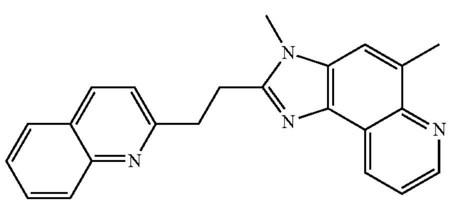 [SMILES: Cc1cc2c(nc(CCc3ccc4ccccc4n3)n2C)c2cccnc12] | MS (ESI): m/z 353 [M + H]⁺; ¹H NMR (400 MHz, CDCl₃): δ 8.97-8.93 (m, 2H), 8.07-8.02 (m, 2H), 7.78 (d, J = 8.0 Hz, 1H), 7.73-7.69 (m, 1H), 7.53-7.49 (m, 3H), 7.30 (d, J = 8.4 Hz, 1H), 3.75 (s, 3H), 3.66-3.54 (m, 4H), 2.89 (s, 3H). |
| 170 | 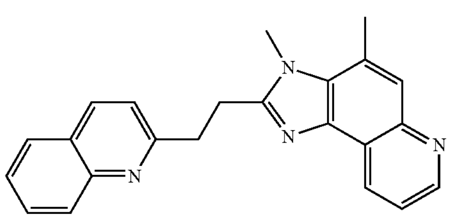 [SMILES: Cc1cc2ncccc2c2nc(CCc3ccc4ccccc4n3)n(C)c12] | MS (ESI): m/z 353 [M + H]⁺; ¹H NMR (400 MHz, CD₃OD): δ 8.87 (dd, ¹J = 8.4 Hz, ²J = 1.2 Hz, 1H), 8.73 (d, ¹J = 8.0 Hz, ²J = 1.6 Hz, 1H), 8.23 (d, J = 8.4 Hz, 1H), 7.97 (d, J = 8.4 Hz, 1H), 7.88 (d, J = 7.2 Hz, 1H), 7.75-7.71 (m, 1H), 7.57-7.52 (m, 3H), 7.44 (d, J = 8.4 Hz, 1H), 4.06 (s, 3H), 3.54 (s, 4H), 2.87 (s, 3H). |

-continued

| Compound No. | Structure | Analytical Data |
|---|---|---|
| 171 | 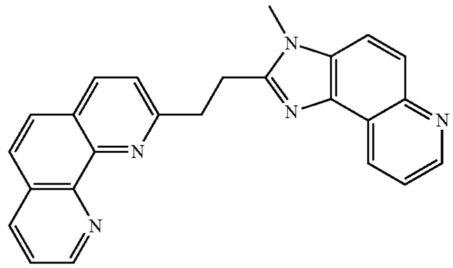 [SMILES: Cn1c(CCc2ccc3ccc4cccnc4c3n2)nc2c3cccnc3ccc21] | MS (ESI): m/z 390 [M + H]+; 1H NMR (400 MHz, CDCl3): δ 9.23 (dd, 1J = 4.4 Hz, 2J = 2.0 Hz, 1H), 8.98 (td, 1J = 8.4 Hz, 2J = 0.8 Hz, 1H), 8.89 (dd, 1J = 4.4 Hz, 2J = 1.6 Hz, 1H), 8.26 (dd, 1J = 8.0 Hz, 2J = 1.6 Hz, 1H), 8.11 (d, J = 8.4 Hz, 1H), 7.92 (d, J = 8.8 Hz, 1H), 7.76 (s, 2H), 7.66-7.60 (m, 2H), 7.55-7.50 (m, 2H), 3.88 (t, J = 7.2 Hz, 2H), 3.76 (s, 3H), 3.69 (t, J = 7.6 Hz, 2H). |
| 172 | 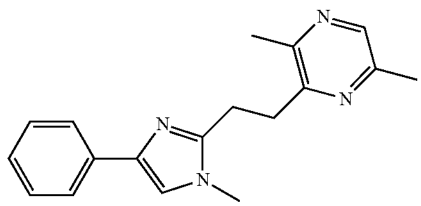 [SMILES: Cc1cnc(C)c(CCc2nc(-c3ccccc3)cn2C)n1] | MS (ESI): m/z 293.1 [M + H]+; 1H NMR (400 MHz, CDCl3): δ 8.16 (s, 1H), 7.72 (d, J = 7.6 Hz, 1H), 7.36-7.32 (m, 2H), 7.22-7.20 (m, 1H), 7.04 (s, 1H), 3.55 (s, 3H), 3.34-3.30 (m, 2H), 3.21-3.17 (m, 2H), 2.51 (s, 3H), 2.49 (s, 3H). |
| 173 | 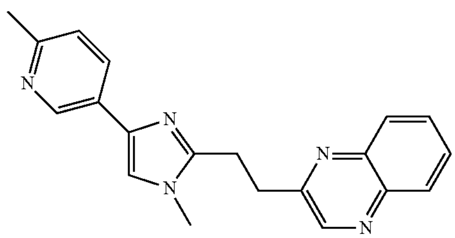 [SMILES: Cc1ccc(-c2cn(C)c(CCc3cnc4ccccc4n3)n2)cn1] | MS (ESI): m/z 330.1 [M + H]+; 1H NMR (400 MHz, CDCl3): δ 8.83 (s, 1H), 7.78 (d, J = 2.4 Hz, 1H), 8.09-8.03 (m, 2H), 7.97-7.95 (m, 1H), 7.76-7.73 (m, 2H), 7.15 (d, J = 8.0 Hz, 1H), 7.09 (s, 1H), 3.61 (s, 3H), 3.62-3.58 (m, 2H), 3.34-3.30 (m, 2H), 2.55 (s, 3H). |
| 174 | 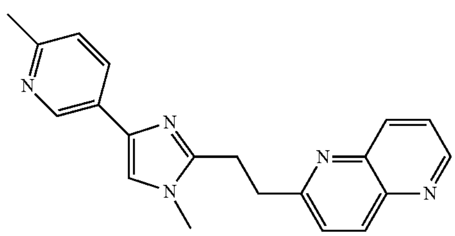 [SMILES: Cc1ccc(-c2cn(C)c(CCc3ccc4ncccc4n3)n2)cn1] | MS (ESI): m/z 330.1 [M + H]+; 1H NMR (400 MHz, CDCl3): δ 8.93 (dd, 1J = 4.0 Hz, 2J = 1.6 Hz, 1H), 8.80 (brd, J = 1.6 Hz, 1H), 8.34 (brd, J = 8.8 Hz, 1H), 8.29 (d, J = 8.8 Hz, 1H), 7.95 (dd, 1J = 4.0 Hz, 2J = 2.8 Hz, 1H), 7.63 (dd, 1J = 8.4 Hz, 2J = 4.0 Hz, 1H), 7.57 (d, J = 8.8 Hz, 1H), 7.08 (s, 1H), 7.15 (d, J = 8.4 Hz, 1H), 3.58 (s, 3H), 3.54 (t, J = 8.0 Hz, 2H), 3.31 (dd, 1J = 8.0 Hz, 2J = 6.4 Hz, 2H), 2.55 (s, 3H). |
| 175 | 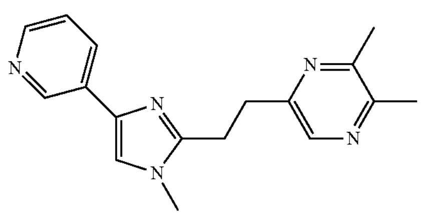 [SMILES: Cc1ncc(CCc2nc(-c3cccnc3)cn2C)nc1C] | MS (ESI): m/z 294.1 [M + H]+; 1H NMR (400 MHz, CDCl3): δ 8.91 (d, J = 1.6 Hz, 1 H), 8.44 (dd, 1J = 4.8 Hz, 2J = 1.6 Hz, 1H), 8.21 (s, 1H), 8.08-8.05 (m, 1H), 7.30-7.28 (m, 1H), 7.12 (s, 1H), 3.58 (s, 3H), 3.29-3.25 (m, 2H), 3.16-3.12 (m, 2H), 2.53 (s, 3H), 2.51 (s, 3H). |
| 176 | 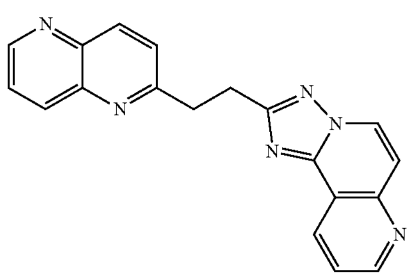 [SMILES: c1cnc2ccc(CCc3nc4c5cccnc5ccn4n3)nc2c1] | MS (ESI): m/z 327 [M + H]+; 1H NMR (400 MHz, CDCl3): δ 9.04 (dd, 1J = 4.8 Hz, 2J = 1.6 Hz, 1H), 8.93 (dd, 1J = 4.8 Hz, 2J = 1.6 Hz, 1H), 8.89 (dd, 1J = 8.0 Hz, 2J = 1.6 Hz, 1H), 8.48 (d, J = 7.2 Hz, 1H), 8.37-8.35 (m, 1H), 8.30 (d, J = 8.4 Hz, 1H), 7.65-7.61 (m, 3H), 7.50 (d, J = 7.2 Hz, 1H), 3.69-3.65 (m, 2H), 3.63-3.58 (m, 2H). |

| Compound No. | Structure | Analytical Data |
|---|---|---|
| 177 | 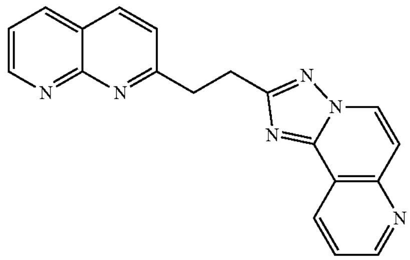 [SMILES: c1cnc2nc(CCc3nc4c5cccnc5ccn4n3)ccc2c1] | MS (ESI): m/z 327 [M + H]$^+$; $^1$H NMR (400 MHz, CDCl$_3$): δ 9.10 (dd, $^1$J = 4.4 Hz, $^2$J = 2.0 Hz, 1H), 9.03 (dd, $^1$J = 4.4 Hz, $^2$J = 2.0 Hz, 1H), 8.92-8.89 (m, 1H), 8.49 (d, J = 7.2 Hz, 1H), 8.17 (dd, $^1$J = 8.0 Hz, $^2$J = 2.0 Hz, 1H), 8.12 (d, J = 8.0 Hz, 1H), 7.63 (t, J = 4.4 Hz, 1H), 7.50 (m, 1H), 7.48 (m, 1H), 7.46 (t, J = 4.4 Hz, 1H), 3.71-3.67 (m, 4H). |
| 178 | 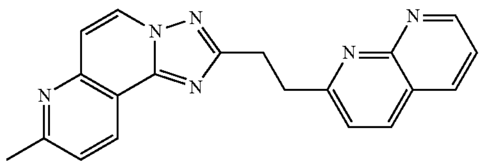 [SMILES: Cc1ccc2c(ccn3nc(CCc4ccc5cccnc5n4)nc23)n1] | MS (ESI): m/z 341 [M + H]$^+$; $^1$H NMR (400 MHz, CDCl$_3$): δ 9.27 (s, 1H), 8.85 (d, J = 7.6 Hz, 1H), 8.79 (d, J = 8.4 Hz, 1H), 8.65 (m, 2H), 7.92 (m, 2H), 7.70 (d, J = 8.4 Hz, 1H), 7.46 (d, J = 7.6 Hz, 1H), 3.77 (m, 2H), 3.65 (m, 2H), 2.78 (s, 3H). |
| 179 | 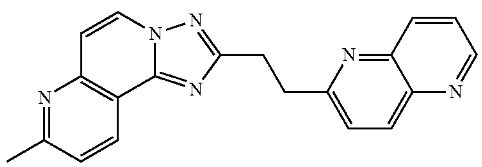 [SMILES: Cc1ccc2c(ccn3nc(CCc4ccc5ncccc5n4)nc23)n1] | MS (ESI): m/z 341 [M + H]$^+$; $^1$H NMR (400 MHz, CD$_3$OD): δ 8.92 (q, J = 1.6 Hz, 1H), 8.75 (d, J = 8.4 Hz, 1H), 8.44 (d, J = 7.6 Hz, 1H), 8.35 (d, J = 7.6 Hz, 1H), 8.29 (d, J = 8.4 Hz, 1H), 7.63 (t, J = 1.6 Hz, 1H), 7.60 (d, J = 1.6 Hz, 1H), 7.50 (d, J = 8.4 Hz, 1H), 7.41 (d, J = 7.6 Hz, 1H), 3.66 (m, 2H), 3.58 (m, 2H), 2.79 (s, 3H). |
| 180 | 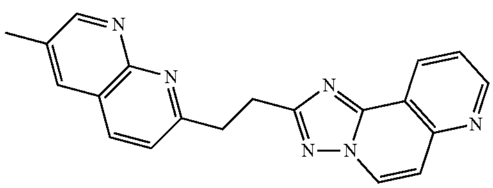 [SMILES: Cc1cnc2nc(CCc3nc4c5cccnc5ccn4n3)ccc2c1] | MS (ESI): m/z 341 [M + H]$^+$; $^1$H NMR (400 MHz, CDCl$_3$): δ 9.03 (dd, $^1$J = 4.4 Hz, $^2$J = 1.2 Hz, 1H), 8.94 (d, J = 2.0 Hz, 1H), 8.91-8.89 (m, 1H), 8.48 (d, J = 7.6 Hz, 1H), 8.03 (d, J = 8.4 Hz, 1H), 7.91 (d, J = 1.2 Hz, 1H), 7.62 (dd, $^1$J = 8.0 Hz, $^2$J = 4.4 Hz, 1H), 7.48 (d, J = 7.6 Hz, 1H), 7.45 (d, J = 8.4 Hz, 1H), 3.67 (s, 4H), 2.54 (s, 3H). |
| 181 | 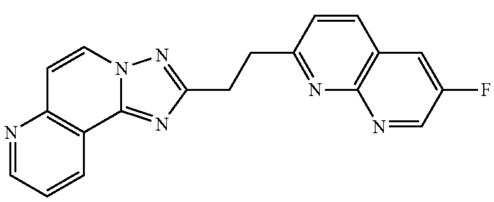 [SMILES: Fc1cnc2nc(CCc3nc4c5cccnc5ccn4n3)ccc2c1] | MS (ESI): m/z 345 [M + H]$^+$; $^1$H NMR (400 MHz, CDCl$_3$): δ 9.04 (dd, $^1$J = 4.4 Hz, $^2$J = 1.2 Hz, 1H), 8.99 (d, J = 3.2 Hz, 1H), 8.89 (dd, $^1$J = 8.0 Hz, $^2$J = 1.2 Hz, 1H), 8.48 (d, J = 7.6 Hz, 1H), 8.10 (d, J = 8.4 Hz, 1H), 7.79 (dd, $^1$J = 7.2 Hz, $^2$J = 2.8 Hz, 1H), 7.63 (dd, $^1$J = 8.0 Hz, $^2$J = 4.4 Hz, 1H), 7.54-7.48 (m, 2H), 3.72-3.63 (m, 4H). |
| 182 | 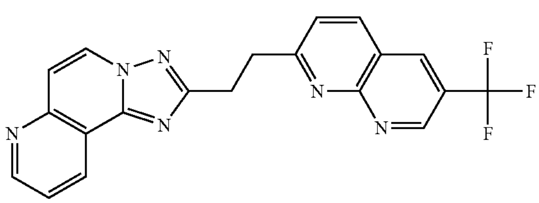 [SMILES: FC(F)(F)c1cnc2nc(CCc3nc4c5cccnc5ccn4n3)ccc2c1] | MS (ESI): m/z 395 [M + H]$^+$; $^1$H NMR (400 MHz, CDCl$_3$): δ 9.30 (d, J = 2.4 Hz, 1H), 9.04 (dd, $^1$J = 4.4 Hz, $^2$J = 1.2 Hz, 1H), 8.89 (dd, $^1$J = 8.0 Hz, $^2$J = 1.2 Hz, 1H), 8.47 (dd, $^1$J = 4.4 Hz, $^2$J = 2.4 Hz, 2H), 8.22 (d, J = 8.0 Hz, 1H), 7.65-7.61 (m, 2H), 7.50 (d, J = 7.2 Hz, 1H), 3.76-3.67 (m, 4H). |
| 183 | 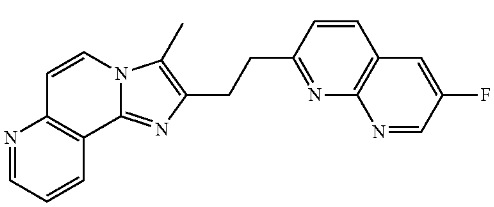 [SMILES: Cc1c(CCc2ccc3cc(F)cnc3n2)nc2c3cccnc3ccn12] | MS (ESI): m/z 358.1 [M + H]$^+$; $^1$H NMR (400 MHz, CDCl$_3$): δ 8.98 (d, J = 2.8 Hz, 1H), 8.89 (dd, $^1$J = 8.0 Hz, $^2$J = 1.6 Hz, 1H), 8.84 (dd, $^1$J = 4.4 Hz, $^2$J = 1.6 Hz, 1H), 8.01 (d, J = 8.4 Hz, 1H), 7.83 (d, J = 7.6 Hz, 1H), 7.76 (dd, $^1$J = 7.6 Hz, $^2$J = 3.2 Hz, 1H), 7.51 (dd, $^1$J = 8.0 Hz, $^2$J = 4.4 Hz, 1H), 7.39 (d, J = 8.4 Hz, 1H), 7.29 (d, J = 7.6 Hz, 1H), 3.56-3.52 (m, 2H), 3.43-3.39 (m, 2H), 2.34 (s, 3H). |

-continued

| Compound No. | Structure | Analytical Data |
|---|---|---|
| 184 | 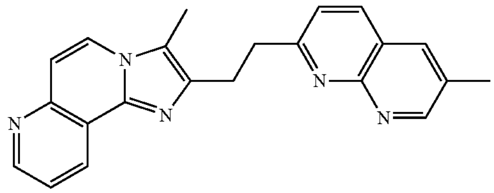 [SMILES: Cc1cnc2nc(CCc3nc4c5cccnc5ccn4c3C)ccc2c1] | MS (ESI): m/z 354.1 [M + H]⁺; ¹H NMR (400 MHz, CDCl₃): δ 8.94 (d, J = 2.4 Hz, 1H), 8.91 (dd, ¹J = 7.6 Hz, ²J = 1.6 Hz, 1H), 8.45 (d, ¹J = 4.4 Hz, ²J = 1.6 Hz, 1H), 7.96 (d, J = 8.4 Hz, 1H), 7.89 (d, J = 1.6 Hz, 1H), 7.94 (d, J = 7.6 Hz, 1H), 7.51 (dd, ¹J = 8.4 Hz, ²J = 4.4 Hz, 1H), 7.33-7.27 (m, 2H), 3.54-3.50 (m, 2H), 3.44-3.40 (m, 2H), 2.54 (s, 3H), 2.34 (s, 3H). |
| 185 | 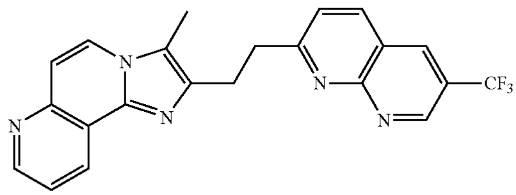 [SMILES: Cc1c(CCc2ccc3cc(C(F)(F)F)cnc3n2)nc2c3cccnc3ccn12] | MS (ESI): m/z 408.1 [M + H]⁺; ¹H NMR (400 MHz, CDCl₃): δ 9.30 (d, J = 2.8 Hz, 1H), 8.91-8.86 (m, 2H), 8.46 (d, J = 1.2 Hz, 1H), 8.15 (d, J = 8.4 Hz, 1H), 7.85 (d, J = 7.6 Hz, 1H), 7.55-7.49 (m, 2H), 7.31 (d, J = 7.2 Hz, 1H), 3.64-3.60 (m, 2H), 3.48-3.44 (m, 2H), 2.34 (s, 3H). |
| 186 | 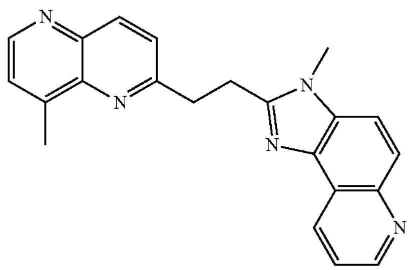 [SMILES: Cc1ccnc2ccc(CCc3nc4c5cccnc5ccc4n3C)nc12] | MS (ESI): m/z 354.1 [M + H]⁺; ¹H NMR (400 MHz, CDCl₃): δ 8.96 (d, J = 8.0 Hz, 1H), 8.91 (d, J = 4.4 Hz, 1H), 8.77 (d, J = 4.4 Hz, 1H), 8.26 (d, J = 8.8 Hz, 1H), 7.97 (d, J = 8.8 Hz, 1H), 7.69 (d, J = 9.2 Hz, 1H), 7.58-7.50 (m, 2H), 7.44 (d, J = 4.4 Hz, 1H), 3.86 (s, 3H), 3.72-3.62 (m, 4H), 2.78 (s, 2H). |
| 187 | 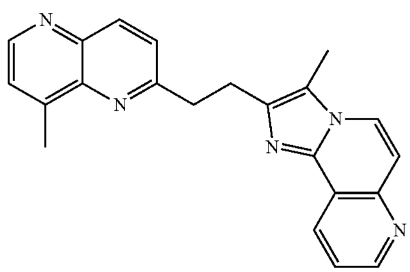 [SMILES: Cc1ccnc2ccc(CCc3nc4c5cccnc5ccn4c3C)nc12] | MS (ESI): m/z 354.1 [M + H]⁺; ¹H NMR (400 MHz, CDCl₃): δ 8.98 (d, J = 7.2 Hz, 1H), 8.88 (d, J = 4.4 Hz, 1H), 8.76 (d, J = 4.4 Hz, 1H), 8.19 (d, J = 8.4 Hz, 1H), 7.85 (d, J = 7.6 Hz, 1H), 7.57-7.43 (m, 3H), 7.34 (d, J = 7.2 Hz, 1H), 3.53 (t, J = 8.0 Hz, 2H), 3.41 (t, J = 8.0 Hz, 1H), 2.84 (s, 3H), 2.31 (s, 3H). |
| 188 | 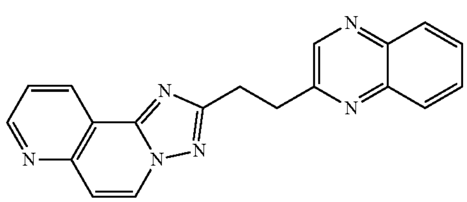 [SMILES: c1ccc2nc(CCc3nc4c5cccnc5ccn4n3)cnc2c1] | MS (ESI): m/z 327 [M + H]⁺; ¹H NMR (400 MHz, CDCl₃): δ 9.04 (dd, ¹J = 4.4 Hz, ²J = 1.6 Hz, 1H), 8.87 (dd, ¹J = 8.0 Hz, ²J = 1.6 Hz, 1H), 8.83 (s, 1H), 8.46 (d, J = 7.6 Hz, 1H), 8.06 (dd, ¹J = 7.2 Hz, ²J = 1.6 Hz, 2H), 7.77-7.69 (m, 2H), 7.62 (dd, ¹J = 8.0 Hz, ²J = 4.4 Hz, 1H), 7.49 (d, J = 7.6 Hz, 1H), 3.70-3.61 (m, 4H). |
| 189 | 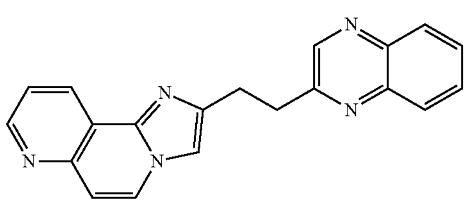 [SMILES: c1ccc2nc(CCc3cn4ccc5ncccc5c4n3)cnc2c1] | MS (ESI): m/z 326 [M + H]⁺; ¹H NMR (400 MHz, CDCl₃): δ 8.94-8.89 (m, 2H), 8.75 (s, 1H), 8.09-8.06 (m, 2H), 8.01 (d, J = 7.6 Hz, 1H), 7.79-7.71 (m, 2H), 7.55 (dd, ¹J = 8.0 Hz, ²J = 4.4 Hz, 1H), 7.34 (s, 1H), 7.29 (d, J = 7.6 Hz, 1H), 3.57 (t, J = 7.2 Hz, 2H), 3.45 (t, J = 7.2 Hz, 2H). |
| 190 | 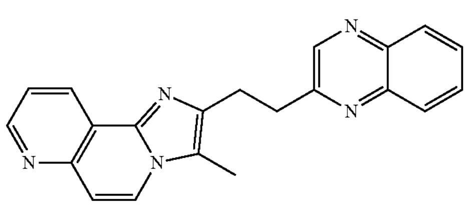 [SMILES: Cc1c(CCc2cnc3ccccc3n2)nc2c3cccnc3ccn12] | MS (ESI): m/z 340 [M + H]⁺; ¹H NMR (400 MHz, CDCl₃): δ 8.90 (d, J = 8.4 Hz, 1H), 8.86 (dd, ¹J = 4.8 Hz, ²J = 1.6 Hz, 1H), 8.65 (s, 1H), 8.09-8.04 (m, 2H), 7.82 (d, J = 7.6 Hz, 1H), 7.78-7.69 (m, 2H), 7.53 (dd, ¹J = 8.0 Hz, ²J = 4.8 Hz, 1H), 7.31 (d, J = 7.6 Hz, 1H), 3.56 (t, J = 7.2 Hz, 2H), 3.39 (t, J = 7.2 Hz, 2H), 2.29 (s, 3H). |

-continued

| Compound No. | Structure | Analytical Data |
|---|---|---|
| 191 | 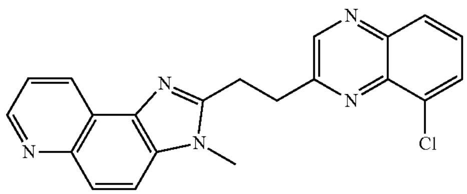 [SMILES: Cn1c(CCc2cnc3cccc(Cl)c3n2)nc2c3cccnc3ccc21] | MS (ESI): m/z 374 [M + H]$^+$; $^1$H NMR (400 MHz, CDCl$_3$): δ 8.96 (s, 1H), 8.90-8.88 (m, 2H), 7.99 (d, J = 8.4 Hz, 1H), 7.93 (d, J = 9.2 Hz, 1H), 7.83 (d, J = 7.2 Hz, 1H), 7.67 (d, J = 9.2 Hz, 1H), 7.62 (d, J = 8.0 Hz, 1H), 7.50 (dd, $^1$J = 8.4 Hz, $^2$J = 4.8 Hz, 1H), 3.94 (s, 3H), 3.85 (t, J = 7.2 Hz, 2H), 3.68 (t, J = 7.2 Hz, 2H). |
| 192 | 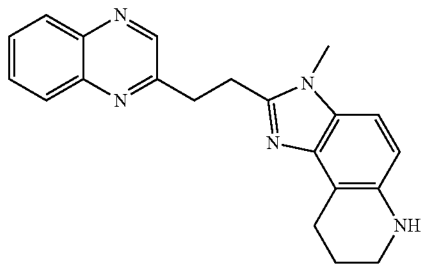 [SMILES: Cn1c(CCc2cnc3ccccc3n2)nc2c3c(ccc21)NCCC3] | MS (ESI): m/z 344 [M + H]$^+$; $^1$H NMR (400 MHz, CDCl$_3$): δ 8.83 (s, 1H), 8.08-8.02 (m, 2H), 7.77-7.70 (m, 2H), 6.90 (d, J = 8.8 Hz, 1H), 6.51 (d, J = 8.8 Hz, 1H), 3.67 (s, 3H), 3.65-3.61 (m, 2H), 3.46 (t, J = 7.2 Hz, 2H), 3.32 (t, J = 5.2 Hz, 2H), 3.13 (t, J = 7.2 Hz, 2H), 2.07-2.00 (m, 2H). |
| 193 | 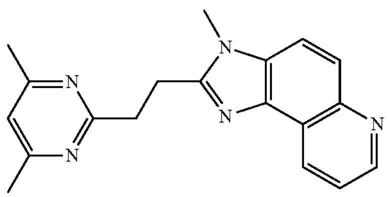 [SMILES: Cc1cc(C)nc(CCc2nc3c4cccnc4ccc3n2C)n1] | MS (ESI): m/z 318 [M + H]$^+$; $^1$H NMR (400 MHz, CDCl$_3$): δ 8.93 (dd, $^1$J = 8.0 Hz, $^2$J = 0.8 Hz, 1H), 8.88 (dd, $^1$J = 4.0 Hz, $^2$J = 1.6 Hz, 1H), 7.95 (d, J = 8.8 Hz, 1H), 7.69 (d, J = 8.8 Hz, 1H), 7.49 (dd, $^1$J = 8.4 Hz, $^2$J = 4.0 Hz, 1H), 6.86 (s, 1H), 3.92 (s, 3H), 3.57-3.49 (m, 4H), 2.43 (s, 6H). |
| 194 | 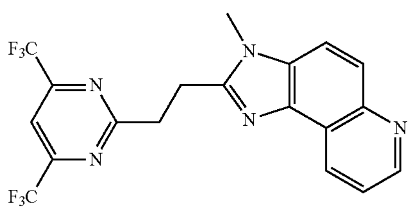 [SMILES: Cn1c(CCc2nc(C(F)(F)F)cc(C(F)(F)F)n2)nc2c3cccnc3ccc21] | MS (ESI): m/z 426 [M + H]$^+$; $^1$H NMR (400 MHz, CDCl$_3$): δ 8.88-8.85 (m, 2H), 7.98 (d, J = 4.4 Hz, 1H), 7.76 (s, 1H), 7.72 (d, J = 4.4 Hz, 1H), 7.51-7.48 (m, 1H), 3.98 (s, 3H), 3.98-3.94 (m, 2H), 3.60 (t, J = 7.2 Hz, 2H). |
| 195 | 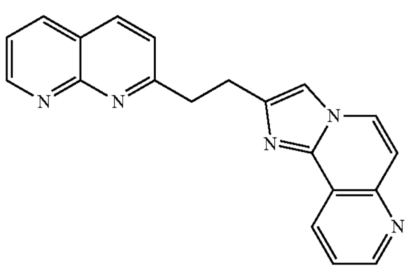 [SMILES: c1cnc2nc(CCc3cn4ccc5ncccc5c4n3)ccc2c1] | MS (ESI): m/z 326 [M + H]$^+$. |
| 196 | 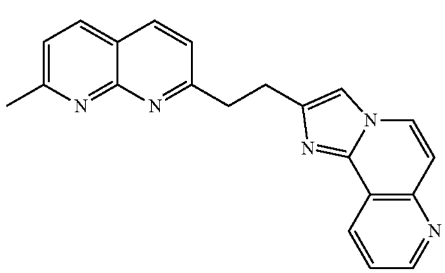 [SMILES: Cc1ccc2ccc(CCc3cn4ccc5ncccc5c4n3)nc2n1] | MS (ESI): m/z 340 [M + H]$^+$; $^1$H NMR (300 MHz, CDCl$_3$): δ 8.91-8.87 (m, 2H), 8.06-8.01 (m, 3H), 7.54 (dd, $^1$J = 8.1 Hz, $^2$J = 1.8 Hz, 1H), 7.40-7.26 (m, 3H), 7.28-7.24 (m, 1H), 3.58-3.48 (m, 4H), 2.84 (s, 3H). |

| Compound No. | Structure | Analytical Data |
|---|---|---|
| 197 | 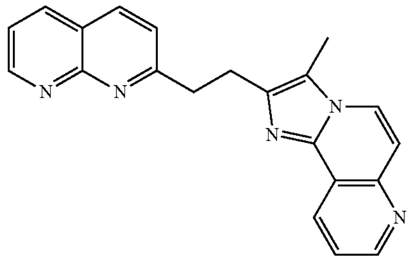 [SMILES: Cc1c(CCc2ccc3cccnc3n2)nc2c3cccnc3ccn12] | MS (ESI): m/z 340 [M + H]$^+$; $^1$H NMR (300 MHz, CDCl$_3$): δ 9.12 (dd, $^1J$ = 4.2 Hz, $^2J$ = 2.1 Hz, 1H), 8.93 (d, J = 8.4 Hz, 1H), 8.87 (dd, $^1J$ = 4.5 Hz, $^2J$ = 1.5 Hz, 1H), 8.18 (d, J = 1.8 Hz, 1H), 8.15 (d, J = 2.1 Hz, 1H), 8.06 (d, J = 8.1 Hz, 1H), 7.87-7.45 (m, 2H), 7.38 (d, J = 8.1 Hz, 1H), 7.32 (d, J = 7.5 Hz, 1H), 3.59-3.42 (m, 4H), 2.37 (s, 3H). |
| 198 | 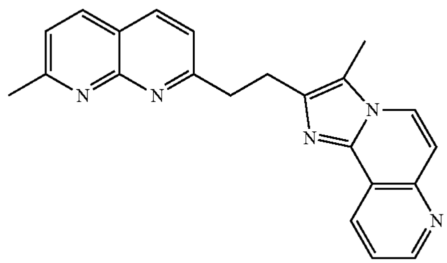 [SMILES: Cc1ccc2ccc(CCc3nc4c5cccnc5ccn4c3C)nc2n1] | MS (ESI): m/z 354.5 [M + H]$^+$; $^1$H NMR (300 MHz, CDCl$_3$): δ 8.95 (d, J = 8.1 Hz, 1H), 8.88 (d, J = 3.9 Hz, 1H), 8.03 (dd, $^1J$ = 10.5 Hz, $^2J$ = 8.7 Hz, 2H), 7.87 (d, J = 7.5 Hz, 1H), 7.55 (dd, $^1J$ = 8.21 Hz, $^2J$ = 4.5 Hz, 1H), 7.38-7.30 (m, 3H), 3.52-3.43 (m, 4H), 2.84 (s, 3H), 2.36 (s, 3H). |
| 199 | 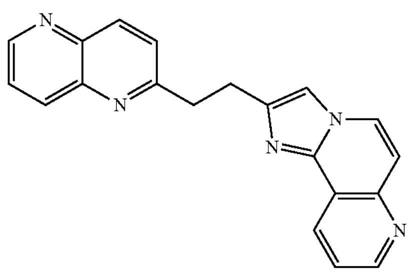 [SMILES: c1cnc2ccc(CCc3cn4ccc5ncccc5c4n3)nc2c1] | MS (ESI): m/z 326 [M + H]$^+$; $^1$H NMR (300 MHz, CDCl$_3$): δ 8.96-8.89 (m, 2H), 8.39 (d, J = 8.4 Hz, 1H), 8.31 (d, J = 8.4 Hz, 1H), 8.02 (d, J = 7.5 Hz, 1H), 7.67-7.53 (m, 3H), 7.35 (s, 1H), 7.32-7.26 (m, 2H), 3.56 (m, 2H), 3.44 (m, 2H). |
| 200 | 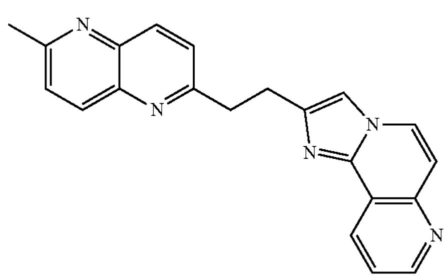 [SMILES: Cc1ccc2nc(CCc3cn4ccc5ncccc5c4n3)ccc2n1] | MS (ESI): m/z 340 [M + H]$^+$; $^1$H NMR (300 MHz, CDCl$_3$): δ 8.93-8.87 (m, 2H), 8.26 (d, J = 8.7 Hz, 1H), 8.21 (d, J = 8.7 Hz, 1H), 8.02 (d, J = 7.5 Hz, 1H), 7.57-7.50 (m, 3H), 7.35-7.25 (m, 2H), 3.55-3.39 (m, 4H), 2.78 (s, 3H). |
| 201 | 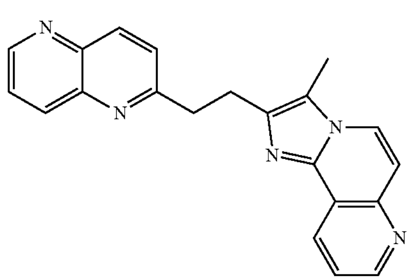 [SMILES: Cc1c(CCc2ccc3ncccc3n2)nc2c3cccnc3ccn12] | MS (ESI): m/z 340 [M + H]$^+$; $^1$H NMR (300 MHz, CDCl$_3$): δ 8.93-8.85 (m, 3H), 8.39 (d, J = 8.4 Hz, 1H), 8.25 (d, J = 8.7 Hz, 1H), 7.84 (d, J = 7.5 Hz, 1H), 7.65 (dd, $^1J$ = 8.4 Hz, $^2J$ = 4.2 Hz, 1H), 7.55 (dd, $^1J$ = 8.1 Hz, $^2J$ = 4.5 Hz, 1H), 7.47 (d, J = 8.7 Hz, 1H), 7.32 (d, J = 7.5 Hz, 1H), 3.54 (m, 2H), 3.38 (m, 2H), 2.24 (s, 3H). |

-continued

| Compound No. | Structure | Analytical Data |
|---|---|---|
| 202 | 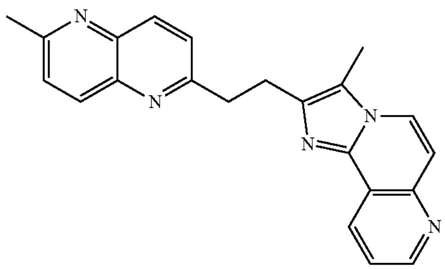 [SMILES: Cc1ccc2nc(CCc3nc4c5cccnc5ccn4c3C)ccc2n1] | MS (ESI): m/z 354.4 [M + H]$^+$; $^1$H NMR (300 MHz, CDCl$_3$): δ 8.95-8.88 (m, 1H), 8.88 (d, J = 3.0 Hz, 1H), 8.27 (d, J = 8.4 Hz, 1H), 8.15 (d, J = 8.7 Hz, 1H), 7.83 (d, J = 7.5 Hz, 1H), 7.57-7.49 (m, 2H), 7.41 (d, J = 8.7 Hz, 1H), 7.32 (d, J = 7.5 Hz, 1H), 3.51 (m, 2H), 3.36 (m, 2H), 2.78 (s, 3H), 2.21 (s, 3H). |
| 203 | 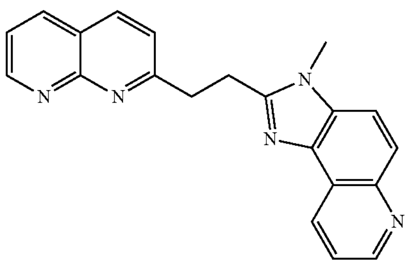 [SMILES: Cn1c(CCc2ccc3cccnc3n2)nc2c3cccnc3ccc21] | MS (ESI): m/z 340 [M + H]$^+$; $^1$H NMR (400 MHz, CDCl$_3$): δ 9.12 (m, 1H), 8.97 (brd, J = 8.0 Hz, 1H), 8.91 (m, 1H), 8.19 (d, J = 8.4 Hz, 1H), 8.12 (d, J = 8.4 Hz, 1H), 7.96 (d, J = 9.2 Hz, 1H), 7.69 (d, J = 8.8 Hz, 1H), 7.55-7.48 (m, 3H), 3.95 (s, 3H), 3.79-3.70 (m, 4H). |
| 204 | 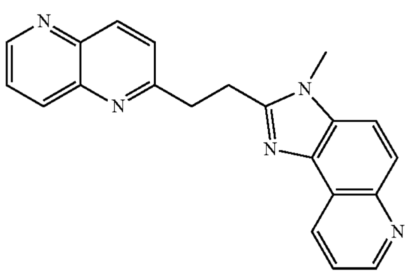 [SMILES: Cn1c(CCc2ccc3ncccc3n2)nc2c3cccnc3ccc21] | MS (ESI): m/z 340.1 [M + H]$^+$; $^1$H NMR (400 MHz, CD$_3$OD): δ 8.83 (dd, $^1$J = 8.4 Hz, $^2$J = 1.2 Hz, 1H), 8.80 (dd, $^1$J = 8.4 Hz, $^2$J = 1.5 Hz, 1H), 8.70 (dd, $^1$J = 4.4 Hz, $^2$J = 1.6 Hz, 1H), 8.28 (brd, J = 8.4 Hz, 1H), 8.22 (brd, J = 8.8 Hz, 1H), 7.85 (d, J = 9.2 Hz, 1H), 7.79 (d, J = 9.6 Hz, 1H), 7.66 (d, J = 8.8 Hz, 1H), 7.65 (d, J = 8.8 Hz, 1H), 7.52 (dd, $^1$J = 8.4 Hz, $^2$J = 4.4 Hz, 1H), 3.86 (s, 3H), 3.59-3.50 (m, 4H). |
| 205 | 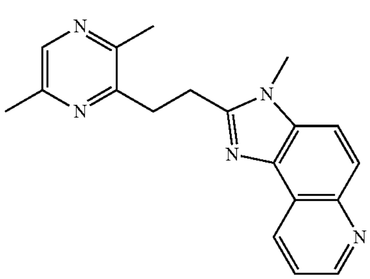 [SMILES: Cc1cnc(C)c(CCc2nc3c4cccnc4ccc3n2C)n1] | MS (ESI): m/z 318.2 [M + H]$^+$; $^1$H NMR (400 MHz, CD$_3$OD): δ 8.81 (ddd, $^1$J = 8.4 Hz, $^2$J = 2.2 Hz, $^3$J = 2.0 Hz, 1H), 8.69 (dd, $^1$J = 4.0 Hz, $^2$J = 1.6 Hz, 1H), 8.05 (s, 1H), 7.84 (d, J = 9.2 Hz, 1H), 7.78 (dd, $^1$J = 8.8 Hz, $^2$J = 0.8 Hz, 1H), 7.51 (dd, $^1$J = 8.4 Hz, $^2$J = 4.4 Hz, 1H), 3.86 (s, 3H), 3.42-3.30 (m, 4H), 2.40 (s, 3H), 2.32 (s, 3H). |
| 206 | 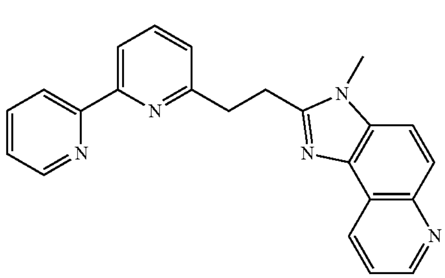 [SMILES: Cn1c(CCc2cccc(-c3ccccn3)n2)nc2c3cccnc3ccc21] | MS (ESI): m/z 366.2 [M + H]$^+$; $^1$H NMR (400 MHz, CD$_3$OD): δ 8.87 (dd, $^1$J = 8.0 Hz, $^2$J = 0.8 Hz, 1H), 8.72 (dd, $^1$J = 8.4 Hz, $^2$J = 1.6 Hz, 1H), 8.47 (brd, J = 8.4 Hz, 1H), 8.00 (d, J = 8.0 Hz, 1H), 7.93 (d, J = 8.0 Hz, 1H), 7.81 (d, J = 9.2 Hz, 1H), 7.77 (d, J = 9.2 Hz, 1H), 7.71 (t, J = 8.0 Hz, 1H), 7.57-7.52 (m, 2H), 7.26-7.22 (m, 2H), 3.73 (d, 3H), 3.48 (m, 2H), 3.38 (m, 2H). |

| Compound No. | Structure | Analytical Data |
|---|---|---|
| 207 | 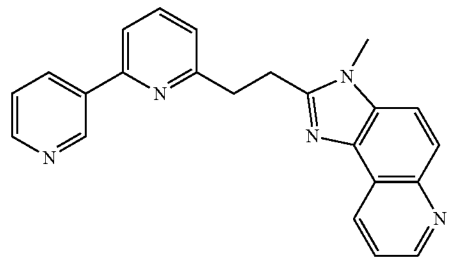 [SMILES: Cn1c(CCc2cccc(-c3cccnc3)n2)nc2c3cccnc3ccc21] | MS (ESI): m/z 366.1 [M + H]+; 1H NMR (400 MHz, CD3OD): δ 8.99 (m, 1H), 8.86 (dd, $^1J$ = 8.4 Hz, $^2J$ = 1.6 Hz, 1H), 8.72 (dd, $^1J$ = 8.8 Hz, $^2J$ = 1.6 Hz, 1H), 8.41 (dd, $^1J$ = 4.8 Hz, $^2J$ = 1.6 Hz, 1H), 8.15 (dt, $^1J$ = 8.0 Hz, $^2J$ = 1.6 Hz, 1H), 7.82 (d, J = 9.2 Hz, 1H), 7.78 (d, J = 9.2 Hz, 1H), 7.73-7.65 (m, 2H), 7.53 (dd, $^1J$ = 8.4 Hz, $^2J$ = 4.4 Hz, 1H), 7.28 (dd, $^1J$ = 8.4 Hz, $^2J$ = 4.8 Hz, 1H), 7.22 (dd, $^1J$ = 7.6 Hz, $^2J$ = 1.6 Hz, 1H), 3.76 (s, 3H), 3.50 (m, 2H), 3.39 (m, 2H). |
| 208 | 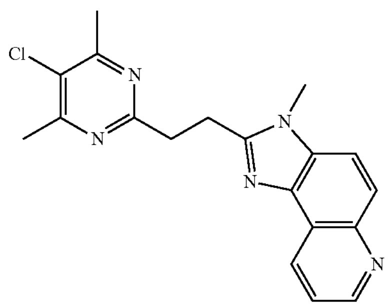 [SMILES: Cc1nc(CCc2nc3c4cccnc4ccc3n2C)nc(C)c1Cl] | MS (ESI): m/z 352.1 [M + H]+; 1H NMR (400 MHz, CDCl3): δ 8.93-8.87 (m, 2H), 7.95 (dd, $^1J$ = 9.2 Hz, $^2J$ = 0.4 Hz, 1H), 7.69 (d, J = 9.2 Hz, 1H), 7.50 (dd, $^1J$ = 8.0 Hz, $^2J$ = 4.4 Hz, 1H), 3.93 (s, 3H), 3.56-3.48 (m, 4H), 2.54 (s, 6H). |
| 209 | 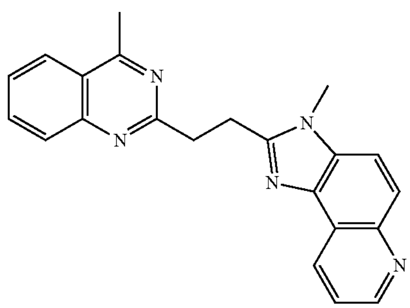 [SMILES: Cc1nc(CCc2nc3c4cccnc4ccc3n2C)nc2ccccc12] | MS (ESI): m/z 354.1 [M + H]+; 1H NMR (400 MHz, CDCl3): δ 8.96 (dd, $^1J$ = 8.4 Hz, $^2J$ = 1.2 Hz, 1H), 8.89 (dd, $^1J$ = 4.4 Hz, $^2J$ = 1.6 Hz, 1H), 8.05 (brd, J = 8.4 Hz, 1H), 7.98 (d, J = 8.8 Hz, 1H), 7.93 (d, J = 8.8 Hz, 1H), 7.84 (ddd, $^1J$ = 8.4 Hz, $^2J$ = 6.8 Hz, $^3J$ = 1.2 Hz, 1H), 7.70 (d, J = 9.2 Hz, 1H), 7.58 (ddd, $^1J$ = 8.4 Hz, $^2J$ = 7.2 Hz, $^3J$ = 1.2 Hz, 1H), 7.52 (dd, $^1J$ = 8.4 Hz, $^2J$ = 4.4 Hz, 1H), 3.98 (s, 3H), 3.76 (m, 2H), 3.67 (m, 2H), 2.91 (s, 3H). |
| 210 | 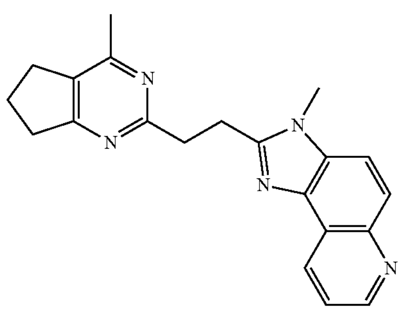 [SMILES: Cc1nc(CCc2nc3c4cccnc4ccc3n2C)nc2c1CCC2] | MS (ESI): m/z 344.1 [M + H]+; 1H NMR (400 MHz, CDCl3): δ 8.91 (brd, J = 8.0 Hz, 1H), 8.87 (dd, $^1J$ = 4.0 Hz, $^2J$ = 1.2 Hz, 1H), 7.93 (d, J = 9.2 Hz, 1H), 7.67 (d, J = 8.8 Hz, 1H), 7.48 (dd, $^1J$ = 8.4 Hz, $^2J$ = 4.4 Hz, 1H), 3.90 (s, 3H), 3.57-3.49 (m, 4H), 2.94 (t, J = 7.6 Hz, 2H), 2.86 (t, J = 7.6 Hz, 2H), 2.38 (s, 3H), 2.10 (quin, J = 7.6 Hz, 2H). |
| 211 | 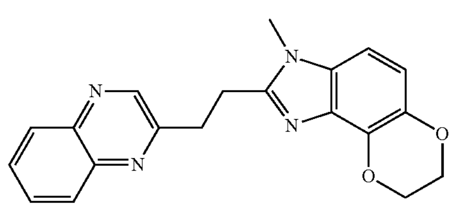 [SMILES: Cn1c(CCc2cnc3ccccc3n2)nc2c3c(ccc21)OCCO3] | MS (ESI): m/z 347.1 [M + H]+; 1H NMR (400 MHz, CDCl3): δ 8.80 (s, 1H), 8.09-8.01 (m, 2H), 7.77-7.69 (m, 2H), 6.82 (d, J = 8.4 Hz, 1H), 6.73 (d, J = 8.8 Hz, 1H), 4.44 (m, 2H), 4.31 (m, 2H), 3.76 (d, J = 8.8 Hz, 1H), 3.74 (d, J = 7.6 Hz, 1H), 3.70 (s, 3H), 3.46 (d, J = 7.6 Hz, 1H), 3.44 (d, J = 9.2 Hz, 1H). |

The following compounds may be made using synthetic methods as disclosed herein. Where applicable a Buchwald coupling (See, e.g., WO 2010/034500) may be used (General Method: Buch).
| Compound No. | Structure | Method of Preparation |
|---|---|---|
| 212 | 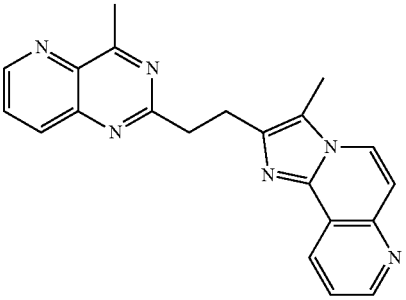 [SMILES: Cc1nc(CCc2nc3c4cccnc4ccn3c2C)nc2cccnc12] | TT, AAA |
| 213 | 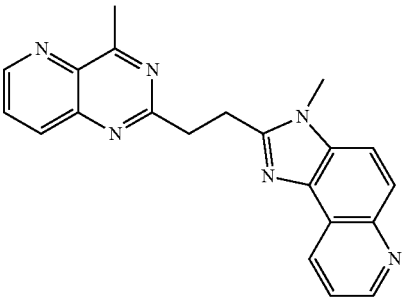 [SMILES: Cc1nc(CCc2nc3c4cccnc4ccc3n2C)nc2cccnc12] | AAA |
| 214 | 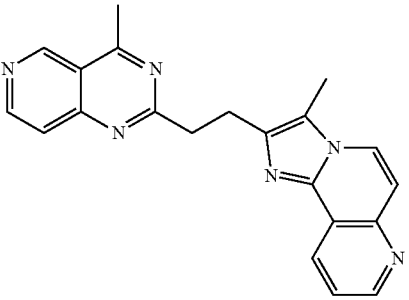 [SMILES: Cc1nc(CCc2nc3c4cccnc4ccn3c2C)nc2ccncc12] | TT, AAA |
| 215 | 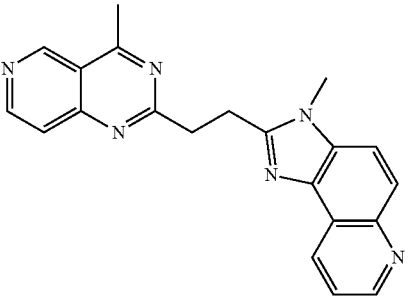 [SMILES: Cc1nc(CCc2nc3c4cccnc4ccc3n2C)nc2ccncc12] | AAA |
| 216 | 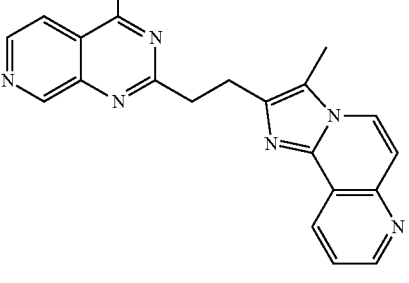 | TT, AAA |

| Compound No. | Structure | Method of Preparation |
|---|---|---|
| 217 | 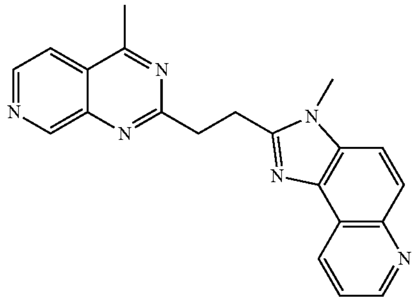 [SMILES: Cc1nc(CCc2nc3c4cccnc4ccc3n2C)nc2cnccc12] | AAA |
| 218 | 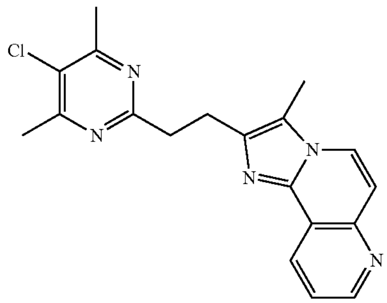 [SMILES: Cc1nc(CCc2nc3c4cccnc4ccn3c2C)nc(C)c1Cl] | TT, AAA |
| 219 | 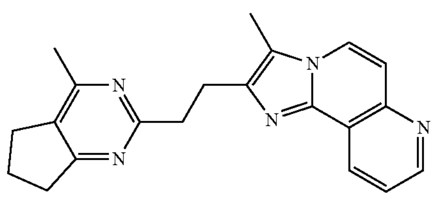 [SMILES: Cc1nc(CCc2nc3c4cccnc4ccn3c2C)nc2c1CCC2] | TT, AAA |
| 220 | 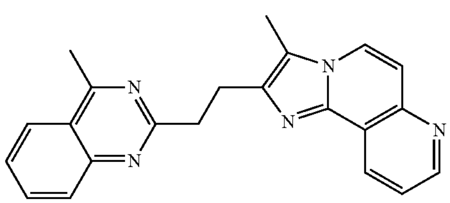 [SMILES: Cc1nc(CCc2nc3c4cccnc4ccn3c2C)nc2ccccc12] | TT, AAA |
| 221 | 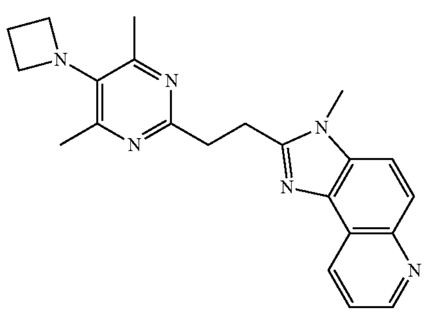 [SMILES: Cc1nc(CCc2nc3c4cccnc4ccc3n2C)nc(C)c1N1CCC1] | AAA |

-continued

| Compound No. | Structure | Method of Preparation |
|---|---|---|
| 222 | 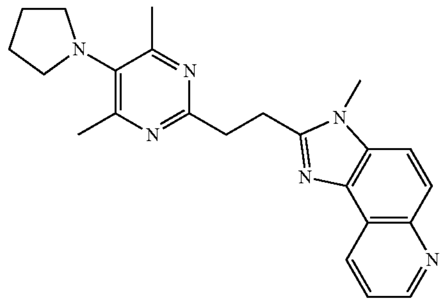 [SMILES: Cc1nc(CCc2nc3c4cccnc4ccc3n2C)nc(C)c1N1CCCC1] | AAA |
| 223 | 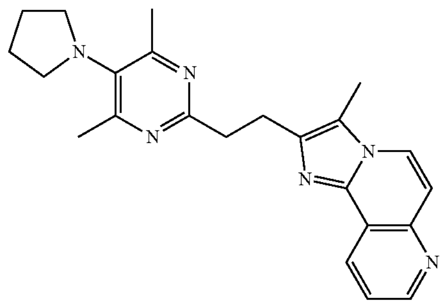 [SMILES: Cc1nc(CCc2nc3c4cccnc4ccn3c2C)nc(C)c1N1CCCC1] | TT, AAA |
| 224 | 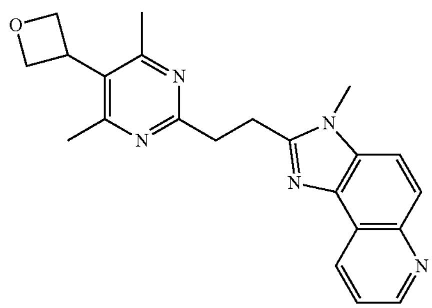 [SMILES: Cc1nc(CCc2nc3c4cccnc4ccc3n2C)nc(C)c1C1COC1] | AAA |
| 225 | 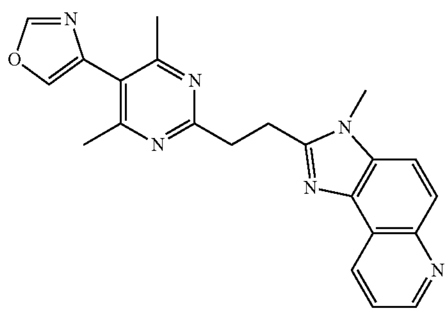 [SMILES: Cc1nc(CCc2nc3c4cccnc4ccc3n2C)nc(C)c1-c1cocn1] | AAA |
| 226 | 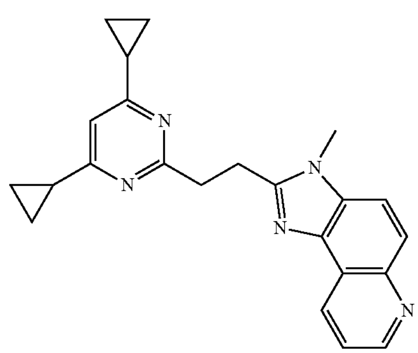 [SMILES: Cn1c(CCc2nc(C3CC3)cc(C3CC3)n2)nc2c3cccnc3ccc21] | AAA |

-continued

| Compound No. | Structure | Method of Preparation |
|---|---|---|
| 227 | 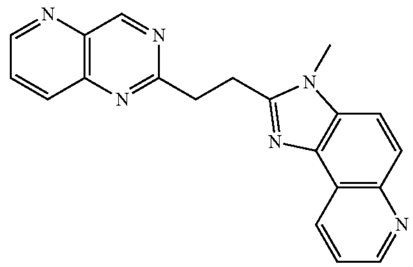 [SMILES: Cn1c(CCc2ncc3ncccc3n2)nc2c3cccnc3ccc21] | AAA |
| 228 | 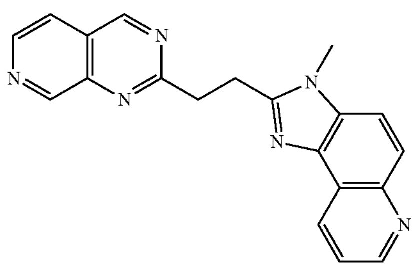 [SMILES: Cn1c(CCc2ncc3ccncc3n2)nc2c3cccnc3ccc21] | AAA |
| 229 | 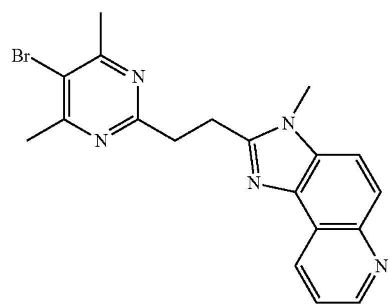 | AAA |
| 230 | 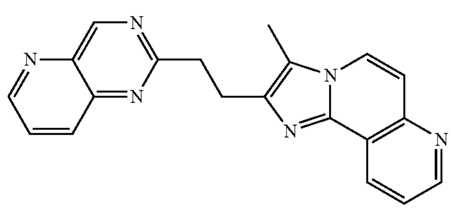 [SMILES: Cc1c(CCc2ncc3ncccc3n2)nc2c3cccnc3ccn12] | TT, AAA |
| 231 | 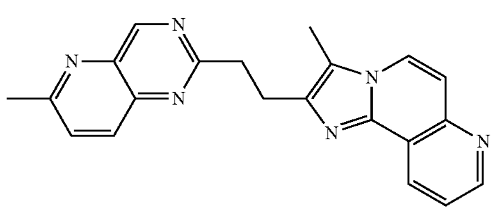 [SMILES: Cc1ccc2nc(CCc3nc4c5cccnc5ccn4c3C)ncc2n1] | TT, AAA |
| 232 | 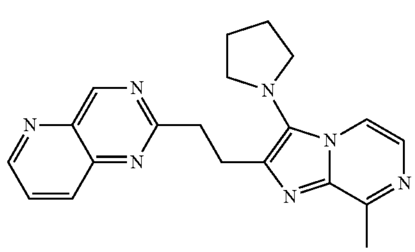 [SMILES: Cc1nccn2c(N3CCCC3)c(CCc3ncc4ncccc4n3)nc12] | XX, NN, Buch, AAA |

-continued

| Compound No. | Structure | Method of Preparation |
|---|---|---|
| 233 | 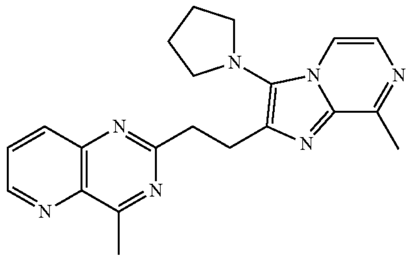 [SMILES: Cc1nc(CCc2nc3c(C)nccn3c2N2CCCC2)nc2cccnc12] | XX, NN, Buch, AAA |
| 234 | 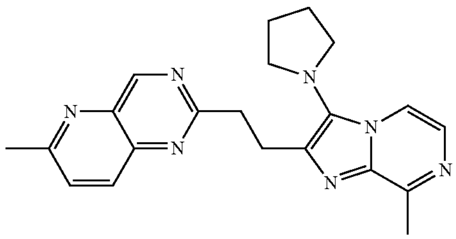 [SMILES: Cc1ccc2nc(CCc3nc4c(C)nccn4c3N3CCCC3)ncc2n1] | XX, NN, Buch, AAA |
| 235 | 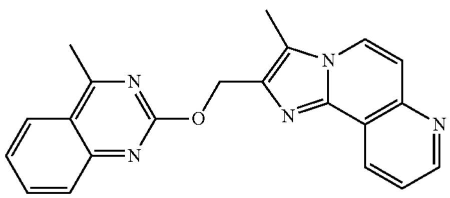 | TT, #18 |
| 236 | 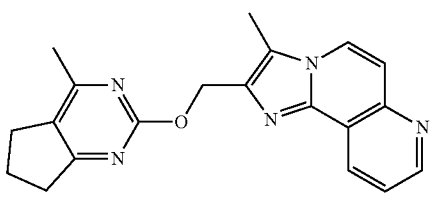 | TT, #18 |
| 237 | 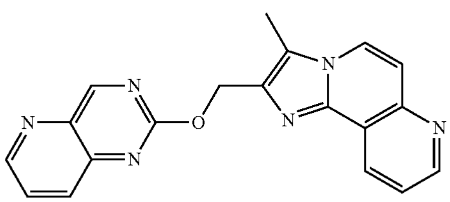 | TT, #18 |
| 238 | 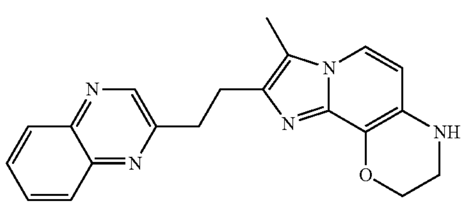 [SMILES: Cc1c(CCc2cnc3ccccc3n2)nc2c3c(ccn12)NCCO3] | II, #16 |
| 239 | 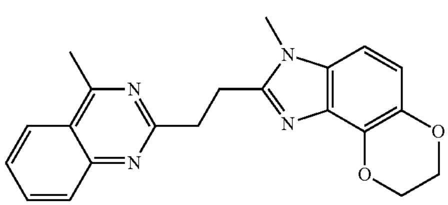 [SMILES: Cc1nc(CCc2nc3c4c(ccc3n2C)OCCO4)nc2ccccc12] | II, AAA |

-continued

| Compound No. | Structure | Method of Preparation |
|---|---|---|
| 240 | 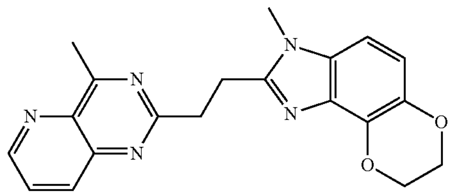 [SMILES: Cc1nc(CCc2nc3c4c(ccc3n2C)OCCO4)nc2cccnc12] | II, AAA |
| 241 | 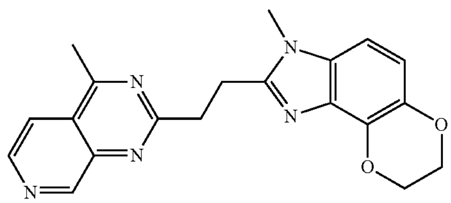 [SMILES: Cc1nc(CCc2nc3c4c(ccc3n2C)OCCO4)nc2cnccc12] | II, AAA |
| 242 | 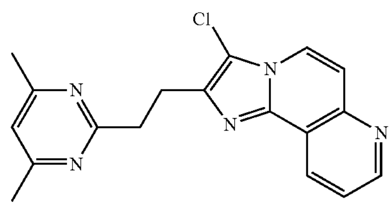 [SMILES: Cc1cc(C)nc(CCc2nc3c4cccnc4ccn3c2Cl)n1] | XX, NN |
| 243 | 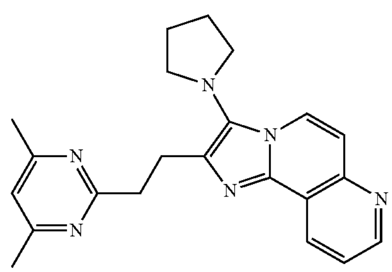 [SMILES: Cc1cc(C)nc(CCc2nc3c4cccnc4ccn3c2N2CCCC2)n1] | XX, NN, Buch, AAA |
| 244 | 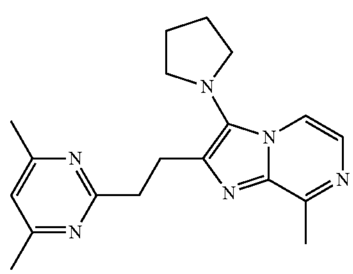 [SMILES: Cc1cc(C)nc(CCc2nc3c(C)nccn3c2N2CCCC2)n1] | XX, NN, Buch, AAA |
| 245 | 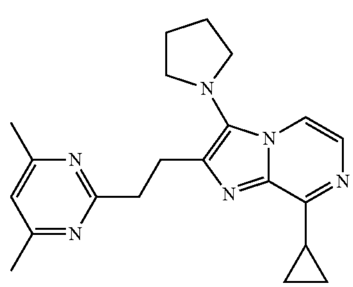 [SMILES: Cc1cc(C)nc(CCc2nc3c(C4CC4)nccn3c2N2CCCC2)n1] | XX, NN, Buch, AAA |

-continued
| Compound No. | Structure | Method of Preparation |
|---|---|---|
| 246 | 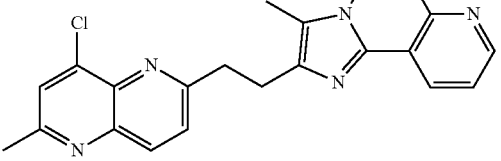 | TT, #25 |
| 247 | 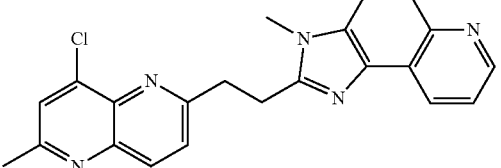 | L1, #25 |
| 248 | 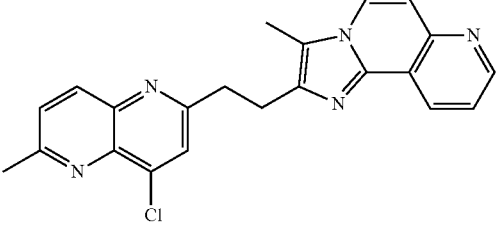 | TT, #25 |
| 249 | 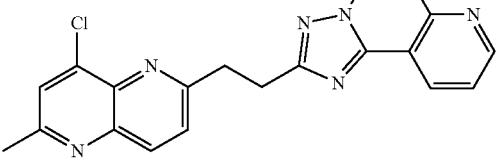 | SS, #25 |
| 250 | 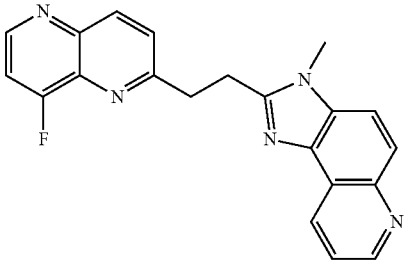 | T |
| 251 | 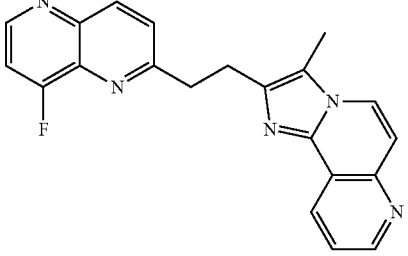 | T, TT |
| 252 | 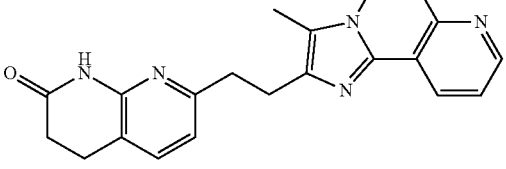 | TT |

-continued

| Compound No. | Structure | Method of Preparation |
|---|---|---|
| 253 | 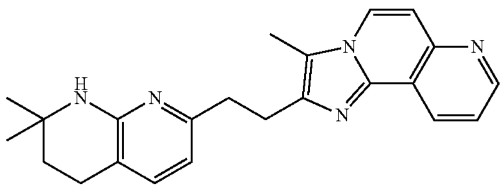 [SMILES: Cc1c(CCc2ccc3c(n2)NC(C)(C)CC3)nc2c3cccnc3ccn12] | TT |
| 254 | 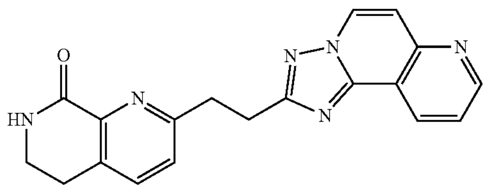 [SMILES: O=C1NCCc2ccc(CCc3nc4c5cccnc5ccn4n3)nc21] | SS |
| 255 | 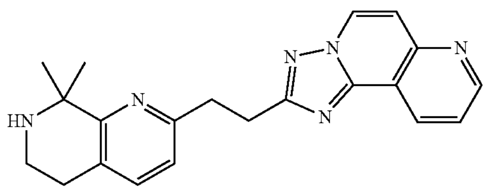 [SMILES: CC1(C)NCCc2ccc(CCc3nc4c5cccnc5ccn4n3)nc21] | SS |
| 256 | 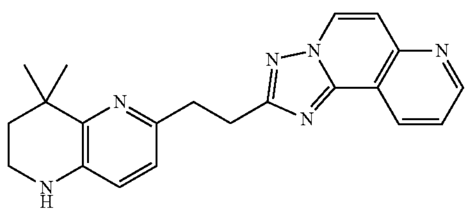 [SMILES: CC1(C)CCNc2ccc(CCc3nc4c5cccnc5ccn4n3)nc21] | SS |
| 257 | 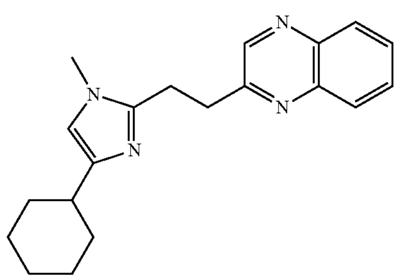 [SMILES: Cn1cc(C2CCCCC2)nc1CCc1cnc2ccccc2n1] | G |
| 258 | 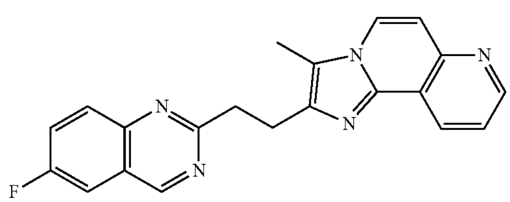 [SMILES: Cc1c(CCc2ncc3cc(F)ccc3n2)nc2c3cccnc3ccn12] | TT, AAA |
| 259 | 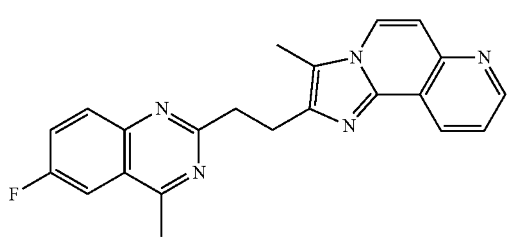 [SMILES: Cc1nc(CCc2nc3c4cccnc4ccn3c2C)nc2ccc(F)cc12] | TT, AAA |

| Compound No. | Structure | Method of Preparation |
|---|---|---|
| 260 | 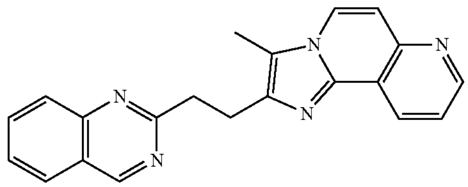 [SMILES: Cc1c(CCc2ncc3ccccc3n2)nc2c3cccnc3ccn12] | TT, AAA |
| 261 | 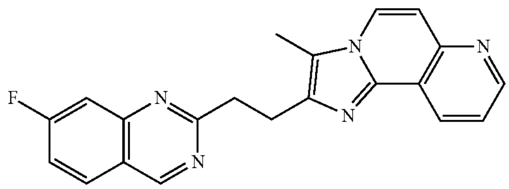 [SMILES: Cc1c(CCc2ncc3ccc(F)cc3n2)nc2c3cccnc3ccn12] | TT, AAA |
| 262 | 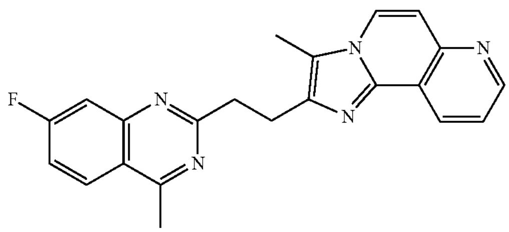 [SMILES: Cc1nc(CCc2nc3c4cccnc4ccn3c2C)nc2cc(F)ccc12] | TT, AAA |
| 263 | 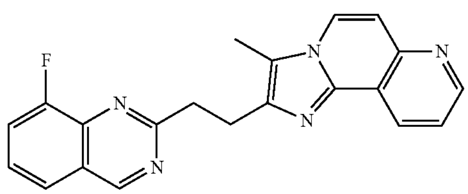 [SMILES: Cc1c(CCc2ncc3cccc(F)c3n2)nc2c3cccnc3ccn12] | TT, AAA |
| 264 | 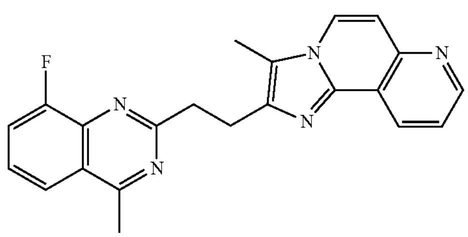 [SMILES: Cc1nc(CCc2nc3c4cccnc4ccn3c2C)nc2c(F)cccc12] | TT, AAA |

C. In Vitro Pharmacology

In one embodiment, the compounds provided herein were assayed for their ability to inhibit human PDE-10A. In one embodiment, the activities of the compounds were determined using the Molecular Devices IMAP PDE Fluorescence Polarization assay using recombinant human PDE-10 enzyme expressed in a baculoviral system. Briefly, 10 µL of a compound (0.2 nM-20 µM) was added to either a 96-well half area black plate or a 384-well black plate along with 10 µL of Fluorescein-labeled cAMP/cGMP substrate as per manufacturer's instructions and 10 µL of PDE enzyme (activity 0.1 U). Following a 40-minute incubation at 37° C., 60 µL of IMAP binding reagent was added. The plate was then read on a Perkin Elmer Victor (480-535 nm). The data was analyzed using Prism Software (GraphPad Inc, San Diego, Calif.).

In one embodiment, the compounds provided herein were run through a whole cell PDE-10 assay to assess their abilities to elevate intracellular concentrations of cAMP after PDE-10 blockade. Briefly, intracellular cGMP levels in HEK293 cells over-expressing PDE-10A were measured in a cell-based assay. Cells were plated into 96-well plates at a density of 100,000 cells per well and incubated at 37° C. overnight. The following day, cells were treated with a compound provided herein in fresh culture medium for 30 minutes. Sodium nitroprusside was then added from a 5× stock to a final concentration of 200 µM and the cells were incubated for 2 minutes exactly. The reaction was then stopped by addition of 200 µL Lysis Reagent A (GE Healthcare) and the intracellular cGMP concentration was determined using a cGMP EIA kit (GE Healthcare) according to the manufacturer's instructions. Data were reported as an $EC_{300}$, which was the concentration of the test compound that elevated intracellular cAMP concentrations 300% above the baseline levels.

IC$_{50}$ (μM) in PDE-10A Enzymatic Assay and EC$_{300}$ (μM) in Cell-Based Assay.

The potency of the compounds provided herein in human PDE-10 inhibition assay (enzyme assay IC$_{50}$) and whole cell PDE-10 assay (EC$_{300}$) is summarized in the table below.

| Compound No. | PDE-10 IC$_{50}$ (μM) | PDE-10 EC$_{300}$ (μM) |
| --- | --- | --- |
| 1 | ++++ | ++++ |
| 2 | ++++ | |
| 3 | ++++ | + |
| 4 | ++++ | ++ |
| 5 | ++++ | +++ |
| 6 | + | |
| 7 | + | |
| 8 | + | ++++ |
| 9 | + | |
| 10 | ++ | |
| 11 | ++++ | ++++ |
| 12 | ++++ | ++ |
| 13 | ++++ | |
| 14 | ++ | |
| 15 | ++ | |
| 16 | ++++ | +++ |
| 17 | ++++ | +++ |
| 18 | ++++ | |
| 19 | ++++ | ++++ |
| 20 | ++++ | +++ |
| 21 | ++ | |
| 22 | + | |
| 23 | ++ | |
| 24 | + | |
| 25 | ++ | |
| 26 | ++ | |
| 27 | ++ | |
| 28 | + | |
| 29 | + | |
| 30 | + | + |
| 31 | ++ | + |
| 32 | + | |
| 33 | + | |
| 34 | ++++ | ++++ |
| 35 | + | |
| 36 | ++++ | ++ |
| 37 | + | |
| 38 | + | |
| 39 | ++++ | ++++ |
| 40 | ++++ | ++++ |
| 41 | ++ | |
| 42 | ++++ | ++++ |
| 43 | ++++ | ++ |
| 44 | +++ | |
| 45 | ++++ | ++++ |
| 46 | ++++ | ++++ |
| 47 | + | |
| 48 | ++++ | ++++ |
| 49 | ++++ | ++++ |
| 50 | ++++ | ++++ |
| 51 | ++++ | ++ |
| 52 | ++++ | ++++ |
| 53 | ++ | |
| 54 | ++ | |
| 55 | ++ | |
| 56 | ++++ | ++++ |
| 57 | ++ | + |
| 58 | +++ | ++ |
| 59 | ++++ | ++ |
| 60 | +++ | ++ |
| 61 | ++++ | ++ |
| 62 | ++ | |
| 63 | + | |
| 64 | ++++ | ++++ |
| 65 | ++ | ++ |
| 66 | +++ | |
| 67 | ++++ | ++++ |
| 68 | ++ | ++ |
| 69 | ++++ | ++ |
| 70 | ++++ | ++ |
| 71 | +++ | |
| 72 | ++++ | ++++ |
| 73 | ++++ | ++++ |
| 74 | ++ | |
| 75 | ++++ | ++++ |
| 76 | ++++ | ++++ |
| 77 | ++++ | ++++ |
| 78 | ++++ | |
| 79 | +++ | ++ |
| 80 | + | |
| 81 | + | |
| 82 | ++ | + |
| 83 | ++ | |
| 84 | ++++ | |
| 85 | ++++ | |
| 86 | ++++ | |
| 87 | ++++ | |
| 88 | ++++ | |
| 89 | ++++ | |
| 90 | ++++ | |
| 91 | ++ | |
| 92 | ++++ | + |
| 93 | ++ | |
| 94 | ++++ | |
| 95 | ++ | |
| 96 | ++ | |
| 97 | ++ | |
| 98 | ++ | |
| 99 | +++ | |
| 100 | ++ | |
| 101 | +++ | |
| 102 | ++++ | ++ |
| 103 | ++++ | + |
| 104 | ++ | |
| 105 | ++ | |
| 106 | +++ | |
| 107 | + | |
| 108 | ++++ | |
| 109 | + | |
| 110 | + | + |
| 111 | ++ | |
| 112 | + | |
| 113 | + | |
| 114 | ++++ | |
| 115 | ++ | |
| 116 | ++++ | |
| 117 | ++ | |
| 118 | ++ | |
| 119 | ++ | |
| 120 | ++++ | ++ |
| 121 | ++ | |
| 122 | + | |
| 123 | ++++ | ++ |
| 124 | ++++ | ++ |
| 125 | ++++ | ++++ |
| 126 | ++++ | |
| 127 | ++++ | |
| 128 | ++++ | |
| 129 | +++ | |
| 130 | +++ | |
| 131 | ++++ | |
| 132 | +++ | |
| 133 | ++++ | |
| 134 | ++++ | ++ |
| 135 | ++++ | |
| 136 | ++++ | |
| 137 | ++++ | |
| 138 | ++++ | |
| 139 | ++ | |
| 140 | ++++ | |
| 141 | ++++ | |
| 142 | ++++ | ++++ |
| 143 | ++++ | |
| 144 | ++++ | ++ |
| 145 | +++ | + |
| 146 | ++++ | ++++ |

-continued

| Compound No. | PDE-10 IC$_{50}$ (µM) | PDE-10 EC$_{300}$ (µM) |
|---|---|---|
| 147 | ++++ | |
| 148 | ++++ | |
| 149 | ++++ | ++++ |
| 150 | ++ | |
| 151 | + | |
| 152 | ++ | |
| 153 | ++++ | |
| 154 | ++++ | |
| 155 | ++++ | +++ |
| 156 | ++++ | |
| 157 | ++++ | |
| 158 | ++++ | |
| 159 | ++++ | |
| 160 | +++ | |
| 161 | ++++ | |
| 162 | ++ | |
| 163 | ++++ | |
| 164 | ++++ | |
| 165 | ++++ | |
| 166 | ++++ | |
| 167 | ++++ | |
| 168 | ++ | |
| 169 | + | |
| 170 | ++++ | |
| 171 | ++++ | |
| 172 | ++++ | |
| 173 | + | |
| 174 | +++ | |
| 175 | ++ | |
| 176 | ++++ | |
| 177 | +++ | |
| 178 | | |
| 179 | | |
| 180 | ++++ | |
| 181 | ++++ | |
| 182 | + | |
| 183 | ++++ | |
| 184 | ++++ | |
| 185 | +++ | |
| 186 | ++++ | |
| 187 | ++++ | |
| 188 | ++++ | |
| 189 | ++++ | |
| 190 | ++++ | |
| 191 | ++++ | |
| 192 | ++++ | |
| 193 | ++++ | ++++ |
| 194 | ++++ | |
| 195 | ++ | |
| 196 | +++ | |
| 197 | ++++ | |
| 198 | +++ | |
| 199 | ++++ | |
| 200 | ++++ | |
| 201 | ++++ | |
| 202 | ++++ | ++++ |
| 203 | ++++ | |
| 204 | ++++ | ++++ |
| 205 | ++++ | |
| 206 | +++ | |
| 207 | ++ | |
| 208 | ++++ | ++++ |
| 209 | ++++ | |
| 210 | ++++ | ++++ |
| 211 | ++++ | ++++ |

IC$_{50}$ or EC$_{300}$ < 0.5 µM ++++;
0.5 < IC$_{50}$ or EC$_{300}$ < 1 µM +++;
1 < IC$_{50}$ or EC$_{300}$ < 10 µM ++;
IC$_{50}$ or EC$_{300}$ > 10 µM +.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated herein by reference in their entireties. Citation or identification of any reference in this application is not an admission that such reference is available as prior art to this application. The full scope of the disclosure is better understood with reference to the appended claims.

What is claimed:

1. A compound of formula (I):

A-L-B    (I), or a pharmaceutically acceptable salt or stereoisomer thereof, wherein L is —C(R$^6$)$_2$—C(R$^6$)$_2$—;

A is

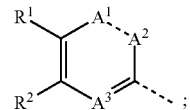

B is

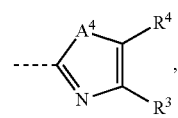 , 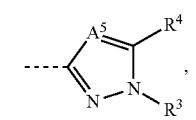 ,

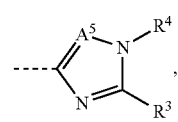 , 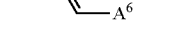

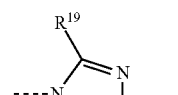 , 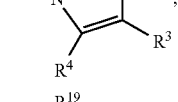 ,

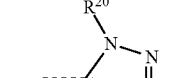 , 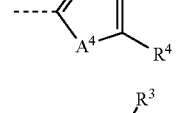 , or

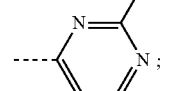 ;

-A$^1$-A$^2$- is —NR$^7$—C(=O)— or —N=CR$^8$—;

A$^3$ is N;

A$^4$ is NR$^5$ or O;

A$^5$ is CR$^5$ or N;

A$^6$ is CR$^5$;

R$^1$ and R$^2$ together with the carbon atoms to which they are attached form a 1,2-phenylene ring optionally substituted with one or more R$^{11}$;

R$^3$ and R$^4$ are each independently (i) hydrogen, cyano, or halo; or (ii) (C$_1$-C$_{10}$)alkyl, (C$_2$-C$_{10}$)alkenyl, (C$_1$-C$_{10}$)alkoxy, (C$_1$-C$_{10}$)aminoalkyl, (C$_1$C$_{10}$)heteroalkyl, (C$_3$-C$_{10}$)cycloalkyl, (6 to 10 membered)aryl, (5 to 10 membered)heteroaryl, (3 to 12 membered)heterocyclyl, hydroxy, amino, imino, amido, or thiol, each of which is optionally substituted with one or more $R^{11}$; or (iii) $R^3$ and $R^4$ together with the atoms to which they are attached form a ring optionally substituted with one or more $R^{11}$;

$R^5$ is (i) hydrogen, cyano, or halo; or (ii) $(C_1-C_{10})$alkyl, $(C_2C_{10})$alkenyl, $(C1-C_{10})$alkoxy, $(C_1-C_{10})$aminoalkyl, $(C_1-C_{10})$heteroalkyl, $(C_3-C_{10})$cycloalkyl, (6 to 10 membered)aryl, (5 to 10 membered)heteroaryl, (3 to 12 membered)heterocyclyl, hydroxy, amino, imino, amido, or thiol, each of which is optionally substituted with one or more $R^{11}$; or (iii) $R^4$ and $R^5$ together with the atoms to which they are attached form a ring optionally substituted with one or more $R^{11}$;

$R^{19}$ is (i) hydrogen, cyano, or halo; or (ii) $(C_1-C_{10})$alkyl, $(C_2-C_{10})$alkenyl, $(C1-C_{10})$alkoxy, $(C_1-C_{10})$aminoalkyl, $(C_1-C_{10})$heteroalkyl, $(C_3-C_{10})$cycloalkyl, (6 to 10 membered)aryl, (5 to 10 membered)heteroaryl, (3 to 12 membered)heterocyclyl, hydroxy, amino, imino, amido, or thiol, each of which is optionally substituted with one or more $R^{11}$;

$R^{20}$ is (i) hydrogen; or (ii) $(C_1-C_{10})$alkyl, $(C_2-C_{10})$alkenyl, $(C_1-C_{10})$heteroalkyl, $(C_3-C_{10})$cycloalkyl, (6 to 10 membered)aryl, or (5 to 10 membered)heteroaryl, (3 to 12 membered)heterocyclyl, each of which is optionally substituted with one or more $R^{11}$;

each occurrence of $R^6$ is independently hydrogen, halo, or $(C_1-C_6)$alkyl optionally substituted with one or more halo;

$R^7$ is hydrogen or $(C_1-C_6)$alkyl optionally substituted with one or more halo;

$R^8$ is (i) hydrogen, cyano, or halo; or (ii) $(C_1-C_{10})$ alkyl, $(C_2-C_{10})$alkenyl, $(C_1-C_{10})$alkoxy, $(C_1-C_{10})$aminoalkyl, $(C_1-C_{10})$heteroalkyl, $(C_3-C_{10})$ cycloalkyl, (6 to 10 membered)aryl, (5 to 10 membered)heteroaryl, (3 to 12 membered) heterocyclyl, hydroxy, amino, imino, amido, or thiol, each of which is optionally substituted with one or more $R^{11}$;

each occurrence of $R^{11}$ is independently hydrogen, halogen, cyano, =O, —$OR^{13}$, —$NR^{13}R^{14}$, —$N(R^{13})C(O)R^{14}$, —$C(O)NR^{13}R^{14}$, —$C(O)R^{13}$, —$C(O)OR^{13}$, —$SR^{13}$, —$S(O)R^{13}$, —$S(O)_2R^{13}$, —$S(O)_2NR^{13}R^{14}$, $(C_1-C_{10})$alkyl optionally substituted with one or more $R^{12}$, $(C_1-C_{10})$heteroalkyl optionally substituted with one or more $R^{12}$, $(C_3-C_{10})$cycloalkyl optionally substituted with one or more $R^{12}$, $(C_7-C_{12})$aralkyl optionally substituted with one or more $R^{12}$, $(C_3-C_{12})$heteroaralkyl optionally substituted with one or more $R^{12}$, (6 to 10 membered)aryl optionally substituted with one or more $R^{12}$, (5 to 10 membered)heteroaryl optionally substituted with one or more $R^{12}$, or (3 to 12 membered) heterocyclyl optionally substituted with one or more $R^{12}$;

each occurrence of $R^{12}$ is independently hydrogen, $(C_1-C_6)$ alkyl optionally substituted with one or more $R^{13}$, $(C_3-C_6)$cycloalkyl optionally substituted with one or more $R^{13}$, halogen, cyano, =O, —$OR^{13}$, —$NR^{13}R^{14}$, —$N(R13)C(O)R^{14}$, —$C(O)R^{13}$, —$C(O)OR^{13}$, —$OC(O)R^{13}$, —$SR^{13}$, —$S(O)R^{13}$, —$S(O)_2R^{13}$, or —$S(O)_2NR^{13}R^{14}$; and each occurrence of $R^{13}$ and $R^{14}$ is independently hydrogen, $(C_1-C_6)$alkyl, $(C_1-C_6)$ heteroalkyl, $(C_3-C_6)$cycloalkyl, $(C_7-C_{10})$aralkyl; $(C_3-C_{12})$heteroaralkyl, (6 to 10 membered)aryl, (5 to 10 membered)heteroaryl, or (3 to 12 membered)heterocyclyl; or $R^{13}$ and $R^{14}$ together may form a 3 to 10 membered ring.

2. The compound of claim 1, or a pharmaceutically acceptable salt or stereoisomer thereof, having formula (I-A):

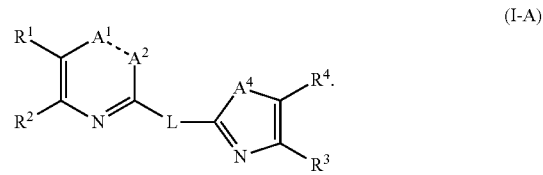

(I-A)

3. The compound of claim 2, wherein

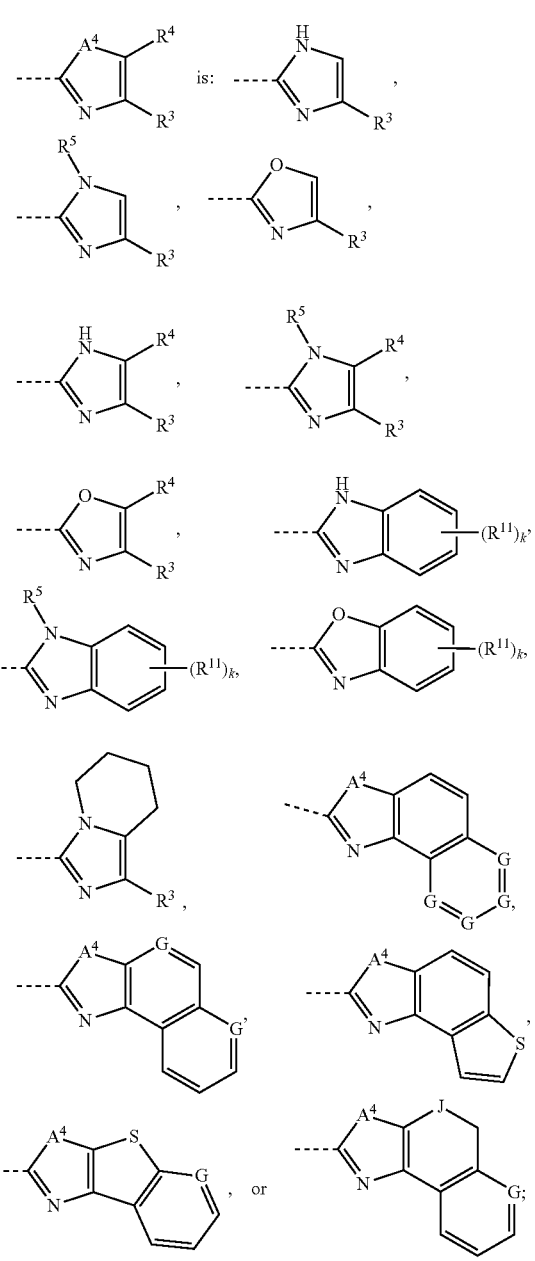

k is 0, 1, 2, 3, or 4;
each occurrence of G is independently CH or N; and
J is O, S, NH or $CH_2$.

4. The compound of claim 3, wherein $R^3$ is (i) hydrogen; or (ii) $(C_1-C_{10})$alkyl, (6 to 10 membered)aryl, or (5 to 10 membered)heteroaryl, each of which is optionally substituted with one or more $R^{11}$.

5. The compound of claim 3, wherein $R^4$ is (i) hydrogen; or (ii) $(C_1-C_{10})$alkyl, (6 to 10 membered)aryl, or (5 to 10 membered)heteroaryl, each of which is optionally substituted with one or more $R^{11}$.

6. The compound of claim 3, wherein $R^5$ is (i) hydrogen; or (ii) $(C_1-C_{10})$alkyl, (6 to 10 membered)aryl, or (5 to 10 membered)heteroaryl, each of which is optionally substituted with one or more $R^{11}$.

7. The compound of claim 3, wherein each occurrence of $R^{11}$ is independently (i) hydrogen; or (ii) $(C_1-C_{10})$alkyl, (6 to 10 membered)aryl, or (5 to 10 membered)heteroaryl, each of which is optionally substituted with one or more $R^{12}$.

8. The compound of claim 2, wherein $A^4$ is $NR^5$; and $R^5$ is (i) hydrogen; or (ii) $(C_1-C_{10})$alkyl, $(C_2-C_{10})$alkenyl, $(C_1-C_{10})$heteroalkyl, $(C_3-C_{10})$cycloalkyl, (6 to 10 membered) aryl, (5 to 10 membered) heteroaryl, or (3 to 12 membered)heterocyclyl, each of which is optionally substituted with one or more $R^{11}$; or (iii) $R^4$ and $R^5$ together with the atoms to which they are attached form a ring optionally substituted with one or more $R^{11}$.

9. The compound of claim 8, wherein $R^5$ is H or $CH_3$.

10. The compound of claim 2, wherein

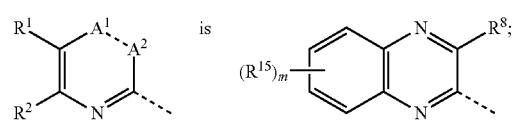

each occurrence of $R^{15}$ is independently: hydrogen, halo, cyano, $-OR^{13}$, $-NR^{13}R^{14}$, $-N(R^{13})C(O)R^{14}$, $-C(O)NR^{13}R^{14}$, $-C(O)R^{13}$, $-OC(O)R^{13}$, $-SR^{13}$, $-S(O)R^{13}$, $-S(O)_2R^{13}$, $-S(O)_2NR^{13}R^{14}$, $(C_1-C_{10})$alkyl optionally substituted with one or more $R^{12}$, $(C_1-C_{10})$heteroalkyl optionally substituted with one or more $R^{12}$, $(C_3-C_{10})$cycloalkyl optionally substituted with one or more $R^{12}$, $(C_7-C_{12})$aralkyl optionally substituted with one or more $R^{12}$, $(C_3-C_{12})$heteroaralkyl optionally substituted with one or more $R^{12}$, (6 to 10 membered)aryl optionally substituted with one or more $R^{12}$, (5 to 10 membered)heteroaryl optionally substituted with one or more $R^{12}$, or (3 to 12 membered)heterocyclyl optionally substituted with one or more $R^{12}$; and m is 0,1,2,3, or 4.

11. The compound of claim 10, wherein $R^8$ is H or $CH_3$.

12. The compound of claim 10, wherein the compound is:

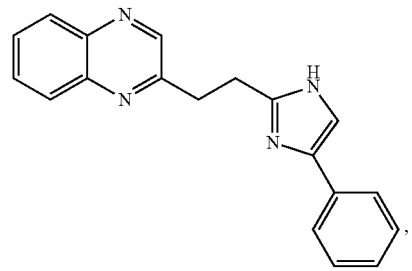

-continued

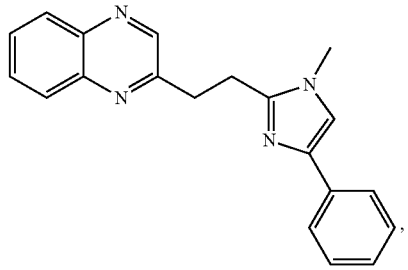

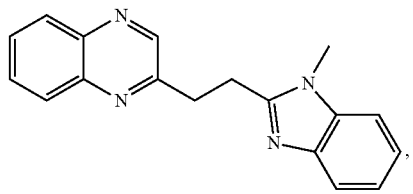

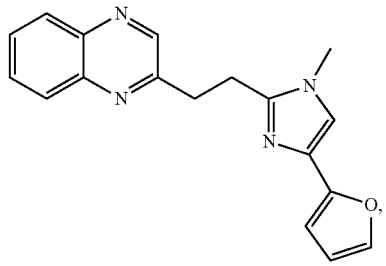

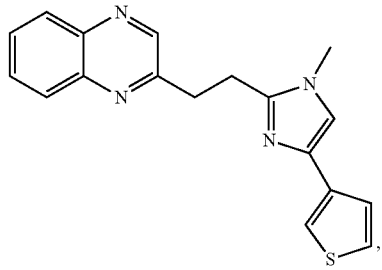

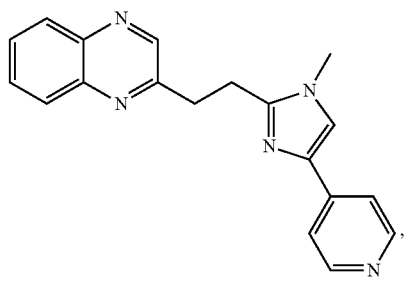

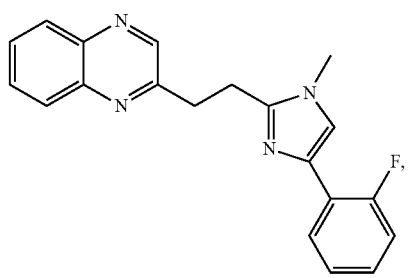

317
-continued
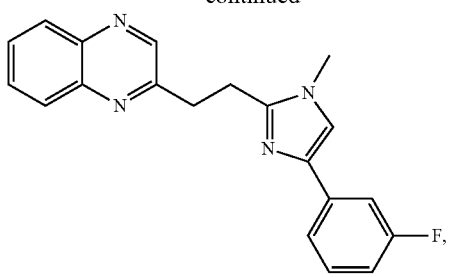
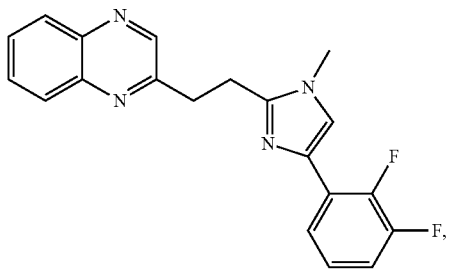
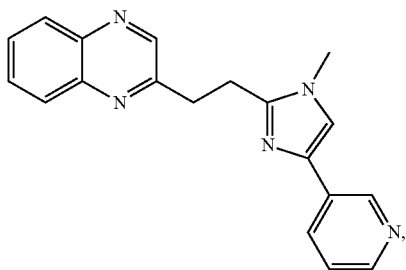
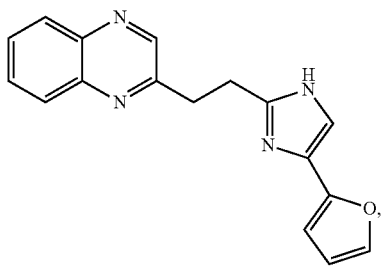
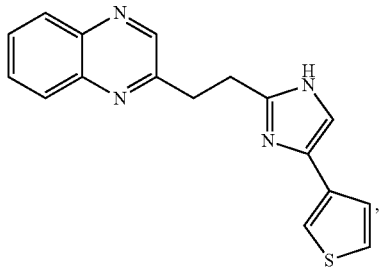
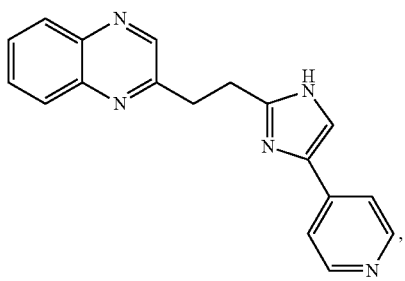
318
-continued
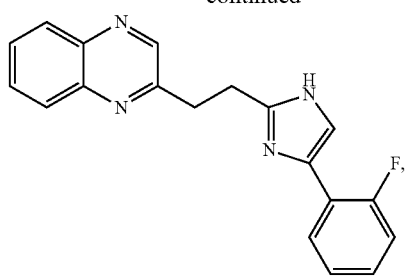
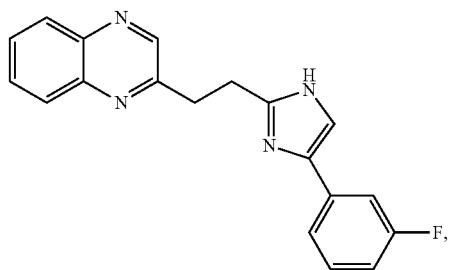
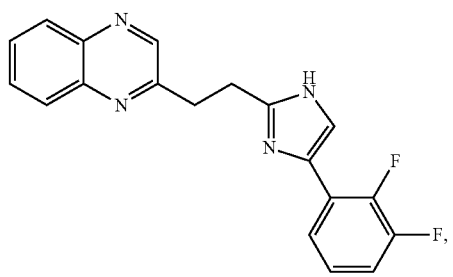
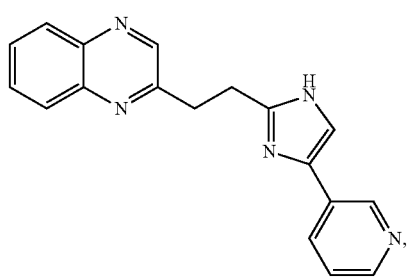
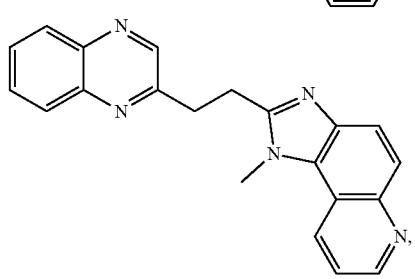
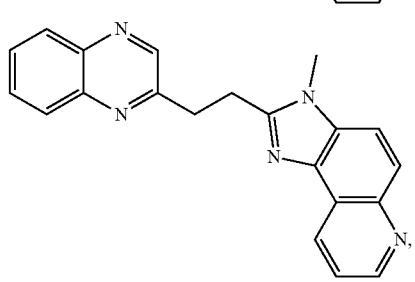

319
-continued
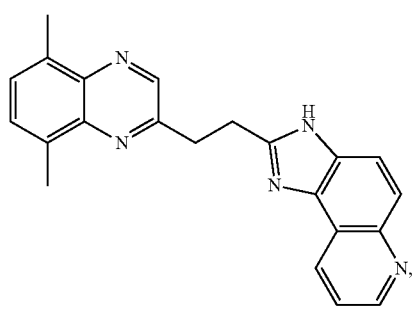
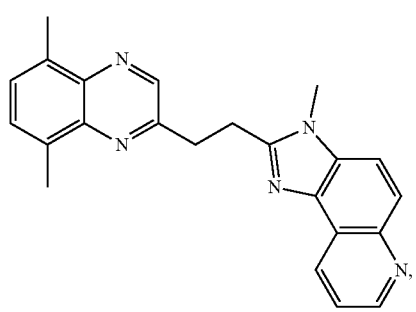
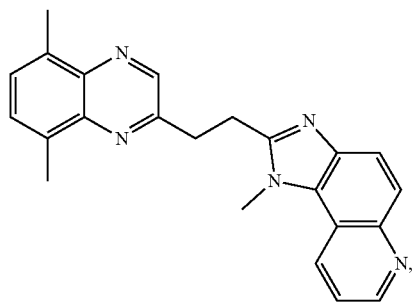
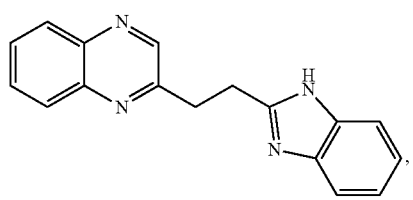
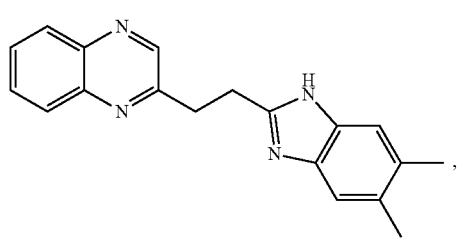
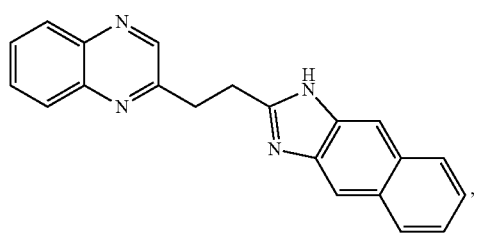
320
-continued
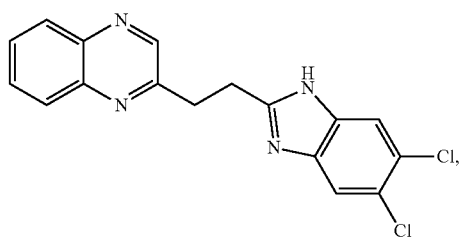
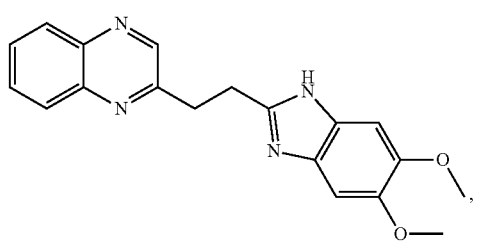
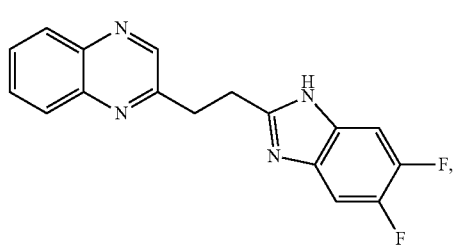
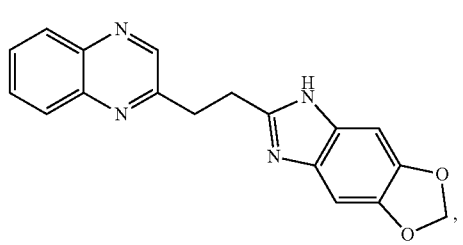
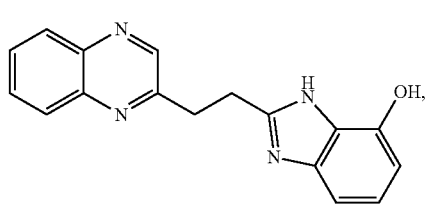
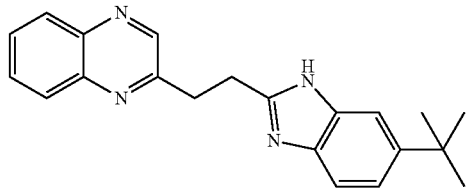
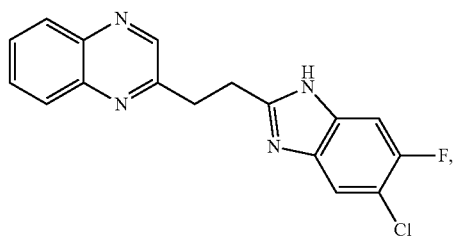

321
-continued
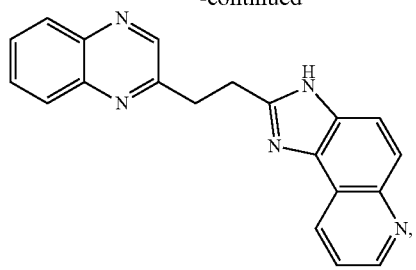
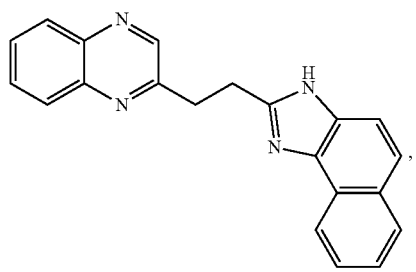
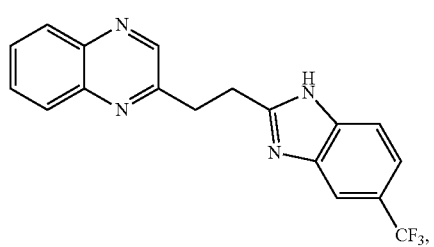
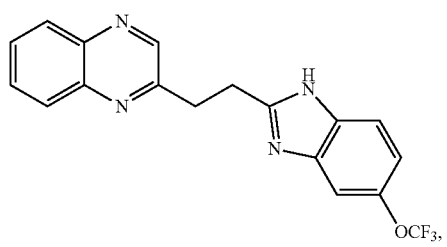
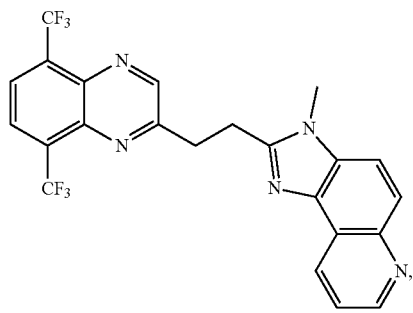
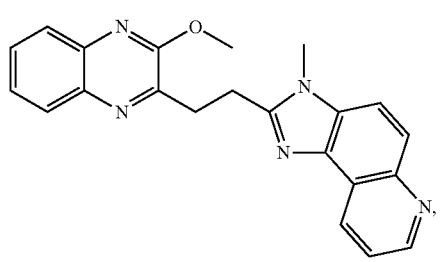
322
-continued
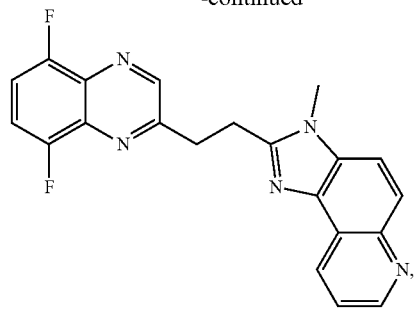
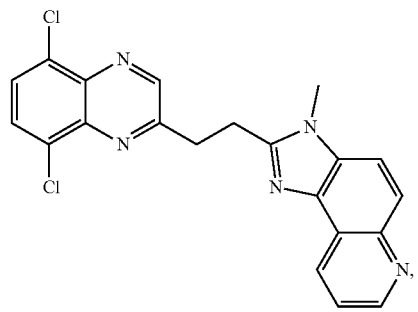
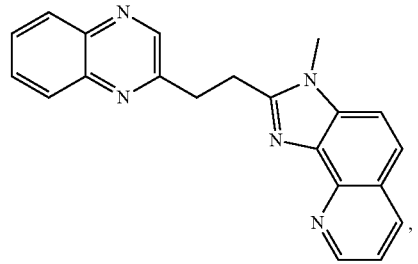
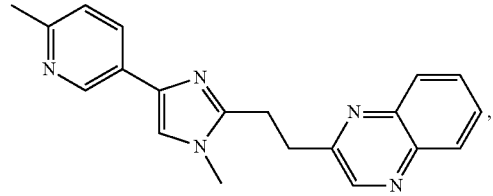
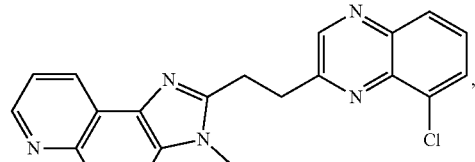
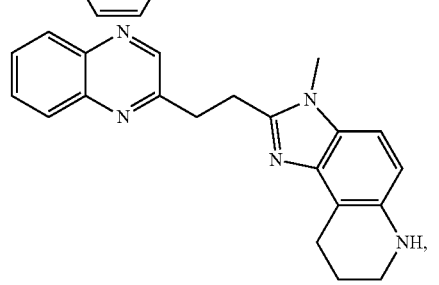
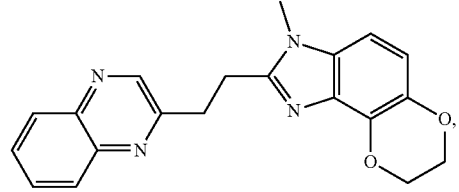

-continued

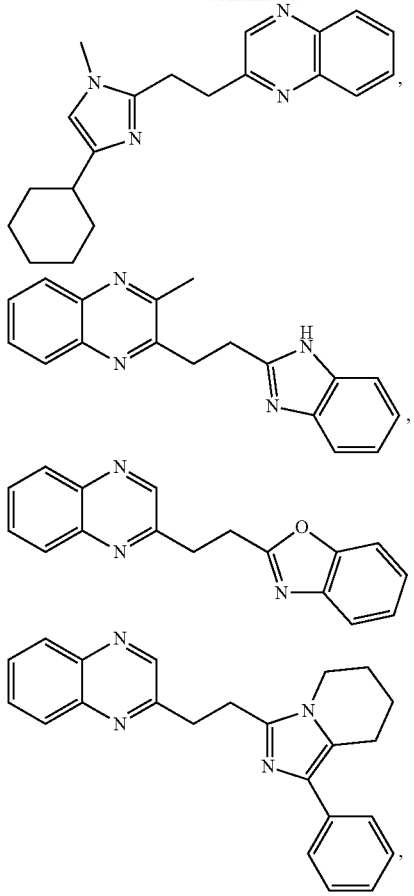

13. The compound of claim 2, wherein

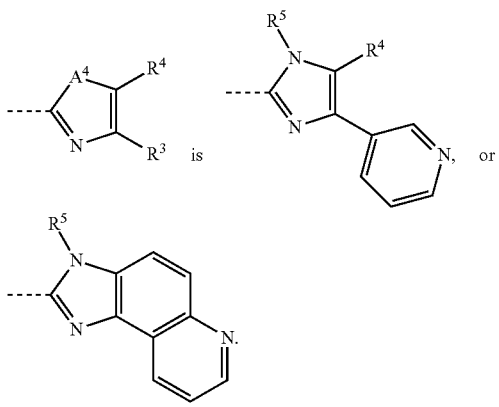

14. The compound of claim 2, wherein the compound is:

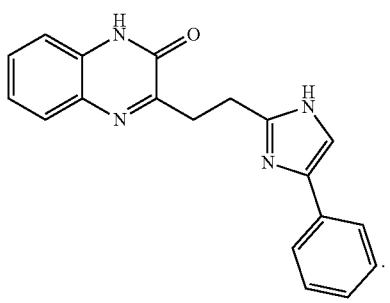 [SMILES: O=c1[nH]c2ccccc2nc1CCc1nc(-c2ccccc2)c[nH]1]

15. The compound of claim 1, wherein
B is

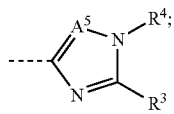

$A^5$ is $CR^5$;

$R^3$ and $R^4$ together with the atoms to which they are attached form an optionally substituted ring.

16. The compound of claim 15, wherein $R^5$ is H or $CH_3$.

17. The compound of claim 15, wherein the compound is:

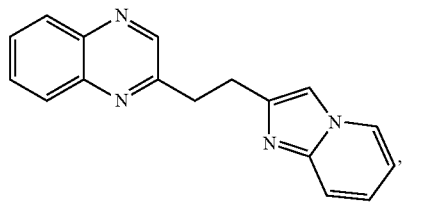

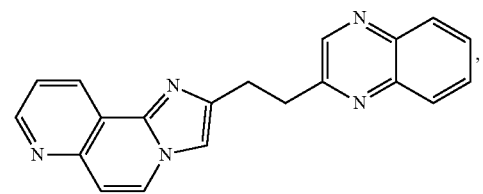

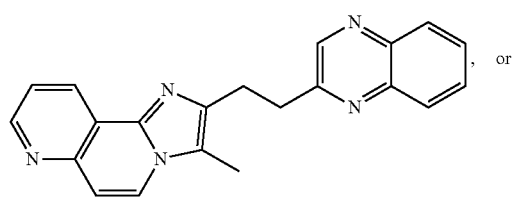

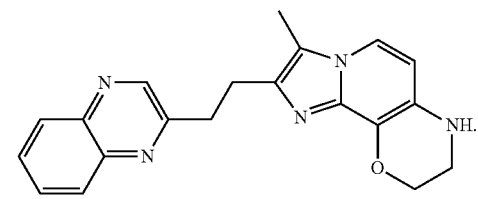

18. The compound of claim 1, wherein
B is

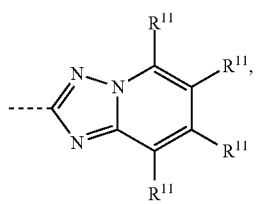

wherein each $R^{11}$ may be the same or different.

19. The compound of claim 18, wherein the compound is:

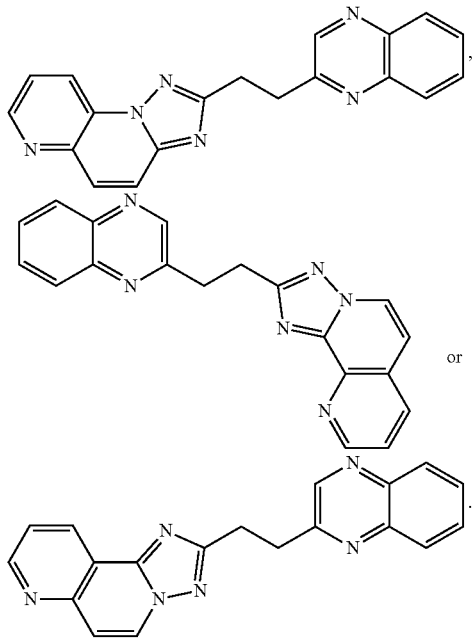

20. The compound of claim 1, having formula (I-B):

D-L-E  (I-B), or a pharmaceutically acceptable salt or stereoisomer thereof, wherein L is —(CH$_2$)$_2$—;

D is

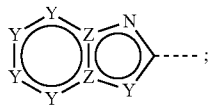

E is:

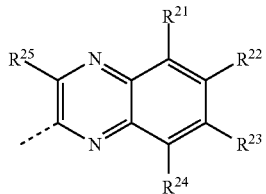

each Y is independently N or CR;
each Z is independently N or C;
provided that D contains 1, 2, 3, or 4 nitrogen ring atoms;
each occurrence of R is independently hydrogen, halo, cyano, (C$_1$-C$_6$)alkyl, (C$_1$-C$_6$)alkoxy, (C$_1$-C$_6$)hydroxyalkyl, aryl, or heteroaryl;
each occurrence of R$^{21}$, R$^{22}$, R$^{23}$, and R$^{24}$ is independently hydrogen, halo, cyano, (C$_1$-C$_6$)alkyl, (C$_2$-C$_6$)alkenyl, (C$_2$-C$_6$)alkynyl, (C$_1$-C$_6$)heteroalkyl, (C$_1$-C$_6$)alkoxy, (C$_1$-C$_6$)aminoalkyl, (C$_1$-C$_6$)hydroxyalkyl, CH$_2$CN, CH$_2$C(O)NH$_2$, (C$_3$-C$_8$)cycloalkyl, aryl, heteroaryl, heterocyclyl, aralkyl, heteroaralkyl, or alkyl-heterocycloalkyl; and R$^{25}$ is hydrogen, halo, cyano, (C$_1$-C$_6$)alkyl, (C$_3$-C$_8$)cycloalkyl, (C$_1$-C$_6$)alkoxy, (C$_1$-C$_6$)hydroxyalkyl, CH$_2$CN, CH$_2$C(O)NH$_2$, (C$_7$-C$_{12}$)aralkyl, or alkyl-heterocycloalkyl.

21. The compound of claim 20, wherein the compound is:

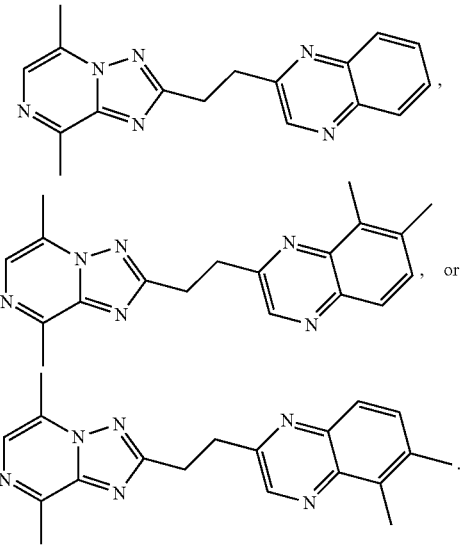

22. The compound of claim 1, wherein L is —CH$_2$—CH$_2$—.

23. A pharmaceutical composition comprising a compound of claim 1, or a pharmaceutically acceptable salt or stereoisomer thereof.

24. A method of inhibiting phosphodiesterase-10A activity in a subject, comprising administering to the subject a therapeutically effective amount of a compound of claim 1, or a pharmaceutically acceptable salt or stereoisomer thereof.

25. A compound, or a pharmaceutically acceptable salt or stereoisomer thereof, wherein the compound is:

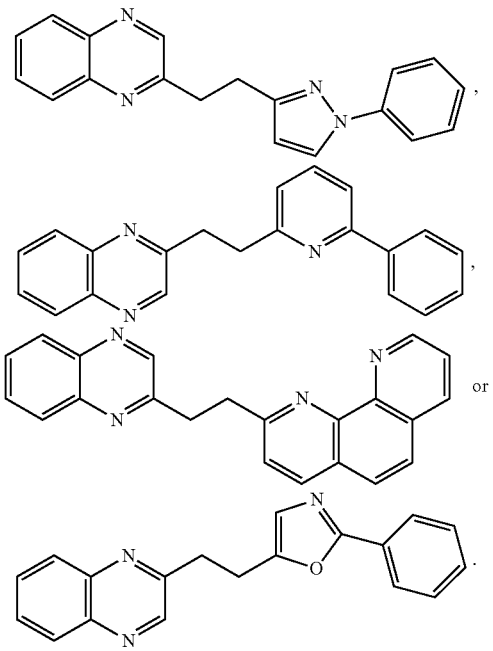

* * * * *